US007020508B2

(12) United States Patent
Stivoric et al.

(10) Patent No.: US 7,020,508 B2
(45) Date of Patent: Mar. 28, 2006

(54) APPARATUS FOR DETECTING HUMAN PHYSIOLOGICAL AND CONTEXTUAL INFORMATION

(75) Inventors: John M. Stivoric, Pittsburgh, PA (US); Scott K. Boehmke, Pittsburgh, PA (US); Eric Teller, Pittsburgh, PA (US); Christopher D. Kasabach, Pittsburgh, PA (US)

(73) Assignee: BodyMedia, Inc., Pittsburgh, PA (US)

( * ) Notice: Subject to any disclaimer, the term of this patent is extended or adjusted under 35 U.S.C. 154(b) by 60 days.

(21) Appl. No.: 10/227,575

(22) Filed: Aug. 22, 2002

(65) Prior Publication Data
US 2004/0039254 A1    Feb. 26, 2004

(51) Int. Cl.
*A61B 5/04* (2006.01)

(52) U.S. Cl. ...................... 600/390; 600/513
(58) Field of Classification Search ................ 600/372, 600/382–384, 386, 388–391, 393, 481, 483, 600/508, 509, 544–547, 549
See application file for complete search history.

(56) References Cited

U.S. PATENT DOCUMENTS

| | | | |
|---|---|---|---|
| 4,031,365 A | 6/1977 | Raggiotti et al. ............ 702/131 |
| 4,052,979 A | 10/1977 | Scherr et al. ................ 600/503 |
| 4,129,125 A | 12/1978 | Lester et al. ................ 600/484 |
| 4,148,304 A | 4/1979 | Mull .......................... 600/549 |
| 4,151,831 A | 5/1979 | Lester ........................ 600/549 |
| 4,192,000 A | 3/1980 | Lipsey | |
| 4,377,171 A | 3/1983 | Wada ......................... 600/549 |
| 4,407,295 A | 10/1983 | Steuer et al. ................ 600/483 |
| 4,488,558 A * | 12/1984 | Simbruner et al. ......... 600/376 |
| 4,509,531 A | 4/1985 | Ward ......................... 600/549 |
| 4,531,527 A | 7/1985 | Reinhold, Jr. et al. ...... 600/509 |
| 4,557,273 A | 12/1985 | Stoller et al. ............... 600/551 |
| 4,608,987 A | 9/1986 | Mills .......................... 600/389 |
| 4,622,979 A | 11/1986 | Katchis et al. .............. 600/515 |
| 4,672,977 A * | 6/1987 | Kroll .......................... 600/528 |
| 4,676,254 A | 6/1987 | Frohn ......................... 600/549 |

(Continued)

FOREIGN PATENT DOCUMENTS

DE    198 32 361 A1    2/2000

(Continued)

OTHER PUBLICATIONS

"Georgia Tech Researchers Develop First 'Smart T-shirt'," Nov. 14, 1997 press release, Georgia Institute of Technology.

(Continued)

*Primary Examiner*—Carl Layno
(74) *Attorney, Agent, or Firm*—Metz Lewis LLC; Barry I. Friedman

(57) ABSTRACT

A detecting apparatus includes a housing support section(s), a housing removably attached thereto, one or more sensors and a processor. An alternate apparatus measures heat flux and includes a known resistivity base member, a processing unit and two temperature measuring devices, one in thermal communication with the body through a thermal energy communicator and the other in thermal communication with the ambient environment. A further alternate apparatus includes a housing or flexible section having an adhesive material on a surface thereof for removably attaching the apparatus to the body. A further alternate apparatus includes a housing having an inner surface having a concave shape in a first direction and convex shape in a second direction substantially perpendicular thereto. Also, an apparatus for detecting heart related parameters includes one or more filtering sensors for generating filtering signals related to the non-heart related motion of the body.

222 Claims, 36 Drawing Sheets

U.S. PATENT DOCUMENTS

| | | | | |
|---|---|---|---|---|
| 4,757,453 A | 7/1988 | Nasiff ................... 73/379.01 |
| RE32,758 E | 10/1988 | Zartman ................... 600/549 |
| 4,784,162 A | 11/1988 | Ricks et al. ............... 600/484 |
| 4,803,625 A | 2/1989 | Fu et al. .................. 600/483 |
| 4,819,860 A | 4/1989 | Hargrove et al. ........... 600/483 |
| 4,827,943 A | 5/1989 | Bornn et al. .............. 600/481 |
| 4,828,257 A | 5/1989 | Dyer et al. .................. 482/5 |
| 4,891,756 A | 1/1990 | Williams, III .............. 708/132 |
| 4,917,108 A | 4/1990 | Mault ..................... 600/531 |
| 4,958,645 A | 9/1990 | Cadell et al. .............. 600/484 |
| 4,966,154 A | 10/1990 | Cooper et al. ............. 600/484 |
| 4,981,139 A | 1/1991 | Pfohl ..................... 600/484 |
| 5,007,427 A | 4/1991 | Suzuki et al. .............. 600/436 |
| 5,012,411 A | 4/1991 | Policastro et al. .......... 600/485 |
| 5,027,824 A | 7/1991 | Dougherty et al. .......... 600/515 |
| 5,038,792 A | 8/1991 | Mault ..................... 600/531 |
| 5,050,612 A | 9/1991 | Matsumura ............... 600/483 |
| 5,072,458 A | 12/1991 | Suzuki ....................... 2/102 |
| 5,111,818 A * | 5/1992 | Suzuki et al. .............. 600/390 |
| 5,148,002 A | 9/1992 | Kuo et al. .................. 219/211 |
| 5,178,155 A | 1/1993 | Mault ..................... 600/531 |
| 5,179,958 A | 1/1993 | Mault ..................... 600/531 |
| 5,216,599 A | 6/1993 | Uebe et al. ................ 600/551 |
| 5,224,479 A | 7/1993 | Sekine ..................... 600/389 |
| 5,263,491 A | 11/1993 | Thornton .................. 600/587 |
| 5,285,398 A | 2/1994 | Janik ...................... 361/683 |
| 5,305,244 A | 4/1994 | Newman et al. ........... 708/141 |
| 5,335,664 A | 8/1994 | Nagashima ............... 600/508 |
| 5,353,793 A * | 10/1994 | Bornn ..................... 600/386 |
| 5,410,471 A | 4/1995 | Alyfuku et al. ........ 364/413.02 |
| 5,435,315 A | 7/1995 | McPhee et al. ............. 600/483 |
| 5,445,149 A | 8/1995 | Rotolo et al. .............. 600/382 |
| 5,458,123 A | 10/1995 | Unger ..................... 600/509 |
| 5,474,090 A | 12/1995 | Begun et al. ............... 600/520 |
| 5,484,389 A | 1/1996 | Stark et al. ................ 601/384 |
| 5,491,651 A | 2/1996 | Janik ...................... 361/683 |
| 5,511,553 A | 4/1996 | Segalowitz ................ 600/508 |
| 5,515,858 A | 5/1996 | Myllymaki ................ 600/301 |
| 5,515,865 A | 5/1996 | Scanlon ................... 600/534 |
| 5,524,618 A | 6/1996 | Pottgen et al. ............. 600/306 |
| 5,555,490 A | 9/1996 | Carroll .................... 361/686 |
| 5,559,497 A | 9/1996 | Hong ................... 340/573.1 |
| 5,566,679 A | 10/1996 | Herriott ................... 600/551 |
| 5,581,238 A | 12/1996 | Chang et al. ............ 340/573.1 |
| 5,581,492 A | 12/1996 | Janik ...................... 361/683 |
| 5,611,085 A | 3/1997 | Rasmussen ................... 2/102 |
| 5,617,477 A | 4/1997 | Boyden ................... 381/309 |
| 5,622,180 A | 4/1997 | Tammi et al. .............. 600/503 |
| 5,645,068 A | 7/1997 | Mezack et al. ............. 600/481 |
| 5,670,944 A | 9/1997 | Myllymaki .............. 340/573.1 |
| 5,673,692 A | 10/1997 | Schulze et al. ............. 600/301 |
| 5,686,516 A | 11/1997 | Tzur ....................... 524/394 |
| 5,687,734 A | 11/1997 | Dempsey et al. ........... 600/509 |
| 5,704,350 A | 1/1998 | Williams, III ............... 600/300 |
| 5,719,743 A | 2/1998 | Jenkins et al. .............. 361/683 |
| 5,724,025 A | 3/1998 | Tavori .................. 340/573.1 |
| 5,726,631 A | 3/1998 | Lin ...................... 340/573.1 |
| 5,741,217 A | 4/1998 | Gero ...................... 600/547 |
| 5,752,976 A | 5/1998 | Duffin et al. ............... 607/32 |
| 5,771,001 A | 6/1998 | Cobb .................... 340/573.1 |
| 5,778,882 A | 7/1998 | Raymond et al. ........... 600/513 |
| 5,798,907 A | 8/1998 | Janik ...................... 361/683 |
| 5,813,766 A | 9/1998 | Chen ...................... 374/141 |
| 5,813,994 A | 9/1998 | Pottgen et al. ............. 600/549 |
| 5,823,975 A | 10/1998 | Stark et al. ................ 600/595 |
| 5,827,180 A | 10/1998 | Goodman ................. 600/300 |
| 5,828,943 A | 10/1998 | Brown .................... 434/258 |
| 5,832,296 A | 11/1998 | Wang et al. .................. 710/3 |
| 5,832,448 A | 11/1998 | Brown ....................... 705/2 |
| 5,836,300 A | 11/1998 | Mault ................. 128/204.23 |
| 5,853,005 A | 12/1998 | Scanlon ................... 600/459 |
| 5,855,550 A | 1/1999 | Lai et al. .................. 600/300 |
| 5,857,967 A | 1/1999 | Frid et al. ................. 600/301 |
| 5,865,733 A | 2/1999 | Malinouskas et al. ....... 600/300 |
| 5,868,669 A | 2/1999 | Iliff ........................ 600/300 |
| 5,868,671 A | 2/1999 | Mahoney ................. 600/382 |
| 5,871,451 A | 2/1999 | Unger et al. ............... 600/509 |
| 5,879,163 A | 3/1999 | Brown et al. .............. 434/236 |
| 5,879,309 A | 3/1999 | Johnson et al. ............. 600/552 |
| 5,884,198 A | 3/1999 | Kese et al. .............. 455/575.6 |
| 5,888,172 A | 3/1999 | Andrus et al. ................ 482/7 |
| 5,897,493 A | 4/1999 | Brown .................... 600/300 |
| 5,899,855 A | 5/1999 | Brown .................... 600/301 |
| 5,902,250 A | 5/1999 | Verrier et al. .............. 600/515 |
| 5,908,396 A | 6/1999 | Hayakawa et al. ......... 600/587 |
| 5,913,310 A | 6/1999 | Brown .................... 128/897 |
| 5,919,141 A | 7/1999 | Money et al. ............. 600/513 |
| 5,929,782 A | 7/1999 | Stark et al. ............ 340/870.01 |
| 5,933,136 A | 8/1999 | Brown ..................... 345/741 |
| 5,951,300 A | 9/1999 | Brown .................... 434/236 |
| 5,956,501 A | 9/1999 | Brown .................... 203/11 |
| 5,960,403 A | 9/1999 | Brown ....................... 705/2 |
| 6,032,119 A | 2/2000 | Brown et al. ................. 705/2 |
| 6,047,203 A | 4/2000 | Sackner et al. ............. 600/388 |
| 6,053,872 A * | 4/2000 | Mohler ................... 600/485 |
| 6,059,692 A | 5/2000 | Hickman ..................... 482/8 |
| 6,067,468 A | 5/2000 | Korenman et al. ......... 600/547 |
| 6,091,973 A | 7/2000 | Colla et al. ................ 600/324 |
| 6,101,407 A | 8/2000 | Groezinger ................ 600/407 |
| 6,101,478 A | 8/2000 | Brown ....................... 705/2 |
| 6,135,107 A | 10/2000 | Mault ................. 128/204.23 |
| 6,138,079 A | 10/2000 | Putnam ..................... 702/50 |
| 6,154,668 A | 11/2000 | Pedersen et al. ............ 600/361 |
| 6,168,563 B1 | 1/2001 | Brown .................... 600/301 |
| 6,184,797 B1 | 2/2001 | Stark et al. ............ 340/870.07 |
| 6,198,394 B1 | 3/2001 | Jacobsen et al. .......... 340/573.1 |
| 6,208,900 B1 * | 3/2001 | Ecker et al. .................. 607/17 |
| 6,225,901 B1 | 5/2001 | Kail, IV .................... 340/539 |
| 6,248,065 B1 | 6/2001 | Brown .................... 600/300 |
| 6,265,978 B1 * | 7/2001 | Atlas ...................... 340/575 |
| 6,285,897 B1 | 9/2001 | Kilcoyne et al. ............ 600/350 |
| 6,290,646 B1 | 9/2001 | Cosentino et al. .......... 600/300 |
| 6,292,698 B1 | 9/2001 | Duffin et al. ................ 607/32 |
| 6,298,218 B1 | 10/2001 | Lowe et al. ................ 455/66.1 |
| 6,306,088 B1 | 10/2001 | Krausman et al. .......... 600/301 |
| 6,312,363 B1 | 11/2001 | Watterson et al. ............ 482/54 |
| 6,315,719 B1 | 11/2001 | Rode et al. ................ 600/300 |
| 6,336,900 B1 | 1/2002 | Alleckson et al. .......... 600/485 |
| 6,341,229 B1 | 1/2002 | Akiva ..................... 600/388 |
| 6,364,834 B1 | 4/2002 | Reuss et al. ............... 600/300 |
| 6,366,871 B1 | 4/2002 | Geva ...................... 702/188 |
| 6,368,287 B1 | 4/2002 | Hadas ..................... 600/529 |
| 6,371,123 B1 | 4/2002 | Stark et al. ................ 128/898 |
| 6,377,162 B1 | 4/2002 | Delestienne et al. ... 340/286.07 |
| 6,385,473 B1 | 5/2002 | Haines et al. .............. 600/393 |
| 6,416,471 B1 | 7/2002 | Kumar et al. .............. 600/300 |
| 6,450,953 B1 | 9/2002 | Place et al. ............... 600/300 |
| 6,454,708 B1 | 9/2002 | Ferguson et al. ........... 600/300 |
| 6,494,829 B1 | 12/2002 | New, Jr. et al. ............. 600/300 |
| 6,527,711 B1 * | 3/2003 | Stivoric et al. ............. 600/300 |
| 6,595,929 B1 * | 7/2003 | Stivoric et al. ............. 600/549 |
| 6,610,012 B1 * | 8/2003 | Mault ...................... 600/437 |
| 6,690,959 B1 * | 2/2004 | Thompson ................. 600/372 |
| 6,755,795 B1 * | 6/2004 | Marmaropoulos et al. .. 600/587 |
| 2001/0029340 A1 | 10/2001 | Mault et al. ............... 600/532 |
| 2001/0044581 A1 | 11/2001 | Mault ...................... 600/437 |
| 2001/0049470 A1 | 12/2001 | Mault et al. ............... 600/300 |
| 2001/0056229 A1 | 12/2001 | Cosentino et al. .......... 600/300 |
| 2002/0019296 A1 * | 2/2002 | Freeman et al. ............... 482/4 |
| 2002/0028995 A1 | 3/2002 | Mault ...................... 600/437 |
| 2002/0088160 A1 * | 7/2002 | Beretta .................... 42/70.08 |
| 2002/0107450 A1 * | 8/2002 | Ogura ..................... 600/490 |
| 2002/0128804 A1 | 9/2002 | Geva ...................... 702/188 |
| 2003/0055460 A1 * | 3/2003 | Owen et al. .................. 607/5 |

| | | | | |
|---|---|---|---|---|
| 2003/0069510 | A1* | 4/2003 | Semler | 600/509 |
| 2003/0083559 | A1* | 5/2003 | Thompson | 600/372 |

FOREIGN PATENT DOCUMENTS

| | | |
|---|---|---|
| DE | 199 11 766 A1 | 9/2000 |
| EP | 0 670 064 B1 | 11/1993 |
| EP | 0 707 825 A2 | 4/1996 |
| GB | 2322952 A | 5/1997 |
| WO | WO 93/01574 | 1/1993 |
| WO | WO 94/25841 | 11/1994 |
| WO | WO 97/06499 | 2/1997 |
| WO | WO 99/27483 | 6/1999 |
| WO | WO 00/11578 | 3/2000 |
| WO | WO 00/26822 | 5/2000 |
| WO | WO 00/32098 | 6/2000 |
| WO | WO 00/47108 | 8/2000 |
| WO | WO 00/51543 | 9/2000 |
| WO | WO 00/52604 | 9/2000 |
| WO | WO 01/08554 | 2/2001 |
| WO | WO 01/26535 | 4/2001 |
| WO | WO 01/26547 | 4/2001 |
| WO | WO 01/28416 | 4/2001 |
| WO | WO 01/28495 | 4/2001 |
| WO | WO 01/28495 A2 | 4/2001 |
| WO | WO 01/39089 | 5/2001 |
| WO | WO 01/52718 | 7/2001 |
| WO | WO 01/56454 | 8/2001 |
| WO | WO 01/82783 | 11/2001 |
| WO | WO 01/82789 | 11/2001 |
| WO | WO 01/89365 A2 | 11/2001 |
| WO | WO 01/89365 A3 | 11/2001 |
| WO | WO 01/89368 A2 | 11/2001 |
| WO | WO 01/89368 A3 | 11/2001 |

OTHER PUBLICATIONS

"Personal Health Monitor for Homes," Timo Tuomisto and Vesa Pentikainen, *ERCIM News*, No. 29, Apr. 1997.

"CYBeR-CARE Announes U.S. Patent Office Allows 25 Additional Claims for its Internet Healthcare Technologies," *BW HealthWire*, Oct. 7, 1999.

"Nearer to the Heart," Briana Krebs, *Washington Post*, Jan. 17, 1999.

"Portable Sensor Provides Remote Monitoring of Heart," *Nikkei Weekly*, Oct. 27, 1998.

"FDA Clears New Dates-Ohmeda 3900/3900P Pulse Oximeter with World's First Remote Fax Capability," *BW HealthWire*, Dec. 3, 1998.

"Estee Soft Announces New Version of LifeConnect, Providing Advanced Telemonitoring Capabilities for the Mobile Practitioner," *Business Wire*, Jan. 20, 1999.

"Matsushita Electric Works to Sell Home Health Check System," *The Nithon Keizai Shimbun*, Dec. 17, 1998.

"A Lightweight Ambulatory Physiological Monitoring Systm" (undated), Ames Research Center, Moffett Field, California.

Warfighter Physiological Status Monitoring, 1999 MOMRP Fact Sheet No. 6, USAMRMC Military Operational Medicine Research Program. |Retrieved from Internet. URL: <http://www.momrp.org/publications/WPSM.pdf>.

Henshaw, D., The H.J. Andrews Climatological Field Measurement Program, Aug. 9, 1997. |Retrieved from Internet. URL : <http://www.fsl.orst.edu/lter/research/component/climate/summary.cfm?sum=clim97&topnav=57>.

"A combined heart rate and movement sensor: proof of concet and preliminary testing study," K. Rennie, T. Rowsell, S.A. Jebb, D. Holburn and N.J. Wareham, European Journal of Clinical Nutrition, May 2000, vol. 54, No. 5, pp. 409-414.

* cited by examiner

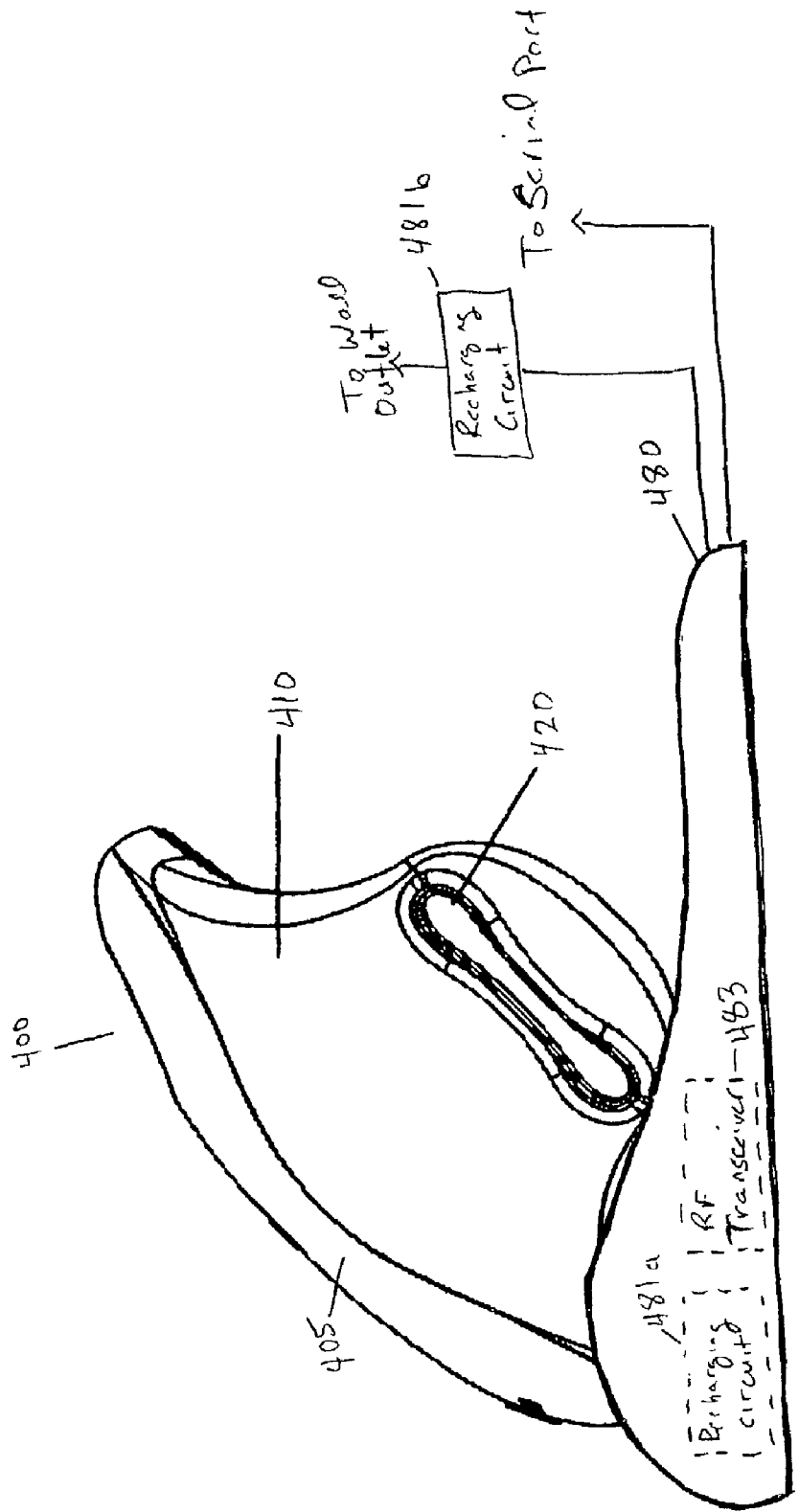

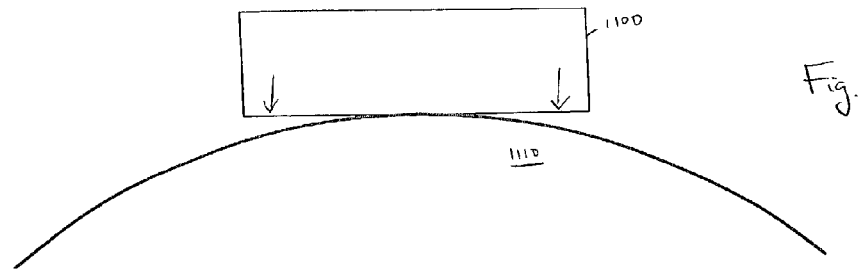
Fig. 36 A
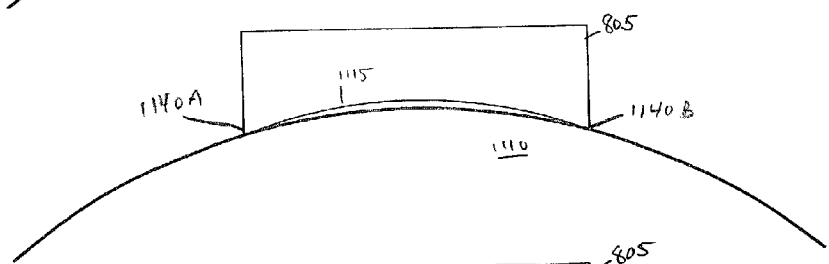
Fig. 36 B
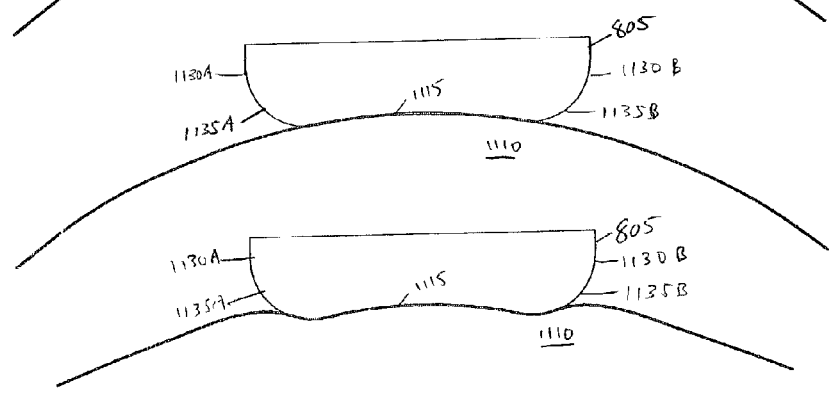
Fig. 36 C
Fig. 36 D
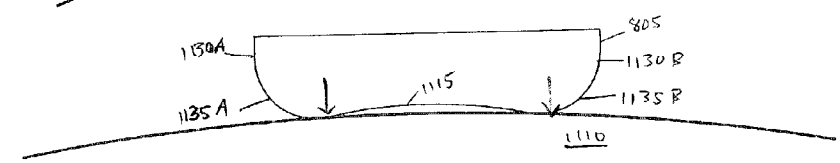
Fig. 36 E
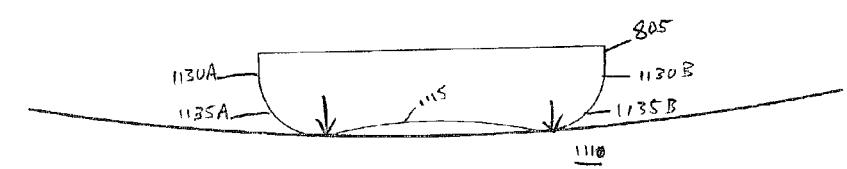
Fig. 36 F
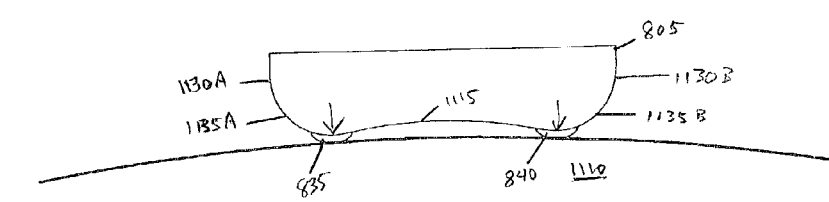
Fig. 36 G
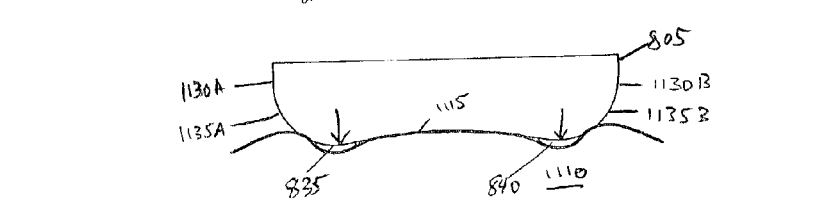
Fig. 36 H

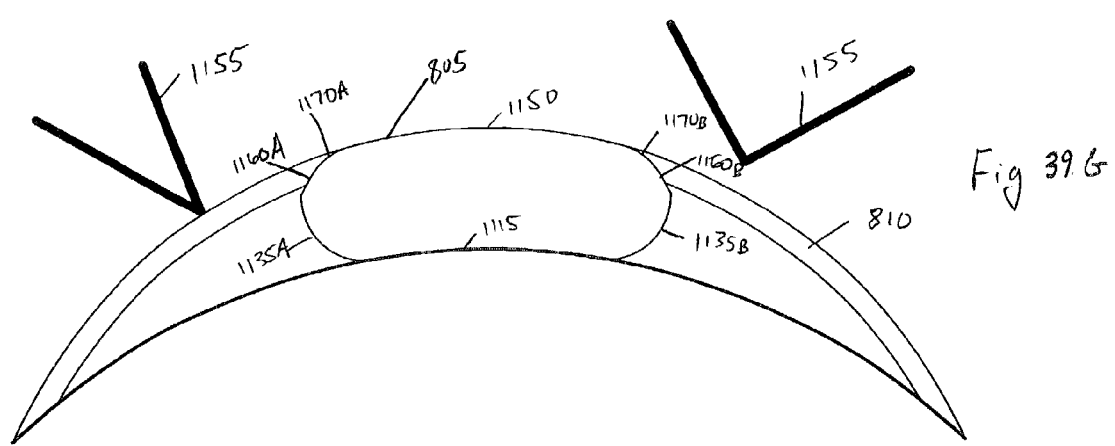

APPARATUS FOR DETECTING HUMAN PHYSIOLOGICAL AND CONTEXTUAL INFORMATION

FIELD OF THE INVENTION

The present invention also relates to a number of embodiments of an apparatus which includes one or more sensors for collecting and storing data relating to an individual's physiological state and various contextual parameters.

BACKGROUND OF THE INVENTION

Research has shown that a large number of the top health problems in society are either caused in whole or in part by an unhealthy lifestyle. More and more, our society requires people to lead fast-paced, achievement-oriented lifestyles that often result in poor eating habits, high stress levels, lack of exercise, poor sleep habits and the inability to find the time to center the mind and relax. Recognizing this fact, people are becoming increasingly interested in establishing a healthier lifestyle.

Traditional medicine, embodied in the form of an HMO or similar organizations, does not have the time, the training, or the reimbursement mechanism to address the needs of those individuals interested in a healthier lifestyle. There have been several attempts to meet the needs of these individuals, including a perfusion of fitness programs and exercise equipment, dietary plans, self-help books, alternative therapies, and most recently, a plethora of health information web sites on the Internet. Each of these attempts are targeted to empower the individual to take charge and get healthy. Each of these attempts, however, addresses only part of the needs of individuals seeking a healthier lifestyle and ignores many of the real barriers that most individuals face when trying to adopt a healthier lifestyle. These barriers include the fact that the individual is often left to himself or herself to find motivation, to implement a plan for achieving a healthier lifestyle, to monitor progress, and to brainstorm solutions when problems arise; the fact that existing programs are directed to only certain aspects of a healthier lifestyle, and rarely come as a complete package; and the fact that recommendations are often not targeted to the unique characteristics of the individual or his life circumstances.

SUMMARY OF THE INVENTION

An apparatus is disclosed for detecting human physiological or contextual information from the body of an individual wearing the apparatus. The apparatus includes a flexible section that is adapted to engage a portion of the wearer's body, and a housing that is removably attached to the flexible section. The housing supports one or more physiological and/or contextual sensors and a processor in electrical communication with the sensors. According to one embodiment, the apparatus may include multiple flexible sections that may be selectively attached to the housing. The apparatus may also have operating parameters that are adjustable depending on the particular flexible section that is attached to the housing at a particular time. The operating parameters, for example, may be adjusted through the interaction of a switch or switches provided on or in the housing and a switch activator or switch activators provided on or in each of the flexible sections. Various structures for removably attaching the housing to the flexible section are described, including, but no limited to, tongues and grooves, adhesives, magnets, and elastic bands. The apparatus may also include a wireless transceiver for transmitting information to and receiving information from a computing device.

Also described is an apparatus that is adapted to measure heat flux between the body of the wearer and the ambient environment. The apparatus includes a housing and a base member having a preselected, known resistivity mounted within the housing. The base member may comprise a printed circuit board. A first temperature measuring device is attached to a first side of the base member and a second temperature measuring device is attached to a second side of the base member. The temperature measuring devices may comprise, for example, a thermistor, a thermocouple, or a thermopile. The apparatus further includes a thermal energy communicator mounted between a portion of the body of the wearer and the first temperature measuring device. The thermal energy communicator may include one or more of a heat conduit, a thermally conductive interface material or materials, and a thermally conductive interface component in various combinations. The second temperature measuring device is in thermal communication with the ambient environment. The apparatus may include a thermal interface material and/or a thermally conductive interface component for providing thermal communication between the ambient environment and the second temperature measuring device. A processing unit is provided in the housing and is in electrical communication with the temperature measuring devices. The apparatus may further include a flexible section attached to the housing adapted to engage a portion of the body of the wearer, or a plurality of flexible sections adapted to be selectively attached to the housing. According to one embodiment, the apparatus has operating parameters that may be adjusted depending on the particular flexible section that is attached to the housing.

An apparatus for detecting, monitoring and reporting at least one of human physiological and contextual information from the body of a wearer is also described. The apparatus includes a housing having an adhesive material on at least a portion of an external surface thereof that enables the housing to be removably attached to a portion of the body of the wearer. At least two physiological and/or contextual sensors are supported by the housing. The physiological sensors are adapted to facilitate the generation of data indicative of one or more physiological parameters of the wearer and the contextual sensors are adapted to facilitate the generation of data indicative of one or more contextual parameters of the wearer. A processor is also included and is an electrical communication with the sensors. The processor generates: (i) derived data from at least one of at least a portion of the data indicative of physiological parameters and at least a portion of the data indicative of contextual parameters; and (ii) analytical status data from at least a portion of at least one of the data indicative of physiological parameters, the data indicative of contextual parameters, the derived data and the analytical status data. The apparatus further includes an electronic memory for retrievably storing at least one of the data indicative of physiological parameters, the data indicative of contextual parameters, the derived data and the analytical status data. The apparatus is adapted to transmit to the wearer at least one of the data indicative of physiological parameters, the data indicative of contextual parameters, the derived data and the analytical status data. The housing may be made of a rigid material or a flexible material, such as a flexible plastic film. The apparatus may include a number of displays for transmitting information, including, but not limited to, an LED or an electrochemical display. The apparatus may further include a wireless transceiver for receiving information from and transmitting information to a computing device. The processor of the apparatus and the computing device may be adapted to engage in shared computing. Furthermore, a computing device may be included in the apparatus for transmitting information to the wearer. The computing device may be coupled to the processor, and the processor may be adapted to cause the computing device to trigger an event upon detection of one or more physiological conditions of the individual. The apparatus may further include various structures for manually entering information into the apparatus, such as a button or a touch pad or keyboard provided on the apparatus or on a computing device coupled to the processor. According to one embodiment, the apparatus monitors the degree to which the wearer has followed a predetermined routine. In this embodiment, the analytical status data comprises feedback to the individual relating to the degree to which the individual has followed the predetermined routine, with the feedback being generated from at least a portion of at least one of the data indicative of one or more physiological parameters of the individual, the derived data, and manually entered data. Also described is an apparatus for detecting human physiological or contextual information from the body of an individual wearing the apparatus that includes a housing having an inner surface for mounting adjacent the body and an outer surface opposite the inner surface. The inner surface includes a longitudinal axis and a transverse axis, with the inner surface being generally concave in a first direction and having an axis of concavity coincident with the longitudinal axis and generally convex in a second direction perpendicular to the first direction and having an axis of concavity coincident with the transverse axis. The inner surface may have first and second lateral ends at opposite ends of the axis of concavity, and the housing may have a first radiused portion adjacent to and including the first lateral end and a second radiused portion adjacent to and including the second lateral end. The inner surface may also have third and fourth lateral ends at opposite ends of the axis of convexity, and the housing may have a third radiused portion adjacent to and including the third lateral end and a fourth radiused portion adjacent to and including the fourth lateral end. Further, the outer surface of the housing may have a convex shape between a first lateral side and a second lateral side of the outer surface. According to one embodiment, the housing includes a width dimension as measured between a first lateral side and a second lateral side of the housing, with at least a portion of the first lateral side and second lateral side each having a taper such that the width dimension generally decreases in a direction from the inner surface to the outer surface. The apparatus may include a flexible section attached to the housing that engages the body of the wearer and has a generally convex outer surface.

Also described is an apparatus for detecting from the body of a wearer parameters relating to the heart of the wearer including an acoustic-based non-ECG heart parameter sensor that generates a first signal including a first acoustic component generated from the motion of the wearers heart and a second acoustic component generated from non-heart related motion of the body of the wearer, such as, for example, from footfalls. The apparatus also includes one or more filtering sensors, such as an accelerometer, for generating a second signal related to the non-heart related motion of the body. The second signal is used to subtract the second acoustic component from the first signal to generate a third signal, with the third signal being used to generate the heart related parameters. The first signal may also include an acoustic component generated from ambient noise, and the apparatus may include an ambient noise sensor. In this configuration, the signal form the ambient noise sensor is used to subtract out the acoustic component generated from ambient noise from the signal that is used to generate the heart related parameters.

In addition, a method is disclosed for detecting from the body of a wearer parameters relating to the heart of the wearer. The method comprises steps of generating a first acoustic signal including a first acoustic component generated from the motion of the wearer's heart and a second acoustic component generated from non-heart related motion of the body of the wearer, generating a second signal related to the non-heart related motion of the body, generating a third signal by using the second signal to subtract the second acoustic component from the first signal, and generating the heart related parameters from the third signal. The first acoustic signal may further include a third acoustic component generated from ambient noise and the method may further comprise generating a fourth signal related to the ambient noise with the step of generating the third signal further comprising using the fourth signal to subtract the third acoustic component from the first signal.

BRIEF DESCRIPTION OF THE DRAWINGS

Further features and advantages of the present invention will be apparent upon consideration of the following detailed description of the present invention, taken in conjunction with the following drawings, in which like reference characters refer to like parts, and in which.

DESCRIPTION OF THE PREFERRED EMBODIMENTS

Figure 1:
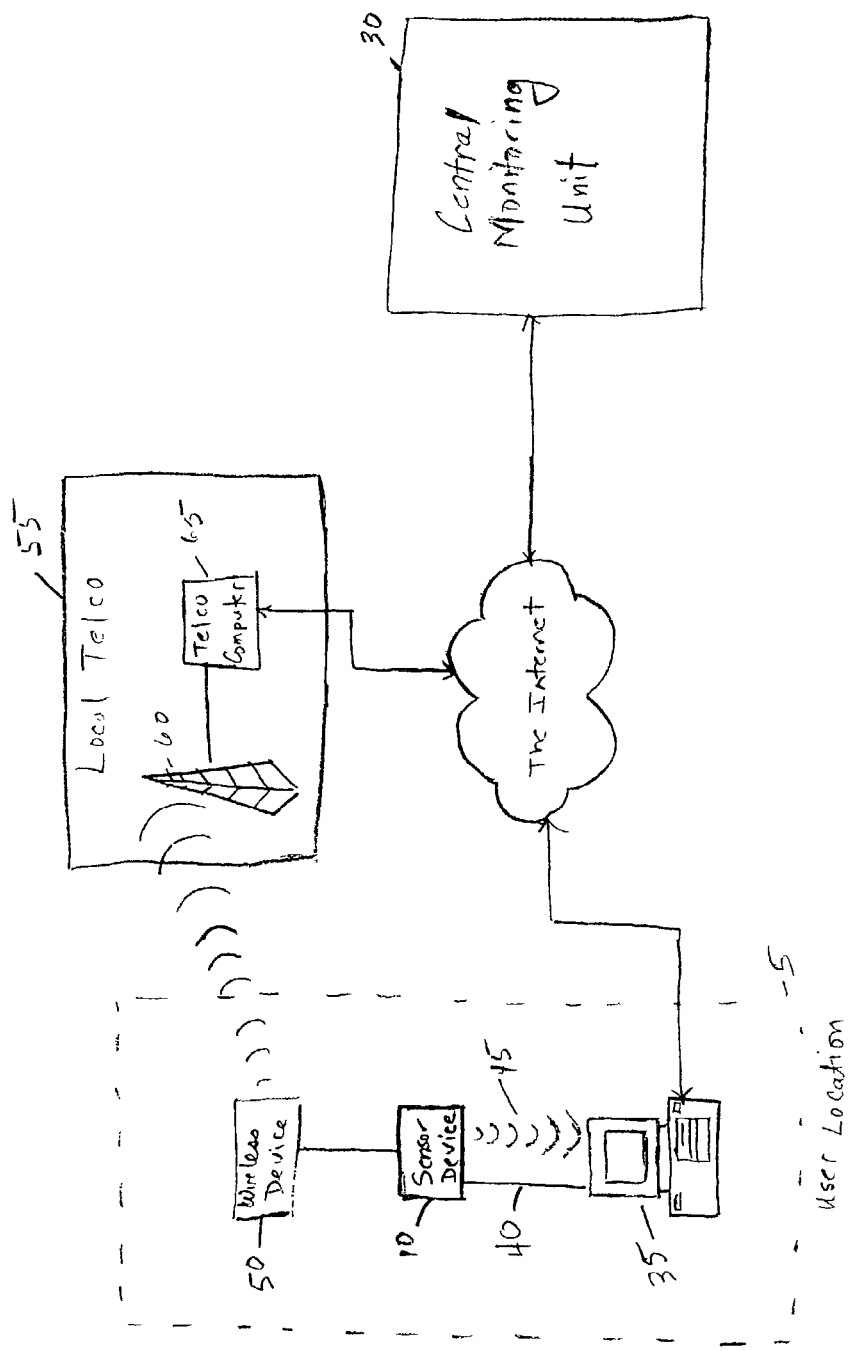
FIG. 1 is a diagram of an embodiment of a system for monitoring physiological data and lifestyle over an electronic network according to the present invention.

In general, according to the present invention, data relating to the physiological state, the lifestyle and certain contextual parameters of an individual is collected and transmitted, either subsequently or in real-time, to a site, preferably remote from the individual, where it is stored for later manipulation and presentation to a recipient, preferably over an electronic network such as the Internet. Contextual parameters as used herein means parameters relating to the environment, surroundings and location of the individual, including, but not limited to, air quality, sound quality, ambient temperature, global positioning and the like. Referring to FIG. 1, located at user location 5 is sensor device 10 adapted to be placed in proximity with at least a portion of the human body. Sensor device 10 is preferably worn by an individual user on his or her body, for example as part of a garment such as a form fitting shirt, or as part of an arm band or the like. Sensor device 10, includes one or more sensors, which are adapted to generate signals in response to physiological characteristics of an individual, and a microprocessor. Proximity as used herein means that the sensors of sensor device 10 are separated from the individual's body by a material or the like, or a distance such that the capabilities of the sensors are not impeded.

Sensor device 10 generates data indicative of various physiological parameters of an individual, such as the individual's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and UV radiation exposure and absorption. In certain cases, the data indicative of the various physiological parameters is the signal or signals themselves generated by the one or more sensors and in certain other cases the data is calculated by the microprocessor based on the signal or signals generated by the one or more sensors. Methods for generating data indicative of various physiological parameters and sensors to be used therefor are well known. Table 1 provides several examples of such well known methods and shows the parameter in question, the method used, the sensor device used, and the signal that is generated. Table 1 also provides an indication as to whether further processing based on the generated signal is required to generate the data.

TABLE 1

| Parameter | Method | Sensor | Signal | Further Processing |
|---|---|---|---|---|
| Heart Rate | EKG | 2 Electrodes | DC Voltage | Yes |
| Pulse Rate | BVP | LED Emitter and Optical Sensor | Change in Resistance | Yes |
| Beat-to-Beat Variability | Heart Rate | 2 Electrodes | DC Voltage | Yes |
| EKG | Skin Surface Potentials | 3–10 Electrodes | DC Voltage | No |
| Respiration Rate | Chest Volume Change | Strain Gauge | Change in Resistance | Yes |
| Skin Temperature | Surface Temperature Probe | Thermistors | Change in Resistance | Yes |
| Core Temperature | Esophageal or Rectal Probe | Thermistors | Change in Resistance | Yes |
| Heat Flow | Heat Flux | Thermopile | DC Voltage | Yes |
| Galvanic Skin Response | Skin Conductance | 2 Electrodes | Change in Resistance | No |
| EMG | Skin Surface Potentials | 3 Electrodes | DC Voltage | No |
| EEG | Skin Surface Potentials | Multiple Electrodes | DC Voltage | Yes |
| EOG | Eye Movement | Thin Film Piezoelectric Sensors | DC Voltage | Yes |
| Blood Pressure | Non-Invasive Korotkuff Sounds | Electronic Sphygromarometer | Change in Resistance | Yes |
| Body Fat | Body Impedance | 2 Active Electrodes | Change in Impedance | Yes |
| Activity in Interpreted G Shocks per Minute | Body Movement | Accelerometer | DC Voltage, Capacitance Changes | Yes |
| Oxygen Consumption | Oxygen Uptake | Electro-chemical | DC Voltage Change | Yes |
| Glucose Level | Non-Invasive | Electro-chemical | DC Voltage Change | Yes |
| Body Position (e.g. supine, erect, sitting) | N/A | Mercury Switch Array | DC Voltage Change | Yes |
| Muscle Pressure | N/A | Thin Film Piezoelectric Sensors | DC Voltage Change | Yes |
| UV Radiation Absorption | N/A | UV Sensitive Photo Cells | DC Voltage Change | Yes |

The types of data listed in Table 1 are intended to be examples of the types of data that can be generated by sensor device 10. It is to be understood that other types of data relating to other parameters can be generated by sensor device 10 without departing from the scope of the present invention.

The microprocessor of sensor device 10 may be programmed to summarize and analyze the data. For example, the microprocessor can be programmed to calculate an average, minimum or maximum heart rate or respiration rate over a defined period of time, such as ten minutes. Sensor device 10 may be able to derive information relating to an individual's physiological state based on the data indicative of one or more physiological parameters. The microprocessor of sensor device 10 is programmed to derive such information using known methods based on the data indicative of one or more physiological parameters. Table 2 provides examples of the type of information that can be derived, and indicates some of the types of data that can be used therefor.

TABLE 2

| Derived Information | Data Used |
|---|---|
| Ovulation | Skin temperature, core temperature, oxygen consumption |
| Sleep onset/wake | Beat-to-beat variability, heart rate, pulse rate, respiration rate, skin temperature, core temperature, heat flow, galvanic skin response, EMG, EEG, EOG, blood pressure, oxygen consumption |
| Calories burned | Heart rate, pulse rate, respiration rate, heat flow, activity, oxygen consumption |
| Basal metabolic rate | Heart rate, pulse rate, respiration rate, heat flow, activity, oxygen consumption |
| Basal temperature | Skin temperature, core temperature |
| Activity level | Heart rate, pulse rate, respiration rate, heat flow, activity, oxygen consumption |
| Stress level | EKG, beat-to-beat variability, heart rate, pulse rate, respiration rate, skin temperature, heat flow, galvanic skin response, EMG, EEG, blood pressure, activity, oxygen consumption |
| Relaxation level | EKG, beat-to-beat variability, heart rate, pulse rate, respiration rate, skin temperature, heat flow, galvanic skin response, EMG, EEG, blood pressure, activity, oxygen consumption |

TABLE 2-continued

| Derived Information | Data Used |
| --- | --- |
| Maximum oxygen consumption rate | EKG, heart rate, pulse rate, respiration rate, heat flow, blood pressure, activity, oxygen consumption |
| Rise time or the time it takes to rise from a resting rate to 85% of a target maximum | Heart rate, pulse rate, heat flow, oxygen consumption |
| Time in zone or the time heart rate was above 85% of a target maximum | Heart rate, pulse rate, heat flow, oxygen consumption |
| Recovery time or the time it takes heart rate to return to a resting rate after heart rate was above 85% of a target maximum | Heart rate, pulse rate, heat flow, oxygen consumption |

Additionally, sensor device 10 may also generate data indicative of various contextual parameters relating to the environment surrounding the individual. For example, sensor device 10 can generate data indicative of the air quality, sound level/quality, light quality or ambient temperature near the individual, or even the global positioning of the individual. Sensor device 10 may include one or more sensors for generating signals in response to contextual characteristics relating to the environment surrounding the individual, the signals ultimately being used to generate the type of data described above. Such sensors are well known, as are methods for generating contextual parametric data such as air quality, sound level/quality, ambient temperature and global positioning.

Figure 2:
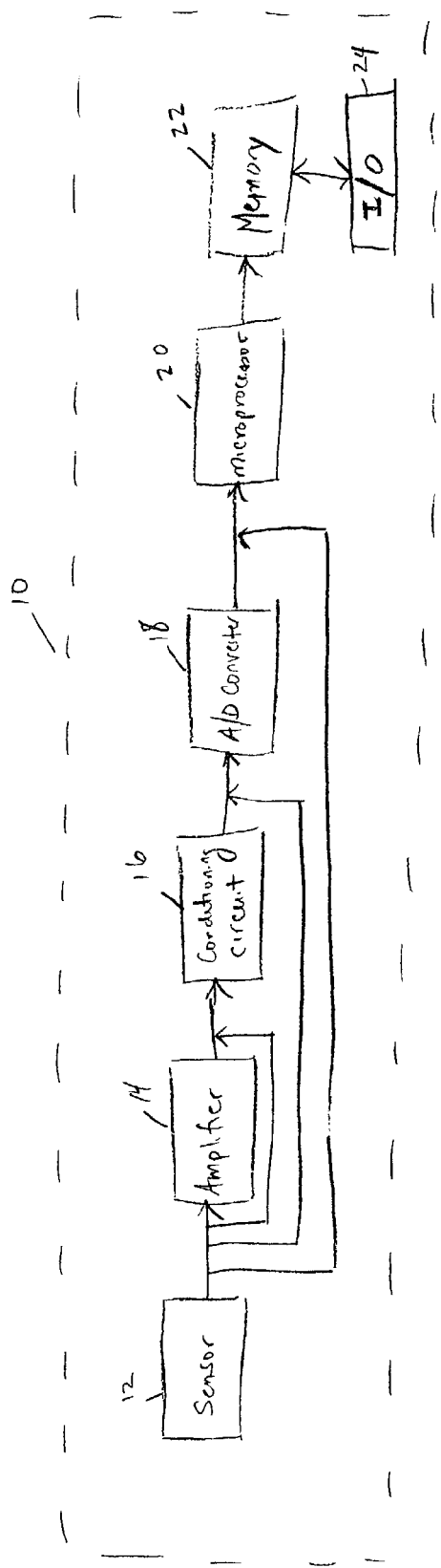
FIG. 2 is a block diagram of an embodiment of the sensor device shown in FIG. 1.

FIG. 2 is a block diagram of an embodiment of sensor device 10. Sensor device 10 includes at least one sensor 12 and microprocessor 20. Depending upon the nature of the signal generated by sensor 12, the signal can be sent through one or more of amplifier 14, conditioning circuit 16, and analog-to-digital converter 18, before being sent to microprocessor 20. For example, where sensor 12 generates an analog signal in need of amplification and filtering, that signal can be sent to amplifier 14, and then on to conditioning circuit 16, which may, for example, be a band pass filter. The amplified and conditioned analog signal can then be transferred to analog-to-digital converter 18, where it is converted to a digital signal. The digital signal is then sent to microprocessor 20. Alternatively, if sensor 12 generates a digital signal, that signal can be sent directly to microprocessor 20.

A digital signal or signals representing certain physiological and/or contextual characteristics of the individual user may be used by microprocessor 20 to calculate or generate data indicative of physiological and/or contextual parameters of the individual user. Microprocessor 20 is programmed to derive information relating to at least one aspect of the individual's physiological state. It should be understood that microprocessor 20 may also comprise other forms of processors or processing devices, such as a microcontroller, or any other device that can be programmed to perform the functionality described herein.

The data indicative of physiological and/or contextual parameters can, according to one embodiment of the present invention, be sent to memory 22, such as flash memory, where it is stored until uploaded in the manner to be described below. Although memory 22 is shown in FIG. 2 as a discrete element, it will be appreciated that it may also be part of microprocessor 20. Sensor device 10 also includes input/output circuitry 24, which is adapted to output and receive as input certain data signals in the manners to be described herein. Thus, memory 22 of the sensor device 10 will build up, over time, a store of data relating to the individual user's body and/or environment. That data is periodically uploaded from sensor device 10 and sent to remote central monitoring unit 30, as shown in FIG. 1, where it is stored in a database for subsequent processing and presentation to the user, preferably through a local or global electronic network such as the Internet. This uploading of data can be an automatic process that is initiated by sensor device 10 periodically or upon the happening of an event such as the detection by sensor device 10 of a heart rate below a certain level, or can be initiated by the individual user or some third party authorized by the user, preferably according to some periodic schedule, such as every day at 10:00 p.m. Alternatively, rather than storing data in memory 22, sensor device 10 may continuously upload data in real time.

The uploading of data from sensor device 10 to central monitoring unit 30 for storage can be accomplished in various ways. In one embodiment, the data collected by sensor device 10 is uploaded by first transferring the data to personal computer 35 shown in FIG. 1 by means of physical connection 40, which, for example, may be a serial connection such as an RS232 or USB port. This physical connection may also be accomplished by using a cradle, not shown, that is electronically coupled to personal computer 35 into which sensor device 10 can be inserted, as is common with many commercially available personal digital assistants. The uploading of data could be initiated by then pressing a button on the cradle or could be initiated automatically upon insertion of sensor device 10. The data collected by sensor device 10 may be uploaded by first transferring the data to personal computer 35 by means of short-range wireless transmission, such as infrared or RF transmission, as indicated at 45.

Once the data is received by personal computer 35, it is optionally compressed and encrypted by any one of a variety of well known methods and then sent out over a local or global electronic network, preferably the Internet, to central monitoring unit 30. It should be noted that personal computer 35 can be replaced by any computing device that has access to and that can transmit and receive data through the electronic network, such as, for example, a personal digital assistant such as the Palm VII sold by Palm, Inc., or the Blackberry 2-way pager sold by Research in Motion, Inc.

Alternatively, the data collected by sensor device 10, after being encrypted and, optionally, compressed by microprocessor 20, may be transferred to wireless device 50, such as a 2-way pager or cellular phone, for subsequent long distance wireless transmission to local telco site 55 using a wireless protocol such as e-mail or as ASCII or binary data. Local telco site 55 includes tower 60 that receives the wireless transmission from wireless device 50 and computer 65 connected to tower 60. According to the preferred embodiment, computer 65 has access to the relevant electronic network, such as the Internet, and is used to transmit the data received in the form of the wireless transmission to the central monitoring unit 30 over the Internet. Although wireless device 50 is shown in FIG. 1 as a discrete device coupled to sensor device 10, it or a device having the same or similar functionality may be embedded as part of sensor device 10.

Sensor device 10 may be provided with a button to be used to time stamp events such as time to bed, wake time, and time of meals. These time stamps are stored in sensor device 10 and are uploaded to central monitoring unit 30 with the rest of the data as described above. The time stamps may include a digitally recorded voice message that, after being uploaded to central monitoring unit 30, are translated using voice recognition technology into text or some other information format that can be used by central monitoring unit 30.

In addition to using sensor device 10 to automatically collect physiological data relating to an individual user, a kiosk could be adapted to collect such data by, for example, weighing the individual, providing a sensing device similar to sensor device 10 on which an individual places his or her hand or another part of his or her body, or by scanning the individual's body using, for example, laser technology or an iStat blood analyzer. The kiosk would be provided with processing capability as described herein and access to the relevant electronic network, and would thus be adapted to send the collected data to the central monitoring unit 30 through the electronic network. A desktop sensing device, again similar to sensor device 10, on which an individual places his or her hand or another part of his or her body may also be provided. For example, such a desktop sensing device could be a blood pressure monitor in which an individual places his or her arm. An individual might also wear a ring having a sensor device 10 incorporated therein. A base, not shown, could then be provided which is adapted to be coupled to the ring. The desktop sensing device or the base just described may then be coupled to a computer such as personal computer 35 by means of a physical or short range wireless connection so that the collected data could be uploaded to central monitoring unit 30 over the relevant electronic network in the manner described above. A mobile device such as, for example, a personal digital assistant, might also be provided with a sensor device 10 incorporated therein. Such a sensor device 10 would be adapted to collect data when mobile device is placed in proximity with the individual's body, such as by holding the device in the palm of one's hand, and upload the collected data to central monitoring unit 30 in any of the ways described herein.

Furthermore, in addition to collecting data by automatically sensing such data in the manners described above, individuals can also manually provide data relating to various life activities that is ultimately transferred to and stored at central monitoring unit 30. An individual user can access a web site maintained by central monitoring unit 30 and can directly input information relating to life activities by entering text freely, by responding to questions posed by the web site, or by clicking through dialog boxes provided by the web site. Central monitoring unit 30 can also be adapted to periodically send electronic mail messages containing questions designed to elicit information relating to life activities to personal computer 35 or to some other device that can receive electronic mail, such as a personal digital assistant, a pager, or a cellular phone. The individual would then provide data relating to life activities to central monitoring unit 30 by responding to the appropriate electronic mail message with the relevant data. Central monitoring unit 30 may also be adapted to place a telephone call to an individual user in which certain questions would be posed to the individual user. The user could respond to the questions by entering information using a telephone keypad, or by voice, in which case conventional voice recognition technology would be used by central monitoring unit 30 to receive and process the response. The telephone call may also be initiated by the user, in which case the user could speak to a person directly or enter information using the keypad or by voice/voice recognition technology. Central monitoring unit 30 may also be given access to a source of information controlled by the user, for example the user's electronic calendar such as that provided with the Outlook product sold by Microsoft Corporation of Redmond, Wash., from which it could automatically collect information. The data relating to life activities may relate to the eating, sleep, exercise, mind centering or relaxation, and/or daily living habits, patterns and/or activities of the individual. Thus, sample questions may include: What did you have for lunch today? What time did you go to sleep last night? What time did you wake up this morning? How long did you run on the treadmill today?

Feedback may also be provided to a user directly through sensor device 10 in a visual form, for example through an LED or LCD or by constructing sensor device 10, at least in part, of a thermochromatic plastic, in the form of an acoustic signal or in the form of tactile feedback such as vibration. Such feedback may be a reminder or an alert to eat a meal or take medication or a supplement such as a vitamin, to engage in an activity such as exercise or meditation, or to drink water when a state of dehydration is detected. Additionally, a reminder or alert can be issued in the event that a particular physiological parameter such as ovulation has been detected, a level of calories burned during a workout has been achieved or a high heart rate or respiration rate has been encountered.

As will be apparent to those of skill in the art, it may be possible to "download" data from central monitoring unit 30 to sensor device 10. The flow of data in such a download process would be substantially the reverse of that described above with respect to the upload of data from sensor device 10. Thus, it is possible that the firmware of microprocessor 20 of sensor device 10 can be updated or altered remotely, i.e., the microprocessor can be reprogrammed, by downloading new firmware to sensor device 10 from central monitoring unit 30 for such parameters as timing and sample rates of sensor device 10. Also, the reminders/alerts provided by sensor device 10 may be set by the user using the web site maintained by central monitoring unit 30 and subsequently downloaded to the sensor device 10.

Figure 3:
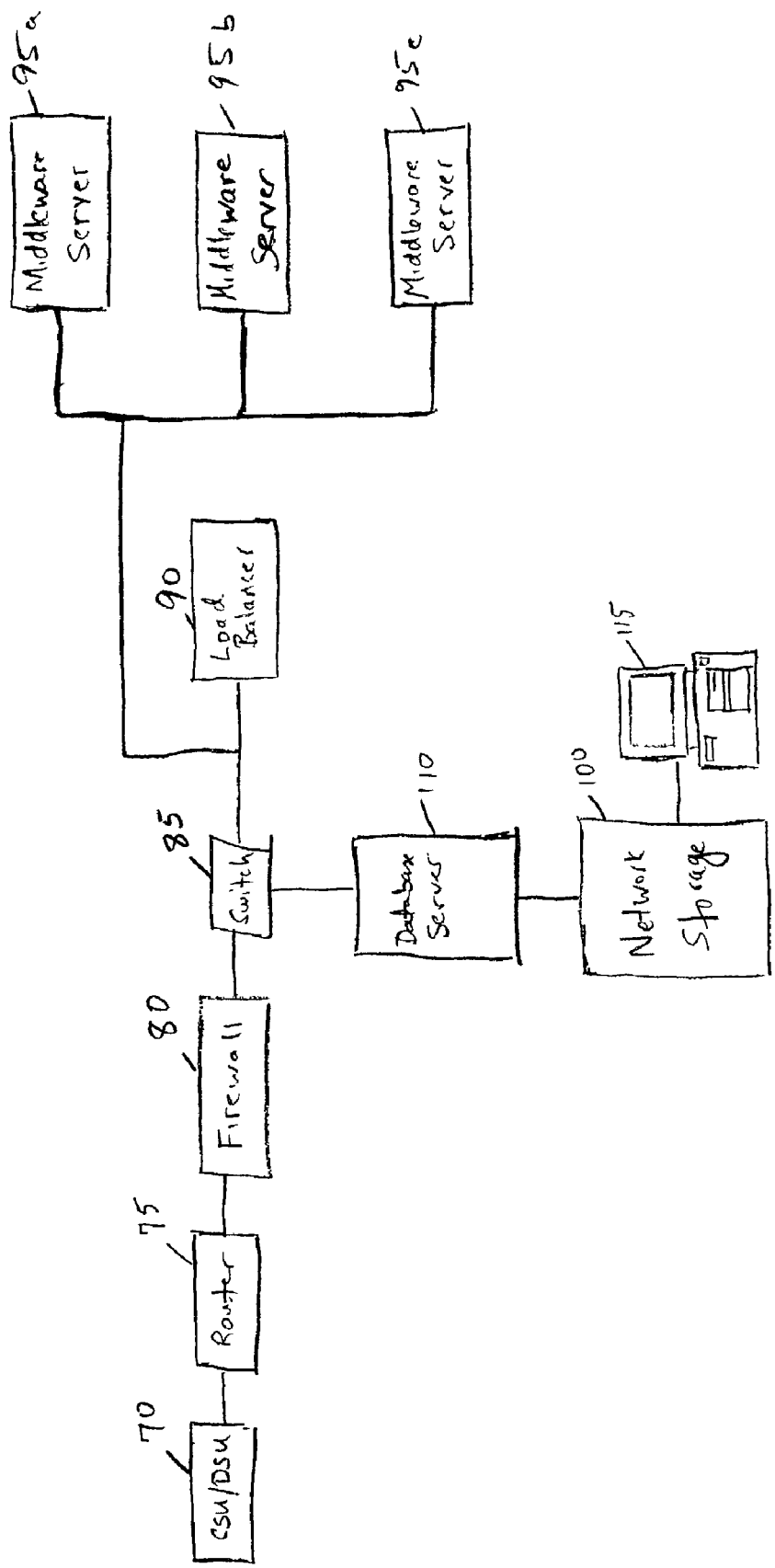
FIG. 3 is a block diagram of an embodiment of the central monitoring unit shown in FIG. 1.

Referring to FIG. 3, a block diagram of an embodiment of central monitoring unit 30 is shown. Central monitoring unit 30 includes CSU/DSU 70 which is connected to router 75, the main function of which is to take data requests or traffic, both incoming and outgoing, and direct such requests and traffic for processing or viewing on the web site maintained by central monitoring unit 30. Connected to router 75 is firewall 80. The main purpose of firewall 80 is to protect the remainder of central monitoring unit 30 from unauthorized or malicious intrusions. Switch 85, connected to firewall 80, is used to direct data flow between middleware servers 95a through 95c and database server 110. Load balancer 90 is provided to spread the workload of incoming requests among the identically configured middleware servers 95a through 95c. Load balancer 90, a suitable example of which is the F5 ServerIron product sold by Foundry Networks, Inc. of San Jose, Calif., analyzes the availability of each middleware server 95a through 95c, and the amount of system resources being used in each middleware server 95a through 95c, in order to spread tasks among them appropriately.

Central monitoring unit 30 includes network storage device 100, such as a storage area network or SAN, which acts as the central repository for data. In particular, network storage device 100 comprises a database that stores all data gathered for each individual user in the manners described above. An example of a suitable network storage device 100 is the Symmetrix product sold by EMC Corporation of Hopkinton, Mass. Although only one network storage device 100 is shown in FIG. 3, it will be understood that multiple network storage devices of various capacities could be used depending on the data storage needs of central monitoring unit 30. Central monitoring unit 30 also includes database server 110 which is coupled to network storage device 100. Database server 110 is made up of two main components: a large scale multiprocessor server and an enterprise type software server component such as the 8/8i component sold by Oracle Corporation of Redwood City, Calif., or the 506 7 component sold by Microsoft Corporation of Redmond, Wash. The primary functions of database server 110 are that of providing access upon request to the data stored in network storage device 100, and populating network storage device 100 with new data. Coupled to network storage device 100 is controller 115, which typically comprises a desktop personal computer, for managing the data stored in network storage device 100.

Middleware servers 95a through 95c, a suitable example of which is the 22OR Dual Processor sold by Sun Microsystems, Inc. of Palo Alto, Calif., each contain software for generating and maintaining the corporate or home web page or pages of the web site maintained by central monitoring unit 30. As is known in the art, a web page refers to a block or blocks of data available on the World-Wide Web comprising a file or files written in Hypertext Markup Language or HTML, and a web site commonly refers to any computer on the Internet running a World-Wide Web server process. The corporate or home web page or pages are the opening or landing web page or pages that are accessible by all members of the general public that visit the site by using the appropriate uniform resource locator or URL. As is known in the art, URLs are the form of address used on the World-Wide Web and provide a standard way of specifying the location of an object, typically a web page, on the Internet. Middleware servers 95a through 95c also each contain software for generating and maintaining the web pages of the web site of central monitoring unit 30 that can only be accessed by individuals that register and become members of central monitoring unit 30. The member users will be those individuals who wish to have their data stored at central monitoring unit 30. Access by such member users is controlled using passwords for security purposes. Preferred embodiments of those web pages are described in detail below and are generated using collected data that is stored in the database of network storage device 100.

Middleware servers 95a through 95c also contain software for requesting data from and writing data to network storage device 100 through database server 110. When an individual user desires to initiate a session with the central monitoring unit 30 for the purpose of entering data into the database of network storage device 100, viewing his or her data stored in the database of network storage device 100, or both, the user visits the home web page of central monitoring unit 30 using a browser program such as Internet Explorer distributed by Microsoft Corporation of Redmond, Wash., and logs in as a registered user. Load balancer 90 assigns the user to one of the middleware servers 95a through 95c, identified as the chosen middleware server. A user will preferably be assigned to a chosen middleware server for each entire session. The chosen middleware server authenticates the user using any one of many well known methods, to ensure that only the true user is permitted to access the information in the database. A member user may also grant access to his or her data to a third party such as a health care provider or a personal trainer. Each authorized third party may be given a separate password and may view the member user's data using a conventional browser. It is therefore possible for both the user and the third party to be the recipient of the data.

When the user is authenticated, the chosen middleware server requests, through database server 110, the individual user's data from network storage device 100 for a predetermined time period. The predetermined time period is preferably thirty days. The requested data, once received from network storage device 100, is temporarily stored by the chosen middleware server in cache memory. The cached data is used by the chosen middleware server as the basis for presenting information, in the form of web pages, to the user again through the user's browser. Each middleware server 95a through 95c is provided with appropriate software for generating such web pages, including software for manipulating and performing calculations utilizing the data to put the data in appropriate format for presentation to the user. Once the user ends his or her session, the data is discarded from cache. When the user initiates a new session, the process for obtaining and caching data for that user as described above is repeated. This caching system thus ideally requires that only one call to the network storage device 100 be made per session, thereby reducing the traffic that database server 110 must handle. Should a request from a user during a particular session require data that is outside of a predetermined time period of cached data already retrieved, a separate call to network storage device 100 may be performed by the chosen middleware server. The predetermined time period should be chosen, however, such that such additional calls are minimized. Cached data may also be saved in cache memory so that it can be reused when a user starts a new session, thus eliminating the need to initiate a new call to network storage device 100.

As described in connection with Table 2, the microprocessor of sensor device 10 may be programmed to derive information relating to an individual's physiological state based on the data indicative of one or more physiological parameters. Central monitoring unit 30, and preferably middleware servers 95a through 95c, may also be similarly programmed to derive such information based on the data indicative of one or more physiological parameters.

It is also contemplated that a user will input additional data during a session, for example, information relating to the user's eating or sleeping habits. This additional data is preferably stored by the chosen middleware server in a cache during the duration of the user's session. When the user ends the session, this additional new data stored in a cache is transferred by the chosen middleware server to database server 110 for population in network storage device 100. Alternatively, in addition to being stored in a cache for potential use during a session, the input data may also be immediately transferred to database server 110 for population in network storage device 100, as part of a write-through cache system which is well known in the art.

Data collected by sensor device 10 shown in FIG. 1 is periodically uploaded to central monitoring unit 30. Either by long distance wireless transmission or through personal computer 35, a connection to central monitoring unit 30 is made through an electronic network, preferably the Internet. In particular, connection is made to load balancer 90 through CSU/DSU 70, router 75, firewall 80 and switch 85. Load balancer 90 then chooses one of the middleware servers 95a through 95c to handle the upload of data, hereafter called the chosen middleware server. The chosen middleware server authenticates the user using any one of many well known methods. If authentication is successful, the data is uploaded to the chosen middleware server as described above, and is ultimately transferred to database server 110 for population in the network storage device 100.

Figure 4:
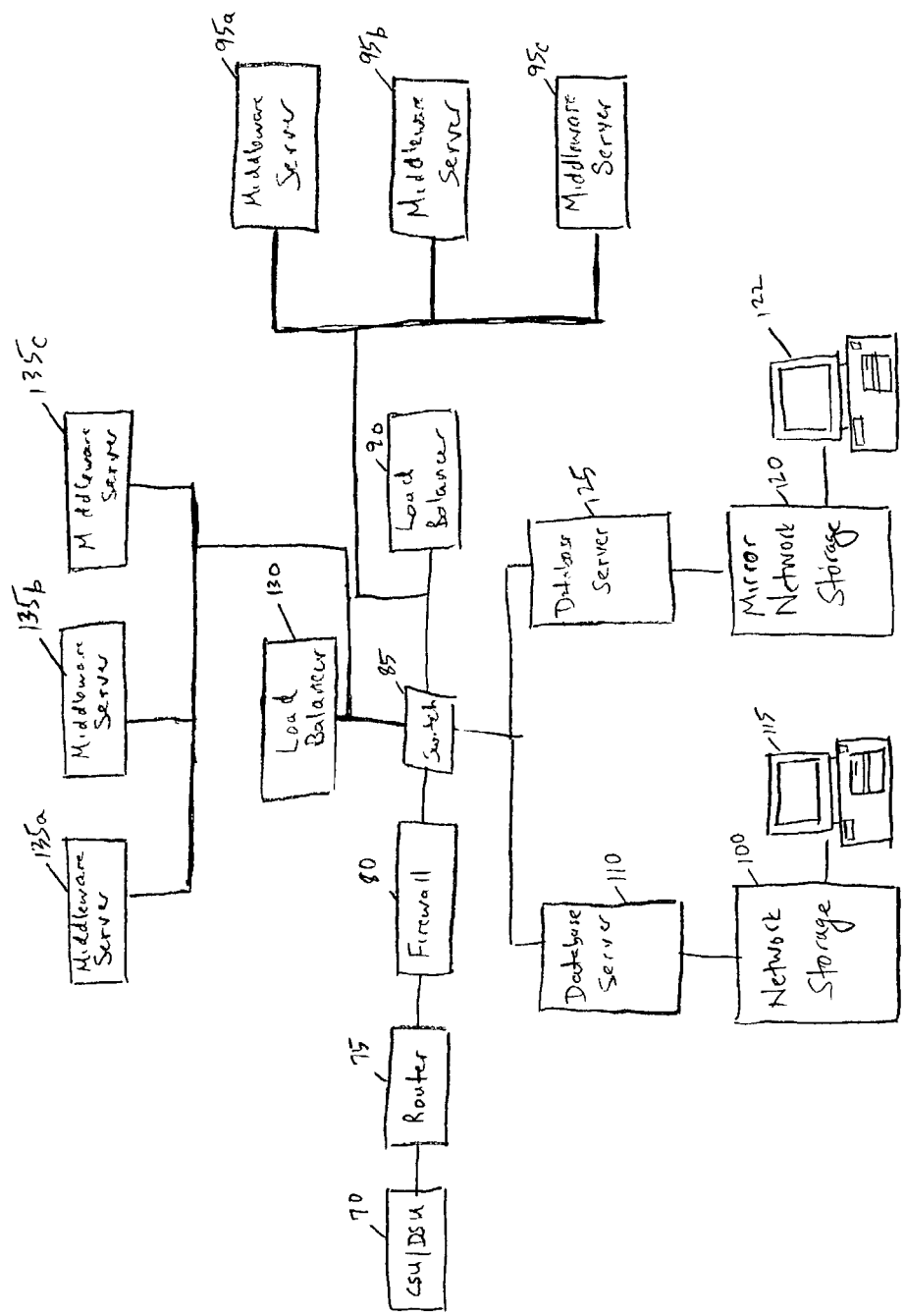
FIG. 4 is a block diagram of an alternate embodiment of the central monitoring unit shown in FIG. 1.

Referring to FIG. 4, an alternate embodiment of central monitoring unit 30 is shown. In addition to the elements shown and described with respect to FIG. 3, the embodiment of the central monitoring unit 30 shown in FIG. 4 includes a mirror network storage device 120 which is a redundant backup of network storage device 100. Coupled to mirror network storage device 120 is controller 122. Data from network storage device 100 is periodically copied to mirror network storage device 120 for data redundancy purposes.

Third parties such as insurance companies or research institutions may be given access, possibly for a fee, to certain of the information stored in mirror network storage device 120. Preferably, in order to maintain the confidentiality of the individual users who supply data to central monitoring unit 30, these third parties are not given access to such user's individual database records, but rather are only given access to the data stored in mirror network storage device 120 in aggregate form. Such third parties may be able to access the information stored in mirror network storage device 120 through the Internet using a conventional browser program. Requests from third parties may come in through CSU/DSU 70, router 75, firewall 80 and switch 85. In the embodiment shown in FIG. 4, a separate load balancer 130 is provided for spreading tasks relating to the accessing and presentation of data from mirror drive array 120 among identically configured middleware servers 135a through 135c. Middleware servers 135a through 135c each contain software for enabling the third parties to, using a browser, formulate queries for information from mirror network storage lo device 120 through separate database server 125. Middleware servers 135a through 135c also contain software for presenting the information obtained from mirror network storage device 120 to the third parties over the Internet in the form of web pages. In addition, the third parties can choose from a series of prepared reports that have information packaged along subject matter lines, such as various demographic categories.

As will be apparent to one of skill in the art, instead of giving these third parties access to the backup data stored in mirror network storage device 120, the third parties may be given access to the data stored in network storage device 100. Also, instead of providing load balancer 130 and middleware servers 135a through 135c, the same functionality, although at a sacrificed level of performance, could be provided by load balancer 90 and middleware servers 95a through 95c.

When an individual user first becomes a registered user or member, that user completes a detailed survey. The purposes of the survey are to: identify unique characteristics/circumstances for each user that they might need to address in order to maximize the likelihood that they will implement and maintain a healthy lifestyle as suggested by central monitoring unit 30; gather baseline data which will be used to set initial goals for the individual user and facilitate the calculation and display of certain graphical data output such as the Health Index pistons; identify unique user characteristics and circumstances that will help central monitoring unit 30 customize the type of content provided to the user in the Health Manager's Daily Dose; and identify unique user characteristics and circumstances that the Health Manager can guide the user to address as possible barriers to a healthy lifestyle through the problem-solving function of the Health Manager.

The specific information to be surveyed may include: key individual temperamental characteristics, including activity level, regularity of eating, sleeping, and bowel habits, initial response to situations, adaptability, persistence, threshold of responsiveness, intensity of reaction, and quality of mood; the user's level of independent functioning, i.e., self-organization and management, socialization, memory, and academic achievement skills; the user's ability to focus and sustain attention, including the user's level of arousal, cognitive tempo, ability to filter distractions, vigilance, and self-monitoring; the user's current health status including current weight, height, and blood pressure, most recent general physician visit, gynecological exam, and other applicable physician/healthcare contacts, current medications and supplements, allergies, and a review of current symptoms and/or health-related behaviors; the user's past health history, i.e., illnesses/surgeries, family history, and social stress events, such as divorce or loss of a job, that have required adjustment by the individual; the user's beliefs, values and opinions about health priorities, their ability to alter their behavior and, what might contribute to stress in their life, and how they manage it; the user's degree of self-awareness, empathy, empowerment, and self-esteem, and the user's current daily routines for eating, sleeping, exercise, relaxation and completing activities of daily living; and the user's perception of the temperamental characteristics of two key persons in their life, for example, their spouse, a friend, a co-worker, or their boss, and whether there are clashes present in their relationships that might interfere with a healthy lifestyle or contribute to stress.

Figure 5:
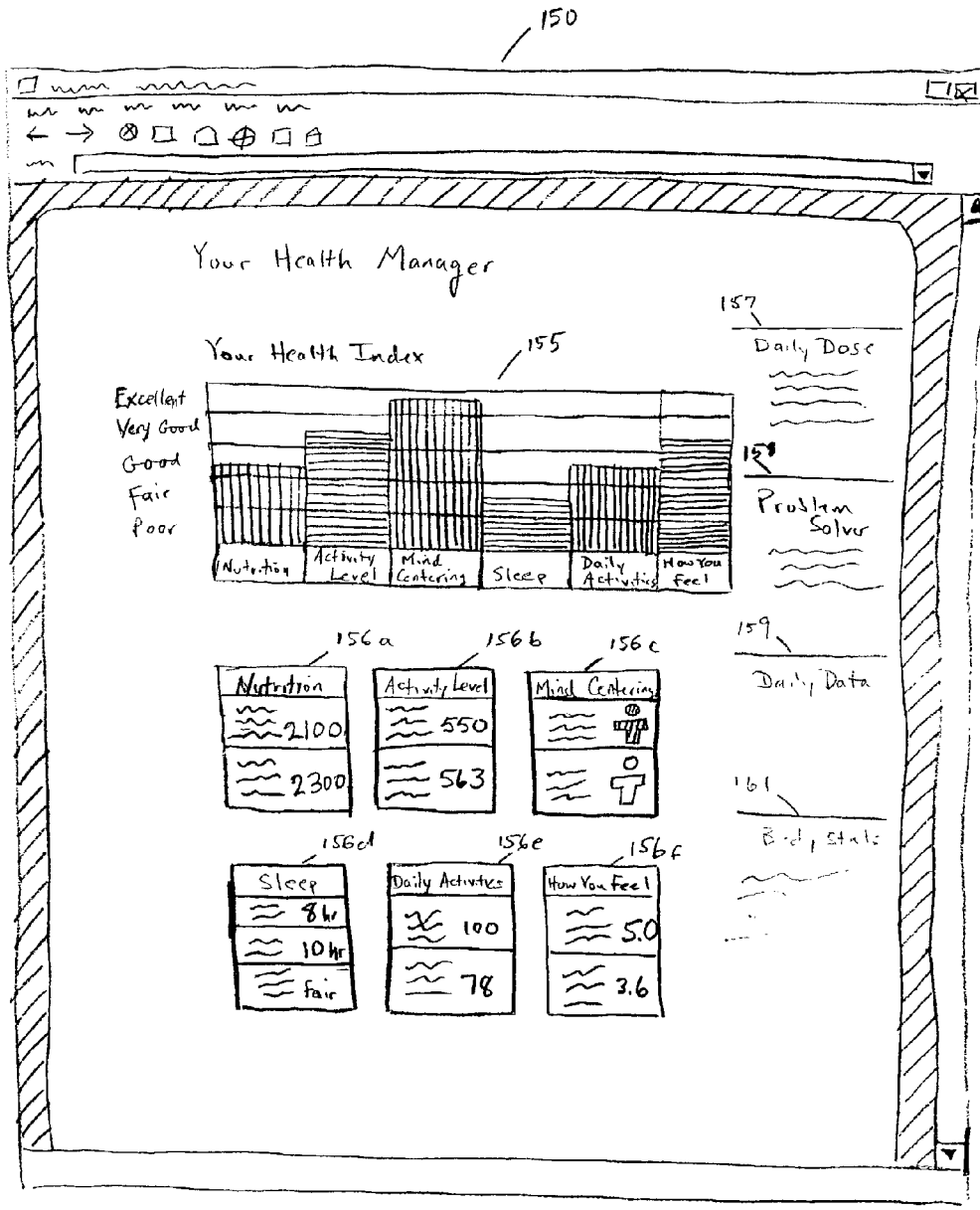
FIG. 5 is a representation of a preferred embodiment of the Health Manager web page according to an aspect of the present invention.

Each member user will have access, through the home web page of central monitoring unit 30, to a series of web pages customized for that user, referred to as the Health Manager. The opening Health Manager web page 150 is shown in FIG. 5. The Health Manager web pages are the main workspace area for the member user. The Health Manager web pages comprise a utility through which central monitoring unit 30 provides various types and forms of data, commonly referred to as analytical status data, to the user that is generated from the data it collects or generates, namely one or more of: the data indicative of various physiological parameters generated by sensor device 10; the data derived from the data indicative of various physiological parameters; the data indicative of various contextual parameters generated by sensor device 10; and the data input by the user. Analytical status data is characterized by the application of certain utilities or algorithms to convert one or more of the data indicative of various physiological parameters generated by sensor device 10, the data derived from the data indicative of various physiological parameters, the data indicative of various contextual parameters generated by sensor device 10, and the data input by the user into calculated health, wellness and lifestyle indicators. For example, based on data input by the user relating to the foods he or she has eaten, things such as calories and amounts of proteins, fats, carbohydrates, and certain vitamins can be calculated. As another example, skin temperature, heart rate, respiration rate, heat flow and/or GSR can be used to provide an indicator to the user of his or her stress level over a desired time period. As still another example, skin temperature, heat flow, beat-to-beat heart variability, heart rate, pulse rate, respiration rate, core temperature, galvanic skin response, EMG, EEG, EOG, blood pressure, oxygen consumption, ambient sound and body movement or motion as detected by a device such as an accelerometer can be used to provide indicators to the user of his or her sleep patterns over a desired time period.

Located on the opening Health Manager web page 150 is Health Index 155. Health Index 155 is a graphical utility used to measure and provide feedback to member users regarding their performance and the degree to which they have succeeded in reaching a healthy daily routine suggested by central monitoring unit 30. Health Index 155 thus provides an indication for the member user to track his or her progress. Health Index 155 includes six categories relating to the user's health and lifestyle: Nutrition, Activity Level, Mind Centering, Sleep, Daily Activities and How You Feel. The Nutrition category relates to what, when and how much a person eats and drinks. The Activity Level category relates to how much a person moves around. The Mind Centering category relates to the quality and quantity of time a person spends engaging in some activity that allows the body to achieve a state of profound relaxation while the mind becomes highly alert and focused. The Sleep category relates to the quality and quantity of a person's sleep. The Daily Activities category relates to the daily responsibilities and health risks people encounter. Finally, the How You Feel category relates to the general perception that a person has about how they feel on a particular day. Each category has an associated level indicator or piston that indicates, preferably on a scale ranging from poor to excellent, how the user is performing with respect to that category.

When each member user completes the initial survey described above, a profile is generated that provides the user with a summary of his or her relevant characteristics and life circumstances. A plan and/or set of goals is provided in the form of a suggested healthy daily routine. The suggested healthy daily routine may include any combination of specific suggestions for incorporating proper nutrition, exercise, mind centering, sleep, and selected activities of daily living in the user's life. Prototype schedules may be offered as guides for how these suggested activities can be incorporated into the user's life. The user may periodically retake the survey, and based on the results, the items discussed above will be adjusted accordingly.

The Nutrition category is calculated from both data input by the user and sensed by sensor device 10. The data input by the user comprises the time and duration of breakfast, lunch, dinner and any snacks, and the foods eaten, the supplements such as vitamins that are taken, and the water and other liquids consumed during a relevant, pre-selected time period. Based upon this data and on stored data relating to known properties of various foods, central monitoring unit 30 calculates well known nutritional food values such as calories and amounts of proteins, fats, carbohydrates, vitamins, etc., consumed.

The Nutrition Health Index piston level is preferably determined with respect to the following suggested healthy daily routine: eat at least three meals; eat a varied diet consisting of 6-11 servings of bread, pasta, cereal, and rice, 2-4 servings fruit, 3-5 servings of vegetables, 2-3 servings of fish, meat, poultry, dry beans, eggs, and nuts, and 2-3 servings of milk, yogurt and cheese; and drink 8 or more 8 ounce glasses of water. This routine may be adjusted based on information about the user, such as sex, age, height and/or weight. Certain nutritional targets may also be set by the user or for the user, relating to daily calories, protein, fiber, fat, carbohydrates, and/or water consumption and percentages of total consumption. Parameters utilized in the calculation of the relevant piston level include the number of meals per day, the number of glasses of water, and the types and amounts of food eaten each day as input by the user.

Figure 6:
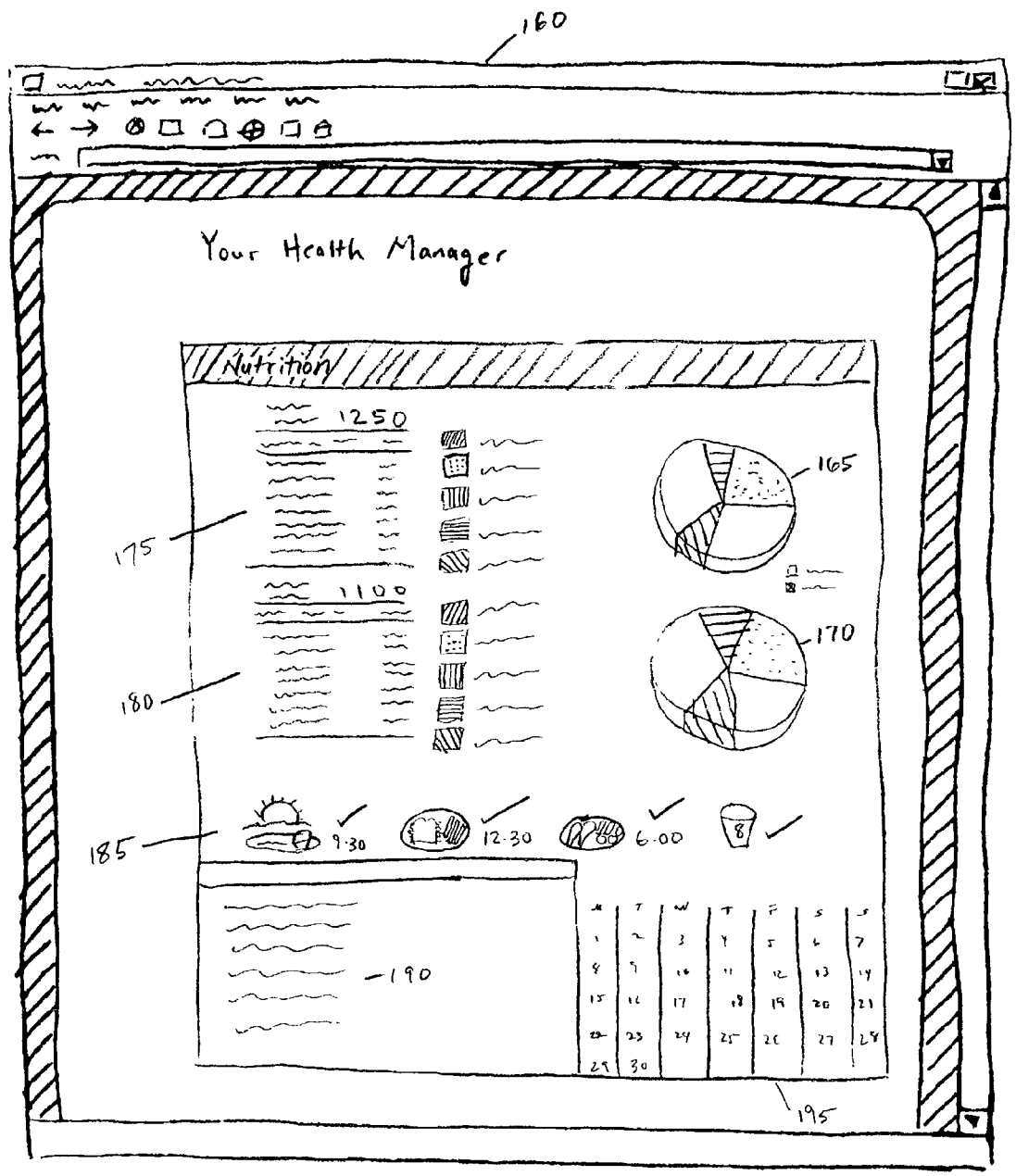
FIG. 6 is a representation of a preferred embodiment of the nutrition web page according to an aspect of the present invention.

Nutritional information is presented to the user through nutrition web page 160 as shown in FIG. 6. The preferred nutritional web page 160 includes nutritional fact charts 165 and 170 which illustrate actual and target nutritional facts, respectively as pie charts, and nutritional intake charts 175 and 180 which show total actual nutritional intake and target nutritional intake, respectively as pie charts. Nutritional fact charts 165 and 170 preferably show a percentage breakdown of items such as carbohydrates, protein and fat, and nutritional intake charts 175 and 180 are preferably broken down to show components such as total and target calories, fat, carbohydrates, protein, and vitamins. Web page 160 also includes meal and water consumption tracking 185 with time entries, hyperlinks 190 which allow the user to directly access nutrition-related news items and articles, suggestions for refining or improving daily routine with respect to nutrition and affiliate advertising elsewhere on the network, and calendar 195 for choosing between views having variable and selectable time periods. The items shown at 190 may be selected and customized based on information learned about the individual in the survey and on their performance as measured by the Health Index.

The Activity Level category of Health Index 155 is designed to help users monitor how and when they move around during the day and utilizes both data input by the user and data sensed by sensor device 10. The data input by the user may include details regarding the user's daily activities, for example the fact that the user worked at a desk from 8 a.m. to 5 p.m. and then took an aerobics class from 6 p.m. to 7 p.m. Relevant data sensed by sensor device 10 may include heart rate, movement as sensed by a device such as an accelerometer, heat flow, respiration rate, calories burned, GSR and hydration level, which may be derived by sensor device 60 or central monitoring unit 30. Calories burned may be calculated in a variety of manners, including: the multiplication of the type of exercise input by the user by the duration of exercise input by the user; sensed motion multiplied by time of motion multiplied by a filter constant; or sensed heat flux multiplied by time multiplied by a filter constant.

The Activity Level Health Index piston level is preferably determined with respect to a suggested healthy daily routine that includes: exercising aerobically for a pre-set time period, preferably 20 minutes, or engaging in a vigorous lifestyle activity for a pre-set time period, preferably one hour, and burning at least a minimum target number of calories, preferably 205 calories, through the aerobic exercise and/or lifestyle activity. The minimum target number of calories may be set according to information about the user, such as sex, age, height and/or weight. Parameters utilized in the calculation of the relevant piston level include the amount of time spent exercising aerobically or engaging in a vigorous lifestyle activity as input by the user and/or sensed by sensor device 10, and the number of calories burned above pre-calculated energy expenditure parameters.

Figure 7:
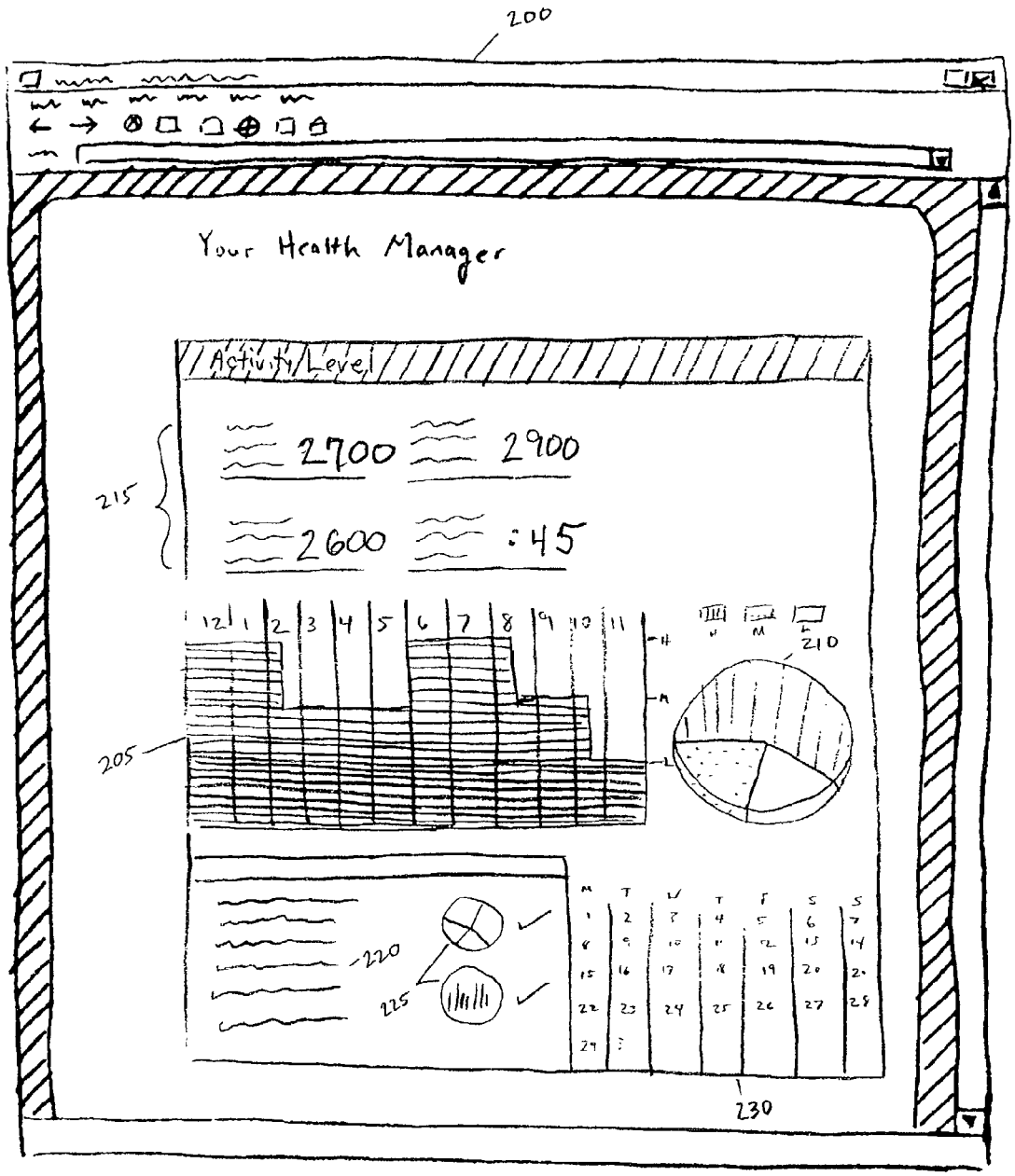
FIG. 7 is a representation of a preferred embodiment of the activity level web page according to an aspect of the present invention.

Information regarding the individual user's movement is presented to the user through activity level web page 200 shown in FIG. 7, which may include activity graph 205 in the form of a bar graph, for monitoring the individual user's activities in one of three categories: high, medium and low intensity with respect to a pre-selected unit of time. Activity percentage chart 210, in the form or a pie chart, may also be provided for showing the percentage of a pre-selected time period, such as one day, that the user spent in each category. Activity level web page 200 may also include calorie section 215 for displaying items such as total calories burned, daily target calories burned, total caloric intake, and duration of aerobic activity. Finally, activity level web page 200 may include at least one hyperlink 220 to allow a user to directly access relevant news items and articles, suggestions for refining or improving daily routine with respect to activity level and affiliate advertising elsewhere on the network. Activity level web page 200 may be viewed in a variety of formats, and may include user-selectable graphs and charts such as a bar graph, pie chart, or both, as selectable by Activity level check boxes 225. Activity level calendar 230 is provided for selecting among views having variable and selectable time periods. The items shown at 220 may be selected and customized based on information learned about the individual in the survey and on their performance as measured by the Health Index.

The Mind Centering category of Health Index 155 is designed to help users monitor the parameters relating to time spent engaging in certain activities which allow the body to achieve a state of profound relaxation while the mind becomes focused, and is based upon both data input by the user and data sensed by the sensor device 10. In particular, a user may input the beginning and end times of relaxation activities such as yoga or meditation. The quality of those activities as determined by the depth of a mind centering event can be measured by monitoring parameters including skin temperature, heart rate, respiration rate, and heat flow as sensed by sensor device 10. Percent change in GSR as derived either by sensor device 10 or central monitoring unit 30 may also be utilized.

The Mind Centering Health Index piston level is preferably calculated with respect to a suggested healthy daily routine that includes participating each day in an activity that allows the body to achieve profound relaxation while the mind stays highly focused for at least fifteen minutes. Parameters utilized in the calculation of the relevant piston level include the amount of time spent in a mind centering activity, and the percent change in skin temperature, heart rate, respiration rate, heat flow or GSR as sensed by sensor device 10 compared to a baseline which is an indication of the depth or quality of the mind centering activity.

Figure 8:
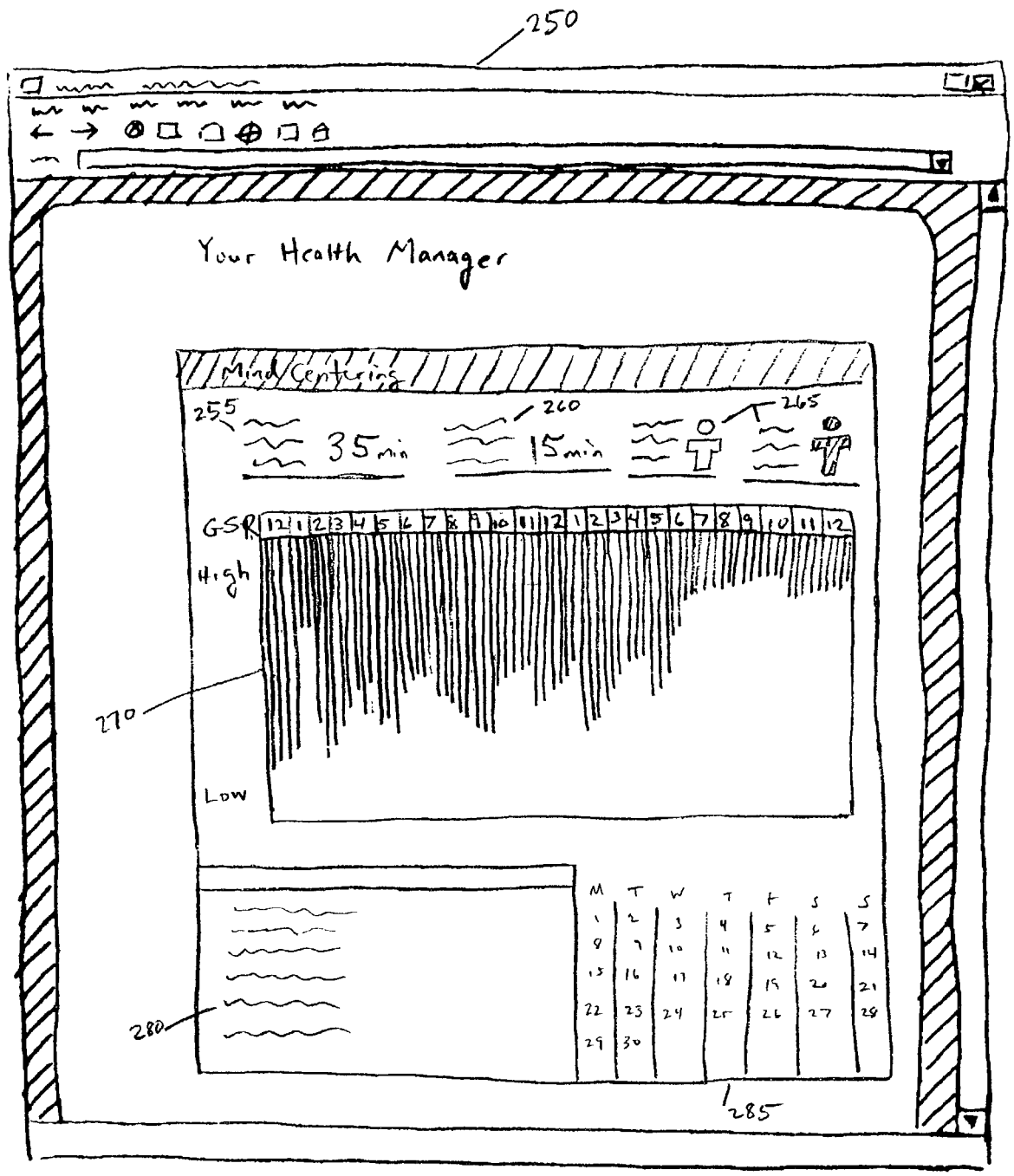
FIG. 8 is a representation of a preferred embodiment of the mind centering web page according to an aspect of the present invention.

Information regarding the time spent on self-reflection and relaxation is presented to the user through mind centering web page 250 shown in FIG. 8. For each mind centering activity, referred to as a session, the preferred mind centering web page 250 includes the time spent during the session, shown at 255, the target time, shown at 260, comparison section 265 showing target and actual depth of mind centering, or focus, and a histogram 270 that shows the overall level of stress derived from such things as skin temperature, heart rate, respiration rate, heat flow and/or GSR. In comparison section 265, the human figure outline showing target focus is solid, and the human figure outline showing actual focus ranges from fuzzy to solid depending on the level of focus. The preferred mind centering web page may also include an indication of the total time spent on mind centering activities, shown at 275, hyperlinks 280 which allow the user to directly access relevant news items and articles, suggestions for refining or improving daily routine with respect to mind centering and affiliate advertising, and a calendar 285 for choosing among views having variable and selectable time periods. The items shown at 280 may be selected and customized based on information learned about the individual in the survey and on their performance as measured by the Health Index.

The Sleep category of Health Index 155 is designed to help users monitor their sleep patterns and the quality of their sleep. It is intended to help users learn about the importance of sleep in their healthy lifestyle and the relationship of sleep to circadian rhythms, being the normal daily variations in body functions. The Sleep category is based upon both data input by the user and data sensed by sensor device 10. The data input by the user for each relevant time interval includes the times the user went to sleep and woke up and a rating of the quality of sleep. As noted in Table 2, the data from sensor device 10 that is relevant includes skin temperature, heat flow, beat-to-beat heart variability, heart rate, pulse rate, respiration rate, core temperature, galvanic skin response, EMG, EEG, EOG, blood pressure, and oxygen consumption. Also relevant is ambient sound and body movement or motion as detected by a device such as an accelerometer. This data can then be used to calculate or derive sleep onset and wake time, sleep interruptions, and the quality and depth of sleep.

The Sleep Health Index piston level is determined with respect to a healthy daily routine including getting a minimum amount, preferably eight hours, of sleep each night and having a predictable bed time and wake time. The specific parameters which determine the piston level calculation include the number of hours of sleep per night and the bed time and wake time as sensed by sensor device 10 or as input by the user, and the quality of the sleep as rated by the user or derived from other data.

Figure 9:
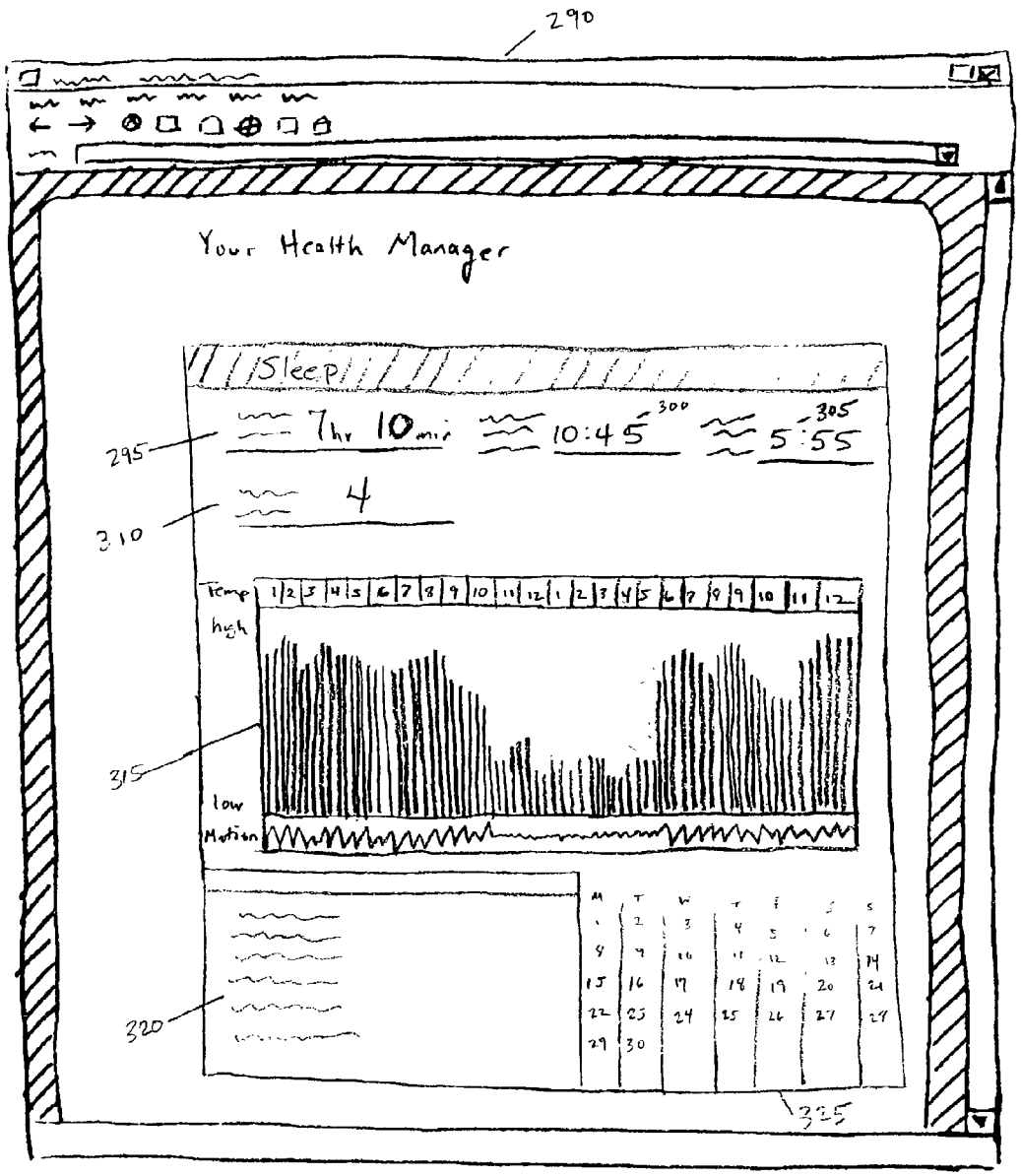
FIG. 9 is a representation of a preferred embodiment of the sleep web page according to an aspect of the present invention.

Information regarding sleep is presented to the user through sleep web page 290 shown in FIG. 9. Sleep web page 290 includes a sleep duration indicator 295, based on either data from sensor device 10 or on data input by the user, together with user sleep time indicator 300 and wake time indicator 305. A quality of sleep rating 310 input by the user may also be utilized and displayed. If more than a one day time interval is being displayed on sleep web page 290, then sleep duration indicator 295 is calculated and displayed as a cumulative value, and sleep time indicator 300, wake time indicator 305 and quality of sleep rating 310 are calculated and illustrated as averages. Sleep web page 290 also includes a user-selectable sleep graph 315 which calculates and displays one sleep related parameter over a pre-selected time interval. For illustrative purposes, FIG. 9 shows heat flow over a one-day period, which tends to be lower during sleeping hours and higher during waking hours. From this information, a person's bio-rhythms can be derived. Sleep graph 315 may also include a graphical representation of data from an accelerometer incorporated in sensor device 10 which monitors the movement of the body. The sleep web page 290 may also include hyperlinks 320 which allow the user to directly access sleep related news items and articles, suggestions for refining or improving daily routine with respect to sleep and affiliate advertising available elsewhere on the network, and a sleep calendar 325 for choosing a relevant time interval. The items shown at 320 may be selected and customized based on information learned about the individual in the survey and on their performance as measured by the Health Index.

The Activities of Daily Living category of Health Index 155 is designed to help users monitor certain health and safety related activities and risks and is based entirely on data input by the user. The Activities of Daily Living category is divided into four sub-categories: personal hygiene, which allows the user to monitor activities such as brushing and flossing his or her teeth and showering; health maintenance, that tracks whether the user is taking prescribed medication or supplements and allows the user to monitor tobacco and alcohol consumption and automobile safety such as seat belt use; personal time, that allows the user to monitor time spent socially with family and friends, leisure, and mind centering activities; and responsibilities, that allows the user to monitor certain work and financial activities such as paying bills and household chores.

The Activities of Daily Living Health Index piston level is preferably determined with respect to the healthy daily routine described below. With respect to personal hygiene, the routine requires that the users shower or bathe each day, brush and floss teeth each day, and maintain regular bowel habits. With respect to health maintenance, the routine requires that the user take medications and vitamins and/or supplements, use a seat belt, refrain from smoking, drink moderately, and monitor health each day with the Health Manager. With respect to personal time, the routine requires the users to spend at least one hour of quality time each day with family and/or friends, restrict work time to a maximum of nine hours a day, spend some time on a leisure or play activity each day, and engage in a mind stimulating activity. With respect to responsibilities, the routine requires the users to do household chores, pay bills, be on time for work, and keep appointments. The piston level is calculated based on the degree to which the user completes a list of daily activities as determined by information input by the user.

Figure 10:
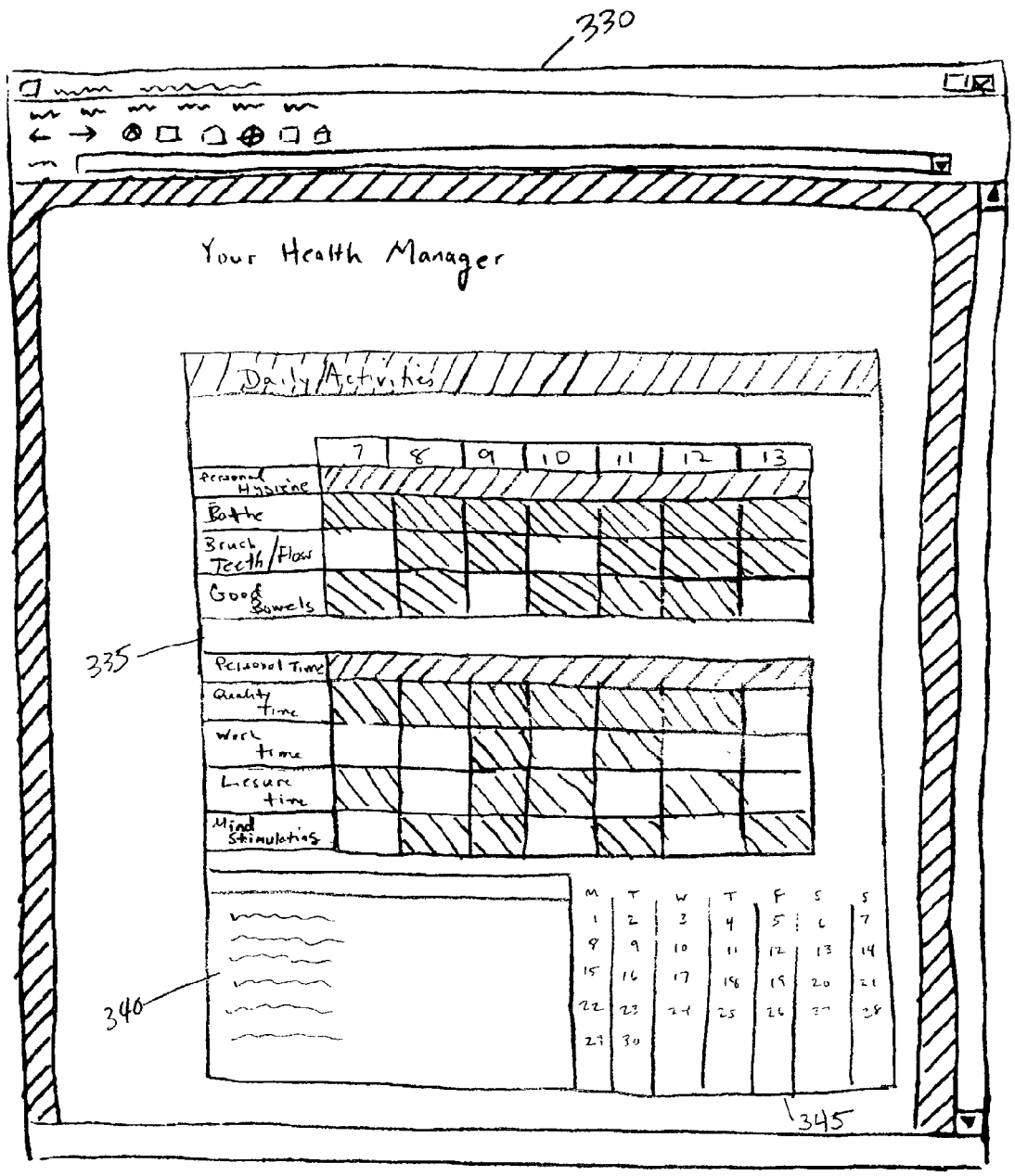
FIG. 10 is a representation of a preferred embodiment of the daily activities web page according to an aspect of the present invention.

Information relating to these activities is presented to the user through daily activities web page 330 shown in FIG. 10. In preferred daily activities web page 330, activities chart 335, selectable for one or more of the sub-categories, shows whether the user has done what is required by the daily routine. A colored or shaded box indicates that the user has done the required activity, and an empty, non-colored or shaded box indicates that the user has not done the activity. Activities chart 335 can be created and viewed in selectable time intervals. For illustrative purposes, FIG. 10 shows the personal hygiene and personal time sub-categories for a particular week. In addition, daily activities web page 330 may include daily activity hyperlinks 340 which allow the user to directly access relevant news items and articles, suggestions for improving or refining daily routine with respect to activities of daily living and affiliate advertising, and a daily activities calendar 345 for selecting a relevant time interval. The items shown at 340 maybe selected and customized based on information learned about the individual in the survey and on their performance as measured by the Health Index.

The How You Feel category of Health Index 155 is designed to allow users to monitor their perception of how they felt on a particular day, and is based on information, essentially a subjective rating, that is input directly by the user. A user provides a rating, preferably on a scale of 1 to 5, with respect to the following nine subject areas: mental sharpness; emotional and psychological well being; energy level; ability to cope with life stresses; appearance; physical well being; self-control; motivation; and comfort in relating to others. Those ratings are averaged and used to calculate the relevant piston level.

Figure 11:
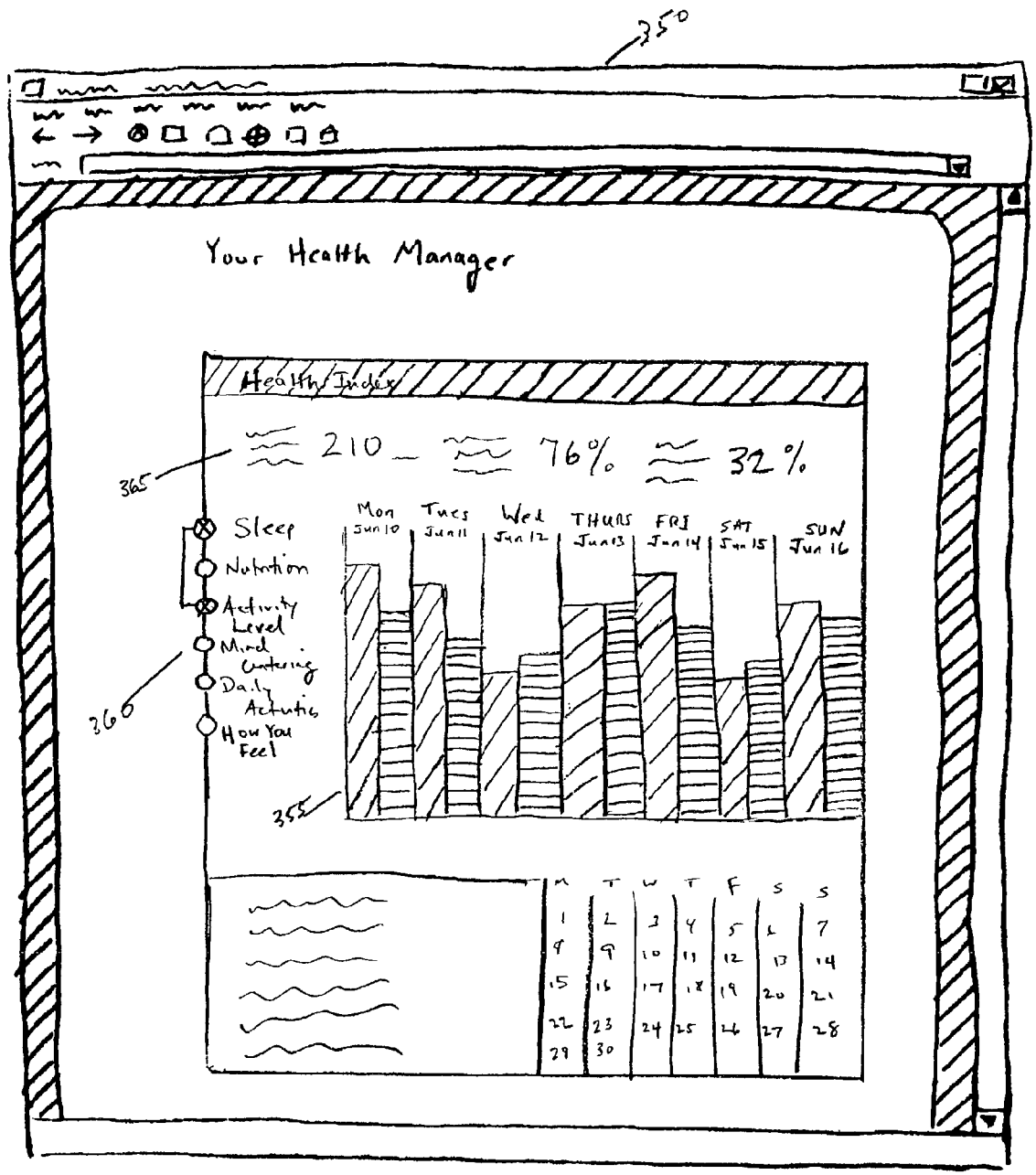
FIG. 11 is a representation of a preferred embodiment of the Health Index web page according to an aspect of the present invention.

Referring to FIG. 11, Health Index web page 350 is shown. Health Index web page 350 enables users to view the performance of their Health Index over a user selectable time interval including any number of consecutive or non-consecutive days. Using Health Index selector buttons 360, the user can select to view the Health Index piston levels for one category, or can view a side-by-side comparison of the Health Index piston levels for two or more categories. For example, a user might want to just turn on Sleep to see if their overall sleep rating improved over the previous month, much in the same way they view the performance of their favorite stock. Alternatively, Sleep and Activity Level might be simultaneously displayed in order to compare and evaluate Sleep ratings with corresponding Activity Level ratings to determine if any day-to-day correlations exist. Nutrition ratings might be displayed with How You Feel for a pre-selected time interval to determine if any correlation exists between daily eating habits and how they felt during that interval. For illustrative purposes, FIG. 11 illustrates a comparison of Sleep and Activity Level piston levels for the week of June 10 through June 16. Health Index web page 350 also includes tracking calculator 365 that displays access information and statistics such as the total number of days the user has logged in and used the Health Manager, the percentage of days the user has used the Health Manager since becoming a subscriber, and percentage of time the user has used the sensor device 10 to gather data.

Referring again to FIG. 5, opening Health Manager web page 150 may include a plurality of user selectable category summaries 156a through 156f, one corresponding to each of the Health Index 155 categories. Each category summary 156a through 156f presents a pre-selected filtered subset of the data associated with the corresponding category. Nutrition category summary 156a displays daily target and actual caloric intake. Activity Level category summary 156b displays daily target and actual calories burned. Mind Centering category summary 156c displays target and actual depth of mind centering or focus. Sleep category summary 156d displays target sleep, actual sleep, and a sleep quality rating. Daily Activities category summary 156e displays a target and actual score based on the percentage of suggested daily activities that are completed. The How You Feel category summary 156f shows a target and actual rating for the day.

Opening Health Manager web page 150 also may include Daily Dose section 157 which provides, on a daily time interval basis, information to the user, including, but not limited to, hyperlinks to news items and articles, commentary and reminders to the user based on tendencies, such as poor nutritional habits, determined from the initial survey. The commentary for Daily Dose 157 may, for example, be a factual statement that drinking 8 glasses of water a day can reduce the risk of colon cancer by as much as 32%, accompanied by a suggestion to keep a cup of water by your computer or on your desk at work and refill often. Opening Health Manager web page 150 also may include a Problem Solver section 158 that actively evaluates the user's performance in each of the categories of Health Index 155 and presents suggestions for improvement. For example, if the system detects that a user's Sleep levels have been low, which suggest that the user has been having trouble sleeping, Problem Solver 158 can provide suggestions for way to improve sleep. Problem Solver 158 also may include the capability of user questions regarding improvements in performance. Opening Health Manager web page 150 may also include a Daily Data section 159 that launches an input dialog box. The input dialog box facilitates input by the user of the various data required by the Health Manager. As is known in the art, data entry may be in the form of selection from pre-defined lists or general free form text input. Finally, opening Health Manager web page 150 may include Body Stats section 161 which may provide information regarding the user's height, weight, body measurements, body mass index or BMI, and vital signs such as heart rate, blood pressure or any of the identified physiological parameters.

Figure 15:
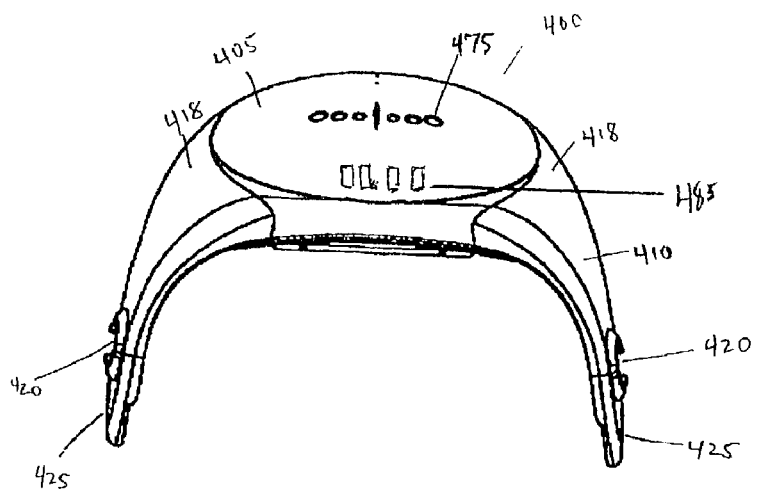
FIG. 15 is a bottom view of a specific embodiment of the sensor device shown in FIG. 1.
Figure 16:
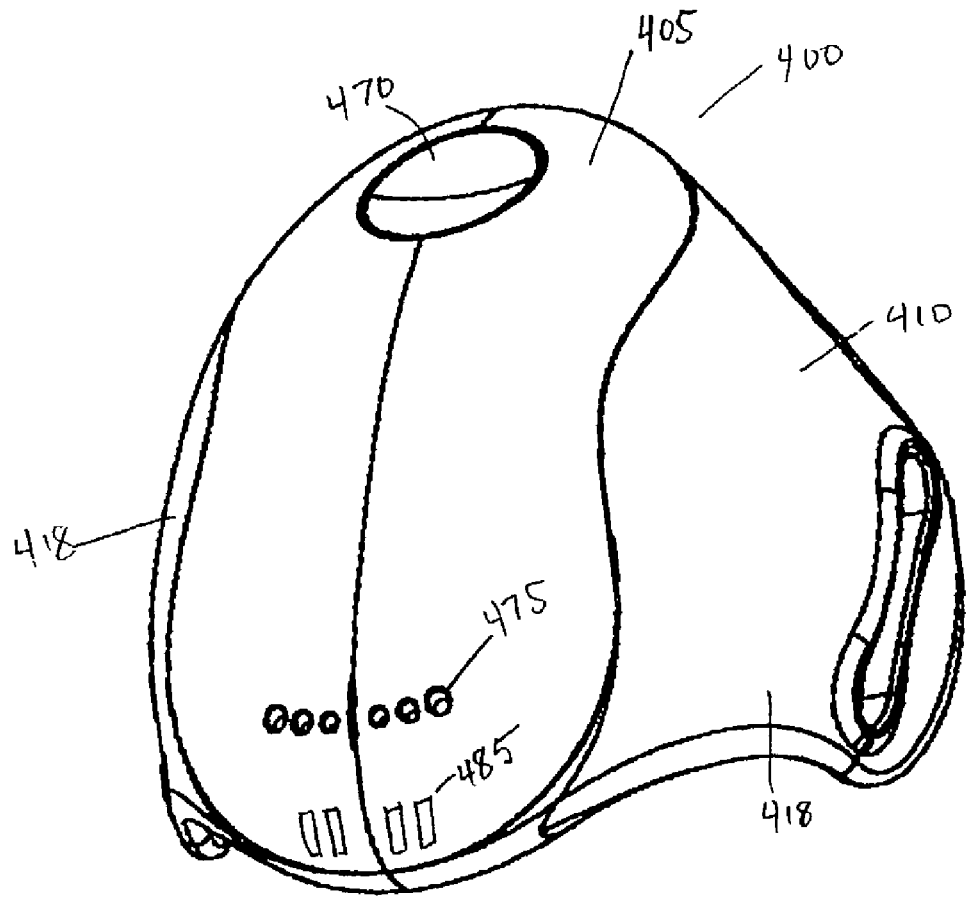
FIGS. 16 and 17 are front perspective views of a specific embodiment of the sensor device shown in FIG. 1.
Figure 17:
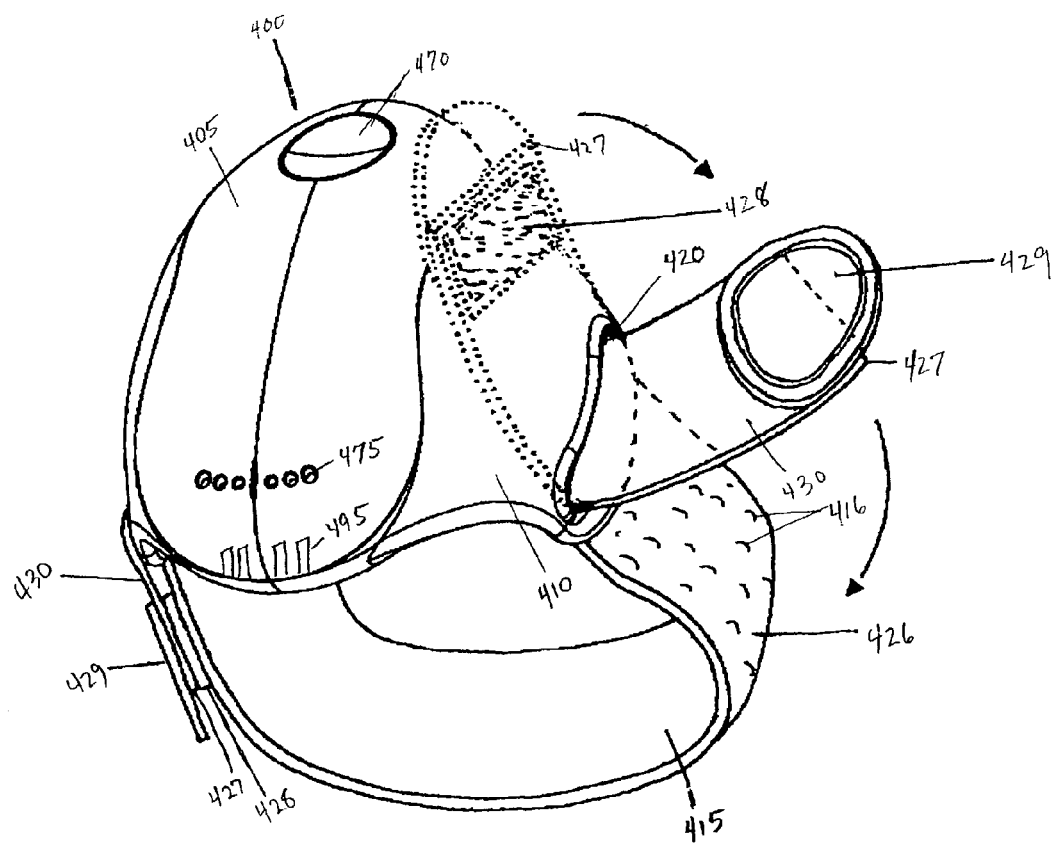

Referring to FIGS. 12–17, a specific embodiment of sensor device 10 is shown which is in the form of an armband adapted to be worn by an individual on his or her upper arm, between the shoulder and the elbow. The specific embodiment of sensor device 10 shown in FIGS. 12–17 will, for convenience, be referred to as armband sensor device 400. Armband sensor device 400 includes computer housing 405, flexible wing body 410, and, as shown in FIG. 17, elastic strap 415. Computer housing 405 and flexible wing body 410 are preferably made of a flexible urethane material or an elastomeric material such as rubber or a rubber-silicone blend by a molding process. Flexible wing body 410 includes first and second wings 418 each having a thru-hole 420 located near the ends 425 thereof. First and second wings 418 are adapted to wrap around a portion of the wearer's upper arm.

Elastic strap 415 is used to removably affix armband sensor device 400 to the individual's upper arm. As seen in FIG. 17, bottom surface 426 of elastic strap 415 is provided with Velcro loops 416 along a portion thereof. Each end 427 of elastic strap 415 is provided with Velcro hook patch 428 on bottom surface 426 and pull tab 429 on top surface 430. A portion of each pull tab 429 extends beyond the edge of each end 427.

In order to wear armband sensor device 400, a user inserts each end 427 of elastic strap 415 into a respective thru-hole 420 of flexible wing body 410. The user then places his arm through the loop created by elastic strap 415, flexible wing body 410 and computer housing 405. By pulling each pull tab 429 and engaging Velcro hook patches 428 with Velcro loops 416 at a desired position along bottom surface 426 of elastic strap 415, the user can adjust elastic strap 415 to fit comfortably. Since Velcro hook patches 428 can be engaged with Velcro loops 416 at almost any position along bottom surface 426, armband sensor device 400 can be adjusted to fit arms of various sizes. Also, elastic strap 415 may be provided in various lengths to accommodate a wider range of arm sizes. As will be apparent to one of skill in the art, other means of fastening and adjusting the size of elastic strap may be used, including, but not limited to, snaps, buttons, or buckles. It is also possible to use two elastic straps that fasten by one of several conventional means including Velcro, snaps, buttons, buckles or the like, or merely a single elastic strap affixed to wings 418.

Alternatively, instead of providing thru-holes 420 in wings 418, loops having the shape of the letter D, not shown, may be attached to ends 425 of wings 418 by one of several conventional means. For example, a pin, not shown, may be inserted through ends 425, wherein the pin engages each end of each loop. In this configuration, the D-shaped loops would serve as connecting points for elastic strap 415, effectively creating a thru-hole between each end 425 of each wing 418 and each loop.

Figure 18:
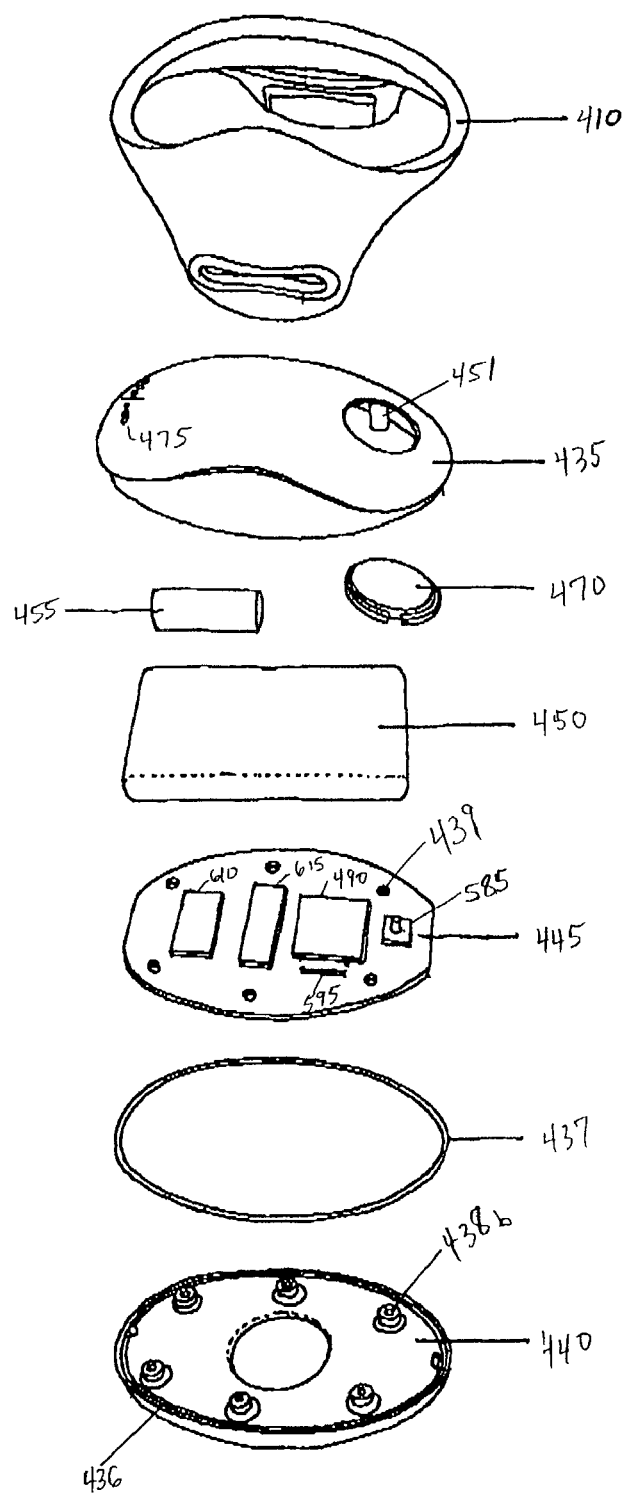
FIG. 18 is an exploded side perspective view of a specific embodiment of the sensor device shown in FIG. 1.

As shown in FIG. 18, which is an exploded view of armband sensor device 400, computer housing 405 includes a top portion 435 and a bottom portion 440. Contained within computer housing 405 are printed circuit board or PCB 445, rechargeable battery 450, preferably a lithium ion battery, and vibrating motor 455 for providing tactile feedback to the wearer, such as those used in pagers, suitable examples of which are the Model 12342 and 12343 motors sold by MG Motors Ltd. of the United Kingdom.

Top portion 435 and bottom portion 440 of computer housing 405 sealingly mate along groove 436 into which O-ring 437 is fit, and may be affixed to one another by screws, not shown, which pass through screw holes 438a and stiffeners 438b of bottom portion 440 and apertures 439 in PCB 445 and into threaded receiving stiffeners 451 of top portion 435. Alternately, top portion 435 and bottom portion 440 may be snap fit together or affixed to one another with an adhesive. Preferably, the assembled computer housing 405 is sufficiently water resistant to permit armband sensor device 400 to be worn while swimming without adversely affecting the performance thereof.

Figure 13:
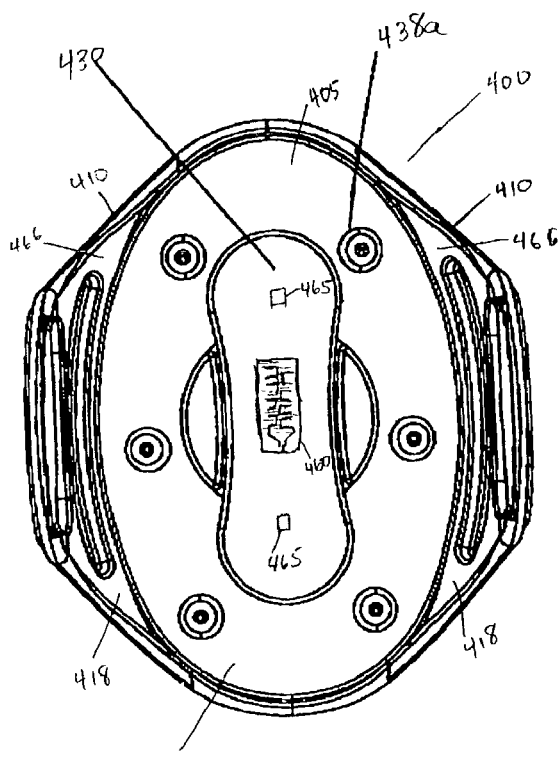
FIG. 13 is a back view of a specific embodiment of the sensor device shown in FIG. 1.

As can be seen in FIG. 13, bottom portion 440 includes, on a bottom side thereof, a raised platform 430. Affixed to raised platform 430 is heat flow or flux sensor 460, a suitable example of which is the micro-foil heat flux sensor sold by RdF Corporation of Hudson, N.H. Heat flux sensor 460 functions as a self-generating thermopile transducer, and preferably includes a carrier made of a polyamide film. Bottom portion 440 may include on a top side thereof, that is on a side opposite the side to which heat flux sensor 460 is affixed, a heat sink, not shown, made of a suitable metallic material such as aluminum. Also affixed to raised platform 430 are GSR sensors 465, preferably comprising electrodes formed of a material such as conductive carbonized rubber, gold or stainless steel. Although two GSR sensors 465 are shown in FIG. 13, it will be appreciated by one of skill in the art that the number of GSR sensors 465 and the placement thereof on raised platform 430 can vary as long as the individual GSR sensors 465, i.e., the electrodes, are electrically isolated from one another. By being affixed to raised platform 430, heat flux sensor 460 and GSR sensors 465 are adapted to be in contact with the wearer's skin when armband sensor device 400 is worn. Bottom portion 440 of computer housing 405 may also be provided with a removable and replaceable soft foam fabric pad, not shown, on a portion of the surface thereof that does not include raised platform 430 and screw holes 438a. The soft foam fabric is intended to contact the wearer's skin and make armband sensor device 400 more comfortable to wear.

Electrical coupling between heat flux sensor 460, GSR sensors 465, and PCB 445 may be accomplished in one of various known methods. For example, suitable wiring, not shown, may be molded into bottom portion 440 of computer housing 405 and then electrically connected, such as by soldering, to appropriate input locations on PCB 445 and to heat flux sensor 460 and GSR sensors 465. Alternatively, rather than molding wiring into bottom portion 440, thru-holes may be provided in bottom portion 440 through which appropriate wiring may pass. The thru-holes would preferably be provided with a water tight seal to maintain the integrity of computer housing 405.

Rather than being affixed to raised platform 430 as shown in FIG. 13, one or both of heat flux sensor 460 and GSR sensors 465 may be affixed to the inner portion 466 of flexible wing body 410 on either or both of wings 418 so as to be in contact with the wearer's skin when armband sensor device 400 is worn. In such a configuration, electrical coupling between heat flux sensor 460 and GSR sensors 465, whichever the case may be, and the PCB 445 may be accomplished through suitable wiring, not shown, molded into flexible wing body 410 that passes through one or more thru-holes in computer housing 405 and that is electrically connected, such as by soldering, to appropriate input locations on PCB 445. Again, the thru-holes would preferably be provided with a water tight seal to maintain the integrity of computer housing 405. Alternatively, rather than providing thru-holes in computer housing 405 through which the wiring passes, the wiring may be captured in computer housing 405 during an overmolding process, described below, and ultimately soldered to appropriate input locations on PCB 445.

As shown in FIGS. 12, 16, 17 and 18, computer housing 405 includes a button 470 that is coupled to and adapted to activate a momentary switch 585 on PCB 445. Button 470 may be used to activate armband sensor device 400 for use, to mark the time an event occurred or to request system status information such as battery level and memory capacity. When button 470 is depressed, momentary switch 585 closes a circuit and a signal is sent to processing unit 490 on PCB 445. Depending on the time interval for which button 470 is depressed, the generated signal triggers one of the events just described. Computer housing 405 also includes LEDs 475, which may be used to indicate battery level or memory capacity or to provide visual feedback to the wearer. Rather than LEDs 475, computer housing 405 may also include a liquid crystal display or LCD to provide battery level, memory capacity or visual feedback information to the wearer. Battery level, memory capacity or feedback information may also be given to the user tactily or audibly.

Armband sensor device 400 may be adapted to be activated for use, that is collecting data, when either of GSR sensors 465 or heat flux sensor 460 senses a particular condition that indicates that armband sensor device 400 has been placed in contact with the user's skin. Also, armband sensor device 400 may be adapted to be activated for use when one or more of heat flux sensor 460, GSR sensors 465, accelerometer 495 or 550, or any other device in communication with armband sensor device 400, alone or in combination, sense a particular condition or conditions that indicate that the armband sensor device 400 has been placed in contact with the user's skin for use. At other times, armband sensor device 400 would be deactivated, thus preserving battery power.

Figure 19:
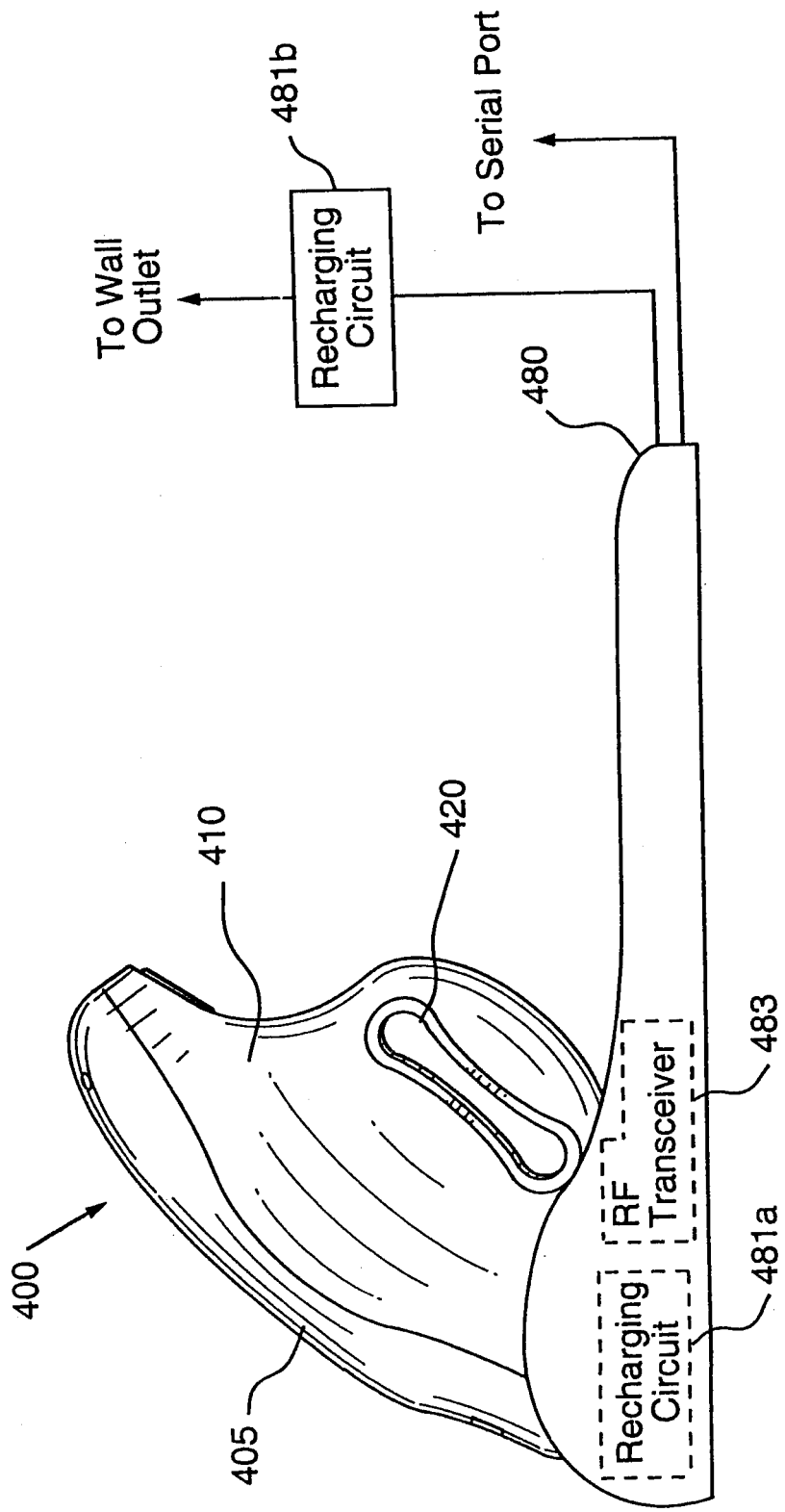
FIG. 19 is a side view of the sensor device shown in FIGS. 12 through 18 inserted into a battery recharger unit.
Figure 20:
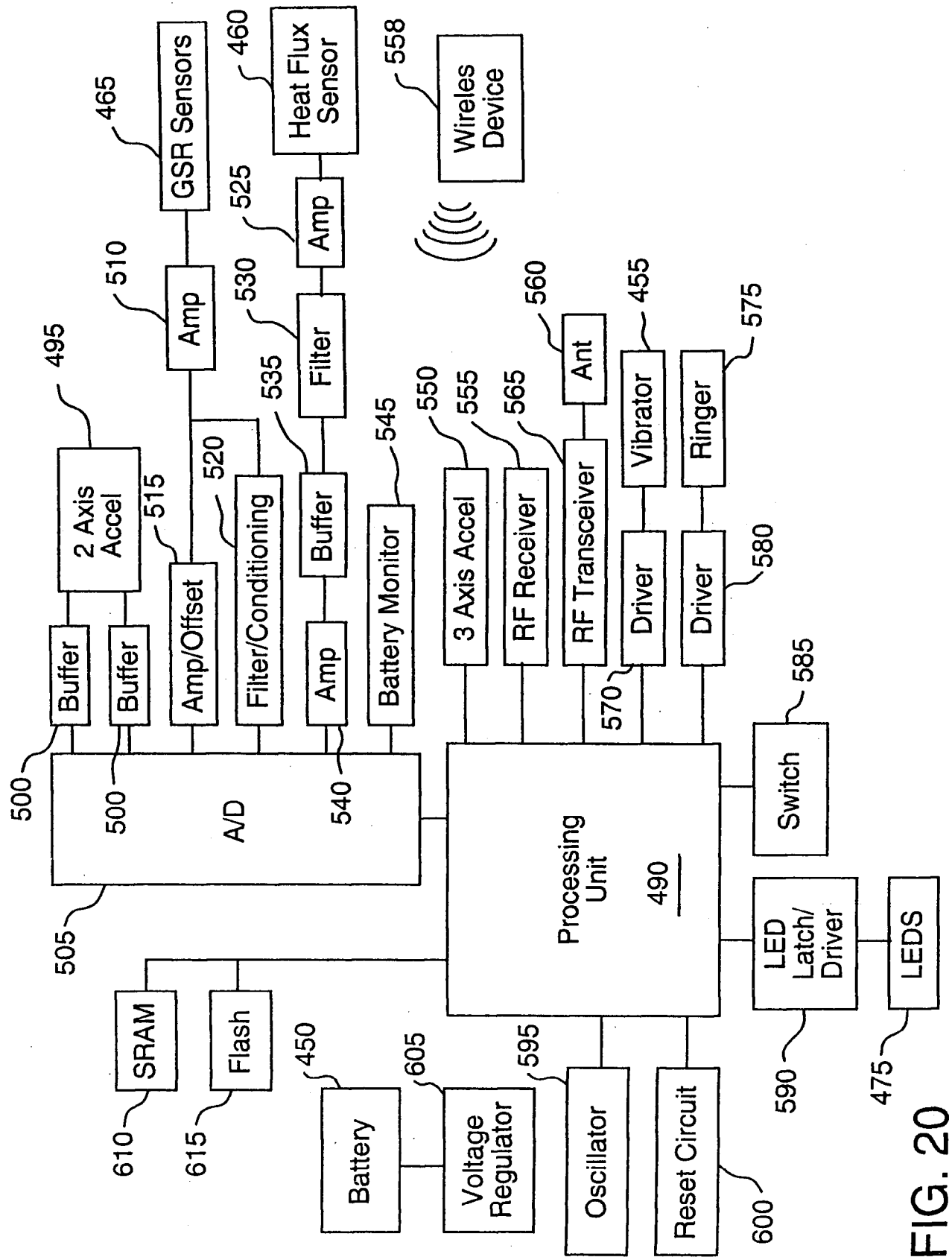
Figure 21:
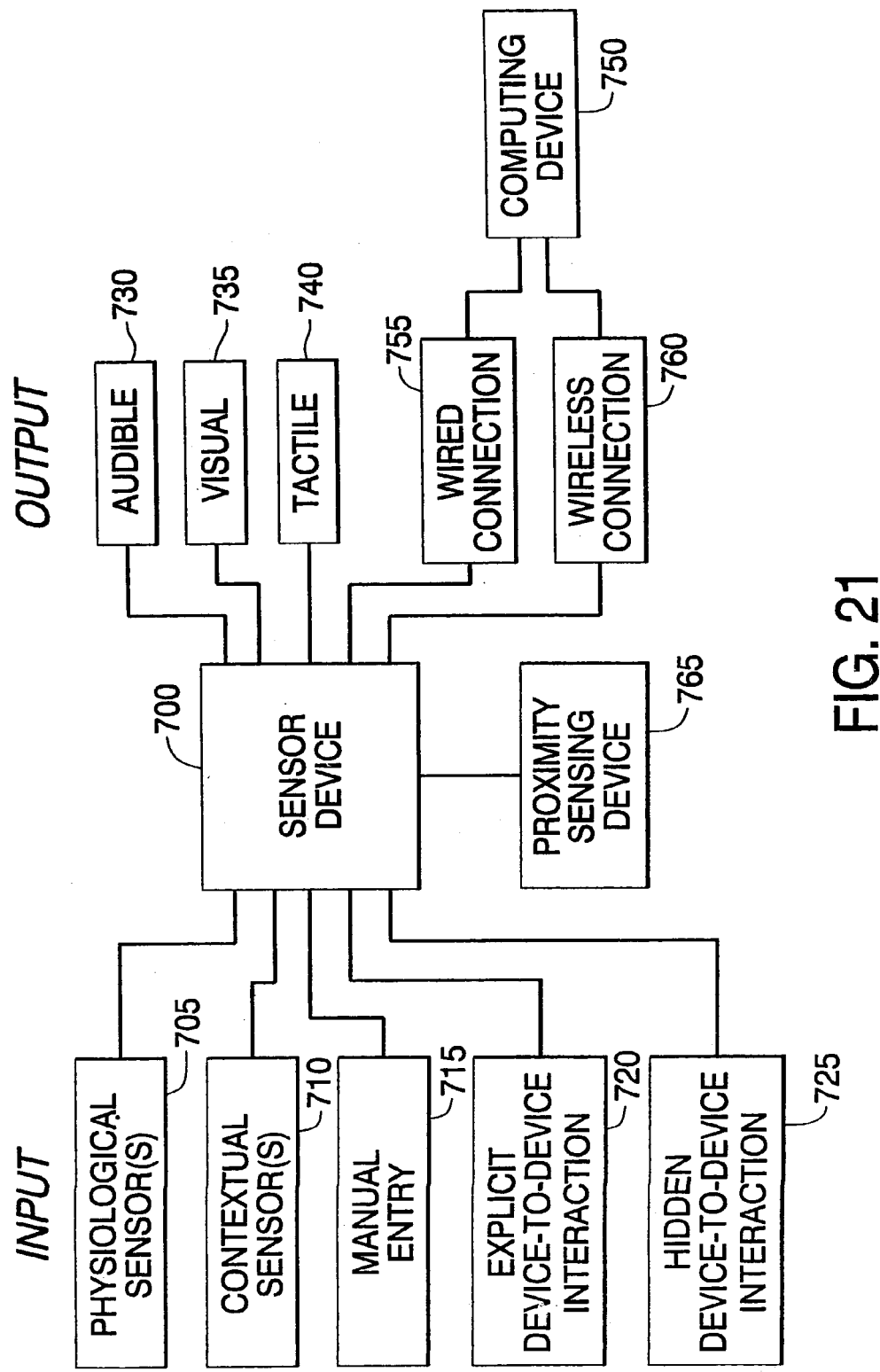
Figure 22:
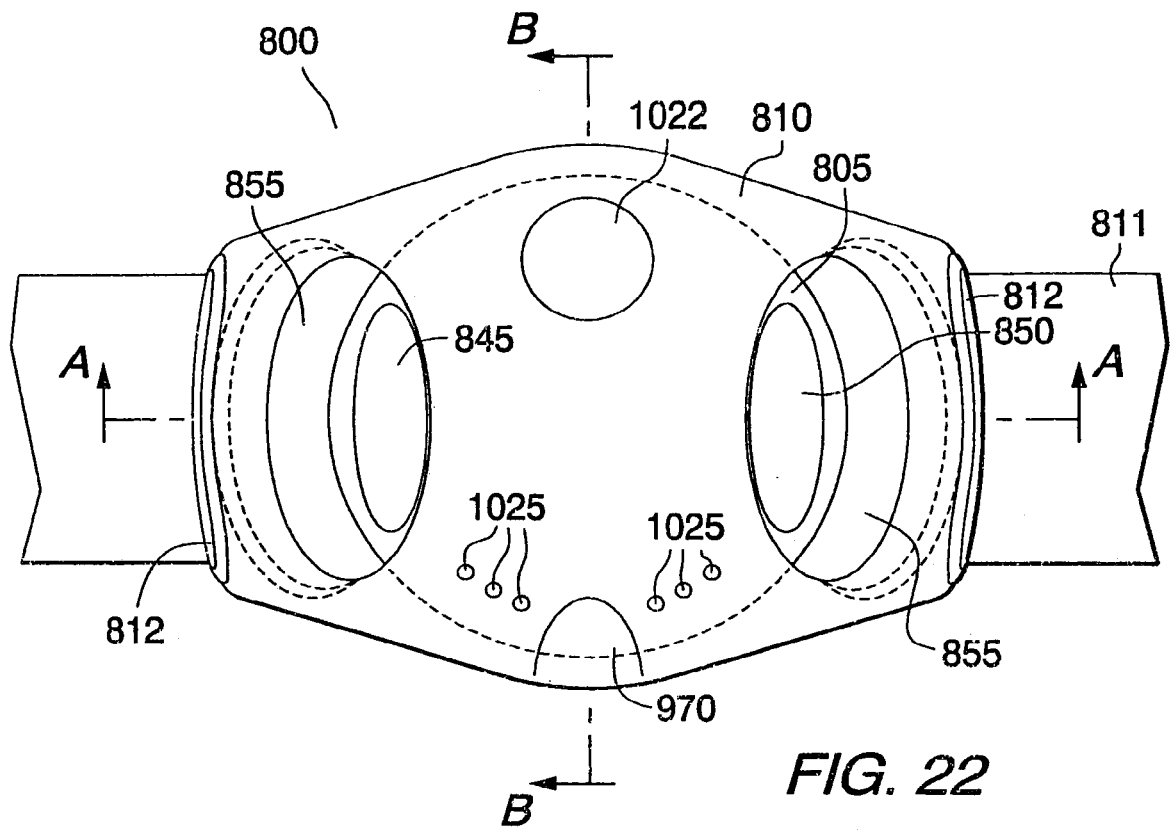
Figure 23:
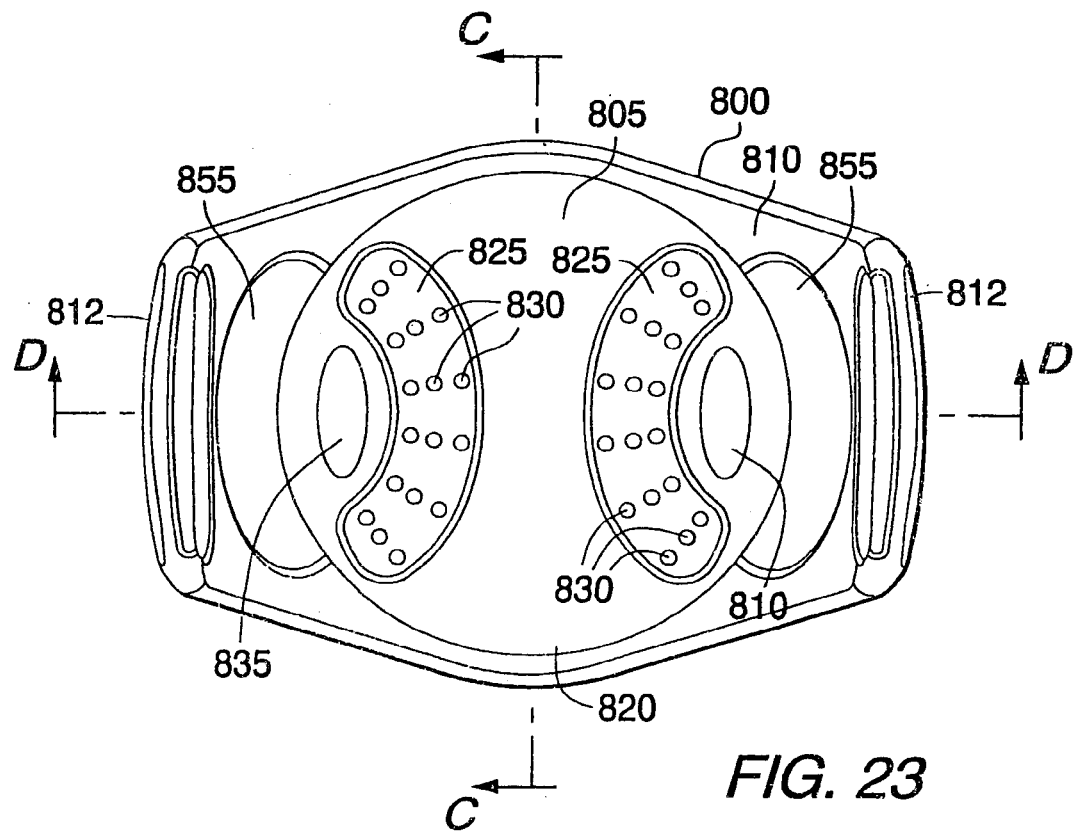
Figure 24:
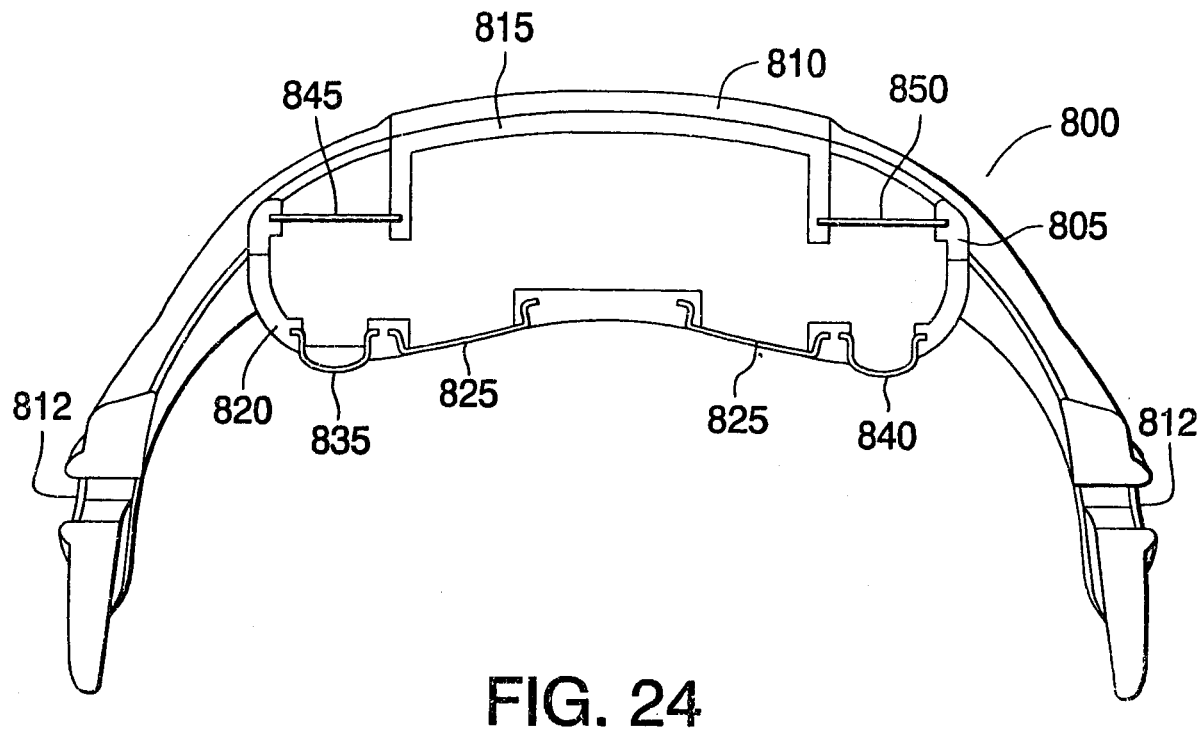
Figure 25:
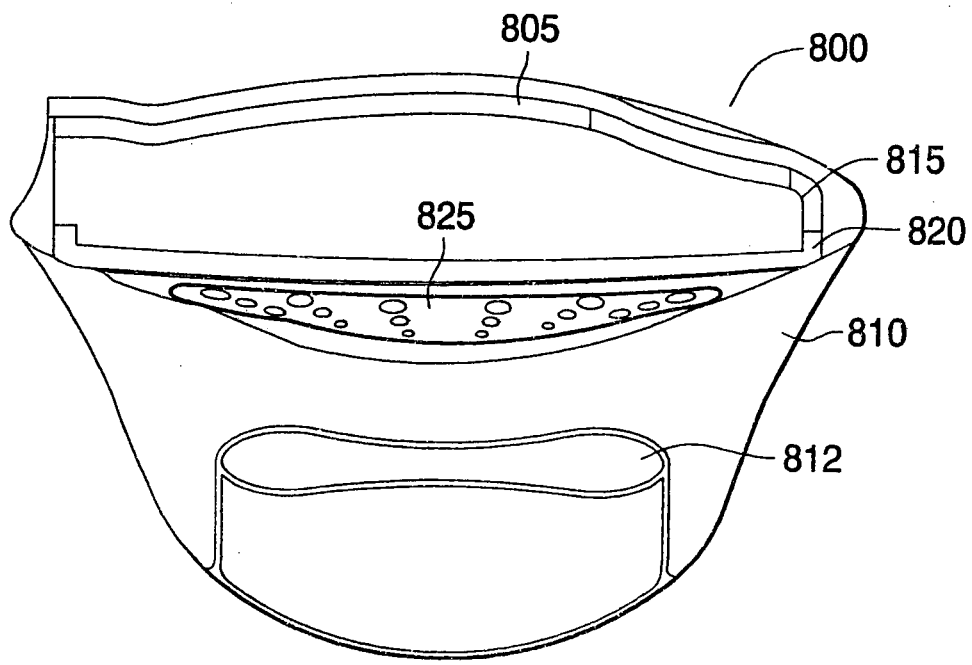
Figure 26:
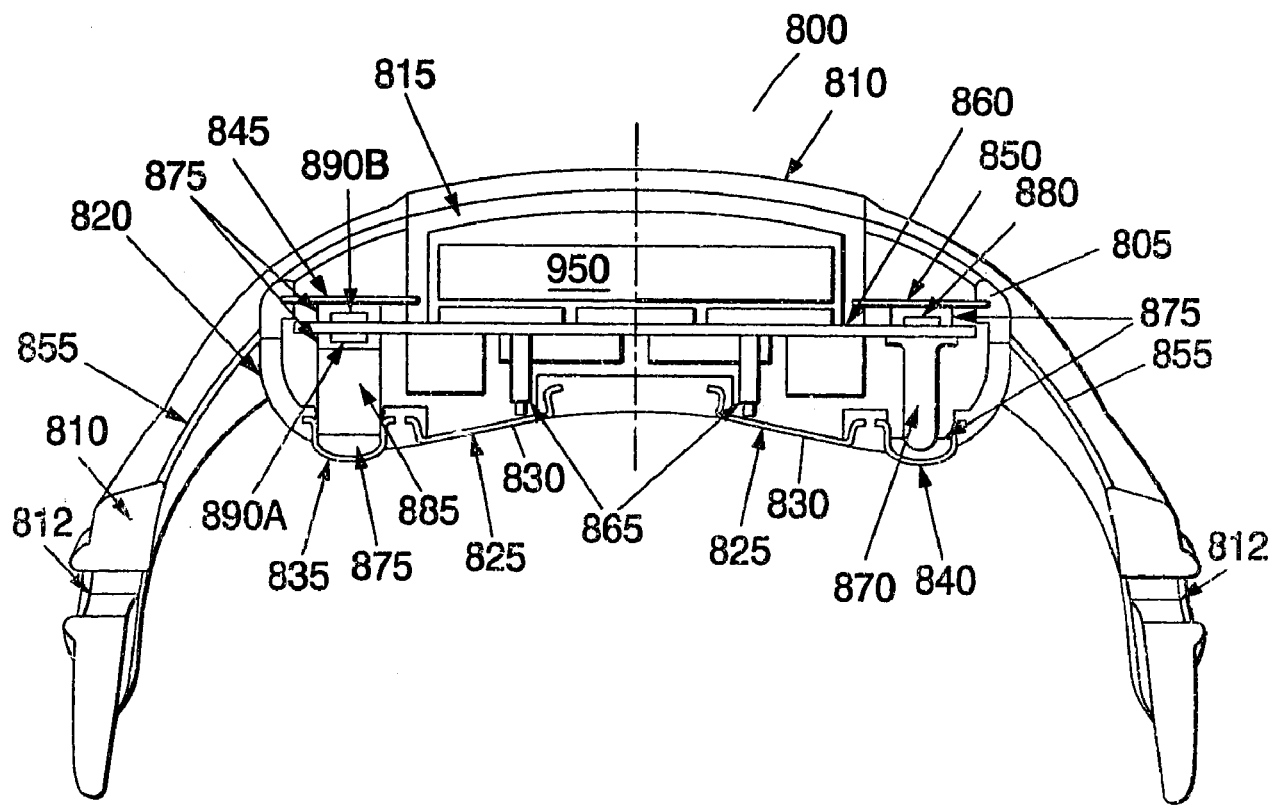
Figure 27:
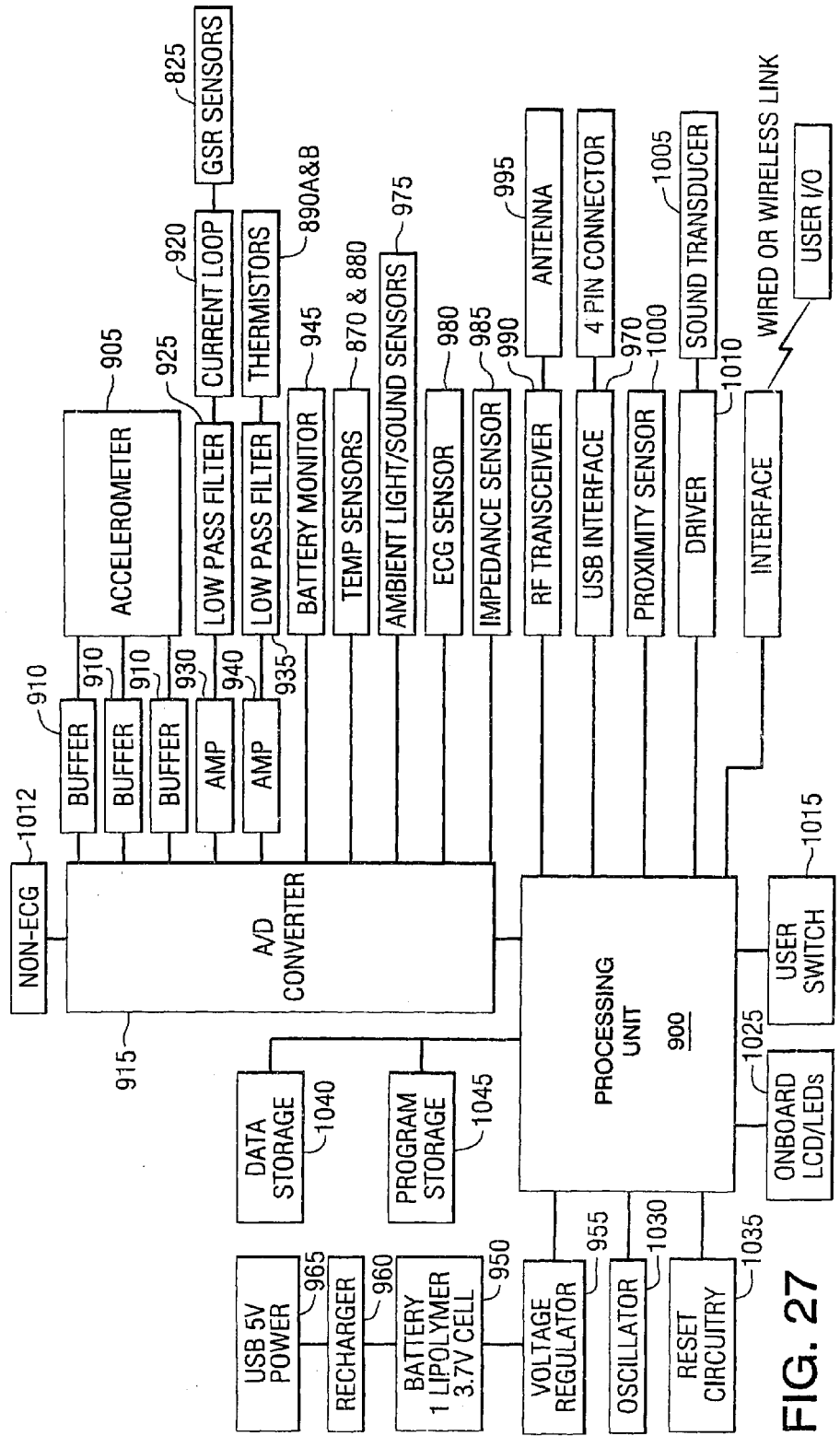
Figure 28:
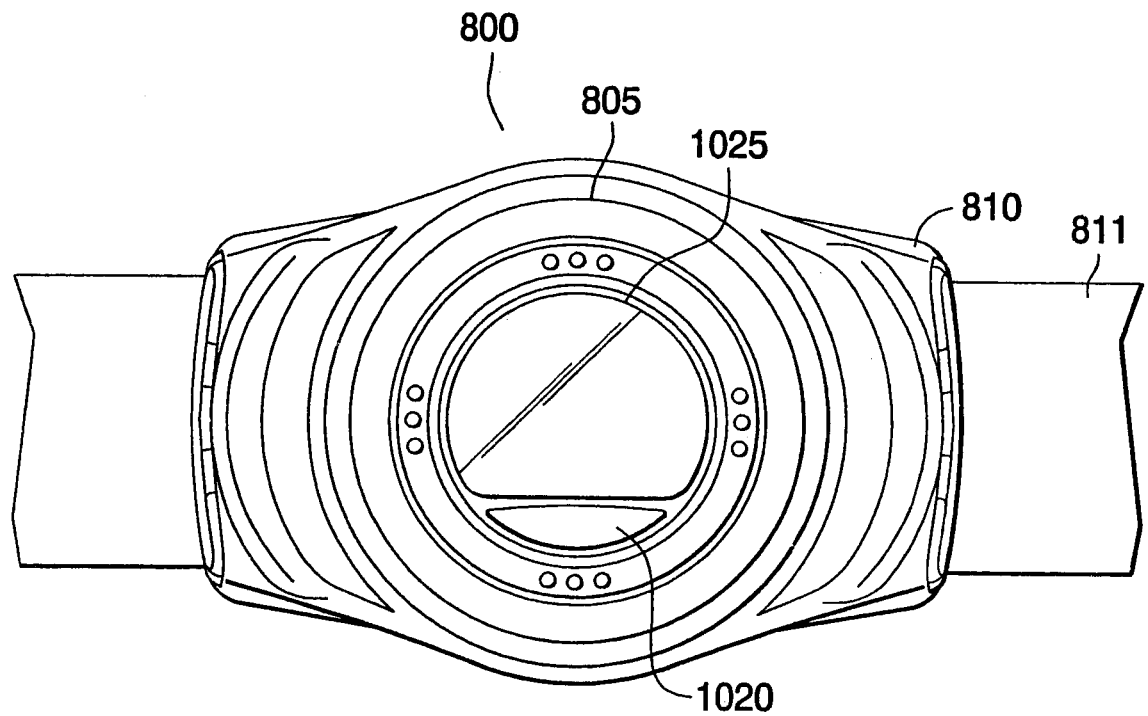
Figure 29:
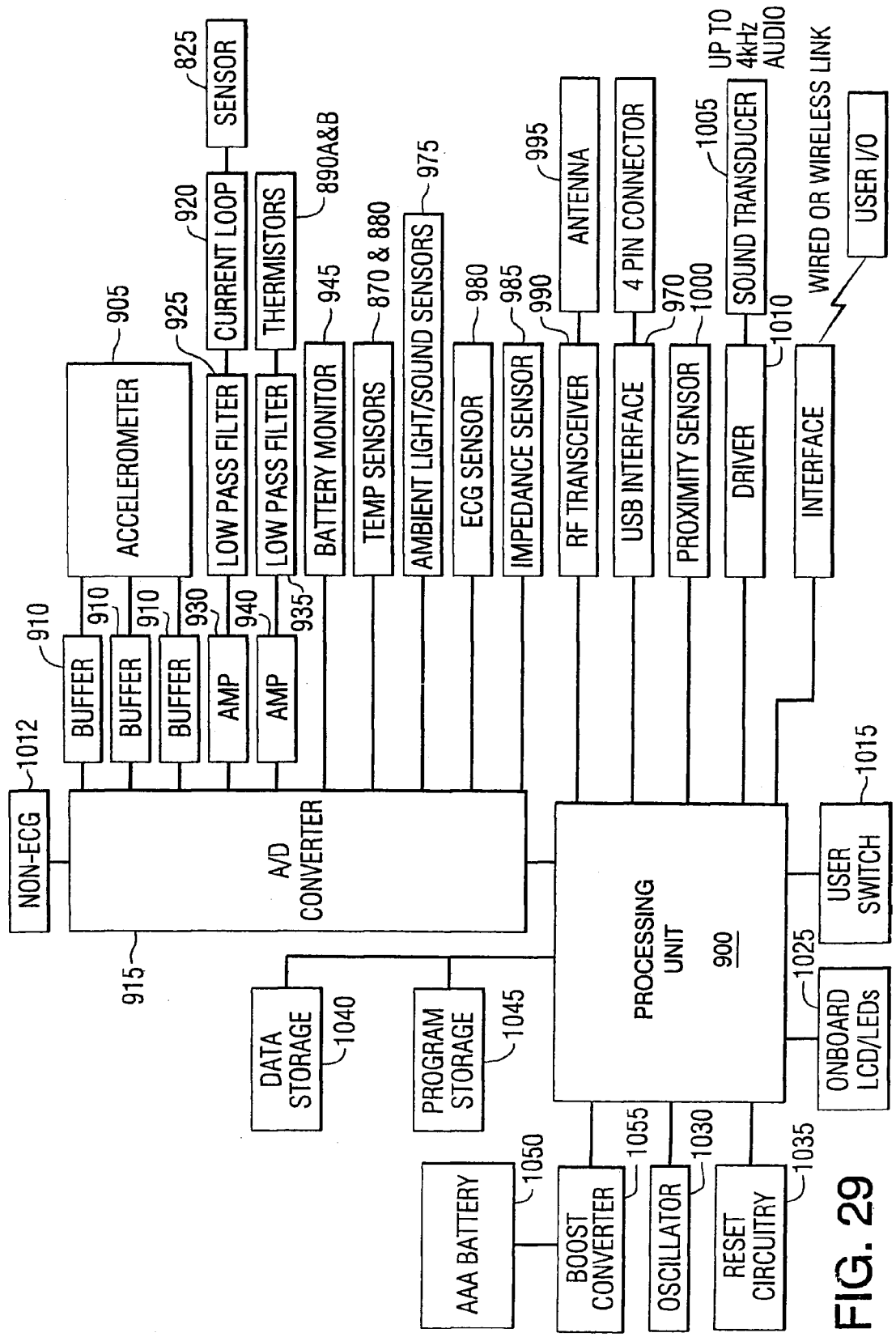
Figure 30:
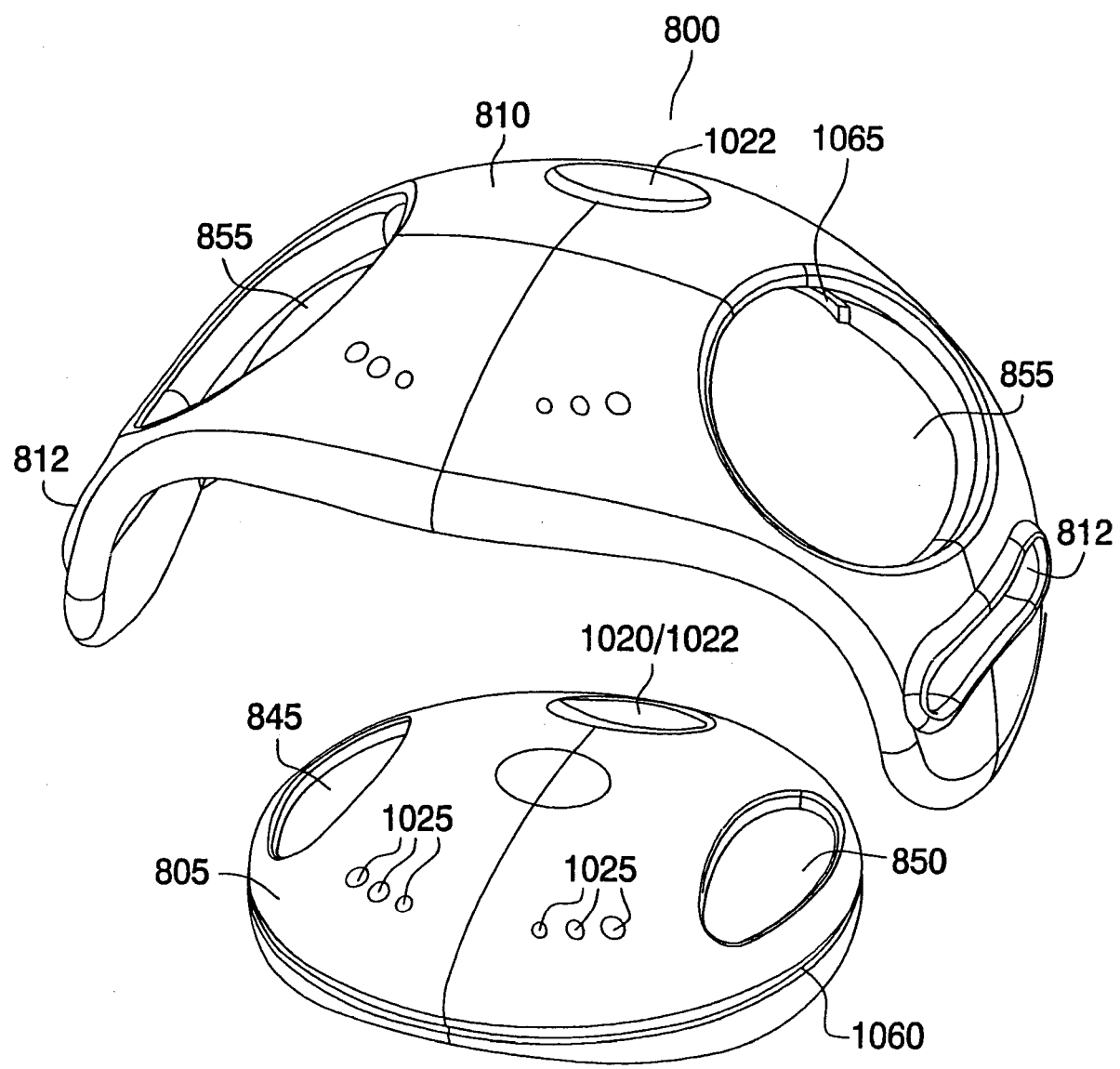
Figure 31:
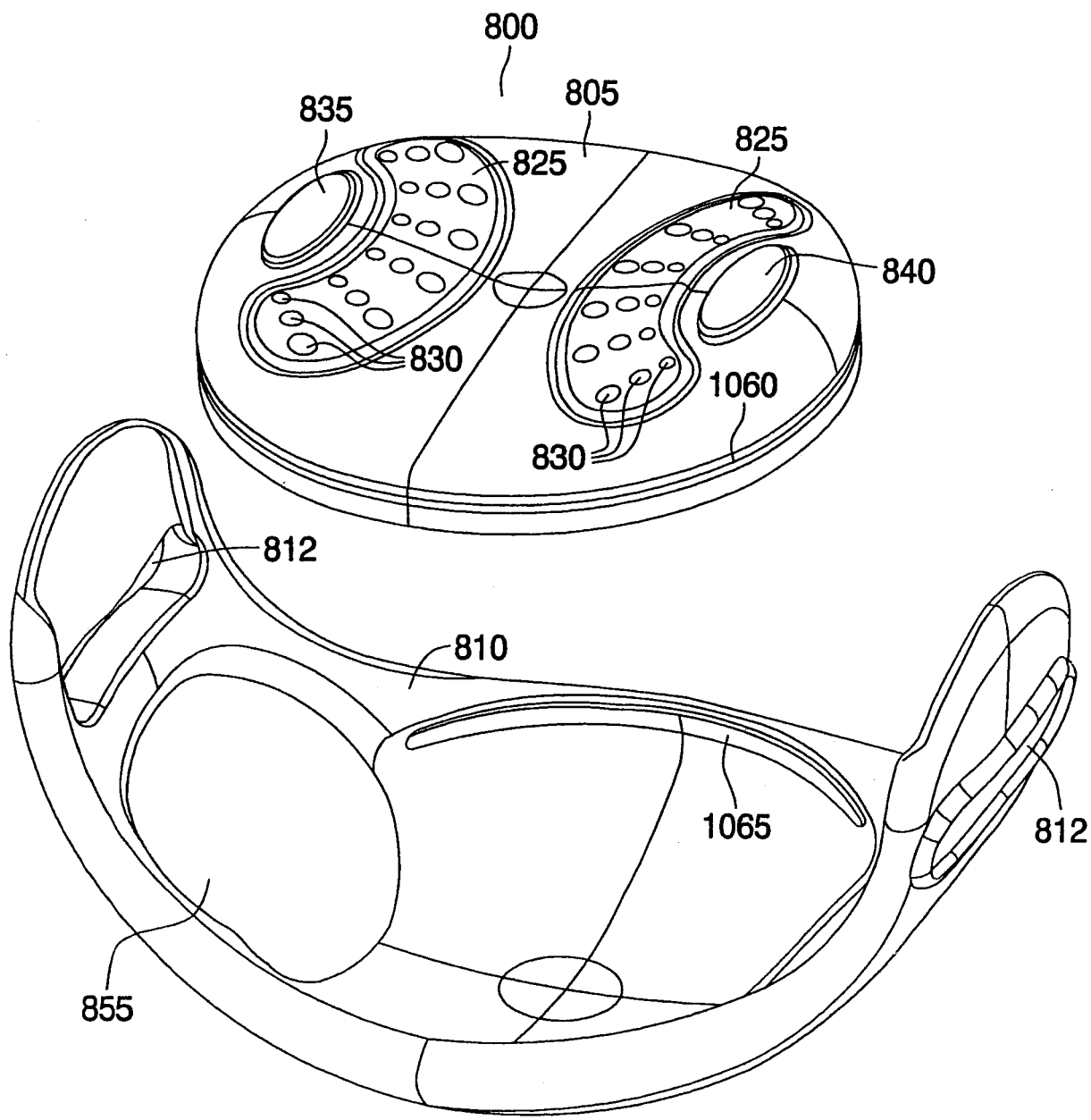
Figure 32:
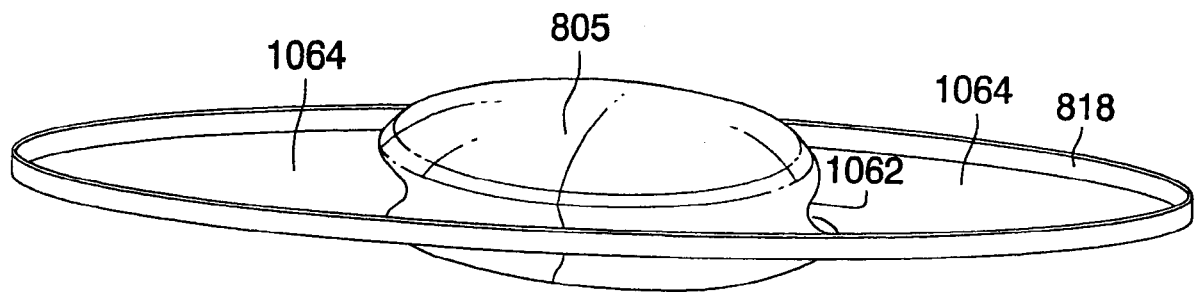
Figure 33:
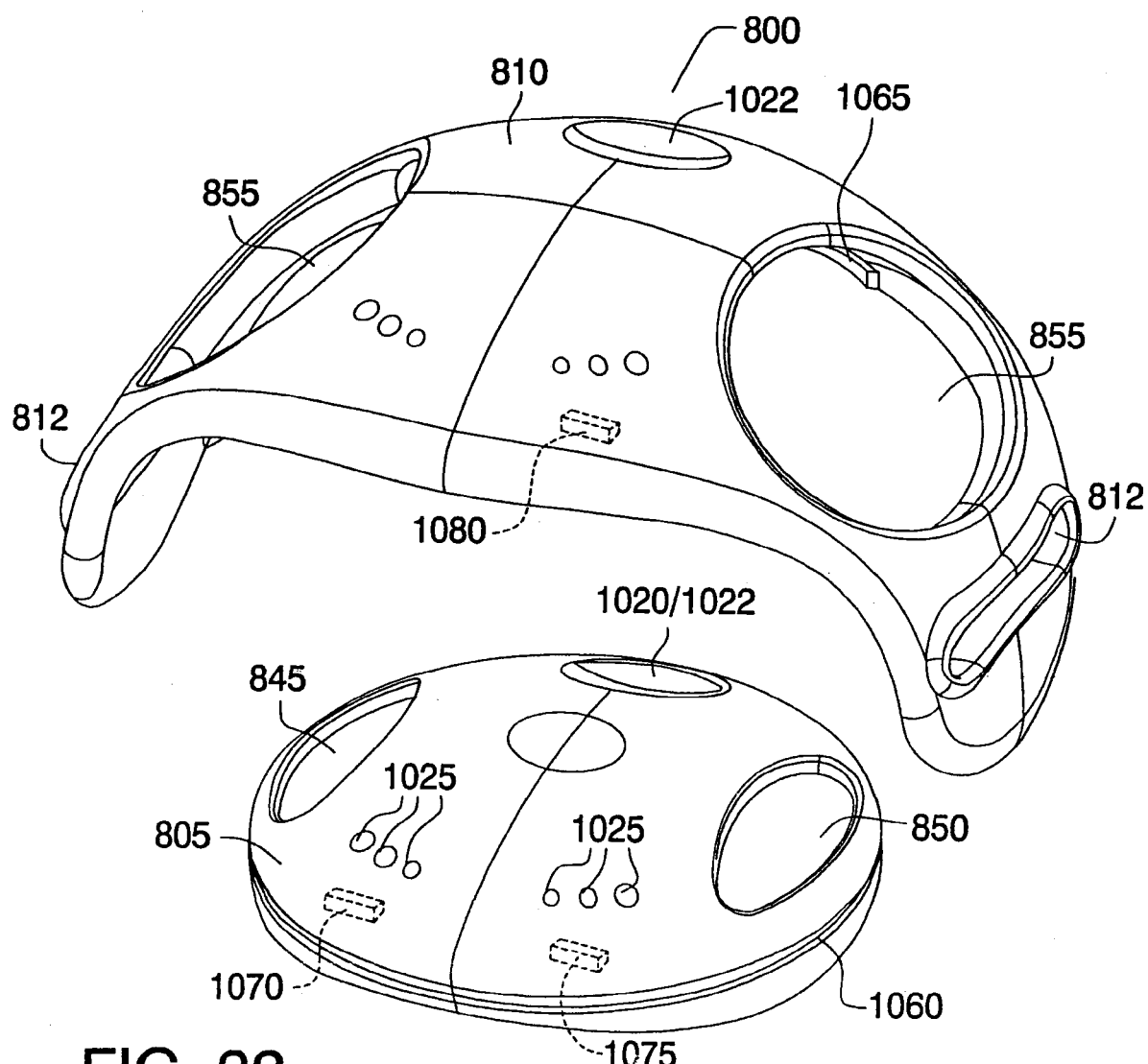
Figure 34:
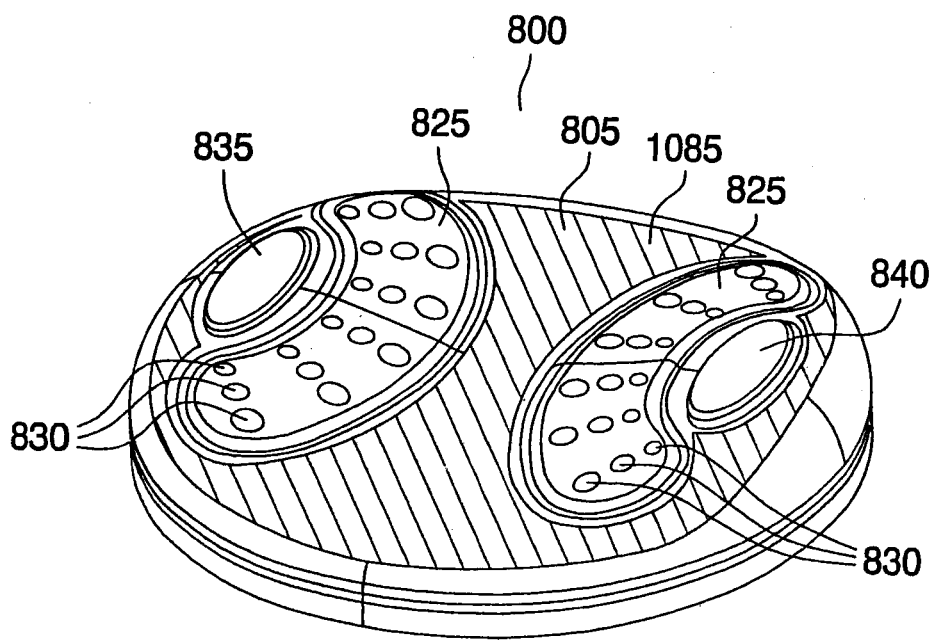
Figure 35A:
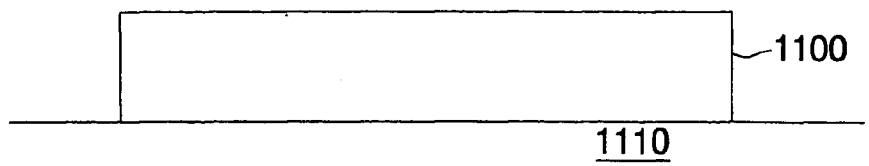
Figure 35B:
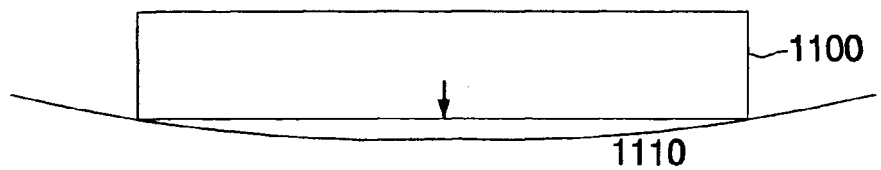
Figure 35C:
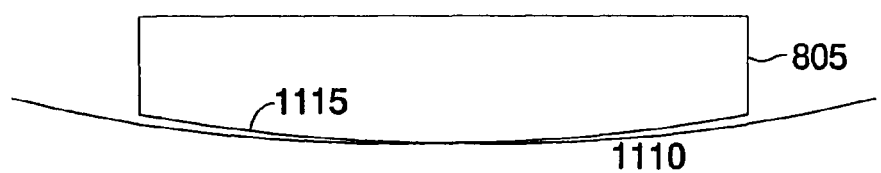
Figure 35D:
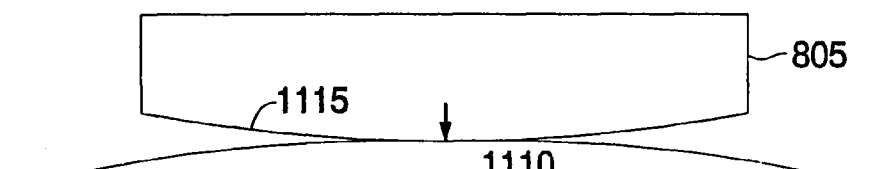
Figure 35E:
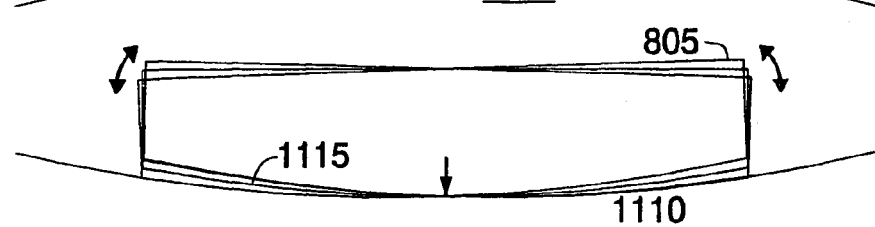
Figure 35F:
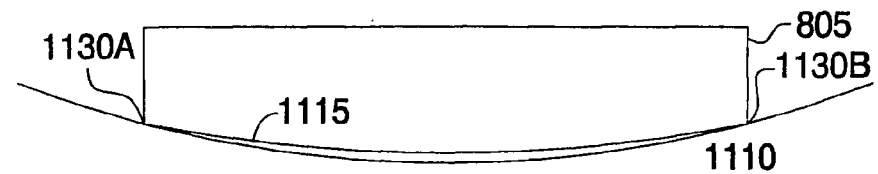
Figure 35G:
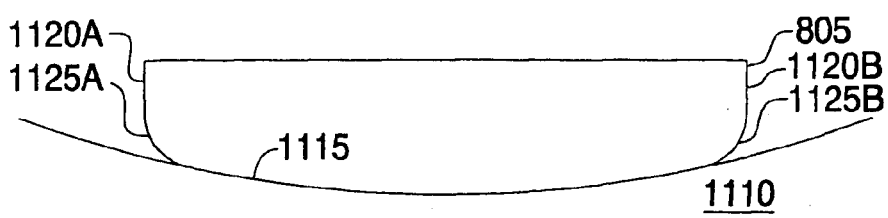
Figure 35H:
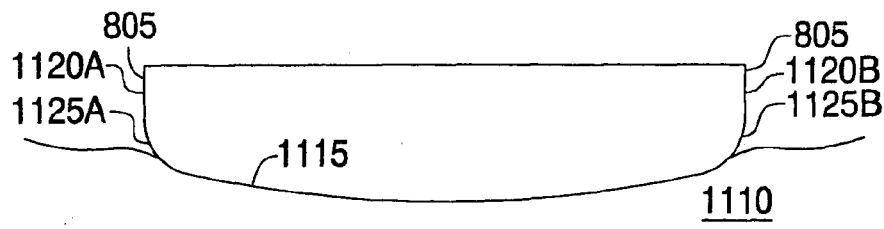

Computer housing 405 is adapted to be coupled to a battery recharger unit 480 shown in FIG. 19 for the purpose of recharging rechargeable battery 450. Computer housing 405 includes recharger contacts 485, shown in FIGS. 12, 15, 16 and 17, that are coupled to rechargeable battery 450. Recharger contacts 485 may be made of a material such as brass, gold or stainless steel, and are adapted to mate with and be electrically coupled to electrical contacts, not shown, provided in battery recharger unit 480 when armband sensor device 400 is placed therein. The electrical contacts provided in battery recharger unit 480 may be coupled to recharging circuit 481 a provided inside battery recharger unit 480. In this configuration, recharging circuit 481 would be coupled to a wall outlet, such as by way of wiring including a suitable plug that is attached or is attachable to battery recharger unit 480. Alternatively, electrical contacts 480 may be coupled to wiring that is attached to or is attachable to battery recharger unit 480 that in turn is coupled to recharging circuit 481b external to battery recharger unit 480. The wiring in this configuration would also include a plug, not shown, adapted to be plugged into a conventional wall outlet.

Figure 20:
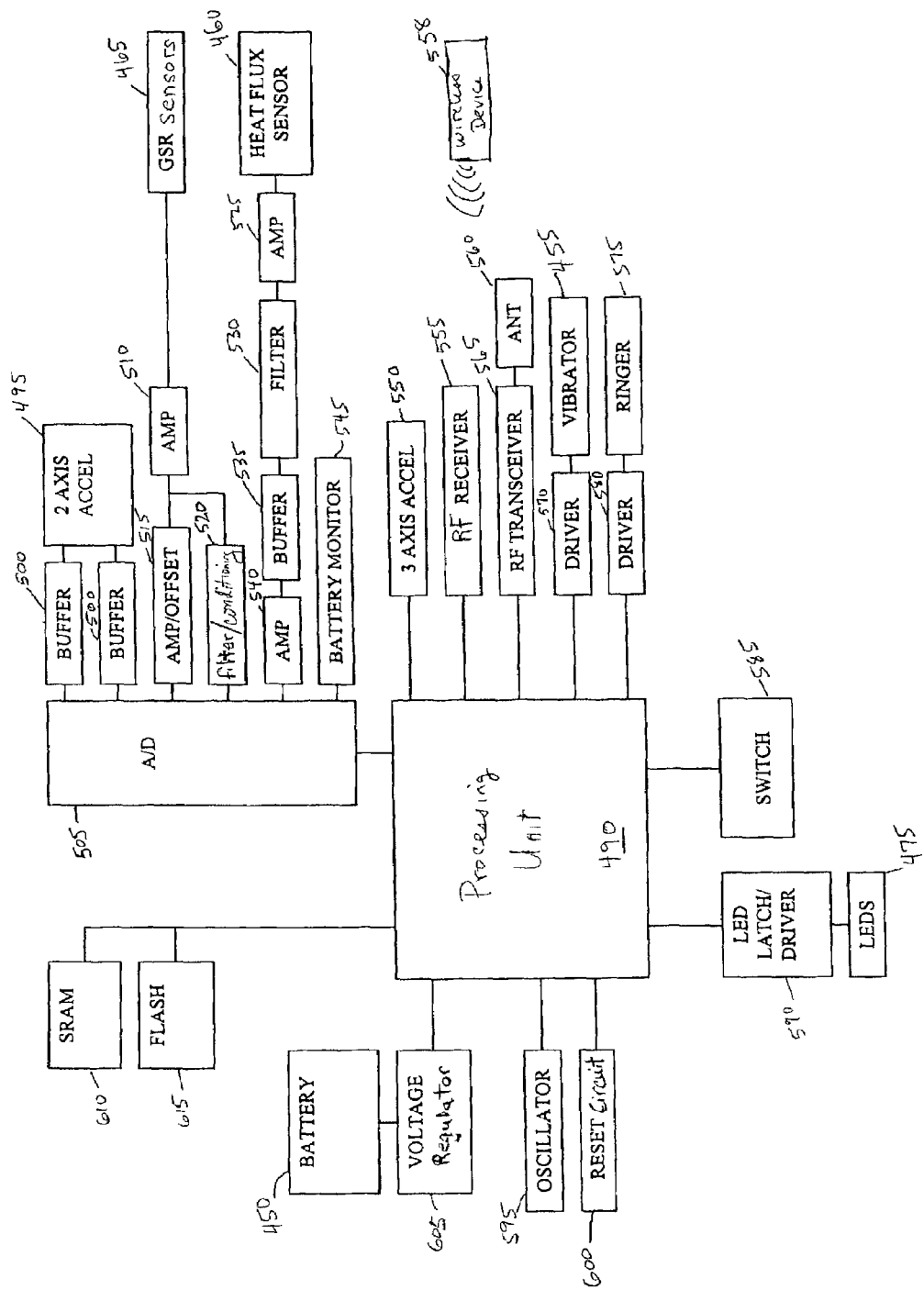
FIG. 20 is a block diagram illustrating all of the components either mounted on or coupled to the printed circuit board forming a part of the sensor device shown in FIGS. 12 through 18.

Also provided inside battery recharger unit 480 is RF transceiver 483 adapted to receive signals from and transmit signals to RF transceiver 565 provided in computer housing 405 and shown in FIG. 20. RF transceiver 483 is adapted to be coupled, for example by a suitable cable, to a serial port, such as an RS 232 port or a USB port, of a device such as personal computer 35 shown in FIG. 1. Thus, data may be uploaded from and downloaded to armband sensor device 400 using RF transceiver 483 and RF transceiver 565. It will be appreciated that although RF transceivers 483 and 565 are shown in FIGS. 19 and 20, other forms of wireless transceivers may be used, such as infrared transceivers. Alternatively, computer housing 405 may be provided with additional electrical contacts, not shown, that would be adapted to mate with and be electrically coupled to additional electrical contacts, not shown, provided in battery recharger unit 480 when armband sensor device 400 is placed therein. The additional electrical contacts in the computer housing 405 would be coupled to the processing unit 490 and the additional electrical contacts provided in battery recharger unit 480 would be coupled to a suitable cable that in turn would be coupled to a serial port, such as an RS R32 port or a USB port, of a device such as personal computer 35. This configuration thus provides an alternate method for uploading of data from and downloading of data to armband sensor device 400 using a physical connection.

FIG. 20 is a schematic diagram that shows the system architecture of armband sensor device 400, and in particular each of the components that is either on or coupled to PCB 445.

As shown in FIG. 17, PCB 445 includes processing unit 490, which may be a microprocessor, a microcontroller, or any other processing device that can be adapted to perform the functionality described herein. Processing unit 490 is adapted to provide all of the functionality described in connection with microprocessor 20 shown in FIG. 2. A suitable example of processing unit 490 is the Dragonball EZ sold by Motorola, Inc. of Schaumburg, Ill. PCB 445 also has thereon a two-axis accelerometer 495, a suitable example of which is the Model ADXL210 accelerometer sold by Analog Devices, Inc. of Norwood, Mass. Two-axis accelerometer 495 is preferably mounted on PCB 445 at an angle such that its sensing axes are offset at an angle substantially equal to 45 degrees from the longitudinal axis of PCB 445 and thus the longitudinal axis of the wearer's arm when armband sensor device 400 is worn. The longitudinal axis of the wearer's arm refers to the axis defined by a straight line drawn from the wearer's shoulder to the wearer's elbow. The output signals of two-axis accelerometer 495 are passed through buffers 500 and input into analog to digital converter 505 that in turn is coupled to processing unit 490. GSR sensors 465 are coupled to amplifier 510 on PCB 445. Amplifier 510 provides amplification and low pass filtering functionality, a suitable example of which is the Model AD8544 amplifier sold by Analog Devices, Inc. of Norwood, Mass. The amplified and filtered signal output by amplifier 510 is input into amp/offset 515 to provide further gain and to remove any bias voltage and into filter/conditioning circuit 520, which in turn are each coupled to analog to digital converter 505. Heat flux sensor 460 is coupled to differential input amplifier 525, such as the Model INA amplifier sold by Burr-Brown Corporation of Tucson, Ariz., and the resulting amplified signal is passed through filter circuit 530, buffer 535 and amplifier 540 before being input to analog to digital converter 505. Amplifier 540 is configured to provide further gain and low pass filtering, a suitable example of which is the Model AD8544 amplifier sold by Analog Devices, Inc. of Norwood, Mass. PCB 445 also includes thereon a battery monitor 545 that monitors the remaining power level of rechargeable battery 450. Battery monitor 545 preferably comprises a voltage divider with a low pass filter to provide average battery voltage. When a user depresses button 470 in the manner adapted for requesting battery level, processing unit 490 checks the output of battery monitor 545 and provides an indication thereof to the user, preferably through LEDs 475, but also possibly through vibrating motor 455 or ringer 575. An LCD may also be used.

PCB 445 may include three-axis accelerometer 550 instead of or in addition to two-axis accelerometer 495. The three-axis accelerometer outputs a signal to processing unit 490. A suitable example of three-axis accelerometer is the μPAM product sold by I.M. Systems, Inc. of Scottsdale, Ariz. Three-axis accelerometer 550 is preferably tilted in the manner described with respect to two-axis accelerometer 495.

PCB 445 also includes RF receiver 555 that is coupled to processing unit 490. RF receiver 555 may be used to receive signals that are output by another device capable of wireless transmission, shown in FIG. 20 as wireless device 558, worn by or located near the individual wearing armband sensor device 400. Located near as used herein means within the transmission range of wireless device 558. For example, wireless device 558 may be a chest mounted heart rate monitor such as the Tempo product sold by Polar Electro of Oulu, Finland. Using such a heart rate monitor, data indicative of the wearer's heart rate can be collected by armband sensor device 400. Antenna 560 and RF transceiver 565 are coupled to processing unit 490 and are provided for purposes of uploading data to central monitoring unit 30 and receiving data downloaded from central monitoring unit 30. RF transceiver 565 and RF receiver 555 may, for example, employ Bluetooth technology as the wireless transmission protocol. Also, other forms of wireless transmission may be used, such as infrared transmission.

The fact that RF Transceiver 565 may be used for wirelessly uploading data from and wirelessly downloading data to armband sensor device 400 is advantageous because it eliminates the need to remove armband sensor device 400 to perform these functions, as would be required with a physical connection. For example, if armband sensor device 400 was being worn under the user's clothing, requiring removal of armband sensor device 400 prior to uploading and/or downloading data increases user inconvenience. In addition, the wearing of armband sensor device 400 has an effect on the user's skin and underlying blood vessels, which in turn may effect any measurements being made with respect thereto. It may be necessary for a period of time during which armband sensor device 400 is worn by the user to elapse before a steady state is achieved and consistent, accurate measurements can be made. By providing armband sensor device 400 with wireless communications capability, data can be uploaded and downloaded without disturbing an established steady state equilibrium condition. For example, programming data for processing unit 490 that controls the sampling characteristics of armband sensor device 400 can be downloaded to armband sensor device 400 without disturbing the steady state equilibrium condition.

In addition, antenna 560 and RF transceiver 565 permit armband sensor device 400 to communicate wirelessly with other devices capable of wireless communication, i.e., transmit information to and receive information from those devices. The devices may include, for example, devices that are implanted in the body of the person using armband sensor device 400, such as an implantable heart pacemaker or an implantable insulin dispensing device, for example the MiniMed® 2007 implantable insulin pump sold by MiniMed Inc. of Northridge, Calif., devices worn on the body of the person using armband sensor device 400, or devices located near the person using armband sensor device 400 at any particular time, such as an electronic scale, a blood pressure monitor, a glucose monitor, a cholesterol monitor or another armband sensor device 400. With this two-way wireless communication capability, armband sensor device 400 may be adapted to transmit information that activates or deactivates such a device for use or information that programs such a device to behave in a particular way. For example, armband sensor device 400 may be adapted to activate a piece of exercise equipment such as a treadmill and program it to operate with certain parameters that are dictated or desired by or optimal for the user of armband sensor device 400. As another example, armband sensor device 400 may be adapted to adjust a computer controlled thermostat in a home based on the detected skin temperature of the wearer or turn off a computer controlled lighting system, television or stereo when the wearer is determined to have fallen asleep.

Vibrating motor 455 is coupled to processing unit 490 through vibrator driver 570 and provides tactile feedback to the wearer. Similarly, ringer 575, a suitable example of which is the Model SMT916A ringer sold by Projects Unlimited, Inc. of Dayton, Ohio, is coupled to processing unit 490 through ringer driver 580, a suitable example of which is the Model MMBTA14 CTI darlington transistor driver sold by Motorola, Inc. of Schaumburg, Ill., and provides audible feedback to the wearer. Feedback may include, for example, celebratory, cautionary and other threshold or event driven messages, such as when a wearer reaches a level of calories burned during a workout.

Also provided on PCB 445 and coupled to processing unit 490 is momentary switch 585. Momentary switch 585 is also coupled to button 470 for activating momentary switch 585. LEDs 475, used to provide various types of feedback information to the wearer, are coupled to processing unit 490 through LED latch/driver 590.

Oscillator 595 is provided on PCB 445 and supplies the system clock to processing unit 490. Reset circuit 600, accessible and triggerable through a pin-hole in the side of computer housing 405, is coupled to processing unit 490 and enables processing unit 490 to be reset to a standard initial setting.

Rechargeable battery 450, which is the main power source for the armband sensor device 400, is coupled to processing unit 490 through voltage regulator 605. Finally, memory functionality is provided for armband sensor device 400 by SRAM 610, which stores data relating to the wearer of armband sensor device 400, and flash memory 615, which stores program and configuration data, provided on PCB 445. SRAM 610 and flash memory 615 are coupled to processing unit 490 and each preferably have at least 512K of memory.

In manufacturing and assembling armband sensor device 400, top portion 435 of computer housing 405 is preferably formed first, such as by a conventional molding process, and flexible wing body 410 is then overmolded on top of top portion 435. That is, top portion 435 is placed into an appropriately shaped mold, i.e., one that, when top portion 435 is placed therein, has a remaining cavity shaped according to the desired shape of flexible wing body 410, and flexible wing body 410 is molded on top of top portion 435. As a result, flexible wing body 410 and top portion 435 will merge or bond together, forming a single unit. Alternatively, top portion 435 of computer housing 405 and flexible wing body 410 may be formed together, such as by molding in a single mold, to form a single unit. The single unit however formed may then be turned over such that the underside of top portion 435 is facing upwards, and the contents of computer housing 405 can be placed into top portion 435, and top portion 435 and bottom portion 440 can be affixed to one another. As still another alternative, flexible wing body 410 may be separately formed, such as by a conventional molding process, and computer housing 405, and in particular top portion 435 of computer housing 405, may be affixed to flexible wing body 410 by one of several known methods, such as by an adhesive, by snap-fitting, or by screwing the two pieces together. Then, the remainder of computer housing 405 would be assembled as described above. It will be appreciated that rather than assembling the remainder of computer housing 405 after top portion 435 has been affixed to flexible wing body 410, the computer housing 405 could be assembled first and then affixed to flexible wing body 410.

Figure 21:
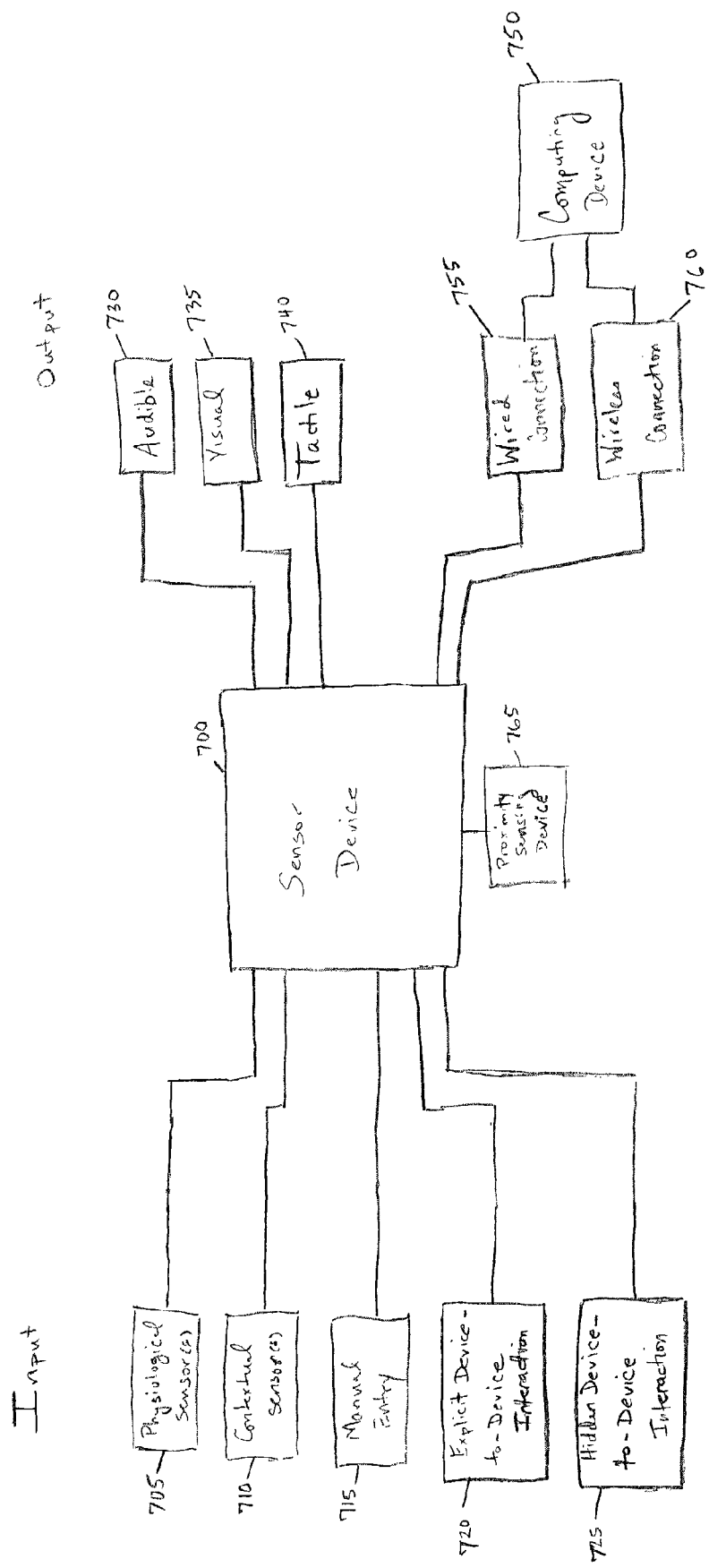
FIG. 21 is a block diagram of an apparatus for monitoring health, wellness and fitness according to an alternate embodiment of the present invention.

Referring to FIG. 21, a block diagram of an alternate embodiment of the present invention is shown. This alternate embodiment includes stand alone sensor device 700 which functions as an independent device, meaning that it is capable of collecting and/or generating the various types of data described herein in connection with sensor device 10 and sensor device 400 and providing analytical status data to the user without interaction with a remotely located apparatus such as central monitoring unit 30. Stand alone sensor device 700 includes a processor that is programmed and/or otherwise adapted to include the utilities and algorithms necessary to create analytical status data from the data indicative of various physiological and/or contextual parameters of the user, the data derived therefrom, and the data input by the user, all of which is stored in and accessed as needed from memory provided in stand alone sensor device 700. Stand alone sensor device 700 may comprise sensor device 10 shown in FIGS. 1 and 2 that includes microprocessor 20 and memory 22 or armband sensor device 400 shown in FIGS. 12–17 that includes processing unit 490 and SRAM 610.

As shown schematically in FIG. 21, data may be input into stand alone sensor device 700 in a number of ways. Stand alone sensor device 700 may include one or more physiological sensors 705 as described herein for facilitating the collection of data indicative of various physiological parameters of the user. Stand alone sensor device 700 may also include one or more contextual sensors 710 as described herein for facilitating the collection of data indicative of various contextual parameters of the user. As indicated by reference number 715, stand alone sensor device 700 may be adapted to enable the manual entry of data by the user. For example, stand alone sensor device 700 may include a data input button, such as a button 470 of armband sensor device 400, through which a user could manually enter information such as information relating to various life activities of the user as described herein or information relating to the operation and/or control of stand alone sensor device 700, for example, the setting of reminders or alerts as described herein. In this example, activation of button 470 may simply record or time stamp that an event such as a meal has occurred, with the wearer needing to assign a meaning to that time stamp through data entry at a later time. Alternatively, activation of button 470 in certain sequences, such as one activation, two successive activations, three successive activations, etc., can be preset to have different specific meanings. A wearer would need to follow a menu or guide of such preset activation sequences to input relevant data. Alternatively, stand alone sensor device 700 may include a more sophisticated means for manual entry of information such as a keypad, a touch screen, a microphone, or a remote control device, for example a remote control device incorporated into a wristwatch. In the case of a microphone, the processor of stand alone sensor device 700 would be provided with well known voice recognition software or the like for converting the input speech into usable data.

As indicated by reference numbers 720 and 725, information comprising data indicative of various physiological and/or contextual parameters and data derived therefrom may be input into stand alone sensor device 700 through interaction with other devices. In addition, information such as handshake data or data indicative of various physiological and/or contextual parameters and data derived therefrom may be output from stand alone sensor device 700 to such other devices. According to one embodiment, the interaction is in the form of wireless communication between stand alone sensor device 700 and another device capable of wireless communication by way of a wireless transceiver provided in stand alone sensor device 700, such as wireless transceiver 565 shown and described in connection with FIG. 20. The device-to-device interaction may, as shown by reference number 720, be explicit, meaning that the user of stand alone sensor device 700 has knowingly initiated the interaction. For example, a user may activate a button on a scale to upload data to stand alone sensor device 700. The device-to-device interaction may also, as shown by reference number 725, be hidden, meaning that the user of stand alone sensor device 700 does not knowingly initiate the interaction. For example, a gym may have a sensor that wirelessly transmits a signal to sensing device 700 when the user enters and leaves the gym to time stamp when the user began and ended a workout.

As shown schematically in FIG. 21, information may be output or transmitted from stand alone sensor device 700 in a number of ways. Such information may include the data indicative of various physiological parameters and/or contextual parameters, the data derived therefrom, the data manually input by the user, the analytical status data, or any combination thereof. As shown by reference numbers 730, 735 and 740, information may be output or transmitted in an audible fashion such as by a series of tones or beeps or a recorded voice by a device such as a speaker, in a visual fashion such as by one or more LEDs, or in a tactile fashion such as by vibration. For example, stand alone sensor device 700 may be adapted to output a tone or tones, light an LED or LEDs, or vibrate as a reminder for an event, such as a reminder to eat or exercise at a particular time, or when a goal has been reached, such as a target number of calories burned during a workout, or a condition has been sensed, such as ovulation. Alternatively, stand alone sensor device 700 may be provided with a more sophisticated visual output means such as an LCD similar to those found on commercially available cell phones, pagers and personal digital assistants. With an LCD or a similar device and the expanded visual output capabilities it would provide, stand alone sensor device 700 may be adapted to output or transmit some or all of the information described in connection with FIGS. 5 through 11 in the same or a similar format. For example, stand alone sensor device 700 could provide analytical status data in the form of the Health Index to the user. As a further alternative, stand alone sensor device 700 may be coupled to computing device 750 such as a personal computer, a cell phone, a pager, a personal digital assistant, another stand alone sensor device 700 or any other device having a processor by either wired connection 755 or wireless connection 760. For example, battery recharger unit 480 shown in FIG. 19 may be used to provide the wired connection 755 or wireless connection 760. In this configuration, the display of the computing device could be used to visually output information from stand alone sensor device 700. It will be appreciated that since computing device 750 includes a sophisticated output means such as an LCD, it may be used to output or transmit to the user some or all of the information described in connection with FIGS. 5 through 11, such as the Health Index, in the same or a similar format.

Also, computing device 750 may in turn be used to control other devices, such as the lights or thermostat in a home, based on data output by stand alone sensor device 700, such as the fact that the wearer has fallen asleep or the fact that the wearer's skin temperature has reached a certain level. In other words, stand alone sensor device 700, and in particular its processor, may be adapted to cause a computing device 750 to trigger an event upon detection of one or more physiological and/or contextual conditions by stand alone sensor device 700. Alternatively, stand alone sensor device 700 may be adapted to cause a computing device 750 to trigger an event based upon information received from another computing device 750.

Stand alone sensor device 700 may be adapted to interact with and influence an interactive electronic media device, such as a video game, or non-interactive electronic media device, such as on a display device such as a DVD or digital video disc player playing a digitally recorded movie. For example, stand alone sensor device 700 may be adapted to transmit information relating to the physiological state of the wearer to the video game, which in turn adjusts the characteristics of the game, such as the level of difficulty. As another example, stand alone sensor device 700 may be adapted to transmit information relating to the physiological state of the wearer to the device displaying the digitally recorded movie which in turn adjusts the characteristics, such as the outcome, of the movie.

Furthermore, stand alone sensor device 700 may include location sensing device 765, such as an ultrasonic or a radio-frequency identification tag, for enabling a computing device 750 to detect the geographic location of stand alone sensor device 700, such as the location of stand alone sensor device 700 within a defined space such as a building. In one embodiment, a location indication causes computing device 750 to trigger an event, such as lowering the temperature in a room corresponding to the indicated location, preferably based on the detection by stand alone sensor device 700 of one or more physiological conditions of the wearer, such as skin temperature. In another embodiment, the location indication causes computing device 750 to trigger an event, such as lowering the temperature in a room corresponding to the indicated location, if stand alone sensor device 700 detects one or more physiological conditions, such as a skin temperature of the wearer being above a certain level. In addition, the input means of the computing device, such as the mouse and keyboard of a personal computer, the keypad of a cell phone or pager, or the touch screen of a personal digital assistant, may be used to manually input information into stand alone sensor device 700.

The different modes of output may be used in combination to provide different types and levels of information to a user. For example, stand alone sensor device 700 could be worn by an individual while exercising and an LED or a tone can be used to signal that a goal of a certain number of calories burned has been reached. The user could then transmit additional data wirelessly from stand alone sensor device 700 to a computing device 750 such as a cell phone after he or she is finished exercising to view data such as heart rate and/or respiration rate over time.

As a further alternative embodiment of the present invention, rather than the processor provided in stand alone sensor device 700 being programmed and/or otherwise adapted to generate the derived data and to include the utilities and algorithms necessary to create analytical status data, computing device 750 could be so programmed. In this embodiment, stand alone sensor device 700 collects and/or generates the data indicative of various physiological and/or contextual parameters of the user, the data manually input by the user, and/or data input as a result of device-to-device interaction shown at 720 and 725, all of which is stored in the memory provided in stand alone sensor device 700. This data is then periodically uploaded to computing device 750 which in turn generates derived data and/or analytical status data. Alternatively, the processor of stand alone sensor device 700 could be programmed to generate the derived data with computing device 750 being programmed and/or otherwise adapted to include the utilities and algorithms necessary to create analytical status data based on data indicative of one or more physiological and/or contextual parameters, data derived therefrom, data manually input by the user and/or data input as a result of device-to-device interaction shown at 720 and 725 uploaded from stand alone sensor device 700. As still a further alternative, the processor of stand alone sensor device 700 could be programmed and/or otherwise adapted to include the utilities and algorithms necessary to create analytical status data based on data indicative of one or more physiological and/or contextual parameters, data derived therefrom, data manually input by the user and/or data input as a result of device-to-device interaction shown at 720 and 725 uploaded from stand alone sensor device 700 with computing device 750 being programmed to generate the derived data. In either alternative, any or all of the data indicative of physiological and/or contextual parameters of the user, the data derived therefrom, the data manually input by the user, the data input as a result of device-to-device interaction shown at 720 and 725 and the analytical status data may then be viewed by the user using the output means of the programmed computing device 750 or another computing device 750 to which the data is downloaded. In the latter alternative, everything but the analytical status data may also be output by stand alone sensor device 700 as described herein.

Computing device 750 in these alternative embodiments may be connected to an electronic network, such as the Internet, to enable it to communicate with central monitoring unit 30 or the like. The programming of computing device 750 that enables it to generate the derived data and/or the analytical status data may, with such a configuration, be modified or replaced by downloading the relevant data to computing device 750 over the electronic network.

As still a further alternative embodiment, computing device 750 may be provided with a custom written plug-in adapted to provide data display functionality through use of a well known browser program. In this embodiment, stand alone sensor device 700 collects and/or generates the data indicative of various physiological and/or contextual parameters of the user, the derived data, the data input by the user, data input as a result of device-to-device interaction shown at 720 and 725, and/or analytical status data based thereon and uploads this data to computing device 750. The plug-in provided in computing device 750 then generates appropriate display pages based on the data which may be viewed by the user using the browser provided with computing device 750. The plug-in may be modified/updated from a source such as central monitoring unit 30 over an electronic network such as the Internet.

Referring to FIGS. 22–26, an alternate embodiment of a sensor device is shown at 800. Sensor device 800 may be a specific embodiment of either sensor device 10 described in connection with FIGS. 1–11 or stand alone sensor device 700 described in connection with FIG. 21. Sensor device 800 includes housing 805 affixed to flexible section 810, which is similar to flexible wing body 410 shown in FIGS. 12–17. Flexible section 810 is adapted to engage, such as by wrapping around or conforming to, at least a portion of the human body, such as the upper arm, to enable sensor device 800, in combination with a removable strap 811 inserted through slots 812 provided in flexible section 810, to be worn on the body. Preferably, flexible section 810 is made of a material having a durometer of between 75 and 85 Shore A. Flexible section 810 may take on a variety of shapes and may be made of a cloth material, a flexible plastic film, or an elastic material having an adhesive similar in structure to a Band-Aid® disposable adhesive bandage. In the embodiment shown in FIGS. 22–26, housing 805 is permanently affixed to flexible section 810, such as by an over molding or co-molding process, through the use of an adhesive material, or by a fastening mechanism such as one or more screws. Housing 805 includes top portion 815 affixed to bottom portion 820 by any known means, including, for example, an adhesive material, screws, snap fittings, sonic welding, or thermal welding. According to a preferred embodiment, a watertight seal is provided between top portion 815 and bottom portion 820. Such a water-tight seal is provided when sonic welding or thermal welding is used. Alternatively, an O-ring could be provided between top portion 815 and bottom portion 820 to create the water-tight seal.

Figure 22:
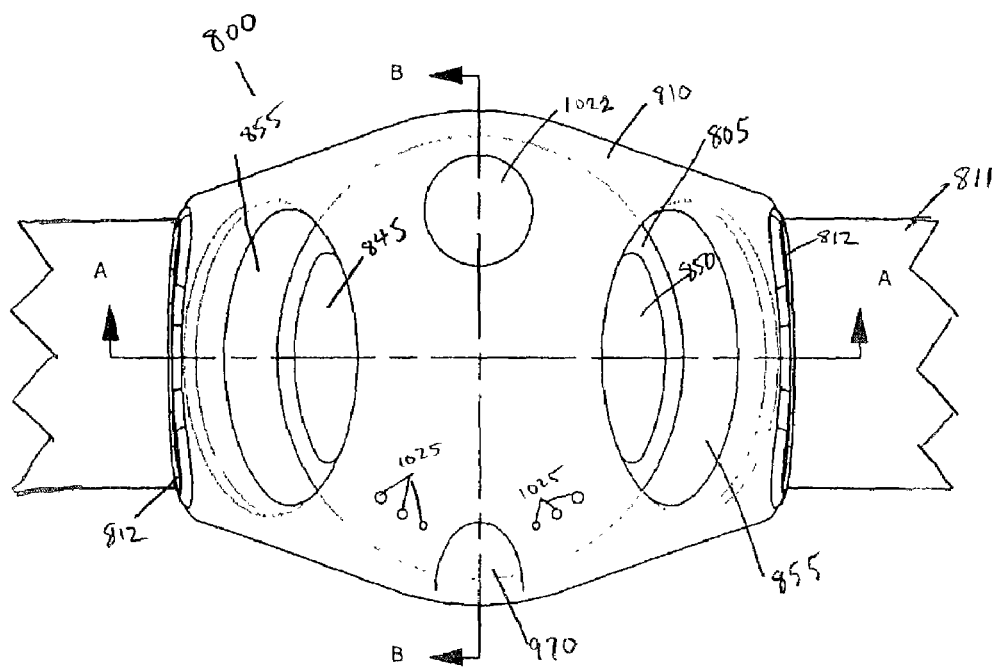
FIG. 22 is a front view of an alternate embodiment of a sensor device according to the present invention.
Figure 23:
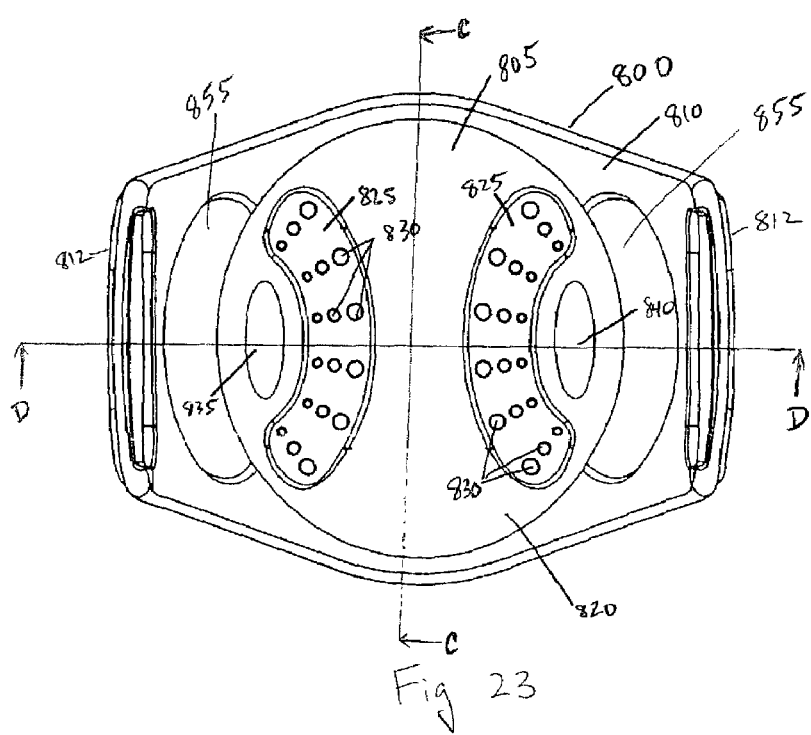
FIG. 23 is a back view of an alternate embodiment of a sensor device according to the present invention.
Figure 24:
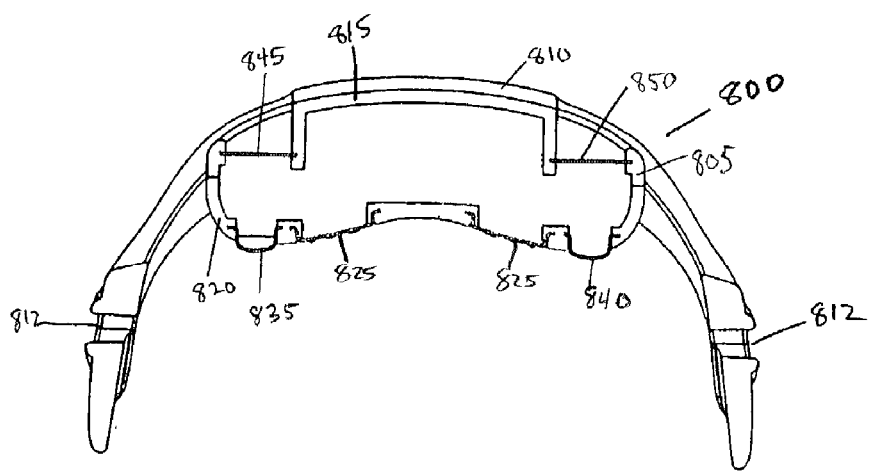
FIG. 24 is a cross-sectional view of the sensor device shown in FIG. 22 taken along lines A—A.
Figure 26:
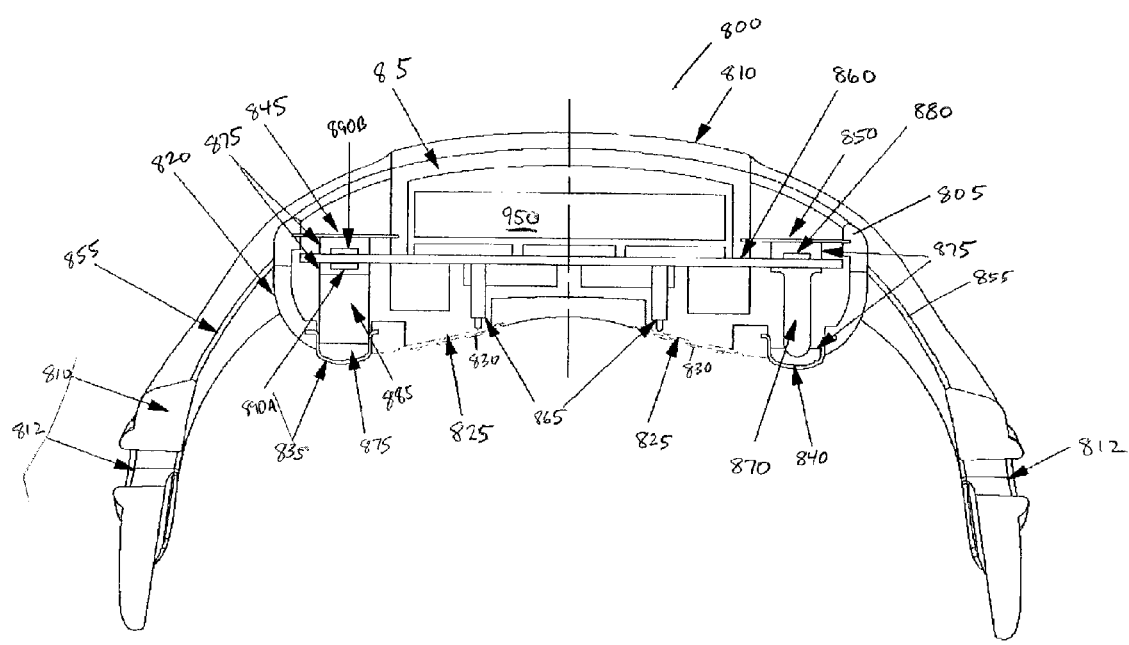
FIG. 26 is a cross-sectional view of the sensor device shown in FIG. 22 taken along lines A—A showing the internal components of the housing of the sensor device.

As can be seen most readily in FIGS. 23, 24 and 26, affixed to bottom portion 820 of housing 805 are GSR sensors 825. GSR sensors 825 measure the conductivity of the skin between two points and may comprise electrodes formed of a material such as stainless steel, gold or a conductive carbonized rubber. Preferably, GSR sensors 825 have an oblong, curved shape as shown in FIG. 23, much like a kidney bean shape, that allows some portion of GSR sensors 825 to maintain contact with the body even if sensor device 800 is rocking or otherwise moving while being worn. Most preferably, GSR sensors 825 include raised bumps 830, or some other three-dimensional textured surface, along the surface thereof to perturb the skin and push between hairs to ensure good contact with the skin. In addition, raised bumps 830 provide channels for the movement of sweat underneath sensor device 800, rather than trapping sweat, no matter the orientation of sensor device with respect to the body. Also affixed to bottom portion 820 are heat flux skin interface component 835 and skin temperature skin interface component 840, each comprising a plate made of a thermally conductive material such as stainless steel. Preferably, heat flux skin interface component 835 and skin temperature skin interface component 840 are made of a material having thermal conduction properties of at least 12.9 W/mK, such as 304 stainless steel. Preferably, GSR sensors 825 are spaced at least 0.44 inches apart from one another, and at least 0.09 inches apart from heat flux skin interface component 835 and skin temperature skin interface component 840. GSR sensors 825, heat flux skin interface component 835 and skin temperature skin interface component 840 are adapted to be in contact with the wearer's skin when sensor device 800 is worn, and facilitate the measurement of GSR, heat flux from the body and skin temperature data. As can be seen most readily in FIGS. 22, 24 and 26, affixed to top portion 815 of housing 805 are heat flux ambient interface component 845 and ambient temperature interface component 850, which also are made of a thermally conductive material such as stainless steel, preferably a material having thermal conduction properties of at least 12.9 W/mK, such as 304 stainless steel. Heat flux ambient interface component 845 and ambient temperature interface component 850 facilitate the measurement of heat flux from the body and ambient temperature, respectively, by providing a thermal interface to the surrounding environment. To further enhance the measurement of these parameters, holes 855 are provided in flexible section 810 to expose heat flux ambient interface component 845 and ambient temperature interface component 850 to the ambient air. Preferably, holes 855 are sized so that flexible section 810 occludes as little skin as possible in the regions surrounding heat flux ambient interface component 845 and ambient temperature interface component 850 so as to allow air flowing off of the skin of the wearer to pass these components.

GSR Sensors 825, heat flux, skin interface component 835, skin temperature skin interface component 840, or any other sensing component that comes into contact with the skin may be provided with a plurality of microneedles for, among other things, enhancing electrical contact with the skin and providing real time access to interstitial fluid in and below the epidermis, which access may be used to measure various parameters such as pH level of the skin through electrochemical, impedance based or other well known methods. Microneedles enhance electrical contact by penetrating the stratum corneum of the skin to reach the epidermis. Such microneedles are well known in the art and may be made of a metal or plastic material. Prior art microneedles are described in, for example, U.S. Pat. No. 6,312,612 owned by the Procter and Gamble Company. Based on the particular application, the number, density, length, width at the point or base, distribution and spacing of the microneedles will vary.

Referring to FIG. 26, which is a cross-section taken along lines A—A in FIG. 22, the internal components of sensor device 800, housed within housing 805, are shown. Printed circuit board or PCB 860 is affixed to top portion 815 of housing 805 and receives and supports the electronic components provided inside housing 805. Affixed to a bottom side of PCB 860 and electronically coupled to GSR sensors 825 are contacts 865, which preferably comprise gold plated contact pins such as the Pogo® contacts available from Everett Charles Technologies in Pomona, Calif. Also affixed to the bottom side of PCB 860 is skin temperature thermistor 870, a suitable example of which is the model 100K6D280 themistor manufactured by BetaTherm Corporation in Shrewsbury, Mass. Skin temperature thermistor 870 is, according to a preferred embodiment, thermally coupled to skin temperature skin interface component 840 by a thermally conductive interface material 875. Thermally conductive interface material 875 may be any type of thermally conductive interface known in the art, including, for example, thermally conductive gap fillers, thermally conductive phase change interface materials, thermally conductive tapes, thermally conductive cure-in-place compounds or epoxies, and thermal greases. Suitable thermally conductive interface materials include a boron nitride filled expanded polytetrafluoroethylene matrix sold under the trademark PolarChip CP8000 by W. L. Gore & Associates, Inc. and a boron nitride and alumina filled silicone elastomer on an adhesive backed 5 mil. (0.013 cm) thick aluminum foil carrier called A574, which is available from the Chomerics division of Parker Hannefin Corp. located in Woburn, Mass. Provided on top of PCB 860 is near-body ambient temperature thermistor 880, a suitable example of which is the model NTHS040ZN0IN100KJ thermistor manufactured by Vishay Intertechnology, Inc. in Malvern, Pa. Near-body ambient temperature thermistor 880 is thermally coupled to ambient temperature interface component 850 by thermally conductive interface material 875.

Still referring to FIG. 26, a preferred embodiment of sensor device 800 includes a particular embodiment of an apparatus for measuring heat flux between a living body and the ambient environment described in U.S. Pat. No. 6,595,929 B2 owned by the assignee hereof, the disclosure of which is incorporated herein by reference in its entirety. Specifically, heat conduit 885 is provided within housing 805. As used herein, the term heat conduit refers to one or more heat conductors which are adapted to singly or jointly transfer heat from one location to another, such as a conductor made of stainless steel. Heat conduit 885 is thermally coupled to heat flux skin interface component 835 by thermally conductive interface material 875. Provided on the bottom side of PCB 860 is a first heat flux thermistor 890A, and provided on the top side of PCB 860 is a second heat flux thermistor 890B. PCB 860 acts as a base member for supporting these components. It will be appreciated that a base member separate and apart from PCB 860 may be substituted therefor as an alternative configuration. A suitable example of both heat flux thermistors 890A and 890B model 100K6D280 thermisor manufactured by BetaTherm Corporation in Shrewsbury, Mass. is the. Heat flux Thermistor 890A and 890B are soldered to pads provided on PCB 860. The second heat flux thermistor 890B is thermally coupled to heat flux ambient interface 845 by thermally conductive interface material 875. As is well-known in the art, PCB 860 is made of a rigid or flexible material, such as a fiberglass, having a preselected, known thermal resistance or resistivity K. The heat flux off of the body of the wearer can be determined by measuring a first voltage V1 with heat flux thermistor 890A and a second voltage V2 with heat flux thermistor 890B. These voltages are then electrically differenced, such as by using a differential amplifier, to provide a voltage value that, as is well known in the art, can be used to calculate the temperature difference (T2−T1) between the top and bottom sides of PCB 860. Heat flux can then be calculated according to the following formula:

Heat Flux=$K(T2-T1)$

The combination of PCB 860 and heat flux thermistors 890A and 890B are thus a form of a heat flux sensor. One advantage of the configuration of the apparatus for measuring heat flux shown in FIG. 26 is that, due to the vertical orientation of the components, assembly of the apparatus for measuring heat flux, and thus sensor device 800 as a whole, is simplified. Also adding to the simplicity is the fact that thermally conductive interface materials that include a thin adhesive layer on one or both sides may be used for thermally conductive interface materials 875, enabling components to be adhered to one another. In addition, thermistors 890A and 890B are relatively inexpensive components, as compared to an integral heat flux sensor such as those commercially available from RdF Corporation of Hudson, N.H., thereby reducing the cost of sensor device 800. Although heat flux thermistors 890A and 890B are described as being provided on PCB 860 in the embodiment shown in FIG. 26, it will be appreciated that any piece of material having a known resistivity K may be used. Furthermore, other temperature measuring devices known in the art, such as a thermocouple or thermopile, may be substituted for heat flux thermistors 890A and 890B. As a further alternative, heat conduit 885 may be omitted such that thermal communication between heat flux thermistor 890A and heat flux skin interface component 835 is provided by one or more pieces of thermally conductive interface material 875. As still a further alternative, heat flux skin interface component 835 may be omitted such that thermal communication between heat flux thermistor 890A and the skin is provided by either or both of heat conduit 885 and one or more pieces of thermally conductive interface material 875. In any of the embodiments described herein, the combination of one or more of heat conduit 885, one or more pieces of thermally conductive interface material 875, and heat flux skin interface component 835 act as a thermal energy communicator for placing heat flux thermistor 890A in thermal communication with the body of the wearer of sensor device 800.

Figure 27:
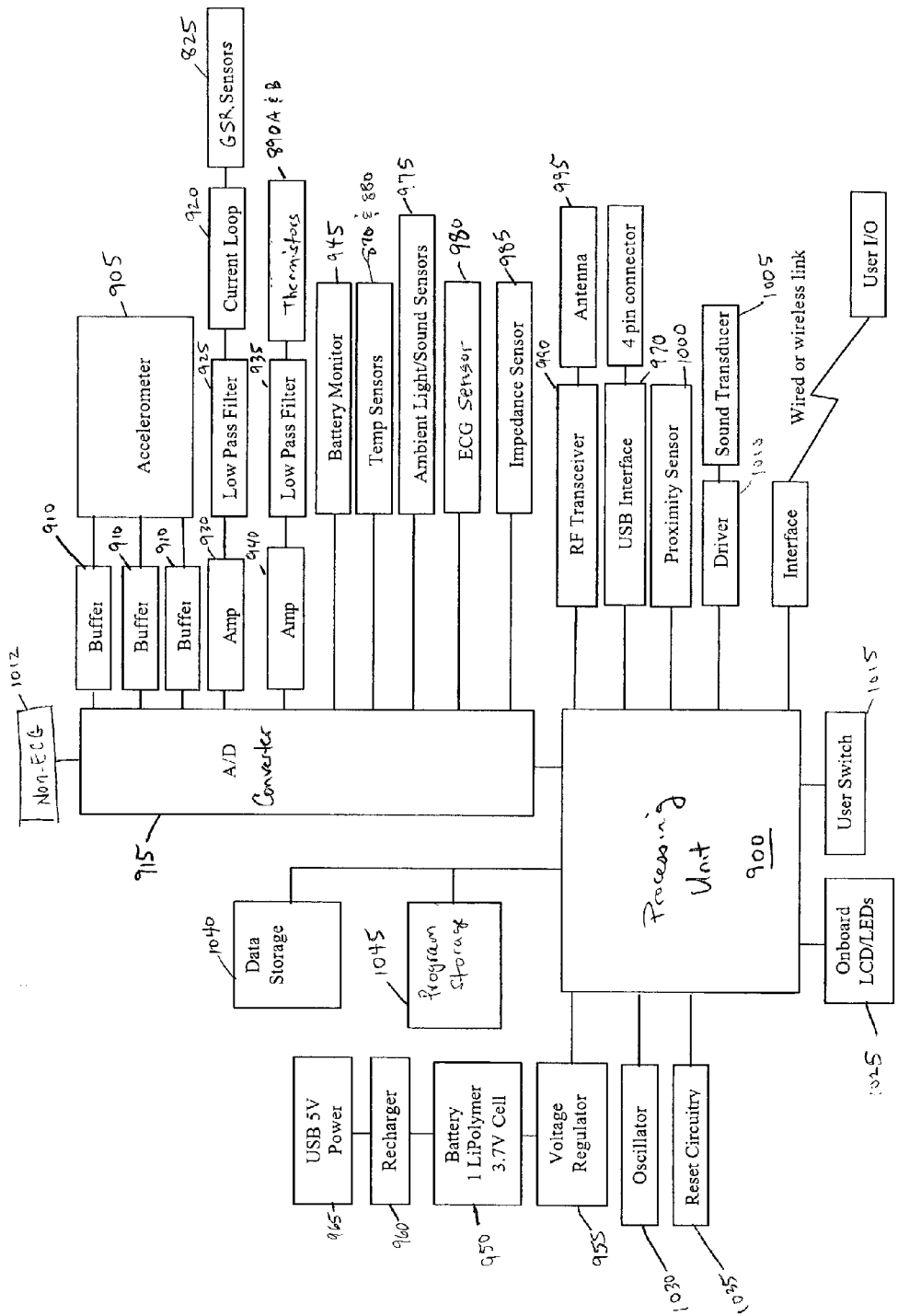
FIG. 27 is a block diagram illustrating the components mounted on or coupled to the printed circuit board forming a part of an embodiment of the sensor device shown in FIGS. 22 through 26.

FIG. 27 is a schematic diagram that shows an embodiment of the system architecture of sensor device 800, and in particular each of the components that is either provided on or coupled to PCB 860.

As shown in FIG. 27, PCB 860 includes processing unit 900, which may be a microprocessor, a microcontroller, or any other processing device that can be adapted to perform the functionality described herein, in particular the functionality described in connection with microprocessor 20 shown in FIG. 2, processing unit 490 shown in FIG. 20, or stand alone sensor device 700 shown in FIG. 21. A suitable example of processing unit 900 is the Dragonball EZ sold by Motorola, Inc. of Schaumburg, Ill. Also provided on PCB 860 is accelerometer 905, which may be either a two-axis or a three-axis accelerometer. A suitable example of a two-axis accelerometer is the Model ADXL202 accelerometer sold by Analog Devices, Inc. of Norwood, Mass., and a suitable example of a three-axis accelerometer is the model ACH-04-08-05 accelerator sold by Measurement Specialties Incorporated in Norristown, Pa. The output signals of accelerometer 905 are passed through buffers 910 and input analog to digital, referred to as A/D, converter 915 that in turn is coupled to processing unit 900. GSR sensors 825 are coupled to A/D converter 915 through current loop 920, low pass filter 925, and amplifier 930. Current loop 920 comprises an opamp and a plurality of resistors, and applies a small, fixed current between the two GSR sensors 825 and measures the voltage across them. The measured voltage is directly proportional to the resistance of the skin in contact with the electrodes. Similarly, heat flux thermistors 890A and 890B are coupled to A/D converter 915 and processing unit 900, where the heat flux calculations are performed, through low pass filter 935 and amplifier 940.

Battery monitor 945, preferably comprising a voltage divider with low pass filter to provide average battery voltage, monitors the remaining power level of rechargeable battery 950. Rechargeable battery 950 is preferably a LiIon/LiPolymer 3.7 V Cell. Rechargeable battery 950, which is the main power source for sensor device 800, is coupled to processing unit 900 through voltage regulator 955. Rechargeable battery 950 may be recharged either using recharger 960 or USB cable 965, both of which may be coupled to sensor device 800 through USB interface 970. Preferably, USB interface 970 is hermetically sealable, such as with a removable plastic or rubber plug, to protect the contacts of USB interface 970 when not in use.

PCB 860 further includes skin temperature thermistor 870 for sensing the temperature of the skin of the wearer of sensor device 800, and near-body ambient temperature thermistor 880 for sensing the ambient temperature in the area near the body of the wearer of sensor device 800. Each of these components is biased and coupled to processing unit 900 through A/D converter 915.

According to a specific embodiment of sensor device 800, PCB 860 may include one or both of an ambient light sensor and an ambient sound sensor, shown at 975 in FIG. 27, coupled to A/D converter 915. The ambient light sensor and ambient sound sensor may be adapted to merely sense the presence or absence of ambient light or sound, the state where a threshold ambient light or sound level has been exceeded, or a reading reflecting the actual level of ambient light or sound. A suitable example of an ambient sound sensor is the WM-60A Condenser Microphone Cartridge sold by Matsushita Electric Corporation of America located in Secaucus, N.J., and suitable examples of an ambient light sensor are the Optek OPR5500 phototransistor and the Optek OPR5910 photodiode sold by Optek Technology, Inc. located in Carrollton, Tex. In addition, PCB 860 may include ECG sensor 980, including two or more electrodes, for measuring the heart rate of the wearer, and impedance sensor 985, also including a plurality of electrodes, for measuring the impedance of the skin of the wearer. Impedance sensor 985 may also be an EMG sensor which gives an indication of the muscular activity of the wearer. The electrodes forming part of ECG sensor 980 or impedance sensor 985 may be dedicated electrodes for such sensors, or may be the electrodes from GSR sensors 825 multiplexed for appropriate measurements. ECG sensor 980 and impedance sensor 985 are each coupled to A/D converter 915.

PCB 860 further includes RF transceiver 990, coupled to processing unit 900, and antenna 995 for wirelessly transmitting and receiving data to and from wireless devices in proximity to sensor device 800. RF transceiver 990 and antenna 995 may be used for transmitting and receiving data to and from a device such as a treadmill being used by a wearer of sensor device 800 or a heart rate monitor worn by the wearer of sensor device 800, or to upload and download data to and from a computing device such as a PDA or a PC. In addition, RF transceiver 990 and antenna 995 may be used to transmit information to a feedback device such as a bone conductivity microphone worn by a fireman to let the fireman know if a condition that may threaten the fireman's safety, such as hydration level or fatigue level, has been sensed by sensor device 800. As described in detail in connection with FIG. 21, stand alone sensor device 700 may be coupled to computing device 750 to enable data to be communicated therebetween. Thus, as a further alternative, RF transceiver 990 and antenna 995 may be used to couple sensor device 800 to a computing device such as computing device 750 shown in FIG. 21. Such a configuration would enable sensor device 800 to transmit data to and receive data from the computing device 750, for example a computing device worn on the wrist. The computing device could be used to enable a user to input data, which may then be stored therein or transmitted to sensor device 800, and to display data, including data transmitted from sensor device 800. The configuration would also allow for computing tasks to be divided between sensor device 800 and computing device 750, referred to herein as shared computing, as described in detail in connection with FIG. 21.

As shown in FIG. 27, PCB 860 may include proximity sensor 1000 which is coupled to processing unit 900 for sensing whether sensor device 800 is being worn on the body. Proximity sensor 1000 may also be used as a way to automatically power on and off sensor device 800. Proximity sensor preferably comprises a capacitor, the electrical capacitance of which changes as sensor device 800 gets closer to the body. PCB 860 may also include sound transducer 1005, such as a ringer, coupled to processing unit 900 through driver 1010.

Sensor device 800 may also be provided with sensors in addition to those shown in FIG. 27, such as those taught by U.S. Pat. No. 5,853,005, the disclosure of which is incorporated herein by reference. The '005 patent teaches a sound transducer coupled to a pad containing an acoustic transmission material. The pad and sound transducer may be used to sense acoustic signals generated by the body which in turn may be converted into signals representative of physiological parameters such as heart rate or respiration rate. In addition, rather than being integrated in sensor device 800 as part of one or more of housing 805, flexible section 810 or strap 811, a sensing apparatus as taught by the '005 patent may be provided separate from sensor device 800 and be coupled, wired or wirelessly, to sensor device 800. According to the '005 patent, the sound or acoustic transducer is preferably a piezoelectric, electret, or condenser-based hydrophone, similar to those used by the Navy in sonar applications, but can be any other type of waterproof pressure and motion sensing type of sensor.

The sensing apparatus as taught by the '005 patent is an example of what shall be referred to herein as a non-ECG heart parameter sensor, meaning that it has the following two qualities: (1) it does not need to make measurements across the torso using at least two contacts separated by some distance; and (2) it does not measure electrical activity of the heart. The sensing apparatus as taught by the '005 patent has been shown to be capable of detecting heart rate information and information relating to individual beats of the heart with high reliability under certain circumstances, depending primarily on factors including the proximity of the apparatus to the heart, the level of ambient noise, and motion related sound artifacts caused by the movement of the body. As a result, the sensing apparatus as taught by the '005 patent is most reliable when worn in an ambient environment with a low level of ambient noise and when the body is not moving.

Certain characteristics, sensors and sensing capabilities of sensor device 800 are able to improve the reliability and accuracy of an acoustic-based non-ECG heart parameter sensor 1012 such as the sensing apparatus as taught by the '005 patent that is incorporated therein or coupled thereto. For example, in one specific embodiment, sensor device 800 is particularly suited to be worn on the upper arm. The upper arm is a good location for a sensor device 800 having an acoustic-based non-ECG heart parameter sensor 1012 incorporated therein because it is near the heart and provides a space for sensor device that allows it to be unobtrusive and comfortable to wear. In addition, ambient sound sensor shown at 975 in FIG. 27 may be used to filter out ambient noise from the signals detected by the acoustic-based non-ECG heart parameter sensor 1012 in order to isolate the sound signal originating from the body. Filtering of the signal produced by an acoustic-based non-ECG heart parameter sensor 1012 such as the sensing apparatus as taught by the '005 patent in this manner may be used both in the case where such an apparatus is incorporated in sensor device 800 and in the case where it is separated from but coupled to sensor device 800 as described above. Furthermore, the sound generated from the motion of the body that is not created by the heart can be accounted for and adjusted for through the use of a sensor or sensors that detect or that may be used to identify body sounds generated as a result of motion of the body, such as accelerometer 905 shown in FIGS. 27 and 29 or the body position or muscle pressure sensors identified in Table 1. For example, footfalls create sound within the body that can lower the signal to noise ratio of an acoustic-based non-ECG heart parameter sensor 1012, which will likely result in false positive and false negative heart beat identifications. As is well known in the art, accelerometer 905 may function as a footfall indicator. Accelerometer 905 may thus be used to filter or subtract out from the signal detected by the acoustic-based non-ECG heart parameter sensor 1012 signals related sound motion artifacts caused by the movement of the body such as by footfalls.

Several methodologies for performing the filtering or subtracting of signals described herein are known to those of ordinary skill in the art. Such filtering or subtracting of signals used in connection with the monitoring of disparate signals, some used for noise cancellation and some used for their direct measure, is also known as data integration.

Sensor device 800 may also be used to put parameters around and provide a context for the readings made by a non-ECG heart parameter sensor 1012 so that inaccurate readings can be identified and compensated for. For example, sensor device 800 may be used to detect real time energy expenditure of the wearer as well as the type of activity in which the wearer is engaging, such as running or riding a bike. Thus, as another example of how the sensors and sensing capabilities of sensor device 800 may be used to increase the reliability and accuracy of a non-ECG heart parameter sensor 1012 through data integration, the energy expenditure and activity type information can be used to provide a context in which the heart related parameters detected by the non-ECG heart parameter sensor 1012 can be assessed and possibly filtered. For example, if sensor device 800 detects that a person is burning 13 calories per minute and is biking, and the non-ECG heart parameter sensor 1012 is indicating that the wearer's heart rate is 60 beats per minute, then it is highly likely that further filtration of the signal from the non-ECG heart parameter sensor 1012 is necessary.

Other well known non-ECG heart parameter sensing devices include, for example, those based on micro-power impulse radar technology, those based on the use of piezo-electric based strain gauges, and those based on plethysmography, which involves the measurement of changes in the size of a body part as modified by the circulation of blood in that part. It will be appreciated that the performance of these devices may also be enhanced through the use of data integration as described herein.

Another sensor that may be incorporated into the sensor device 800 measures the pressure with which sensor device 800 is held against the body of the wearer. Such a sensor could be capacitive or resistive in nature. One such instantiation places a piezo-resistive strain gauge on the back of the enclosure to measure the small deflection of the plastic as increasing force is applied. Data gathered from such a sensor can be used to compensate the readings of other sensors in sensor device 800 according to the readings of such a sensor.

Figure 28:
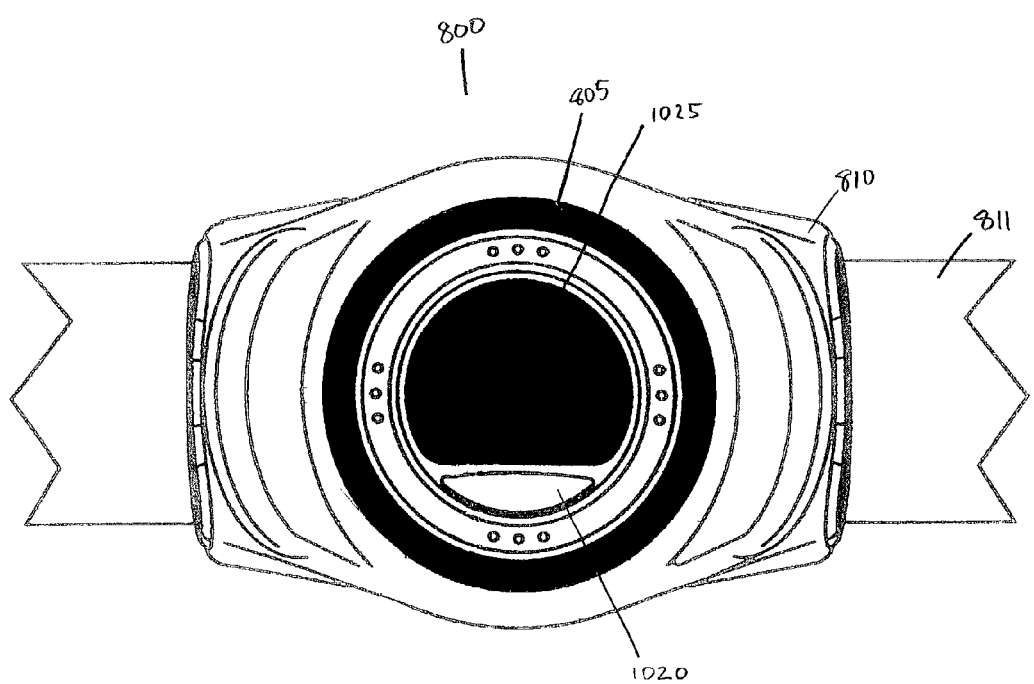
FIG. 28 is a front view of an alternate embodiment of a sensor device according to the present invention including an LCD.

Also provided on PCB 860 and coupled to processing unit 900 is switch 1015. Switch 1015 is also coupled to button 1020 provided on housing 805. Button 1020, by activating switch 1015, may be used to enter information into sensor device 800, such as a time stamp to mark the occurrence of an event such as taking medication. Preferably, button 1020 has a tactile, positive dtent feedback when depressed, and a concave shape to prevent accidental depression. Also, in the embodiment shown in FIGS. 22–26, flexible section 810 includes membrane 1022 that covers and seals button 1020. In the embodiments shown in FIGS. 30–32, a similar membrane 1022 may be provided on flexible section 810, and, preferably, also on housing 805 such that button 1020 is sealed when housing 805 is removed from flexible section 810. Alternatively, a hole may be provided in flexible section 810 exposing button 1020 and membrane 1022 when housing 805 is attached to flexible section 810. In addition, coupled to processing unit 900 on PCB 860 are LCDs and/or LEDs 1025 for outputting information to the wearer. FIG. 28 shows an alternate embodiment of sensor device 800 in which LCD 1025 is provided on a top face of housing 805. As an alternative to LCDs or LEDs 1025, sensor device 800 may include a prior art electrochemical display that retains its ability to display information even when power is no longer being provided thereto. Such a display is described in U.S. Pat. No. 6,368,287 B1, the disclosure of which is incorporated herein by reference, and includes a plurality of markers comprising a miniature heating element and a coating of heat sensitive material. When current is passed through one of the heating elements, it heats up, thereby inducing a change in the color of the coating material. The color change is permanent, even after the heating element cools down. Such displays are relatively inexpensive and thus are well adapted for use in embodiments of sensor device 800 that are designed to be disposable, possibly single use, items.

Oscillator 1030 is provided on PCB 860 and supplies the system clock to processing unit 900. Reset circuit 1035 is coupled to processing unit 900 and enables processing unit to be reset to a standard initial setting.

Finally, non-volatile data storage device 1040, such as a FLASH memory chip, is provided for storing information collected and/or generated by sensor device 800. Preferably, data storage device 1040 includes at least 128K of memory. Non-volatile program storage device 1045, such as a FLASH ROM chip, is provided for storing the programs required to operate sensor device 800.

As an alternative, a microprocessor with integral A/D converters, data storage, and program storage may be substituted for processing unit 900, A/D converter 915, data storage device 1040 and non-volatile memory 1045. A suitable example of such a microprocessor is the Texas Instruments Model MSP430 processor.

Any component forming a part of sensor device 800 that comes in contact with the wearer's skin should not, in a preferred embodiment, degrade in durometer, elasticity, color or other physical or chemical properties when exposed to skin oils, perspiration, deodorant, suntan oils or lotions, skin moisturizers, perfume or isopropyl alcohol. In addition, such components preferably are hypoallergenic.

Figure 29:
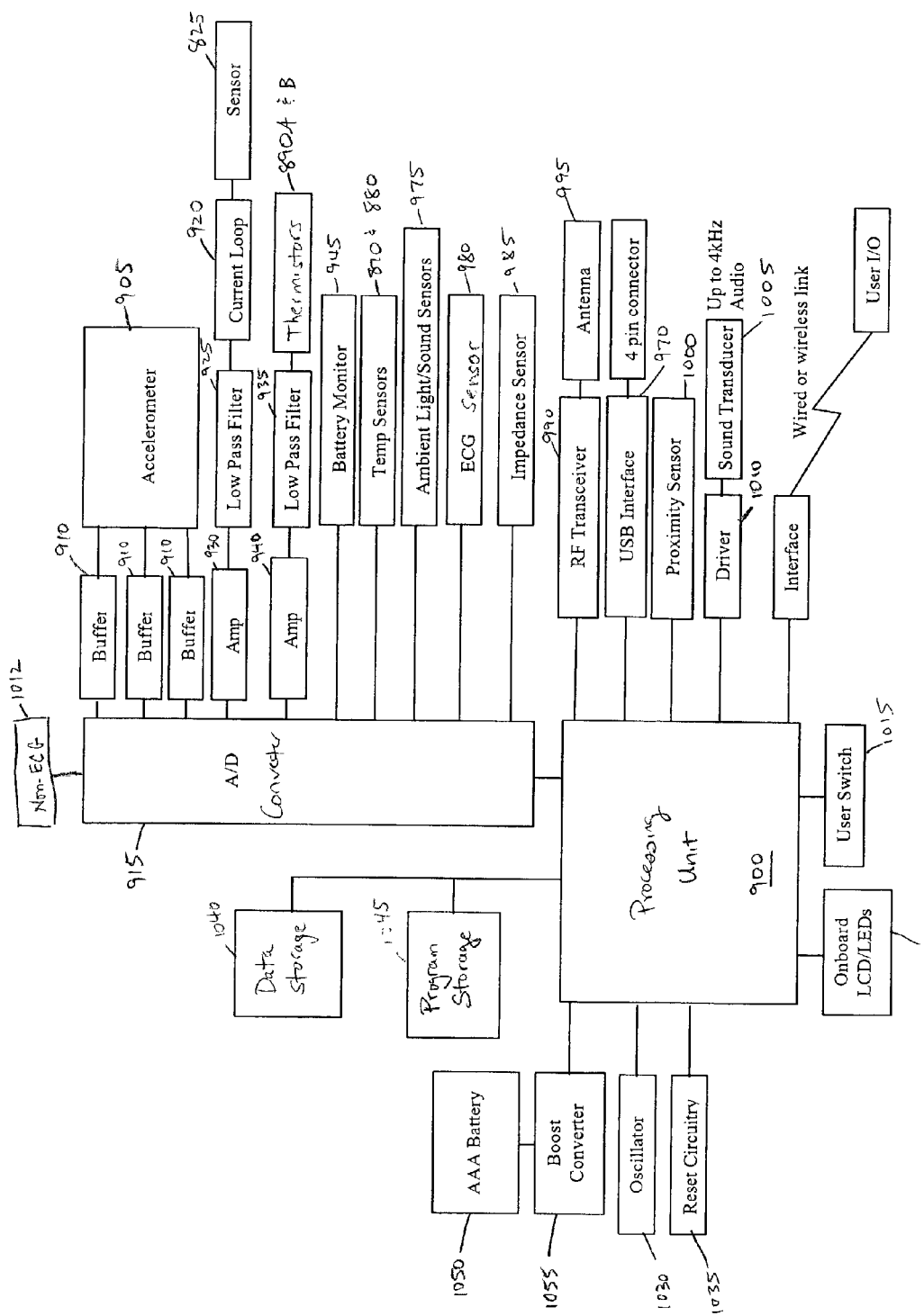
FIG. 29 is a block diagram illustrating the components mounted on or coupled to the printed circuit board forming a part of an alternate embodiment of the sensor device shown in FIGS. 22 through 26.

FIG. 29 shows an alternate embodiment of PCB 860 in which rechargeable battery 950, voltage regulator 955, recharger 960 and USB cable 965 have been replaced by disposable AAA battery 1050 and boost converter 1055. Boost converter 1055 uses an inductor to boost the voltage of AAA battery 1050 to the 3.0–3.3 V required to run the electronics on PCB 860. A suitable boost converter 1055 is the model MAX1724 sold by Maxim Integrated Products, Inc. of Sunnydale, Calif.

Figure 30:
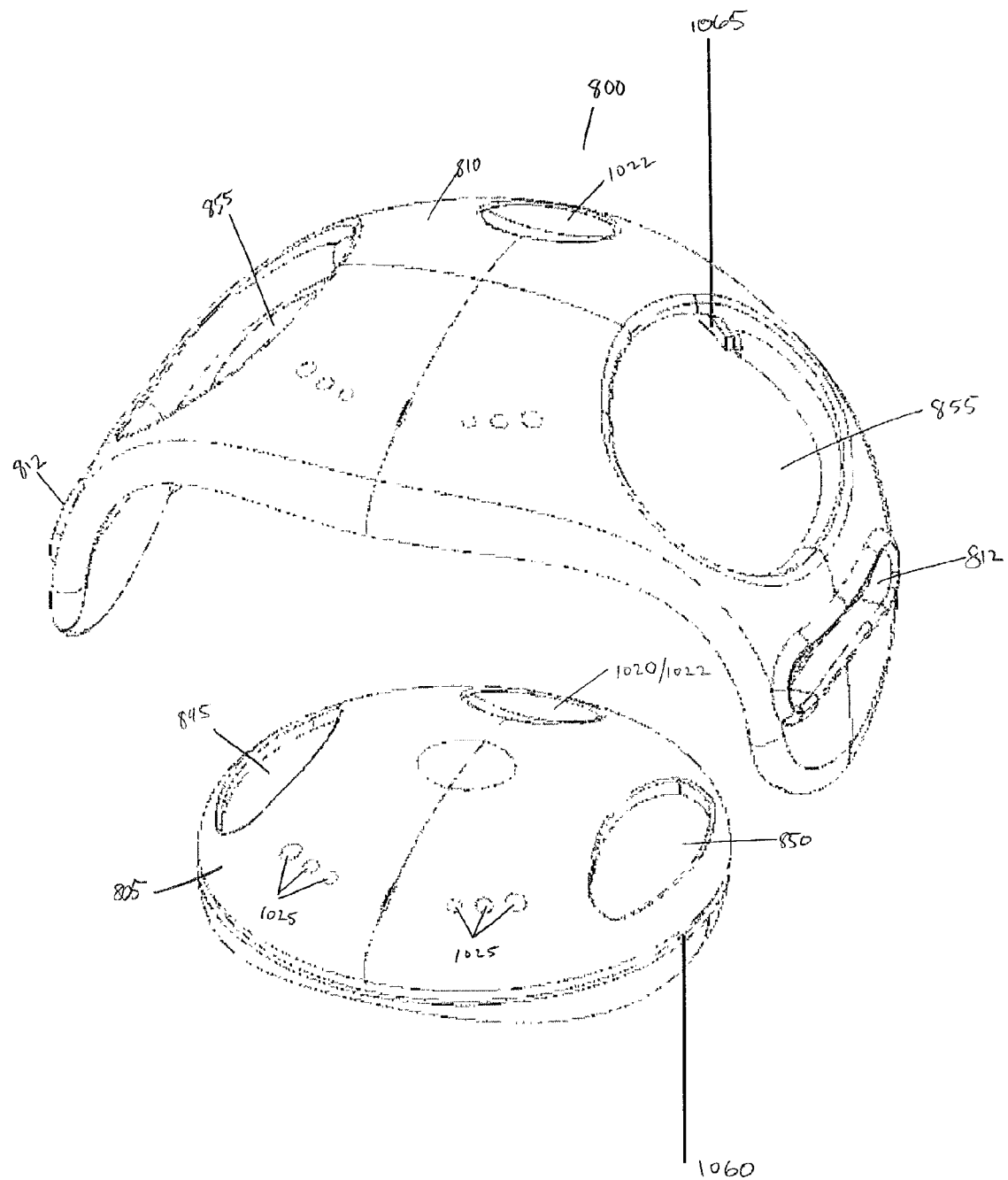
FIGS. 30 and 31 are isometric views of an alternate embodiment of a sensor device according to the present invention having a housing adapted to be removably attached to a flexible section.
Figure 31:
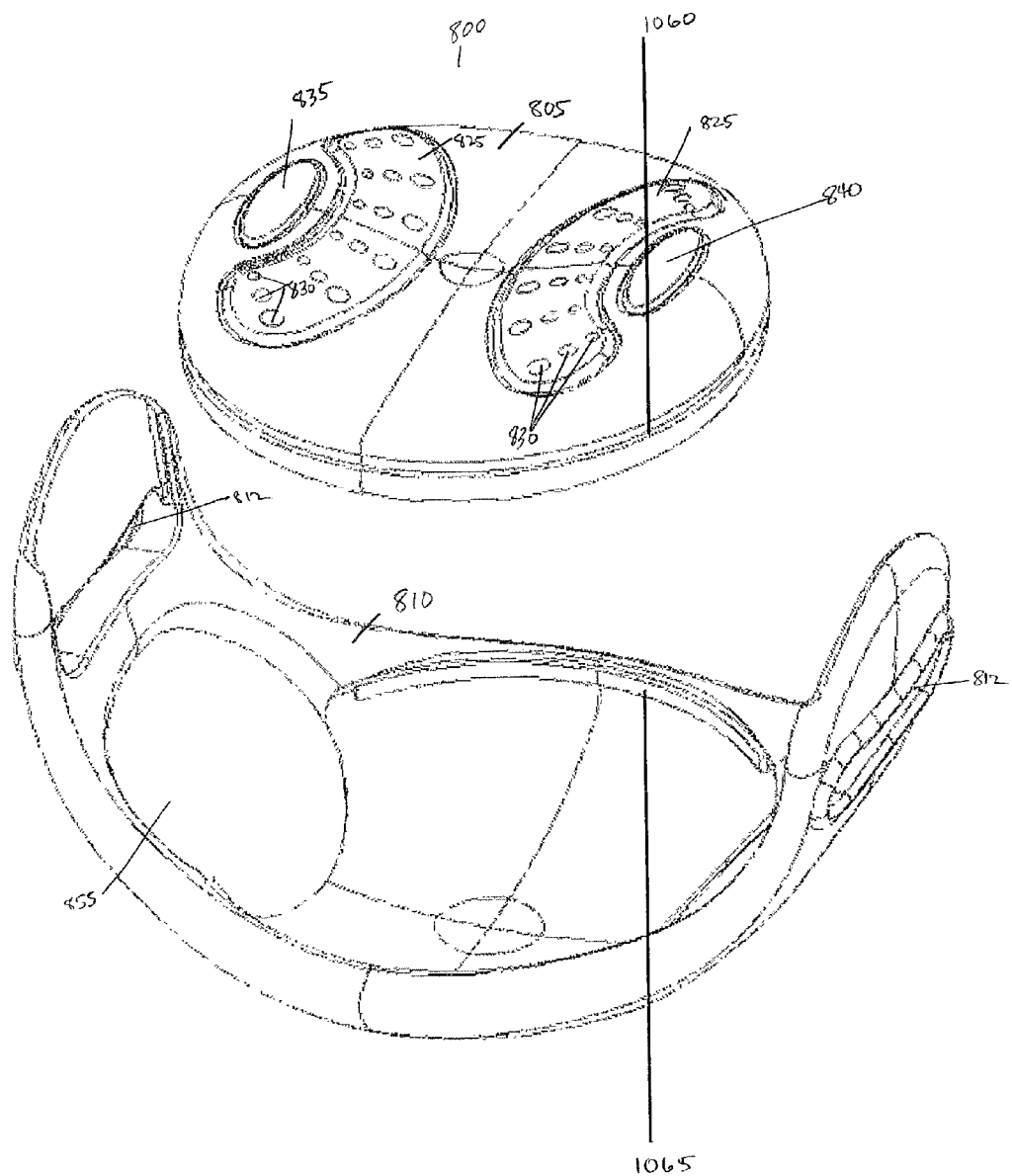
Figure 32:
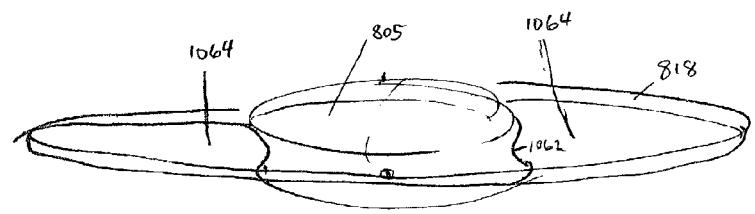
FIG. 32 is an isometric view of a further alternate embodiment of a sensor device according to the present invention having a housing adapted to be removably attached to a flexible section.
Figure 40A:
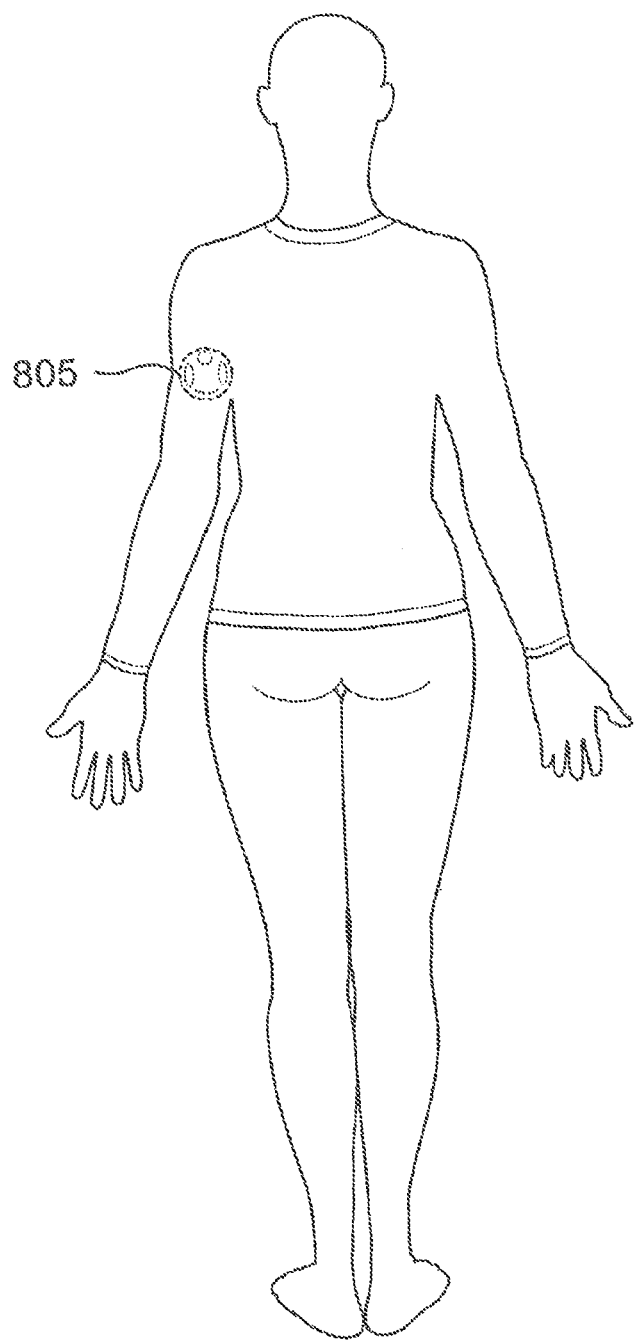
FIG. 40A is an elevational drawing of the sensor device mounted within a garment on the upper arm of a wearer.
Figure 40B:
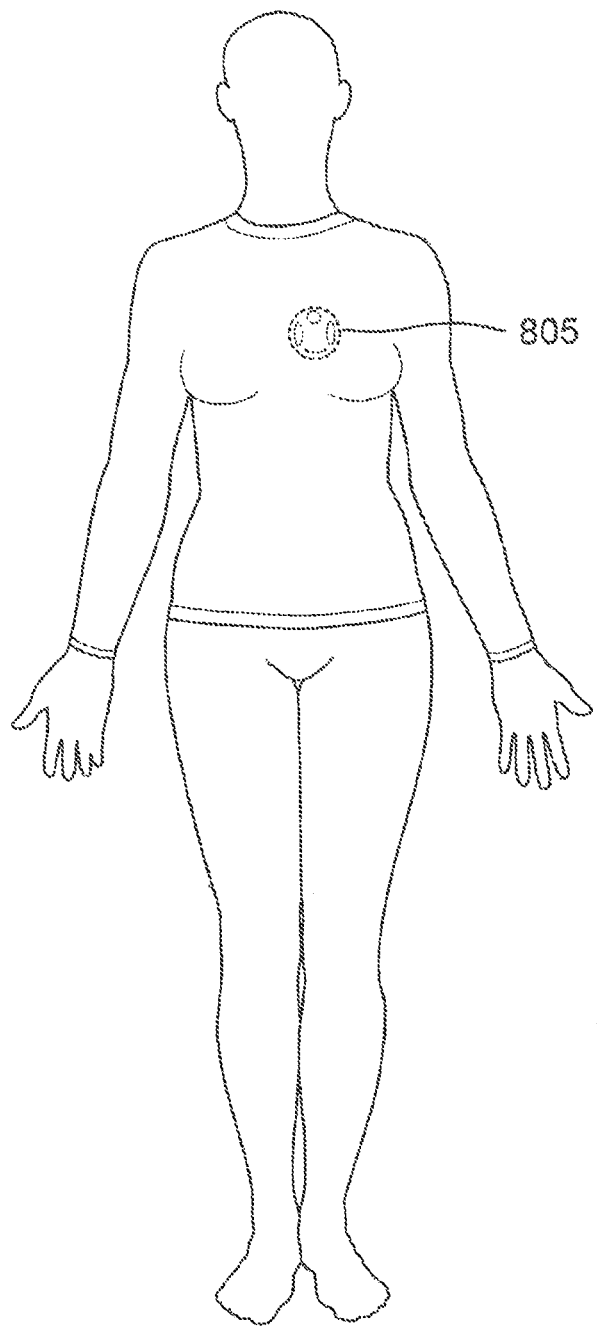
FIG. 40B is an elevational drawing of the sensor device mounted within a garment on the left chest area of a wearer.

Referring to FIGS. 30 and 31, an alternate embodiment of sensor device 800 is shown in which housing 805 is removably attached to flexible section 810. As shown in FIGS. 30 and 31, housing 805 is provided with groove 1060 along the outer edge thereof which is adapted to receive therein tongue 1065 provided on the bottom side of flexible section 810 for securely but removably attaching housing 805 to flexible section 810. Through the interaction of groove 1060 and tongue 1065, housing 805 may thus be readily popped in and out of flexible section 810. Such a configuration enables housing 805 to be readily attached to multiple flexible sections having sizes and shapes that are different than flexible section 810 as long as the flexible section includes a tongue similar to tongue 1065. Such alternate flexible sections may be sized and shaped to fit on particular parts of the body, such as the calf or thigh, and may comprise a garment such as a shirt having the tongue or tongues located in places of interest, such as the upper arm or upper left chest, the latter enabling housing 805 to be positioned over the heart of the wearer, as shown in FIGS. 40A and 40B, owned by the assignee of the present application and incorporated herein by reference, identifies several locations on the body that are particularly well adapted to receive particularly sized and shaped sensor devices so as to avoid interference with the motion and flexibility of the body. As will be appreciated by those of skill in the art, groove 1060 and tongue 1065 may be swapped such that groove 1060 is provided in flexible section 810 and tongue 1065 is provided on housing 805. As will also be appreciated by those of skill in the art, multiple alternative structures exist for securely but removably attaching housing 805 to flexible section 810. These alternative structures include, without limitation, temporary adhesives, screws, a tight fit between having 805 and flexible section 810 that holds the two together by friction, magnets provided in each of housing 805 and flexible section 810, well-known snaps and snapping mechanisms, a threaded portion provided on housing 805 adapted to be received by threads in flexible section 810, an O-ring or similar elastic band adapted to fit around a portion of flexible section 810 and into a groove provided in housing 805 when flexible section 810 is placed over housing 805, or merely pressure when housing 805 is placed on the body and flexible section 810 is placed thereover and attached to the body such as by strap 811. Referring to FIG. 32, a still further alternative structure for removably securing flexible section 810 to housing 805 is shown in which flexible section 810 comprises and elastic or similar band that is adapted to fit into a groove 1062 provided in housing 805. Housing 805 and flexible section 810 may then be placed on the body and held in place by strap 811 or the like inserted through gaps 1064 between housing 805 and flexible section 810.

Figure 33:
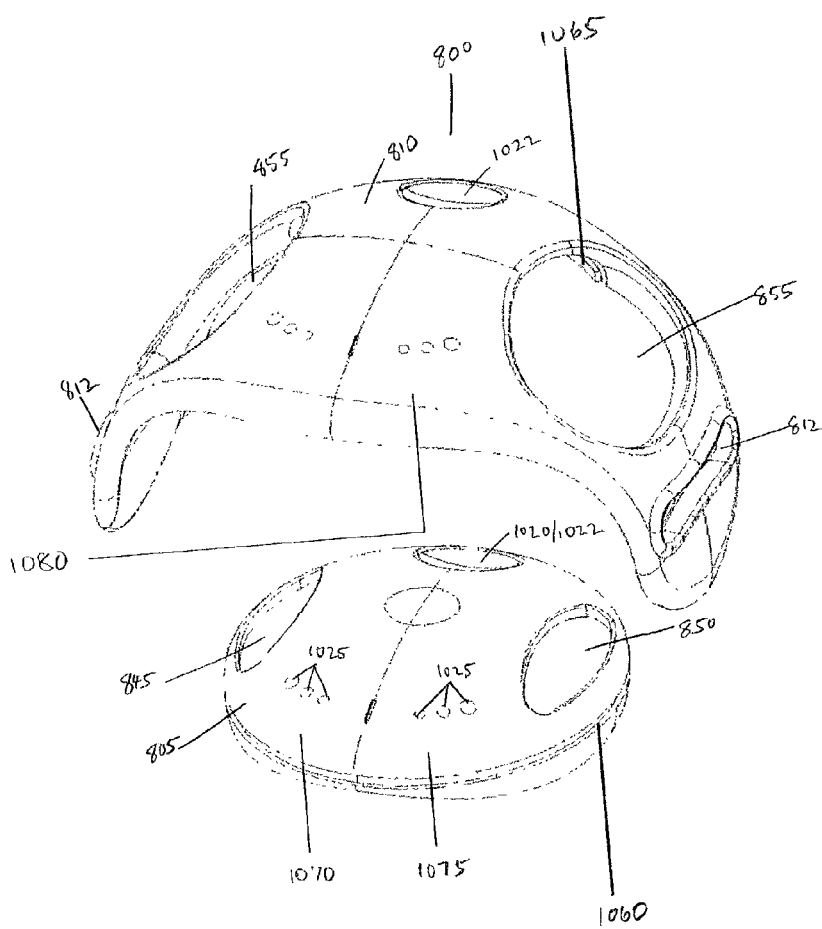
FIG. 33 is an isometric view of an embodiment of a sensor device having adjustable operating parameters according to an aspect of the present invention.

FIG. 33 shows an alternate embodiment of sensor device 800 as shown in FIGS. 30 and 31 that is adapted to automatically adjust or alter the operating parameters of sensor device 800, such as its functionality, settings or capabilities, depending on the particular flexible section to which housing 805 is attached. For example, the calculation of a parameter, such as energy expenditure, may depend on information that is particular each individual, such as age, height, weight, and sex. Rather than having each individual enter that information in sensor device 800 each time he or she wants to wear the device, each individual that is going to wear the device could enter the information once and have their own flexible section that causes sensor device to make measurements based on his or her particular information. Alternatively, the memory in sensor device 800 for storage of user data may be divided into several compartments, one for each user, so as to avoid co-mingling of user data. Sensor device 800 may be adapted to alter where collected data is stored depending on the particular flexible section that is being used. In addition, sensor device 800 may be calibrated and recalibrated differently over time depending on the particular flexible section to which housing 805 is attached as it learns about each particular wearer and his or her habits, demographics and/or activities.

According to a particular embodiment, housing 805 is provided with first magnetic switch 1070 and second magnetic switch 1075, each on PCB 860. Provided on or inside flexible section 810, such as by an insert molding technique, is magnet 1080. Magnet 1080 is positioned on or inside flexible section 810 such that it aligns with and thereby activates one of first magnetic switch 1080 and second magnetic switch 1075 when housing 805 is attached to flexible section 810. In the embodiment shown in FIG. 33, second magnetic switch 1075 will be activated. A second flexible section 810 similar to flexible section 810 shown in FIG. 33 will also be provided, the difference being that the magnet 1080 provided therewith will be positioned such that first magnetic switch 1070 is activated when housing 805, the same housing 805 shown in FIG. 33, is attached to the second flexible section 810. Housing 805, and in particular processing unit 900, may be programmed to alter its functionality, settings or capabilities depending on which one of first magnetic switch 1070 and second magnetic switch 1075 is activated, i.e., which particular flexible section 810 is being used. Thus, a husband and wife may share a single housing 805 but have different flexible wings 810 with magnets 1080 located in different places. In such a case, housing 805 may be programmed to operate with functionality, settings or capabilities particular to the husband when first magnetic switch 1070 is activated, and with functionality, settings or capabilities particular to the wife when second magnetic switch 1075 is activated. Although only two magnetic switches are shown in FIG. 33, it will be appreciated that multiple magnetic switches and multiple flexible sections may be used to allow sensor device 800 to be programmed for multiple wearers, such as an entire family, with each family member having his or her own flexible section. As still a further alternative, multiple flexible sections may be provided that are adapted to be worn on different parts of the body, each having a magnet placed in a different location. Housing 805 may then be programmed to have functionality, settings or capabilities particular to the type of sensing to be done on each different part of the body, with magnetic switches placed so as to be activated when housing 805 is attached to the appropriate flexible section. Sensor device 800 according to this embodiment is thus a "smart" device. As will be appreciated by one of skill in the art, many alternatives to first and second magnetic switches 1070 and 1075 and magnet 1080 may be used to provide the functionality described in connection with FIG. 33. Such alternatives include, without limitation, mechanical switches provided in housing 805 that are activated by a protruding portion, such as a pin, provided at a particular location on flexible section 810, optical switches comprising an array of light sensors provided in housing 805 that are activated when the surrounding light is blocked, reflected or filtered in a particular way with one or more translucent sections and a single opaque, reflective or filtering section being selectively provided on flexible section 810 at particular locations, the translucent sections not activating the corresponding optical switches and the opaque, reflective or filtering section activating the corresponding optical switch, electronic switches provided in housing 805 activated by a conductor provided in particular locations in flexible section 810. As still a further alternative, housing 805 may be provided with multiple switches and each flexible section 810 may be provided with one or more switch activators positioned to activate certain selected switches. The operating parameters of housing 805 would in this embodiment be adapted to change depending upon the particular set of one or more switches that are activated. This embodiment thus employs an encoding scheme to alter the operating parameters of housing 805 depending on which flexible section 810 is used. As still a further alternative, housing 805 may be provided with a single switch adapted to alter the operating parameters of housing 805 depending upon the way in which or state in which it is activated, such as by the properties of the switch activators. For example, the switch may be a magnetic switch that is activated a plurality of different ways depending upon the magnetic level or strength of the magnet provided in each flexible section 810. A plurality of flexible sections 810 could then be provided, each having a magnet of a different strength. In addition, any particular flexible section 810 may be provided with a plurality of magnets having different strengths with each magnet being able to activate the switch in housing 805 in a different manner. Such a flexible section 810 would be able to selectively trigger different operating parameters of housing 805, such as by rotating a portion of flexible wing 805 to align a particular magnet with the switch. As an alternative, the switch could be an electrical switch and the switch activators could be conductors having different resistances. The switch would, in this embodiment, be activated in different ways depending on the measured resistance of the switch activator that closes the circuit.

Figure 34:
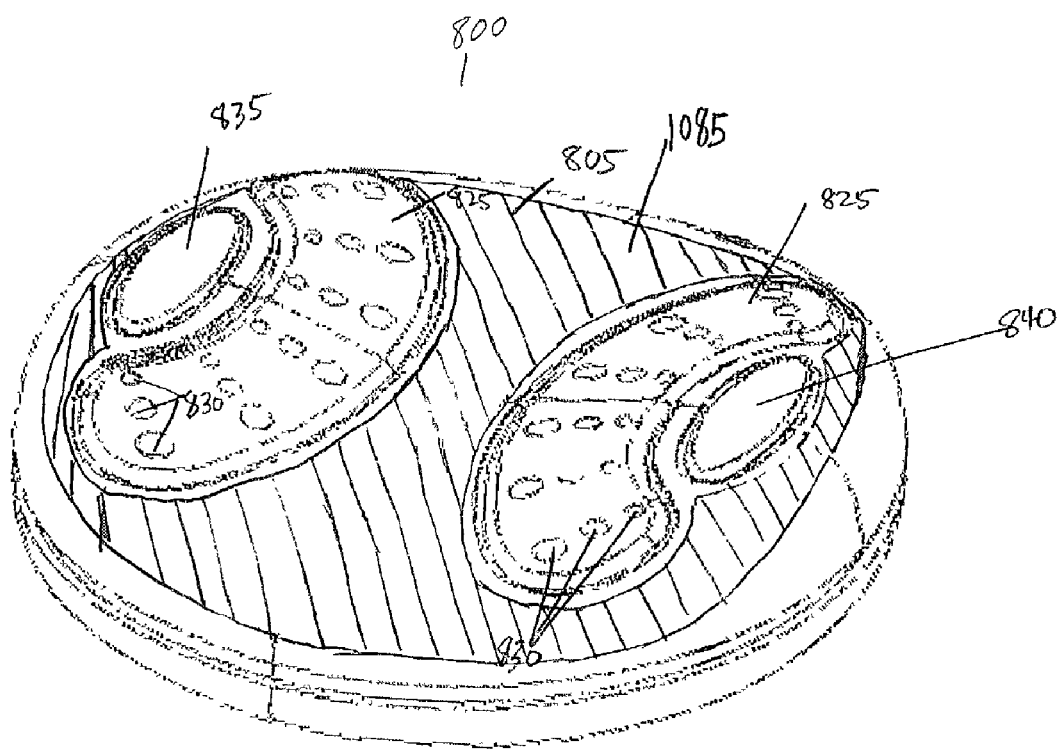
FIG. 34 is an isometric view of an alternate embodiment of a sensor device according to the present invention having a housing having an adhesive material on an external surface thereof for removably attaching the housing to the body.

Referring to FIG. 34, as still a further embodiment of sensor device 800, housing 805 may be provided with adhesive material 1085 on a back side thereof to enable housing 805 to be removably attached to selected portions of the body, such as the upper left chest over the heart, without flexible section 810. Adhesive material 1085 may be any well-known adhesive that would securely attach housing 805 to the body and enable it to be worn for a period of time, but that would also readily enable housing 805 to be removed from the body after use. Adhesive material 1085 may comprise, for example, a double sided adhesive foam backing that would allow for comfortable attachment of housing 805 to the body. Furthermore, housing 805 may be made of a well-known flexible plastic film or the like, such as that taught in U.S. Pat. No. 6,368,287 B1, the disclosure of which is incorporated herein by reference, that would, due to low cost, enable sensor device 800 to be disposable. Such a disposable sensor device may also include an electro-chemical display described above to enhance its disposability. In an embodiment adapted for placement over the upper left chest or any other appropriate region for detecting heart related parameters, sensor device 800 would include one or more sensors described herein for sensing heart related parameters such as heart rate, beat-to-beat or interbeat variability, ECG or EKG, pulse oximetry, heart sounds, such as detected with a microphone, and mechanical action of the heart, such as detected with ultrasound or micro-pulse radar devices.

Figure 35A:
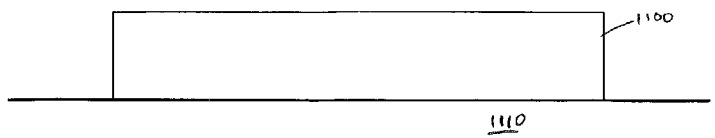
FIGS. 35A and B are cross-sectional views of a housing for a prior art sensor device.
Figure 35B:
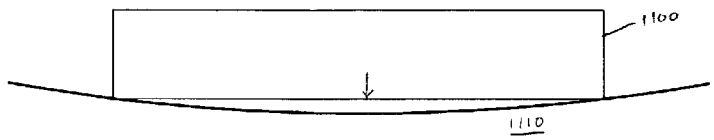
FIGS. 35C through H are cross-sectional views of various embodiments of a housing for a sensor device according to an aspect of the present invention taken along lines C—C in FIG. 23.

FIGS. 35A–H and 36A–H illustrate aspects of the present invention relating to the ergonomic design of sensor device 800. Referring to FIGS. 35A and 35B, a housing 1100 of a prior art sensor device having a rectangular cross-section is shown resting on the body 1110 of a wearer of the prior art sensor device. As seen in FIG. 35B, when body 1110 flexes and forms a concavity, as may happen many times each minute on various parts of the body or for extended periods of time depending on the position of various body parties during particular activities, a significant portion of housing 1100 is caused to be removed from body 1110. When housing 1100 is caused to be removed in this manner, the ability of the prior art sensor device to accurately make measurements and collect data will be jeopardized, especially for any readings to be taken near the center of the cross-section indicated by the arrows in FIG. 35B.

Figure 35C:
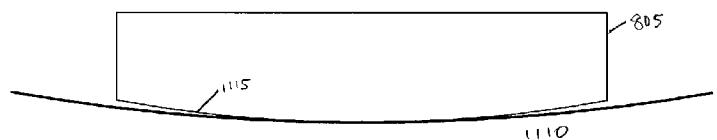
Figure 35D:
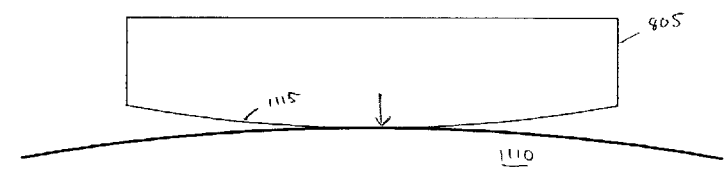
Figure 35E:
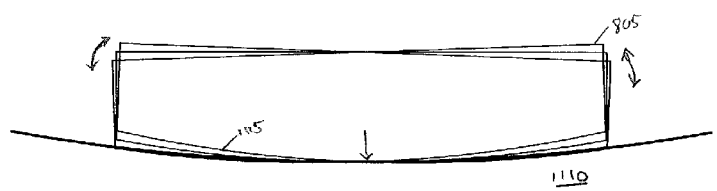
Figure 35F:
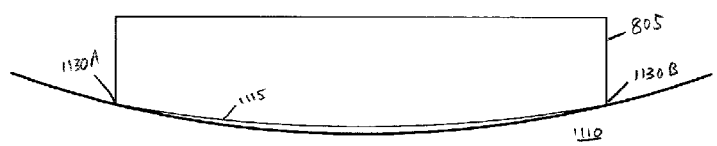
Figure 35G:
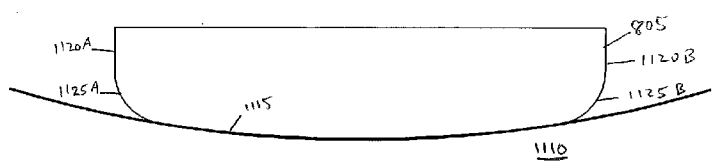
Figure 35H:

FIGS. 35C–H illustrate a cross-section of housing 805 of sensor device 800 taken along lines C—C shown in FIG. 23 according to various aspects of the present invention. The cross-section shown in FIGS. 35C–H is taken near the middle portion of housing 805 shown in FIG. 23 between GSR sensors 825. As seen in FIG. 35C, bottom surface 1115 of housing 805 is provided with a generally convex shape such that, when body 1110 flexes and forms a concavity, a substantial portion of bottom surface 1115 of housing 805 remains in contact with body 1110 by fitting into the concavity. As seen in FIG. 35D, when body 1110 flexes in the opposite direction so as to create a convexity, the center portion of housing 805, indicated by the arrow in FIG. 35D, remains in contact with body 1110. As shown in FIG. 35E, this is true even if housing 805 were to rock within the concavity formed in body 1110. Referring to FIG. 35F, body 1110 may, at times, flex to an extreme degree, i.e., more than the anticipated maximum that it was designed for, such that, even if bottom surface 1115 is provided with a convex shape, it may still cause bottom surface 1115 to be removed from body 1110. A solution to this problem is illustrated in FIG. 35G, wherein the lateral ends 1120A and 1120B of housing 805 are provided with radiused portions 1125A and 1125B, respectively adjacent to and including opposite lateral ends of bottom surface 1115. Radiused portions 1125A and 1125B enable housing 805 to sit lower and fit into the concavity created when body 1110 flexes to an extreme degree. In addition, radiused portions 1125A and 1125B provide for more comfortable wear as they eliminate sharp edges 1130A and 1130B shown in FIG. 35F that contact body 1110. FIG. 35H shows how body 1110 will tend to conform to the shape of housing 805 due at least in part to the viscosity of the skin when body 1110 is in a relaxed condition.

Figure 36A:
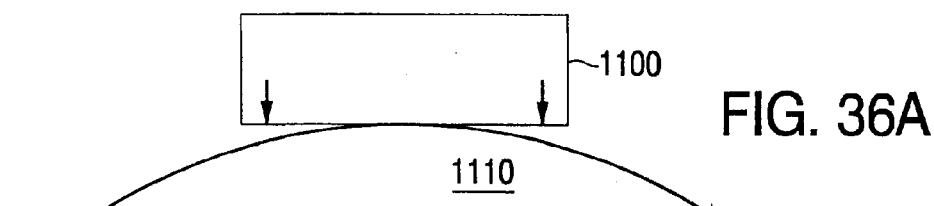
FIG. 36A is a cross-sectional view of a housing for a prior art sensor device.
Figure 36B:
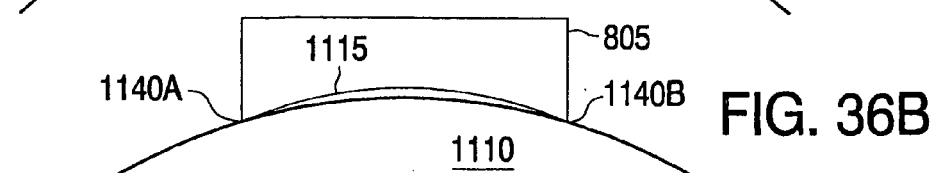
FIGS. 36B through H are cross-sectional views of various embodiments of a housing for a sensor device according to an aspect of the present invention taken along lines D—D in FIG. 23.
Figure 36C:
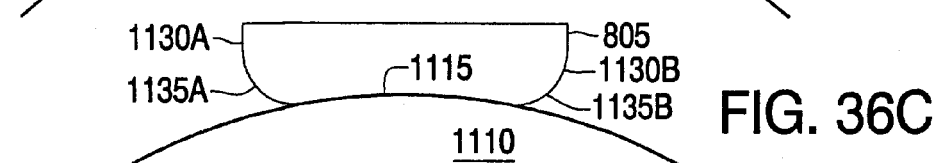
Figure 36D:
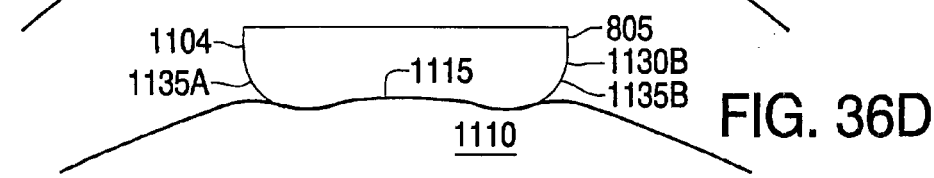
Figure 36E:
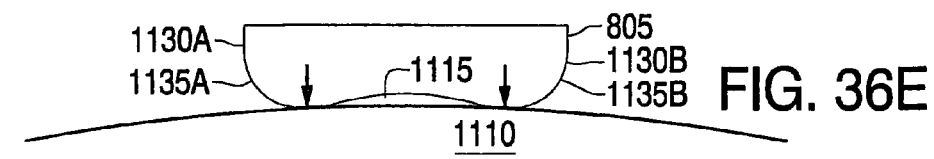
Figure 36F:
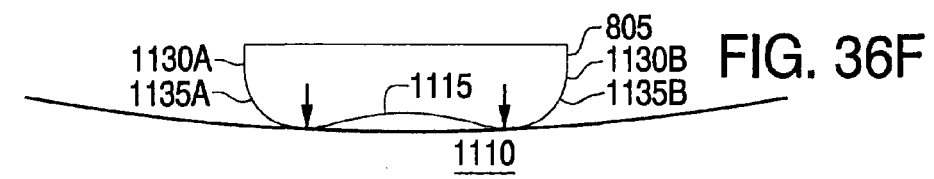
Figure 36G:
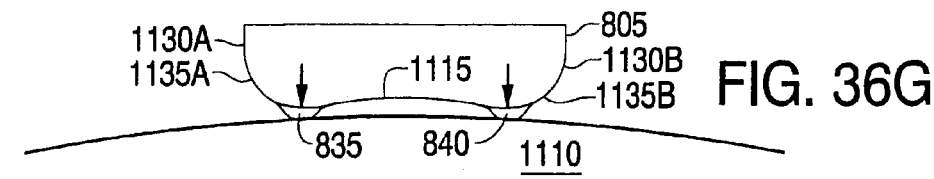
Figure 36H:
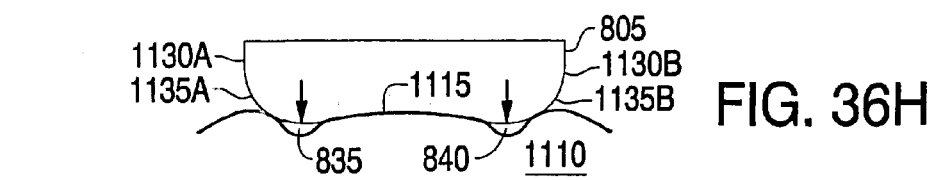
Figure 37:
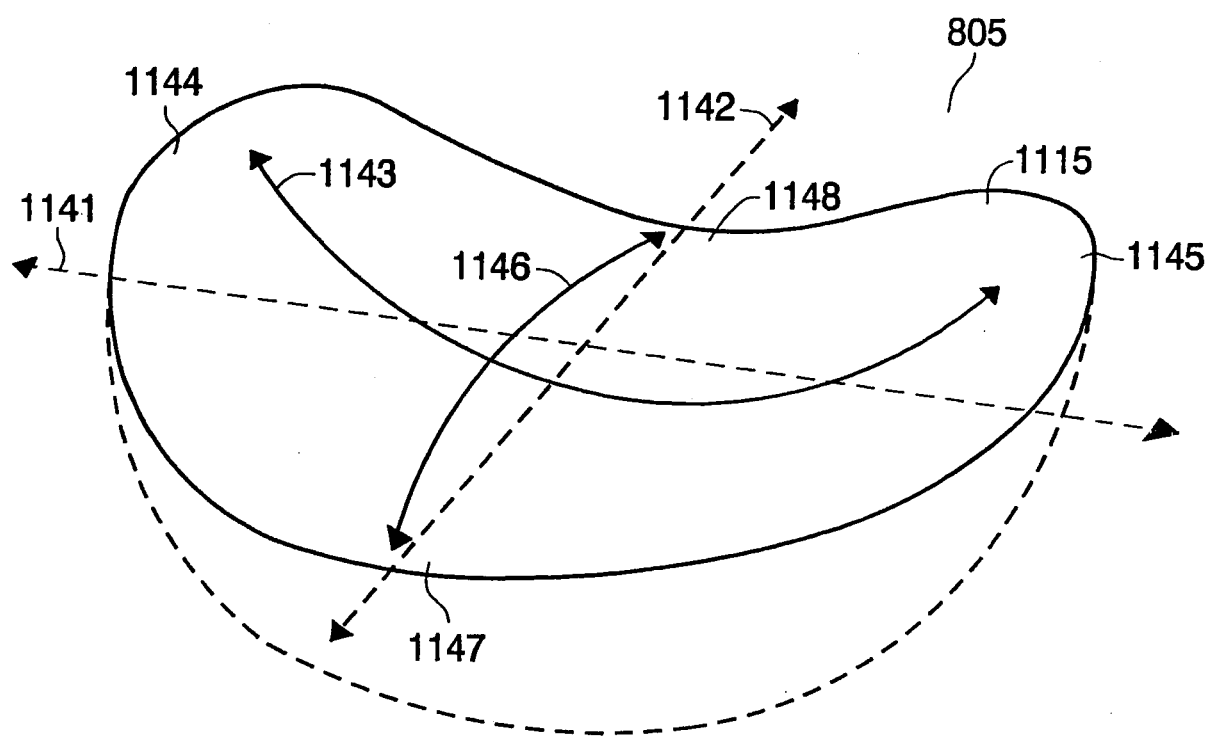
Figure 38A:
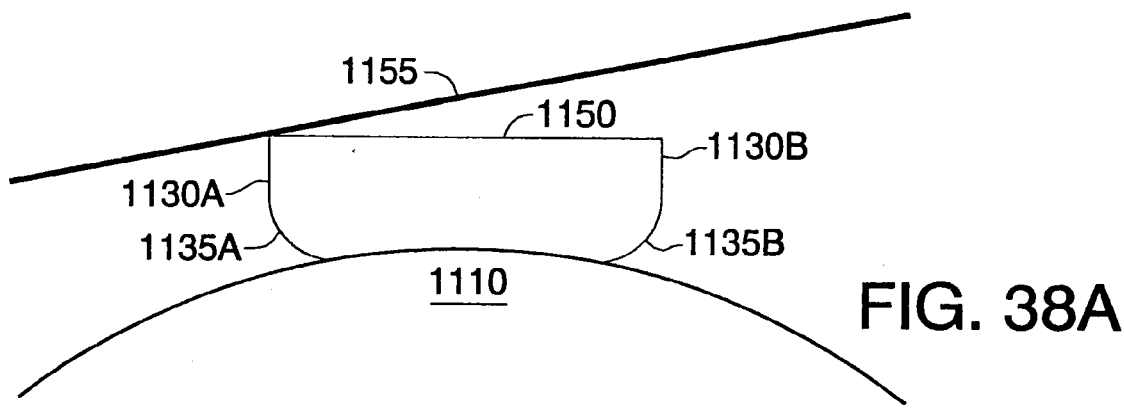
Figure 38B:
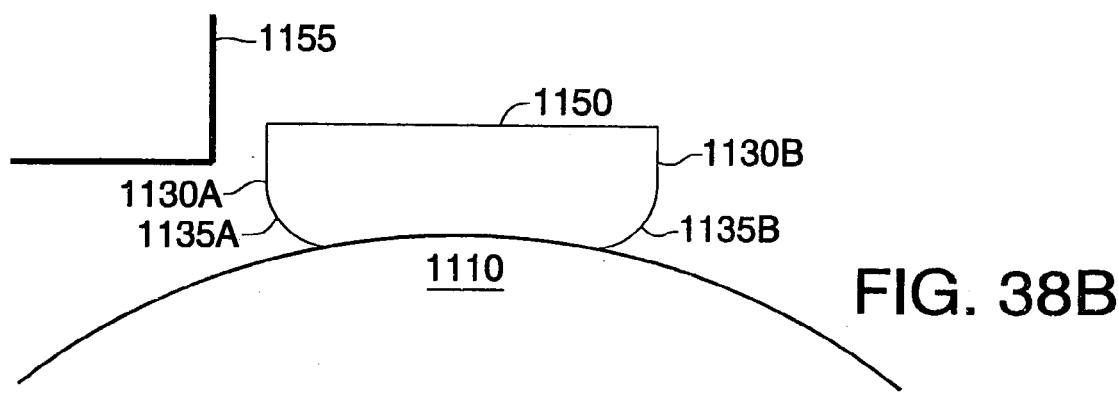
Figure 38C:
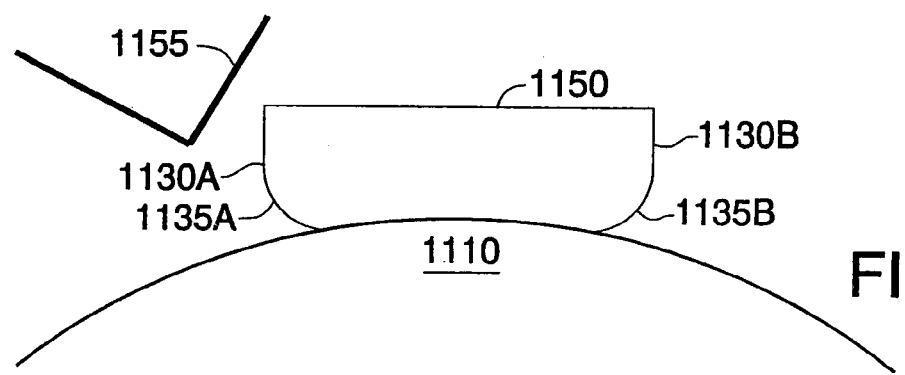
Figure 38D:
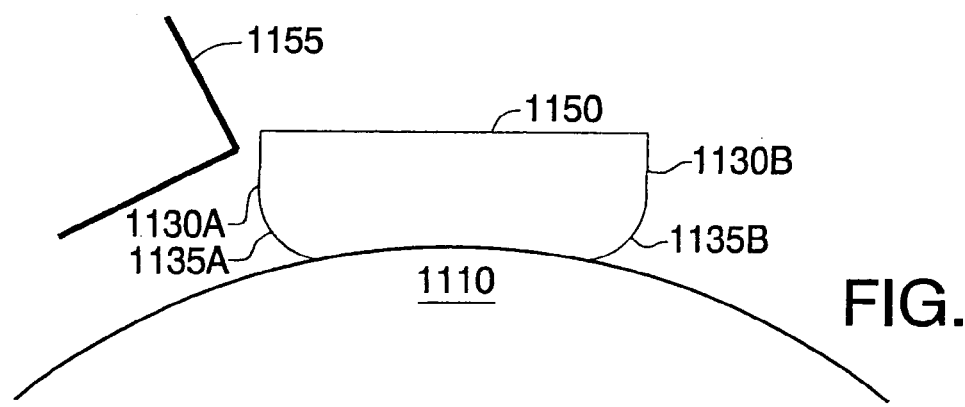

FIG. 36A shows a cross-section of housing 1100 of prior art sensor device taken along a line perpendicular to the line on which the cross-section shown in FIGS. 35A and 35B was taken. As seen in FIG. 36A, when housing 1100 is placed on a convex portion of body 1110, significant portions of housing 1100, specifically the lateral ends thereof indicated by the arrows in FIG. 36A, are not in contact body 1110. FIGS. 36B–H show a cross-section of housing 805 according to various aspects of the present invention taken along lines D—D shown in FIG. 23. As seen in FIG. 36B, bottom surface 1115 of housing 805 is provided with a generally concave shape adapted to receive the convex portion of body 1110. Referring to FIG. 36C, lateral ends 1130A and 1130B may be provided with radiused portions 1135A and 1135B adjacent to and including opposite lateral ends of bottom surface 1115, which allow housing 805 to rest in closer contact with body 1110, even when body 1110 flexes to an extreme degree, i.e., more than the anticipated maximum that it was designed for, and remove sharp edges 1140A and 1140B shown in FIG. 36B, providing for more comfortable wear. As shown in FIG. 36D, body 1110 will tend to conform to the shape of housing 805 when body 1110 is in a relaxed condition. As shown in FIGS. 36E and 36F, good contact with body 1110 is maintained at the points illustrated by the arrows when body 1110 is flexed in a manner that decreases the convex shape thereof or that creates a convexity therein. Thus, it will be appreciated that it is advantageous to place sensors or sensing elements at the points indicated by the arrows because those points will tend to remain in contact with body 1110. FIGS. 36G and 36H, showing, for example, heat flux skin interface lo component 835 and skin temperature skin interface component 840 placed at the points indicated by the arrows, illustrate this point. As seen in FIGS. 36G and 36H, there is more than point contact between body 1110 and skin temperature skin interface component 840.

Figure 37:
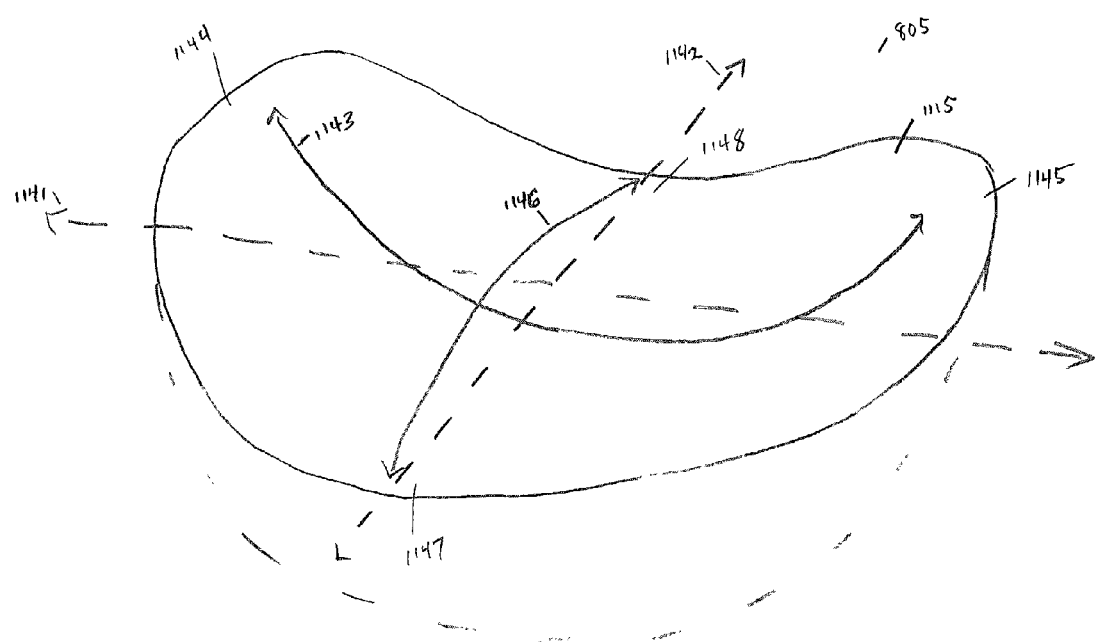
FIG. 37 is an isometric view of an embodiment of a housing for a sensor device according to the present invention having a bottom or inner surface having a concavity in one direction and a convexity in another direction.
Figure 38A:
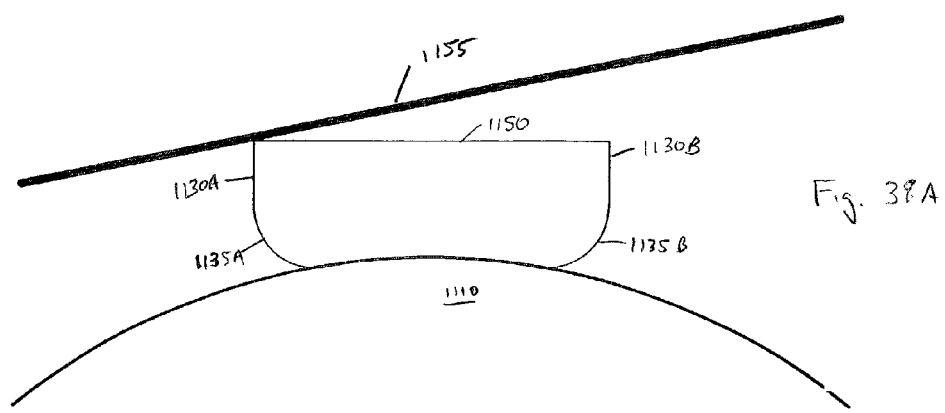
FIGS. 38A through D are cross-sectional views of a housing for a sensor device having a flat top surface and flat lateral ends.
Figure 38B:
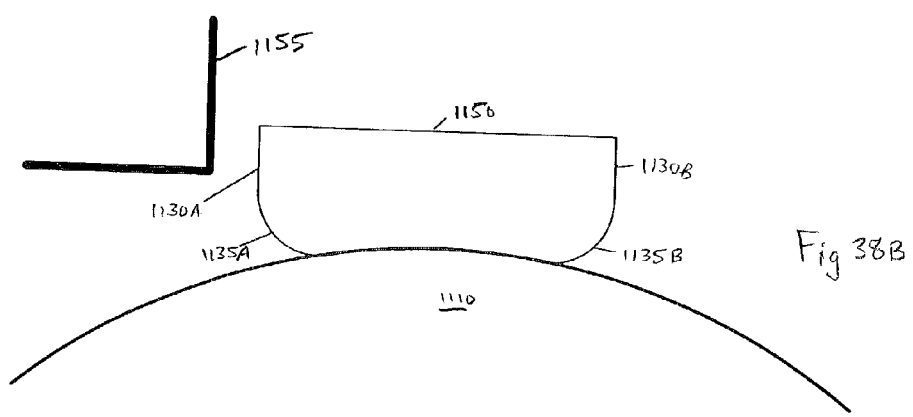
Figure 38C:
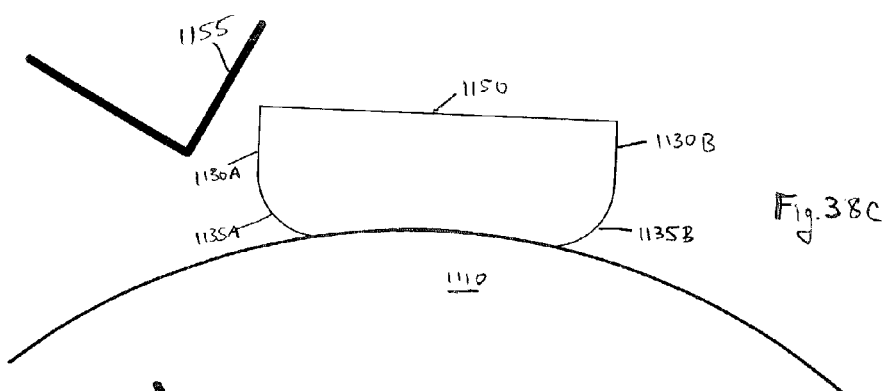
Figure 38D:
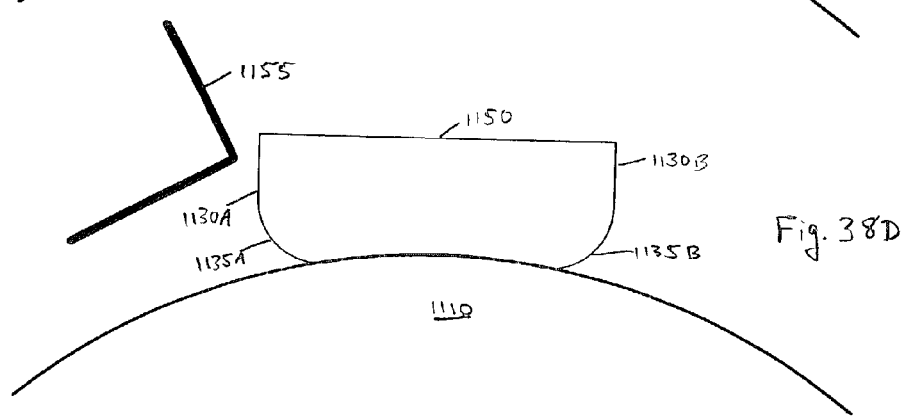

FIG. 37 is an isometric view of housing 805 according to an embodiment of the present invention in which bottom surface 1115 has both the generally convex shape shown in FIGS. 35C–H and the generally concave shape shown in FIGS. 36B–H. Specifically, bottom surface 1115, which is the inner surface of housing 805 for mounting adjacent to the body of the wearer, includes a longitudinal axis 1141 and a transverse axis 1142. Bottom surface 115 has a generally concave shape having an axis of concavity 1143 that is coincident with longitudinal axis 1141, meaning that it runs in a first direction from first lateral end 1144 of inner surface 1115 to second lateral end 1145 of inner surface 1115. Bottom surface 1115 has a generally convex shape having an axis of convexity 1146 that is coincident with transverse axis 1142, meaning that it runs in a second direction from third lateral end 1147 of inner surface 1115 to fourth lateral end 1148 of inner surface 1115. As seen if FIG. 37, the first and second directions, and longitudinal axis 1141 and transverse axis 1142, are generally perpendicular to one another.

Figure 39A:
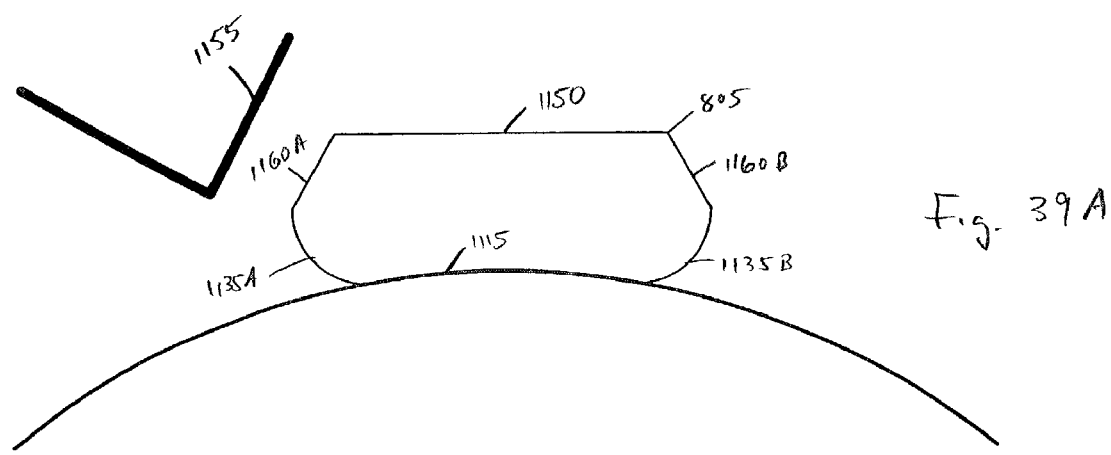
FIGS. 39A through F are cross-sectional views of various embodiments of a housing for a sensor device having surfaces designed to deflect objects and prevent movement of the housing.
Figure 39B:
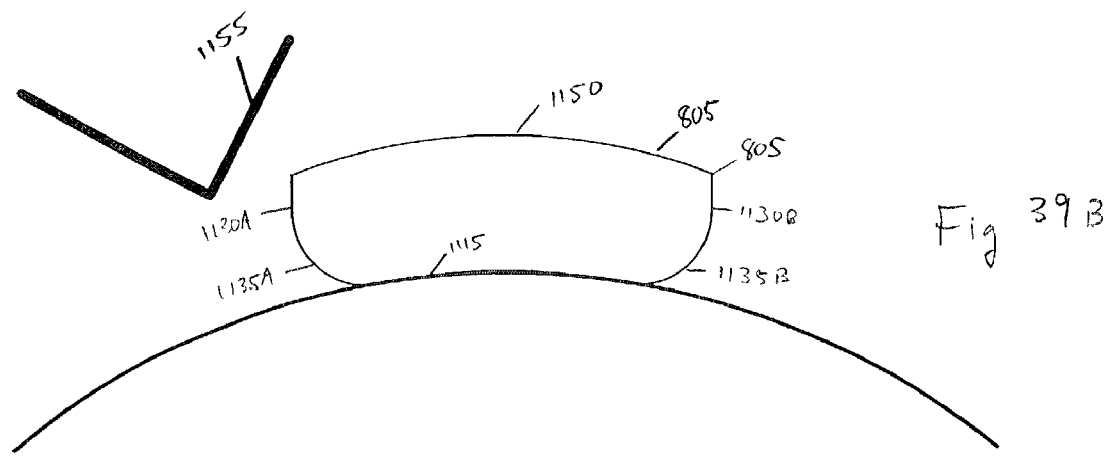
Figure 39C:
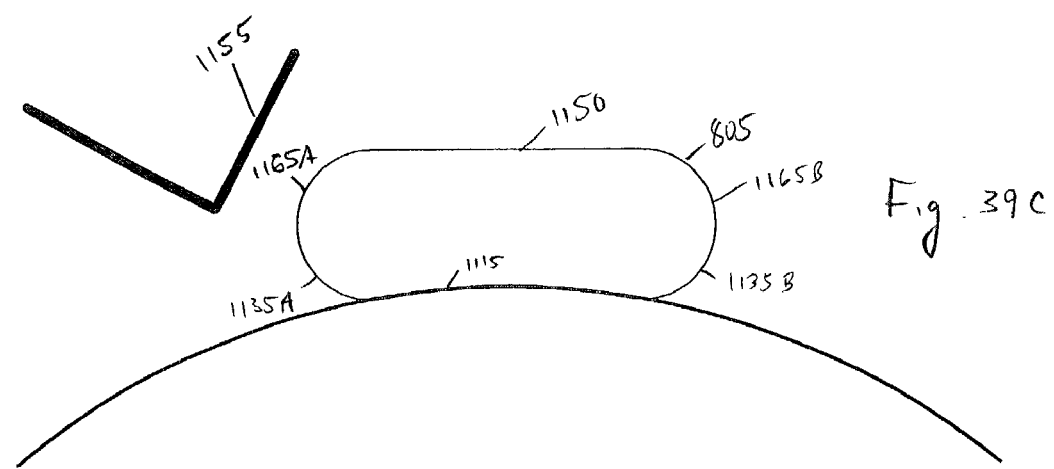
Figure 39:
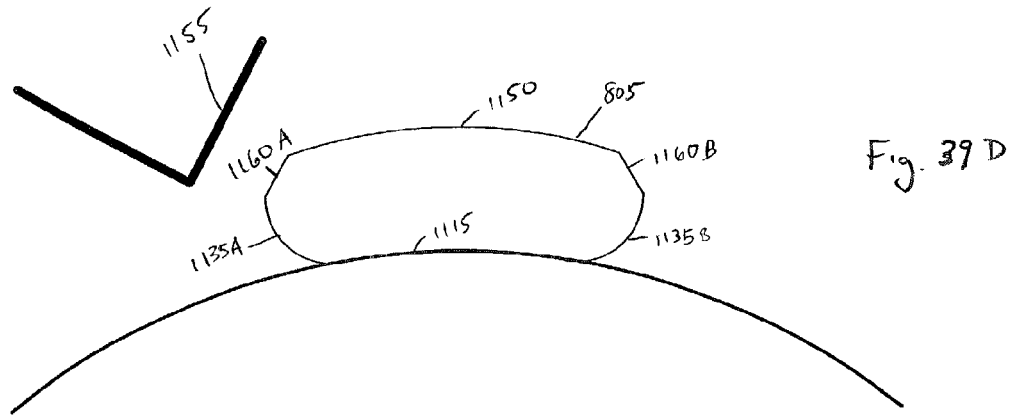
FIG. 39G is a cross-sectional view of the housing shown in FIG. 39E attached to a flexible section.
Figure 39:
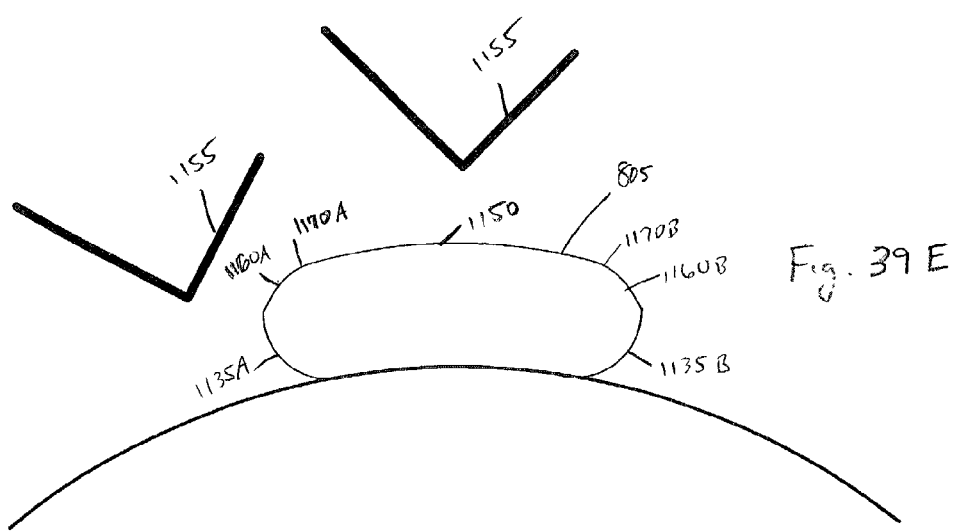
Figure 39:
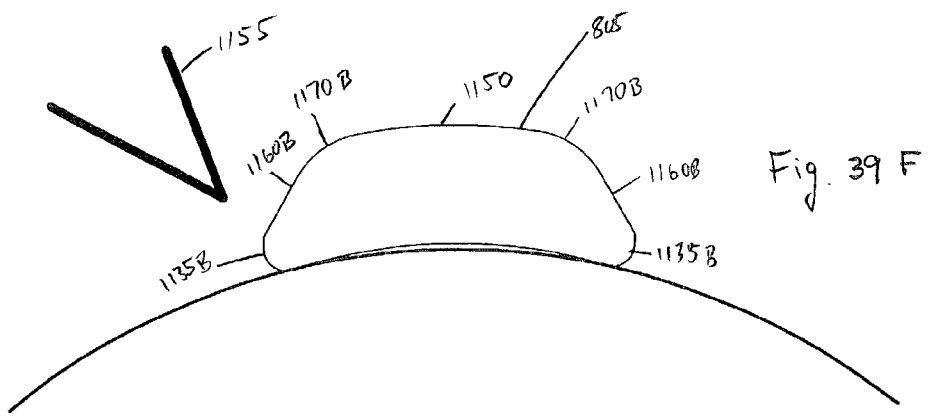
Figure 1:
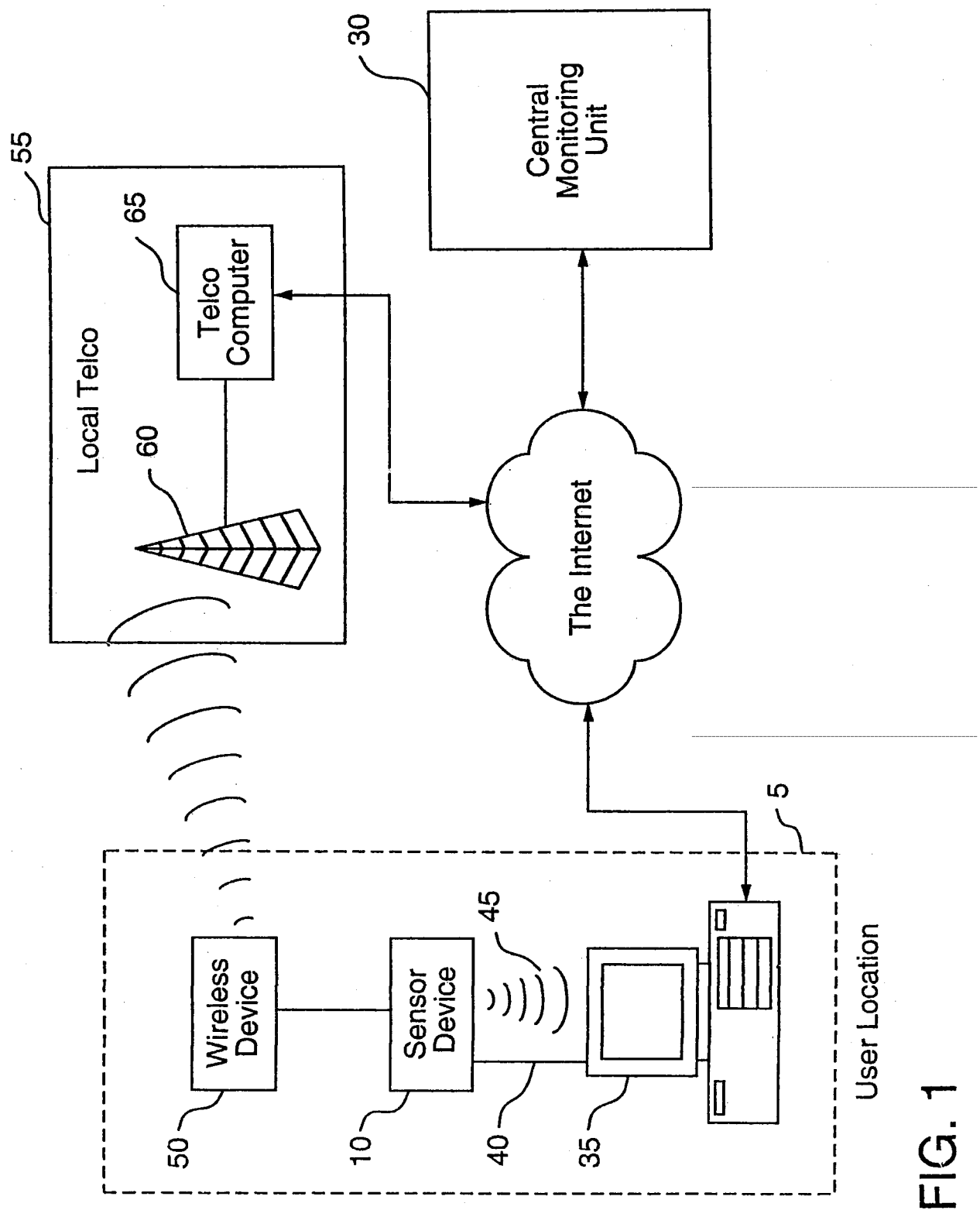
Figure 2:
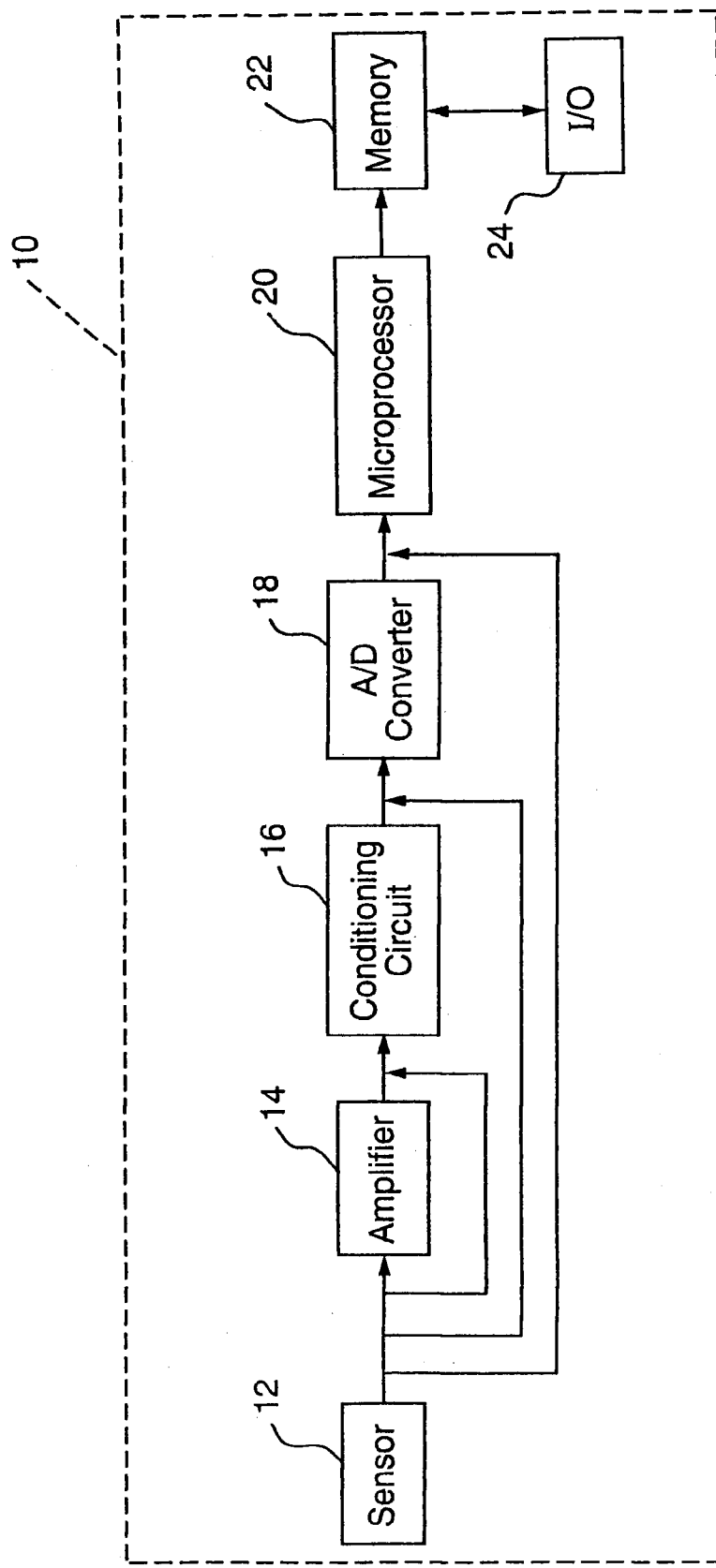
Figure 3:
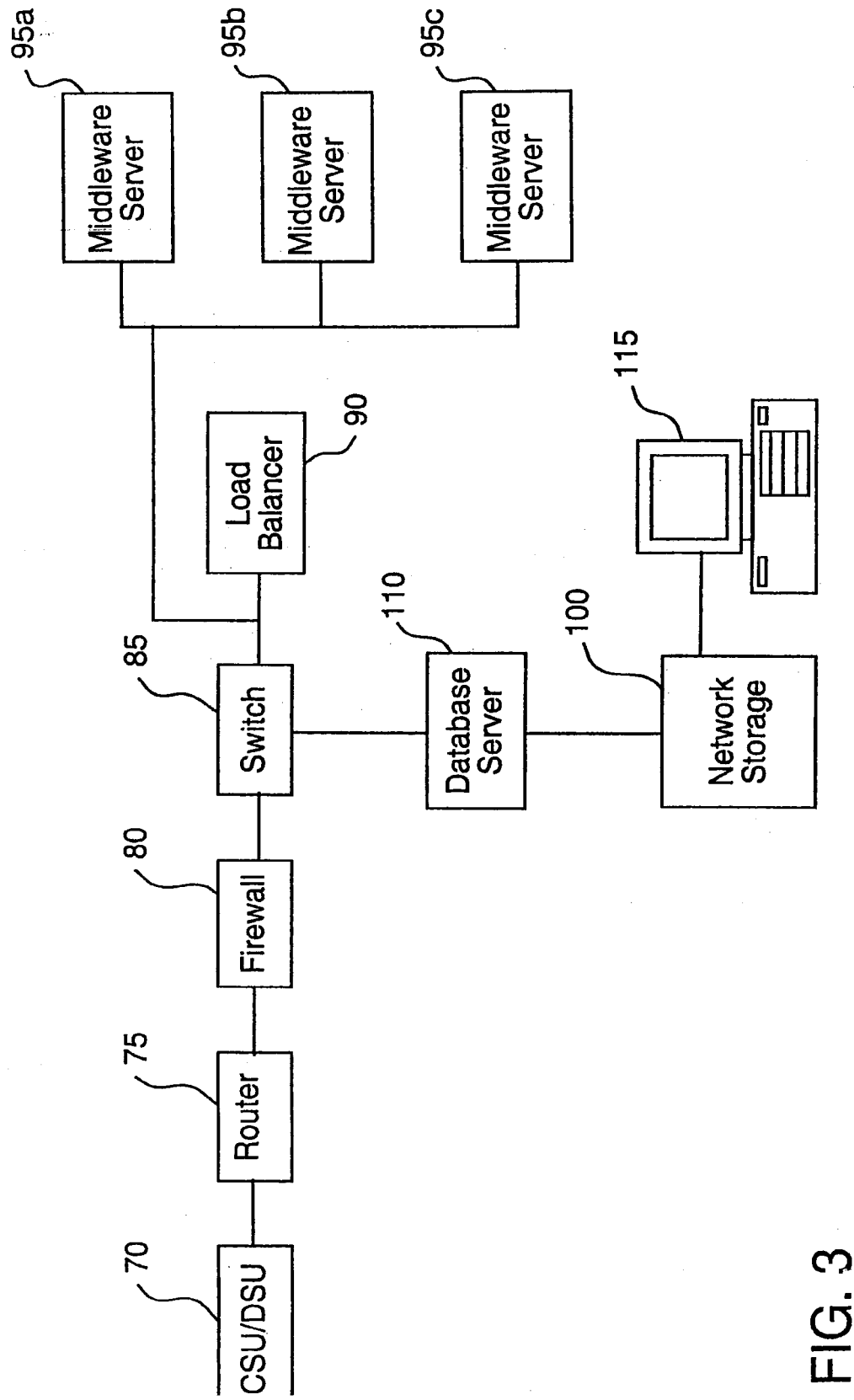
Figure 4:
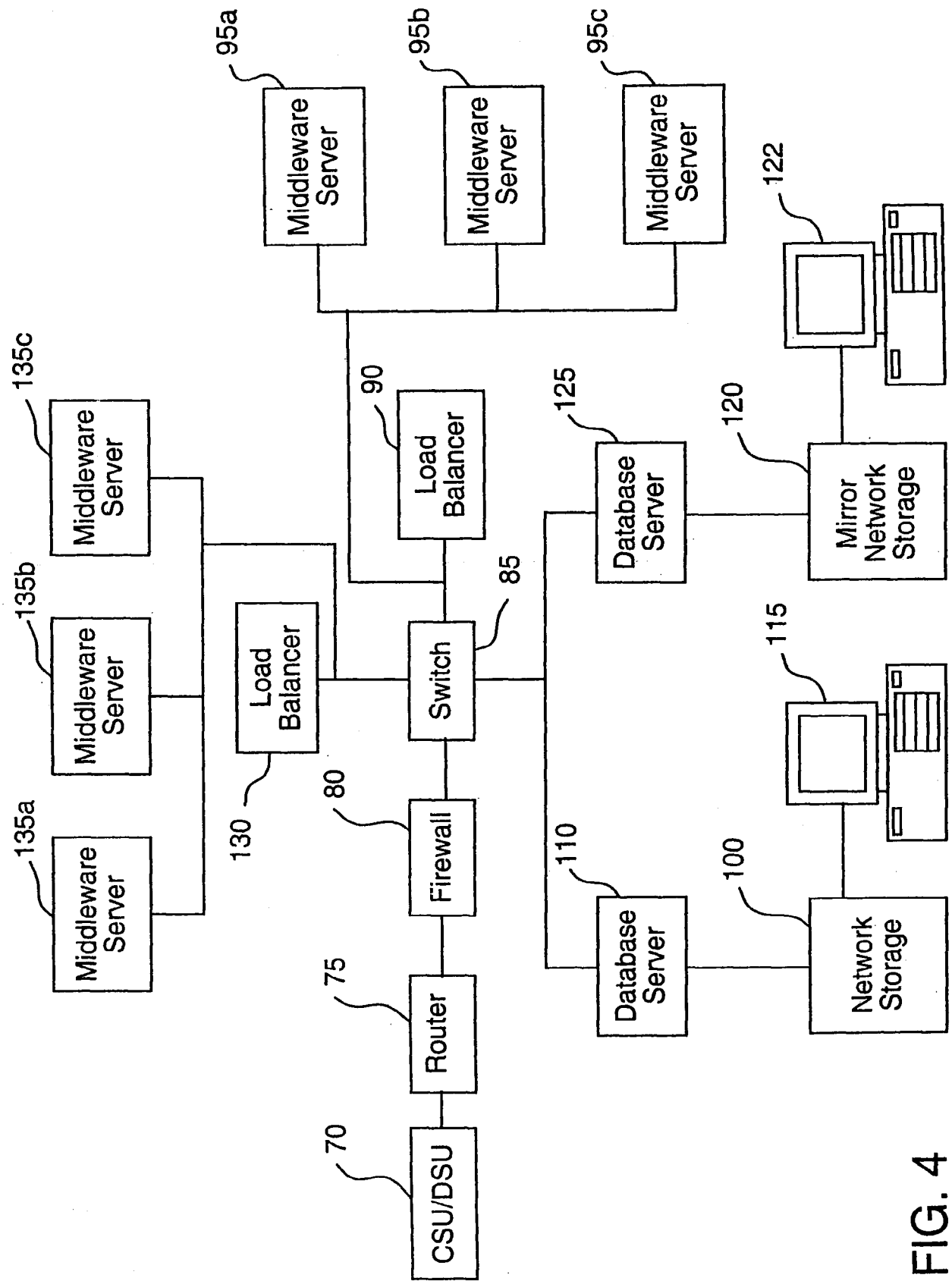
Figure 5:
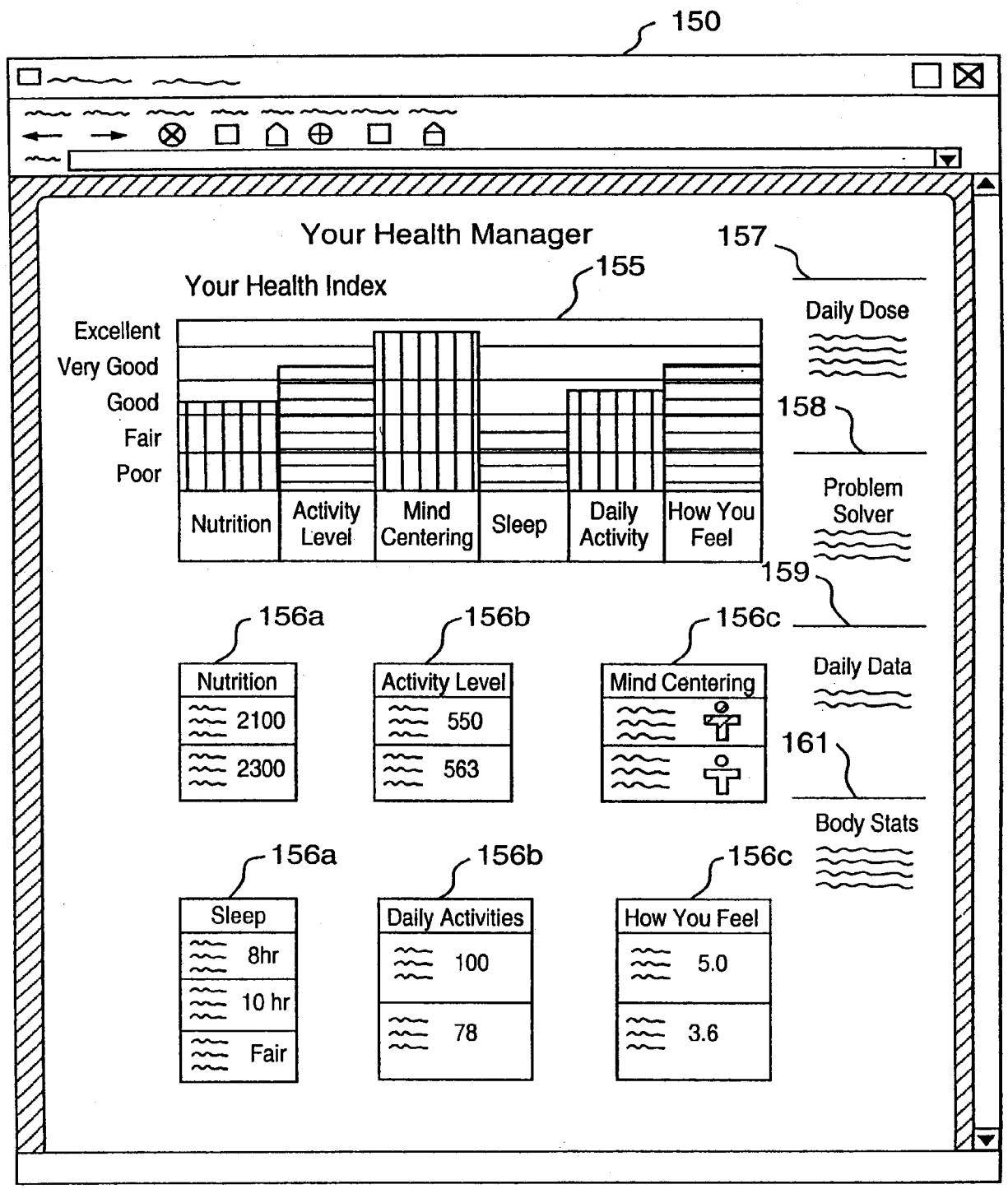
Figure 6:
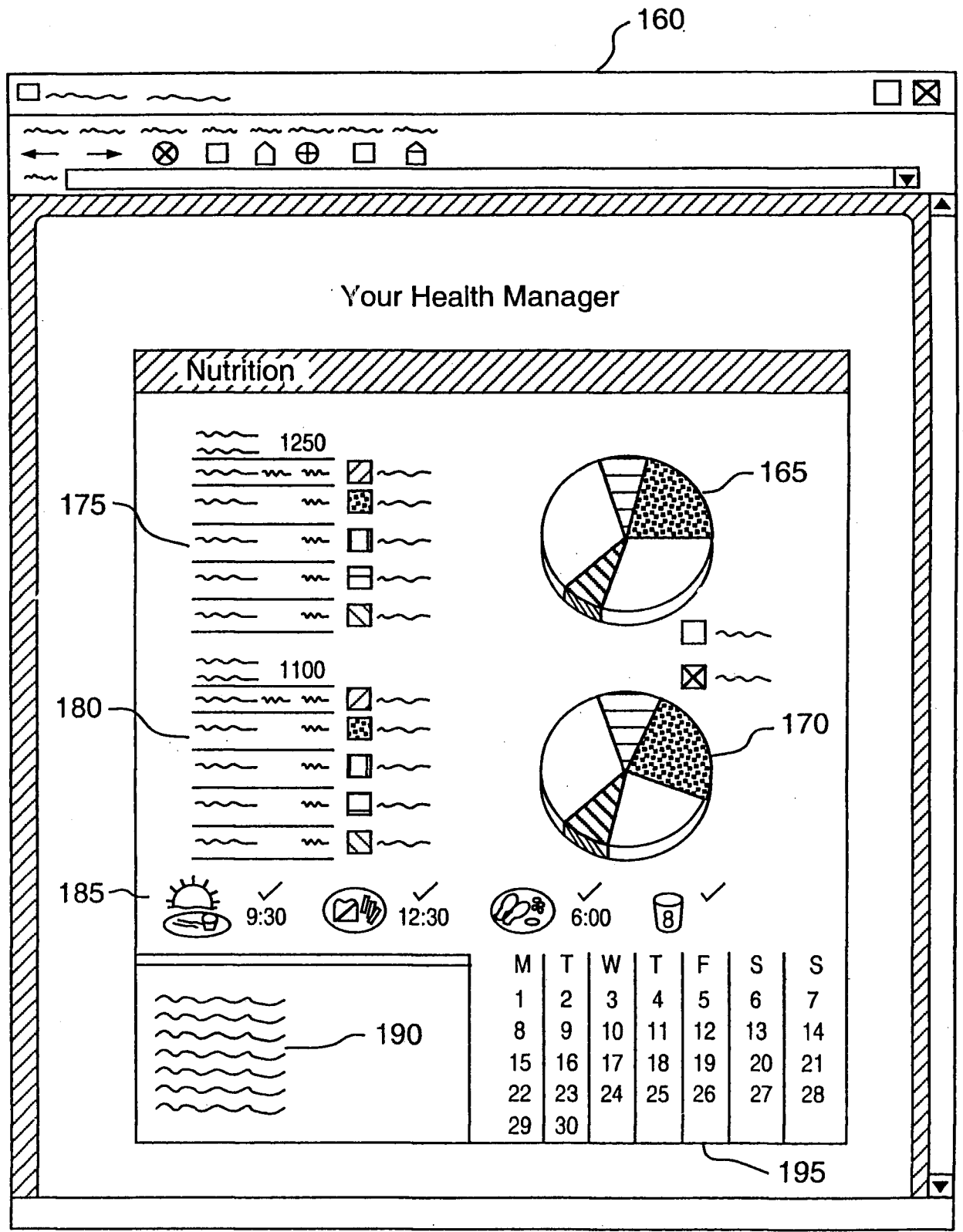
Figure 7:
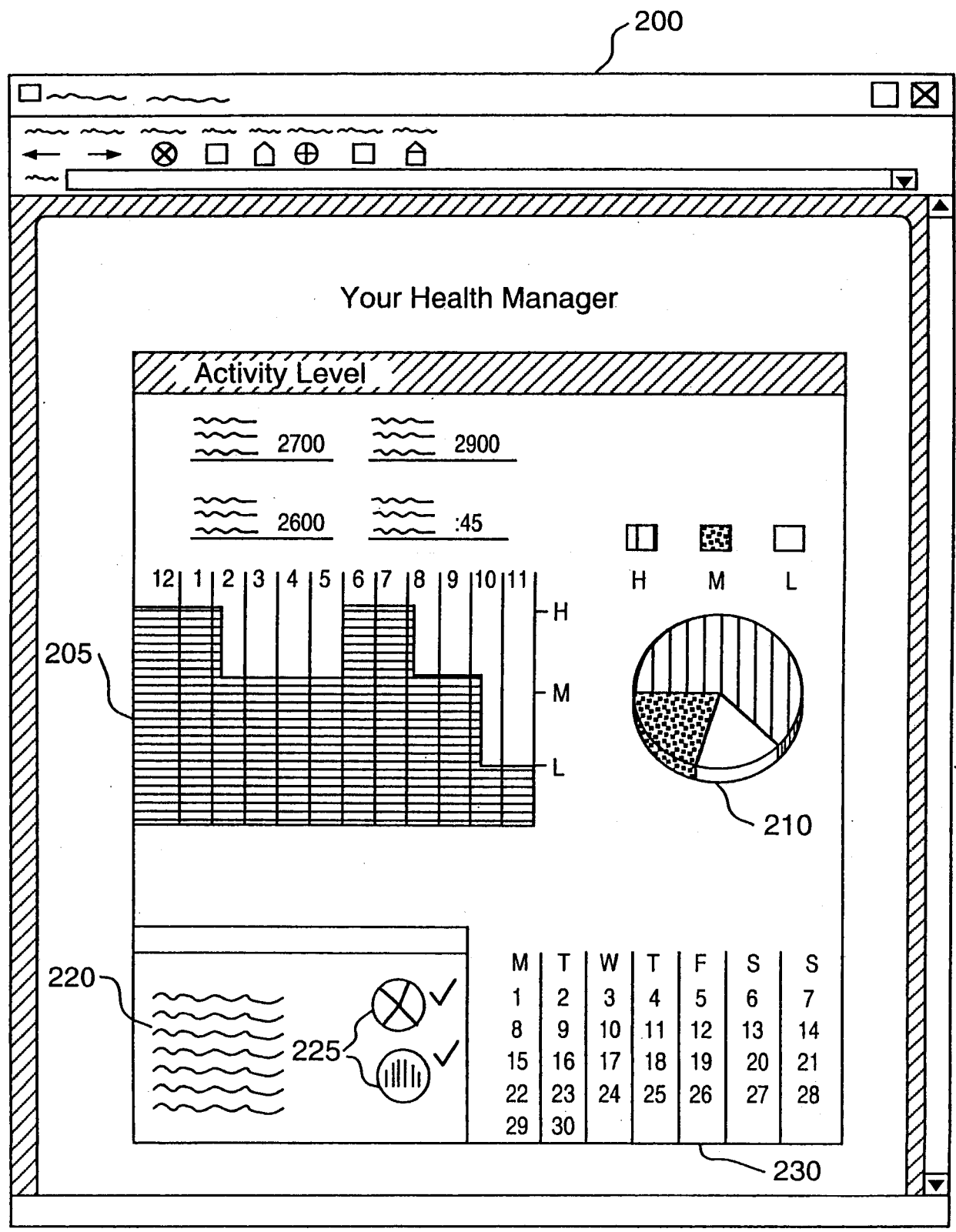
Figure 8:
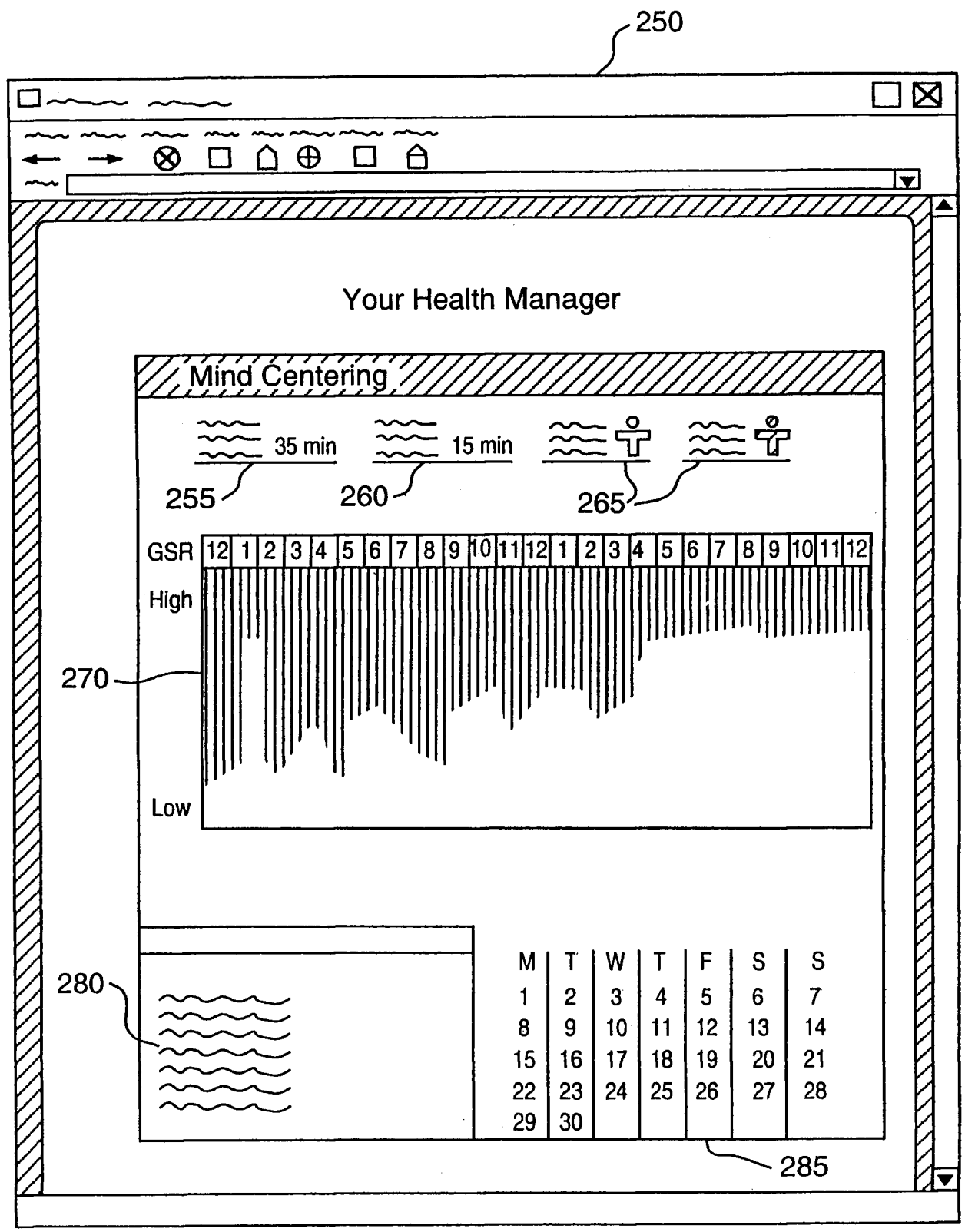
Figure 9:
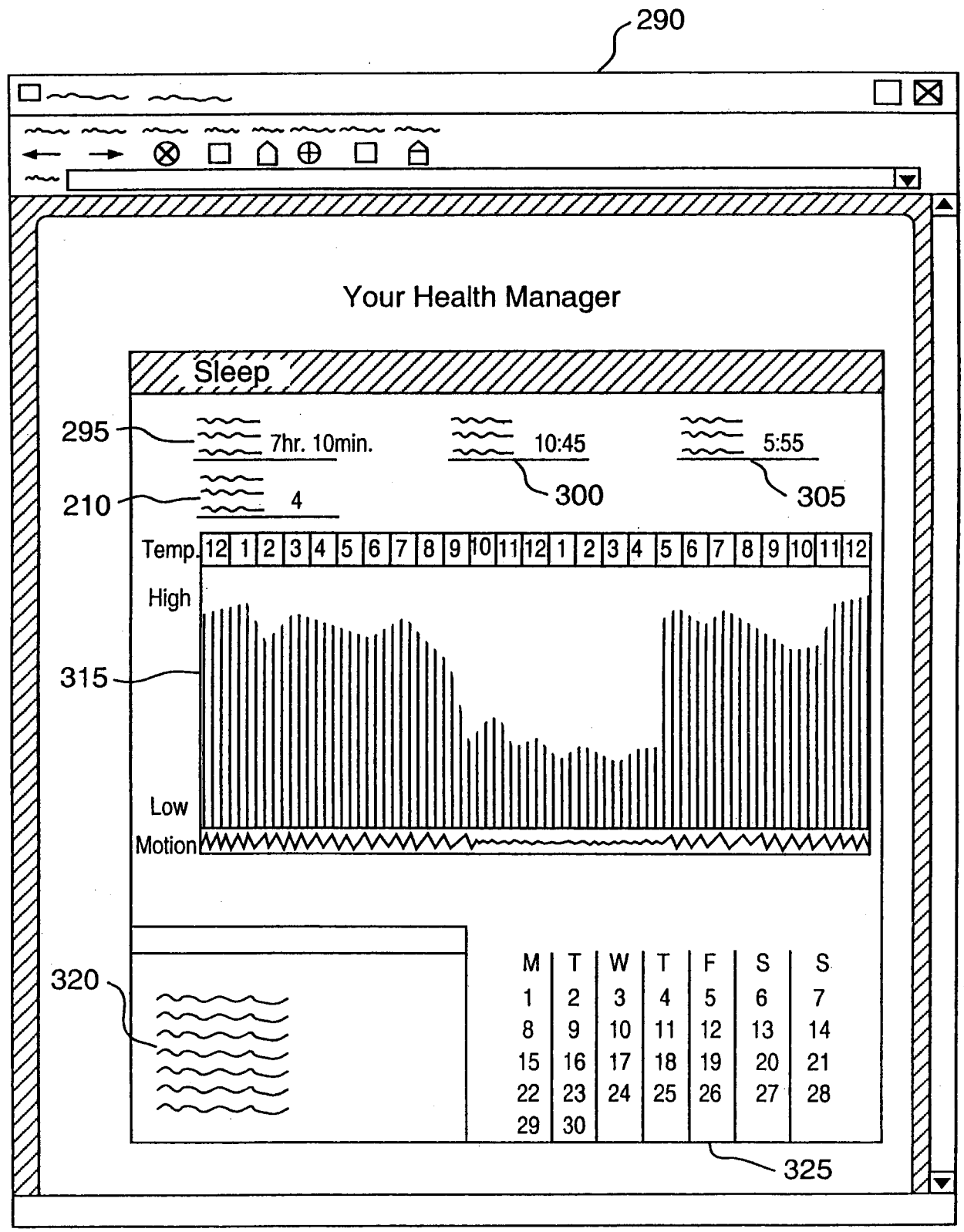
Figure 10:
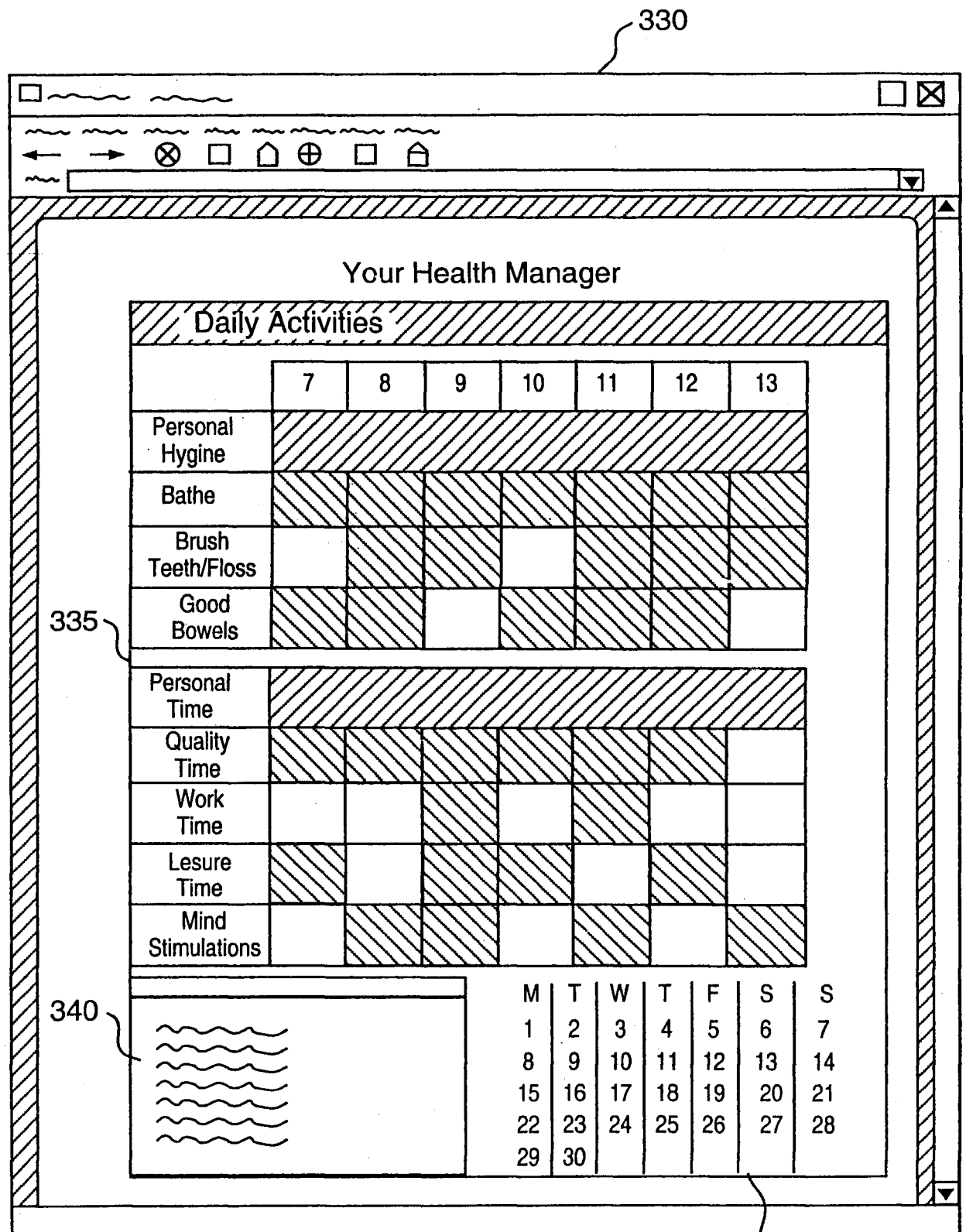
Figure 11:
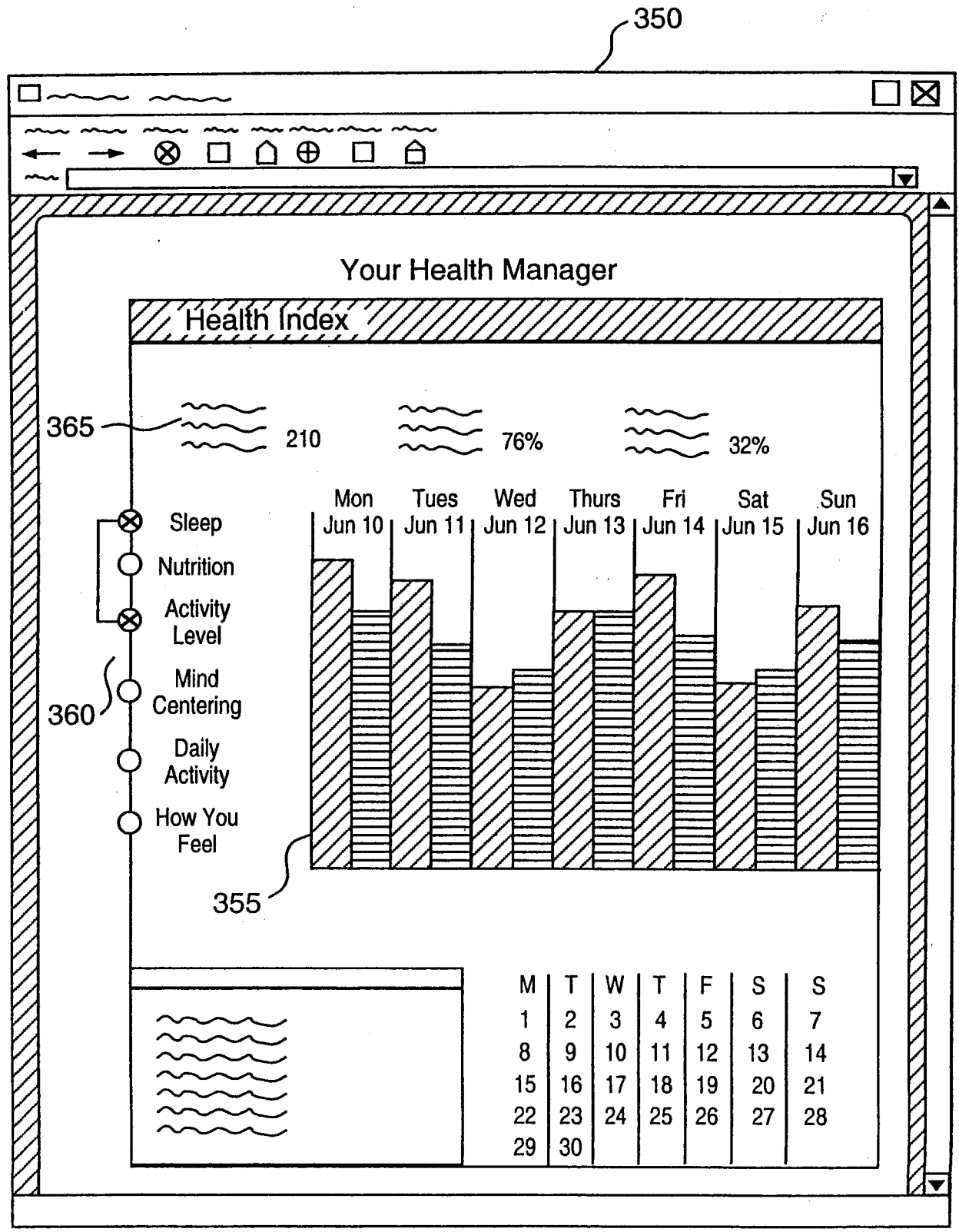
Figure 12:
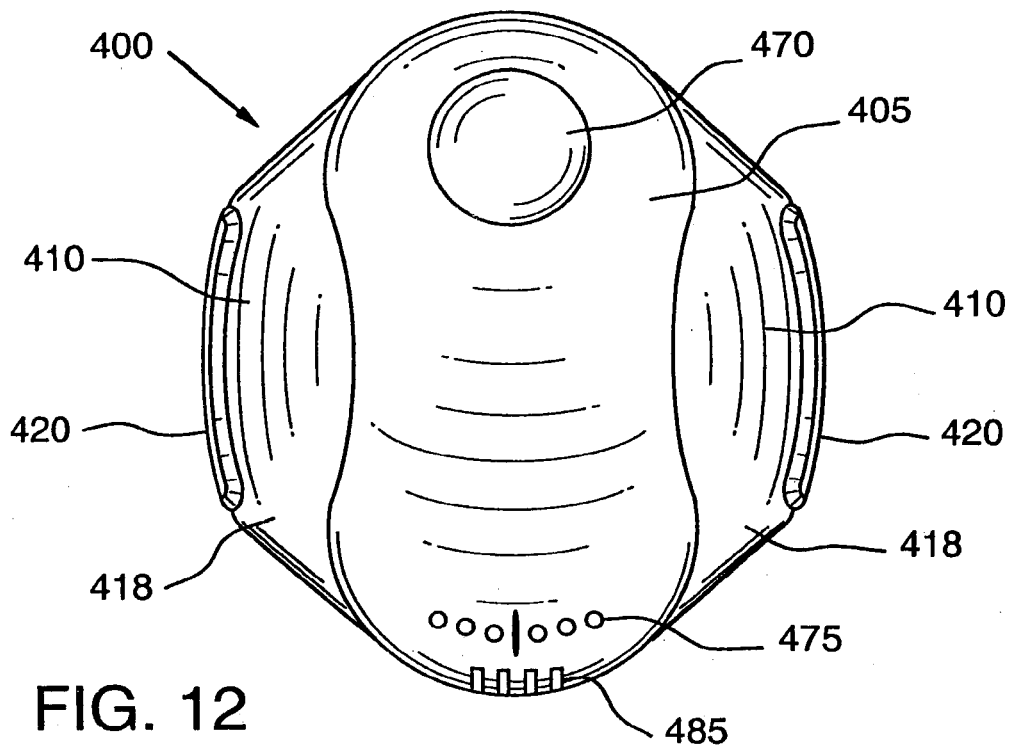
Figure 13:
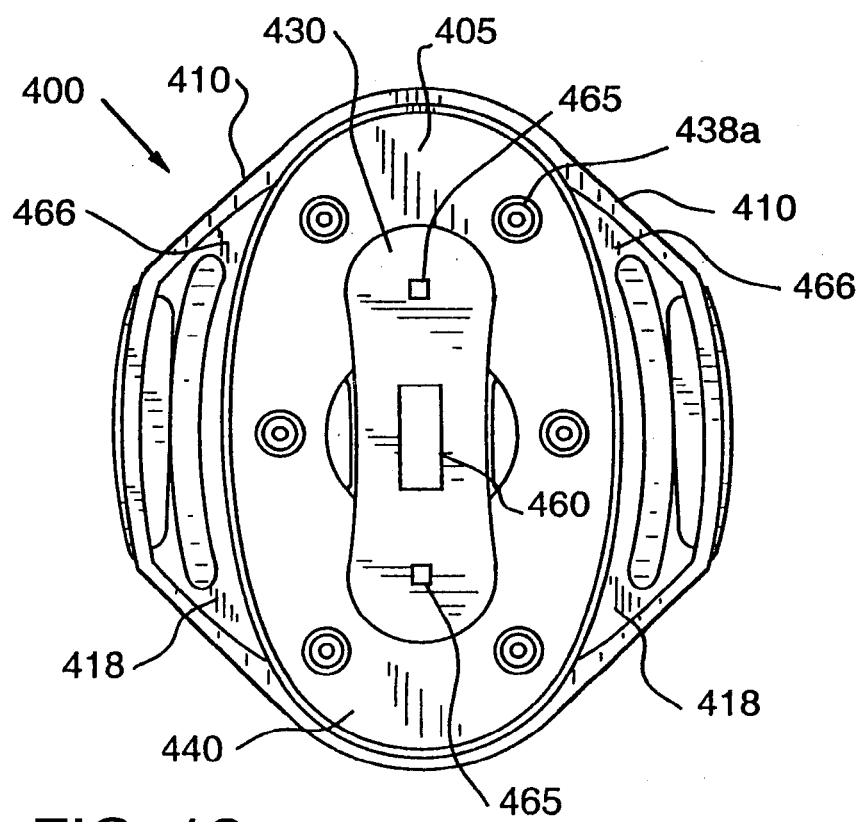
Figure 14:
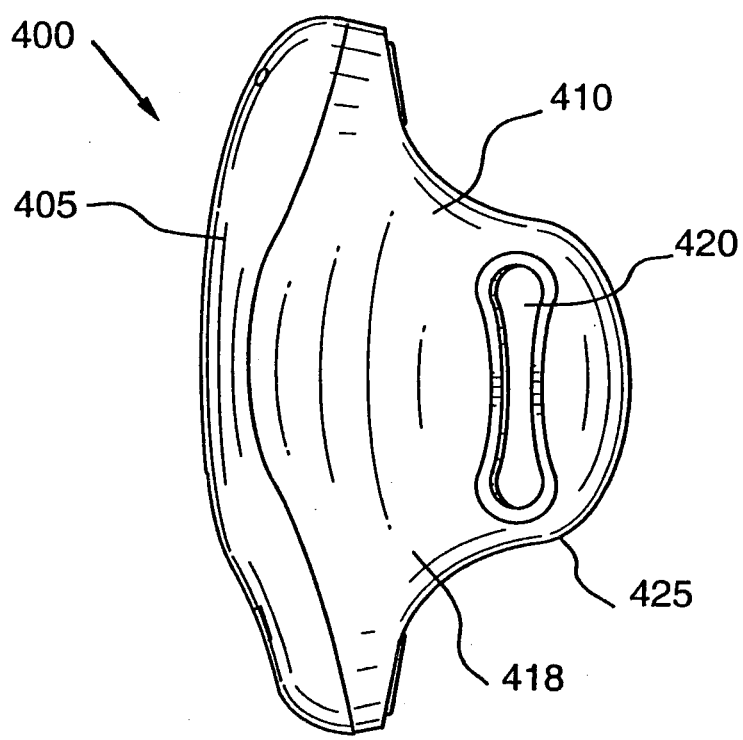
Figure 15:
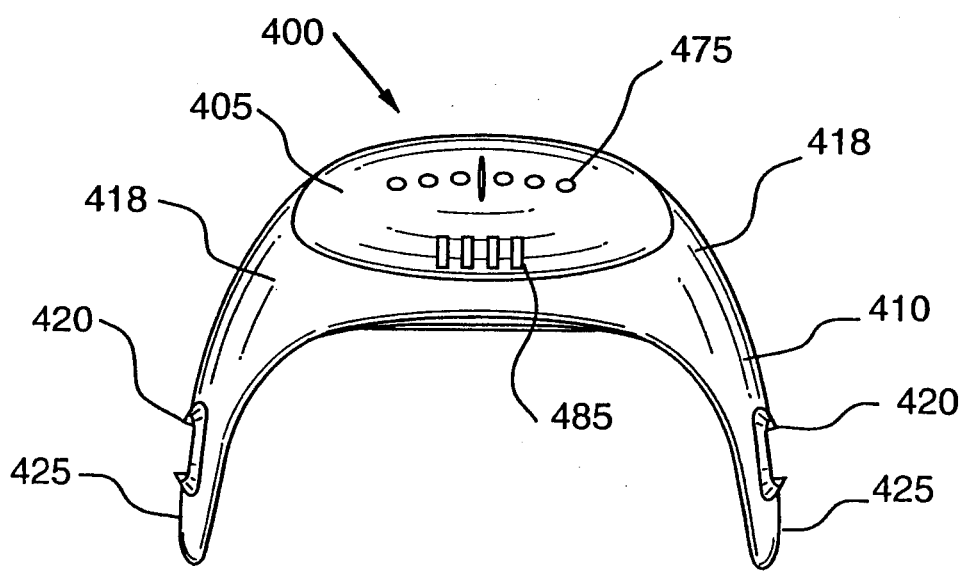
Figure 16:
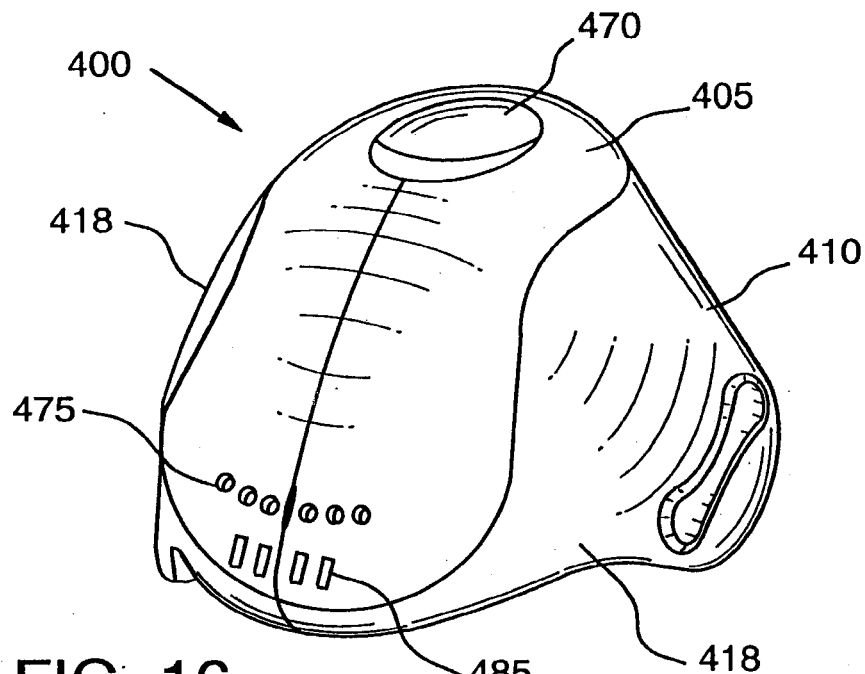
Figure 17:
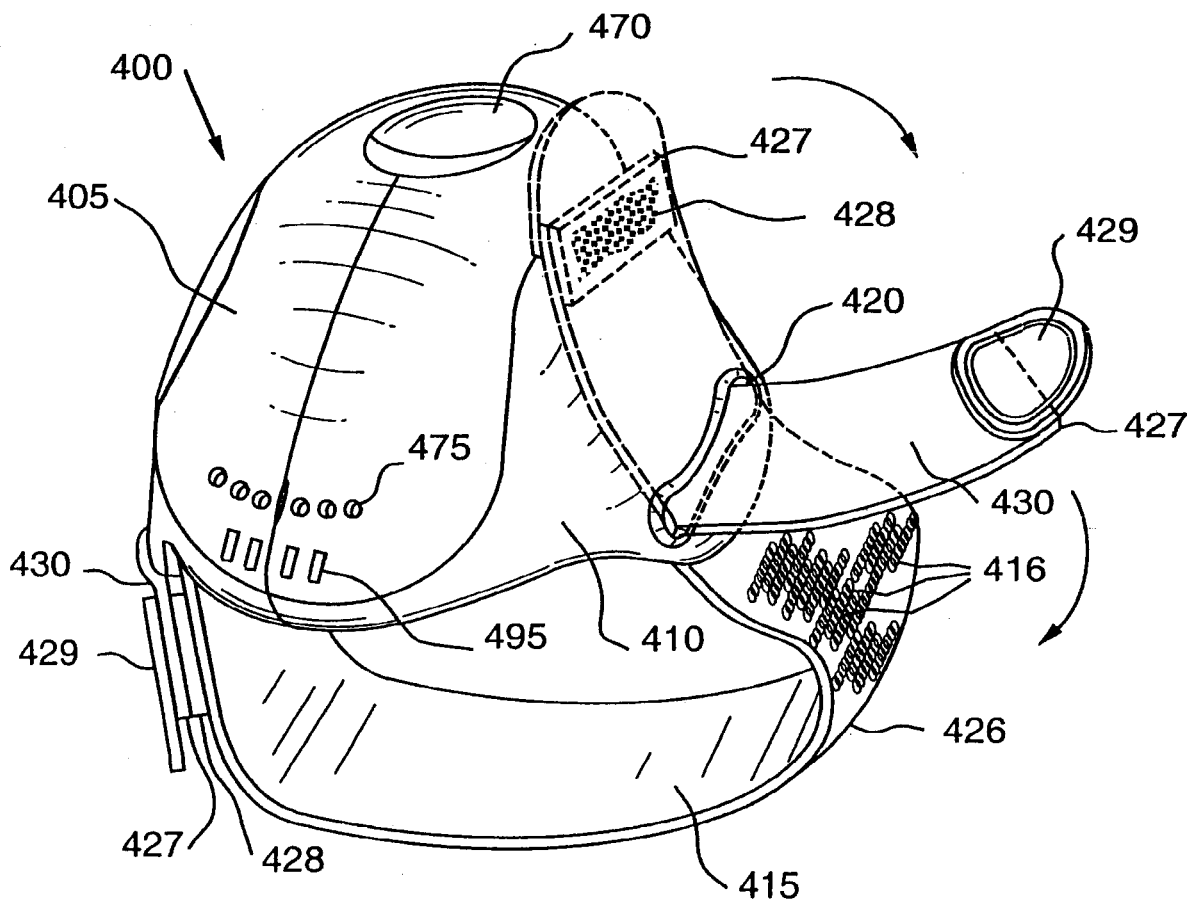
Figure 18:
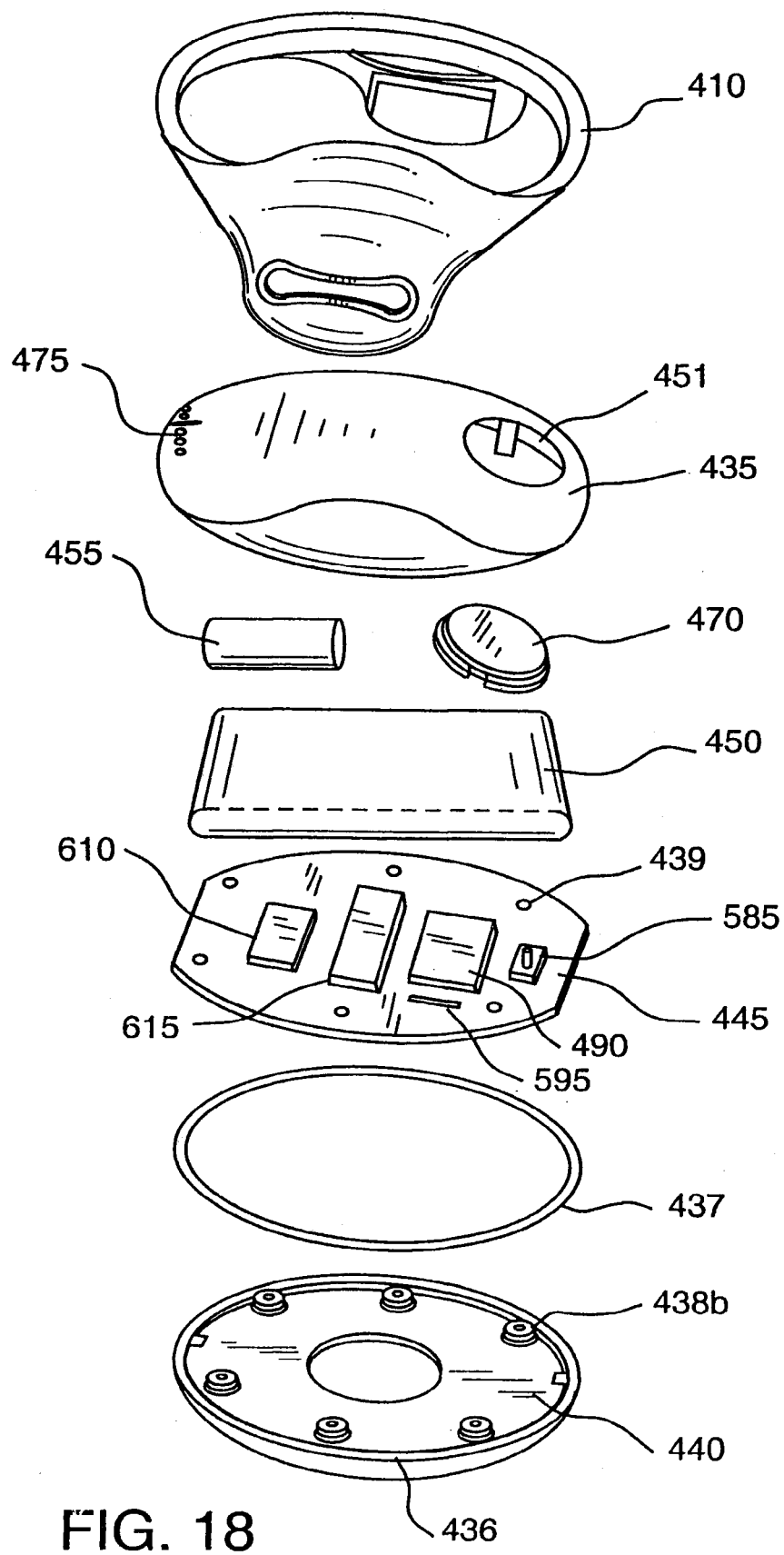
Figure 39A:
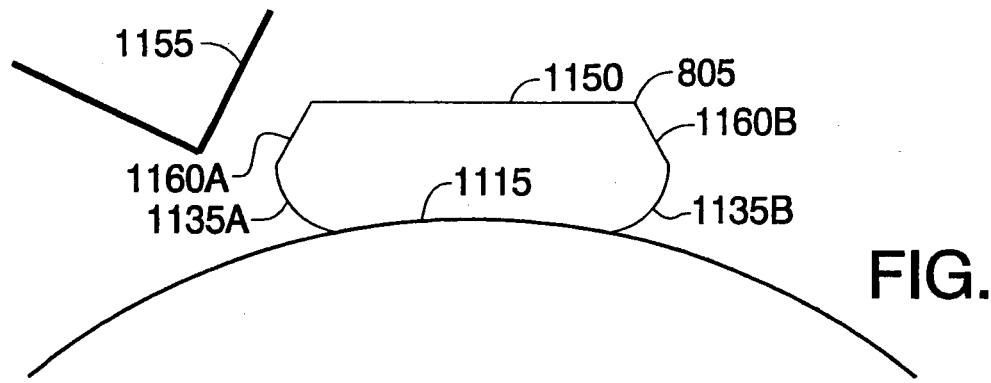
Figure 39B:
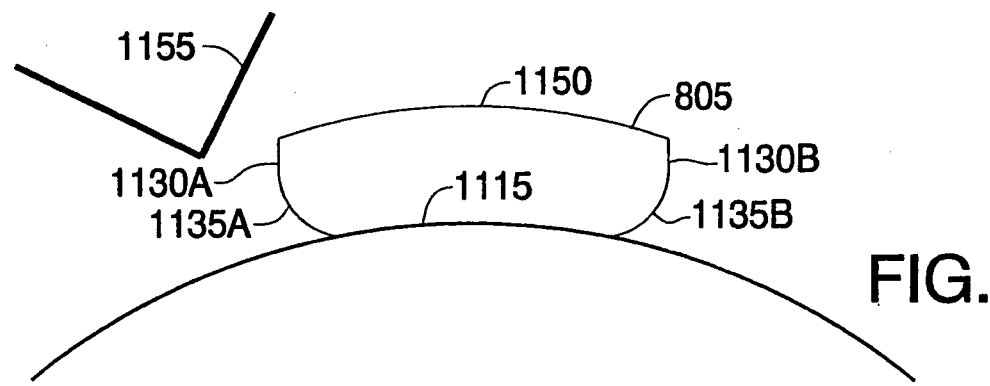
Figure 39C:
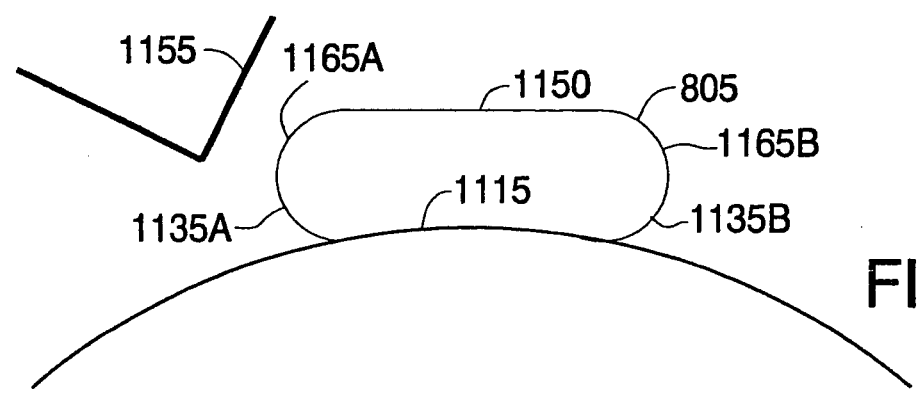
Figure 39D:
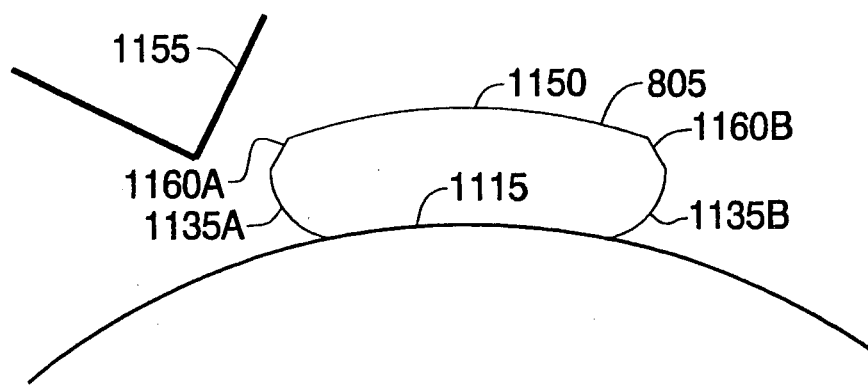
Figure 39E:
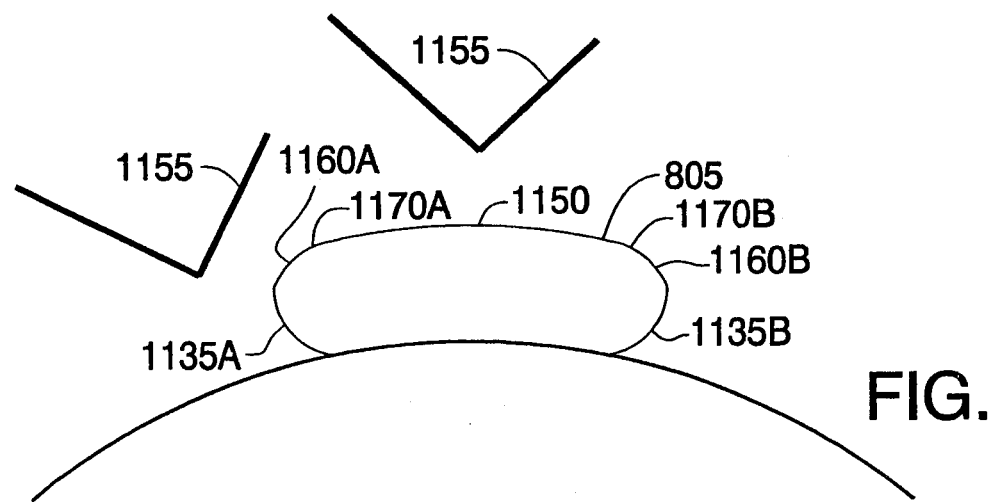
Figure 39F:
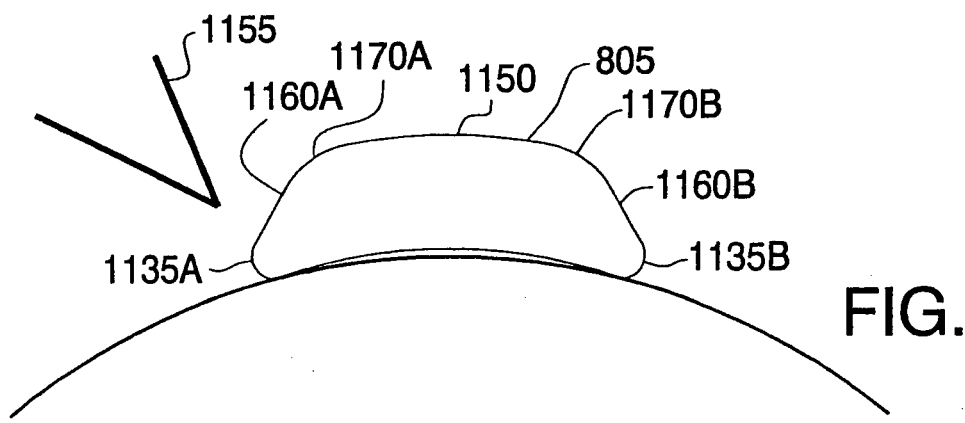
Figure 39G:
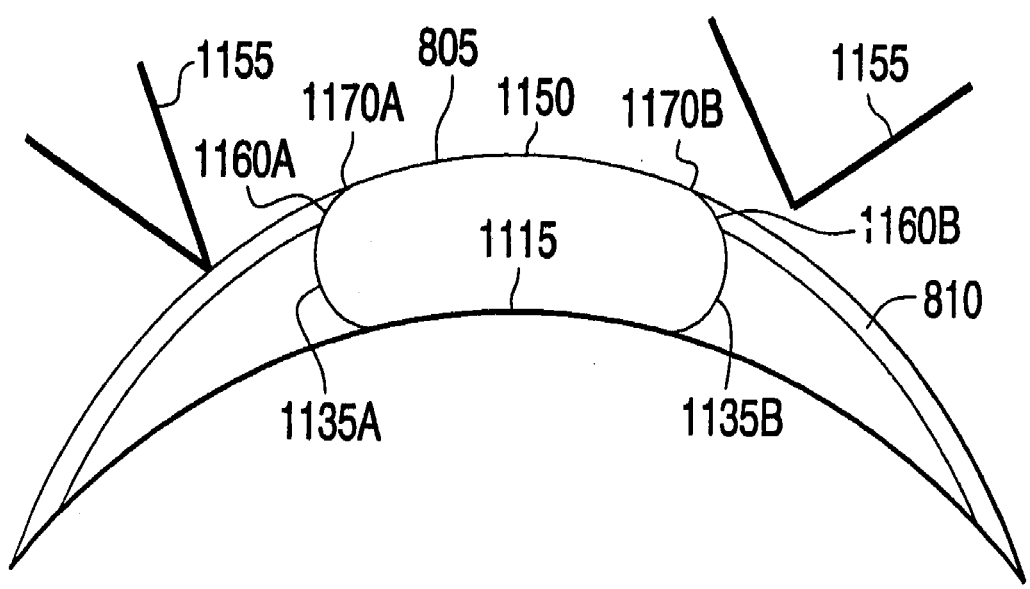
Figure 1:
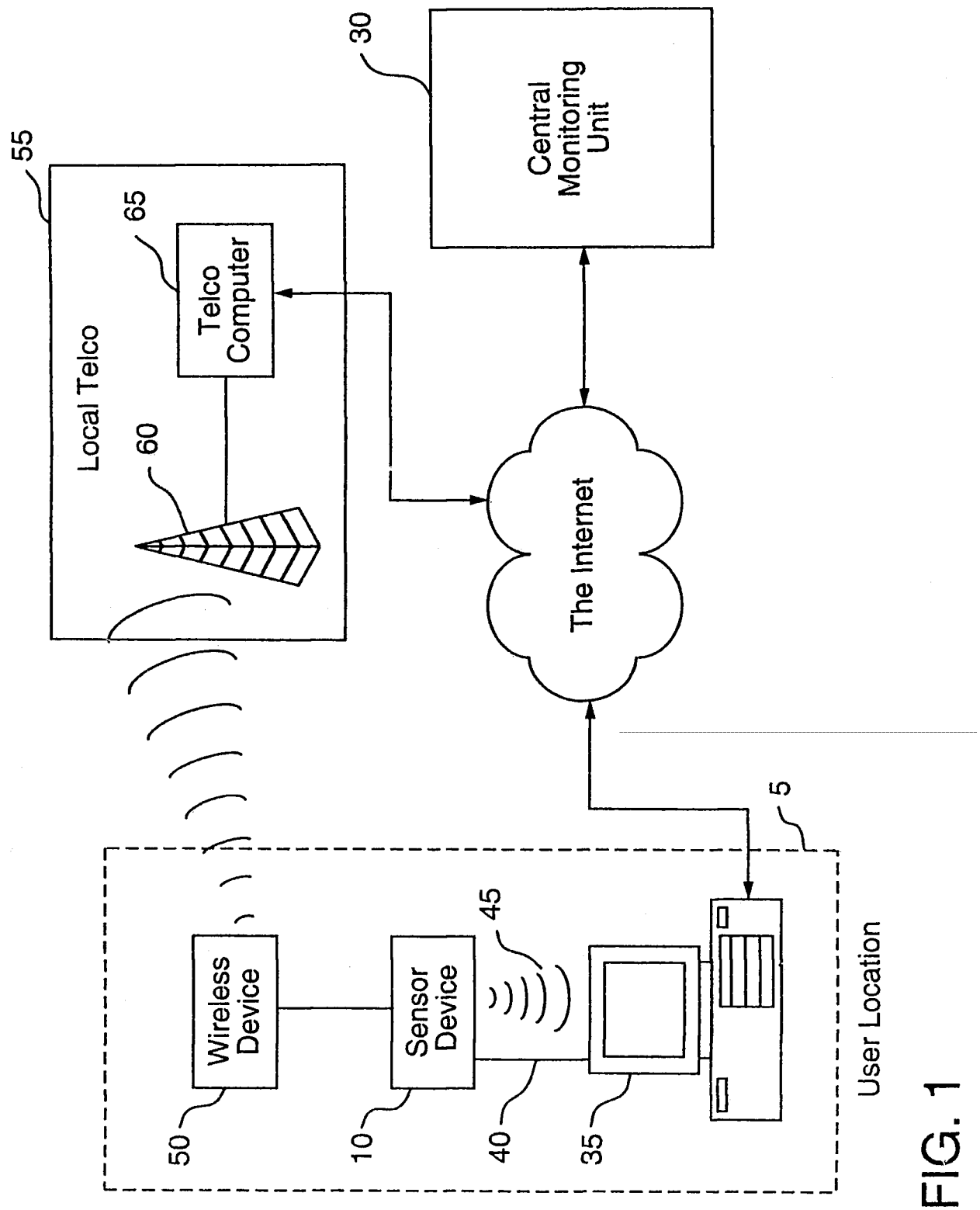
Figure 2:
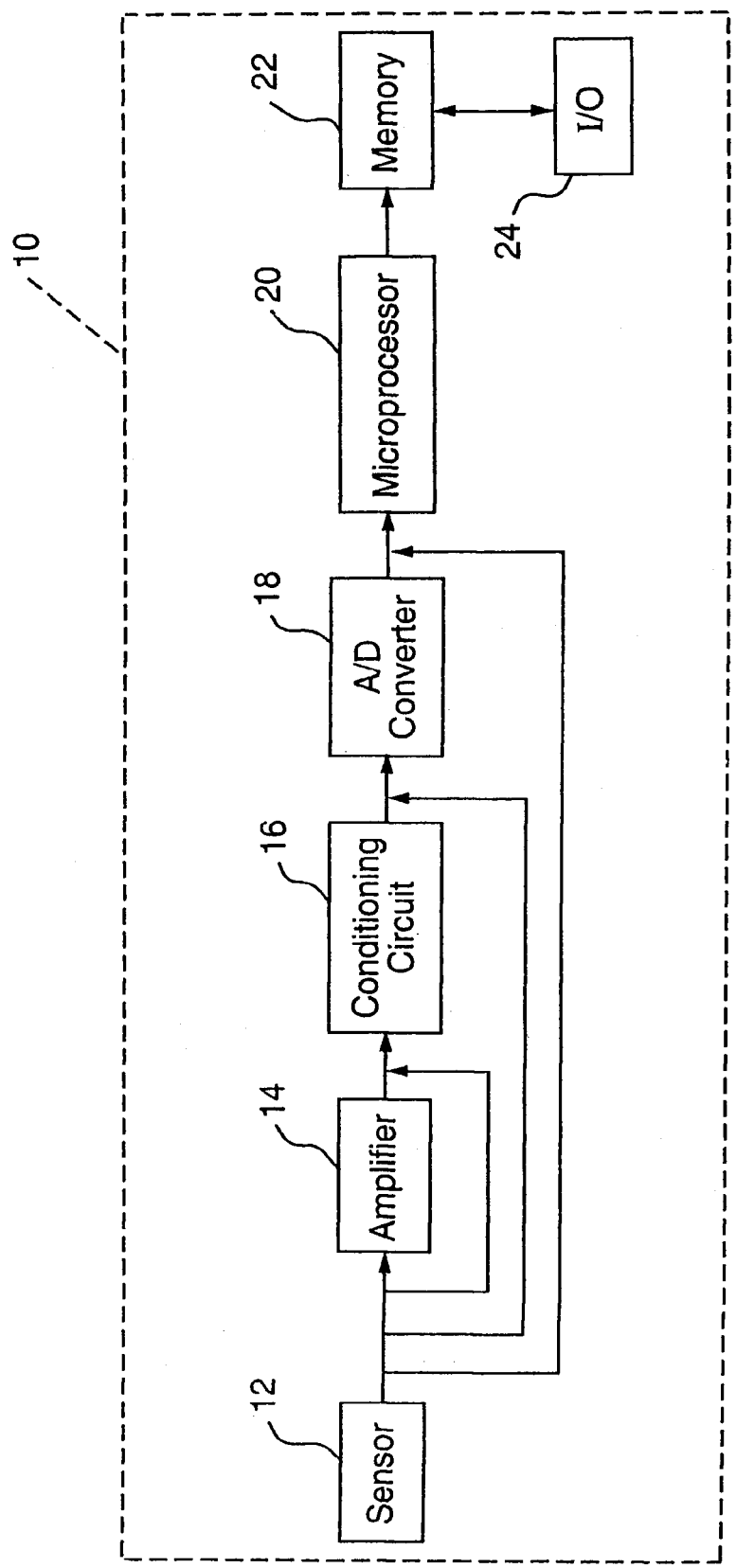
Figure 3:
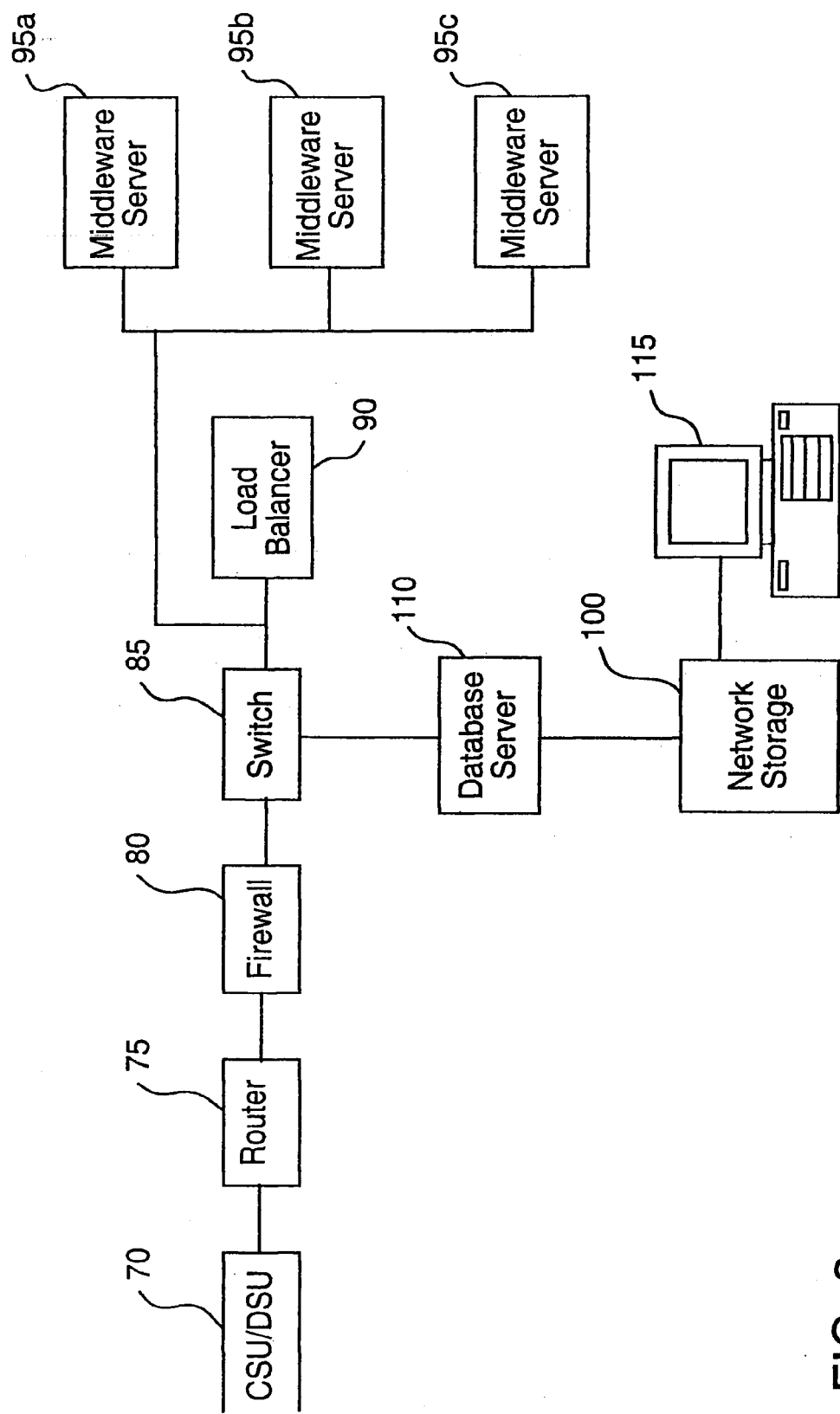
Figure 4:
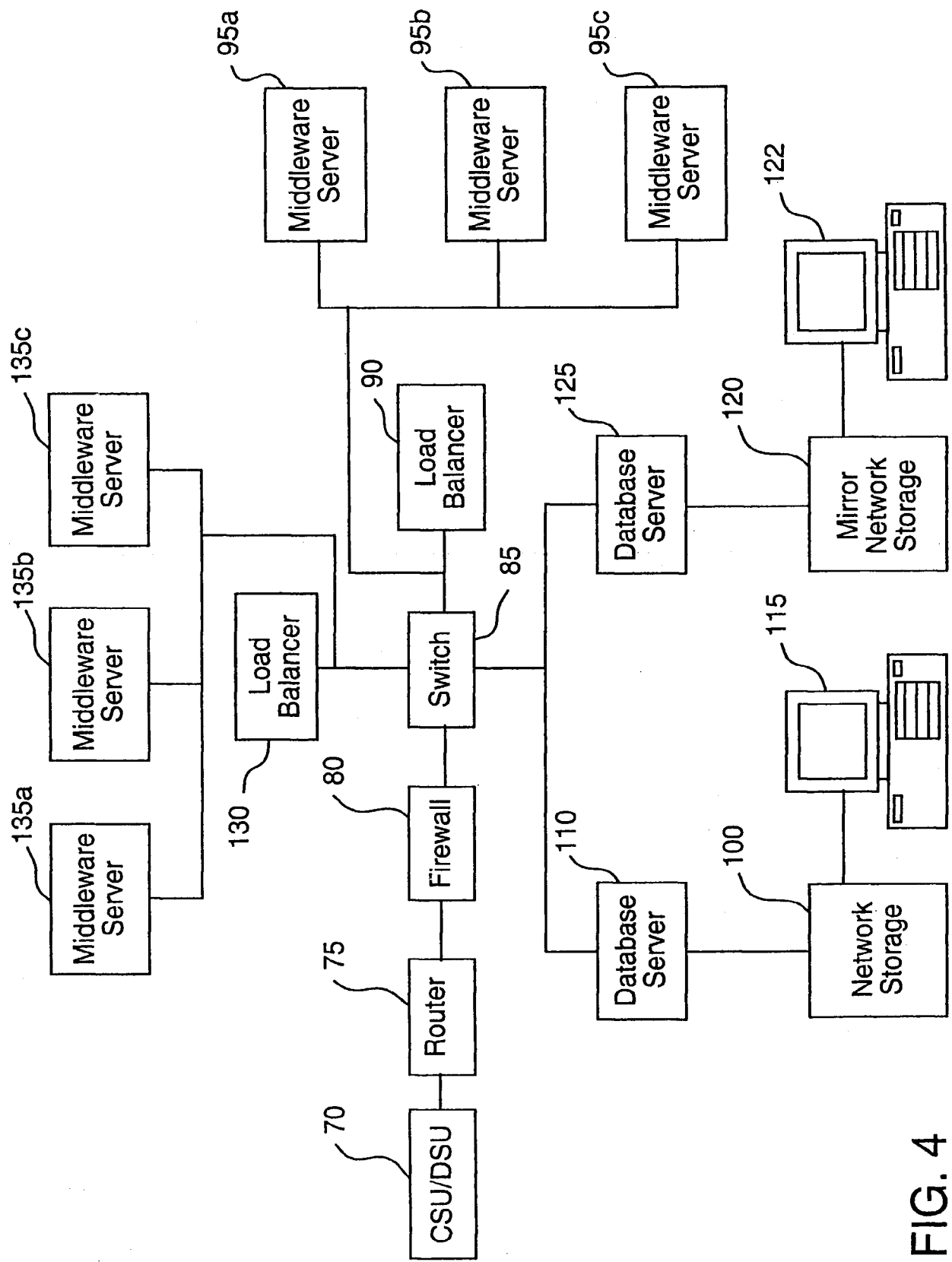
Figure 5:
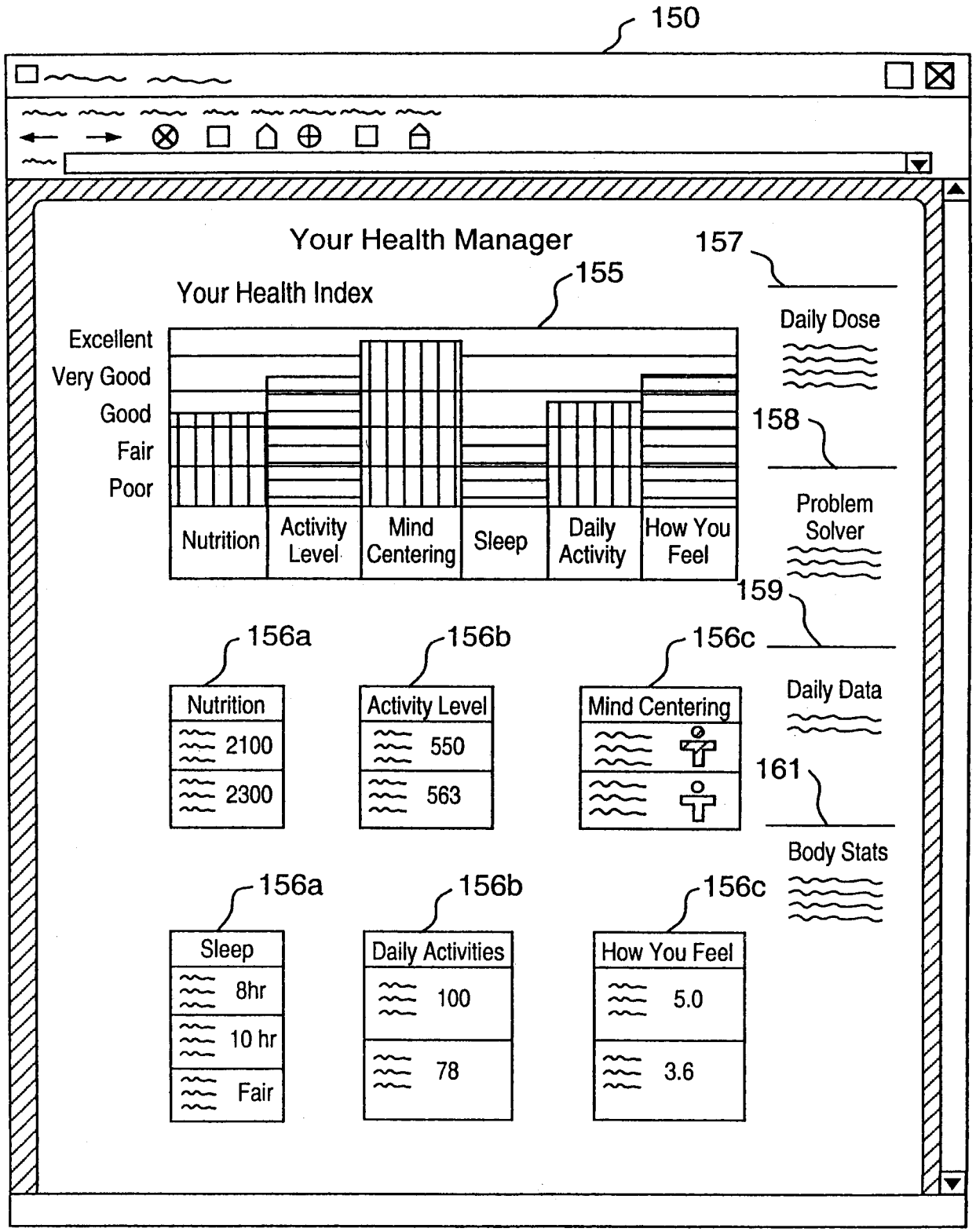
Figure 6:
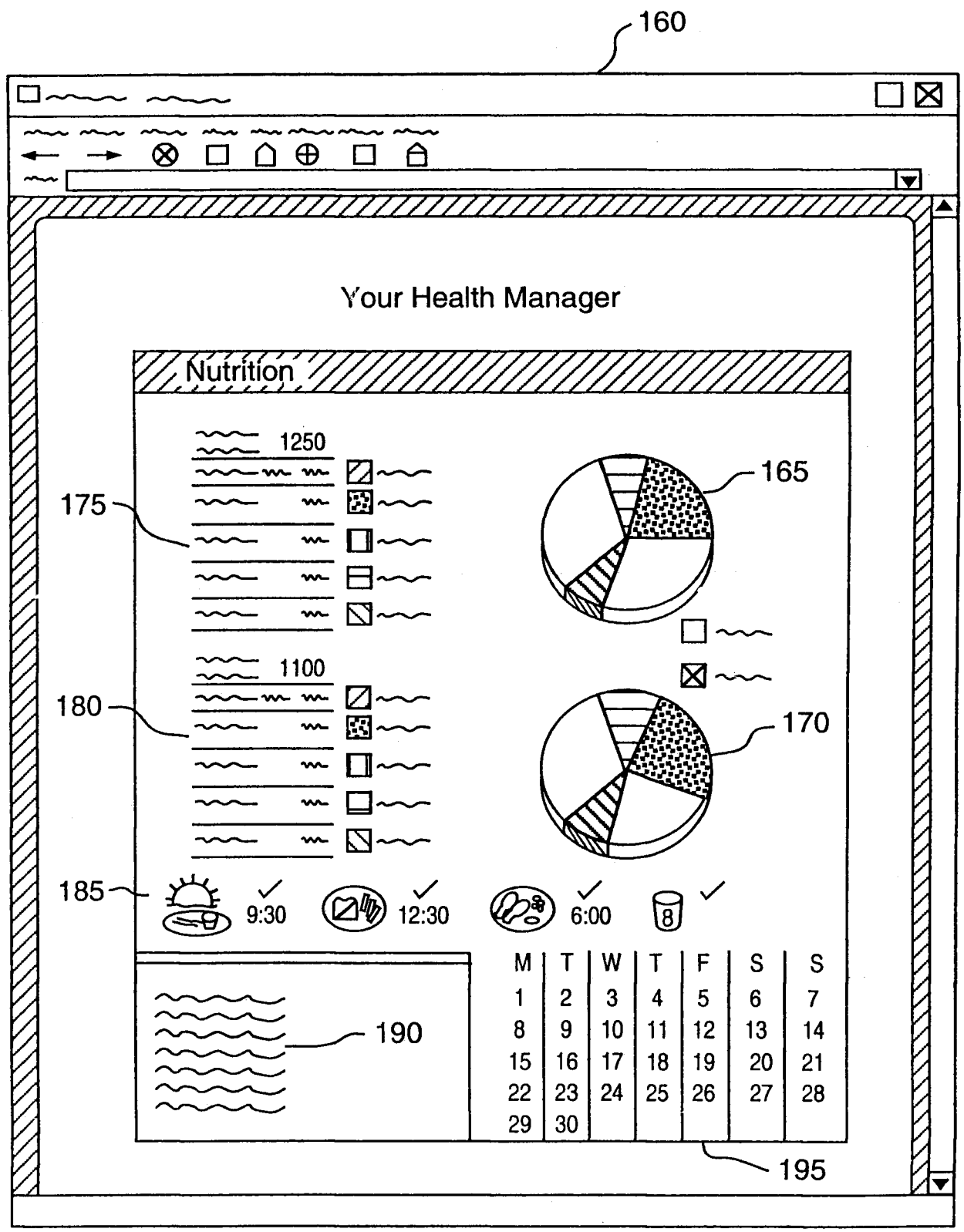
Figure 7:
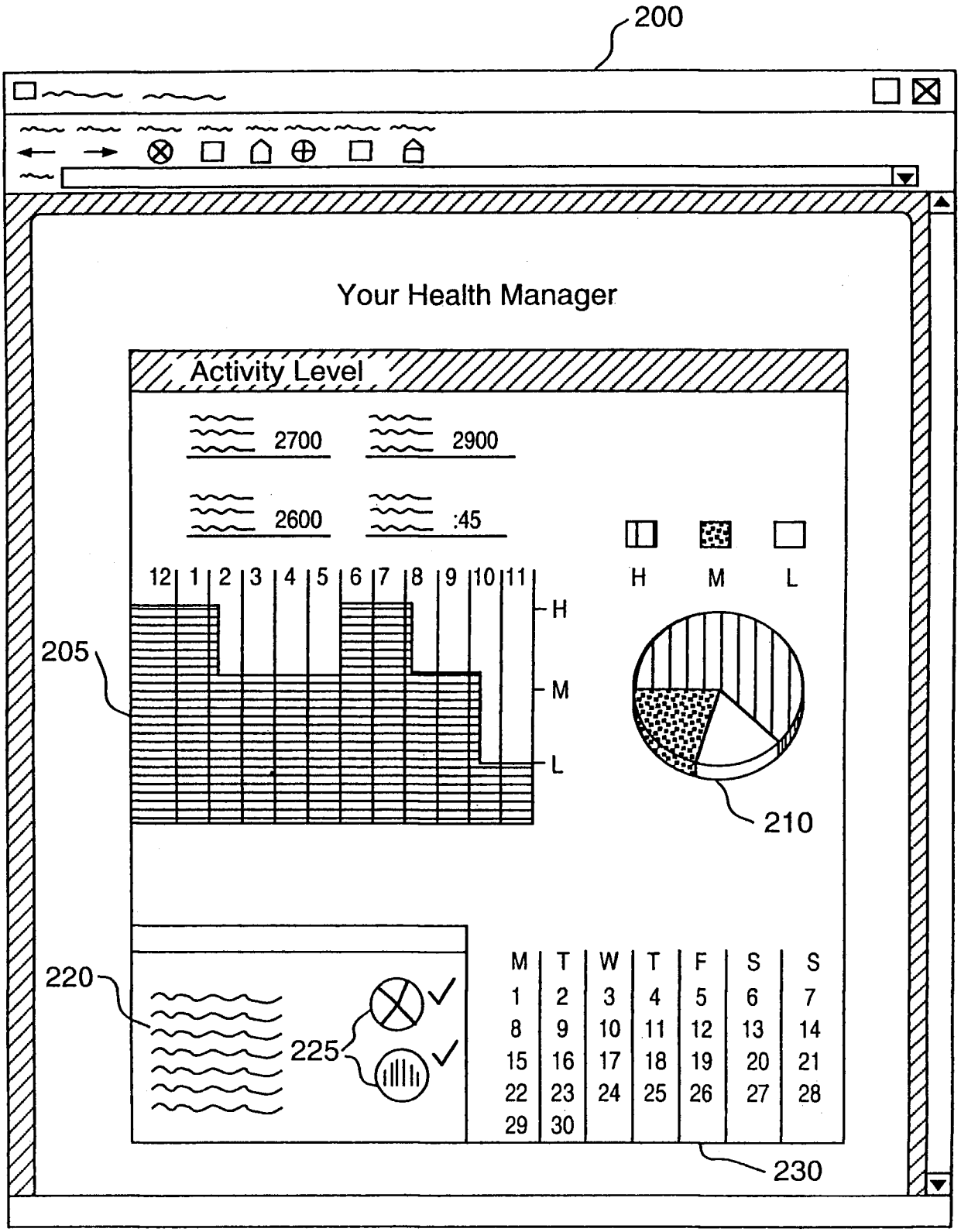
Figure 8:
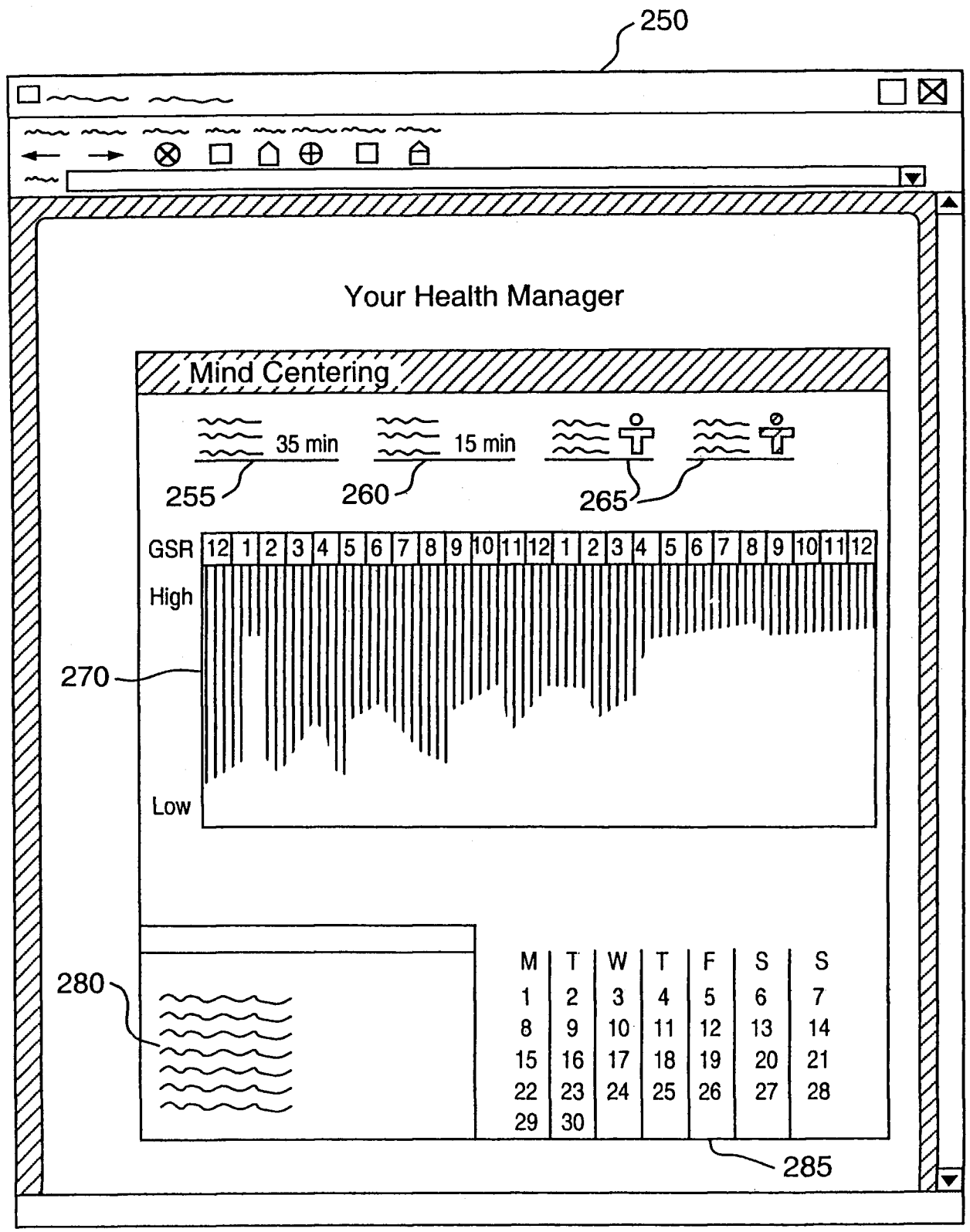
Figure 9:
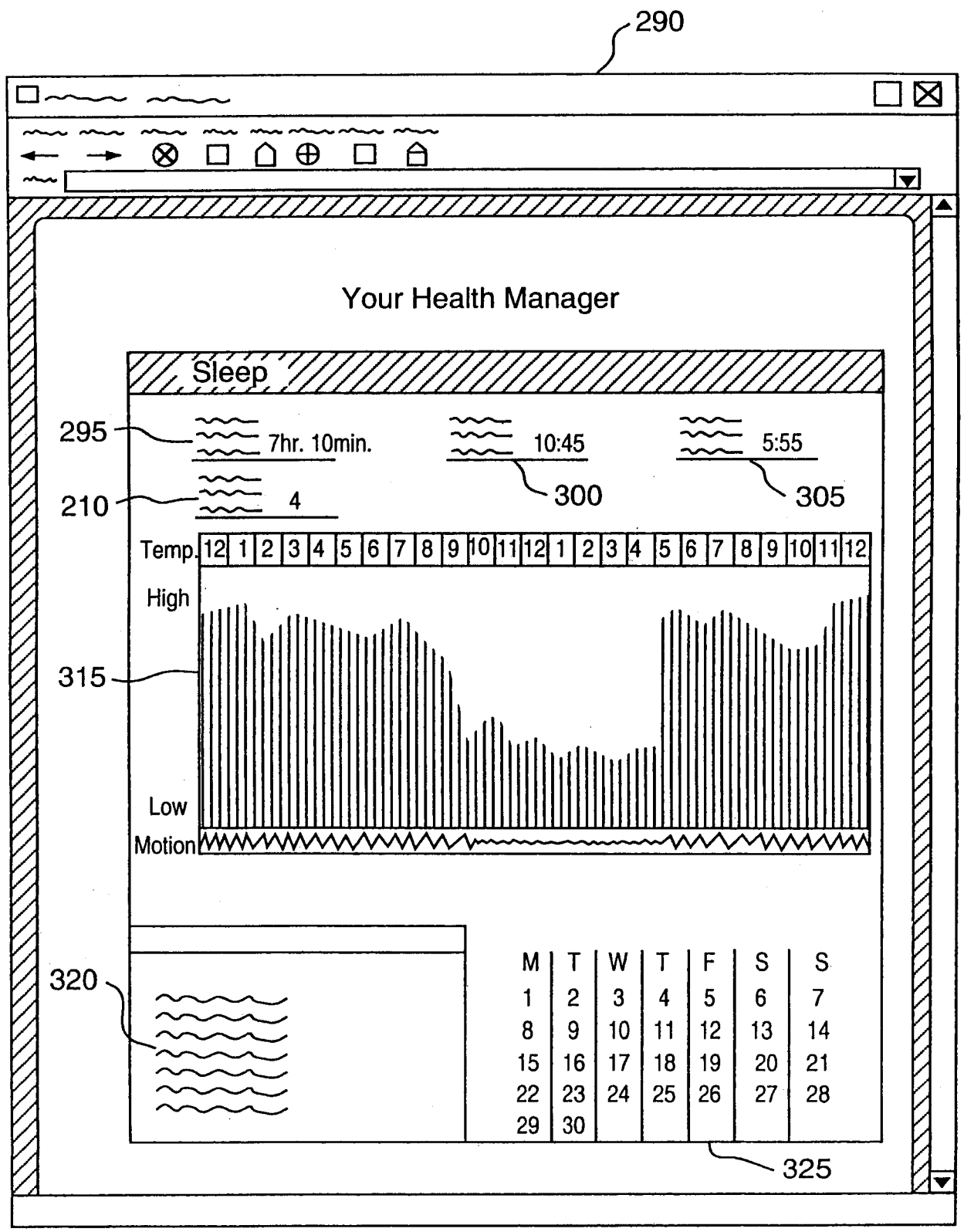
Figure 10:
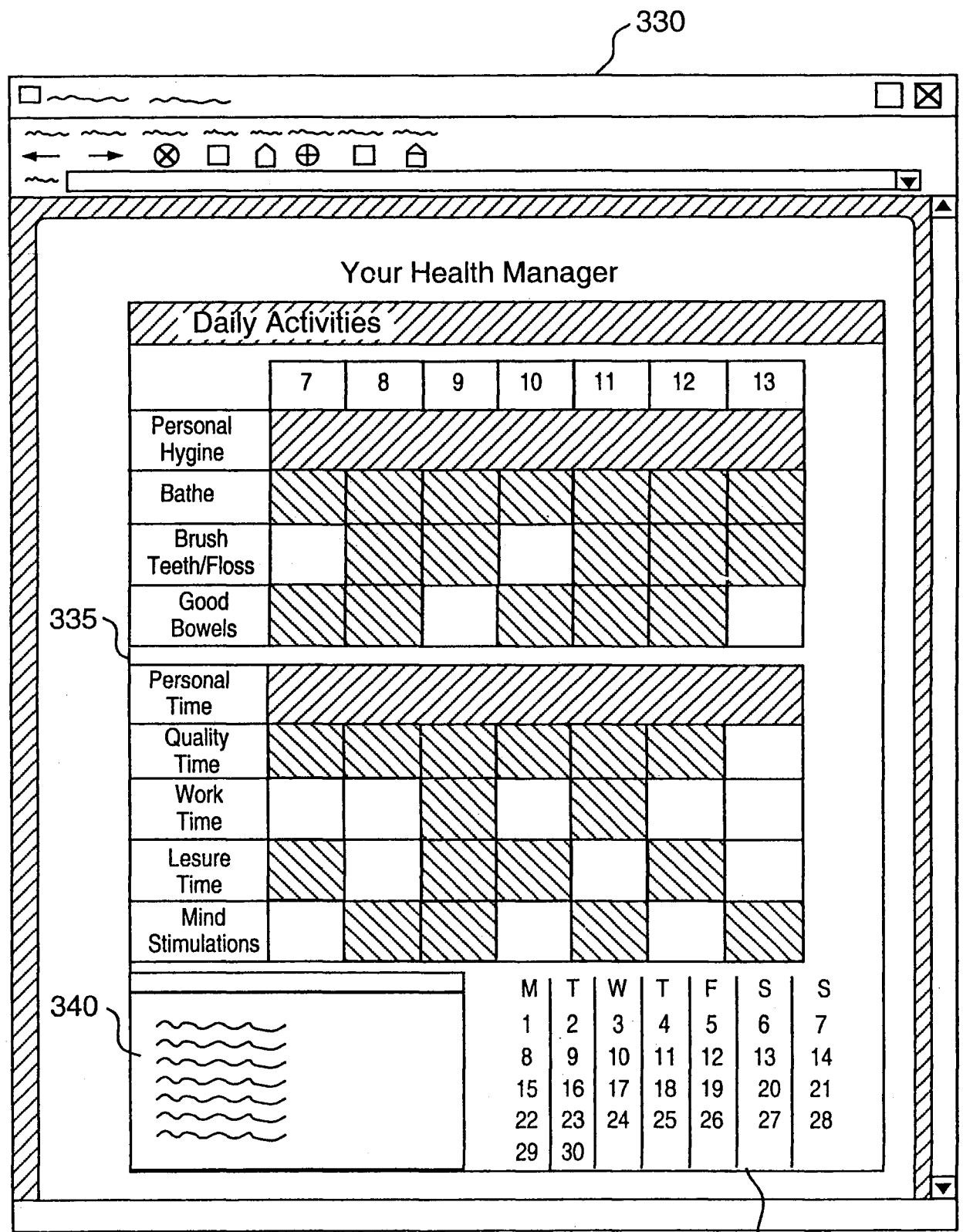
Figure 11:
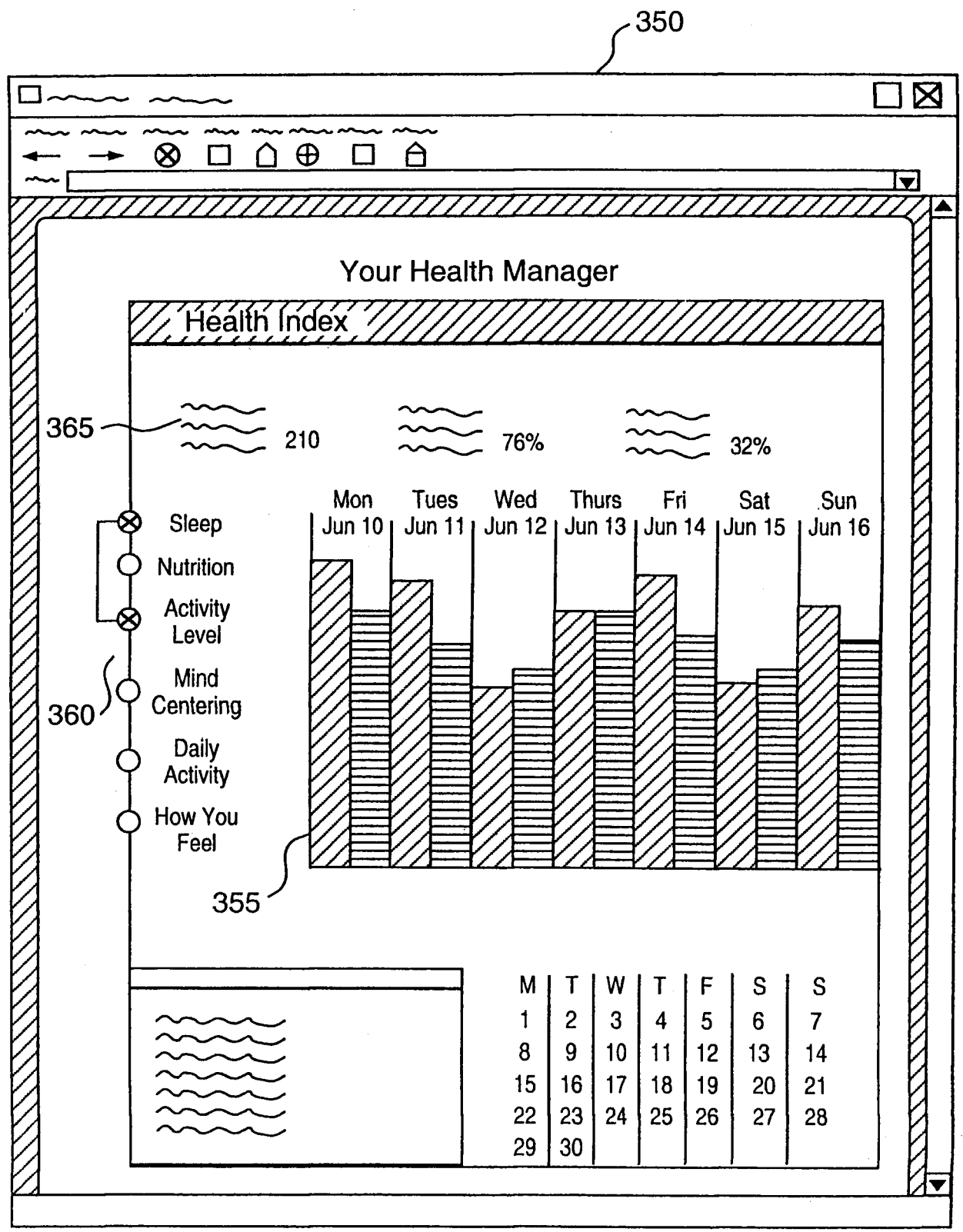
Figure 12:
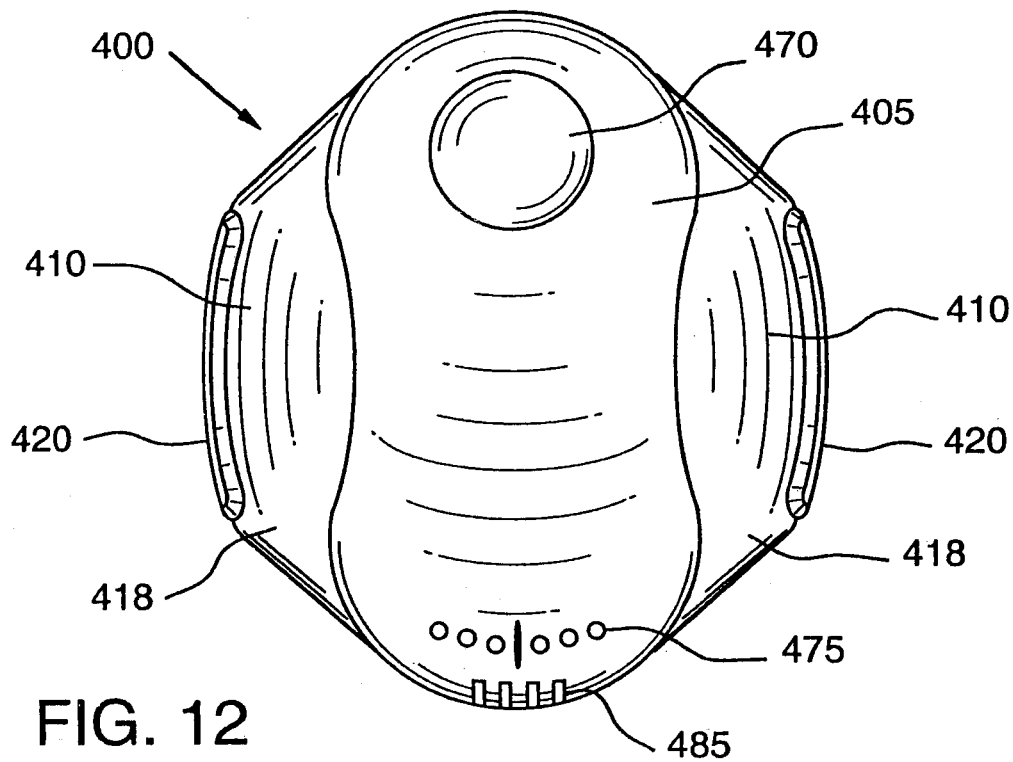
Figure 13:
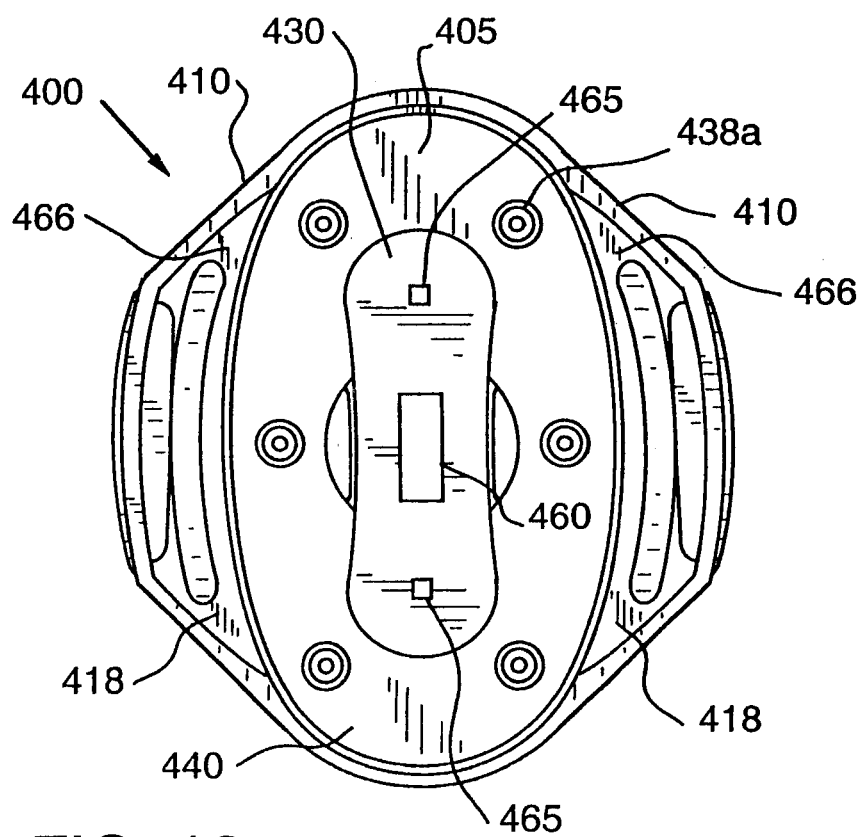
Figure 14:
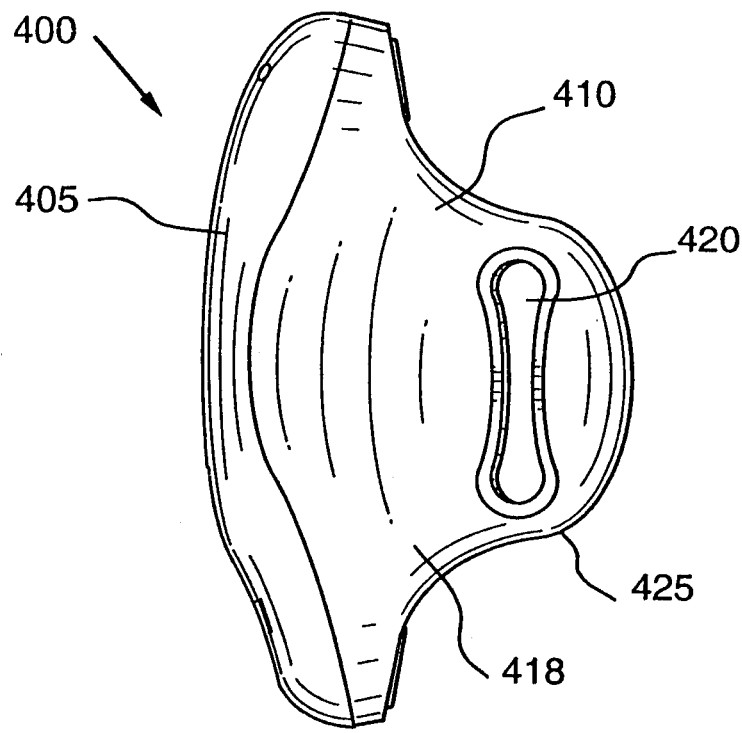
Figure 15:
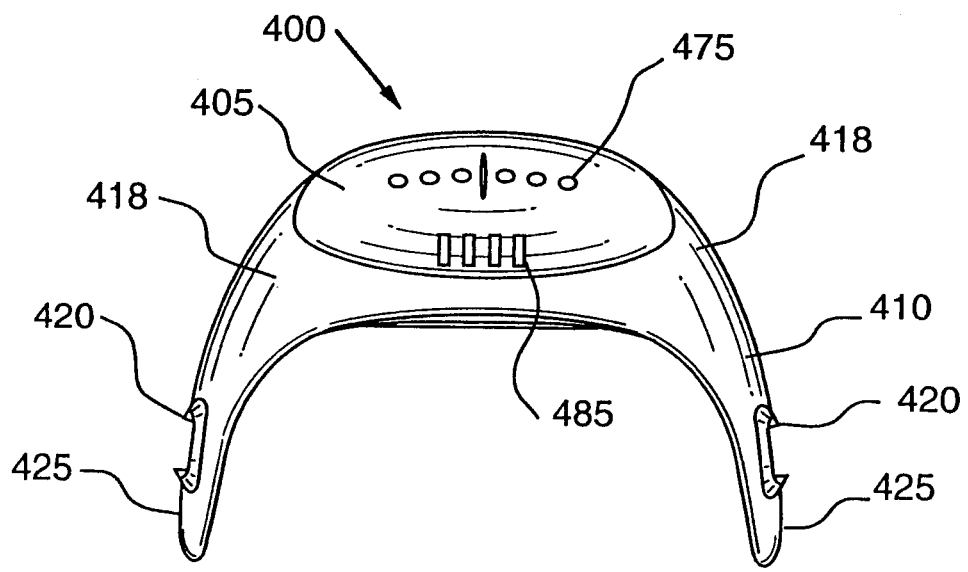
Figure 16:
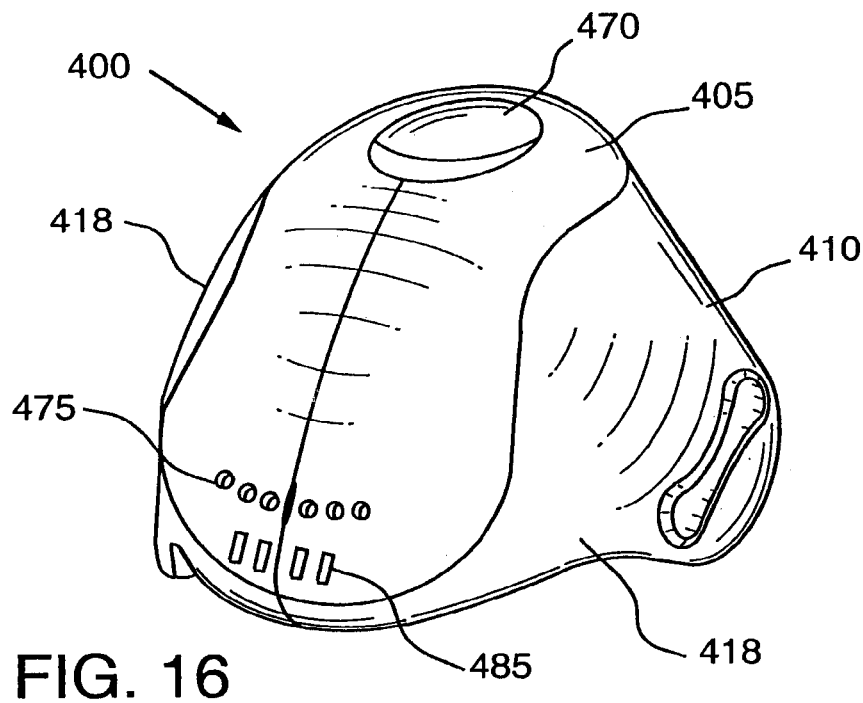
Figure 17:
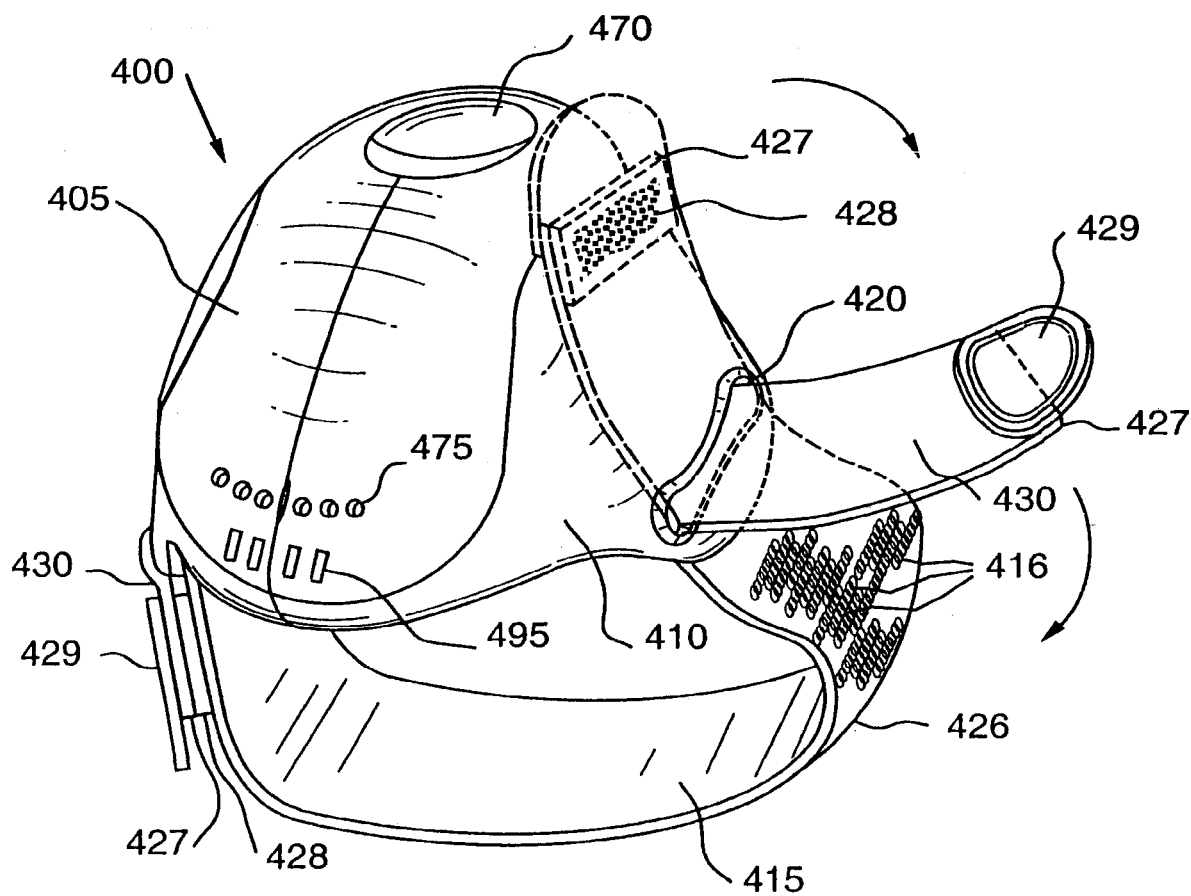
Figure 18:
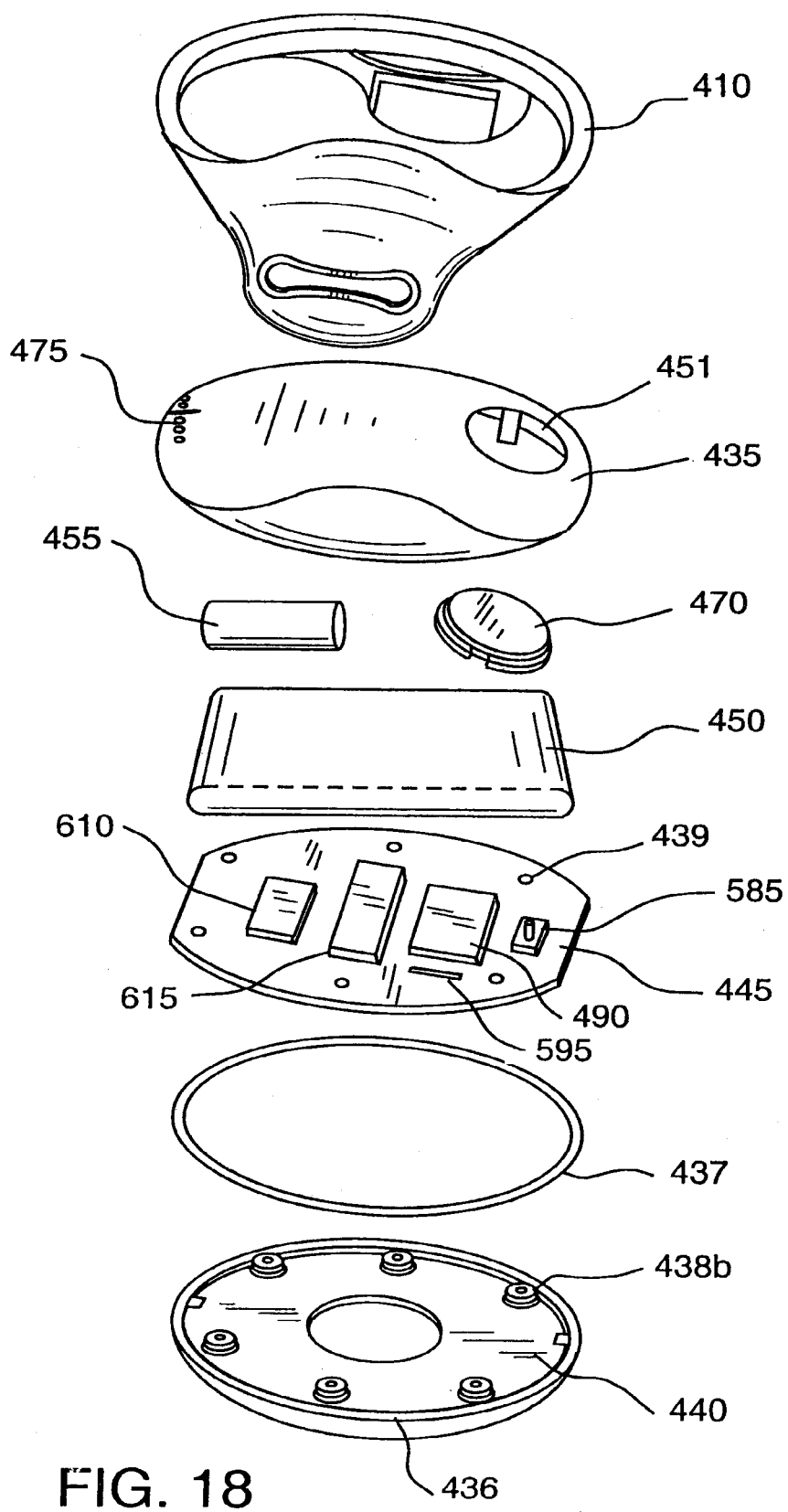
Figure 19:
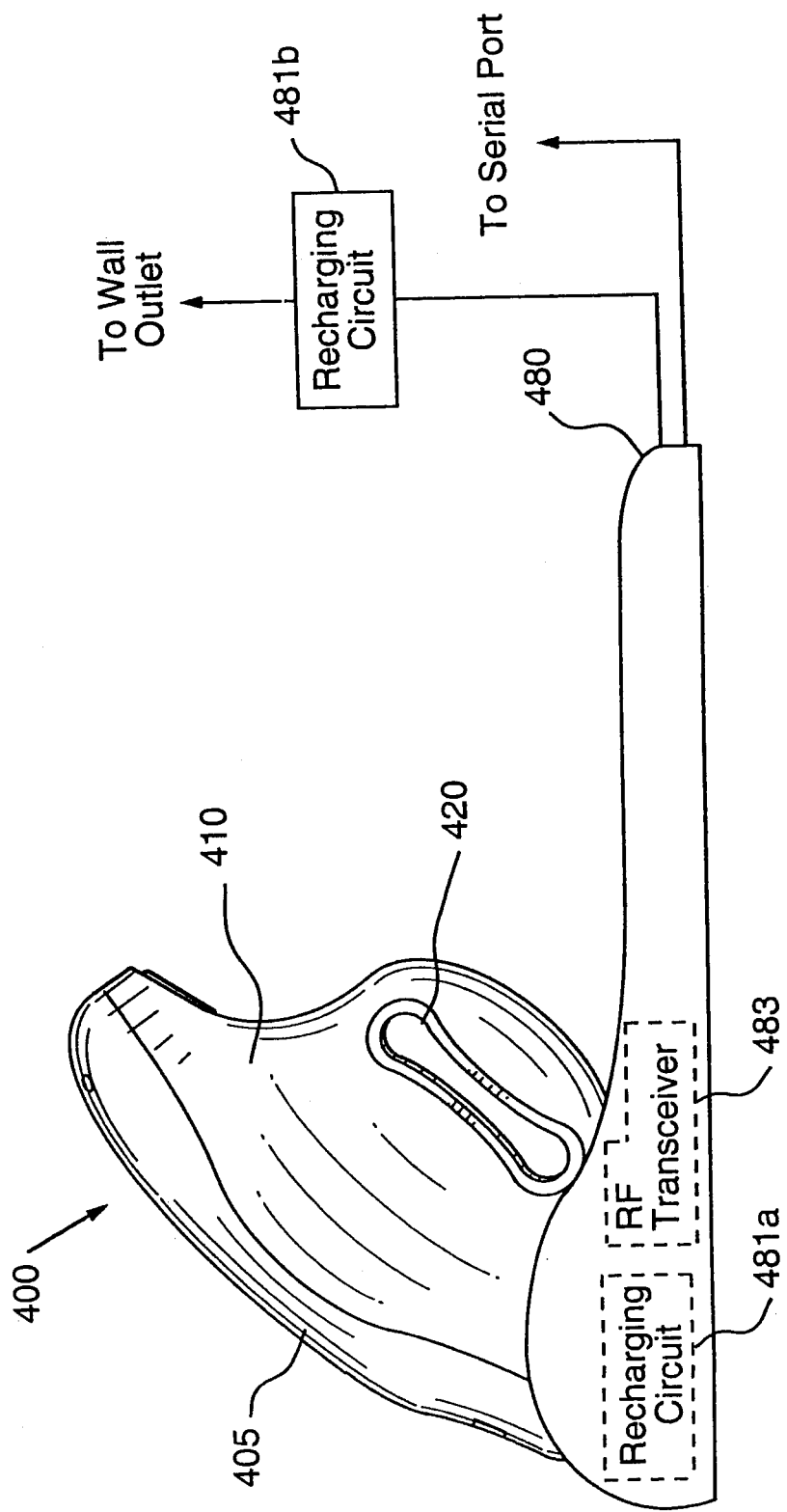
Figure 20:
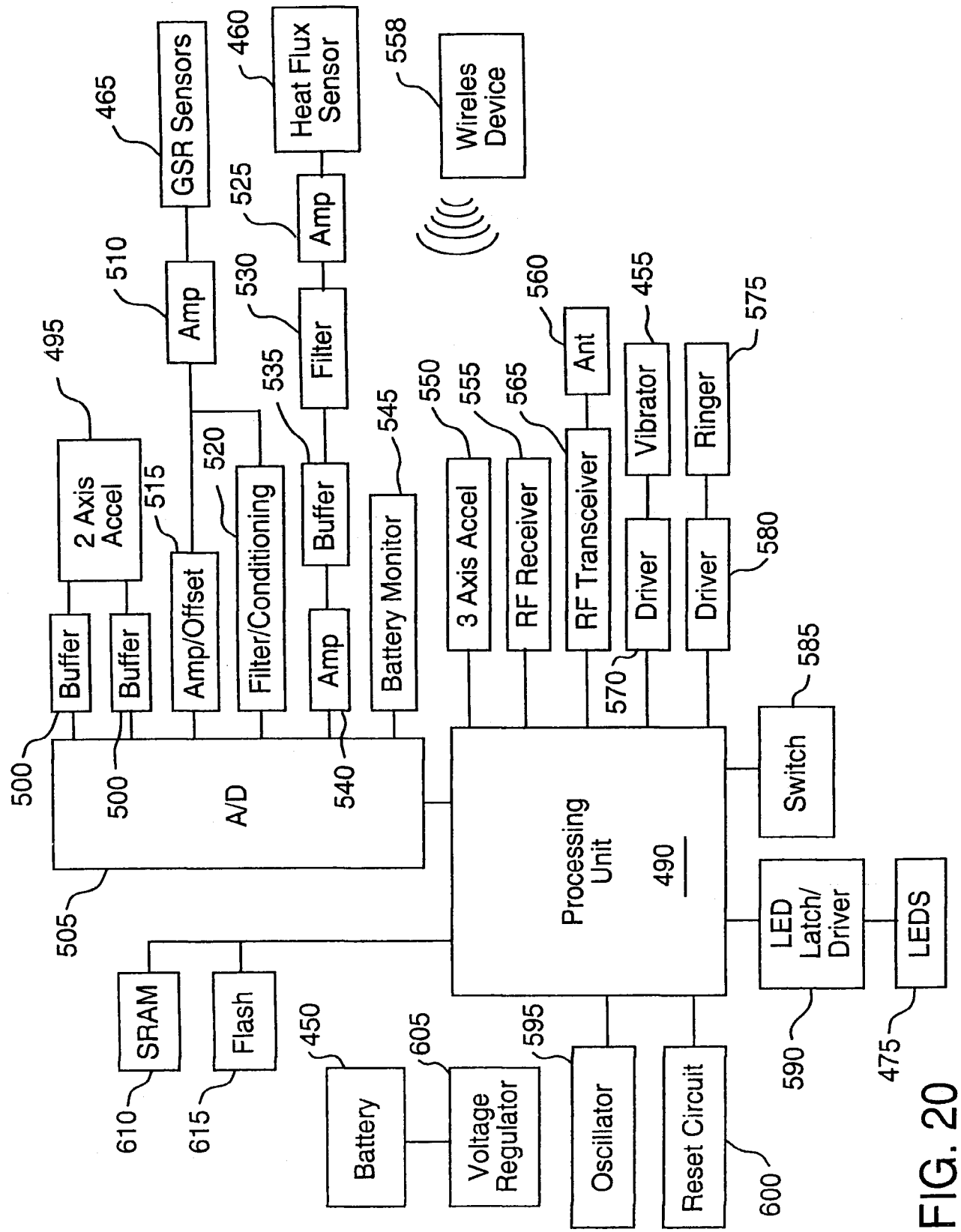
Figure 21:
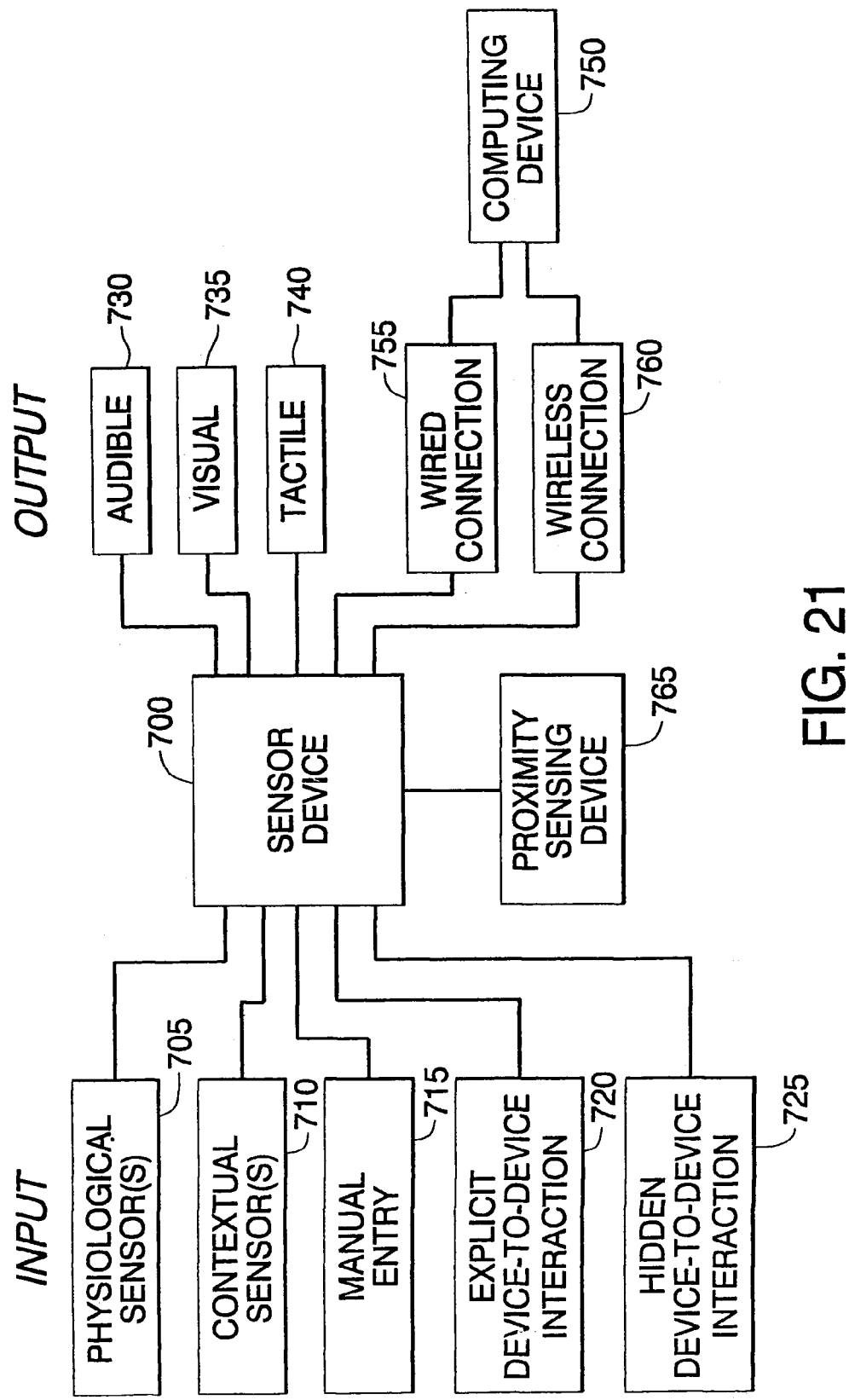
Figure 22:
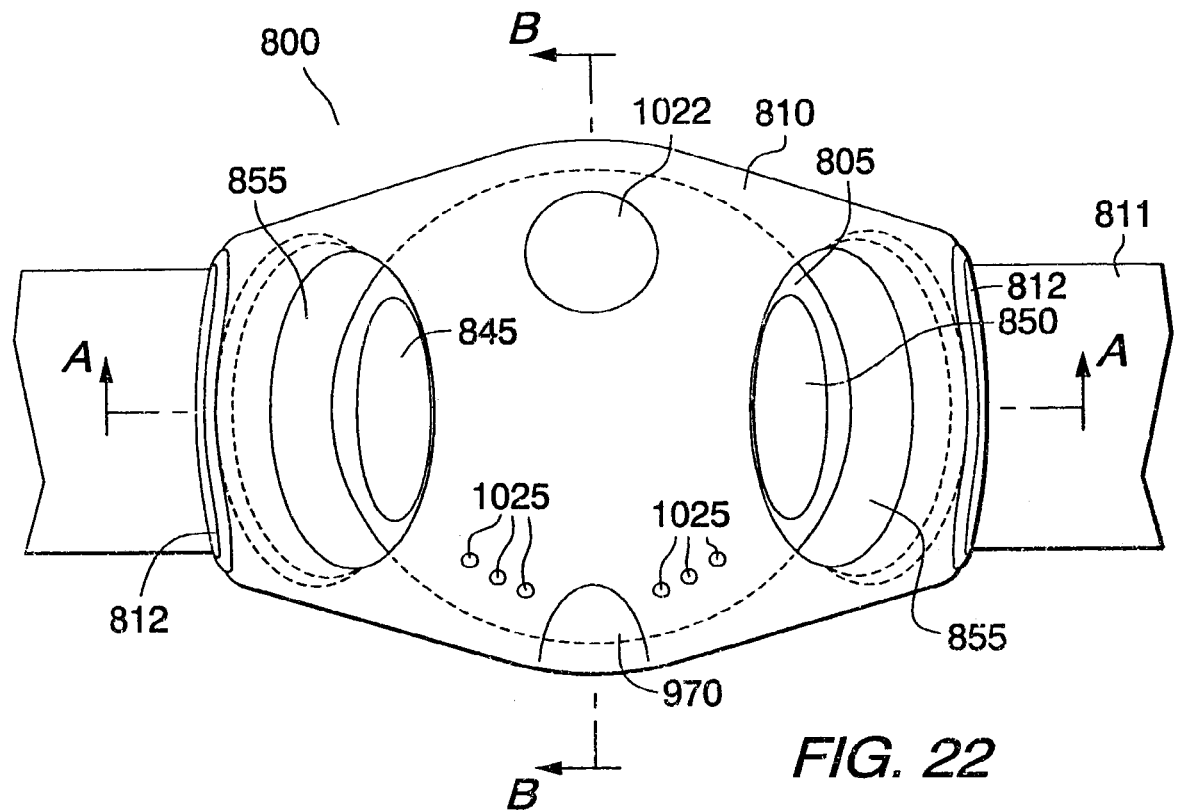
Figure 23:
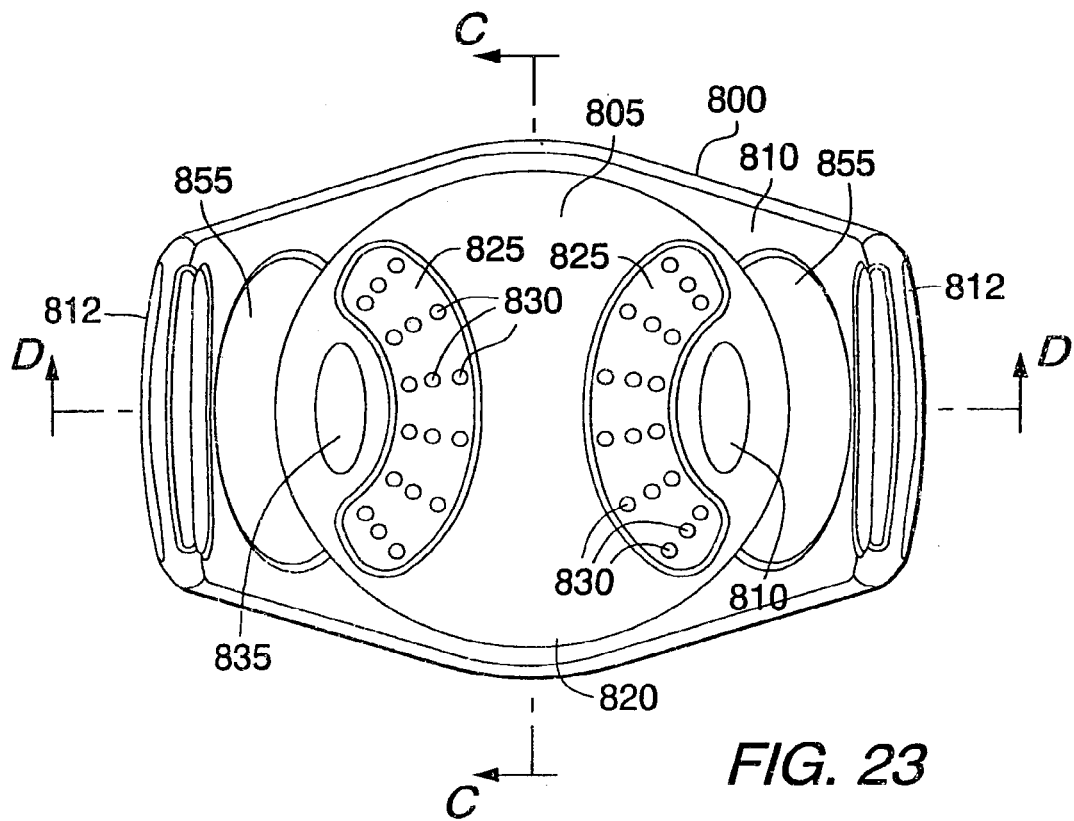
Figure 24:
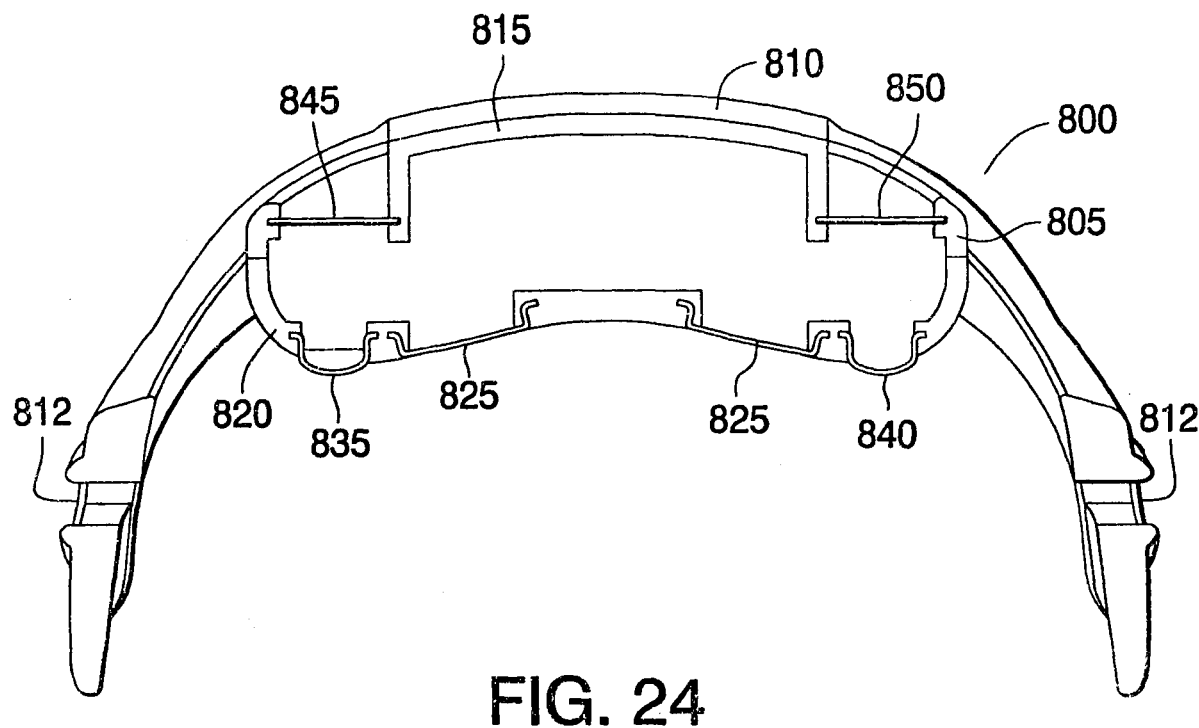
Figure 25:
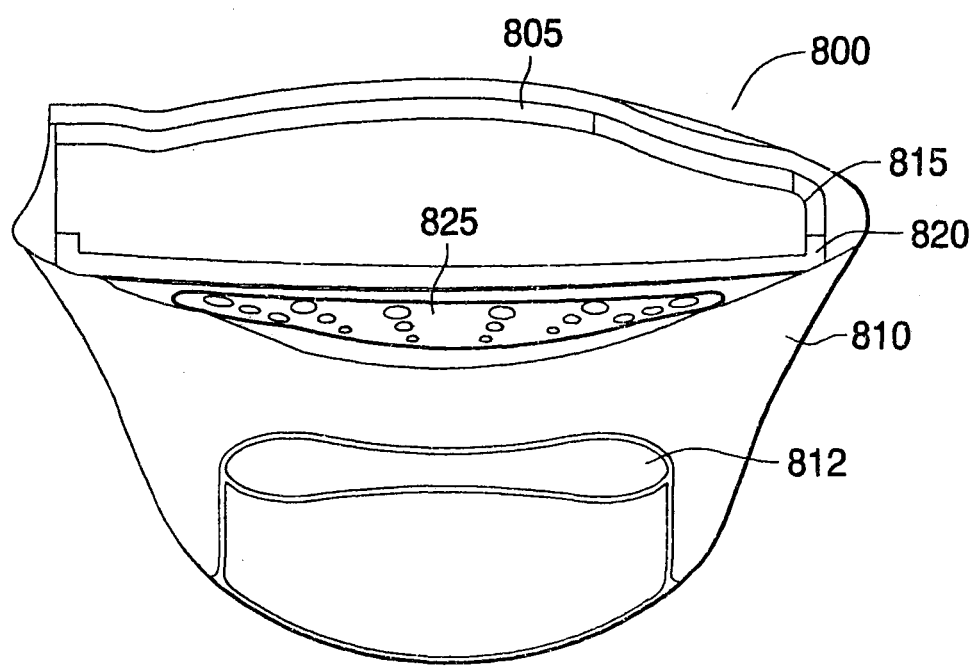
Figure 26:
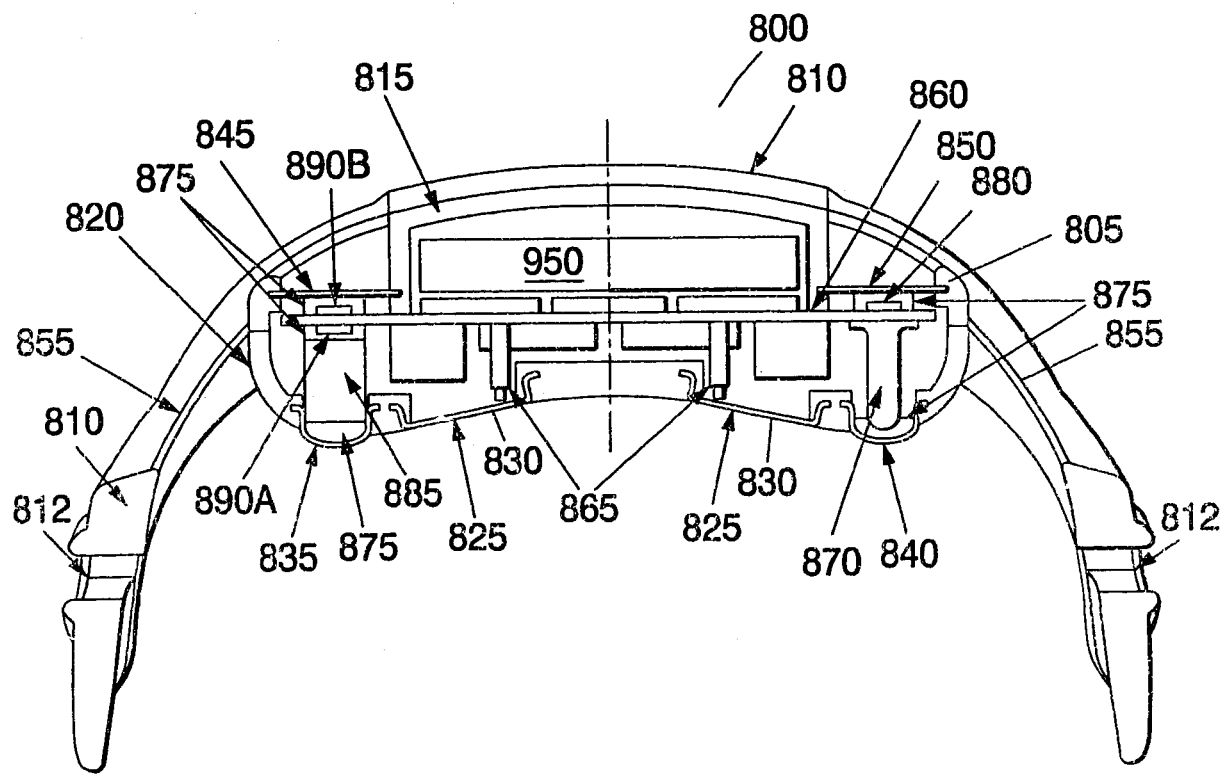
Figure 27:
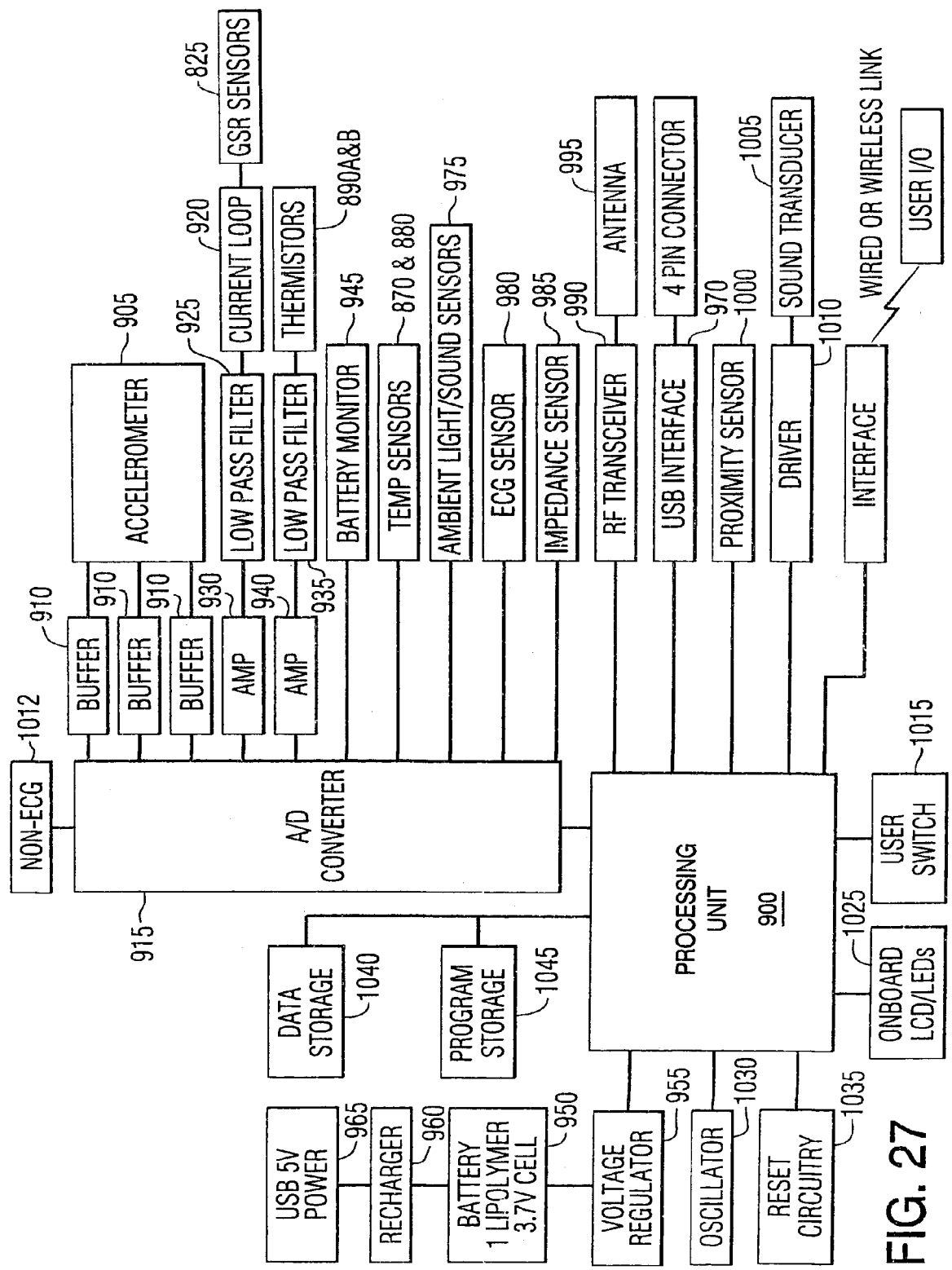
Figure 28:
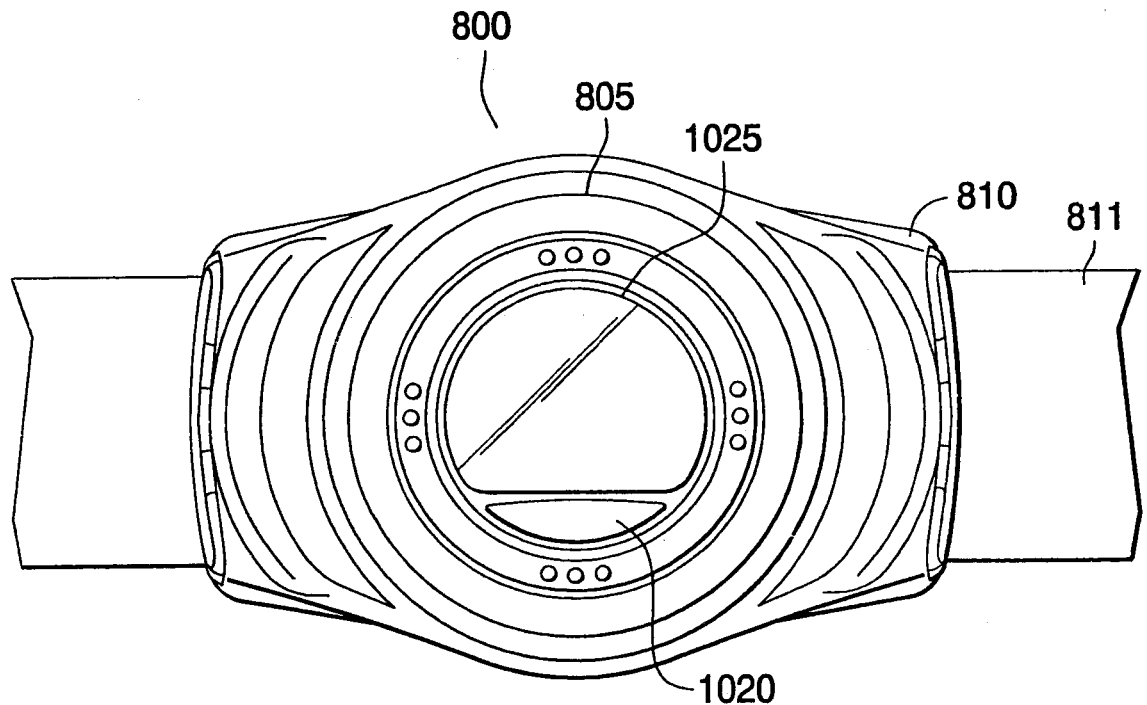
Figure 29:
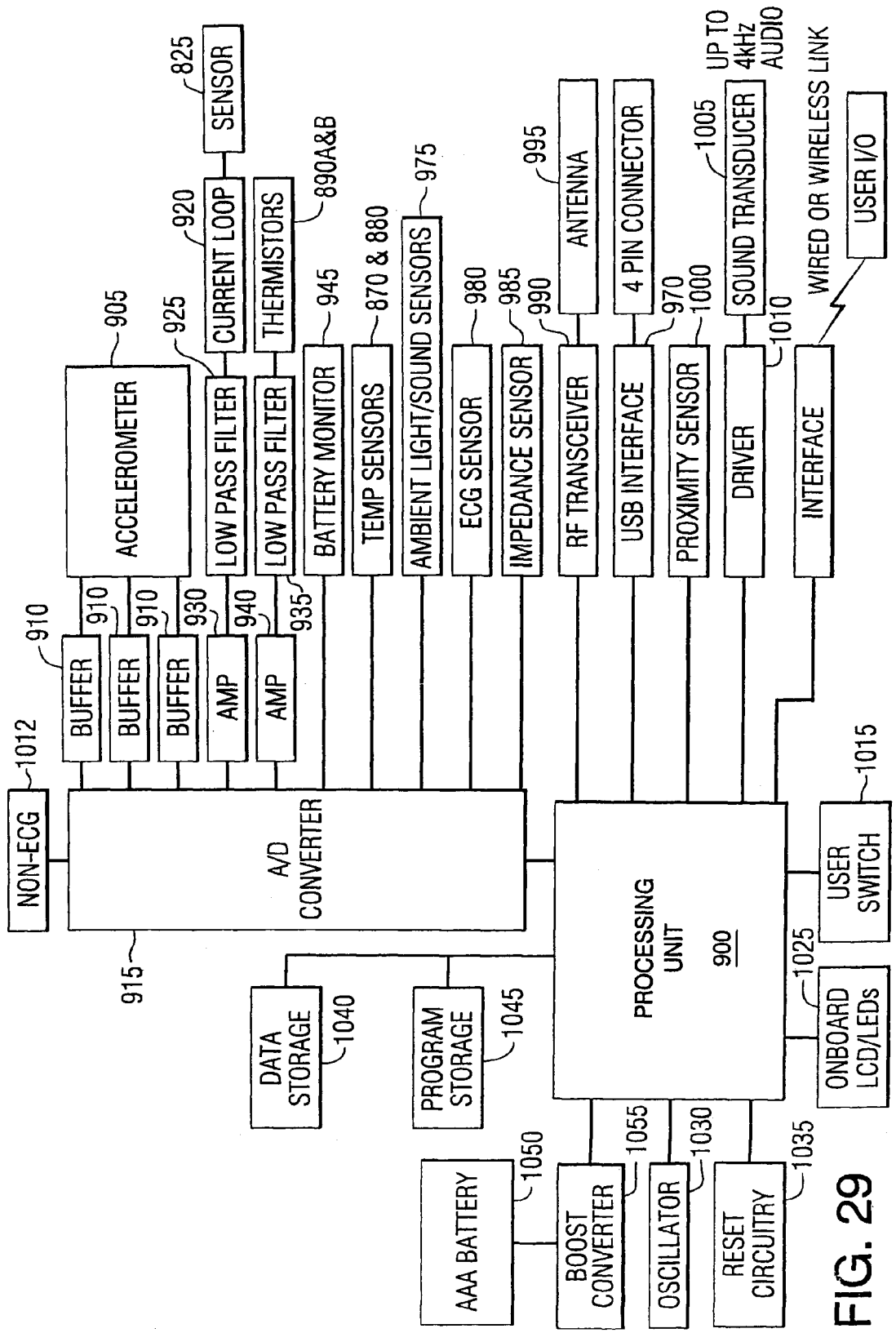
Figure 30:
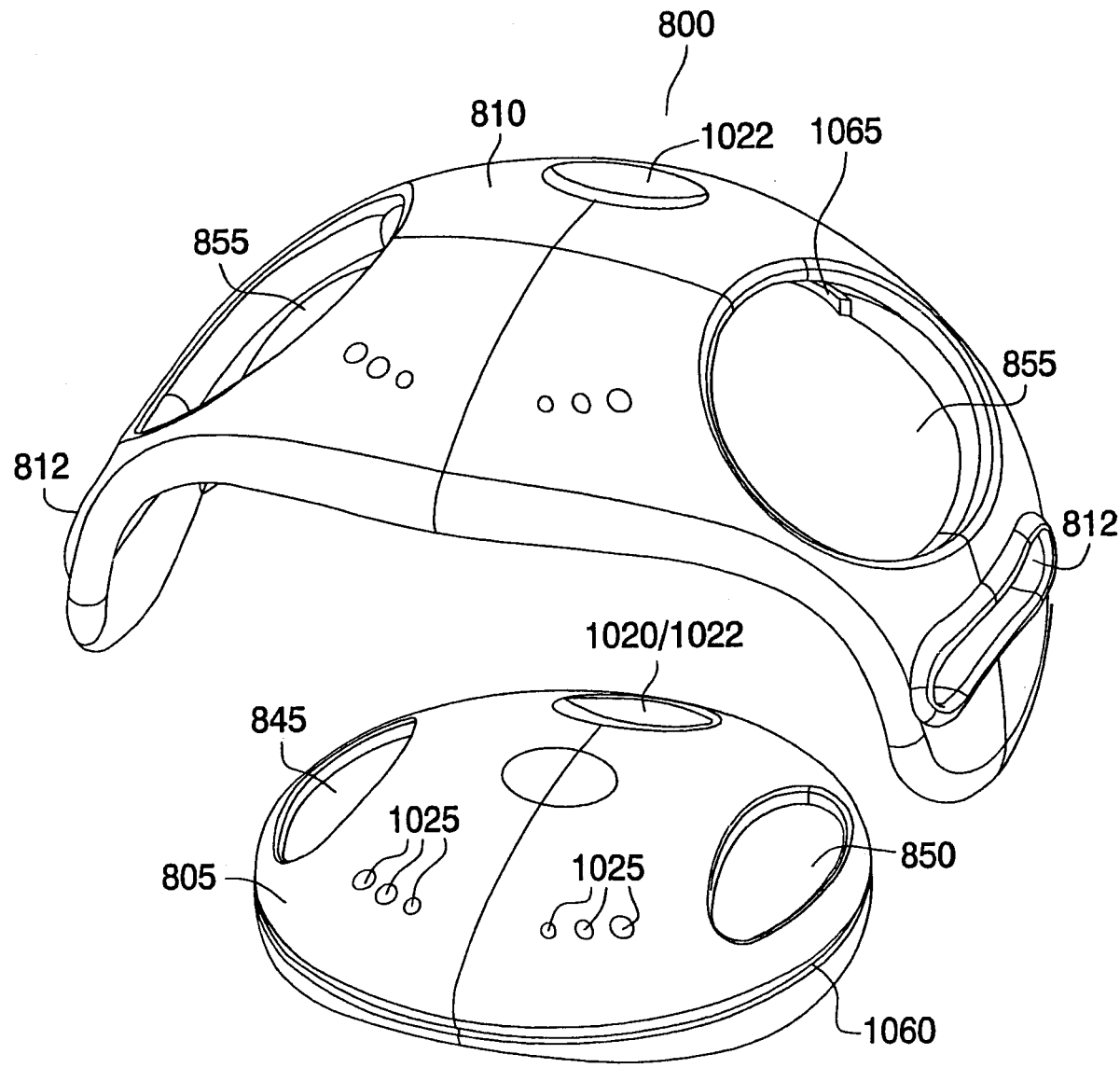
Figure 31:
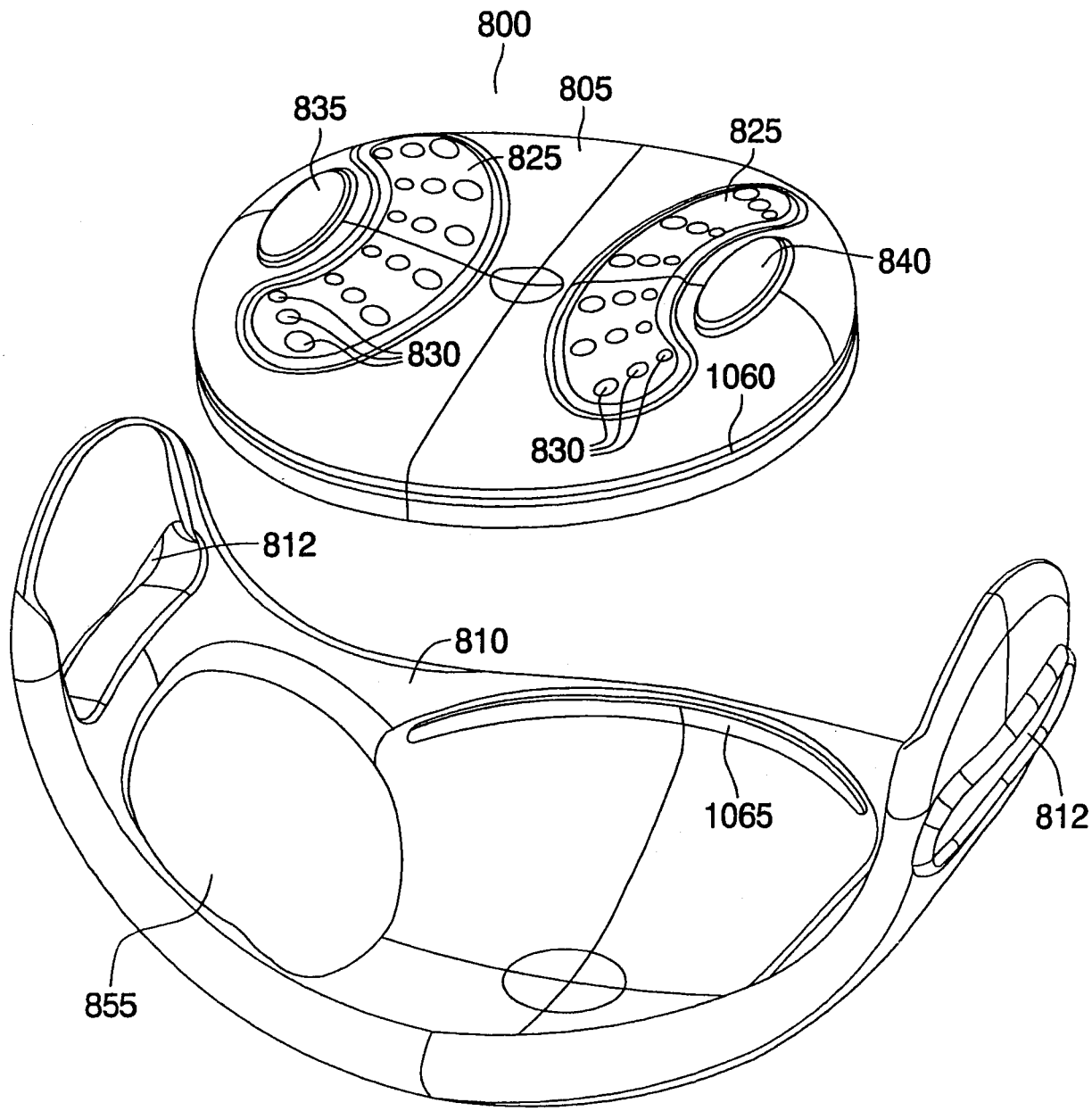
Figure 32:
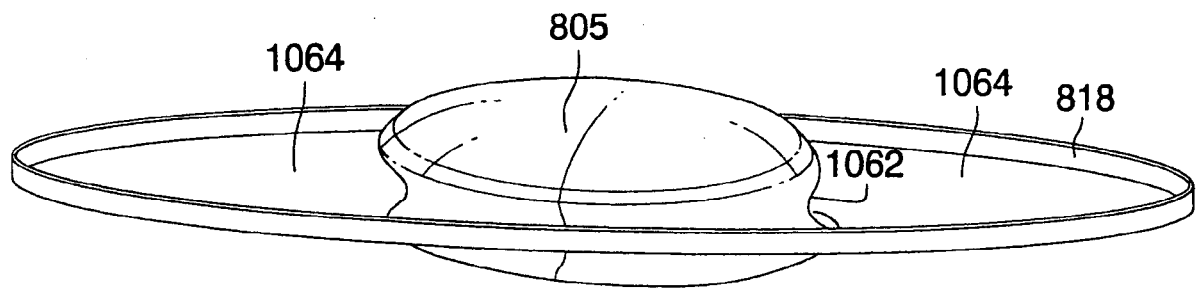
Figure 33:
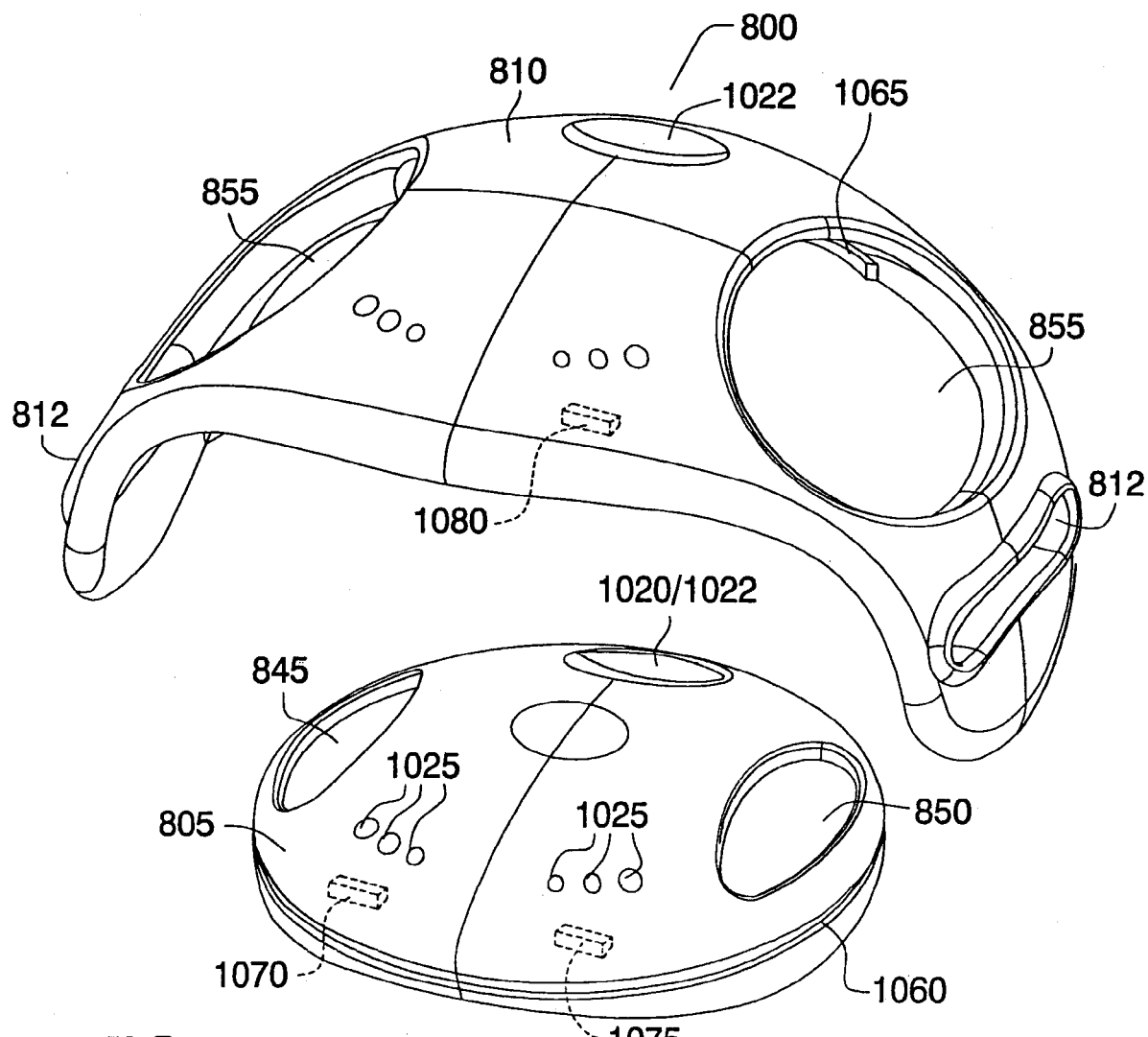
Figure 34:
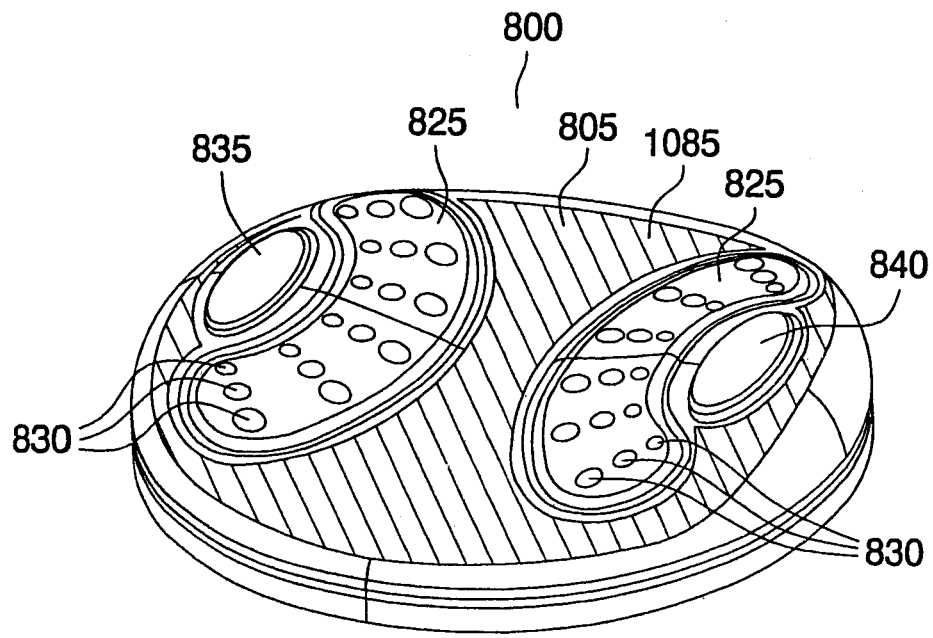
Figure 35A:
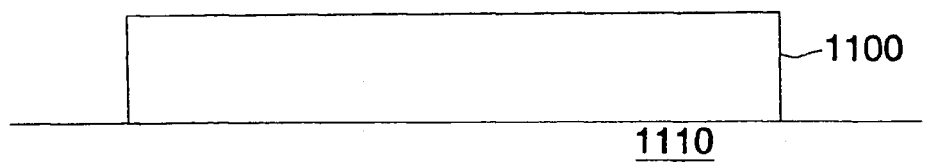
Figure 35B:
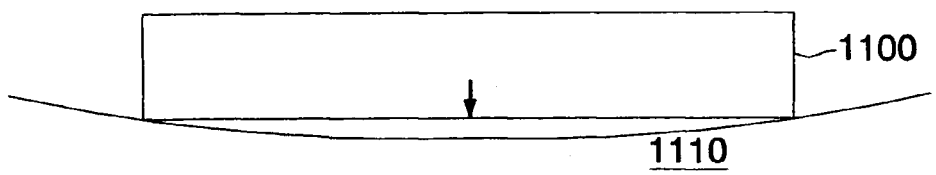
Figure 35C:
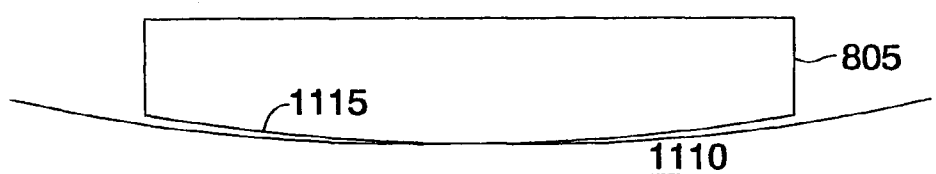
Figure 35D:
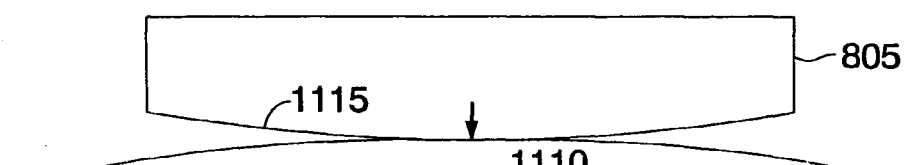
Figure 35E:
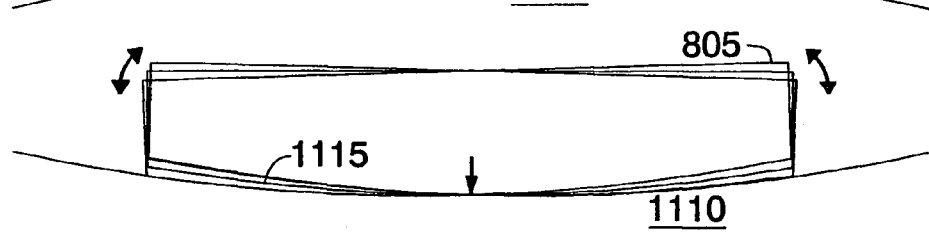
Figure 35F:
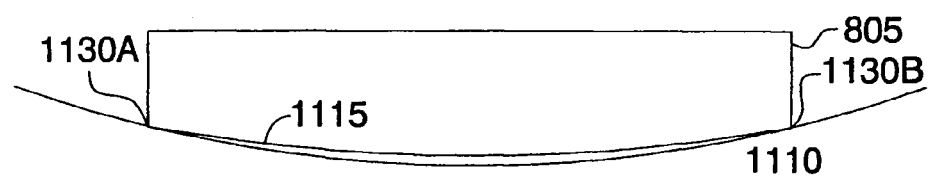
Figure 35G:
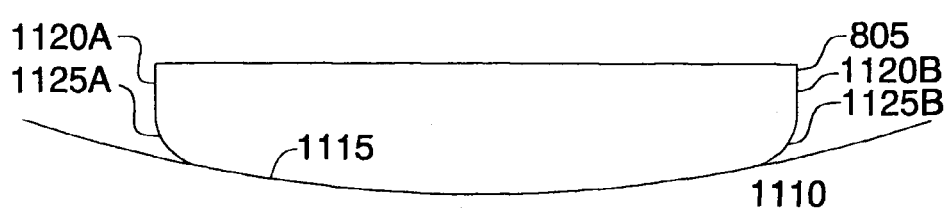
Figure 35H:
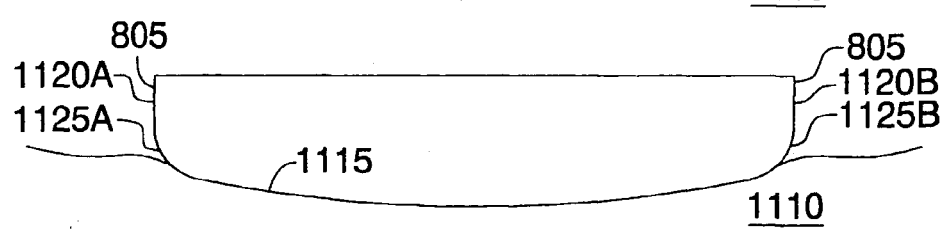
Figure 36A:
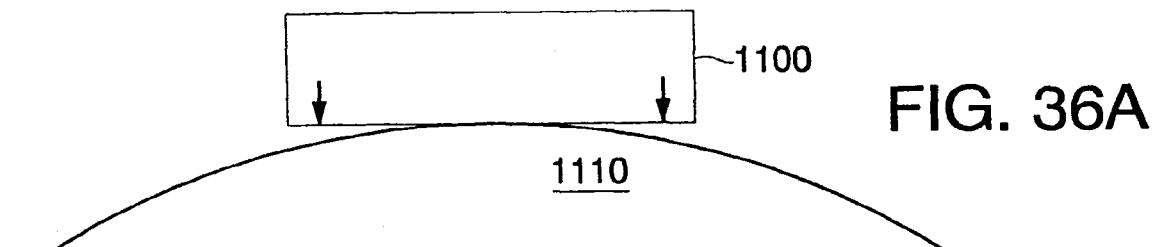
Figure 36B:
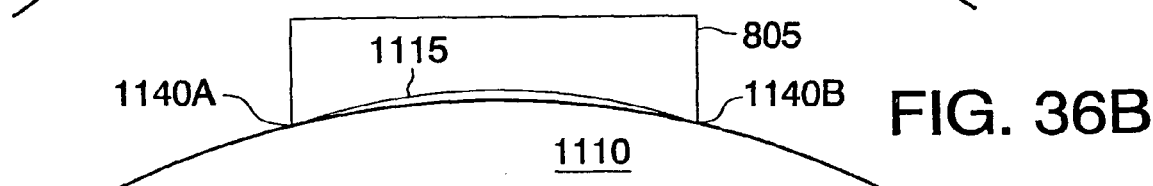
Figure 36C:
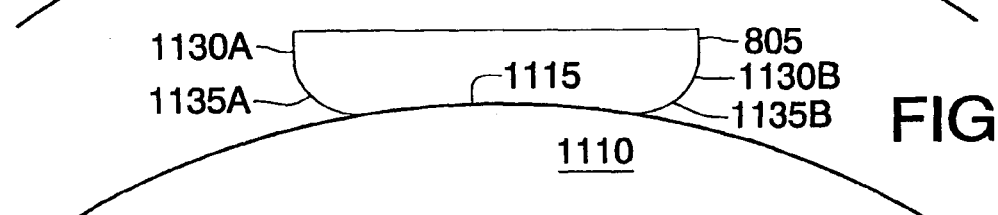
Figure 36D:
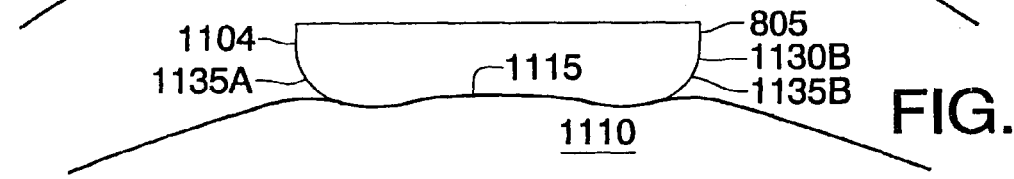
Figure 36E:
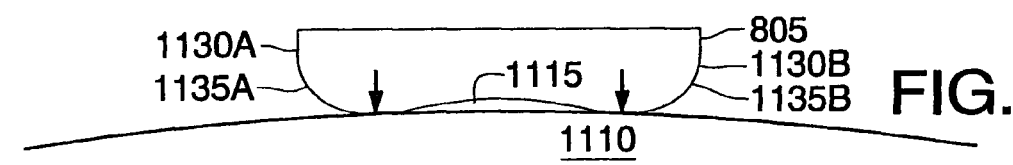
Figure 36F:
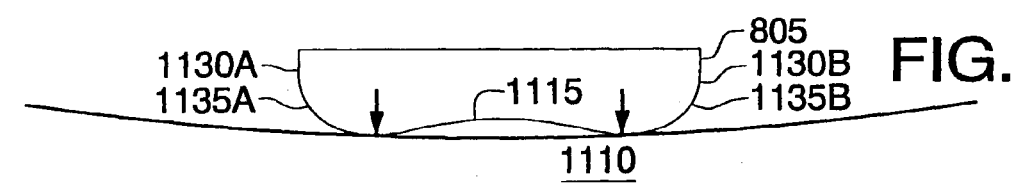
Figure 36G:
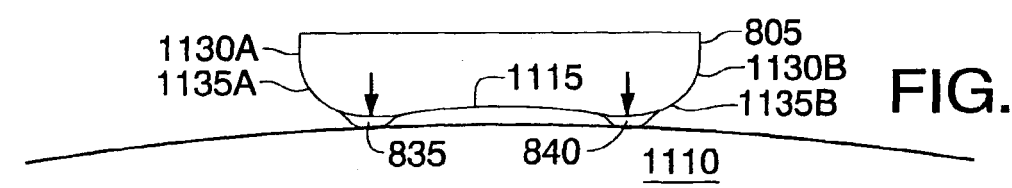
Figure 36H:
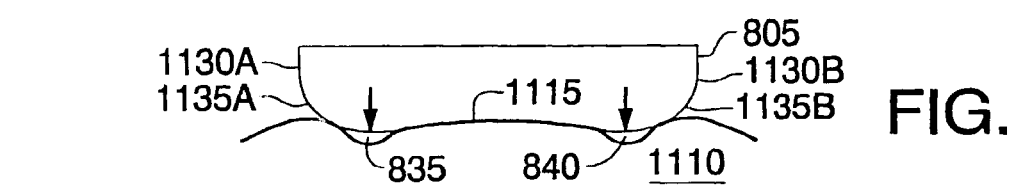
Figure 37:
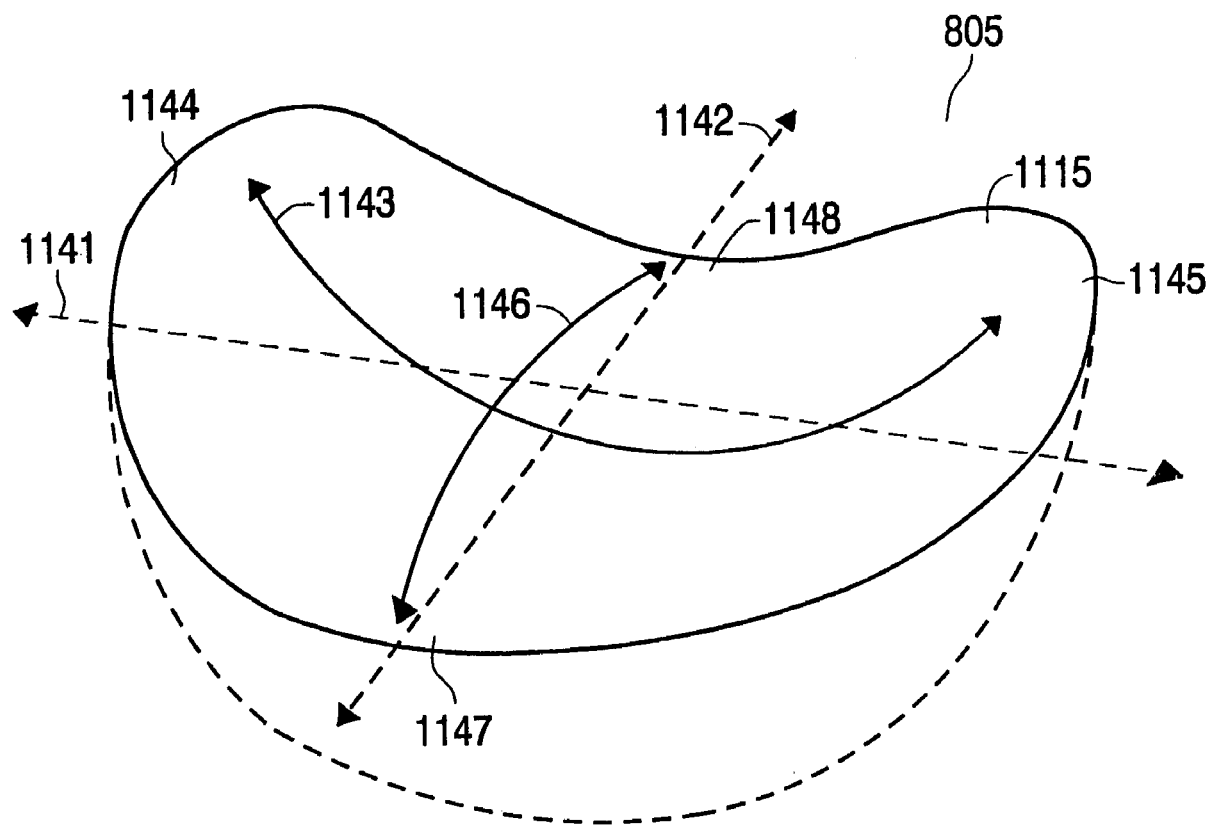
Figure 38A:
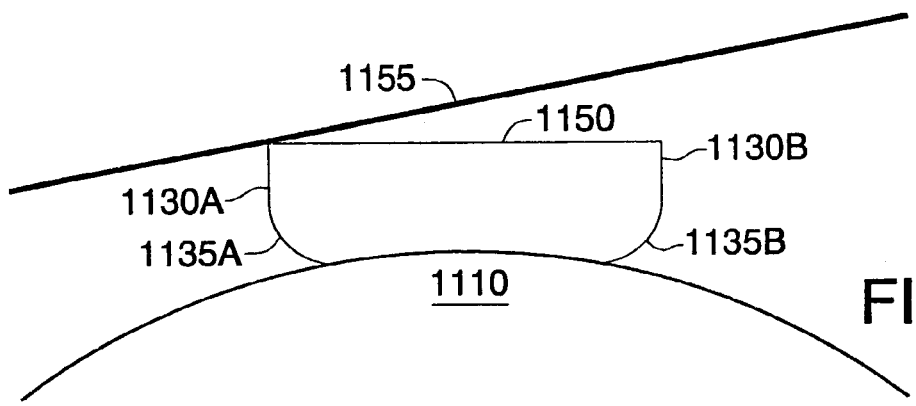
Figure 38B:
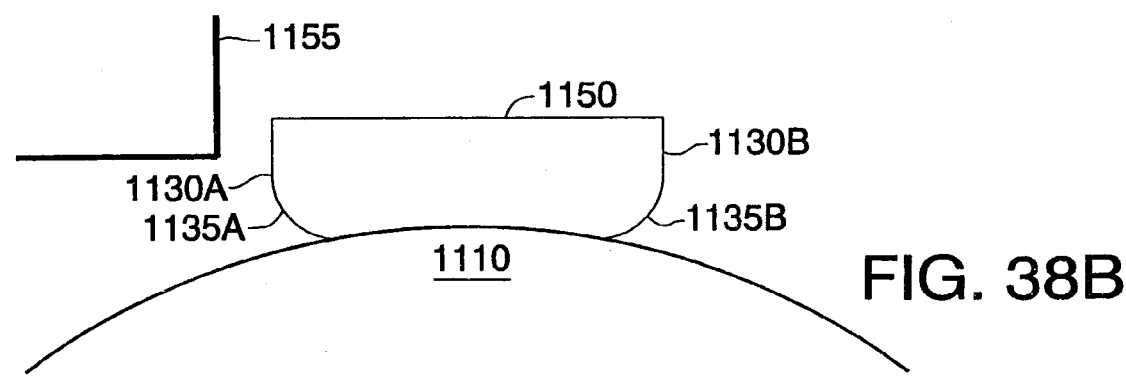
Figure 38C:
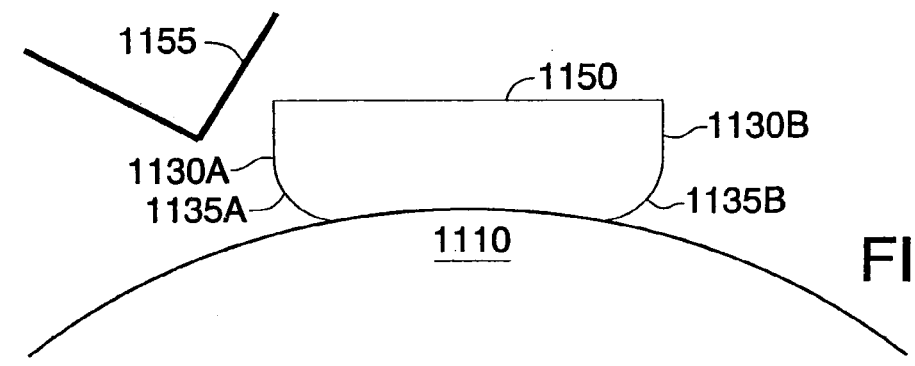
Figure 38D:
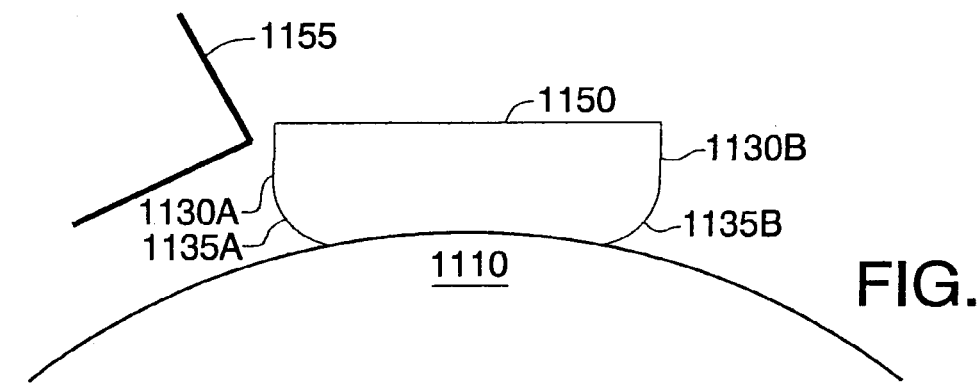
Figure 39A:
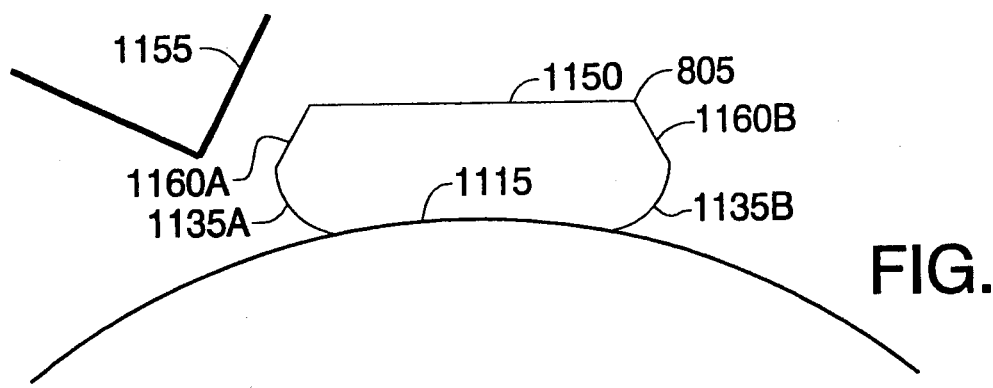
Figure 39B:
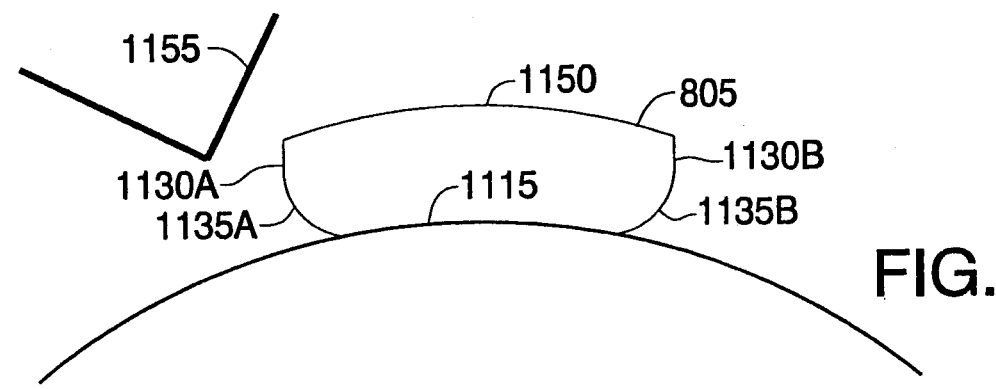
Figure 39C:
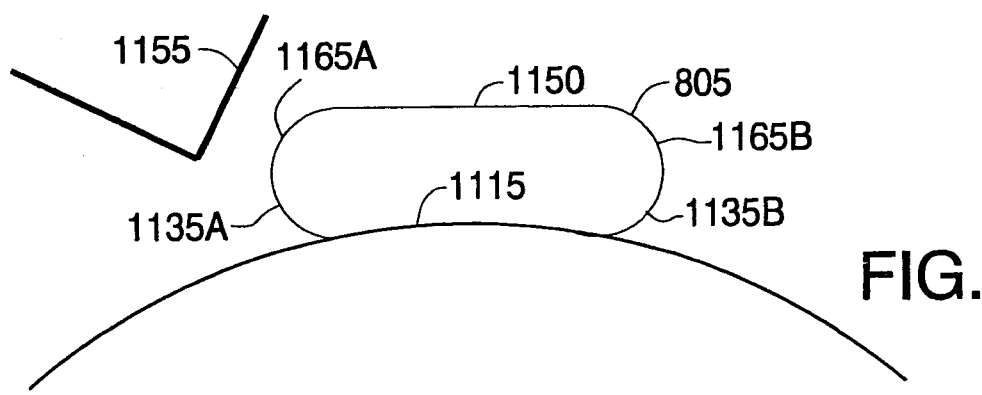
Figure 39D:
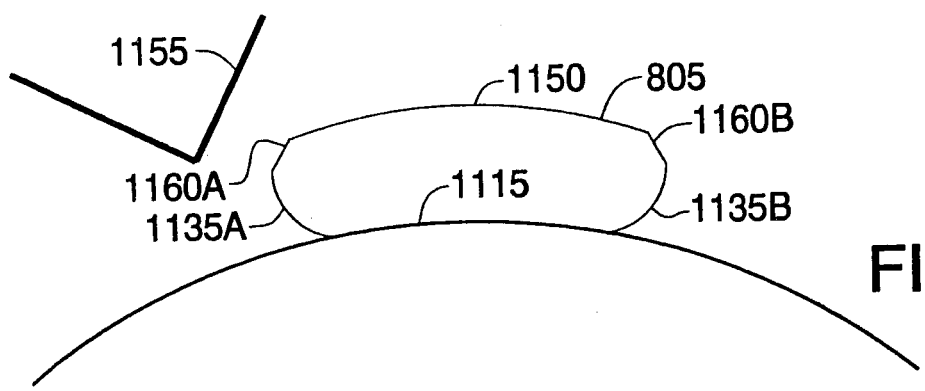
Figure 39E:
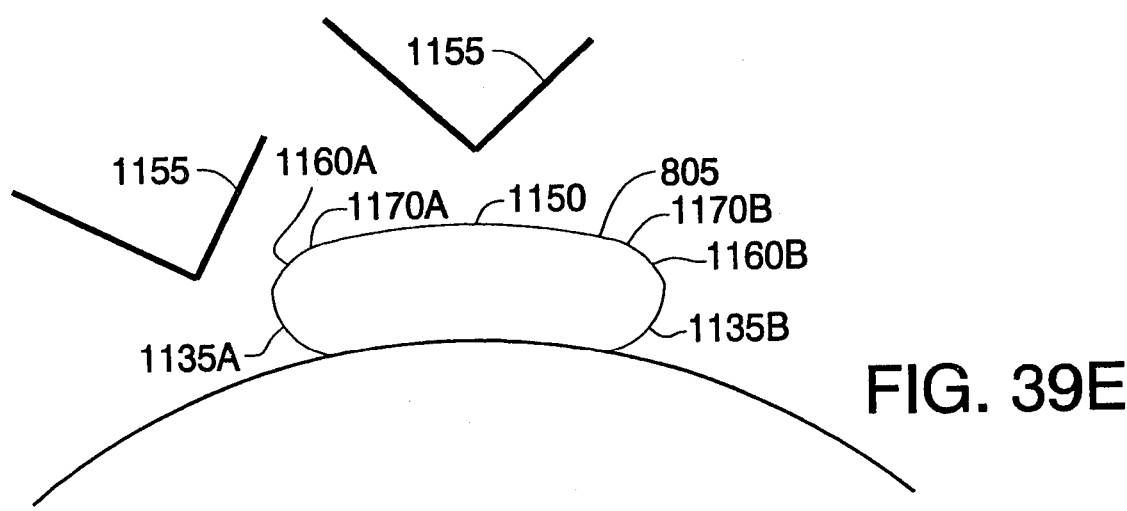
Figure 39F:
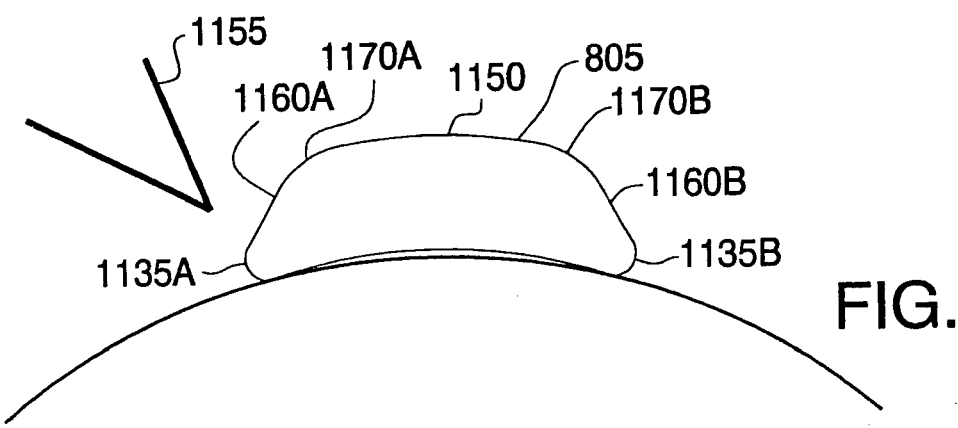
Figure 39G:
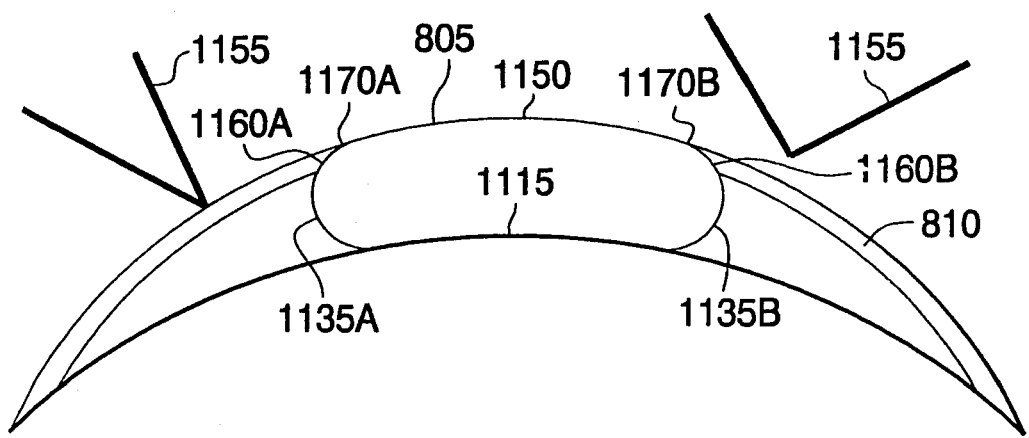

Referring to FIGS. 38A–D, it will be appreciated that housing 805 having a flat top surface 1150 and flat lateral ends 1130A and 1130B may tend to be jostled and bumped by object 1155, such as a wall or door or the corner or edge of a drawer, cabinet or desk, thereby moving housing 805 on body 1110 because such flat surfaces are not well adapted to deflect object 1155. Movement of housing 805 on body 1110 will detrimentally effect the ability of sensor device 800 to accurately make measurements and collect data. FIGS. 39A–G illustrate various aspects of the present invention that are adapted to deflect object 1155 and substantially prevent movement to of housing 805 on body 1110. In addition, the forms shown in FIGS. 39A–G increase the durability of sensor device 800 and make it easier to put on and wear clothing and the like, such as a wetsuit, over sensor device 800. As seen in FIG. 39A, housing 805 may have tapered sides 1160A and 1160B such that the width of housing 805 decreases in the direction from bottom surface 1115 to top surface 1150. Alternatively, referring to FIG. 39B, top surface 1150 of housing 805 may have a convex shape. As a further alternative, as seen in FIG. 39C, housing 805 may be provided with radiused portions 1165A and 1165B that meet with radiused portions 1135A and 1135B such that the lateral ends of housing 805 have a substantially semicircular shape. As shown in FIG. 39D, housing 805 may have both tapered sides 1160A and 1160B and a top surface 1150 with a convex shape. FIG. 39E is a modification of housing 805 shown in FIG. 39E in which the points 1170A and 1170B where radiused portions 1135A and 1135B meet tapered sides 1160A and 1160B, respectively, are themselves radiused. FIG. 39F is a variation of housing 805 shown in FIG. 39E having elongated tapered sides 1160A and 1160B. FIG. 39G shows how the ability of housing 805, such as the embodiment shown in FIG. 39E, to deflect object 1155 may be enhanced by the addition of flexible section 810 having a substantially convex outer surface. In addition, an air channel is provided between flexible section 810 and body 1110 to allow for heat to flow away from body 1110.

The terms and expressions which have been employed herein are used as terms of description and not as limitation, and there is no intention in the use of such terms and expressions of excluding equivalents of the features shown and described or portions thereof, it being recognized that various modifications are possible within the scope of the invention claimed. Although particular embodiments of the present invention have been illustrated in the foregoing detailed description, it is to be further understood that the present invention is not to be limited to just the embodiments disclosed, but that they are capable of numerous rearrangements, modifications and substitutions.

What is claimed is:

1. An apparatus for detecting at least one of human physiological and contextual information from the body of a wearer, comprising:
    a flexible section for engaging at least a portion of said body;
    a housing removably attached to and supported by said flexible section;
    a strap attached to said flexible section for securing said flexible section to said body;
    one or more sensors supported by said housing, said one or more sensors selected from the group consisting of physiological sensors and contextual sensors; and
    a processing unit supported by said housing in electronic communication with said one or more sensors.

2. An apparatus according to claim 1, further comprising a groove provided in said housing and a tongue provided on said flexible section, said groove being suitable to receive said tongue.

3. An apparatus according to claim 1, further comprising a tongue provided on said housing and a groove provided in said flexible section, said groove being suitable to receive said tongue.

4. An apparatus according to claim 1, further comprising an adhesive material for removably attaching said housing to said flexible section.

5. An apparatus according to claim 1, further comprising a magnet supported by each of said housing and said flexible section.

6. An apparatus according to claim 1, further comprising a stretchable band and a groove provided in said housing, said band suitable to fit around a portion of said flexible section and into said groove when said flexible section is placed over said housing.

7. An apparatus according to claim 1, said housing further comprising a display.

8. An apparatus according to claim 1, said one or more sensors comprising at least one of a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

9. An apparatus according to claim 1, said one or more sensors comprising at least two sensors.

10. An apparatus for detecting at least one of human physiological and contextual information from the body of a wearer, comprising:
    a housing support section for engaging at least a portion of said body;
    a housing removably attached to and supported by said housing support section;
    one or more sensors supported by said housing, said one or more sensors selected from the group consisting of physiological sensors and contextual sensors;
    a processing unit supported by said housing in electronic communication with said one or more sensors; and
    one or more additional housing support sections that may be selectively removably attached to said housing.

11. An apparatus according to claim 10, said housing support section and at least one of said additional housing support sections being suitable to engage different body portions of said wearer.

12. An apparatus according to claim 10, said apparatus having adjustable operating parameters, further comprising means for adjusting said operating parameters depending on the particular one of said housing support section and said one or more additional housing support sections to which said housing is removably attached.

13. An apparatus according to claim 12, said means for adjusting said operating parameters comprising a plurality of switches supported by said housing and a switch activator supported by said housing support section and each of said additional housing support sections, said switches being coupled to said processing unit, said operating parameters being adjusted in dependence on the particular one of said switches that is activated.

14. An apparatus according to claim 13, each of said switch activators being supported by a respective one of said housing support section and said additional housing support sections in a position such that a different one of said switches is activated depending on the particular one of said housing support section and said additional housing support sections to which said housing is removably attached.

15. An apparatus according to claim 13, said switches comprising magnetic switches and said switch activators each comprising a magnet.

16. An apparatus according to claim 13, said switches comprising mechanical switches.

17. An apparatus according to claim 16, each of said switch activators comprising a protruding element.

18. An apparatus according to claim 13, said switches comprising optical switches, said switch activators comprising one of means for obscuring light, means for reflecting light and means for filtering light.

19. An apparatus according to claim 13, said switches comprising electrical switches and said switch activators each comprising a conductor.

20. An apparatus according to claim 12, said means for adjusting said operating parameters comprising a plurality of switches supported by said housing and one or more switch activators supported by each of said housing support section and said additional housing support sections, said operating parameters being adjusted in dependence on the particular one or more of said switches that are activated.

21. An apparatus according to claim 12, said means for adjusting said operating parameters comprising a switch supported by said housing and at least one switch activator supported by each of said housing support section and said additional housing support sections, said switch being activatable according to a plurality of states depending upon a property of the particular switch activator activating said switch, said operating parameters being adjusted in dependence on said activation state of said switch.

22. An apparatus according to claim 10, further comprising a groove provided in said housing and a tongue provided on said housing support section and each of said additional housing support sections, said groove being suitable to receive each of said tongues.

23. An apparatus according to claim 10, further comprising a tongue provided on said housing and a groove provided in said housing support section and each of said additional housing support sections, said grooves being suitable to receive said tongue.

24. An apparatus according to claim 10, further comprising an adhesive material for removably attaching said housing to said housing support section and said additional housing support sections.

25. An apparatus according to claim 10, further comprising a magnet supported by each of said housing, said housing support section and said additional housing support sections.

26. An apparatus according to claim 10, further comprising a stretchable band and a groove provided in said housing, said stretchable band suitable to fit around a portion of one of said housing support section and said additional housing support section and into said groove when said one of said housing support section and said additional housing support sections is placed over said housing.

27. An apparatus according to claim 10, further comprising a wireless communications device for at least one of receiving information from and transmitting information to a computing device.

28. An apparatus according to claim 27, said computing device display information to an individual and enabling said individual to input information.

29. An apparatus according to claim 28, said computing device and said processing unit being adapted to engage in shared computing.

30. An apparatus according to claim 10, at least one of said housing section and said additional housing support sections comprising a garment.

31. An apparatus according to claim 30, said one or more sensors comprising a sensor for sensing one or more heart related parameters.

32. An apparatus according to claim 31, said one or more heart related parameters including at least one of heart rate, beat-to-beat variability, ECG, pulse oximetry, heart-related sounds and parameters relating to the mechanical action of the heart.

33. An apparatus according to claim 32, at least one of said additional housing support sections being suitable to engage a portion of said body comprising the left chest.

34. An apparatus according to claim 10, said housing support section and said one or more additional housing support sections each comprising a flexible section.

35. An apparatus according to claim 10, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

36. An apparatus for detecting at least one of human physiological and contextual information from the body of a wearer, comprising:
　a self-contained housing suitable to be worn on the left chest portion of said body;
　one or more sensors within said housing, said one or more sensors selected from the group consisting of physiological sensors and contextual sensors; and
　a processing unit within said housing in electronic communication with said one or more sensors;
　said one or more sensors comprising a sensor for sensing one or more heart related parameters including at least one of heart rate, beat-to-beat variability, ECG, pulse oximetry, heart-related sounds, and parameters relating to the mechanical action of the heart.

37. An apparatus according to claim 36, further comprising a housing support section for engaging at least a portion of said body, said housing being attached to said housing support section.

38. An apparatus according to claim 37, said housing support section comprising a flexible section.

39. An apparatus according to claim 38, said housing being selectively removably attached to said housing support section.

40. An apparatus according to claim 36, wherein said sensors generate data indicative of at least a detected parameter of the wearer and said processing unit generates derived data comprising a derived parameter based on said detected parameter, being an individual status parameter that cannot be directly detected by one of said one or more sensors.

41. An apparatus for detecting at least one of human physiological and contextual information from the body of a wearer which is mounted on said body in conjunction with a garment, comprising:

a housing;

a garment suitable to be worn on a portion of the body which restrains and supports said housing in a position proximate to the left chest of said body;

one or more sensors supported by said housing, said one or more sensors selected from the group consisting of physiological sensors and contextual sensors; and a processing unit supported by said housing in electronic communication with said one or more sensors;

said one or more sensors comprising a sensor for sensing one or more heart related parameters including at least one of heart rate, beat-to-beat variability, ECU, pulse oximetry, heart-related sounds, and parameters relating to the mechanical action of the heart.

42. An apparatus for detecting at least one of human physiological and contextual information from the body of a wearer in an ambient environment, comprising:

a housing;

a base member having a preselected resistivity mounted within said housing;

a first temperature measuring device attached to a first side of said base member;

a thermal energy communicator mounted adjacent to said first temperature measuring device for placing said first temperature measuring device in thermal communication with a portion of said body, said thermal energy communicator being located between said first temperature measuring device and said portion of said body when said apparatus is being worn on said body;

a second temperature measuring device attached to a second side of said base member, said second temperature measuring device in thermal communication with said ambient environment; and a processing unit provided in said housing, said first and second temperature measuring devices being in electronic communication with said processing unit;

wherein said apparatus is adapted to measure heat flux between said body and said ambient environment.

43. An apparatus according to claim 42, said first temperature measuring device comprising a first thermistor and said second temperature measuring device comprising a second thermistor.

44. An apparatus according to claim 43, said first thermistor measuring a first voltage, said second thermistor measuring a second voltage, said first voltage and said second voltage being used to generate a temperature difference (T2−T1), said heat flux being calculated according to the following formula:

heat flux $=K(T2-T1)$, wherein $K$ is said preselected resistivity.

45. An apparatus according to claim 42, said first temperature measuring device measuring a first parameter, said second temperature measuring device measuring a second parameter, said first parameter and said second parameter being used to generate a temperature difference (T2−T1), said heat flux being calculated according to the following formula:

heat flux $=K(T2-T1)$, wherein $K$ is said preselected resistivity.

46. An apparatus according to claim 42, said thermal energy communicator comprising a heat conduit having a first surface in thermal communication with said body portion when said apparatus is being worn and a second surface in thermal communication with said first temperature measuring device.

47. An apparatus according to claim 46, said thermal energy communicator further comprising a skin-side thermally conductive interface component in thermal communication with said body portion when said apparatus is being worn and said first surface of said heat conduit.

48. An apparatus according to claim 47, said skin-side thermally conductive interface component comprising a stainless steel plate.

49. An apparatus according to claim 47, said thermal energy communicator further comprising a first skin-side thermally conductive interface material located between said first thermally conductive interface component and said first surface of said heat conduit, and a second skin-side thermally conductive interface material located between said second surface of said heat conduit and said first temperature measuring device.

50. An apparatus according to claim 49, said first and second skin-side thermally conductive interface materials selected from the group consisting of thermally conductive gap fillers, thermally conductive phase change interface materials, thermally conductive tapes, thermally conductive cure-in-place compounds and epoxies, and thermal greases.

51. An apparatus according to claim 49, said skin-side thermally conductive interface component, said first skin-side thermally conductive interface material, said heat conduit, said second skin-side thermally conductive interface material, said first temperature measuring device, said base member, and said second temperature measuring device attached to one another along a direction substantially normal to said first and second side of said base member.

52. An apparatus according to claim 51, said base member comprising a printed circuit board.

53. An apparatus according to claim 52, said processing unit being attached to said printed circuit board.

54. An apparatus according to claim 42, further comprising an ambient-side thermally conductive interface component in thermal communication with said ambient environment and said second temperature measuring device.

55. An apparatus according to claim 54, further comprising an ambient-side thermally conductive interface material located between said ambient-side thermally conductive interface component and said second temperature measuring device.

56. An apparatus according to claim 55, said ambient-side thermally conductive interface material selected from the group consisting of thermally conductive gap fillers, thermally conductive phase change interface materials, thermally conductive tapes, thermally conductive cure-in-place compounds and epoxies, and thermal greases.

57. An apparatus according to claim 54, said ambient-side thermally conductive interface component comprising a stainless steel plate.

58. An apparatus according to claim 54, further comprising a housing support section for holding said housing in engagement with said body of said wearer, said housing support section exposing said ambient-side thermally conductive interface component to said ambient environment.

59. An apparatus according to claim 42, said thermal energy communicator comprising a thermally conductive interface material in thermal communication with said body portion when said apparatus is worn and said first temperature measuring device.

60. An apparatus according to claim 59, said thermally conductive interface material selected from the group consisting of thermally conductive gap fillers, thermally conductive phase change interface materials, thermally conductive tapes, thermally conductive cure-in-place compounds and epoxies, and thermal greases.

61. An apparatus according to claim 42, further comprising a housing support section attached to said housing, said housing support section being suitable to engage at least a portion of said body of said wearer.

62. An apparatus according to claim 42, further comprising a housing support section for engaging at least a portion of said body of said wearer, said housing support section being removably attached to said housing.

63. An apparatus according to claim 42, further comprising a plurality of housing support sections each suitable to engage at least a portion of said body of said wearer, and means for removably attaching said housing to any one of said housing support sections.

64. An apparatus according to claim 63, said apparatus having adjustable operating parameters, further comprising means for adjusting said operating parameters depending on the particular one of said housing support sections to which said housing is removably attached.

65. An apparatus for detecting at least one of human physiological and contextual information from the body of a wearer in an ambient environment, comprising:
  a housing;
  a printed circuit board supported by said housing, said printed circuit board having a preselected resistivity;
  a first thermistor attached to a first side of said printed circuit board and a second thermistor attached to a second side of said printed circuit board;
  a processing unit supported by said housing, said first thermistor and said second thermistor in electrical communication with said processing unit;
  a heat conduit, said heat conduit having a first surface and a second surface;
  a first thermally conductive interface component, said first thermally conductive interface component being in thermal communication with said body of said wearer when said apparatus is being worn;
  a second thermally conductive interface component in thermal communication with said ambient environment when said apparatus is being worn; and
  a first thermally conductive interface material located between said first thermally conductive interface component and said first surface of said heat conduit, a second thermally conductive interface material located between said second surface of said heat conduit and said first thermistor, and a third thermally conductive interface material located between said second thermistor and said second thermally conductive interface component;
    wherein said apparatus is adapted to measure heat flux between said body and said ambient environment.

66. An apparatus according to claim 65, said first thermally conductive interface component, said first thermally conductive interface material, said heat conduit, said second thermally conductive interface material, said first thermistor, said printed circuit board, said second thermistor, said third thermally conductive interface material and said second thermally conductive interface component attached to one another along a direction substantially normal to said first and second sides of said printed circuit board.

67. An apparatus according to claim 65, further comprising a housing support section for holding said housing in engagement with said body of said wearer, said housing support section exposing said second thermally conductive interface component to said ambient environment.

68. An apparatus for detecting, monitoring and reporting at least one of human physiological and contextual information from the body of a wearer, comprising:
  a housing having an adhesive material on at least a portion of an external surface thereof, said adhesive material enabling said housing to be removably attached to a portion of said body;
  at least two sensors supported by said housing selected from the group consisting of physiological sensors and contextual sensors, said physiological sensors adapted to facilitate the generation of data indicative of one or more detected physiological parameters of said wearer, said contextual sensors adapted to facilitate the generation of data indicative of one or more detected contextual parameters of said wearer;
  a processing unit in electrical communication with said sensors, said processing unit being adapted to generate at least one of: (i) derived data from at least one of at least a portion of said data indicative of physiological parameters, (ii) derived data from at least a portion of said data indicative of contextual parameters, said derived data comprising a calculated parameter based on at least one of said detected parameters, being an individual status parameter that cannot be directly detected by any of said at least two sensors and (iii) analytical status data from at least a portion of at least one of said data indicative of physiological parameters, said data indicative of contextual parameters and said derived data;
  an electronic memory in electrical communication with said processing unit for retrievably storing at least one of said data indicative of physiological parameters, data indicative of contextual parameters, derived data and analytical status data; and
  means for transmitting to an individual at least one of said data indicative of physiological parameters, data indicative of contextual parameters, derived data and analytical status data.

69. An apparatus according to claim 68, said housing being made of a rigid material.

70. An apparatus according to claim 69, said analytical status data being generated from at least a portion of said manually entered information.

71. An apparatus according to claim 68, said housing being made of a flexible material.

72. An apparatus according to claim 71, said flexible material comprising a flexible plastic film.

73. An apparatus according to claim 68, said means for transmitting comprising an electrochemical display.

74. An apparatus according to claim 68, said portion of said body comprising the left chest, said data indicative of one or more physiological parameters of said wearer comprising heart related parameters.

75. An apparatus according to claim 74, said housing being made of a flexible material.

76. An apparatus according to claim 75, said flexible material comprising a flexible plastic film.

77. An apparatus according to claim 76, said means for transmitting comprising an electrochemical display.

78. An apparatus according to claim 68, further comprising a wireless communications device for at least one of receiving information from and transmitting information to a computing device.

79. An apparatus according to claim 78, said processing unit and said computing device adapted to engage in shared computing.

80. An apparatus according to claim 68, said means for transmitting comprising a computing device coupled to said processing unit.

81. An apparatus according to claim 80, said computing device being coupled to said processing unit by a physical connection.

82. An apparatus according to claim 80, said computing device being coupled to said processing unit by a wireless connection.

83. An apparatus according to claim 69, further comprising means for manually entering information into said apparatus.

84. An apparatus according to claim 83, said apparatus monitoring the degree to which said individual has followed a predetermined routine, said analytical status data comprising feedback to said individual relating to the degree to which said individual has followed said predetermined routine, said feedback being generated from at least a portion of at least one of said data indicative of one or more physiological parameters of said individual, said derived data and said manually entered data.

85. An apparatus according to claim 84, wherein said routine comprises a plurality of categories and said feedback is generated and provided with respect to each of said categories.

86. An apparatus according to claim 68, said means for transmitting comprising a computing device coupled to said processing unit, said processing unit being adapted to cause said computing device to trigger an event upon detection of one or more physiological conditions of said wearer.

87. An apparatus according to claim 68, said processing unit being adapted to cause a computing device to trigger an event upon detection of one or more physiological conditions of said individual.

88. An apparatus according to claim 68, said at least two sensors being selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

89. An apparatus for detecting at least one of human physiological and contextual information from the body of a wearer, comprising:
 a housing, said housing having an inner surface for mounting adjacent said body and an outer surface opposite said inner surface;
 said inner surface having a longitudinal axis and a transverse axis, said inner surface being generally concave in a first direction and having an axis of concavity coincident with said longitudinal axis, said inner surface being generally convex in a second direction generally perpendicular to said first direction and having an axis of convexity coincident with said transverse axis.

90. An apparatus according to claim 89, said inner surface having first and second lateral ends located at opposite ends of said axis of concavity, said housing having a first radiused portion adjacent to and including said first lateral end and a second radiused portion adjacent to and including said second lateral end.

91. An apparatus according to claim 90, said inner surface having third and fourth lateral ends located at opposite ends of said axis of convexity, said housing having a third radiused portion adjacent to and including said third lateral end and a fourth radiused portion adjacent to and including said fourth lateral end.

92. An apparatus according to claim 90, further comprising one or more sensors located adjacent to at least one of said first and second lateral ends.

93. An apparatus according to claim 90, said outer surface having a convex shape between a first lateral side and a second lateral side of said outer surface.

94. An apparatus according to claim 93, said housing having a width dimension as measured between a first lateral side and a second lateral side of said housing, at least a portion of said first lateral side and said second lateral side each having a taper such that said width dimension gradually decreases in a third direction from said inner surface to said outer surface.

95. An apparatus according to claim 93, said housing having a third radiused portion adjacent to and including said first lateral side of said outer surface and a fourth radiused portion adjacent to and including said second lateral side of said outer surface.

96. An apparatus according to claim 94, said housing having a third radiused portion adjacent to and including said first lateral side of said outer surface and a fourth radiused portion adjacent to and including said second lateral side of said outer surface.

97. An apparatus according to claim 89, said outer surface having a convex shape between a first lateral side and a second lateral side of said outer surface.

98. An apparatus according to claim 97, said housing having a width dimension as measured between a first lateral side and a second lateral side of said housing, at least a portion of said first lateral side and said second lateral side each having a taper such that said width dimension gradually decreases in a third direction from said inner surface to said outer surface.

99. An apparatus according to claim 89, further comprising a housing support section attached to said housing for engaging said body of said wearer, said housing support section having a generally convex outer surface.

100. An apparatus according to claim 89, further comprising one or more sensor supported by said housing, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

101. An apparatus for detecting at least one of human physiological and contextual information from the body of a wearer, comprising:
 a housing suitable to be worn on said body;
 one or more sensors supported by said housing, said one or more sensors selected from the group consisting of physiological sensors and contextual sensors; and
 a processing unit supported by said housing in electronic communication with said one or more sensors, said one or more sensors comprising a sensor for measuring GSR including at least two electrical contacts, said electrical contacts having a textured surface.

102. An apparatus according to claim 101, said textured surface comprising a plurality of raised bumps.

103. An apparatus according to claim 101, said electrical contacts having an oblong, curved shape.

104. An apparatus according to claim 101, said sensor for measuring GSR further comprising a current loop for applying a current between said electrical contacts and measuring a voltage across said electrical contacts.

105. An apparatus according to claim 101, further comprising a housing support section for engaging at least a portion of said body, said housing being attached to said housing support section.

106. An apparatus according to claim 105, said housing support section comprising a flexible section.

107. An apparatus according to claim 106, said housing being selectively removably attached to said housing support section.

108. An apparatus for detecting at least one of human physiological and contextual information from the body of a wearer, comprising:
   a housing suitable to be worn on said body;
   one or more sensors supported by said housing, said one or more sensors selected from the group consisting of physiological sensors and contextual sensors;
   a processing unit supported by said housing in electronic communication with said one or more sensors; and
   a proximity sensor for sensing whether said apparatus is being worn.

109. An apparatus according to claim 108, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.
   a proximity sensor for sensing whether said apparatus is being worn.

110. An apparatus according to claim 108, further comprising a housing support section for engaging at least a portion of said body, said housing being attached to said housing support section.

111. An apparatus according to claim 110, said housing support section comprising a flexible section.

112. An apparatus according to claim 111, said housing being selectively removably attached to said housing support section.

113. An apparatus for detecting at least one of human physiological and contextual information from the body of a wearer, comprising:
   a housing suitable to be worn on said body;
   one or more sensors supported by said housing, said one or more sensors selected from the group consisting of physiological sensors and contextual sensors;
   a processing unit supported by said housing in electronic communication with said one or more sensors; and
   a proximity sensor for automatically powering said apparatus on and off.

114. An apparatus according to claim 113, further comprising a housing support section for engaging at least a portion of said body, said housing being attached to said housing support section.

115. An apparatus according to claim 114, said housing support section comprising a flexible section.

116. An apparatus according to claim 115, said housing being selectively removably attached to said housing support section.

117. An apparatus according to claim 113, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

118. An apparatus for detecting at least one of human physiological and contextual information from the body of a wearer, comprising:
   a housing suitable to be worn on said body;
   one or more sensors supported by said housing, said one or more sensors selected from the group consisting of physiological sensors and contextual sensors, said sensors generating data indicative of at least a detected parameter of the wearer;
   a processing unit supported by said housing in electronic communication with said one or more sensors generating derived data comprising a calculated parameter based on said detected parameter, being an individual status parameter that cannot be directly detected by one of said one or more sensors, said processing unit being in electronic communication with a feedback device for providing feedback information to a wearer of said device.

119. An apparatus according to claim 118, further comprising a housing support section for engaging at least a portion of said body, said housing being attached to and supported by said housing support section.

120. An apparatus according to claim 119, said housing support section comprising a flexible section.

121. An apparatus according to claim 120, said housing being selectively removably attached to said housing support section.

122. An apparatus according to claim 118, said one or more sensors comprising two sensors supported by said housing.

123. An apparatus according to claim 118, further comprising at least one additional sensor in electrical communication with said processing unit.

124. An apparatus according to claim 123, wherein said additional sensor is external to said housing.

125. An apparatus according to claim 118, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor and a sensor for measuring heart related parameters.

126. A method for detecting from the body of a wearer parameters relating to the heart of the wearer, comprising:
   generating a first physiological acoustic signal including a first physiological acoustic component generated from the motion of said heart and a second physiological acoustic component generated from non-heart related motion of said body of said wearer, said non-heart related motion comprising footfalls of said wearer;
   generating a second signal related to said non-heart related motion of said body;
   generating a third signal by using said second signal to subtract at least a portion said second physiological acoustic component from said first signal; and
   generating said heart related parameters from said third signal.

127. A method according to claim 126, wherein said information relating to said footfalls is generated using an accelerometer.

128. An apparatus for detecting, monitoring and reporting at least one of human physiological and contextual information from the body of a wearer, comprising:
a housing having an adhesive material on at least a portion of an external surface thereof, said adhesive material enabling said housing to be removably attached to a portion of said body;
at least two sensors supported by said housing, said at least two sensors being selected from the group consisting of physiological sensors and contextual sensors, said sensors generating data indicative of at least a first parameter and a second parameter of the wearer;
a processor, said processor generating derived data based on said data indicative of at least a first parameter and a second parameter, said derived data comprising a third parameter of said wearer, said third parameter being an individual status parameter that cannot be directly detected by any of said at least two sensors;
a memory for retrievably storing at least one of said data indicative of at least a first parameter and a second parameter and said derived data; and
means for transmitting to an individual at least one of said data indicative of at least a first parameter and a second parameter and said derived data.

129. An apparatus according to claim 128, said housing being made of a rigid material.

130. An apparatus according to claim 128, said housing being made of a flexible material.

131. An apparatus according to claim 130, said flexible material comprising a flexible plastic film.

132. An apparatus according to claim 128, said means for transmitting comprising an electrochemical display.

133. An apparatus according to claim 128, said portion of said body comprising the left chest, said data indicative of at least a first parameter and a second parameter of the wearer comprising heart related parameters, said derived data relating to the heart of said wearer.

134. An apparatus according to claim 133, said housing being made of a flexible material.

135. An apparatus according to claim 133, said flexible material comprising a flexible plastic film.

136. An apparatus according to claim 133, said means for transmitting comprising an electrochemical display.

137. An apparatus according to claim 128, further comprising a wireless communications device for at least one of receiving information from and transmitting information to a computing device.

138. An apparatus according to claim 137, said processor and said computing device adapted to engage in shared computing.

139. An apparatus according to claim 128, said means for transmitting comprising a computing device in electronic communication with said processor.

140. An apparatus according to claim 128, said means for transmitting comprising a computing device in electronic communication with said processor, said processor being adapted to cause said computing device to trigger an event upon detection of one or more physiological conditions of said individual.

141. An apparatus according to claim 128, said processor being adapted to cause a computing device to trigger an event upon detection of one or more physiological conditions of said wearer.

142. An apparatus according to claim 128, said at least two sensors being selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

143. An apparatus for detecting at least one of human physiological and contextual information from the body of a wearer, comprising:
a housing suitable to be worn on said body;
housing support section for engaging at least a portion of said body, said housing being attached to said housing support section;
one or more sensors supported by said housing, said one or more sensors selected from the group consisting of physiological sensors and contextual sensors; and
a processing unit supported by said housing in electronic communication with said one or more sensors, said one or more sensors comprising a sensing component for contacting the skin of a wearer, said sensing component comprising a plurality of microneedles.

144. An apparatus according to claim 143, said housing support section comprising a flexible section.

145. An apparatus according to claim 144, said housing being selectively removably attached to said housing support section.

146. An apparatus for detecting at least one of human physiological and contextual information from the body of a wearer, comprising:
a self-contained housing suitable to be worn on said body:
one or more sensors within said housing, said one or more sensors selected from the group consisting of physiological sensors and contextual sensors; and
a processing unit within said housing in electronic communication with said one or more sensors, said one or more sensors comprising one or more electrical contacts, said electrical contacts having a textured surface.

147. An apparatus according to claim 146, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

148. An apparatus according to claim 146, said textured surface comprising a plurality of raised bumps.

149. An apparatus according to claim 146, further comprising a housing support section for engaging at least a portion of said body, said housing being attached to said housing support section.

150. An apparatus according to claim 149, said housing support section comprising a flexible section.

151. An apparatus according to claim 150, said housing being selectively removably attached to said housing support section.

152. An apparatus for detecting at least one of human physiological and contextual information from the body of a wearer, comprising:
a housing suitable to be worn on said body;
a housing support section for engaging at least a portion of said body, said housing being attached to said housing support section;

one or more sensors supported by said housing, said one or more sensors selected from the group consisting of physiological sensors and contextual sensors; and a processing unit supported by said housing in electronic communication with said one or more sensors and with a sensing component placed in contact with the skin of said wearer, said sensing component comprising a plurality of microneedles.

153. An apparatus according to claim 152, said housing support section comprising a flexible section.

154. An apparatus according to claim 153, said housing being selectively removably attached to said housing support section.

155. An apparatus for detecting at least one of human physiological and contextual information from the body of a wearer, comprising:

a housing suitable to be worn on said body;

one or more sensors supported by said housing, said one or more sensors comprising at least one of: an ambient temperature sensor, an ambient light sensor, an ambient sound sensor, an EMG sensor, a skin impedance sensor and a heat flux sensor;

a processing unit supported by said housing in electronic communication with said one or more sensors; and a wireless transceiver for receiving information from and transmitting information to a computing device, said computing device displaying information to an individual and enabling said individual to input information, said computing device and said processing unit being adapted to engage in shared computing.

156. An apparatus according to claim 155, further comprising a housing support section for engaging at least a portion of said body, said housing being attached to said housing support section.

157. An apparatus according to claim 156, said housing support section comprising a flexible section.

158. An apparatus according to claim 157, said housing being selectively removably attached to said housing support section.

159. An apparatus according to claim 155, further comprising two sensors.

160. An apparatus according to claim 155, wherein said sensors generate data indicative of at least a detected parameter of the wearer and said processing unit generates derived data comprising a derived parameter based on said detected parameter, being an individual status parameter that cannot be directly detected by one of said one or more sensors.

161. An apparatus for detecting at least one of human physiological and contextual information from the body of a wearer, comprising:

a housing suitable to be worn on said body;

one or more sensors supported by said housing, said one or more sensors further comprising at least one of: a sensor for measuring GSR including at least two electrical contacts, a skin temperature sensor, an ambient temperature sensor, an accelerometer, an ambient light sensor, an ambient sound sensor, an EMG sensor, an ECU sensor, a skin impedance sensor, a heat flux sensor, and a sensor for measuring heart related parameters; and a processing unit supported by said housing in electronic communication with said one or more sensors, said one or more sensors comprising a sensing component for contacting the skin of said wearer, said sensing component comprising a plurality of microneedles.

162. An apparatus for detecting at least one of human physiological and contextual information from the body of a wearer, comprising:

a housing suitable to be worn on said body;

an ECG sensor and an accelerometer supported by said housing;

a processing unit supported by said housing in electronic communication with said sensors, said processing unit being in electronic communication with a feedback device for providing feedback information to a wearer of said device.

163. An apparatus for detecting at least one of human physiological and contextual information from the body of a wearer, comprising:

a self-contained housing suitable to be worn on the upper arm portion of said body;

one or more sensors within said housing, said one or more sensors selected from the group consisting of physiological sensors and contextual sensors, said one or more sensors comprising at least one of: an ambient temperature sensor, an ambient light sensor, an ambient sound sensor, an EMG sensor, a skin impedance sensor, and a heat flux sensor; and a processing unit within said housing in electronic communication with said one or more sensors.

164. An apparatus for detecting at least one of human physiological and contextual information from the body of a wearer, comprising:

a housing support section for engaging at least a portion of said body, said housing support section having an adhesive material on a surface thereof for attaching said housing support section to said body;

a housing located between said housing support section and said body, said housing being held against said body by said housing support section;

one or more sensors supported by said housing, said one or more sensors selected from the group consisting of physiological sensors and contextual sensors; and a processing unit supported by said housing in electronic communication with said one or more sensors.

165. An apparatus according to claim 164, said housing support section comprising a flexible section.

166. An apparatus according to claim 164, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

167. An apparatus according to claim 164, said housing being selectively removably attached to said housing support section.

168. An apparatus according to claim 164, said housing having an inner surface for mounting adjacent said body and an outer surface opposite said inner surface, said inner surface having a generally concave cross section.

169. An apparatus according to claim 164, said housing having an inner surface for mounting adjacent said body and an outer surface opposite said inner surface, said inner surface having a generally convex cross section.

170. An apparatus according to claim 164, said housing having an inner surface for mounting adjacent said body and an outer surface opposite said inner surface, said inner surface having a longitudinal axis and a transverse axis, said inner surface being generally concave in a first direction and having an axis of concavity coincident with said longitudinal axis, said inner surface being generally convex in a second direction generally perpendicular to said first direction and having an axis of convexity coincident with said transverse axis.

171. An apparatus for detecting at least one of human physiological and contextual information from the body of a wearer, comprising:
- a housing, said housing engaging said body;
- one or more sensors supported by said housing, said one or more sensors selected from the group consisting of physiological sensors and contextual sensors;
- a processing unit supported by said housing in electronic communication with said one or more sensors;
- a housing support section placed over said housing, said housing support section engaging said body and securing said housing in place against said body by way of pressure alone.

172. An apparatus according to claim 171, said housing support section comprising a flexible section.

173. An apparatus according to claim 171, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

174. An apparatus according to claim 171, said housing having an inner surface for mounting adjacent said body and an outer surface opposite said inner surface, said inner surface having a generally concave cross section.

175. An apparatus according to claim 171, said housing having an inner surface for mounting adjacent said body and an outer surface opposite said inner surface, said inner surface having a generally convex cross section.

176. An apparatus according to claim 171, said housing having an inner surface for mounting adjacent said body and an outer surface opposite said inner surface, said inner surface having a longitudinal axis and a transverse axis, said inner surface being generally concave in a first direction and having an axis of concavity coincident with said longitudinal axis, said inner surface being generally convex in a second direction generally perpendicular to said first direction and having an axis of convexity coincident with said transverse axis.

177. An apparatus for detecting at least one of human physiological and contextual information from the body of a wearer, comprising:
- a housing suitable to be worn on said body;
- one or more sensors supported by said housing, said one or more sensors selected from the group consisting of physiological sensors and contextual sensors;
- a processing unit supported by said housing in electronic communication with said one or more sensors, said processing unit being in electronic communication with a feedback device having a sensor for providing feedback information to a wearer of said device.

178. An apparatus for detecting at least one of human physiological and contextual information from the body of a wearer, comprising:
- a housing;
- a housing support section comprising a flexible section for receiving and supporting the insertion of said housing, said housing support section engaging at least a portion of said body;
- one or more sensors supported by said housing, said one or more sensors selected from the group consisting of physiological sensors and contextual sensors; and
- a processing unit supported by said housing in electronic communication with said one or more sensors, said processing unit being in electronic communication with a feedback device for providing feedback information to a wearer of said device.

179. An apparatus according to claim 178, said housing being selectively removably attached to said housing support section.

180. An apparatus for detecting at least one of human physiological and contextual information from the body of a wearer, comprising:
- a housing suitable to be worn on a portion of said body;
- a housing support section for engaging at least a portion of said body, said housing being attached to said housing support section;
- one or more sensors supported by said housing, said one or more sensors selected from the group consisting of physiological sensors and contextual sensors; and
- a processing unit supported by said housing in electronic communication with said one or more sensors;
- said one or more sensors comprising a sensor for sensing one or more heart related parameters including at least one of heart rate, beat-to-beat variability, ECG, pulse oximetry, heart-related sounds, and parameters relating to the mechanical action of the heart, said portion of said body comprising the left chest.

181. An apparatus according to claim 180, said housing support section comprising a flexible section.

182. An apparatus according to claim 180, said housing being selectively removably attached to said housing support section.

183. An apparatus for detecting at least one of human physiological and contextual information from the body of a wearer, comprising:
- a housing suitable to be worn on said body;
- a housing support section comprising a flexible section for engaging at least a portion of said body, said housing being selectively removably attached to said housing support section;
- one or more sensors supported by said housing, said one or more sensors selected from the group consisting of physiological sensors and contextual sensors; and
- a processing unit supported by said housing in electronic communication with said one or more sensors, said one or more sensors comprising one or more electrical contacts, said electrical contacts having a textured surface comprising a plurality of raised bumps.

184. An apparatus for detecting at least one of human physiological and contextual information from the body of a wearer, comprising:
- a housing suitable to be worn on said body;
- one or more sensors supported by said housing, said one or more sensors selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters; and
- a processing unit supported by said housing in electronic communication with said one or more sensors and with a sensing component placed in contact with the skin of said wearer, said sensing component comprising a plurality of microneedles.

185. An apparatus for detecting, monitoring and reporting at least one of human physiological and contextual information from the body of a wearer, comprising:
  a housing having an adhesive material on at least a portion of an external surface thereof, said adhesive material enabling said housing to be removably attached to a portion of said body;
  at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;
  a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;
  an electronic memory in electrical communication with said processing unit for retrievably storing at least one of said data indicative of physiological parameters, data indicative of contextual parameters, derived data and analytical status data; and
  an electrochemical display for transmitting to an individual at least one of said data indicative of physiological parameters, data indicative of contextual parameters, derived data and analytical status data.

186. An apparatus for detecting, monitoring and reporting at least one of human physiological and contextual information from the body of a wearer, comprising:
  a flexible housing comprising plastic film, said flexible housing having an adhesive material on at least a portion of an external surface thereof, said adhesive material enabling said housing to be removably attached to the left chest area of said body;
  at least two sensors supported by said housing selected from the group consisting of physiological sensors and contextual sensors, said physiological sensors adapted to facilitate the generation of data indicative of one or more heart related physiological parameters of said wearer, said contextual sensors adapted to facilitate the generation of data indicative of one or more contextual parameters of said wearer;
  a processing unit in electrical communication with said sensors, said processing unit being adapted to generate at least one of: (i) derived data from at least one of at least a portion of said data indicative of said heart related physiological parameters and at least a portion of said data indicative of contextual parameters, and (ii) analytical status data from at least a portion of at least one of said data indicative of said heart related physiological parameters, said data indicative of contextual parameters and said derived data;
  an electronic memory in electrical communication with said processing unit for retrievably storing at least one of said data indicative of said heart related physiological parameters, data indicative of contextual parameters, derived data and analytical status data; and
  an electrochemical display for transmitting to an individual at least one of said data indicative of said heart related physiological parameters, data indicative of contextual parameters, derived data and analytical status data.

187. An apparatus for detecting, monitoring and reporting at least one of human physiological and contextual information from the body of a wearer, comprising:
  a housing having an adhesive material on at least a portion of an external surface thereof, said adhesive material enabling said housing to be removably attached to a portion of said body;
  at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;
  a processing unit in electrical communication with said sensors, said processing unit being adapted to generate at least one of: (i) derived data from at least one of at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;
  an electronic memory in electrical communication with said processing unit for retrievably storing at least one of said data indicative of physiological parameters, data indicative of contextual parameters, derived data and analytical status data;
  means for transmitting to an individual at least one of said data indicative of physiological parameters, data indicative of contextual parameters, derived data and analytical status data; and
  a wireless communications device for at least one of receiving information from and transmitting information to a computing device
  wherein said processing unit and said computing device are adapted to engage in shared computing.

188. An apparatus for detecting, monitoring and reporting at least one of human physiological and contextual information from the body of a wearer, comprising:
  a housing having an adhesive material on at least a portion of an external surface thereof, said adhesive material enabling said housing to be removably attached to a portion of said body;
  at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;
  a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and a computing device coupled to said processing unit by a physical connection for transmitting to an individual at least one of said data indicative of physiological parameters, data indicative of contextual parameters, derived data and analytical status data.

189. An apparatus for detecting, monitoring and reporting at least one of human physiological and contextual information from the body of a wearer, comprising:

a rigid housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and means for transmitting to an individual at least one of said data indicative of physiological parameters, data indicative of contextual parameters, derived data and analytical status data.

190. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data;

means for transmitting to an individual at least one of said data indicative of physiological parameters, data indicative of contextual parameters, derived data and analytical status data; and means for manually entering information into said apparatus.

191. An apparatus for detecting, monitoring and reporting at least one of human physiological and contextual information from the body of a wearer, comprising:

a rigid housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data;

means for transmitting to an individual at least one of said data indicative of physiological parameters, data indicative of contextual parameters, derived data and analytical status data; and means for manually entering information into said apparatus, said analytical status data being generated from at least a portion of manually entered information.

192. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and a computing device coupled to said processing unit for transmitting to an individual at least one of said data indicative of physiological parameters, data indicative of contextual parameters, derived data and analytical status data;

wherein said processing unit is adapted to cause said computing device to trigger an event upon detection of one or more physiological conditions of said wearer.

193. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data and to cause a computing device to trigger an event upon detection of one or more physiological conditions of said wearer;

an electronic memory in electrical communication with said processing unit for retrievably storing at least one of said data indicative of physiological parameters, data indicative of contextual parameters, derived data and analytical status data; and means for transmitting to an individual at least one of said data indicative of physiological parameters, data indicative of contextual parameters, derived data and analytical status data.

194. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least one of at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data;

means for transmitting to an individual at least one of said data indicative of physiological parameters, data indicative of contextual parameters, derived data and analytical status data; and means for manually entering information into said apparatus;

said apparatus monitoring the degree to which said individual has followed a predetermined routine, said analytical status data comprising feedback to said individual relating to the degree to which said individual has followed said predetermined routine, said feedback being generated from at least a portion of at least one of said data indicative of one or more physiological parameters of said individual, said derived data and said manually entered data.

195. An apparatus according to claim 194, wherein said routine comprises a plurality of categories and said feedback is generated and provided with respect to each of said categories.

196. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters, said sensors adapted to facilitate the generation of data indicative of one or more physiological parameters or contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and means for transmitting to an individual at least one of said data indicative of physiological parameters, data indicative of contextual parameters, derived data and analytical status data.

197. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of physiological sensors and contextual sensors, said sensors generating data indicative of at least a first parameter and a second parameter of the wearer;

a processor, said processor generating derived data based on said data indicative of at least a first parameter and a second parameter;

a memory for retrievably storing at least one of said data indicative of at least a first parameter and a second parameter and said derived data; and an electrochemical display for transmitting to an individual at least one of said data indicative of at least a first parameter and a second parameter and said derived data.

198. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a the left chest area of said body;

at least two sensors supported by said housing, said at least two sensors being selected from the group consisting of physiological sensors and contextual sensors, said sensors generating data indicative of at least a first heart related parameter and a second heart related parameter of the wearer;

a processor, said processor generating derived data based on at least a portion of said first and second parameters, said derived data comprising heart related derived data;

a memory for retrievably storing at least one of said data indicative of at least a first heart related parameter and a second heart related parameter and said heart related derived data; and an electrochemical display for transmitting to an individual at least one of said data indicative of at least a first heart related parameter, said data indicative of at least a second heart related parameter, and said derived data.

199. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of physiological sensors and contextual sensors, said sensors generating data indicative of at least a first parameter and a second parameter of the wearer;

a processor, said processor generating derived data based on said data indicative of at least a first parameter and a second parameter;

a memory for retrievably storing at least one of said data indicative of at least a first parameter and a second parameter and said derived data;

means for transmitting to an individual at least one of said data indicative of at least a first parameter and a second parameter and said derived data; and a wireless communications device for at least one of receiving information from and transmitting information to a computing device, wherein said processor and said computing device adapted to engage in shared computing.

200. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of physiological sensors and contextual sensors, said sensors generating data indicative of at least a first parameter and a second parameter of the wearer;

a processor, said processor generating derived data based on said data indicative of at least a first parameter and a second parameter;

a memory for retrievably storing at least one of said data indicative of at least a first parameter and a second parameter and said derived data; and a computing device in electronic communication with said processor for transmitting to an individual at least one of said data indicative of at least a first parameter and a second parameter and said derived data, said processor being adapted to cause said computing device to trigger an event upon detection of one or more physiological conditions of said individual.

201. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of physiological sensors and contextual sensors, said sensors generating data indicative of at least a first parameter and a second parameter of the wearer;

a processor, said processor generating derived data based on said data indicative of at least a first parameter and a second parameter and adapted to cause a computing device to trigger an event upon detection of one or more physiological conditions of said wearer;

a memory for retrievably storing at least one of said data indicative of at least a first parameter and a second parameter and said derived data; and means for transmitting to an individual at least one of said data indicative of at least a first parameter and a second parameter and said derived data.

202. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters, said sensors generating data indicative of at least a first parameter and a second parameter of the wearer;

a processor, said processor generating derived data based on said data indicative of at least a first parameter and a second parameter;

a memory for retrievably storing at least one of said data indicative of at least a first parameter and a second parameter and said derived data; and means for transmitting to an individual at least one of said data indicative of at least a first parameter and a second parameter and said derived data.

203. An apparatus for detecting from the body of a wearer parameters relating to the heart of the wearer, comprising:

an acoustic-based non-ECG heart parameter sensor that generates a first signal including a first acoustic component generated from the motion of said heart and a second acoustic component generated from footfalls created by said body of said wearer; and one or more filtering accelerometer sensors for generating a second signal related to said footfalls created by said body, said second signal being used to subtract at least a portion of said second acoustic component from said first signal to generate a third signal, said third signal being used to generate said heart related parameters.

204. An apparatus for detecting from the body of a wearer parameters relating to the heart of the wearer, comprising:

an acoustic-based non-ECG heart parameter sensor that generates a first signal including a first acoustic component generated from the motion of said heart and a second acoustic component generated from non-heart related motion of said body of said wearer, said first signal further including a third acoustic component generated from ambient noise;

one or more filtering sensors for generating a second signal related to said non-heart related motion of said body, said second signal being used to subtract at least a portion of said second acoustic component from said first signal to generate a third signal, said third signal being used to generate said heart related parameters; and an ambient noise sensor that generates a fourth signal related to said ambient noise, said fourth signal being used to subtract at least a portion of said third acoustic component from said first signal to generate said third signal.

205. A method for detecting from the body of a wearer parameters relating to the heart of the wearer, comprising:

generating a first acoustic signal including a first acoustic component generated from the motion of said heart and a second acoustic component generated from footfalls created by said body of said wearer;

generating a second signal related to said footfalls;

generating a third signal by using said second signal to subtract at least a portion said second acoustic component from said first signal; and generating said heart related parameters from said third signal.

206. A method according to claim 205, wherein said information relating to said footfalls is generated using an accelerometer.

207. A method for detecting from the body of a wearer parameters relating to the heart of the wearer, comprising:

generating a first acoustic signal including a first acoustic component generated from the motion of said heart and a second acoustic component generated from non-heart related motion of said body of said wearer, said first acoustic signal further including a third acoustic component generated from ambient noise;

generating a second signal related to said non-heart related motion of said body;

generating a third signal by using said second signal to subtract at least a portion said second acoustic component from said first signal;

generating said heart related parameters from said third signal; and generating a fourth signal related to said ambient noise, said step of generating said third signal further comprising using said fourth signal to subtract at least a portion of said third acoustic component from said first signal.

208. An apparatus for detecting at least one of human physiological and contextual information from the body of a wearer which is mounted on said body in conjunction with a garment, comprising:

a housing;

a garment suitable to be worn on a portion of the body which restrains and supports said housing in a position proximate to the upper arm of said body;

one or more sensors supported by said housing, said one or more sensors selected from the group consisting of physiological sensors and contextual sensors; and a processing unit supported by said housing in electronic communication with said one or more sensors;

said one or more sensors comprising a sensor for sensing one or more heart related parameters including at least one of pulse oximetry, heart-related sounds, and parameters relating to the mechanical action of the heart.

209. An apparatus for detecting at least one of human physiological and contextual information from the body of a wearer, comprising:

a self-contained housing suitable to be worn on the upper arm portion of said body;

one or more sensors within said housing, said one or more sensors selected from the group consisting of physiological sensors and contextual sensors; and a processing unit within said housing in electronic communication with said one or more sensors;

said one or more sensors comprising a sensor for sensing one or more heart related parameters including at least one of pulse oximetry, heart-related sounds, and parameters relating to the mechanical action of the heart.

210. An apparatus for detecting from the body of a wearer parameters relating to the heart of the wearer, comprising:

an acoustic-based non-ECG heart parameter sensor that generates a first signal including a first physiological acoustic component generated from the motion of said heart, a second physiological acoustic component generated from non-heart related motion of said body of said wearer, and a third acoustic component generated from ambient noise; and one or more filtering sensors for generating a second signal related to said non-heart related motion of said body and a third signal related to said ambient noise, said second signal being used to subtract at least a portion of said second physiological acoustic component from said first signal and said third signal being used to subtract at least a portion of said third acoustic component from said first signal to generate a fourth signal, said fourth signal being used to generate said heart related parameters.

211. An apparatus according to claim 210, said acoustic-based non-ECG heart parameter sensor including a sound transducer coupled to a pad containing an acoustic transmission material.

212. A method for detecting from the body of a wearer parameters relating to the heart of the wearer, comprising:

generating a first physiological acoustic signal including a first physiological acoustic component generated from the motion of said heart, a second acoustic component generated from non-heart related motion of said body, and a third acoustic component generated from ambient noise;

generating a second signal related to said non-heart related motion of said body;

generating a third signal related to said ambient noise;

generating a fourth signal by (i) using said second signal to subtract at least a portion of said second acoustic component from said first signal, and (ii) using said third signal to subtract at least a portion of said third acoustic component from said first signal;

generating said heart related parameters from said fourth signal.

213. An apparatus for detecting at least one of human physiological and contextual information from the body of a wearer, comprising:

a housing support section for engaging at least a portion of said body a housing removably attached to and supported by said housing support section;

a strap attached to said housing support section for securing said housing support section to said body;

one or more sensors supported by said housing, said one or more sensors selected from the group consisting of physiological sensors and contextual sensors; and a processing unit supported by said housing in electronic communication with said one or more sensors.

214. An apparatus according to claim 213, said one or more sensors comprising at least one of a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

215. An apparatus according to claim 213, said housing support section comprising a flexible section.

216. An apparatus according to claim 215, said housing being selectively removably attached to said housing support section.

217. An apparatus for detecting at least one of human physiological and contextual information from the body of a wearer, comprising:

a housing suitable to be worn on said body;

housing support section for engaging at least a portion of said body, said housing being attached to said housing support section;

one or more sensors supported by said housing, said one or more sensors selected from the group consisting of physiological sensors and contextual sensors;

a processing unit supported by said housing in electronic communication with said one or more sensors; and a wireless transceiver for receiving information from and transmitting information to a computing device, said computing device displaying information to an individual and enabling said individual to input information, said computing device and said processing unit being adapted to engage in shared computing.

218. An apparatus according to claim 217, said housing support section comprising a flexible section.

219. An apparatus according to claim 218, said housing being selectively removably attached to said housing support section.

220. An apparatus for detecting at least one of human physiological and contextual information from the body of a wearer, comprising:

a housing suitable to be worn on said body;

one or more sensors supported by said housing, said one or more sensors selected from the group consisting of physiological sensors and contextual sensors, said sensors generate data indicative of at least a detected parameter of the wearer;

a processing unit supported by said housing in electronic communication with said one or more sensors and generating derived data comprising a derived parameter based on said detected parameter, being an individual status parameter that cannot be directly detected by one of said one or more sensors.; and a wireless transceiver for receiving information from and transmitting information to a computing device, said computing device displaying information to an individual and enabling said individual to input information, said computing device and said processing unit being adapted to engage in shared computing.

221. An apparatus for detecting from the body of a wearer parameters relating to the heart of the wearer, comprising:

an acoustic-based non-ECG heart parameter sensor that generates a first signal including a first physiological acoustic component generated from the motion of said heart and a second physiological acoustic component generated from non-heart related motion of said body of said wearer, said non-heart related motion comprising footfalls of said wearer; and one or more filtering sensors comprising an accelerometer for generating a second signal related to said non-heart related motion of said body, said second signal being used to subtract at least a portion of said second physiological acoustic component from said first signal to generate a third signal, said third signal being used to generate said heart related parameters.

222. An apparatus according to claim 221, said acoustic-based non-ECG heart parameter sensor including a sound transducer coupled to a pad containing an acoustic transmission material.

* * * * *

UNITED STATES PATENT AND TRADEMARK OFFICE
CERTIFICATE OF CORRECTION

| | |
|---|---|
| PATENT NO. | : 7,020,508 B2 |
| APPLICATION NO. | : 10/227575 |
| DATED | : March 28, 2006 |
| INVENTOR(S) | : Stivoric et al. |

It is certified that error appears in the above-identified patent and that said Letters Patent is hereby corrected as shown below:

On title page Item [56]
On page 2, under References Cited, U.S. Patent Documents, "2002/0088160 A1, 7/2002, Baretta, 72/70.08" should be -- 2003/0088160 A1, 5/2003, Halleck et al, 600/300 --.

Column 1, line 66, "but no limited to" should read -- but not limited to --.

Column 4, line 1, "form" should be -- from --.

Column 15, line 32, after "storage" delete "lo".

Column 18, line 58, "or a pie chart" should read -- of a pie chart --.

Column 25, line 34, "481 a" should be -- 481a --.

Column 25, line 41, "481*b*" should be -- 481b --.

Column 27, line 27, "effect" should be -- affect --.

Column 34, line 34, "themistor" should be -- thermistor --.

Column 35, line 12, before "model" insert -- is the --.

Column 35, line 12, "thermisor" should be -- thermistor --.

Column 35, line 13, after "Mass." delete -- is the. --.

Column 36, line 40, "LiIon" should be -- LiIon --.

Column 37, line 52, after "sensor" insert -- 1000 --.

Column 38, line 35, after "device" insert -- 800 --.

Column 39, line 49, "dtent" should be -- detent --.

Column 40, line 14, after the second occurrence of "processing unit" insert -- 900 --.

Column 40, line 64, "40B," should be -- 40B. --.

Column 40, line 65, before "owned by the assignee" insert -- U.S. Pat. No. 6,527,711, --.

Column 41, line 10, delete "having" and insert -- housing --.

UNITED STATES PATENT AND TRADEMARK OFFICE
CERTIFICATE OF CORRECTION

PATENT NO. : 7,020,508 B2
APPLICATION NO. : 10/227575
DATED : March 28, 2006
INVENTOR(S) : Stivoric et al.

It is certified that error appears in the above-identified patent and that said Letters Patent is hereby corrected as shown below:

Column 41, line 24, "and" should read -- an --.

Column 41, line 42, after "device" insert -- 800 --.

Column 43, line 44, "355B" should read -- 35B --.

Column 43, line 47, delete "parties" and insert -- parts --.

Column 44, line 28, after "contact" insert -- with --.

Column 44, line 51, after "interface" delete "lo".

Column 44, line 64, "Bottom surface 115" should be -- Bottom surface 1115 --.

Column 45, line 6, "As seen if" should read -- As seen in --.

Column 45, line 20, after "movement" delete -- to --.

Column 48, line 6, "display" should read -- displaying --.

Column 49, line 16, "ECU" should read -- ECG --.

Column 54, line 48, "sensor" should read -- sensors --.

Column 56, line 64, after "portion" insert -- of --.

Column 59, line 60, "ECU" should read -- ECG --.

Column 69, line 35, "attached to a the" should read -- attached to the --.

Column 73, line 40, after "body" insert -- ; --.

UNITED STATES PATENT AND TRADEMARK OFFICE
CERTIFICATE OF CORRECTION

PATENT NO. : 7,020,508 B2
APPLICATION NO. : 10/227575
DATED : March 28, 2006
INVENTOR(S) : Stivoric et al.

It is certified that error appears in the above-identified patent and that said Letters Patent is hereby corrected as shown below:

Column 73, lines 40-41, "a housing removably attached to and supported by said housing support section;" should be a separate subsection of claim 213.

Signed and Sealed this

Fourth Day of September, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,020,508 B2 | |
| APPLICATION NO. | : 10/227575 | |
| DATED | : March 28, 2006 | |
| INVENTOR(S) | : John M. Stivoric et al. | |

It is certified that error appears in the above-identified patent and that said Letters Patent is hereby corrected as shown below:

Delete the title and substitute therefore the attached title page consisting of the corrected number of drawing sheets in patent.

Delete drawing sheets 1-36 and substitute therefore the attached drawing sheets 1-35.

Delete the entire specification and claims and replace with the attached reprinted specification and claims.

This certificate supersedes the Certificate of Correction issued September 4, 2007.

Signed and Sealed this
First Day of March, 2011

David J. Kappos
*Director of the United States Patent and Trademark Office*

(12) United States Patent
Stivoric et al.

(10) Patent No.: US 7,020,508 B2
(45) Date of Patent: Mar. 28, 2006

(54) APPARATUS FOR DETECTING HUMAN PHYSIOLOGICAL AND CONTEXTUAL INFORMATION

(75) Inventors: John M. Stivoric, Pittsburgh, PA (US); Scott K. Boehmke, Pittsburgh, PA (US); Eric Teller, Pittsburgh, PA (US); Christopher D. Kasabach, Pittsburgh, PA (US)

(73) Assignee: BodyMedia, Inc., Pittsburgh, PA (US)

(*) Notice: Subject to any disclaimer, the term of this patent is extended or adjusted under 35 U.S.C. 154(b) by 60 days.

(21) Appl. No.: 10/227,575

(22) Filed: Aug. 22, 2002

(65) Prior Publication Data
US 2004/0039254 A1 Feb. 26, 2004

(51) Int. Cl.
*A61B 5/04* (2006.01)
(52) U.S. Cl. .................................. 600/390; 600/513
(58) Field of Classification Search .............. 600/372, 600/382–384, 386, 388–391, 393, 481, 483, 600/508, 509, 544–547, 549
See application file for complete search history.

(56) References Cited

U.S. PATENT DOCUMENTS

| 4,031,365 A | 6/1977 | Raggiotti et al. | 702/131 |
|---|---|---|---|
| 4,052,979 A | 10/1977 | Scherr et al. | 600/503 |
| 4,129,125 A | 12/1978 | Lester et al. | 600/484 |
| 4,148,304 A | 4/1979 | Mull | 600/549 |
| 4,151,831 A | 5/1979 | Lester | 600/549 |
| 4,192,000 A | 3/1980 | Lipsey | |
| 4,377,171 A | 3/1983 | Wada | 600/549 |
| 4,407,295 A | 10/1983 | Steuer et al. | 600/483 |
| 4,488,558 A * | 12/1984 | Simbruner et al. | 600/376 |
| 4,509,531 A | 4/1985 | Ward | 600/549 |
| 4,531,527 A | 7/1985 | Reinhold, Jr. et al. | 600/509 |
| 4,557,273 A | 12/1985 | Stoller et al. | 600/551 |
| 4,608,987 A | 9/1986 | Mills | 600/389 |
| 4,622,979 A | 11/1986 | Katchis et al. | 600/515 |
| 4,672,977 A * | 6/1987 | Kroll | 600/528 |
| 4,676,254 A | 6/1987 | Frohn | 600/549 |

(Continued)

FOREIGN PATENT DOCUMENTS

DE  198 32 361 A1  2/2000

(Continued)

OTHER PUBLICATIONS

"Georgia Tech Researchers Develop First 'Smart T-shirt'," Nov. 14, 1997 press release, Georgia Institute of Technology.

(Continued)

*Primary Examiner*—Carl Layno
(74) *Attorney, Agent, or Firm*—Metz Lewis LLC; Barry I. Friedman

(57) ABSTRACT

A detecting apparatus includes a housing support section(s), a housing removably attached thereto, one or more sensors and a processor. An alternate apparatus measures heat flux and includes a known resistivity base member, a processing unit and two temperature measuring devices, one in thermal communication with the body through a thermal energy communicator and the other in thermal communication with the ambient environment. A further alternate apparatus includes a housing or flexible section having an adhesive material on a surface thereof for removably attaching the apparatus to the body. A further alternate apparatus includes a housing having an inner surface having a concave shape in a first direction and convex shape in a second direction substantially perpendicular thereto. Also, an apparatus for detecting heart related parameters includes one or more filtering sensors for generating filtering signals related to the non-heart related motion of the body.

222 Claims, 35 Drawing Sheets

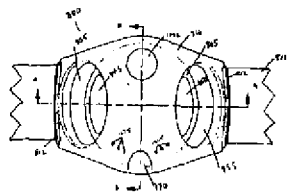

APPARATUS FOR DETECTING HUMAN PHYSIOLOGICAL AND CONTEXTUAL INFORMATION

FIELD OF THE INVENTION

The present invention also relates to a number of embodiments of an apparatus which includes one or more sensors for collecting and storing data relating to an individual's physiological state and various contextual parameters.

BACKGROUND OF THE INVENTION

Research has shown that a large number of the top health problems in society are either caused in whole or in part by an unhealthy lifestyle. More and more, our society requires people to lead fast-paced, achievement-oriented lifestyles that often result in poor eating habits, high stress levels, lack of exercise, poor sleep habits and the inability to find the time to center the mind and relax. Recognizing this fact, people are becoming increasingly interested in establishing a healthier lifestyle.

Traditional medicine, embodied in the form of an HMO or similar organizations, does not have the time, the training, or the reimbursement mechanism to address the needs of those individuals interested in a healthier lifestyle. There have been several attempts to meet the needs of these individuals, including a perfusion of fitness programs and exercise equipment, dietary plans, self-help books, alternative therapies, and most recently, a plethora of health information web sites on the Internet. Each of these attempts are targeted to empower the individual to take charge and get healthy. Each of these attempts, however, addresses only part of the needs of individuals seeking a healthier lifestyle and ignores many of the real barriers that most individuals face when trying to adopt a healthier lifestyle. These barriers include the fact that the individual is often left to himself or herself to find motivation, to implement a plan for achieving a healthier lifestyle, to monitor progress, and to brainstorm solutions when problems arise; the fact that existing programs are directed to only certain aspects of a healthier lifestyle, and rarely come as a complete package; and the fact that recommendations are often not targeted to the unique characteristics of the individual or his life circumstances.

SUMMARY OF THE INVENTION

An apparatus is disclosed for detecting human physiological or contextual information from the body of an individual wearing the apparatus. The apparatus includes a flexible section that is adapted to engage a portion of the wearer's body, and a housing that is removably attached to the flexible section. The housing supports one or more physiological and/or contextual sensors and a processor in electrical communication with the sensors. According to one embodiment, the apparatus may include multiple flexible sections that may be selectively attached to the housing. The apparatus may also have operating parameters that are adjustable depending on the particular flexible section that is attached to the housing at a particular time. The operating parameters, for example, may be adjusted through the interaction of a switch or switches provided on or in the housing and a switch activator or switch activators provided on or in each of the flexible sections. Various structures for removably attaching the housing to the flexible section are described, including, but not limited to, tongues and grooves, adhesives, magnets, and elastic bands. The apparatus may also include a wireless transceiver for transmitting information to and receiving information from a computing device.

Also described is an apparatus that is adapted to measure heat flux between the body of the wearer and the ambient environment. The apparatus includes a housing and a base member having a preselected, known resistivity mounted within the housing. The base member may comprise a printed circuit board. A first temperature measuring device is attached to a first side of the base member and a second temperature measuring device is attached to a second side of the base member. The temperature measuring devices may comprise, for example, a thermistor, a thermocouple, or a thermopile. The apparatus further includes a thermal energy communicator mounted between a portion of the body of the wearer and the first temperature measuring device. The thermal energy communicator may include one or more of a heat conduit, a thermally conductive interface material or materials, and a thermally conductive interface component in various combinations. The second temperature measuring device is in thermal communication with the ambient environment. The apparatus may include a thermal interface material and/or a thermally conductive interface component for providing thermal communication between the ambient environment and the second temperature measuring device. A processing unit is provided in the housing and is in electrical communication with the temperature measuring devices. The apparatus may further include a flexible section attached to the housing adapted to engage a portion of the body of the wearer, or a plurality of flexible sections adapted to be selectively attached to the housing. According to one embodiment, the apparatus has operating parameters that may be adjusted depending on the particular flexible section that is attached to the housing.

An apparatus for detecting, monitoring and reporting at least one of human physiological and contextual information from the body of a wearer is also described. The apparatus includes a housing having an adhesive material on at least a portion of an external surface thereof that enables the housing to be removably attached to a portion of the body of the wearer. At least two physiological and/or contextual sensors are supported by the housing. The physiological sensors are adapted to facilitate the generation of data indicative of one or more physiological parameters of the wearer and the contextual sensors are adapted to facilitate the generation of data indicative of one or more contextual parameters of the wearer. A processor is also included and is an electrical communication with the sensors. The processor generates: (i) derived data from at least one of at least a portion of the data indicative of physiological parameters and at least a portion of the data indicative of contextual parameters; and (ii) analytical status data from at least a portion of at least one of the data indicative of physiological parameters, the data indicative of contextual parameters, the derived data and the analytical status data. The apparatus further includes an electronic memory for retrievably storing at least one of the data indicative of physiological parameters, the data indicative of contextual parameters, the derived data and the analytical status data. The apparatus is adapted to transmit to the wearer at least one of the data indicative of physiological parameters, the data indicative of contextual parameters, the derived data and the analytical status data. The housing may be made of a rigid material or a flexible material, such as a flexible plastic film. The apparatus may include a number of displays for transmitting information, including, but not limited to, an LED or an electrochemical display. The apparatus may further include a wireless transceiver for receiving information from and transmitting information to a computing device. The processor of the apparatus and the computing device may be adapted to engage in shared computing. Furthermore, a computing device may be included in the apparatus for transmitting information to the wearer. The computing device may be coupled to the processor, and the processor may be adapted to cause the computing device to trigger an event upon detection of one or more physiological conditions of the individual. The apparatus may further include various structures for manually entering information into the apparatus, such as a button or a touch pad or keyboard provided on the apparatus or on a computing device coupled to the processor. According to one embodiment, the apparatus monitors the degree to which the wearer has followed a predetermined routine. In this embodiment, the analytical status data comprises feedback to the individual relating to the degree to which the individual has followed the predetermined routine, with the feedback being generated from at least a portion of at least one of the data indicative of one or more physiological parameters of the individual, the derived data, and manually entered data. Also described is an apparatus for detecting human physiological or contextual information from the body of an individual wearing the apparatus that includes a housing having an inner surface for mounting adjacent the body and an outer surface opposite the inner surface. The inner surface includes a longitudinal axis and a transverse axis, with the inner surface being generally concave in a first direction and having an axis of concavity coincident with the longitudinal axis and generally convex in a second direction perpendicular to the first direction and having an axis of concavity coincident with the transverse axis. The inner surface may have first and second lateral ends at opposite ends of the axis of concavity, and the housing may have a first radiused portion adjacent to and including the first lateral end and a second radiused portion adjacent to and including the second lateral end. The inner surface may also have third and fourth lateral ends at opposite ends of the axis of convexity, and the housing may have a third radiused portion adjacent to and including the third lateral end and a fourth radiused portion adjacent to and including the fourth lateral end. Further, the outer surface of the housing may have a convex shape between a first lateral side and a second lateral side of the outer surface. According to one embodiment, the housing includes a width dimension as measured between a first lateral side and a second lateral side of the housing, with at least a portion of the first lateral side and second lateral side each having a taper such that the width dimension generally decreases in a direction from the inner surface to the outer surface. The apparatus may include a flexible section attached to the housing that engages the body of the wearer and has a generally convex outer surface.

Also described is an apparatus for detecting from the body of a wearer parameters relating to the heart of the wearer including an acoustic-based non-ECG heart parameter sensor that generates a first signal including a first acoustic component generated from the motion of the wearers heart and a second acoustic component generated from non-heart related motion of the body of the wearer, such as, for example, from footfalls. The apparatus also includes one or more filtering sensors, such as an accelerometer, for generating a second signal related to the non-heart related motion of the body. The second signal is used to subtract the second acoustic component from the first signal to generate a third signal, with the third signal being used to generate the heart related parameters. The first signal may also include an acoustic component generated from ambient noise, and the apparatus may include an ambient noise sensor. In this configuration, the signal from the ambient noise sensor is used to subtract out the acoustic component generated from ambient noise from the signal that is used to generate the heart related parameters.

In addition, a method is disclosed for detecting from the body of a wearer parameters relating to the heart of the wearer. The method comprises steps of generating a first acoustic signal including a first acoustic component generated from the motion of the wearer's heart and a second acoustic component generated from non-heart related motion of the body of the wearer, generating a second signal related to the non-heart related motion of the body, generating a third signal by using the second signal to subtract the second acoustic component from the first signal, and generating the heart related parameters from the third signal. The first acoustic signal may further include a third acoustic component generated from ambient noise and the method may further comprise generating a fourth signal related to the ambient noise with the step of generating the third signal further comprising using the fourth signal to subtract the third acoustic component from the first signal.

BRIEF DESCRIPTION OF THE DRAWINGS

Figure 12:
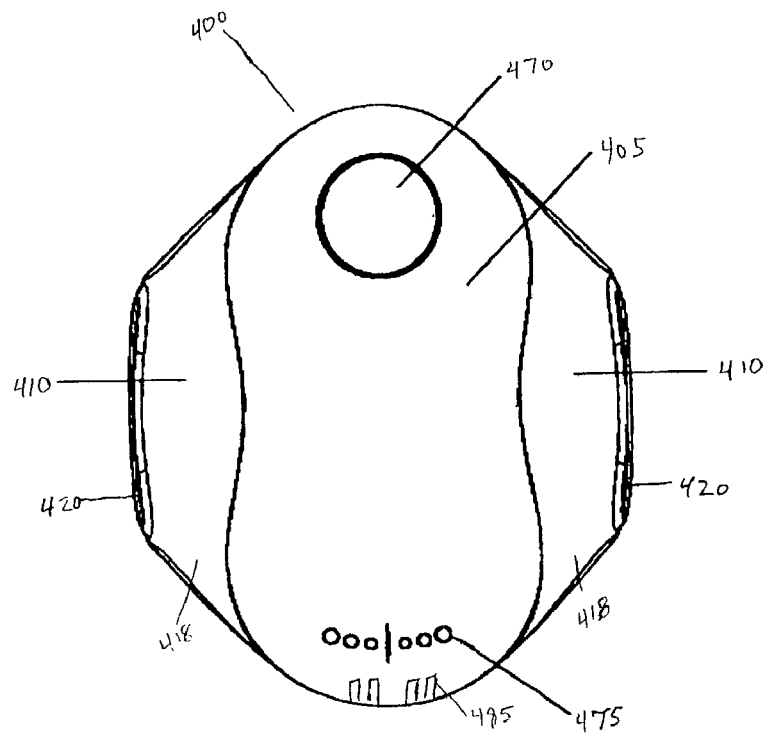
FIG. 12 is a front view of a specific embodiment of the sensor device shown in FIG. 1.
Figure 14:
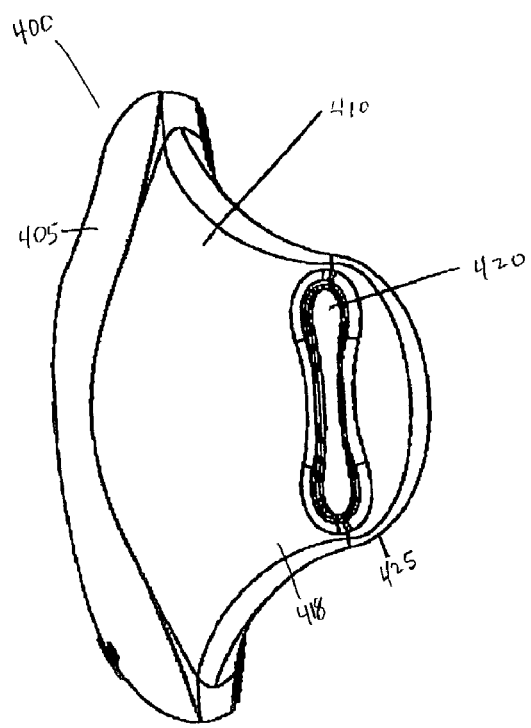
FIG. 14 is a side view of a specific embodiment of the sensor device shown in FIG. 1.
Figure 25:
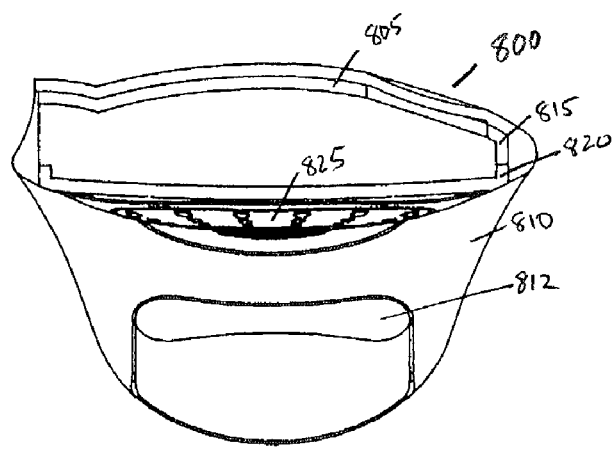
FIG. 25 is a cross-sectional view of the sensor device shown in FIG. 22 taken along lines B—B.

Further features and advantages of the present invention will be apparent upon consideration of the following detailed description of the present invention, taken in conjunction with the following drawings, in which like reference characters refer to like parts, and in which:

FIG. 1 is a diagram of an embodiment of a system for monitoring physiological data and lifestyle over an electronic network according to the present invention;

FIG. 2 is a block diagram of an embodiment of the sensor device shown in FIG. 1;

FIG. 3 is a block diagram of an embodiment of the central monitoring unit shown in FIG. 1;

FIG. 4 is a block diagram of an alternate embodiment of the central monitoring unit shown in FIG. 1;

FIG. 5 is a representation of a preferred embodiment of the Health Manager web page according to an aspect of the present invention;

FIG. 6 is a representation of a preferred embodiment of the nutrition web page according to an aspect of the present invention;

FIG. 7 is a representation of a preferred embodiment of the activity level web page according to an aspect of the present invention;

FIG. 8 is a representation of a preferred embodiment of the mind centering web page according to an aspect of the present invention;

FIG. 9 is a representation of a preferred embodiment of the sleep web page according to an aspect of the present invention;

FIG. 10 is a representation of a preferred embodiment of the daily activities web page according to an aspect of the present invention;

FIG. 11 is a representation of a preferred embodiment of the Health Index web page according to an aspect of the present invention;

FIG. 12 is a front view of a specific embodiment of the sensor device shown in FIG. 1;

FIG. 13 is a back view of a specific embodiment of the sensor device shown in FIG. 1;

FIG. 14 is a side view of a specific embodiment of the sensor device shown in FIG. 1;

FIG. 15 is a bottom view of a specific embodiment of the sensor device shown in FIG. 1;

FIGS. 16 and 17 are front perspective views of a specific embodiment of the sensor device shown in FIG. 1;

FIG. 18 is an exploded side perspective view of a specific embodiment of the sensor device shown in FIG. 1;

FIG. 19 is a side view of the sensor device shown in FIGS. 12 through 18 inserted into a battery recharger unit;

FIG. 20 is a block diagram illustrating all of the components either mounted on or coupled to the printed circuit board forming a part of the sensor device shown in FIGS. 12 through 18; and FIG. 21 is a block diagram of an apparatus for monitoring health, wellness and fitness according to an alternate embodiment of the present invention;

FIG. 22 is a front view of an alternate embodiment of a sensor device according to the present invention;

FIG. 23 is a back view of an alternate embodiment of a sensor device according to the present invention;

FIG. 24 is a cross-sectional view of the sensor device shown in FIG. 22 taken along lines A—A;

FIG. 25 is a cross-sectional view of the sensor device shown in FIG. 22 taken along lines B—B;

FIG. 26 is a cross-sectional view of the sensor device shown in FIG. 22 taken along lines A—A showing the internal components of the housing of the sensor device;

FIG. 27 is a block diagram illustrating the components mounted on or coupled to the printed circuit board forming a part of an embodiment of the sensor device shown in FIGS. 22 through 26;

FIG. 28 is a front view of an alternate embodiment of a sensor device according to the present invention including an LCD;

FIG. 29 is a block diagram illustrating the components mounted on or coupled to the printed circuit board forming a part of an alternate embodiment of the sensor device shown in FIGS. 22 through 26;

FIGS. 30 and 31 are isometric views of an alternate embodiment of a sensor device according to the present invention having a housing adapted to be removably attached to a flexible section;

FIG. 32 is an isometric view of a further alternate embodiment of a sensor device according to the present invention having a housing adapted to be removably attached to a flexible section;

FIG. 33 is an isometric view of an embodiment of a sensor device having adjustable operating parameters according to an aspect of the present invention;

FIG. 34 is an isometric view of an alternate embodiment of a sensor device according to the present invention having a housing having an adhesive material on an external surface thereof for removably attaching the housing to the body;

FIGS. 35A and B are cross-sectional views of a housing for a prior art sensor device;

FIGS. 35C through H are cross-sectional views of various embodiments of a housing for a sensor device according to an aspect of the present invention taken along lines C—C in FIG. 23.

FIG. 36A is a cross-sectional view of a housing for a prior art sensor device;

FIGS. 36B through H are cross-sectional views of various embodiments of a housing for a sensor device according to an aspect of the present invention taken along lines D—D in FIG. 23;

FIG. 37 is an isometric view of an embodiment of a housing for a sensor device according to the present invention having a bottom or inner surface having a concavity in one direction and a convexity in another direction;

FIGS. 38A through D are cross-sectional views of a housing for a sensor device having a flat top surface and flat lateral ends;

FIGS. 39A through F are cross-sectional views of various embodiments of a housing for a sensor device having surfaces designed to deflect objects and prevent movement of the housing; and FIG. 39G is a cross-sectional view of the housing shown in FIG. 39E attached to a flexible section.

FIG. 40A is an elevational drawing of the sensor device mounted within a garment on the upper arm of a wearer.

FIG. 40B is an elevational drawing of the sensor device mounted within a garment on the left chest area of a wearer.

DESCRIPTION OF THE PREFERRED EMBODIMENTS

In general, according to the present invention, data relating to the physiological state, the lifestyle and certain contextual parameters of an individual is collected and transmitted, either subsequently or in real-time, to a site, preferably remote from the individual, where it is stored for later manipulation and presentation to a recipient, preferably over an electronic network such as the Internet. Contextual parameters as used herein means parameters relating to the environment, surroundings and location of the individual, including, but not limited to, air quality, sound quality, ambient temperature, global positioning and the like. Referring to FIG. 1, located at user location 5 is sensor device 10 adapted to be placed in proximity with at least a portion of the human body. Sensor device 10 is preferably worn by an individual user on his or her body, for example as part of a garment such as a form fitting shirt, or as part of an arm band or the like. Sensor device 10, includes one or more sensors, which are adapted to generate signals in response to physiological characteristics of an individual, and a microprocessor. Proximity as used herein means that the sensors of sensor device 10 are separated from the individual's body by a material or the like, or a distance such that the capabilities of the sensors are not impeded.

Sensor device 10 generates data indicative of various physiological parameters of an individual, such as the individual's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and UV radiation exposure and absorption. In certain cases, the data indicative of the various physiological parameters is the signal or signals themselves generated by the one or more sensors and in certain other cases the data is calculated by the microprocessor based on the signal or signals generated by the one or more sensors. Methods for generating data indicative of various physiological parameters and sensors to be used therefor are well known. Table 1 provides several examples of such well known methods and shows the parameter in question, the method used, the sensor device used, and the signal that is generated. Table 1 also provides an indication as to whether further processing based on the generated signal is required to generate the data.

TABLE 1

| Parameter | Method | Sensor | Signal | Further Processing |
|---|---|---|---|---|
| Heart Rate | EKG | 2 Electrodes | DC Voltage | Yes |
| Pulse Rate | BVP | LED Emitter and Optical Sensor | Change in Resistance | Yes |
| Beat-to-Beat Variability | Heart Rate | 2 Electrodes | DC Voltage | Yes |
| EKG | Skin Surface Potentials | 3-10 Electrodes | DC Voltage | No |
| Respiration Rate | Chest Volume Change | Strain Gauge | Change in Resistance | Yes |
| Skin Temperature | Surface Temperature Probe | Thermistors | Change in Resistance | Yes |
| Core Temperature | Esophageal or Rectal Probe | Thermistors | Change in Resistance | Yes |
| Heat Flow | Heat Flux | Thermopile | DC Voltage | Yes |
| Galvanic Skin Response | Skin Conductance | 2 Electrodes | Change in Resistance | No |
| EMG | Skin Surface Potentials | 3 Electrodes | DC Voltage | No |
| EEG | Skin Surface Potentials | Multiple Electrodes | DC Voltage | Yes |
| EOG | Eye Movement | Thin Film Piezoelectric Sensors | DC Voltage | Yes |
| Blood Pressure | Non-Invasive Korotkoff Sounds | Electronic Sphygmomarometer | Change in Resistance | Yes |
| Body Fat | Body Impedance | 2 Active Electrodes | Change in Impedance | Yes |
| Activity in Interpreted G Shocks per Minute | Body Movement | Accelerometer | DC Voltage, Capacitance Changes | Yes |
| Oxygen Consumption | Oxygen Uptake | Electro-chemical | DC Voltage Change | Yes |
| Glucose Level | Non-Invasive | Electro-chemical | DC Voltage Change | Yes |
| Body Position (e.g. supine, erect, sitting) | N/A | Mercury Switch Array | DC Voltage Change | Yes |
| Muscle Pressure | N/A | Thin Film Piezoelectric Sensors | DC Voltage Change | Yes |
| UV Radiation Absorption | N/A | UV Sensitive Photo Cells | DC Voltage Change | Yes |

The types of data listed in Table 1 are intended to be examples of the types of data that can be generated by sensor device 10. It is to be understood that other types of data relating to other parameters can be generated by sensor device 10 without departing from the scope of the present invention.

The microprocessor of sensor device 10 may be programmed to summarize and analyze the data. For example, the microprocessor can be programmed to calculate an average, minimum or maximum heart rate or respiration rate over a defined period of time, such as ten minutes. Sensor device 10 may be able to derive information relating to an individual's physiological state based on the data indicative of one or more physiological parameters. The microprocessor of sensor device 10 is programmed to derive such information using known methods based on the data indicative of one or more physiological parameters. Table 2 provides examples of the type of information that can be derived, and indicates some of the types of data that can be used therefor.

TABLE 2

| Derived Information | Data Used |
|---|---|
| Ovulation | Skin temperature, core temperature, oxygen consumption |

TABLE 2-continued

| Derived Information | Data Used |
|---|---|
| Sleep onset/wake | Beat-to-beat variability, heart rate, pulse rate, respiration rate, skin temperature, core temperature, heat flow, galvanic skin response, EMG, EEG, EOG, blood pressure, oxygen consumption |
| Calories burned | Heart rate, pulse rate, respiration rate, heat flow, activity, oxygen consumption |
| Basal metabolic rate | Heart rate, pulse rate, respiration rate, heat flow, activity, oxygen consumption |
| Basal temperature | Skin temperature, core temperature |
| Activity level | Heart rate, pulse rate, respiration rate, heat flow, activity, oxygen consumption |
| Stress level | EKG, beat-to-beat variability, heart rate, pulse rate, respiration rate, skin temperature, heat flow, galvanic skin response, EMG, EEG, blood pressure, activity, oxygen consumption |
| Relaxation level | EKG, beat-to-beat variability, heart rate, pulse rate, respiration rate, skin temperature, heat flow, galvanic skin response, EMG, EEG, blood pressure, activity, oxygen consumption |

TABLE 2-continued

| Derived Information | Data Used |
| --- | --- |
| Maximum oxygen consumption rate | EKG, heart rate, pulse rate, respiration rate, heat flow, blood pressure, activity, oxygen consumption |
| Rise time or the time it takes to rise from a resting rate to 85% of a target maximum | Heart rate, pulse rate, heat flow, oxygen consumption |
| Time in zone or the time heart rate was above 85% of a target maximum | Heart rate, pulse rate, heat flow, oxygen consumption |
| Recovery time or the time it takes heart rate to return to a resting rate after heart rate was above 85% of a target maximum | Heart rate, pulse rate, heat flow, oxygen consumption |

Additionally, sensor device 10 may also generate data indicative of various contextual parameters relating to the environment surrounding the individual. For example, sensor device 10 can generate data indicative of the air quality, sound level/quality, light quality or ambient temperature near the individual, or even the global positioning of the individual. Sensor device 10 may include one or more sensors for generating signals in response to contextual characteristics relating to the environment surrounding the individual, the signals ultimately being used to generate the type of data described above. Such sensors are well known, as are methods for generating contextual parametric data such as air quality, sound level/quality, ambient temperature and global positioning.

FIG. 2 is a block diagram of an embodiment of sensor device 10. Sensor device 10 includes at least one sensor 12 and microprocessor 20. Depending upon the nature of the signal generated by sensor 12, the signal can be sent through one or more of amplifier 14, conditioning circuit 16, and analog-to-digital converter 18, before being sent to microprocessor 20. For example, where sensor 12 generates an analog signal in need of amplification and filtering, that signal can be sent to amplifier 14, and then on to conditioning circuit 16, which may, for example, be a band pass filter. The amplified and conditioned analog signal can then be transferred to analog-to-digital converter 18, where it is converted to a digital signal. The digital signal is then sent to microprocessor 20. Alternatively, if sensor 12 generates a digital signal, that signal can be sent directly to microprocessor 20.

A digital signal or signals representing certain physiological and/or contextual characteristics of the individual user may be used by microprocessor 20 to calculate or generate data indicative of physiological and/or contextual parameters of the individual user. Microprocessor 20 is programmed to derive information relating to at least one aspect of the individual's physiological state. It should be understood that microprocessor 20 may also comprise other forms of processors or processing devices, such as a microcontroller, or any other device that can be programmed to perform the functionality described herein.

The data indicative of physiological and/or contextual parameters can, according to one embodiment of the present invention, be sent to memory 22, such as flash memory, where it is stored until uploaded in the manner to be described below. Although memory 22 is shown in FIG. 2 as a discrete element, it will be appreciated that it may also be part of microprocessor 20. Sensor device 10 also includes input/output circuitry 24, which is adapted to output and receive as input certain data signals in the manners to be described herein. Thus, memory 22 of the sensor device 10 will build up, over time, a store of data relating to the individual user's body and/or environment. That data is periodically uploaded from sensor device 10 and sent to remote central monitoring unit 30, as shown in FIG. 1, where it is stored in a database for subsequent processing and presentation to the user, preferably through a local or global electronic network such as the Internet. This uploading of data can be an automatic process that is initiated by sensor device 10 periodically or upon the happening of an event such as the detection by sensor device 10 of a heart rate below a certain level, or can be initiated by the individual user or some third party authorized by the user, preferably according to some periodic schedule, such as every day at 10:00 p.m. Alternatively, rather than storing data in memory 22, sensor device 10 may continuously upload data in real time.

The uploading of data from sensor device 10 to central monitoring unit 30 for storage can be accomplished in various ways. In one embodiment, the data collected by sensor device 10 is uploaded by first transferring the data to personal computer 35 shown in FIG. 1 by means of physical connection 40, which, for example, may be a serial connection such as an RS232 or USB port. This physical connection may also be accomplished by using a cradle, not shown, that is electronically coupled to personal computer 35 into which sensor device 10 can be inserted, as is common with many commercially available personal digital assistants. The uploading of data could be initiated by then pressing a button on the cradle or could be initiated automatically upon insertion of sensor device 10. The data collected by sensor device 10 may be uploaded by first transferring the data to personal computer 35 by means of short-range wireless transmission, such as infrared or RF transmission, as indicated at 45.

Once the data is received by personal computer 35, it is optionally compressed and encrypted by any one of a variety of well known methods and then sent out over a local or global electronic network, preferably the Internet, to central monitoring unit 30. It should be noted that personal computer 35 can be replaced by any computing device that has access to and that can transmit and receive data through the electronic network, such as, for example, a personal digital assistant such as the Palm VII sold by Palm, Inc., or the Blackberry 2-way pager sold by Research in Motion, Inc.

Alternatively, the data collected by sensor device 10, after being encrypted and, optionally, compressed by microprocessor 20, may be transferred to wireless device 50, such as a 2-way pager or cellular phone, for subsequent long distance wireless transmission to local telco site 55 using a wireless protocol such as e-mail or as ASCII or binary data. Local telco site 55 includes tower 60 that receives the wireless transmission from wireless device 50 and computer 65 connected to tower 60. According to the preferred embodiment, computer 65 has access to the relevant electronic network, such as the Internet, and is used to transmit the data received in the form of the wireless transmission to the central monitoring unit 30 over the Internet. Although wireless device 50 is shown in FIG. 1 as a discrete device coupled to sensor device 10, it or a device having the same or similar functionality may be embedded as part of sensor device 10.

Sensor device 10 may be provided with a button to be used to time stamp events such as time to bed, wake time, and time of meals. These time stamps are stored in sensor device 10 and are uploaded to central monitoring unit 30 with the rest of the data as described above. The time stamps may include a digitally recorded voice message that, after being uploaded to central monitoring unit 30, are translated using voice recognition technology into text or some other information format that can be used by central monitoring unit 30.

In addition to using sensor device 10 to automatically collect physiological data relating to an individual user, a kiosk could be adapted to collect such data by, for example, weighing the individual, providing a sensing device similar to sensor device 10 on which an individual places his or her hand or another part of his or her body, or by scanning the individual's body using, for example, laser technology or an iStat blood analyzer. The kiosk would be provided with processing capability as described herein and access to the relevant electronic network, and would thus be adapted to send the collected data to the central monitoring unit 30 through the electronic network. A desktop sensing device, again similar to sensor device 10, on which an individual places his or her hand or another part of his or her body may also be provided. For example, such a desktop sensing device could be a blood pressure monitor in which an individual places his or her arm. An individual might also wear a ring having a sensor device 10 incorporated therein. A base, not shown, could then be provided which is adapted to be coupled to the ring. The desktop sensing device or the base just described may then be coupled to a computer such as personal computer 35 by means of a physical or short range wireless connection so that the collected data could be uploaded to central monitoring unit 30 over the relevant electronic network in the manner described above. A mobile device such as, for example, a personal digital assistant, might also be provided with a sensor device 10 incorporated therein. Such a sensor device 10 would be adapted to collect data when mobile device is placed in proximity with the individual's body, such as by holding the device in the palm of one's hand, and upload the collected data to central monitoring unit 30 in any of the ways described herein.

Furthermore, in addition to collecting data by automatically sensing such data in the manners described above, individuals can also manually provide data relating to various life activities that is ultimately transferred to and stored at central monitoring unit 30. An individual user can access a web site maintained by central monitoring unit 30 and can directly input information relating to life activities by entering text freely, by responding to questions posed by the web site, or by clicking through dialog boxes provided by the web site. Central monitoring unit 30 can also be adapted to periodically send electronic mail messages containing questions designed to elicit information relating to life activities to personal computer 35 or to some other device that can receive electronic mail, such as a personal digital assistant, a pager, or a cellular phone. The individual would then provide data relating to life activities to central monitoring unit 30 by responding to the appropriate electronic mail message with the relevant data. Central monitoring unit 30 may also be adapted to place a telephone call to an individual user in which certain questions would be posed to the individual user. The user could respond to the questions by entering information using a telephone keypad, or by voice, in which case conventional voice recognition technology would be used by central monitoring unit 30 to receive and process the response. The telephone call may also be initiated by the user, in which case the user could speak to a person directly or enter information using the keypad or by voice/voice recognition technology. Central monitoring unit 30 may also be given access to a source of information controlled by the user, for example the user's electronic calendar such as that provided with the Outlook product sold by Microsoft Corporation of Redmond, Wash., from which it could automatically collect information. The data relating to life activities may relate to the eating, sleep, exercise, mind centering or relaxation, and/or daily living habits, patterns and/or activities of the individual. Thus, sample questions may include: What did you have for lunch today? What time did you go to sleep last night? What time did you wake up this morning? How long did you run on the treadmill today?

Feedback may also be provided to a user directly through sensor device 10 in a visual form, for example through an LED or LCD or by constructing sensor device 10, at least in part, of a thermochromatic plastic, in the form of an acoustic signal or in the form of tactile feedback such as vibration. Such feedback may be a reminder or an alert to eat a meal or take medication or a supplement such as a vitamin, to engage in an activity such as exercise or meditation, or to drink water when a state of dehydration is detected. Additionally, a reminder or alert can be issued in the event that a particular physiological parameter such as ovulation has been detected, a level of calories burned during a workout has been achieved or a high heart rate or respiration rate has been encountered.

As will be apparent to those of skill in the art, it may be possible to "download" data from central monitoring unit 30 to sensor device 10. The flow of data in such a download process would be substantially the reverse of that described above with respect to the upload of data from sensor device 10. Thus, it is possible that the firmware of microprocessor 20 of sensor device 10 can be updated or altered remotely, i.e., the microprocessor can be reprogrammed, by downloading new firmware to sensor device 10 from central monitoring unit 30 for such parameters as timing and sample rates of sensor device 10. Also, the reminders/alerts provided by sensor device 10 may be set by the user using the web site maintained by central monitoring unit 30 and subsequently downloaded to the sensor device 10.

Referring to FIG. 3, a block diagram of an embodiment of central monitoring unit 30 is shown. Central monitoring unit 30 includes CSU/DSU 70 which is connected to router 75, the main function of which is to take data requests or traffic, both incoming and outgoing, and direct such requests and traffic for processing or viewing on the web site maintained by central monitoring unit 30. Connected to router 75 is firewall 80. The main purpose of firewall 80 is to protect the remainder of central monitoring unit 30 from unauthorized or malicious intrusions. Switch 85, connected to firewall 80, is used to direct data flow between middleware servers 95a through 95c and database server 110. Load balancer 90 is provided to spread the workload of incoming requests among the identically configured middleware servers 95a through 95c. Load balancer 90, a suitable example of which is the F5 ServerIron product sold by Foundry Networks, Inc. of San Jose, Calif., analyzes the availability of each middleware server 95a through 95c, and the amount of system resources being used in each middleware server 95a through 95c, in order to spread tasks among them appropriately.

Central monitoring unit 30 includes network storage device 100, such as a storage area network or SAN, which acts as the central repository for data. In particular, network storage device 100 comprises a database that stores all data gathered for each individual user in the manners described above. An example of a suitable network storage device 100 is the Symmetrix product sold by EMC Corporation of Hopkinton, Mass. Although only one network storage device 100 is shown in FIG. 3, it will be understood that multiple network storage devices of various capacities could be used depending on the data storage needs of central monitoring unit 30. Central monitoring unit 30 also includes database server 110 which is coupled to network storage device 100. Database server 110 is made up of two main components: a large scale multiprocessor server and an enterprise type software server component such as the 8/8i component sold by Oracle Corporation of Redwood City, Calif., or the 506 7 component sold by Microsoft Corporation of Redmond, Wash. The primary functions of database server 110 are that of providing access upon request to the data stored in network storage device 100, and populating network storage device 100 with new data. Coupled to network storage device 100 is controller 115, which typically comprises a desktop personal computer, for managing the data stored in network storage device 100.

Middleware servers 95a through 95c, a suitable example of which is the 22OR Dual Processor sold by Sun Microsystems, Inc. of Palo Alto, Calif., each contain software for generating and maintaining the corporate or home web page or pages of the web site maintained by central monitoring unit 30. As is known in the art, a web page refers to a block or blocks of data available on the World-Wide Web comprising a file or files written in Hypertext Markup Language or HTML, and a web site commonly refers to any computer on the Internet running a World-Wide Web server process. The corporate or home web page or pages are the opening or landing web page or pages that are accessible by all members of the general public that visit the site by using the appropriate uniform resource locator or URL. As is known in the art, URLs are the form of address used on the World-Wide Web and provide a standard way of specifying the location of an object, typically a web page, on the Internet. Middleware servers 95a through 95c also each contain software for generating and maintaining the web pages of the web site of central monitoring unit 30 that can only be accessed by individuals that register and become members of central monitoring unit 30. The member users will be those individuals who wish to have their data stored at central monitoring unit 30. Access by such member users is controlled using passwords for security purposes. Preferred embodiments of those web pages are described in detail below and are generated using collected data that is stored in the database of network storage device 100.

Middleware servers 95a through 95c also contain software for requesting data from and writing data to network storage device 100 through database server 110. When an individual user desires to initiate a session with the central monitoring unit 30 for the purpose of entering data into the database of network storage device 100, viewing his or her data stored in the database of network storage device 100, or both, the user visits the home web page of central monitoring unit 30 using a browser program such as Internet Explorer distributed by Microsoft Corporation of Redmond, Wash., and logs in as a registered user. Load balancer 90 assigns the user to one of the middleware servers 95a through 95c, identified as the chosen middleware server. A user will preferably be assigned to a chosen middleware server for each entire session. The chosen middleware server authenticates the user using any one of many well known methods, to ensure that only the true user is permitted to access the information in the database. A member user may also grant access to his or her data to a third party such as a health care provider or a personal trainer. Each authorized third party may be given a separate password and may view the member user's data using a conventional browser. It is therefore possible for both the user and the third party to be the recipient of the data.

When the user is authenticated, the chosen middleware server requests, through database server 110, the individual user's data from network storage device 100 for a predetermined time period. The predetermined time period is preferably thirty days. The requested data, once received from network storage device 100, is temporarily stored by the chosen middleware server in cache memory. The cached data is used by the chosen middleware server as the basis for presenting information, in the form of web pages, to the user again through the user's browser. Each middleware server 95a through 95c is provided with appropriate software for generating such web pages, including software for manipulating and performing calculations utilizing the data to put the data in appropriate format for presentation to the user. Once the user ends his or her session, the data is discarded from cache. When the user initiates a new session, the process for obtaining and caching data for that user as described above is repeated. This caching system thus ideally requires that only one call to the network storage device 100 be made per session, thereby reducing the traffic that database server 110 must handle. Should a request from a user during a particular session require data that is outside of a predetermined time period of cached data already retrieved, a separate call to network storage device 100 may be performed by the chosen middleware server. The predetermined time period should be chosen, however, such that such additional calls are minimized. Cached data may also be saved in cache memory so that it can be reused when a user starts a new session, thus eliminating the need to initiate a new call to network storage device 100.

As described in connection with Table 2, the microprocessor of sensor device 10 may be programmed to derive information relating to an individual's physiological state based on the data indicative of one or more physiological parameters. Central monitoring unit 30, and preferably middleware servers 95a through 95c, may also be similarly programmed to derive such information based on the data indicative of one or more physiological parameters.

It is also contemplated that a user will input additional data during a session, for example, information relating to the user's eating or sleeping habits. This additional data is preferably stored by the chosen middleware server in a cache during the duration of the user's session. When the user ends the session, this additional new data stored in a cache is transferred by the chosen middleware server to database server 110 for population in network storage device 100. Alternatively, in addition to being stored in a cache for potential use during a session, the input data may also be immediately transferred to database server 110 for population in network storage device 100, as part of a write-through cache system which is well known in the art.

Data collected by sensor device 10 shown in FIG. 1 is periodically uploaded to central monitoring unit 30. Either by long distance wireless transmission or through personal computer 35, a connection to central monitoring unit 30 is made through an electronic network, preferably the Internet. In particular, connection is made to load balancer 90 through CSU/DSU 70, router 75, firewall 80 and switch 85. Load balancer 90 then chooses one of the middleware servers 95a through 95c to handle the upload of data, hereafter called the chosen middleware server. The chosen middleware server authenticates the user using any one of many well known methods. If authentication is successful, the data is uploaded to the chosen middleware server as described above, and is ultimately transferred to database server 110 for population in the network storage device 100.

Referring to FIG. 4, an alternate embodiment of central monitoring unit 30 is shown. In addition to the elements shown and described with respect to FIG. 3, the embodiment of the central monitoring unit 30 shown in FIG. 4 includes a mirror network storage device 120 which is a redundant backup of network storage device 100. Coupled to mirror network storage device 120 is controller 122. Data from network storage device 100 is periodically copied to mirror network storage device 120 for data redundancy purposes.

Third parties such as insurance companies or research institutions may be given access, possibly for a fee, to certain of the information stored in mirror network storage device 120. Preferably, in order to maintain the confidentiality of the individual users who supply data to central monitoring unit 30, these third parties are not given access to such user's individual database records, but rather are only given access to the data stored in mirror network storage device 120 in aggregate form. Such third parties may be able to access the information stored in mirror network storage device 120 through the Internet using a conventional browser program. Requests from third parties may come in through CSU/DSU 70, router 75, firewall 80 and switch 85. In the embodiment shown in FIG. 4, a separate load balancer 130 is provided for spreading tasks relating to the accessing and presentation of data from mirror drive array 120 among identically configured middleware servers 135a through 135c. Middleware servers 135a through 135c each contain software for enabling the third parties to, using a browser, formulate queries for information from mirror network storage device 120 through separate database server 125. Middleware servers 135a through 135c also contain software for presenting the information obtained from mirror network storage device 120 to the third parties over the Internet in the form of web pages. In addition, the third parties can choose from a series of prepared reports that have information packaged along subject matter lines, such as various demographic categories.

As will be apparent to one of skill in the art, instead of giving these third parties access to the backup data stored in mirror network storage device 120, the third parties may be given access to the data stored in network storage device 100. Also, instead of providing load balancer 130 and middleware servers 135a through 135c, the same functionality, although at a sacrificed level of performance, could be provided by load balancer 90 and middleware servers 95a through 95c.

When an individual user first becomes a registered user or member, that user completes a detailed survey. The purposes of the survey are to: identify unique characteristics/circumstances for each user that they might need to address in order to maximize the likelihood that they will implement and maintain a healthy lifestyle as suggested by central monitoring unit 30; gather baseline data which will be used to set initial goals for the individual user and facilitate the calculation and display of certain graphical data output such as the Health Index pistons; identify unique user characteristics and circumstances that will help central monitoring unit 30 customize the type of content provided to the user in the Health Manager's Daily Dose; and identify unique user characteristics and circumstances that the Health Manager can guide the user to address as possible barriers to a healthy lifestyle through the problem-solving function of the Health Manager.

The specific information to be surveyed may include: key individual temperamental characteristics, including activity level, regularity of eating, sleeping, and bowel habits, initial response to situations, adaptability, persistence, threshold of responsiveness, intensity of reaction, and quality of mood; the user's level of independent functioning, i.e., self-organization and management, socialization, memory, and academic achievement skills; the user's ability to focus and sustain attention, including the user's level of arousal, cognitive tempo, ability to filter distractions, vigilance, and self-monitoring; the user's current health status including current weight, height, and blood pressure, most recent general physician visit, gynecological exam, and other applicable physician/healthcare contacts, current medications and supplements, allergies, and a review of current symptoms and/or health-related behaviors; the user's past health history, i.e., illnesses/surgeries, family history, and social stress events, such as divorce or loss of a job, that have required adjustment by the individual; the user's beliefs, values and opinions about health priorities, their ability to alter their behavior and, what might contribute to stress in their life, and how they manage it; the user's degree of self-awareness, empathy, empowerment, and self-esteem, and the user's current daily routines for eating, sleeping, exercise, relaxation and completing activities of daily living; and the user's perception of the temperamental characteristics of two key persons in their life, for example, their spouse, a friend, a co-worker, or their boss, and whether there are clashes present in their relationships that might interfere with a healthy lifestyle or contribute to stress.

Each member user will have access, through the home web page of central monitoring unit 30, to a series of web pages customized for that user, referred to as the Health Manager. The opening Health Manager web page 150 is shown in FIG. 5. The Health Manager web pages are the main workspace area for the member user. The Health Manager web pages comprise a utility through which central monitoring unit 30 provides various types and forms of data, commonly referred to as analytical status data, to the user that is generated from the data it collects or generates, namely one or more of: the data indicative of various physiological parameters generated by sensor device 10; the data derived from the data indicative of various physiological parameters; the data indicative of various contextual parameters generated by sensor device 10; and the data input by the user. Analytical status data is characterized by the application of certain utilities or algorithms to convert one or more of the data indicative of various physiological parameters generated by sensor device 10, the data derived from the data indicative of various physiological parameters, the data indicative of various contextual parameters generated by sensor device 10, and the data input by the user into calculated health, wellness and lifestyle indicators. For example, based on data input by the user relating to the foods he or she has eaten, things such as calories and amounts of proteins, fats, carbohydrates, and certain vitamins can be calculated. As another example, skin temperature, heart rate, respiration rate, heat flow and/or GSR can be used to provide an indicator to the user of his or her stress level over a desired time period. As still another example, skin temperature, heat flow, beat-to-beat heart variability, heart rate, pulse rate, respiration rate, core temperature, galvanic skin response, EMG, EEG, EOG, blood pressure, oxygen consumption, ambient sound and body movement or motion as detected by a device such as an accelerometer can be used to provide indicators to the user of his or her sleep patterns over a desired time period.

Located on the opening Health Manager web page 150 is Health Index 155. Health Index 155 is a graphical utility used to measure and provide feedback to member users regarding their performance and the degree to which they have succeeded in reaching a healthy daily routine suggested by central monitoring unit 30. Health Index 155 thus provides an indication for the member user to track his or her progress. Health Index 155 includes six categories relating to the user's health and lifestyle: Nutrition, Activity Level, Mind Centering, Sleep, Daily Activities and How You Feel. The Nutrition category relates to what, when and how much a person eats and drinks. The Activity Level category relates to how much a person moves around. The Mind Centering category relates to the quality and quantity of time a person spends engaging in some activity that allows the body to achieve a state of profound relaxation while the mind becomes highly alert and focused. The Sleep category relates to the quality and quantity of a person's sleep. The Daily Activities category relates to the daily responsibilities and health risks people encounter. Finally, the How You Feel category relates to the general perception that a person has about how they feel on a particular day. Each category has an associated level indicator or piston that indicates, preferably on a scale ranging from poor to excellent, how the user is performing with respect to that category.

When each member user completes the initial survey described above, a profile is generated that provides the user with a summary of his or her relevant characteristics and life circumstances. A plan and/or set of goals is provided in the form of a suggested healthy daily routine. The suggested healthy daily routine may include any combination of specific suggestions for incorporating proper nutrition, exercise, mind centering, sleep, and selected activities of daily living in the user's life. Prototype schedules may be offered as guides for how these suggested activities can be incorporated into the user's life. The user may periodically retake the survey, and based on the results, the items discussed above will be adjusted accordingly.

The Nutrition category is calculated from both data input by the user and sensed by sensor device 10. The data input by the user comprises the time and duration of breakfast, lunch, dinner and any snacks, and the foods eaten, the supplements such as vitamins that are taken, and the water and other liquids consumed during a relevant, pre-selected time period. Based upon this data and on stored data relating to known properties of various foods, central monitoring unit 30 calculates well known nutritional food values such as calories and amounts of proteins, fats, carbohydrates, vitamins, etc., consumed.

The Nutrition Health Index piston level is preferably determined with respect to the following suggested healthy daily routine: eat at least three meals; eat a varied diet consisting of 6–11 servings of bread, pasta, cereal, and rice, 2–4 servings fruit, 3–5 servings of vegetables, 2–3 servings of fish, meat, poultry, dry beans, eggs, and nuts, and 2–3 servings of milk, yogurt and cheese; and drink 8 or more 8 ounce glasses of water. This routine may be adjusted based on information about the user, such as sex, age, height and/or weight. Certain nutritional targets may also be set by the user or for the user, relating to daily calories, protein, fiber, fat, carbohydrates, and/or water consumption and percentages of total consumption. Parameters utilized in the calculation of the relevant piston level include the number of meals per day, the number of glasses of water, and the types and amounts of food eaten each day as input by the user.

Nutritional information is presented to the user through nutrition web page 160 as shown in FIG. 6. The preferred nutritional web page 160 includes nutritional fact charts 165 and 170 which illustrate actual and target nutritional facts, respectively as pie charts, and nutritional intake charts 175 and 180 which show total actual nutritional intake and target nutritional intake, respectively as pie charts. Nutritional fact charts 165 and 170 preferably show a percentage breakdown of items such as carbohydrates, protein and fat, and nutritional intake charts 175 and 180 are preferably broken down to show components such as total and target calories, fat, carbohydrates, protein, and vitamins. Web page 160 also includes meal and water consumption tracking 185 with time entries, hyperlinks 190 which allow the user to directly access nutrition-related news items and articles, suggestions for refining or improving daily routine with respect to nutrition and affiliate advertising elsewhere on the network, and calendar 195 for choosing between views having variable and selectable time periods. The items shown at 190 may be selected and customized based on information learned about the individual in the survey and on their performance as measured by the Health Index.

The Activity Level category of Health Index 155 is designed to help users monitor how and when they move around during the day and utilizes both data input by the user and data sensed by sensor device 10. The data input by the user may include details regarding the user's daily activities, for example the fact that the user worked at a desk from 8 a.m. to 5 p.m. and then took an aerobics class from 6 p.m. to 7 p.m. Relevant data sensed by sensor device 10 may include heart rate, movement as sensed by a device such as an accelerometer, heat flow, respiration rate, calories burned, GSR and hydration level, which may be derived by sensor device 60 or central monitoring unit 30. Calories burned may be calculated in a variety of manners, including: the multiplication of the type of exercise input by the user by the duration of exercise input by the user; sensed motion multiplied by time of motion multiplied by a filter constant; or sensed heat flux multiplied by time multiplied by a filter constant.

The Activity Level Health Index piston level is preferably determined with respect to a suggested healthy daily routine that includes: exercising aerobically for a pre-set time period, preferably 20 minutes, or engaging in a vigorous lifestyle activity for a pre-set time period, preferably one hour, and burning at least a minimum target number of calories, preferably 205 calories, through the aerobic exercise and/or lifestyle activity. The minimum target number of calories may be set according to information about the user, such as sex, age, height and/or weight. Parameters utilized in the calculation of the relevant piston level include the amount of time spent exercising aerobically or engaging in a vigorous lifestyle activity as input by the user and/or sensed by sensor device 10, and the number of calories burned above pre-calculated energy expenditure parameters.

Information regarding the individual user's movement is presented to the user through activity level web page 200 shown in FIG. 7, which may include activity graph 205 in the form of a bar graph, for monitoring the individual user's activities in one of three categories: high, medium and low intensity with respect to a pre-selected unit of time. Activity percentage chart 210, in the form of a pie chart, may also be provided for showing the percentage of a pre-selected time period, such as one day, that the user spent in each category. Activity level web page 200 may also include calorie section 215 for displaying items such as total calories burned, daily target calories burned, total caloric intake, and duration of aerobic activity. Finally, activity level web page 200 may include at least one hyperlink 220 to allow a user to directly access relevant news items and articles, suggestions for refining or improving daily routine with respect to activity level and affiliate advertising elsewhere on the network. Activity level web page 200 may be viewed in a variety of formats, and may include user-selectable graphs and charts such as a bar graph, pie chart, or both, as selectable by Activity level check boxes 225. Activity level calendar 230 is provided for selecting among views having variable and selectable time periods. The items shown at 220 may be selected and customized based on information learned about the individual in the survey and on their performance as measured by the Health Index.

The Mind Centering category of Health Index 155 is designed to help users monitor the parameters relating to time spent engaging in certain activities which allow the body to achieve a state of profound relaxation while the mind becomes focused, and is based upon both data input by the user and data sensed by the sensor device 10. In particular, a user may input the beginning and end times of relaxation activities such as yoga or meditation. The quality of those activities as determined by the depth of a mind centering event can be measured by monitoring parameters including skin temperature, heart rate, respiration rate, and heat flow as sensed by sensor device 10. Percent change in GSR as derived either by sensor device 10 or central monitoring unit 30 may also be utilized.

The Mind Centering Health Index piston level is preferably calculated with respect to a suggested healthy daily routine that includes participating each day in an activity that allows the body to achieve profound relaxation while the mind stays highly focused for at least fifteen minutes. Parameters utilized in the calculation of the relevant piston level include the amount of time spent in a mind centering activity, and the percent change in skin temperature, heart rate, respiration rate, heat flow or GSR as sensed by sensor device 10 compared to a baseline which is an indication of the depth or quality of the mind centering activity.

Information regarding the time spent on self-reflection and relaxation is presented to the user through mind centering web page 250 shown in FIG. 8. For each mind centering activity, referred to as a session, the preferred mind centering web page 250 includes the time spent during the session, shown at 255, the target time, shown at 260, comparison section 265 showing target and actual depth of mind centering, or focus, and a histogram 270 that shows the overall level of stress derived from such things as skin temperature, heart rate, respiration rate, heat flow and/or GSR. In comparison section 265, the human figure outline showing target focus is solid, and the human figure outline showing actual focus ranges from fuzzy to solid depending on the level of focus. The preferred mind centering web page may also include an indication of the total time spent on mind centering activities, shown at 275, hyperlinks 280 which allow the user to directly access relevant news items and articles, suggestions for refining or improving daily routine with respect to mind centering and affiliate advertising, and a calendar 285 for choosing among views having variable and selectable time periods. The items shown at 280 may be selected and customized based on information learned about the individual in the survey and on their performance as measured by the Health Index.

The Sleep category of Health Index 155 is designed to help users monitor their sleep patterns and the quality of their sleep. It is intended to help users learn about the importance of sleep in their healthy lifestyle and the relationship of sleep to circadian rhythms, being the normal daily variations in body functions. The Sleep category is based upon both data input by the user and data sensed by sensor device 10. The data input by the user for each relevant time interval includes the times the user went to sleep and woke up and a rating of the quality of sleep. As noted in Table 2, the data from sensor device 10 that is relevant includes skin temperature, heat flow, beat-to-beat heart variability, heart rate, pulse rate, respiration rate, core temperature, galvanic skin response, EMG, EEG, EOG, blood pressure, and oxygen consumption. Also relevant is ambient sound and body movement or motion as detected by a device such as an accelerometer. This data can then be used to calculate or derive sleep onset and wake time, sleep interruptions, and the quality and depth of sleep.

The Sleep Health Index piston level is determined with respect to a healthy daily routine including getting a minimum amount, preferably eight hours, of sleep each night and having a predictable bed time and wake time. The specific parameters which determine the piston level calculation include the number of hours of sleep per night and the bed time and wake time as sensed by sensor device 10 or as input by the user, and the quality of the sleep as rated by the user or derived from other data.

Information regarding sleep is presented to the user through sleep web page 290 shown in FIG. 9. Sleep web page 290 includes a sleep duration indicator 295, based on either data from sensor device 10 or on data input by the user, together with user sleep time indicator 300 and wake time indicator 305. A quality of sleep rating 310 input by the user may also be utilized and displayed. If more than a one day time interval is being displayed on sleep web page 290, then sleep duration indicator 295 is calculated and displayed as a cumulative value, and sleep time indicator 300, wake time indicator 305 and quality of sleep rating 310 are calculated and illustrated as averages. Sleep web page 290 also includes a user-selectable sleep graph 315 which calculates and displays one sleep related parameter over a pre-selected time interval. For illustrative purposes, FIG. 9 shows heat flow over a one-day period, which tends to be lower during sleeping hours and higher during waking hours. From this information, a person's bio-rhythms can be derived. Sleep graph 315 may also include a graphical representation of data from an accelerometer incorporated in sensor device 10 which monitors the movement of the body. The sleep web page 290 may also include hyperlinks 320 which allow the user to directly access sleep related news items and articles, suggestions for refining or improving daily routine with respect to sleep and affiliate advertising available elsewhere on the network, and a sleep calendar 325 for choosing a relevant time interval. The items shown at 320 may be selected and customized based on information learned about the individual in the survey and on their performance as measured by the Health Index.

The Activities of Daily Living category of Health Index 155 is designed to help users monitor certain health and safety related activities and risks and is based entirely on data input by the user. The Activities of Daily Living category is divided into four sub-categories: personal hygiene, which allows the user to monitor activities such as brushing and flossing his or her teeth and showering; health maintenance, that tracks whether the user is taking prescribed medication or supplements and allows the user to monitor tobacco and alcohol consumption and automobile safety such as seat belt use; personal time, that allows the user to monitor time spent socially with family and friends, leisure, and mind centering activities; and responsibilities, that allows the user to monitor certain work and financial activities such as paying bills and household chores.

The Activities of Daily Living Health Index piston level is preferably determined with respect to the healthy daily routine described below. With respect to personal hygiene, the routine requires that the users shower or bathe each day, brush and floss teeth each day, and maintain regular bowel habits. With respect to health maintenance, the routine requires that the user take medications and vitamins and/or supplements, use a seat belt, refrain from smoking, drink moderately, and monitor health each day with the Health Manager. With respect to personal time, the routine requires the users to spend at least one hour of quality time each day with family and/or friends, restrict work time to a maximum of nine hours a day, spend some time on a leisure or play activity each day, and engage in a mind stimulating activity. With respect to responsibilities, the routine requires the users to do household chores, pay bills, be on time for work, and keep appointments. The piston level is calculated based on the degree to which the user completes a list of daily activities as determined by information input by the user.

Information relating to these activities is presented to the user through daily activities web page 330 shown in FIG. 10. In preferred daily activities web page 330, activities chart 335, selectable for one or more of the sub-categories, shows whether the user has done what is required by the daily routine. A colored or shaded box indicates that the user has done the required activity, and an empty, non-colored or shaded box indicates that the user has not done the activity. Activities chart 335 can be created and viewed in selectable time intervals. For illustrative purposes, FIG. 10 shows the personal hygiene and personal time sub-categories for a particular week. In addition, daily activities web page 330 may include daily activity hyperlinks 340 which allow the user to directly access relevant news items and articles, suggestions for improving or refining daily routine with respect to activities of daily living and affiliate advertising, and a daily activities calendar 345 for selecting a relevant time interval. The items shown at 340 maybe selected and customized based on information learned about the individual in the survey and on their performance as measured by the Health Index.

The How You Feel category of Health Index 155 is designed to allow users to monitor their perception of how they felt on a particular day, and is based on information, essentially a subjective rating, that is input directly by the user. A user provides a rating, preferably on a scale of 1 to 5, with respect to the following nine subject areas: mental sharpness; emotional and psychological well being; energy level; ability to cope with life stresses; appearance; physical well being; self-control; motivation; and comfort in relating to others. Those ratings are averaged and used to calculate the relevant piston level.

Referring to FIG. 11, Health Index web page 350 is shown. Health Index web page 350 enables users to view the performance of their Health Index over a user selectable time interval including any number of consecutive or non-consecutive days. Using Health Index selector buttons 360, the user can select to view the Health Index piston levels for one category, or can view a side-by-side comparison of the Health Index piston levels for two or more categories. For example, a user might want to just turn on Sleep to see if their overall sleep rating improved over the previous month, much in the same way they view the performance of their favorite stock. Alternatively, Sleep and Activity Level might be simultaneously displayed in order to compare and evaluate Sleep ratings with corresponding Activity Level ratings to determine if any day-to-day correlations exist. Nutrition ratings might be displayed with How You Feel for a pre-selected time interval to determine if any correlation exists between daily eating habits and how they felt during that interval. For illustrative purposes, FIG. 11 illustrates a comparison of Sleep and Activity Level piston levels for the week of June 10 through June 16. Health Index web page 350 also includes tracking calculator 365 that displays access information and statistics such as the total number of days the user has logged in and used the Health Manager, the percentage of days the user has used the Health Manager since becoming a subscriber, and percentage of time the user has used the sensor device 10 to gather data.

Referring again to FIG. 5, opening Health Manager web page 150 may include a plurality of user selectable category summaries 156a through 156f, one corresponding to each of the Health Index 155 categories. Each category summary 156a through 156f presents a pre-selected filtered subset of the data associated with the corresponding category. Nutrition category summary 156a displays daily target and actual caloric intake. Activity Level category summary 156b displays daily target and actual calories burned. Mind Centering category summary 156c displays target and actual depth of mind centering or focus. Sleep category summary 156d displays target sleep, actual sleep, and a sleep quality rating. Daily Activities category summary 156e displays a target and actual score based on the percentage of suggested daily activities that are completed. The How You Feel category summary 156f shows a target and actual rating for the day.

Opening Health Manager web page 150 also may include Daily Dose section 157 which provides, on a daily time interval basis, information to the user, including, but not limited to, hyperlinks to news items and articles, commentary and reminders to the user based on tendencies, such as poor nutritional habits, determined from the initial survey. The commentary for Daily Dose 157 may, for example, be a factual statement that drinking 8 glasses of water a day can reduce the risk of colon cancer by as much as 32%, accompanied by a suggestion to keep a cup of water by your computer or on your desk at work and refill often. Opening Health Manager web page 150 also may include a Problem Solver section 158 that actively evaluates the user's performance in each of the categories of Health Index 155 and presents suggestions for improvement. For example, if the system detects that a user's Sleep levels have been low, which suggest that the user has been having trouble sleeping, Problem Solver 158 can provide suggestions for way to improve sleep. Problem Solver 158 also may include the capability of user questions regarding improvements in performance. Opening Health Manager web page 150 may also include a Daily Data section 159 that launches an input dialog box. The input dialog box facilitates input by the user of the various data required by the Health Manager. As is known in the art, data entry may be in the form of selection from pre-defined lists or general free form text input. Finally, opening Health Manager web page 150 may include Body Stats section 161 which may provide information regarding the user's height, weight, body measurements, body mass index or BMI, and vital signs such as heart rate, blood pressure or any of the identified physiological parameters.

Referring to FIGS. 12–17, a specific embodiment of sensor device 10 is shown which is in the form of an armband adapted to be worn by an individual on his or her upper arm, between the shoulder and the elbow. The specific embodiment of sensor device 10 shown in FIGS. 12–17 will, for convenience, be referred to as armband sensor device 400. Armband sensor device 400 includes computer housing 405, flexible wing body 410, and, as shown in FIG. 17, elastic strap 415. Computer housing 405 and flexible wing body 410 are preferably made of a flexible urethane material or an elastomeric material such as rubber or a rubber-silicone blend by a molding process. Flexible wing body 410 includes first and second wings 418 each having a thru-hole 420 located near the ends 425 thereof. First and second wings 418 are adapted to wrap around a portion of the wearer's upper arm.

Elastic strap 415 is used to removably affix armband sensor device 400 to the individual's upper arm. As seen in FIG. 17, bottom surface 426 of elastic strap 415 is provided with Velcro loops 416 along a portion thereof. Each end 427 of elastic strap 415 is provided with Velcro hook patch 428 on bottom surface 426 and pull tab 429 on top surface 430. A portion of each pull tab 429 extends beyond the edge of each end 427.

In order to wear armband sensor device 400, a user inserts each end 427 of elastic strap 415 into a respective thru-hole 420 of flexible wing body 410. The user then places his arm through the loop created by elastic strap 415, flexible wing body 410 and computer housing 405. By pulling each pull tab 429 and engaging Velcro hook patches 428 with Velcro loops 416 at a desired position along bottom surface 426 of elastic strap 415, the user can adjust elastic strap 415 to fit comfortably. Since Velcro hook patches 428 can be engaged with Velcro loops 416 at almost any position along bottom surface 426, armband sensor device 400 can be adjusted to fit arms of various sizes. Also, elastic strap 415 may be provided in various lengths to accommodate a wider range of arm sizes. As will be apparent to one of skill in the art, other means of fastening and adjusting the size of elastic strap may be used, including, but not limited to, snaps, buttons, or buckles. It is also possible to use two elastic straps that fasten by one of several conventional means including Velcro, snaps, buttons, buckles or the like, or merely a single elastic strap affixed to wings 418.

Alternatively, instead of providing thru-holes 420 in wings 418, loops having the shape of the letter D, not shown, may be attached to ends 425 of wings 418 by one of several conventional means. For example, a pin, not shown, may be inserted through ends 425, wherein the pin engages each end of each loop. In this configuration, the D-shaped loops would serve as connecting points for elastic strap 415, effectively creating a thru-hole between each end 425 of each wing 418 and each loop.

As shown in FIG. 18, which is an exploded view of armband sensor device 400, computer housing 405 includes a top portion 435 and a bottom portion 440. Contained within computer housing 405 are printed circuit board or PCB 445, rechargeable battery 450, preferably a lithium ion battery, and vibrating motor 455 for providing tactile feedback to the wearer, such as those used in pagers, suitable examples of which are the Model 12342 and 12343 motors sold by MG Motors Ltd. of the United Kingdom.

Top portion 435 and bottom portion 440 of computer housing 405 sealingly mate along groove 436 into which O-ring 437 is fit, and may be affixed to one another by screws, not shown, which pass through screw holes 438a and stiffeners 438b of bottom portion 440 and apertures 439 in PCB 445 and into threaded receiving stiffeners 451 of top portion 435. Alternately, top portion 435 and bottom portion 440 may be snap fit together or affixed to one another with an adhesive. Preferably, the assembled computer housing 405 is sufficiently water resistant to permit armband sensor device 400 to be worn while swimming without adversely affecting the performance thereof.

As can be seen in FIG. 13, bottom portion 440 includes, on a bottom side thereof, a raised platform 430. Affixed to raised platform 430 is heat flow or flux sensor 460, a suitable example of which is the micro-foil heat flux sensor sold by RdF Corporation of Hudson, N.H. Heat flux sensor 460 functions as a self-generating thermopile transducer, and preferably includes a carrier made of a polyamide film. Bottom portion 440 may include on a top side thereof, that is on a side opposite the side to which heat flux sensor 460 is affixed, a heat sink, not shown, made of a suitable metallic material such as aluminum. Also affixed to raised platform 430 are GSR sensors 465, preferably comprising electrodes formed of a material such as conductive carbonized rubber, gold or stainless steel. Although two GSR sensors 465 are shown in FIG. 13, it will be appreciated by one of skill in the art that the number of GSR sensors 465 and the placement thereof on raised platform 430 can vary as long as the individual GSR sensors 465, i.e., the electrodes, are electrically isolated from one another. By being affixed to raised platform 430, heat flux sensor 460 and GSR sensors 465 are adapted to be in contact with the wearer's skin when armband sensor device 400 is worn. Bottom portion 440 of computer housing 405 may also be provided with a removable and replaceable soft foam fabric pad, not shown, on a portion of the surface thereof that does not include raised platform 430 and screw holes 438a. The soft foam fabric is intended to contact the wearer's skin and make armband sensor device 400 more comfortable to wear.

Electrical coupling between heat flux sensor 460, GSR sensors 465, and PCB 445 may be accomplished in one of various known methods. For example, suitable wiring, not shown, may be molded into bottom portion 440 of computer housing 405 and then electrically connected, such as by soldering, to appropriate input locations on PCB 445 and to heat flux sensor 460 and GSR sensors 465. Alternatively, rather than molding wiring into bottom portion 440, thru-holes may be provided in bottom portion 440 through which appropriate wiring may pass. The thru-holes would preferably be provided with a water tight seal to maintain the integrity of computer housing 405.

Rather than being affixed to raised platform 430 as shown in FIG. 13, one or both of heat flux sensor 460 and GSR sensors 465 may be affixed to the inner portion 466 of flexible wing body 410 on either or both of wings 418 so as to be in contact with the wearer's skin when armband sensor device 400 is worn. In such a configuration, electrical coupling between heat flux sensor 460 and GSR sensors 465, whichever the case may be, and the PCB 445 may be accomplished through suitable wiring, not shown, molded into flexible wing body 410 that passes through one or more thru-holes in computer housing 405 and that is electrically connected, such as by soldering, to appropriate input locations on PCB 445. Again, the thru-holes would preferably be provided with a water tight seal to maintain the integrity of computer housing 405. Alternatively, rather than providing thru-holes in computer housing 405 through which the wiring passes, the wiring may be captured in computer housing 405 during an overmolding process, described below, and ultimately soldered to appropriate input locations on PCB 445.

As shown in FIGS. 12, 16, 17 and 18, computer housing 405 includes a button 470 that is coupled to and adapted to activate a momentary switch 585 on PCB 445. Button 470 may be used to activate armband sensor device 400 for use, to mark the time an event occurred or to request system status information such as battery level and memory capacity. When button 470 is depressed, momentary switch 585 closes a circuit and a signal is sent to processing unit 490 on PCB 445. Depending on the time interval for which button 470 is depressed, the generated signal triggers one of the events just described. Computer housing 405 also includes LEDs 475, which may be used to indicate battery level or memory capacity or to provide visual feedback to the wearer. Rather than LEDs 475, computer housing 405 may also include a liquid crystal display or LCD to provide battery level, memory capacity or visual feedback information to the wearer. Battery level, memory capacity or feedback information may also be given to the user tactily or audibly.

Armband sensor device 400 may be adapted to be activated for use, that is collecting data, when either of GSR sensors 465 or heat flux sensor 460 senses a particular condition that indicates that armband sensor device 400 has been placed in contact with the user's skin. Also, armband sensor device 400 may be adapted to be activated for use when one or more of heat flux sensor 460, GSR sensors 465, accelerometer 495 or 550, or any other device in communication with armband sensor device 400, alone or in combination, sense a particular condition or conditions that indicate that the armband sensor device 400 has been placed in contact with the user's skin for use. At other times, armband sensor device 400 would be deactivated, thus preserving battery power.

Computer housing 405 is adapted to be coupled to a battery recharger unit 480 shown in FIG. 19 for the purpose of recharging rechargeable battery 450. Computer housing 405 includes recharger contacts 485, shown in FIGS. 12, 15, 16 and 17, that are coupled to rechargeable battery 450. Recharger contacts 485 may be made of a material such as brass, gold or stainless steel, and are adapted to mate with and be electrically coupled to electrical contacts, not shown, provided in battery recharger unit 480 when armband sensor device 400 is placed therein. The electrical contacts provided in battery recharger unit 480 may be coupled to recharging circuit 481a provided inside battery recharger unit 480. In this configuration, recharging circuit 481 would be coupled to a wall outlet, such as by way of wiring including a suitable plug that is attached or is attachable to battery recharger unit 480. Alternatively, electrical contacts 480 may be coupled to wiring that is attached to or is attachable to battery recharger unit 480 that in turn is coupled to recharging circuit 481b external to battery recharger unit 480. The wiring in this configuration would also include a plug, not shown, adapted to be plugged into a conventional wall outlet.

Also provided inside battery recharger unit 480 is RF transceiver 483 adapted to receive signals from and transmit signals to RF transceiver 565 provided in computer housing 405 and shown in FIG. 20. RF transceiver 483 is adapted to be coupled, for example by a suitable cable, to a serial port, such as an RS 232 port or a USB port, of a device such as personal computer 35 shown in FIG. 1. Thus, data may be uploaded from and downloaded to armband sensor device 400 using RF transceiver 483 and RF transceiver 565. It will be appreciated that although RF transceivers 483 and 565 are shown in FIGS. 19 and 20, other forms of wireless transceivers may be used, such as infrared transceivers. Alternatively, computer housing 405 may be provided with additional electrical contacts, not shown, that would be adapted to mate with and be electrically coupled to additional electrical contacts, not shown, provided in battery recharger unit 480 when armband sensor device 400 is placed therein. The additional electrical contacts in the computer housing 405 would be coupled to the processing unit 490 and the additional electrical contacts provided in battery recharger unit 480 would be coupled to a suitable cable that in turn would be coupled to a serial port, such as an RS R32 port or a USB port, of a device such as personal computer 35. This configuration thus provides an alternate method for uploading of data from and downloading of data to armband sensor device 400 using a physical connection.

FIG. 20 is a schematic diagram that shows the system architecture of armband sensor device 400, and in particular each of the components that is either on or coupled to PCB 445.

As shown in FIG. 17, PCB 445 includes processing unit 490, which may be a microprocessor, a microcontroller, or any other processing device that can be adapted to perform the functionality described herein. Processing unit 490 is adapted to provide all of the functionality described in connection with microprocessor 20 shown in FIG. 2. A suitable example of processing unit 490 is the Dragonball EZ sold by Motorola, Inc. of Schaumburg, Ill. PCB 445 also has thereon a two-axis accelerometer 495, a suitable example of which is the Model ADXL210 accelerometer sold by Analog Devices, Inc. of Norwood, Mass. Two-axis accelerometer 495 is preferably mounted on PCB 445 at an angle such that its sensing axes are offset at an angle substantially equal to 45 degrees from the longitudinal axis of PCB 445 and thus the longitudinal axis of the wearer's arm when armband sensor device 400 is worn. The longitudinal axis of the wearer's arm refers to the axis defined by a straight line drawn from the wearer's shoulder to the wearer's elbow. The output signals of two-axis accelerometer 495 are passed through buffers 500 and input into analog to digital converter 505 that in turn is coupled to processing unit 490. GSR sensors 465 are coupled to amplifier 510 on PCB 445. Amplifier 510 provides amplification and low pass filtering functionality, a suitable example of which is the Model AD8544 amplifier sold by Analog Devices, Inc. of Norwood, Mass. The amplified and filtered signal output by amplifier 510 is input into amp/offset 515 to provide further gain and to remove any bias voltage and into filter/conditioning circuit 520, which in turn are each coupled to analog to digital converter 505. Heat flux sensor 460 is coupled to differential input amplifier 525, such as the Model INA amplifier sold by Burr-Brown Corporation of Tucson, Ariz., and the resulting amplified signal is passed through filter circuit 530, buffer 535 and amplifier 540 before being input to analog to digital converter 505. Amplifier 540 is configured to provide further gain and low pass filtering, a suitable example of which is the Model AD8544 amplifier sold by Analog Devices, Inc. of Norwood, Mass. PCB 445 also includes thereon a battery monitor 545 that monitors the remaining power level of rechargeable battery 450. Battery monitor 545 preferably comprises a voltage divider with a low pass filter to provide average battery voltage. When a user depresses button 470 in the manner adapted for requesting battery level, processing unit 490 checks the output of battery monitor 545 and provides an indication thereof to the user, preferably through LEDs 475, but also possibly through vibrating motor 455 or ringer 575. An LCD may also be used.

PCB 445 may include three-axis accelerometer 550 instead of or in addition to two-axis accelerometer 495. The three-axis accelerometer outputs a signal to processing unit 490. A suitable example of three-axis accelerometer is the µPAM product sold by I.M. Systems, Inc. of Scottsdale, Ariz. Three-axis accelerometer 550 is preferably tilted in the manner described with respect to two-axis accelerometer 495.

PCB 445 also includes RF receiver 555 that is coupled to processing unit 490. RF receiver 555 may be used to receive signals that are output by another device capable of wireless transmission, shown in FIG. 20 as wireless device 558, worn by or located near the individual wearing armband sensor device 400. Located near as used herein means within the transmission range of wireless device 558. For example, wireless device 558 may be a chest mounted heart rate monitor such as the Tempo product sold by Polar Electro of Oulu, Finland. Using such a heart rate monitor, data indicative of the wearer's heart rate can be collected by armband sensor device 400. Antenna 560 and RF transceiver 565 are coupled to processing unit 490 and are provided for purposes of uploading data to central monitoring unit 30 and receiving data downloaded from central monitoring unit 30. RF transceiver 565 and RF receiver 555 may, for example, employ Bluetooth technology as the wireless transmission protocol. Also, other forms of wireless transmission may be used, such as infrared transmission.

The fact that RF Transceiver 565 may be used for wirelessly uploading data from and wirelessly downloading data to armband sensor device 400 is advantageous because it eliminates the need to remove armband sensor device 400 to perform these functions, as would be required with a physical connection. For example, if armband sensor device 400 was being worn under the user's clothing, requiring removal of armband sensor device 400 prior to uploading and/or downloading data increases user inconvenience. In addition, the wearing of armband sensor device 400 has an effect on the user's skin and underlying blood vessels, which in turn may affect any measurements being made with respect thereto. It may be necessary for a period of time during which armband sensor device 400 is worn by the user to elapse before a steady state is achieved and consistent, accurate measurements can be made. By providing armband sensor device 400 with wireless communications capability, data can be uploaded and downloaded without disturbing an established steady state equilibrium condition. For example, programming data for processing unit 490 that controls the sampling characteristics of armband sensor device 400 can be downloaded to armband sensor device 400 without disturbing the steady state equilibrium condition.

In addition, antenna 560 and RF transceiver 565 permit armband sensor device 400 to communicate wirelessly with other devices capable of wireless communication, i.e., transmit information to and receive information from those devices. The devices may include, for example, devices that are implanted in the body of the person using armband sensor device 400, such as an implantable heart pacemaker or an implantable insulin dispensing device, for example the MiniMed® 2007 implantable insulin pump sold by MiniMed Inc. of Northridge, Calif., devices worn on the body of the person using armband sensor device 400, or devices located near the person using armband sensor device 400 at any particular time, such as an electronic scale, a blood pressure monitor, a glucose monitor, a cholesterol monitor or another armband sensor device 400. With this two-way wireless communication capability, armband sensor device 400 may be adapted to transmit information that activates or deactivates such a device for use or information that programs such a device to behave in a particular way. For example, armband sensor device 400 may be adapted to activate a piece of exercise equipment such as a treadmill and program it to operate with certain parameters that are dictated or desired by or optimal for the user of armband sensor device 400. As another example, armband sensor device 400 may be adapted to adjust a computer controlled thermostat in a home based on the detected skin temperature of the wearer or turn off a computer controlled lighting system, television or stereo when the wearer is determined to have fallen asleep.

Vibrating motor 455 is coupled to processing unit 490 through vibrator driver 570 and provides tactile feedback to the wearer. Similarly, ringer 575, a suitable example of which is the Model SMT916A ringer sold by Projects Unlimited, Inc. of Dayton, Ohio, is coupled to processing unit 490 through ringer driver 580, a suitable example of which is the Model MMBTA14 CTI darlington transistor driver sold by Motorola, Inc. of Schaumburg, Ill., and provides audible feedback to the wearer. Feedback may include, for example, celebratory, cautionary and other threshold or event driven messages, such as when a wearer reaches a level of calories burned during a workout.

Also provided on PCB 445 and coupled to processing unit 490 is momentary switch 585. Momentary switch 585 is also coupled to button 470 for activating momentary switch 585. LEDs 475, used to provide various types of feedback information to the wearer, are coupled to processing unit 490 through LED latch/driver 590.

Oscillator 595 is provided on PCB 445 and supplies the system clock to processing unit 490. Reset circuit 600, accessible and triggerable through a pin-hole in the side of computer housing 405, is coupled to processing unit 490 and enables processing unit 490 to be reset to a standard initial setting.

Rechargeable battery 450, which is the main power source for the armband sensor device 400, is coupled to processing unit 490 through voltage regulator 605. Finally, memory functionality is provided for armband sensor device 400 by SRAM 610, which stores data relating to the wearer of armband sensor device 400, and flash memory 615, which stores program and configuration data, provided on PCB 445. SRAM 610 and flash memory 615 are coupled to processing unit 490 and each preferably have at least 512K of memory.

In manufacturing and assembling armband sensor device 400, top portion 435 of computer housing 405 is preferably formed first, such as by a conventional molding process, and flexible wing body 410 is then overmolded on top of top portion 435. That is, top portion 435 is placed into an appropriately shaped mold, i.e., one that, when top portion 435 is placed therein, has a remaining cavity shaped according to the desired shape of flexible wing body 410, and flexible wing body 410 is molded on top of top portion 435. As a result, flexible wing body 410 and top portion 435 will merge or bond together, forming a single unit. Alternatively, top portion 435 of computer housing 405 and flexible wing body 410 may be formed together, such as by molding in a single mold, to form a single unit. The single unit however formed may then be turned over such that the underside of top portion 435 is facing upwards, and the contents of computer housing 405 can be placed into top portion 435, and top portion 435 and bottom portion 440 can be affixed to one another. As still another alternative, flexible wing body 410 may be separately formed, such as by a conventional molding process, and computer housing 405, and in particular top portion 435 of computer housing 405, may be affixed to flexible wing body 410 by one of several known methods, such as by an adhesive, by snap-fitting, or by screwing the two pieces together. Then, the remainder of computer housing 405 would be assembled as described above. It will be appreciated that rather than assembling the remainder of computer housing 405 after top portion 435 has been affixed to flexible wing body 410, the computer housing 405 could be assembled first and then affixed to flexible wing body 410.

Referring to FIG. 21, a block diagram of an alternate embodiment of the present invention is shown. This alternate embodiment includes stand alone sensor device 700 which functions as an independent device, meaning that it is capable of collecting and/or generating the various types of data described herein in connection with sensor device 10 and sensor device 400 and providing analytical status data to the user without interaction with a remotely located apparatus such as central monitoring unit 30. Stand alone sensor device 700 includes a processor that is programmed and/or otherwise adapted to include the utilities and algorithms necessary to create analytical status data from the data indicative of various physiological and/or contextual parameters of the user, the data derived therefrom, and the data input by the user, all of which is stored in and accessed as needed from memory provided in stand alone sensor device 700. Stand alone sensor device 700 may comprise sensor device 10 shown in FIGS. 1 and 2 that includes microprocessor 20 and memory 22 or armband sensor device 400 shown in FIGS. 12-17 that includes processing unit 490 and SRAM 610.

As shown schematically in FIG. 21, data may be input into stand alone sensor device 700 in a number of ways. Stand alone sensor device 700 may include one or more physiological sensors 705 as described herein for facilitating the collection of data indicative of various physiological parameters of the user. Stand alone sensor device 700 may also include one or more contextual sensors 710 as described herein for facilitating the collection of data indicative of various contextual parameters of the user. As indicated by reference number 715, stand alone sensor device 700 may be adapted to enable the manual entry of data by the user. For example, stand alone sensor device 700 may include a data input button, such as a button 470 of armband sensor device 400, through which a user could manually enter information such as information relating to various life activities of the user as described herein or information relating to the operation and/or control of stand alone sensor device 700, for example, the setting of reminders or alerts as described herein. In this example, activation of button 470 may simply record or time stamp that an event such as a meal has occurred, with the wearer needing to assign a meaning to that time stamp through data entry at a later time. Alternatively, activation of button 470 in certain sequences, such as one activation, two successive activations, three successive activations, etc., can be preset to have different specific meanings. A wearer would need to follow a menu or guide of such preset activation sequences to input relevant data. Alternatively, stand alone sensor device 700 may include a more sophisticated means for manual entry of information such as a keypad, a touch screen, a microphone, or a remote control device, for example a remote control device incorporated into a wristwatch. In the case of a microphone, the processor of stand alone sensor device 700 would be provided with well known voice recognition software or the like for converting the input speech into usable data.

As indicated by reference numbers 720 and 725, information comprising data indicative of various physiological and/or contextual parameters and data derived therefrom may be input into stand alone sensor device 700 through interaction with other devices. In addition, information such as handshake data or data indicative of various physiological and/or contextual parameters and data derived therefrom may be output from stand alone sensor device 700 to such other devices. According to one embodiment, the interaction is in the form of wireless communication between stand alone sensor device 700 and another device capable of wireless communication by way of a wireless transceiver provided in stand alone sensor device 700, such as wireless transceiver 565 shown and described in connection with FIG. 20. The device-to-device interaction may, as shown by reference number 720, be explicit, meaning that the user of stand alone sensor device 700 has knowingly initiated the interaction. For example, a user may activate a button on a scale to upload data to stand alone sensor device 700. The device-to-device interaction may also, as shown by reference number 725, be hidden, meaning that the user of stand alone sensor device 700 does not knowingly initiate the interaction. For example, a gym may have a sensor that wirelessly transmits a signal to sensing device 700 when the user enters and leaves the gym to time stamp when the user began and ended a workout.

As shown schematically in FIG. 21, information may be output or transmitted from stand alone sensor device 700 in a number of ways. Such information may include the data indicative of various physiological parameters and/or contextual parameters, the data derived therefrom, the data manually input by the user, the analytical status data, or any combination thereof. As shown by reference numbers 730, 735 and 740, information may be output or transmitted in an audible fashion such as by a series of tones or beeps or a recorded voice by a device such as a speaker, in a visual fashion such as by one or more LEDs, or in a tactile fashion such as by vibration. For example, stand alone sensor device 700 may be adapted to output a tone or tones, light an LED or LEDs, or vibrate as a reminder for an event, such as a reminder to eat or exercise at a particular time, or when a goal has been reached, such as a target number of calories burned during a workout, or a condition has been sensed, such as ovulation. Alternatively, stand alone sensor device 700 may be provided with a more sophisticated visual output means such as an LCD similar to those found on commercially available cell phones, pagers and personal digital assistants. With an LCD or a similar device and the expanded visual output capabilities it would provide, stand alone sensor device 700 may be adapted to output or transmit some or all of the information described in connection with FIGS. 5 through 11 in the same or a similar format. For example, stand alone sensor device 700 could provide analytical status data in the form of the Health Index to the user. As a further alternative, stand alone sensor device 700 may be coupled to computing device 750 such as a personal computer, a cell phone, a pager, a personal digital assistant, another stand alone sensor device 700 or any other device having a processor by either wired connection 755 or wireless connection 760. For example, battery recharger unit 480 shown in FIG. 19 may be used to provide the wired connection 755 or wireless connection 760. In this configuration, the display of the computing device could be used to visually output information from stand alone sensor device 700. It will be appreciated that since computing device 750 includes a sophisticated output means such as an LCD, it may be used to output or transmit to the user some or all of the information described in connection with FIGS. 5 through 11, such as the Health Index, in the same or a similar format.

Also, computing device 750 may in turn be used to control other devices, such as the lights or thermostat in a home, based on data output by stand alone sensor device 700, such as the fact that the wearer has fallen asleep or the fact that the wearer's skin temperature has reached a certain level. In other words, stand alone sensor device 700, and in particular its processor, may be adapted to cause a computing device 750 to trigger an event upon detection of one or more physiological and/or contextual conditions by stand alone sensor device 700. Alternatively, stand alone sensor device 700 may be adapted to cause a computing device 750 to trigger an event based upon information received from another computing device 750.

Stand alone sensor device 700 may be adapted to interact with and influence an interactive electronic media device, such as a video game, or non-interactive electronic media device, such as on a display device such as a DVD or digital video disc player playing a digitally recorded movie. For example, stand alone sensor device 700 may be adapted to transmit information relating to the physiological state of the wearer to the video game, which in turn adjusts the characteristics of the game, such as the level of difficulty. As another example, stand alone sensor device 700 may be adapted to transmit information relating to the physiological state of the wearer to the device displaying the digitally recorded movie which in turn adjusts the characteristics, such as the outcome, of the movie.

Furthermore, stand alone sensor device 700 may include location sensing device 765, such as an ultrasonic or a radio-frequency identification tag, for enabling a computing device 750 to detect the geographic location of stand alone sensor device 700, such as the location of stand alone sensor device 700 within a defined space such as a building. In one embodiment, a location indication causes computing device 750 to trigger an event, such as lowering the temperature in a room corresponding to the indicated location, preferably based on the detection by stand alone sensor device 700 of one or more physiological conditions of the wearer, such as skin temperature. In another embodiment, the location indication causes computing device 750 to trigger an event, such as lowering the temperature in a room corresponding to the indicated location, if stand alone sensor device 700 detects one or more physiological conditions, such as a skin temperature of the wearer being above a certain level. In addition, the input means of the computing device, such as the mouse and keyboard of a personal computer, the keypad of a cell phone or pager, or the touch screen of a personal digital assistant, may be used to manually input information into stand alone sensor device 700.

The different modes of output may be used in combination to provide different types and levels of information to a user. For example, stand alone sensor device 700 could be worn by an individual while exercising and an LED or a tone can be used to signal that a goal of a certain number of calories burned has been reached. The user could then transmit additional data wirelessly from stand alone sensor device 700 to a computing device 750 such as a cell phone after he or she is finished exercising to view data such as heart rate and/or respiration rate over time.

As a further alternative embodiment of the present invention, rather than the processor provided in stand alone sensor device 700 being programmed and/or otherwise adapted to generate the derived data and to include the utilities and algorithms necessary to create analytical status data, computing device 750 could be so programmed. In this embodiment, stand alone sensor device 700 collects and/or generates the data indicative of various physiological and/or contextual parameters of the user, the data manually input by the user, and/or data input as a result of device-to-device interaction shown at 720 and 725, all of which is stored in the memory provided in stand alone sensor device 700. This data is then periodically uploaded to computing device 750 which in turn generates derived data and/or analytical status data. Alternatively, the processor of stand alone sensor device 700 could be programmed to generate the derived data with computing device 750 being programmed and/or otherwise adapted to include the utilities and algorithms necessary to create analytical status data based on data indicative of one or more physiological and/or contextual parameters, data derived therefrom, data manually input by the user and/or data input as a result of device-to-device interaction shown at 720 and 725 uploaded from stand alone sensor device 700. As still a further alternative, the processor of stand alone sensor device 700 could be programmed and/or otherwise adapted to include the utilities and algorithms necessary to create analytical status data based on data indicative of one or more physiological and/or contextual parameters, data derived therefrom, data manually input by the user and/or data input as a result of device-to-device interaction shown at 720 and 725 uploaded from stand alone sensor device 700 with computing device 750 being programmed to generate the derived data. In either alternative, any or all of the data indicative of physiological and/or contextual parameters of the user, the data derived therefrom, the data manually input by the user, the data input as a result of device-to-device interaction shown at 720 and 725 and the analytical status data may then be viewed by the user using the output means of the programmed computing device 750 or another computing device 750 to which the data is downloaded. In the latter alternative, everything but the analytical status data may also be output by stand alone sensor device 700 as described herein.

Computing device 750 in these alternative embodiments may be connected to an electronic network, such as the Internet, to enable it to communicate with central monitoring unit 30 or the like. The programming of computing device 750 that enables it to generate the derived data and/or the analytical status data may, with such a configuration, be modified or replaced by downloading the relevant data to computing device 750 over the electronic network.

As still a further alternative embodiment, computing device 750 may be provided with a custom written plug-in adapted to provide data display functionality through use of a well known browser program. In this embodiment, stand alone sensor device 700 collects and/or generates the data indicative of various physiological and/or contextual parameters of the user, the derived data, the data input by the user, data input as a result of device-to-device interaction shown at 720 and 725, and/or analytical status data based thereon and uploads this data to computing device 750. The plug-in provided in computing device 750 then generates appropriate display pages based on the data which may be viewed by the user using the browser provided with computing device 750. The plug-in may be modified/updated from a source such as central monitoring unit 30 over an electronic network such as the Internet.

Referring to FIGS. 22–26, an alternate embodiment of a sensor device is shown at 800. Sensor device 800 may be a specific embodiment of either sensor device 10 described in connection with FIGS. 1–11 or stand alone sensor device 700 described in connection with FIG. 21. Sensor device 800 includes housing 805 affixed to flexible section 810, which is similar to flexible wing body 410 shown in FIGS. 12–17. Flexible section 810 is adapted to engage, such as by wrapping around or conforming to, at least a portion of the human body, such as the upper arm, to enable sensor device 800, in combination with a removable strap 811 inserted through slots 812 provided in flexible section 810, to be worn on the body. Preferably, flexible section 810 is made of a material having a durometer of between 75 and 85 Shore A. Flexible section 810 may take on a variety of shapes and may be made of a cloth material, a flexible plastic film, or an elastic material having an adhesive similar in structure to a Band-Aid® disposable adhesive bandage. In the embodiment shown in FIGS. 22–26, housing 805 is permanently affixed to flexible section 810, such as by an over molding or co-molding process, through the use of an adhesive material, or by a fastening mechanism such as one or more screws. Housing 805 includes top portion 815 affixed to bottom portion 820 by any known means, including, for example, an adhesive material, screws, snap fittings, sonic welding, or thermal welding. According to a preferred embodiment, a watertight seal is provided between top portion 815 and bottom portion 820. Such a water-tight seal is provided when sonic welding or thermal welding is used. Alternatively, an O-ring could be provided between top portion 815 and bottom portion 820 to create the water-tight seal.

As can be seen most readily in FIGS. 23, 24 and 26, affixed to bottom portion 820 of housing 805 are GSR sensors 825. GSR sensors 825 measure the conductivity of the skin between two points and may comprise electrodes formed of a material such as stainless steel, gold or a conductive carbonized rubber. Preferably, GSR sensors 825 have an oblong, curved shape as shown in FIG. 23, much like a kidney bean shape, that allows some portion of GSR sensors 825 to maintain contact with the body even if sensor device 800 is rocking or otherwise moving while being worn. Most preferably, GSR sensors 825 include raised bumps 830, or some other three-dimensional textured surface, along the surface thereof to perturb the skin and push between hairs to ensure good contact with the skin. In addition, raised bumps 830 provide channels for the movement of sweat underneath sensor device 800, rather than trapping sweat, no matter the orientation of sensor device with respect to the body. Also affixed to bottom portion 820 are heat flux skin interface component 835 and skin temperature skin interface component 840, each comprising a plate made of a thermally conductive material such as stainless steel. Preferably, heat flux skin interface component 835 and skin temperature skin interface component 840 are made of a material having thermal conduction properties of at least 12.9 W/mK, such as 304 stainless steel. Preferably, GSR sensors 825 are spaced at least 0.44 inches apart from one another, and at least 0.09 inches apart from heat flux skin interface component 835 and skin temperature skin interface component 840. GSR sensors 825, heat flux skin interface component 835 and skin temperature skin interface component 840 are adapted to be in contact with the wearer's skin when sensor device 800 is worn, and facilitate the measurement of GSR, heat flux from the body and skin temperature data. As can be seen most readily in FIGS. 22, 24 and 26, affixed to top portion 815 of housing 805 are heat flux ambient interface component 845 and ambient temperature interface component 850, which also are made of a thermally conductive material such as stainless steel, preferably a material having thermal conduction properties of at least 12.9 W/mK, such as 304 stainless steel. Heat flux ambient interface component 845 and ambient temperature interface component 850 facilitate the measurement of heat flux from the body and ambient temperature, respectively, by providing a thermal interface to the surrounding environment. To further enhance the measurement of these parameters, holes 855 are provided in flexible section 810 to expose heat flux ambient interface component 845 and ambient temperature interface component 850 to the ambient air. Preferably, holes 855 are sized so that flexible section 810 occludes as little skin as possible in the regions surrounding heat flux ambient interface component 845 and ambient temperature interface component 850 so as to allow air flowing off of the skin of the wearer to pass these components.

GSR Sensors 825, heat flux, skin interface component 835, skin temperature skin interface component 840, or any other sensing component that comes into contact with the skin may be provided with a plurality of microneedles for, among other things, enhancing electrical contact with the skin and providing real time access to interstitial fluid in and below the epidermis, which access may be used to measure various parameters such as pH level of the skin through electrochemical, impedance based or other well known methods. Microneedles enhance electrical contact by penetrating the stratum corneum of the skin to reach the epidermis. Such microneedles are well known in the art and may be made of a metal or plastic material. Prior art microneedles are described in, for example, U.S. Pat. No. 6,312,612 owned by the Procter and Gamble Company. Based on the particular application, the number, density, length, width at the point or base, distribution and spacing of the microneedles will vary.

Referring to FIG. 26, which is a cross-section taken along lines A—A in FIG. 22, the internal components of sensor device 800, housed within housing 805, are shown. Printed circuit board or PCB 860 is affixed to top portion 815 of housing 805 and receives and supports the electronic components provided inside housing 805. Affixed to a bottom side of PCB 860 and electronically coupled to GSR sensors 825 are contacts 865, which preferably comprise gold plated contact pins such as the Pogo® contacts available from Everett Charles Technologies in Pomona, Calif. Also affixed to the bottom side of PCB 860 is skin temperature thermistor 870, a suitable example of which is the model 100K6D280 thermistor manufactured by BetaTherm Corporation in Shrewsbury, Mass. Skin temperature thermistor 870 is, according to a preferred embodiment, thermally coupled to skin temperature skin interface component 840 by a thermally conductive interface material 875. Thermally conductive interface material 875 may be any type of thermally conductive interface known in the art, including, for example, thermally conductive gap fillers, thermally conductive phase change interface materials, thermally conductive tapes, thermally conductive cure-in-place compounds or epoxies, and thermal greases. Suitable thermally conductive interface materials include a boron nitride filled expanded polytetrafluoroethylene matrix sold under the trademark PolarChip CP8000 by W. L. Gore & Associates, Inc. and a boron nitride and alumina filled silicone elastomer on an adhesive backed 5 mil. (0.013 cm) thick aluminum foil carrier called A574, which is available from the Chomerics division of Parker Hannefin Corp. located in Woburn, Mass. Provided on top of PCB 860 is near-body ambient temperature thermistor 880, a suitable example of which is the model NTHS040ZN0IN100KJ thermistor manufactured by Vishay Intertechnology, Inc. in Malvern, Pa. Near-body ambient temperature thermistor 880 is thermally coupled to ambient temperature interface component 850 by thermally conductive interface material 875.

Still referring to FIG. 26, a preferred embodiment of sensor device 800 includes a particular embodiment of an apparatus for measuring heat flux between a living body and the ambient environment described in U.S. Pat. No. 6,595,929 B2 owned by the assignee hereof, the disclosure of which is incorporated herein by reference in its entirety. Specifically, heat conduit 885 is provided within housing 805. As used herein, the term heat conduit refers to one or more heat conductors which are adapted to singly or jointly transfer heat from one location to another, such as a conductor made of stainless steel. Heat conduit 885 is thermally coupled to heat flux skin interface component 835 by thermally conductive interface material 875. Provided on the bottom side of PCB 860 is a first heat flux thermistor 890A, and provided on the top side of PCB 860 is a second heat flux thermistor 890B. PCB 860 acts as a base member for supporting these components. It will be appreciated that a base member separate and apart from PCB 860 may be substituted therefor as an alternative configuration. A suitable example of both heat flux thermistors 890A and 890B is the model 100K6D280 thermistor manufactured by Beta Therm Corporation in Shrewsbury, Mass. Heat flux Thermistor 890A and 890B are soldered to pads provided on PCB 860. The second heat flux thermistor 890B is thermally coupled to heat flux ambient interface 845 by thermally conductive interface material 875. As is well-known in the art, PCB 860 is made of a rigid or flexible material, such as a fiberglass, having a preselected, known thermal resistance or resistivity K. The heat flux off of the body of the wearer can be determined by measuring a first voltage V1 with heat flux thermistor 890A and a second voltage V2 with heat flux thermistor 890B. These voltages are then electrically differenced, such as by using a differential amplifier, to provide a voltage value that, as is well known in the art, can be used to calculate the temperature difference (T2−T1) between the top and bottom sides of PCB 860. Heat flux can then be calculated according to the following formula:

Heat Flux=$K(T2-T1)$

The combination of PCB 860 and heat flux thermistors 890A and 890B are thus a form of a heat flux sensor. One advantage of the configuration of the apparatus for measuring heat flux shown in FIG. 26 is that, due to the vertical orientation of the components, assembly of the apparatus for measuring heat flux, and thus sensor device 800 as a whole, is simplified. Also adding to the simplicity is the fact that thermally conductive interface materials that include a thin adhesive layer on one or both sides may be used for thermally conductive interface materials 875, enabling components to be adhered to one another. In addition, thermistors 890A and 890B are relatively inexpensive components, as compared to an integral heat flux sensor such as those commercially available from RdF Corporation of Hudson, N.H., thereby reducing the cost of sensor device 800. Although heat flux thermistors 890A and 890B are described as being provided on PCB 860 in the embodiment shown in FIG. 26, it will be appreciated that any piece of material having a known resistivity K may be used. Furthermore, other temperature measuring devices known in the art, such as a thermocouple or thermopile, may be substituted for heat flux thermistors 890A and 890B. As a further alternative, heat conduit 885 may be omitted such that thermal communication between heat flux thermistor 890A and heat flux skin interface component 835 is provided by one or more pieces of thermally conductive interface material 875. As still a further alternative, heat flux skin interface component 835 may be omitted such that thermal communication between heat flux thermistor 890A and the skin is provided by either or both of heat conduit 885 and one or more pieces of thermally conductive interface material 875. In any of the embodiments described herein, the combination of one or more of heat conduit 885, one or more pieces of thermally conductive interface material 875, and heat flux skin interface component 835 act as a thermal energy communicator for placing heat flux thermistor 890A in thermal communication with the body of the wearer of sensor device 800.

FIG. 27 is a schematic diagram that shows an embodiment of the system architecture of sensor device 800, and in particular each of the components that is either provided on or coupled to PCB 860.

As shown in FIG. 27, PCB 860 includes processing unit 900, which may be a microprocessor, a microcontroller, or any other processing device that can be adapted to perform the functionality described herein, in particular the functionality described in connection with microprocessor 20 shown in FIG. 2, processing unit 490 shown in FIG. 20, or stand alone sensor device 700 shown in FIG. 21. A suitable example of processing unit 900 is the Dragonball EZ sold by Motorola, Inc. of Schaumburg, Ill. Also provided on PCB 860 is accelerometer 905, which may be either a two-axis or a three-axis accelerometer. A suitable example of a two-axis accelerometer is the Model ADXL202 accelerometer sold by Analog Devices, Inc. of Norwood, Mass., and a suitable example of a three-axis accelerometer is the model ACH-04-08-05 accelerator sold by Measurement Specialties Incorporated in Norristown, Pa. The output signals of accelerometer 905 are passed through buffers 910 and input analog to digital, referred to as A/D, converter 915 that in turn is coupled to processing unit 900. GSR sensors 825 are coupled to A/D converter 915 through current loop 920, low pass filter 925, and amplifier 930. Current loop 920 comprises an opamp and a plurality of resistors, and applies a small, fixed current between the two GSR sensors 825 and measures the voltage across them. The measured voltage is directly proportional to the resistance of the skin in contact with the electrodes. Similarly, heat flux thermistors 890A and 890B are coupled to A/D converter 915 and processing unit 900, where the heat flux calculations are performed, through low pass filter 935 and amplifier 940.

Battery monitor 945, preferably comprising a voltage divider with low pass filter to provide average battery voltage, monitors the remaining power level of rechargeable battery 950. Rechargeable battery 950 is preferably a LiIon/LiPolymer 3.7 V Cell. Rechargeable battery 950, which is the main power source for sensor device 800, is coupled to processing unit 900 through voltage regulator 955. Rechargeable battery 950 may be recharged either using recharger 960 or USB cable 965, both of which may be coupled to sensor device 800 through USB interface 970. Preferably, USB interface 970 is hermetically sealable, such as with a removable plastic or rubber plug, to protect the contacts of USB interface 970 when not in use.

PCB 860 further includes skin temperature thermistor 870 for sensing the temperature of the skin of the wearer of sensor device 800, and near-body ambient temperature thermistor 880 for sensing the ambient temperature in the area near the body of the wearer of sensor device 800. Each of these components is biased and coupled to processing unit 900 through A/D converter 915.

According to a specific embodiment of sensor device 800, PCB 860 may include one or both of an ambient light sensor and an ambient sound sensor, shown at 975 in FIG. 27, coupled to A/D converter 915. The ambient light sensor and ambient sound sensor may be adapted to merely sense the presence or absence of ambient light or sound, the state where a threshold ambient light or sound level has been exceeded, or a reading reflecting the actual level of ambient light or sound. A suitable example of an ambient sound sensor is the WM-60A Condenser Microphone Cartridge sold by Matsushita Electric Corporation of America located in Secaucus, N.J., and suitable examples of an ambient light sensor are the Optek OPR5500 phototransistor and the Optek OPR5910 photodiode sold by Optek Technology, Inc. located in Carrollton, Tex. In addition, PCB 860 may include ECG sensor 980, including two or more electrodes, for measuring the heart rate of the wearer, and impedance sensor 985, also including a plurality of electrodes, for measuring the impedance of the skin of the wearer. Impedance sensor 985 may also be an EMG sensor which gives an indication of the muscular activity of the wearer. The electrodes forming part of ECG sensor 980 or impedance sensor 985 may be dedicated electrodes for such sensors, or may be the electrodes from GSR sensors 825 multiplexed for appropriate measurements. ECG sensor 980 and impedance sensor 985 are each coupled to A/D converter 915.

PCB 860 further includes RF transceiver 990, coupled to processing unit 900, and antenna 995 for wirelessly transmitting and receiving data to and from wireless devices in proximity to sensor device 800. RF transceiver 990 and antenna 995 may be used for transmitting and receiving data to and from a device such as a treadmill being used by a wearer of sensor device 800 or a heart rate monitor worn by the wearer of sensor device 800, or to upload and download data to and from a computing device such as a PDA or a PC. In addition, RF transceiver 990 and antenna 995 may be used to transmit information to a feedback device such as a bone conductivity microphone worn by a fireman to let the fireman know if a condition that may threaten the fireman's safety, such as hydration level or fatigue level, has been sensed by sensor device 800. As described in detail in connection with FIG. 21, stand alone sensor device 700 may be coupled to computing device 750 to enable data to be communicated therebetween. Thus, as a further alternative, RF transceiver 990 and antenna 995 may be used to couple sensor device 800 to a computing device such as computing device 750 shown in FIG. 21. Such a configuration would enable sensor device 800 to transmit data to and receive data from the computing device 750, for example a computing device worn on the wrist. The computing device could be used to enable a user to input data, which may then be stored therein or transmitted to sensor device 800, and to display data, including data transmitted from sensor device 800. The configuration would also allow for computing tasks to be divided between sensor device 800 and computing device 750, referred to herein as shared computing, as described in detail in connection with FIG. 21.

As shown in FIG. 27, PCB 860 may include proximity sensor 1000 which is coupled to processing unit 900 for sensing whether sensor device 800 is being worn on the body. Proximity sensor 1000 may also be used as a way to automatically power on and off sensor device 800. Proximity sensor 1000 preferably comprises a capacitor, the electrical capacitance of which changes as sensor device 800 gets closer to the body. PCB 860 may also include sound transducer 1005, such as a ringer, coupled to processing unit 900 through driver 1010.

Sensor device 800 may also be provided with sensors in addition to those shown in FIG. 27, such as those taught by U.S. Pat. No. 5,853,005, the disclosure of which is incorporated herein by reference. The '005 patent teaches a sound transducer coupled to a pad containing an acoustic transmission material. The pad and sound transducer may be used to sense acoustic signals generated by the body which in turn may be converted into signals representative of physiological parameters such as heart rate or respiration rate. In addition, rather than being integrated in sensor device 800 as part of one or more of housing 805, flexible section 810 or strap 811, a sensing apparatus as taught by the '005 patent may be provided separate from sensor device 800 and be coupled, wired or wirelessly, to sensor device 800. According to the '005 patent, the sound or acoustic transducer is preferably a piezoelectric, electret, or condenser-based hydrophone, similar to those used by the Navy in sonar applications, but can be any other type of waterproof pressure and motion sensing type of sensor.

The sensing apparatus as taught by the '005 patent is an example of what shall be referred to herein as a non-ECG heart parameter sensor, meaning that it has the following two qualities: (1) it does not need to make measurements across the torso using at least two contacts separated by some distance; and (2) it does not measure electrical activity of the heart. The sensing apparatus as taught by the '005 patent has been shown to be capable of detecting heart rate information and information relating to individual beats of the heart with high reliability under certain circumstances, depending primarily on factors including the proximity of the apparatus to the heart, the level of ambient noise, and motion related sound artifacts caused by the movement of the body. As a result, the sensing apparatus as taught by the '005 patent is most reliable when worn in an ambient environment with a low level of ambient noise and when the body is not moving.

Certain characteristics, sensors and sensing capabilities of sensor device 800 are able to improve the reliability and accuracy of an acoustic-based non-ECG heart parameter sensor 1012 such as the sensing apparatus as taught by the '005 patent that is incorporated therein or coupled thereto. For example, in one specific embodiment, sensor device 800 is particularly suited to be worn on the upper arm. The upper arm is a good location for a sensor device 800 having an acoustic-based non-ECG heart parameter sensor 1012 incorporated therein because it is near the heart and provides a space for sensor device 800 that allows it to be unobtrusive and comfortable to wear. In addition, ambient sound sensor shown at 975 in FIG. 27 may be used to filter out ambient noise from the signals detected by the acoustic-based non-ECG heart parameter sensor 1012 in order to isolate the sound signal originating from the body. Filtering of the signal produced by an acoustic-based non-ECG heart parameter sensor 1012 such as the sensing apparatus as taught by the '005 patent in this manner may be used both in the case where such an apparatus is incorporated in sensor device 800 and in the case where it is separated from but coupled to sensor device 800 as described above. Furthermore, the sound generated from the motion of the body that is not created by the heart can be accounted for and adjusted for through the use of a sensor or sensors that detect or that may be used to identify body sounds generated as a result of motion of the body, such as accelerometer 905 shown in FIGS. 27 and 29 or the body position or muscle pressure sensors identified in Table 1. For example, footfalls create sound within the body that can lower the signal to noise ratio of an acoustic-based non-ECG heart parameter sensor 1012, which will likely result in false positive and false negative heart beat identifications. As is well known in the art, accelerometer 905 may function as a footfall indicator. Accelerometer 905 may thus be used to filter or subtract out from the signal detected by the acoustic-based non-ECG heart parameter sensor 1012 signals related sound motion artifacts caused by the movement of the body such as by footfalls.

Several methodologies for performing the filtering or subtracting of signals described herein are known to those of ordinary skill in the art. Such filtering or subtracting of signals used in connection with the monitoring of disparate signals, some used for noise cancellation and some used for their direct measure, is also known as data integration.

Sensor device 800 may also be used to put parameters around and provide a context for the readings made by a non-ECG heart parameter sensor 1012 so that inaccurate readings can be identified and compensated for. For example, sensor device 800 may be used to detect real time energy expenditure of the wearer as well as the type of activity in which the wearer is engaging, such as running or riding a bike. Thus, as another example of how the sensors and sensing capabilities of sensor device 800 may be used to increase the reliability and accuracy of a non-ECG heart parameter sensor 1012 through data integration, the energy expenditure and activity type information can be used to provide a context in which the heart related parameters detected by the non-ECG heart parameter sensor 1012 can be assessed and possibly filtered. For example, if sensor device 800 detects that a person is burning 13 calories per minute and is biking, and the non-ECG heart parameter sensor 1012 is indicating that the wearer's heart rate is 60 beats per minute, then it is highly likely that further filtration of the signal from the non-ECG heart parameter sensor 1012 is necessary.

Other well known non-ECG heart parameter sensing devices include, for example, those based on micro-power impulse radar technology, those based on the use of piezoelectric based strain gauges, and those based on plethysmography, which involves the measurement of changes in the size of a body part as modified by the circulation of blood in that part. It will be appreciated that the performance of these devices may also be enhanced through the use of data integration as described herein.

Another sensor that may be incorporated into the sensor device 800 measures the pressure with which sensor device 800 is held against the body of the wearer. Such a sensor could be capacitive or resistive in nature. One such instantiation places a piezo-resistive strain gauge on the back of the enclosure to measure the small deflection of the plastic as increasing force is applied. Data gathered from such a sensor can be used to compensate the readings of other sensors in sensor device 800 according to the readings of such a sensor.

Also provided on PCB 860 and coupled to processing unit 900 is switch 1015. Switch 1015 is also coupled to button 1020 provided on housing 805. Button 1020, by activating switch 1015, may be used to enter information into sensor device 800, such as a time stamp to mark the occurrence of an event such as taking medication. Preferably, button 1020 has a tactile, positive detent feedback when depressed, and a concave shape to prevent accidental depression. Also, in the embodiment shown in FIGS. 22-26, flexible section 810 includes membrane 1022 that covers and seals button 1020. In the embodiments shown in FIGS. 30-32, a similar membrane 1022 may be provided on flexible section 810, and, preferably, also on housing 805 such that button 1020 is sealed when housing 805 is removed from flexible section 810. Alternatively, a hole may be provided in flexible section 810 exposing button 1020 and membrane 1022 when housing 805 is attached to flexible section 810. In addition, coupled to processing unit 900 on PCB 860 are LCDs and/or LEDs 1025 for outputting information to the wearer. FIG. 28 shows an alternate embodiment of sensor device 800 in which LCD 1025 is provided on a top face of housing 1.

As an alternative to LCDs or LEDs 1025, sensor device 800 may include a prior art electrochemical display that retains its ability to display information even when power is no longer being provided thereto. Such a display is described in U.S. Pat. No. 6,368,287 B1, the disclosure of which is incorporated herein by reference, and includes a plurality of markers comprising a miniature heating element and a coating of heat sensitive material. When current is passed through one of the heating elements, it heats up, thereby inducing a change in the color of the coating material. The color change is permanent, even after the heating element cools down. Such displays are relatively inexpensive and thus are well adapted for use in embodiments of sensor device 800 that are designed to be disposable, possibly single use, items.

Oscillator 1030 is provided on PCB 860 and supplies the system clock to processing unit 900. Reset circuit 1035 is coupled to processing unit 900 and enables processing unit 900 to be reset to a standard initial setting.

Finally, non-volatile data storage device 1040, such as a FLASH memory chip, is provided for storing information collected and/or generated by sensor device 800. Preferably, data storage device 1040 includes at least 128K of memory. Non-volatile program storage device 1045, such as a FLASH ROM chip, is provided for storing the programs required to operate sensor device 800.

As an alternative, a microprocessor with integral A/D converters, data storage, and program storage may be substituted for processing unit 900, A/D converter 915, data storage device 1040 and non-volatile memory 1045. A suitable example of such a microprocessor is the Texas Instruments Model MSP430 processor.

Any component forming a part of sensor device 800 that comes in contact with the wearer's skin should not, in a preferred embodiment, degrade in durometer, elasticity, color or other physical or chemical properties when exposed to skin oils, perspiration, deodorant, suntan oils or lotions, skin moisturizers, perfume or isopropyl alcohol. In addition, such components preferably are hypoallergenic.

FIG. 29 shows an alternate embodiment of PCB 860 in which rechargeable battery 950, voltage regulator 955, recharger 960 and USB cable 965 have been replaced by disposable AAA battery 1050 and boost converter 1055. Boost converter 1055 uses an inductor to boost the voltage of AAA battery 1050 to the 3.0–3.3 V required to run the electronics on PCB 860. A suitable boost converter 1055 is the model MAX1724 sold by Maxim Integrated Products, Inc. of Sunnydale, Calif.

Referring to FIGS. 30 and 31, an alternate embodiment of sensor device 800 is shown in which housing 805 is removably attached to flexible section 810. As shown in FIGS. 30 and 31, housing 805 is provided with groove 1060 along the outer edge thereof which is adapted to receive therein tongue 1065 provided on the bottom side of flexible section 810 for securely but removably attaching housing 805 to flexible section 810. Through the interaction of groove 1060 and tongue 1065, housing 805 may thus be readily popped in and out of flexible section 810. Such a configuration enables housing 805 to be readily attached to multiple flexible sections having sizes and shapes that are different than flexible section 810 as long as the flexible section includes a tongue similar to tongue 1065. Such alternate flexible sections may be sized and shaped to fit on particular parts of the body, such as the calf or thigh, and may comprise a garment such as a shirt having the tongue or tongues located in places of interest, such as the upper arm or upper left chest, the latter enabling housing 805 to be positioned over the heart of the wearer, as shown in FIGS. 40A and 40B. U.S. Pat. No. 6,527,711, owned by the assignee of the present application and incorporated herein by reference, identifies several locations on the body that are particularly well adapted to receive particularly sized and shaped sensor devices so as to avoid interference with the motion and flexibility of the body. As will be appreciated by those of skill in the art, groove 1060 and tongue 1065 may be swapped such that groove 1060 is provided in flexible section 810 and tongue 1065 is provided on housing 805. As will also be appreciated by those of skill in the art, multiple alternative structures exist for securely but removably attaching housing 805 to flexible section 810. These alternative structures include, without limitation, temporary adhesives, screws, a tight fit between housing 805 and flexible section 810 that holds the two together by friction, magnets provided in each of housing 805 and flexible section 810, well-known snaps and snapping mechanisms, a threaded portion provided on housing 805 adapted to be received by threads in flexible section 810, an O-ring or similar elastic band adapted to fit around a portion of flexible section 810 and into a groove provided in housing 805 when flexible section 810 is placed over housing 805, or merely pressure when housing 805 is placed on the body and flexible section 810 is placed thereover and attached to the body such as by strap 811. Referring to FIG. 32, a still further alternative structure for removably securing flexible section 810 to housing 805 is shown in which flexible section 810 comprises an elastic or similar band that is adapted to fit into a groove 1062 provided in housing 805. Housing 805 and flexible section 810 may then be placed on the body and held in place by strap 811 or the like inserted through gaps 1064 between housing 805 and flexible section 810.

FIG. 33 shows an alternate embodiment of sensor device 800 as shown in FIGS. 30 and 31 that is adapted to automatically adjust or alter the operating parameters of sensor device 800, such as its functionality, settings or capabilities, depending on the particular flexible section to which housing 805 is attached. For example, the calculation of a parameter, such as energy expenditure, may depend on information that is particular each individual, such as age, height, weight, and sex. Rather than having each individual enter that information in sensor device 800 each time he or she wants to wear the device 800, each individual that is going to wear the device could enter the information once and have their own flexible section that causes sensor device 800 to make measurements based on his or her particular information. Alternatively, the memory in sensor device 800 for storage of user data may be divided into several compartments, one for each user, so as to avoid co-mingling of user data. Sensor device 800 may be adapted to alter where collected data is stored depending on the particular flexible section that is being used. In addition, sensor device 800 may be calibrated and recalibrated differently over time depending on the particular flexible section to which housing 805 is attached as it learns about each particular wearer and his or her habits, demographics and/or activities.

According to a particular embodiment, housing 805 is provided with first magnetic switch 1070 and second magnetic switch 1075, each on PCB 860. Provided on or inside flexible section 810, such as by an insert molding technique, is magnet 1080. Magnet 1080 is positioned on or inside flexible section 810 such that it aligns with and thereby activates one of first magnetic switch 1080 and second magnetic switch 1075 when housing 805 is attached to flexible section 810. In the embodiment shown in FIG. 33, second magnetic switch 1075 will be activated. A second flexible section 810 similar to flexible section 810 shown in FIG. 33 will also be provided, the difference being that the magnet 1080 provided therewith will be positioned such that first magnetic switch 1070 is activated when housing 805, the same housing 805 shown in FIG. 33, is attached to the second flexible section 810. Housing 805, and in particular processing unit 900, may be programmed to alter its functionality, settings or capabilities depending on which one of first magnetic switch 1070 and second magnetic switch 1075 is activated, i.e., which particular flexible section 810 is being used. Thus, a husband and wife may share a single housing 805 but have different flexible wings 810 with magnets 1080 located in different places. In such a case, housing 805 may be programmed to operate with functionality, settings or capabilities particular to the husband when first magnetic switch 1070 is activated, and with functionality, settings or capabilities particular to the wife when second magnetic switch 1075 is activated. Although only two magnetic switches are shown in FIG. 33, it will be appreciated that multiple magnetic switches and multiple flexible sections may be used to allow sensor device 800 to be programmed for multiple wearers, such as an entire family, with each family member having his or her own flexible section. As still a further alternative, multiple flexible sections may be provided that are adapted to be worn on different parts of the body, each having a magnet placed in a different location. Housing 805 may then be programmed to have functionality, settings or capabilities particular to the type of sensing to be done on each different part of the body, with magnetic switches placed so as to be activated when housing 805 is attached to the appropriate flexible section. Sensor device 800 according to this embodiment is thus a "smart" device. As will be appreciated by one of skill in the art, many alternatives to first and second magnetic switches 1070 and 1075 and magnet 1080 may be used to provide the functionality described in connection with FIG. 33. Such alternatives include, without limitation, mechanical switches provided in housing 805 that are activated by a protruding portion, such as a pin, provided at a particular location on flexible section 810, optical switches comprising an array of light sensors provided in housing 805 that are activated when the surrounding light is blocked, reflected or filtered in a particular way with one or more translucent sections and a single opaque, reflective or filtering section being selectively provided on flexible section 810 at particular locations, the translucent sections not activating the corresponding optical switches and the opaque, reflective or filtering section activating the corresponding optical switch, electronic switches provided in housing 805 activated by a conductor provided in particular locations in flexible section 810. As still a further alternative, housing 805 may be provided with multiple switches and each flexible section 810 may be provided with one or more switch activators positioned to activate certain selected switches. The operating parameters of housing 805 would in this embodiment be adapted to change depending upon the particular set of one or more switches that are activated. This embodiment thus employs an encoding scheme to alter the operating parameters of housing 805 depending on which flexible section 810 is used. As still a further alternative, housing 805 may be provided with a single switch adapted to alter the operating parameters of housing 805 depending upon the way in which or state in which it is activated, such as by the properties of the switch activators. For example, the switch may be a magnetic switch that is activated a plurality of different ways depending upon the magnetic level or strength of the magnet provided in each flexible section 810. A plurality of flexible sections 810 could then be provided, each having a magnet of a different strength. In addition, any particular flexible section 810 may be provided with a plurality of magnets having different strengths with each magnet being able to activate the switch in housing 805 in a different manner. Such a flexible section 810 would be able to selectively trigger different operating parameters of housing 805, such as by rotating a portion of flexible wing 805 to align a particular magnet with the switch. As an alternative, the switch could be an electrical switch and the switch activators could be conductors having different resistances. The switch would, in this embodiment, be activated in different ways depending on the measured resistance of the switch activator that closes the circuit.

Referring to FIG. 34, as still a further embodiment of sensor device 800, housing 805 may be provided with adhesive material 1085 on a back side thereof to enable housing 805 to be removably attached to selected portions of the body, such as the upper left chest over the heart, without flexible section 810. Adhesive material 1085 may be any well-known adhesive that would securely attach housing 805 to the body and enable it to be worn for a period of time, but that would also readily enable housing 805 to be removed from the body after use. Adhesive material 1085 may comprise, for example, a double sided adhesive foam backing that would allow for comfortable attachment of housing 805 to the body. Furthermore, housing 805 may be made of a well-known flexible plastic film or the like, such as that taught in U.S. Pat. No. 6,368,287 B1, the disclosure of which is incorporated herein by reference, that would, due to low cost, enable sensor device 800 to be disposable. Such a disposable sensor device may also include an electrochemical display described above to enhance its disposability. In an embodiment adapted for placement over the upper left chest or any other appropriate region for detecting heart related parameters, sensor device 800 would include one or more sensors described herein for sensing heart related parameters such as heart rate, beat-to-beat or interbeat variability, ECG or EKG, pulse oximetry, heart sounds, such as detected with a microphone, and mechanical action of the heart, such as detected with ultrasound or micro-pulse radar devices.

FIGS. 35A–H and 36A–H illustrate aspects of the present invention relating to the ergonomic design of sensor device 800. Referring to FIGS. 35A and 35B, a housing 1100 of a prior art sensor device having a rectangular cross-section is shown resting on the body 1110 of a wearer of the prior art sensor device. As seen in FIG. 35B, when body 1110 flexes and forms a concavity, as may happen many times each minute on various parts of the body or for extended periods of time depending on the position of various body parts during particular activities, a significant portion of housing 1100 is caused to be removed from body 1110. When housing 1100 is caused to be removed in this manner, the ability of the prior art sensor device to accurately make measurements and collect data will be jeopardized, especially for any readings to be taken near the center of the cross-section indicated by the arrows in FIG. 35B.

FIGS. 35C–H illustrate a cross-section of housing 805 of sensor device 800 taken along lines C—C shown in FIG. 23 according to various aspects of the present invention. The cross-section shown in FIGS. 35C–H is taken near the middle portion of housing 805 shown in FIG. 23 between GSR sensors 825. As seen in FIG. 35C, bottom surface 1115 of housing 805 is provided with a generally convex shape such that, when body 1110 flexes and forms a concavity, a substantial portion of bottom surface 1115 of housing 805 remains in contact with body 1110 by fitting into the concavity. As seen in FIG. 35D, when body 1110 flexes in the opposite direction so as to create a convexity, the center portion of housing 805, indicated by the arrow in FIG. 35D, remains in contact with body 1110. As shown in FIG. 35E, this is true even if housing 805 were to rock within the concavity formed in body 1110. Referring to FIG. 35F, body 1110 may, at times, flex to an extreme degree, i.e., more than the anticipated maximum that it was designed for, such that, even if bottom surface 1115 is provided with a convex shape, it may still cause bottom surface 1115 to be removed from body 1110. A solution to this problem is illustrated in FIG. 35G, wherein the lateral ends 1120A and 1120B of housing 805 are provided with radiused portions 1125A and 1125B, respectively adjacent to and including opposite lateral ends of bottom surface 1115. Radiused portions 1125A and 1125B enable housing 805 to sit lower and fit into the concavity created when body 1110 flexes to an extreme degree. In addition, radiused portions 1125A and 1125B provide for more comfortable wear as they eliminate sharp edges 1130A and 1130B shown in FIG. 35F that contact body 1110. FIG. 35H shows how body 1110 will tend to conform to the shape of housing 805 due at least in part to the viscosity of the skin when body 1110 is in a relaxed condition.

FIG. 36A shows a cross-section of housing 1100 of prior art sensor device taken along a line perpendicular to the line on which the cross-section shown in FIGS. 35A and 35B was taken. As seen in FIG. 36A, when housing 1100 is placed on a convex portion of body 1110, significant portions of housing 1100, specifically the lateral ends thereof indicated by the arrows in FIG. 36A, are not in contact with body 1110. FIGS. 36B–H show a cross-section of housing 805 according to various aspects of the present invention taken along lines D—D shown in FIG. 23. As seen in FIG. 36B, bottom surface 1115 of housing 805 is provided with a generally concave shape adapted to receive the convex portion of body 1110. Referring to FIG. 36C, lateral ends 1130A and 1130B may be provided with radiused portions 1135A and 1135B adjacent to and including opposite lateral ends of bottom surface 1115, which allow housing 805 to rest in closer contact with body 1110, even when body 1110 flexes to an extreme degree, i.e., more than the anticipated maximum that it was designed for, and remove sharp edges 1140A and 1140B shown in FIG. 36B, providing for more comfortable wear. As shown in FIG. 36D, body 1110 will tend to conform to the shape of housing 805 when body 1110 is in a relaxed condition. As shown in FIGS. 36E and 36F, good contact with body 1110 is maintained at the points illustrated by the arrows when body 1110 is flexed in a manner that decreases the convex shape thereof or that creates a convexity therein. Thus, it will be appreciated that it is advantageous to place sensors or sensing elements at the points indicated by the arrows because those points will tend to remain in contact with body 1110. FIGS. 36G and 36H, showing, for example, heat flux skin interface component 835 and skin temperature skin interface component 840 placed at the points indicated by the arrows, illustrate this point. As seen in FIGS. 36G and 36H, there is more than point contact between body 1110 and skin temperature skin interface component 840.

FIG. 37 is an isometric view of housing 805 according to an embodiment of the present invention in which bottom surface 1115 has both the generally convex shape shown in FIGS. 35C–H and the generally concave shape shown in FIGS. 36B–H. Specifically, bottom surface 1115, which is the inner surface of housing 805 for mounting adjacent to the body of the wearer, includes a longitudinal axis 1141 and a transverse axis 1142. Bottom surface 1115 has a generally concave shape having an axis of concavity 1143 that is coincident with longitudinal axis 1141, meaning that it runs in a first direction from first lateral end 1144 of inner surface 1115 to second lateral end 1145 of inner surface 1115. Bottom surface 1115 has a generally convex shape having an axis of convexity 1146 that is coincident with transverse axis 1142, meaning that it runs in a second direction from third lateral end 1147 of inner surface 1115 to fourth lateral end 1148 of inner surface 1115. As seen in FIG. 37, the first and second directions, and longitudinal axis 1141 and transverse axis 1142, are generally perpendicular to one another.

Referring to FIGS. 38A–D, it will be appreciated that housing 805 having a flat top surface 1150 and flat lateral ends 1130A and 1130B may tend to be jostled and bumped by object 1155, such as a wall or door or the corner or edge of a drawer, cabinet or desk, thereby moving housing 805 on body 1110 because such flat surfaces are not well adapted to deflect object 1155. Movement of housing 805 on body 1110 will detrimentally effect the ability of sensor device 800 to accurately make measurements and collect data. FIGS. 39A–G illustrate various aspects of the present invention that are adapted to deflect object 1155 and substantially prevent movement of housing 805 on body 1110. In addition, the forms shown in FIGS. 39A–G increase the durability of sensor device 800 and make it easier to put on and wear clothing and the like, such as a wetsuit, over sensor device 800. As seen in FIG. 39A, housing 805 may have tapered sides 1160A and 1160B such that the width of housing 805 decreases in the direction from bottom surface 1115 to top surface 1150. Alternatively, referring to FIG. 39B, top surface 1150 of housing 805 may have a convex shape. As a further alternative, as seen in FIG. 39C, housing 805 may be provided with radiused portions 1165A and 1165B that meet with radiused portions 1135A and 1135B such that the lateral ends of housing 805 have a substantially semicircular shape. As shown in FIG. 39D, housing 805 may have both tapered sides 1160A and 1160B and a top surface 1150 with a convex shape. FIG. 39E is a modification of housing 805 shown in FIG. 39E in which the points 1170A and 1170B where radiused portions 1135A and 1135B meet tapered sides 1160A and 1160B, respectively, are themselves radiused. FIG. 39F is a variation of housing 805 shown in FIG. 39E having elongated tapered sides 1160A and 1160B. FIG. 39G shows how the ability of housing 805, such as the embodiment shown in FIG. 39E, to deflect object 1155 may be enhanced by the addition of flexible section 810 having a substantially convex outer surface. In addition, an air channel is provided between flexible section 810 and body 1110 to allow for heat to flow away from body 1110.

The terms and expressions which have been employed herein are used as terms of description and not as limitation, and there is no intention in the use of such terms and expressions of excluding equivalents of the features shown and described or portions thereof, it being recognized that various modifications are possible within the scope of the invention claimed. Although particular embodiments of the present invention have been illustrated in the foregoing detailed description, it is to be further understood that the present invention is not to be limited to just the embodiments disclosed, but that they are capable of numerous rearrangements, modifications and substitutions.

What is claimed is:

1. An apparatus for detecting at least one of human physiological and contextual information from the body of a wearer, comprising:
    a flexible section for engaging at least a portion of said body;
    a housing removably attached to and supported by said flexible section;
    a strap attached to said flexible section for securing said flexible section to said body;
    one or more sensors supported by said housing, said one or more sensors selected from the group consisting of physiological sensors and contextual sensors; and
    a processing unit supported by said housing in electronic communication with said one or more sensors.

2. An apparatus according to claim 1, further comprising a groove provided said housing and a tongue provided on said flexible section, said groove being suitable to receive said tongue.

3. An apparatus according to claim 1, further comprising a tongue provided on said housing and a groove provided in said flexible section, said groove being suitable to receive said tongue.

4. An apparatus according to claim 1, further comprising an adhesive material for removably attaching said housing to said flexible section.

5. An apparatus according to claim 1, further comprising a magnet supported by each of said housing and said flexible section.

6. An apparatus according to claim 1, further comprising a stretchable band and a groove provided in said housing, said band suitable to fit around a portion of said flexible section and into said groove when said flexible section is placed over said housing.

7. An apparatus according to claim 1, said housing further comprising a display.

8. An apparatus according to claim 1, said one or more sensors comprising at least one of a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

9. An apparatus according to claim 1, said one or more sensors comprising at least two sensors.

10. An apparatus for detecting at least one of human physiological and contextual information from the body of a wearer, comprising:
    a housing support section for engaging at least a portion of said body;
    a housing removably attached to and supported by said housing support section;
    one or more sensors supported by said housing, said one or more sensors selected from the group consisting of physiological sensors and contextual sensors;
    a processing unit supported by said housing in electronic communication with said one or more sensors; and
    one or more additional housing support sections that may be selectively removably attached to said housing.

11. An apparatus according to claim 10, said housing support section and at least one of said additional housing support sections being suitable to engage different body portions of said wearer.

12. An apparatus according to claim 10, said apparatus having adjustable operating parameters, further comprising means for adjusting said operating parameters depending on the particular one of said housing support section and said one or more additional housing support sections to which said housing is removably attached.

13. An apparatus according to claim 12, said means for adjusting said operating parameters comprising a plurality of switches supported by said housing and a switch activator supported by said housing support section and each of said additional housing support sections, said switches being coupled to said processing unit, said operating parameters being adjusted in dependence on the particular one of said switches that is activated.

14. An apparatus according to claim 13, each of said switch activators being supported by a respective one of said housing support section and said additional housing support sections in a position such that a different one of said switches is activated depending on the particular one of said housing support section and said additional housing support sections to which said housing is removably attached.

15. An apparatus according to claim 13, said switches comprising magnetic switches and said switch activators each comprising a magnet.

16. An apparatus according to claim 13, said switches comprising mechanical switches.

17. An apparatus according to claim 16, each of said switch activators comprising a protruding element.

18. An apparatus according to claim 13, said switches comprising optical switches, said switch activators comprising one of means for obscuring light, means for reflecting light and means for filtering light.

19. An apparatus according to claim 13, said switches comprising electrical switches and said switch activators each comprising a conductor.

20. An apparatus according to claim 12, said means for adjusting said operating parameters comprising a plurality of switches supported by said housing and one or more switch activators supported by each of said housing support section and said additional housing support sections, said operating parameters being adjusted in dependence on the particular one or more of said switches that are activated.

21. An apparatus according to claim 12, said means for adjusting said operating parameters comprising a switch supported by said housing and at least one switch activator supported by each of said housing support section and said additional housing support sections, said switch being activatable according to a plurality of states depending upon a property of the particular switch activator activating said switch, said operating parameters being adjusted in dependence on said activation state of said switch.

22. An apparatus according to claim 10, further comprising a groove provided in said housing and a tongue provided on said housing support section and each of said additional housing support sections, said groove being suitable to receive each of said tongues.

23. An apparatus according to claim 10, further comprising a tongue provided on said housing and a groove provided in said housing support section and each of said additional housing support sections, said grooves being suitable to receive said tongue.

24. An apparatus according to claim 10, further comprising an adhesive material for removably attaching said housing to said housing support section and said additional housing support sections.

25. An apparatus according to claim 10, further comprising a magnet supported by each of said housing, said housing support section and said additional housing support sections.

26. An apparatus according to claim 10, further comprising a stretchable band and a groove provided in said housing, said stretchable band suitable to fit around a portion of one of said housing support section and said additional housing support section and into said groove when said one of said housing support section and said additional housing support sections is placed over said housing.

27. An apparatus according to claim 10, further comprising a wireless communications device for at least one of receiving information from and transmitting information to a computing device.

28. An apparatus according to claim 27, said computing device displaying information to an individual and enabling said individual to input information.

29. An apparatus according to claim 28, said computing device and said processing unit being adapted to engage in shared computing.

30. An apparatus according to claim 10, at least one of said housing section and said additional housing support sections comprising a garment.

31. An apparatus according to claim 30, said one or more sensors comprising a sensor for sensing one or more heart related parameters.

32. An apparatus according to claim 31, said one or more heart related parameters including at least one of heart rate, beat-to-beat variability, ECG, pulse oximetry, heart-related sounds and parameters relating to the mechanical action of the heart.

33. An apparatus according to claim 32, at least one of said additional housing support sections being suitable to engage a portion of said body comprising the left chest.

34. An apparatus according to claim 10, said housing support section and said one or more additional housing support sections each comprising a flexible section.

35. An apparatus according to claim 10, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

36. An apparatus for detecting at least one of human physiological and contextual information from the body of a wearer, comprising:
   a self-contained housing suitable to be worn on the left chest portion of said body;
   one or more sensors within said housing, said one or more sensors selected from the group consisting of physiological sensors and contextual sensors; and
   a processing unit within said housing in electronic communication with said one or more sensors;
   said one or more sensors comprising a sensor for sensing one or more heart related parameters including at least one of heart rate, beat-to-beat variability, ECG, pulse oximetry, heart-related sounds, and parameters relating to the mechanical action of the heart.

37. An apparatus according to claim 36, further comprising a housing support section for engaging at least a portion of said body, said housing being attached to said housing support section.

38. An apparatus according to claim 37, said housing support section comprising a flexible section.

39. An apparatus according to claim 38, said housing being selectively removably attached to said housing support section.

40. An apparatus according to claim 36, wherein said sensors generate data indicative of at least a detected parameter of the wearer and said processing unit generates derived data comprising a derived parameter based on said detected parameter, being an individual status parameter that cannot be directly detected by one of said one or more sensors.

41. An apparatus for detecting at least one of human physiological and contextual information from the body of a wearer which is mounted on said body in conjunction with a garment, comprising:

a housing;

a garment suitable to be worn on a portion of the body which restrains and supports said housing in a position proximate to the left chest of said body;

one or more sensors supported by said housing, said one or more sensors selected from the group consisting of physiological sensors and contextual sensors; and a processing unit supported by said housing in electronic communication with said one or more sensors;

said one or more sensors comprising a sensor for sensing one or more heart related parameters including at least one of heart rate, beat-to-beat variability, ECG, pulse oximetry, heart-related sounds, and parameters relating to the mechanical action of the heart.

42. An apparatus for detecting at least one of human physiological and contextual information from the body of a wearer in an ambient environment, comprising:

a housing;

a base member having a preselected resistivity mounted within said housing;

a first temperature measuring device attached to a first side of said base member;

a thermal energy communicator mounted adjacent to said first temperature measuring device for placing said first temperature measuring device in thermal communication with a portion of said body, said thermal energy communicator being located between said first temperature measuring device and said portion of said body when said apparatus is being worn on said body;

a second temperature measuring device attached to a second side of said base member, said second temperature measuring device in thermal communication with said ambient environment; and a processing unit provided in said housing, said first and second temperature measuring devices being in electronic communication with said processing unit;

wherein said apparatus is adapted to measure heat flux between said body and said ambient environment.

43. An apparatus according to claim 42, said first temperature measuring device comprising a first thermistor and said second temperature measuring device comprising a second thermistor.

44. An apparatus according to claim 43, said first thermistor measuring a first voltage, said second thermistor measuring a second voltage, said first voltage and said second voltage being used to generate a temperature difference (T2–T1), said heat flux being calculated according to the following formula:

heat flux $=K(T2-T1)$, wherein $K$ is said preselected resistivity.

45. An apparatus according to claim 42, said first temperature measuring device measuring a first parameter, said second temperature measuring device measuring a second parameter, said first parameter and said second parameter being used to generate a temperature difference (T2–T1), said heat flux being calculated according to the following formula:

heat flux $=K(T2-T1)$, wherein $K$ is said preselected resistivity.

46. An apparatus according to claim 42, said thermal energy communicator comprising a heat conduit having a first surface in thermal communication with said body portion when said apparatus is being worn and a second surface in thermal communication with said first temperature measuring device.

47. An apparatus according to claim 46, said thermal energy communicator further comprising a skin-side thermally conductive interface component in thermal communication with said body portion when said apparatus is being worn and said first surface of said heat conduit.

48. An apparatus according to claim 47, said skin-side thermally conductive interface component comprising a stainless steel plate.

49. An apparatus according to claim 47, said thermal energy communicator further comprising a first skin-side thermally conductive interface material located between said first thermally conductive interface component and said first surface of said heat conduit, and a second skin-side thermally conductive interface material located between said second surface of said heat conduit and said first temperature measuring device.

50. An apparatus according to claim 49, said first and second skin-side thermally conductive interface materials selected from the group consisting of thermally conductive gap fillers, thermally conductive phase change interface materials, thermally conductive tapes, thermally conductive cure-in-place compounds and epoxies, and thermal greases.

51. An apparatus according to claim 49, said skin-side thermally conductive interface component, said first skin-side thermally conductive interface material, said heat conduit, said second skin-side thermally conductive interface material, said first temperature measuring device, said base member, and said second temperature measuring device attached to one another along a direction substantially normal to said first and second side of said base member.

52. An apparatus according to claim 51, said base member comprising a printed circuit board.

53. An apparatus according to claim 52, said processing unit being attached to said printed circuit board.

54. An apparatus according to claim 42, further comprising an ambient-side thermally conductive interface component in thermal communication with said ambient environment and said second temperature measuring device.

55. An apparatus according to claim 54, further comprising an ambient-side thermally conductive interface material located between said ambient-side thermally conductive interface component and said second temperature measuring device.

56. An apparatus according to claim 55, said ambient-side thermally conductive interface material selected from the group consisting of thermally conductive gap fillers, thermally conductive phase change interface materials, thermally conductive tapes, thermally conductive cure-in-place compounds and epoxies, and thermal greases.

57. An apparatus according to claim 54, said ambient-side thermally conductive interface component comprising a stainless steel plate.

58. An apparatus according to claim 54, further comprising a housing support section for holding said housing in engagement with said body of said wearer, said housing support section exposing said ambient-side thermally conductive interface component to said ambient environment.

59. An apparatus according to claim 42, said thermal energy communicator comprising a thermally conductive interface material in thermal communication with said body portion when said apparatus is worn and said first temperature measuring device.

60. An apparatus according to claim 59, said thermally conductive interface material selected from the group consisting of thermally conductive gap fillers, thermally conductive phase change interface materials, thermally conductive tapes, thermally conductive cure-in-place compounds and epoxies, and thermal greases.

61. An apparatus according to claim 42, further comprising a housing support section attached to said housing, said housing support section being suitable to engage at least a portion of said body of said wearer.

62. An apparatus according to claim 42, further comprising a housing support section for engaging at least a portion of said body of said wearer, said housing support section being removably attached to said housing.

63. An apparatus according to claim 42, further comprising a plurality of housing support sections each suitable to engage at least a portion of said body of said wearer, and means for removably attaching said housing to any one of said housing support sections.

64. An apparatus according to claim 63, said apparatus having adjustable operating parameters, further comprising means for adjusting said operating parameters depending on the particular one of said housing support sections to which said housing is removably attached.

65. An apparatus for detecting at least one of human physiological and contextual information from the body of a wearer in an ambient environment, comprising:
  a housing;
  a printed circuit board supported by said housing, said printed circuit board having a preselected resistivity;
  a first thermistor attached to a first side of said printed circuit board and a second thermistor attached to a second side of said printed circuit board;
  a processing unit supported by said housing, said first thermistor and said second thermistor in electrical communication with said processing unit;
  a heat conduit, said heat conduit having a first surface and a second surface;
  a first thermally conductive interface component, said first thermally conductive interface component being in thermal communication with said body of said wearer when said apparatus is being worn;
  a second thermally conductive interface component in thermal communication with said ambient environment when said apparatus is being worn; and
  a first thermally conductive interface material located between said first thermally conductive interface component and said first surface of said heat conduit, a second thermally conductive interface material located between said second surface of said heat conduit and said first thermistor, and a third thermally conductive interface material located between said second thermistor and said second thermally conductive interface component;
    wherein said apparatus is adapted to measure heat flux between said body and said ambient environment.

66. An apparatus according to claim 65, said first thermally conductive interface component, said first thermally conductive interface material, said heat conduit, said second thermally conductive interface material, said first thermistor, said printed circuit board, said second thermistor, said third thermally conductive interface material and said second thermally conductive interface component attached to one another along a direction substantially normal to said first and second sides of said printed circuit board.

67. An apparatus according to claim 65, further comprising a housing support section for holding said housing in engagement with said body of said wearer, said housing support section exposing said second thermally conductive interface component to said ambient environment.

68. An apparatus for detecting, monitoring and reporting at least one of human physiological and contextual information from the body of a wearer, comprising:
  a housing having an adhesive material on at least a portion of an external surface thereof, said adhesive material enabling said housing to be removably attached to a portion of said body;
  at least two sensors supported by said housing selected from the group consisting of physiological sensors and contextual sensors, said physiological sensors adapted to facilitate the generation of data indicative of one or more detected physiological parameters of said wearer, said contextual sensors adapted to facilitate the generation of data indicative of one or more detected contextual parameters of said wearer;
  a processing unit in electrical communication with said sensors, said processing unit being adapted to generate at least one of: (i) derived data from at least one of at least a portion of said data indicative of physiological parameters, (ii) derived data from at least a portion of said data indicative of contextual parameters, said derived data comprising a calculated parameter based on at least one of said detected parameters, being an individual status parameter that cannot be directly detected by any of said at least two sensors and (iii) analytical status data from at least a portion of at least one of said data indicative of physiological parameters, said data indicative of contextual parameters and said derived data;
  an electronic memory in electrical communication with said processing unit for retrievably storing at least one of said data indicative of physiological parameters, data indicative of contextual parameters, derived data and analytical status data; and
  means for transmitting to an individual at least one of said data indicative of physiological parameters, data indicative of contextual parameters, derived data and analytical status data.

69. An apparatus according to claim 68, said housing being made of a rigid material.

70. An apparatus according to claim 69, said analytical status data being generated from at least a portion of said manually entered information.

71. An apparatus according to claim 68, said housing being made of a flexible material.

72. An apparatus according to claim 71, said flexible material comprising a flexible plastic film.

73. An apparatus according to claim 68, said means for transmitting comprising an electrochemical display.

74. An apparatus according to claim 68, said portion of said body comprising the left chest, said data indicative of one or more physiological parameters of said wearer comprising heart related parameters.

75. An apparatus according to claim 74, said housing being made of a flexible material.

76. An apparatus according to claim 75, said flexible material comprising a flexible plastic film.

77. An apparatus according to claim 76, said means for transmitting comprising an electrochemical display.

78. An apparatus according to claim 68, further comprising a wireless communications device for at least one of receiving information from and transmitting information to a computing device.

79. An apparatus according to claim 78, said processing unit and said computing device adapted to engage in shared computing.

80. An apparatus according to claim 68, said means for transmitting comprising a computing device coupled to said processing unit.

81. An apparatus according to claim 80, said computing device being coupled to said processing unit by a physical connection.

82. An apparatus according to claim 80, said computing device being coupled to said processing unit by a wireless connection.

83. An apparatus according to claim 69, further comprising means for manually entering information into said apparatus.

84. An apparatus according to claim 83, said apparatus monitoring the degree to which said individual has followed a predetermined routine, said analytical status data comprising feedback to said individual relating to the degree to which said individual has followed said predetermined routine, said feedback being generated from at least a portion of at least one of said data indicative of one or more physiological parameters of said individual, said derived data and said manually entered data.

85. An apparatus according to claim 84, wherein said routine comprises a plurality of categories and said feedback is generated and provided with respect to each of said categories.

86. An apparatus according to claim 68, said means for transmitting comprising a computing device coupled to said processing unit, said processing unit being adapted to cause said computing device to trigger an event upon detection of one or more physiological conditions of said wearer.

87. An apparatus according to claim 68, said processing unit being adapted to cause a computing device to trigger an event upon detection of one or more physiological conditions of said individual.

88. An apparatus according to claim 68, said at least two sensors being selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

89. An apparatus for detecting at least one of human physiological and contextual information from the body of a wearer, comprising:
a housing, said housing having an inner surface for mounting adjacent said body and an outer surface opposite said inner surface;
said inner surface having a longitudinal axis and a transverse axis, said inner surface being generally concave in a first direction and having an axis of concavity coincident with said longitudinal axis, said inner surface being generally convex in a second direction generally perpendicular to said first direction and having an axis of convexity coincident with said transverse axis.

90. An apparatus according to claim 89, said inner surface having first and second lateral ends located at opposite ends of said axis of concavity, said housing having a first radiused portion adjacent to and including said first lateral end and a second radiused portion adjacent to and including said second lateral end.

91. An apparatus according to claim 90, said inner surface having third and fourth lateral ends located at opposite ends of said axis of convexity, said housing having a third radiused portion adjacent to and including said third lateral end and a fourth radiused portion adjacent to and including said fourth lateral end.

92. An apparatus according to claim 90, further comprising one or more sensors located adjacent to at least one of said first and second lateral ends.

93. An apparatus according to claim 90, said outer surface having a convex shape between a first lateral side and a second lateral side of said outer surface.

94. An apparatus according to claim 93, said housing having a width dimension as measured between a first lateral side and a second lateral side of said housing, at least a portion of said first lateral side and said second lateral side each having a taper such that said width dimension gradually decreases in a third direction from said inner surface to said outer surface.

95. An apparatus according to claim 93, said housing having a third radiused portion adjacent to and including said first lateral side of said outer surface and a fourth radiused portion adjacent to and including said second lateral side of said outer surface.

96. An apparatus according to claim 94, said housing having a third radiused portion adjacent to and including said first lateral side of said outer surface and a fourth radiused portion adjacent to and including said second lateral side of said outer surface.

97. An apparatus according to claim 89, said outer surface having a convex shape between a first lateral side and a second lateral side of said outer surface.

98. An apparatus according to claim 97, said housing having a width dimension as measured between a first lateral side and a second lateral side of said housing, at least a portion of said first lateral side and said second lateral side each having a taper such that said width dimension gradually decreases in a third direction from said inner surface to said outer surface.

99. An apparatus according to claim 89, further comprising a housing support section attached to said housing for engaging said body of said wearer, said housing support section having a generally convex outer surface.

100. An apparatus according to claim 89, further comprising one or more sensors supported by said housing, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

101. An apparatus for detecting at least one of human physiological and contextual information from the body of a wearer, comprising:
a housing suitable to be worn on said body;
one or more sensors supported by said housing, said one or more sensors selected from the group consisting of physiological sensors and contextual sensors; and
a processing unit supported by said housing in electronic communication with said one or more sensors, said one or more sensors comprising a sensor for measuring GSR including at least two electrical contacts, said electrical contacts having a textured surface.

102. An apparatus according to claim 101, said textured surface comprising a plurality of raised bumps.

103. An apparatus according to claim 101, said electrical contacts having an oblong, curved shape.

104. An apparatus according to claim 101, said sensor for measuring GSR further comprising a current loop for applying a current between said electrical contacts and measuring a voltage across said electrical contacts.

105. An apparatus according to claim 101, further comprising a housing support section for engaging at least a portion of said body, said housing being attached to said housing support section.

106. An apparatus according to claim 105, said housing support section comprising a flexible section.

107. An apparatus according to claim 106, said housing being selectively removably attached to said housing support section.

108. An apparatus for detecting at least one of human physiological and contextual information from the body of a wearer, comprising:
  a housing suitable to be worn on said body;
  one or more sensors supported by said housing, said one or more sensors selected from the group consisting of physiological sensors and contextual sensors;
  a processing unit supported by said housing in electronic communication with said one or more sensors; and
  a proximity sensor for sensing whether said apparatus is being worn.

109. An apparatus according to claim 108, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.
  a proximity sensor for sensing whether said apparatus is being worn.

110. An apparatus according to claim 108, further comprising a housing support section for engaging at least a portion of said body, said housing being attached to said housing support section.

111. An apparatus according to claim 110, said housing support section comprising a flexible section.

112. An apparatus according to claim 111, said housing being selectively removably attached to said housing support section.

113. An apparatus for detecting at least one of human physiological and contextual information from the body of a wearer, comprising:
  a housing suitable to be worn on said body;
  one or more sensors supported by said housing, said one or more sensors selected from the group consisting of physiological sensors and contextual sensors;
  a processing unit supported by said housing in electronic communication with said one or more sensors; and
  a proximity sensor for automatically powering said apparatus on and off.

114. An apparatus according to claim 113, further comprising a housing support section for engaging at least a portion of said body, said housing being attached to said housing support section.

115. An apparatus according to claim 114, said housing support section comprising a flexible section.

116. An apparatus according to claim 115, said housing being selectively removably attached to said housing support section.

117. An apparatus according to claim 113, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

118. An apparatus for detecting at least one of human physiological and contextual information from the body of a wearer, comprising:
  a housing suitable to be worn on said body;
  one or more sensors supported by said housing, said one or more sensors selected from the group consisting of physiological sensors and contextual sensors, said sensors generating data indicative of at least a detected parameter of the wearer;
  a processing unit supported by said housing in electronic communication with said one or more sensors generating derived data comprising a calculated parameter based on said detected parameter, being an individual status parameter that cannot be directly detected by one of said one or more sensors, said processing unit being in electronic communication with a feedback device for providing feedback information to a wearer of said device.

119. An apparatus according to claim 118, further comprising a housing support section for engaging at least a portion of said body, said housing being attached to and supported by said housing support section.

120. An apparatus according to claim 119, said housing support section comprising a flexible section.

121. An apparatus according to claim 120, said housing being selectively removably attached to said housing support section.

122. An apparatus according to claim 118, said one or more sensors comprising two sensors supported by said housing.

123. An apparatus according to claim 118, further comprising at least one additional sensor in electrical communication with said processing unit.

124. An apparatus according to claim 123, wherein said additional sensor is external to said housing.

125. An apparatus according to claim 118, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor and a sensor for measuring heart related parameters.

126. A method for detecting from the body of a wearer parameters relating to the heart of the wearer, comprising:
  generating a first physiological acoustic signal including a first physiological acoustic component generated from the motion of said heart and a second physiological acoustic component generated from non-heart related motion of said body of said wearer, said non-heart related motion comprising footfalls of said wearer;
  generating a second signal related to said non-heart related motion of said body;
  generating a third signal by using said second signal to subtract at least a portion of said second physiological acoustic component from said first signal; and
  generating said heart related parameters from said third signal.

127. A method according to claim 126, wherein said information relating to said footfalls is generated using an accelerometer.

128. An apparatus for detecting, monitoring and reporting at least one of human physiological and contextual information from the body of a wearer, comprising:
- a housing having an adhesive material on at least a portion of an external surface thereof, said adhesive material enabling said housing to be removably attached to a portion of said body;
- at least two sensors supported by said housing, said at least two sensors being selected from the group consisting of physiological sensors and contextual sensors, said sensors generating data indicative of at least a first parameter and a second parameter of the wearer;
- a processor, said processor generating derived data based on said data indicative of at least a first parameter and a second parameter, said derived data comprising a third parameter of said wearer, said third parameter being an individual status parameter that cannot be directly detected by any of said at least two sensors;
- a memory for retrievably storing at least one of said data indicative of at least a first parameter and a second parameter and said derived data; and
- means for transmitting to an individual at least one of said data indicative of at least a first parameter and a second parameter and said derived data.

129. An apparatus according to claim 128, said housing being made of a rigid material.

130. An apparatus according to claim 128, said housing being made of a flexible material.

131. An apparatus according to claim 130, said flexible material comprising a flexible plastic film.

132. An apparatus according to claim 128, said means for transmitting comprising an electrochemical display.

133. An apparatus according to claim 128, said portion of said body comprising the left chest, said data indicative of at least a first parameter and a second parameter of the wearer comprising heart related parameters, said derived data relating to the heart of said wearer.

134. An apparatus according to claim 133, said housing being made of a flexible material.

135. An apparatus according to claim 133, said flexible material comprising a flexible plastic film.

136. An apparatus according to claim 133, said means for transmitting comprising an electrochemical display.

137. An apparatus according to claim 128, further comprising a wireless communications device for at least one of receiving information from and transmitting information to a computing device.

138. An apparatus according to claim 137, said processor and said computing device adapted to engage in shared computing.

139. An apparatus according to claim 128, said means for transmitting comprising a computing device in electronic communication with said processor.

140. An apparatus according to claim 128, said means for transmitting comprising a computing device in electronic communication with said processor, said processor being adapted to cause said computing device to trigger an event upon detection of one or more physiological conditions of said individual.

141. An apparatus according to claim 128, said processor being adapted to cause a computing device to trigger an event upon detection of one or more physiological conditions of said wearer.

142. An apparatus according to claim 128, said at least two sensors being selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

143. An apparatus for detecting at least one of human physiological and contextual information from the body of a wearer, comprising:
- a housing suitable to be worn on said body;
- housing support section for engaging at least a portion of said body, said housing being attached to said housing support section;
- one or more sensors supported by said housing, said one or more sensors selected from the group consisting of physiological sensors and contextual sensors; and
- a processing unit supported by said housing in electronic communication with said one or more sensors, said one or more sensors comprising a sensing component for contacting the skin of a wearer, said sensing component comprising a plurality of microneedles.

144. An apparatus according to claim 143, said housing support section comprising a flexible section.

145. An apparatus according to claim 144, said housing being selectively removably attached to said housing support section.

146. An apparatus for detecting at least one of human physiological and contextual information from the body of a wearer, comprising:
- a self-contained housing suitable to be worn on said body:
- one or more sensors within said housing, said one or more sensors selected from the group consisting of physiological sensors and contextual sensors; and
- a processing unit within said housing in electronic communication with said one or more sensors, said one or more sensors comprising one or more electrical contacts, said electrical contacts having a textured surface.

147. An apparatus according to claim 146, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

148. An apparatus according to claim 146, said textured surface comprising a plurality of raised bumps.

149. An apparatus according to claim 146, further comprising a housing support section for engaging at least a portion of said body, said housing being attached to said housing support section.

150. An apparatus according to claim 149, said housing support section comprising a flexible section.

151. An apparatus according to claim 150, said housing being selectively removably attached to said housing support section.

152. An apparatus for detecting at least one of human physiological and contextual information from the body of a wearer, comprising:
- a housing suitable to be worn on said body;
- a housing support section for engaging at least a portion of said body, said housing being attached to said housing support section;

one or more sensors supported by said housing, said one or more sensors selected from the group consisting of physiological sensors and contextual sensors; and
a processing unit supported by said housing in electronic communication with said one or more sensors and with a sensing component placed in contact with the skin of said wearer, said sensing component comprising a plurality of microneedles.

153. An apparatus according to claim 152, said housing support section comprising a flexible section.

154. An apparatus according to claim 153, said housing being selectively removably attached to said housing support section.

155. An apparatus for detecting at least one of human physiological and contextual information from the body of a wearer, comprising:
a housing suitable to be worn on said body;
one or more sensors supported by said housing, said one or more sensors comprising at least one of: an ambient temperature sensor, an ambient light sensor, an ambient sound sensor, an EMG sensor, a skin impedance sensor and a heat flux sensor;
a processing unit supported by said housing in electronic communication with said one or more sensors; and
a wireless transceiver for receiving information from and transmitting information to a computing device, said computing device displaying information to an individual and enabling said individual to input information, said computing device and said processing unit being adapted to engage in shared computing.

156. An apparatus according to claim 155, further comprising a housing support section for engaging at least a portion of said body, said housing being attached to said housing support section.

157. An apparatus according to claim 156, said housing support section comprising a flexible section.

158. An apparatus according to claim 157, said housing being selectively removably attached to said housing support section.

159. An apparatus according to claim 155, further comprising two sensors.

160. An apparatus according to claim 155, wherein said sensors generate data indicative of at least a detected parameter of the wearer and said processing unit generates derived data comprising a derived parameter based on said detected parameter, being an individual status parameter that cannot be directly detected by one of said one or more sensors.

161. An apparatus for detecting at least one of human physiological and contextual information from the body of a wearer, comprising:
a housing suitable to be worn on said body;
one or more sensors supported by said housing, said one or more sensors further comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters; and
a processing unit supported by said housing in electronic communication with said one or more sensors, said one or more sensors comprising a sensing component for contacting the skin of said wearer, said sensing component comprising a plurality of microneedles.

162. An apparatus for detecting at least one of human physiological and contextual information from the body of a wearer, comprising:
a housing suitable to be worn on said body;
an ECG sensor and an accelerometer supported by said housing;
a processing unit supported by said housing in electronic communication with said sensors, said processing unit being in electronic communication with a feedback device for providing feedback information to a wearer of said device.

163. An apparatus for detecting at least one of human physiological and contextual information from the body of a wearer, comprising:
a self-contained housing suitable to be worn on the upper arm portion of said body;
one or more sensors within said housing, said one or more sensors selected from the group consisting of physiological sensors and contextual sensors, said one or more sensors comprising at least one of: an ambient temperature sensor, an ambient light sensor, an ambient sound sensor, an EMG sensor, a skin impedance sensor, and a heat flux sensor; and
a processing unit within said housing in electronic communication with said one or more sensors.

164. An apparatus for detecting at least one of human physiological and contextual information from the body of a wearer, comprising:
a housing support section for engaging at least a portion of said body, said housing support section having an adhesive material on a surface thereof for attaching said housing support section to said body;
a housing located between said housing support section and said body, said housing being held against said body by said housing support section;
one or more sensors supported by said housing, said one or more sensors selected from the group consisting of physiological sensors and contextual sensors; and
a processing unit supported by said housing in electronic communication with said one or more sensors.

165. An apparatus according to claim 164, said housing support section comprising a flexible section.

166. An apparatus according to claim 164, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

167. An apparatus according to claim 164, said housing being selectively removably attached to said housing support section.

168. An apparatus according to claim 164, said housing having an inner surface for mounting adjacent said body and an outer surface opposite said inner surface, said inner surface having a generally concave cross section.

169. An apparatus according to claim 164, said housing having an inner surface for mounting adjacent said body and an outer surface opposite said inner surface, said inner surface having a generally convex cross section.

170. An apparatus according to claim 164, said housing having an inner surface for mounting adjacent said body and an outer surface opposite said inner surface, said inner surface having a longitudinal axis and a transverse axis, said inner surface being generally concave in a first direction and having an axis of concavity coincident with said longitudinal axis, said inner surface being generally convex in a second direction generally perpendicular to said first direction and having an axis of convexity coincident with said transverse axis.

171. An apparatus for detecting at least one of human physiological and contextual information from the body of a wearer, comprising:
 a housing, said housing engaging said body;
 one or more sensors supported by said housing, said one or more sensors selected from the group consisting of physiological sensors and contextual sensors;
 a processing unit supported by said housing in electronic communication with said one or more sensors;
 a housing support section placed over said housing, said housing support section engaging said body and securing said housing in place against said body by way of pressure alone.

172. An apparatus according to claim 171, said housing support section comprising a flexible section.

173. An apparatus according to claim 171, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

174. An apparatus according to claim 171, said housing having an inner surface for mounting adjacent said body and an outer surface opposite said inner surface, said inner surface having a generally concave cross section.

175. An apparatus according to claim 171, said housing having an inner surface for mounting adjacent said body and an outer surface opposite said inner surface, said inner surface having a generally convex cross section.

176. An apparatus according to claim 171, said housing having an inner surface for mounting adjacent said body and an outer surface opposite said inner surface, said inner surface having a longitudinal axis and a transverse axis, said inner surface being generally concave in a first direction and having an axis of concavity coincident with said longitudinal axis, said inner surface being generally convex in a second direction generally perpendicular to said first direction and having an axis of convexity coincident with said transverse axis.

177. An apparatus for detecting at least one of human physiological and contextual information from the body of a wearer, comprising:
 a housing suitable to be worn on said body;
 one or more sensors supported by said housing, said one or more sensors selected from the group consisting of physiological sensors and contextual sensors;
 a processing unit supported by said housing in electronic communication with said one or more sensors, said processing unit being in electronic communication with a feedback device having a sensor for providing feedback information to a wearer of said device.

178. An apparatus for detecting at least one of human physiological and contextual information from the body of a wearer, comprising:
 a housing;
 a housing support section comprising a flexible section for receiving and supporting the insertion of said housing, said housing support section engaging at least a portion of said body;
 one or more sensors supported by said housing, said one or more sensors selected from the group consisting of physiological sensors and contextual sensors; and
 a processing unit supported by said housing in electronic communication with said one or more sensors, said processing unit being in electronic communication with a feedback device for providing feedback information to a wearer of said device.

179. An apparatus according to claim 178, said housing being selectively removably attached to said housing support section.

180. An apparatus for detecting at least one of human physiological and contextual information from the body of a wearer, comprising:
 a housing suitable to be worn on a portion of said body;
 a housing support section for engaging at least a portion of said body, said housing being attached to said housing support section;
 one or more sensors supported by said housing, said one or more sensors selected from the group consisting of physiological sensors and contextual sensors; and
 a processing unit supported by said housing in electronic communication with said one or more sensors;
 said one or more sensors comprising a sensor for sensing one or more heart related parameters including at least one of heart rate, beat-to-beat variability, ECG, pulse oximetry, heart-related sounds, and parameters relating to the mechanical action of the heart, said portion of said body comprising the left chest.

181. An apparatus according to claim 180, said housing support section comprising a flexible section.

182. An apparatus according to claim 180, said housing being selectively removably attached to said housing support section.

183. An apparatus for detecting at least one of human physiological and contextual information from the body of a wearer, comprising:
 a housing suitable to be worn on said body;
 a housing support section comprising a flexible section for engaging at least a portion of said body, said housing being selectively removably attached to said housing support section;
 one or more sensors supported by said housing, said one or more sensors selected from the group consisting of physiological sensors and contextual sensors; and
 a processing unit supported by said housing in electronic communication with said one or more sensors, said one or more sensors comprising one or more electrical contacts, said electrical contacts having a textured surface comprising a plurality of raised bumps.

184. An apparatus for detecting at least one of human physiological and contextual information from the body of a wearer, comprising:
 a housing suitable to be worn on said body;
 one or more sensors supported by said housing, said one or more sensors selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters; and
 a processing unit supported by said housing in electronic communication with said one or more sensors and with a sensing component placed in contact with the skin of said wearer, said sensing component comprising a plurality of microneedles.

185. An apparatus for detecting, monitoring and reporting at least one of human physiological and contextual information from the body of a wearer, comprising:
 a housing having an adhesive material on at least a portion of an external surface thereof, said adhesive material enabling said housing to be removably attached to a portion of said body;
 at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;
 a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;
 an electronic memory in electrical communication with said processing unit for retrievably storing at least one of said data indicative of physiological parameters, data indicative of contextual parameters, derived data and analytical status data; and
 an electrochemical display for transmitting to an individual at least one of said data indicative of physiological parameters, data indicative of contextual parameters, derived data and analytical status data.

186. An apparatus for detecting, monitoring and reporting at least one of human physiological and contextual information from the body of a wearer, comprising:
 a flexible housing comprising plastic film, said flexible housing having an adhesive material on at least a portion of an external surface thereof, said adhesive material enabling said housing to be removably attached to the left chest area of said body;
 at least two sensors supported by said housing selected from the group consisting of physiological sensors and contextual sensors, said physiological sensors adapted to facilitate the generation of data indicative of one or more heart related physiological parameters of said wearer, said contextual sensors adapted to facilitate the generation of data indicative of one or more contextual parameters of said wearer;
 a processing unit in electrical communication with said sensors, said processing unit being adapted to generate at least one of: (i) derived data from at least one of at least a portion of said data indicative of said heart related physiological parameters and at least a portion of said data indicative of contextual parameters, and (ii) analytical status data from at least a portion of at least one of said data indicative of said heart related physiological parameters, said data indicative of contextual parameters and said derived data;
 an electronic memory in electrical communication with said processing unit for retrievably storing at least one of said data indicative of said heart related physiological parameters, data indicative of contextual parameters, derived data and analytical status data; and
 an electrochemical display for transmitting to an individual at least one of said data indicative of said heart related physiological parameters, data indicative of contextual parameters, derived data and analytical status data.

187. An apparatus for detecting, monitoring and reporting at least one of human physiological and contextual information from the body of a wearer, comprising:
 a housing having an adhesive material on at least a portion of an external surface thereof, said adhesive material enabling said housing to be removably attached to a portion of said body;
 at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;
 a processing unit in electrical communication with said sensors, said processing unit being adapted to generate at least one of: (i) derived data from at least one of at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;
 an electronic memory in electrical communication with said processing unit for retrievably storing at least one of said data indicative of physiological parameters, data indicative of contextual parameters, derived data and analytical status data;
 means for transmitting to an individual at least one of said data indicative of physiological parameters, data indicative of contextual parameters, derived data and analytical status data; and
 a wireless communications device for at least one of receiving information from and transmitting information to a computing device
 wherein said processing unit and said computing device are adapted to engage in shared computing.

188. An apparatus for detecting, monitoring and reporting at least one of human physiological and contextual information from the body of a wearer, comprising:
 a housing having an adhesive material on at least a portion of an external surface thereof, said adhesive material enabling said housing to be removably attached to a portion of said body;
 at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;
 a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and a computing device coupled to said processing unit by a physical connection for transmitting to an individual at least one of said data indicative of physiological parameters, data indicative of contextual parameters, derived data and analytical status data.

189. An apparatus for detecting, monitoring and reporting at least one of human physiological and contextual information from the body of a wearer, comprising:

a rigid housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and means for transmitting to an individual at least one of said data indicative of physiological parameters, data indicative of contextual parameters, derived data and analytical status data.

190. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data;

means for transmitting to an individual at least one of said data indicative of physiological parameters, data indicative of contextual parameters, derived data and analytical status data; and means for manually entering information into said apparatus.

191. An apparatus for detecting, monitoring and reporting at least one of human physiological and contextual information from the body of a wearer, comprising:

a rigid housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data;

means for transmitting to an individual at least one of said data indicative of physiological parameters, data indicative of contextual parameters, derived data and analytical status data; and means for manually entering information into said apparatus, said analytical status data being generated from at least a portion of manually entered information.

192. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and a computing device coupled to said processing unit for transmitting to an individual at least one of said data indicative of physiological parameters, data indicative of contextual parameters, derived data and analytical status data;

wherein said processing unit is adapted to cause said computing device to trigger an event upon detection of one or more physiological conditions of said wearer.

193. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data and to cause a computing device to trigger an event upon detection of one or more physiological conditions of said wearer;

an electronic memory in electrical communication with said processing unit for retrievably storing at least one of said data indicative of physiological parameters, data indicative of contextual parameters, derived data and analytical status data; and means for transmitting to an individual at least one of said data indicative of physiological parameters, data indicative of contextual parameters, derived data and analytical status data.

194. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least one of at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data;

means for transmitting to an individual at least one of said data indicative of physiological parameters, data indicative of contextual parameters, derived data and analytical status data; and means for manually entering information into said apparatus;

said apparatus monitoring the degree to which said individual has followed a predetermined routine, said analytical status data comprising feedback to said individual relating to the degree to which said individual has followed said predetermined routine, said feedback being generated from at least a portion of at least one of said data indicative of one or more physiological parameters of said individual, said derived data and said manually entered data.

195. An apparatus according to claim 194, wherein said routine comprises a plurality of categories and said feedback is generated and provided with respect to each of said categories.

196. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters, said sensors adapted to facilitate the generation of data indicative of one or more physiological parameters or contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and means for transmitting to an individual at least one of said data indicative of physiological parameters, data indicative of contextual parameters, derived data and analytical status data.

197. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of physiological sensors and contextual sensors, said sensors generating data indicative of at least a first parameter and a second parameter of the wearer;

a processor, said processor generating derived data based on said data indicative of at least a first parameter and a second parameter;

a memory for retrievably storing at least one of said data indicative of at least a first parameter and a second parameter and said derived data; and an electrochemical display for transmitting to an individual at least one of said data indicative of at least a first parameter and a second parameter and said derived data.

198. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to the left chest area of said body;

at least two sensors supported by said housing, said at least two sensors being selected from the group consisting of physiological sensors and contextual sensors, said sensors generating data indicative of at least a first heart related parameter and a second heart related parameter of the wearer;

a processor, said processor generating derived data based on at least a portion of said first and second parameters, said derived data comprising heart related derived data;

a memory for retrievably storing at least one of said data indicative of at least a first heart related parameter and a second heart related parameter and said heart related derived data; and an electrochemical display for transmitting to an individual at least one of said data indicative of at least a first heart related parameter, said data indicative of at least a second heart related parameter, and said derived data.

199. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of physiological sensors and contextual sensors, said sensors generating data indicative of at least a first parameter and a second parameter of the wearer;

a processor, said processor generating derived data based on said data indicative of at least a first parameter and a second parameter;

a memory for retrievably storing at least one of said data indicative of at least a first parameter and a second parameter and said derived data;

means for transmitting to an individual at least one of said data indicative of at least a first parameter and a second parameter and said derived data; and a wireless communications device for at least one of receiving information from and transmitting information to a computing device, wherein said processor and said computing device adapted to engage in shared computing.

200. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of physiological sensors and contextual sensors, said sensors generating data indicative of at least a first parameter and a second parameter of the wearer;

a processor, said processor generating derived data based on said data indicative of at least a first parameter and a second parameter;

a memory for retrievably storing at least one of said data indicative of at least a first parameter and a second parameter and said derived data; and a computing device in electronic communication with said processor for transmitting to an individual at least one of said data indicative of at least a first parameter and a second parameter and said derived data, said processor being adapted to cause said computing device to trigger an event upon detection of one or more physiological conditions of said individual.

201. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of physiological sensors and contextual sensors, said sensors generating data indicative of at least a first parameter and a second parameter of the wearer;

a processor, said processor generating derived data based on said data indicative of at least a first parameter and a second parameter and adapted to cause a computing device to trigger an event upon detection of one or more physiological conditions of said wearer;

a memory for retrievably storing at least one of said data indicative of at least a first parameter and a second parameter and said derived data; and means for transmitting to an individual at least one of said data indicative of at least a first parameter and a second parameter and said derived data.

202. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters, said sensors generating data indicative of at least a first parameter and a second parameter of the wearer;

a processor, said processor generating derived data based on said data indicative of at least a first parameter and a second parameter;

a memory for retrievably storing at least one of said data indicative of at least a first parameter and a second parameter and said derived data; and means for transmitting to an individual at least one of said data indicative of at least a first parameter and a second parameter and said derived data.

203. An apparatus for detecting from the body of a wearer parameters relating to the heart of the wearer, comprising:

an acoustic-based non-ECG heart parameter sensor that generates a first signal including a first acoustic component generated from the motion of said heart and a second acoustic component generated from footfalls created by said body of said wearer; and one or more filtering accelerometer sensors for generating a second signal related to said footfalls created by said body, said second signal being used to subtract at least a portion of said second acoustic component from said first signal to generate a third signal, said third signal being used to generate said heart related parameters.

204. An apparatus for detecting from the body of a wearer parameters relating to the heart of the wearer, comprising:

an acoustic-based non-ECG heart parameter sensor that generates a first signal including a first acoustic component generated from the motion of said heart and a second acoustic component generated from non-heart related motion of said body of said wearer, said first signal further including a third acoustic component generated from ambient noise;

one or more filtering sensors for generating a second signal related to said non-heart related motion of said body, said second signal being used to subtract at least a portion of said second acoustic component from said first signal to generate a third signal, said third signal being used to generate said heart related parameters; and an ambient noise sensor that generates a fourth signal related to said ambient noise, said fourth signal being used to subtract at least a portion of said third acoustic component from said first signal to generate said third signal.

205. A method for detecting from the body of a wearer parameters relating to the heart of the wearer, comprising:

generating a first acoustic signal including a first acoustic component generated from the motion of said heart and a second acoustic component generated from footfalls created by said body of said wearer;

generating a second signal related to said footfalls;

generating a third signal by using said second signal to subtract at least a portion said second acoustic component from said first signal; and generating said heart related parameters from said third signal.

206. A method according to claim 205, wherein said information relating to said footfalls is generated using an accelerometer.

207. A method for detecting from the body of a wearer parameters relating to the heart of the wearer, comprising:

generating a first acoustic signal including a first acoustic component generated from the motion of said heart and a second acoustic component generated from non-heart related motion of said body of said wearer, said first acoustic signal further including a third acoustic component generated from ambient noise;

generating a second signal related to said non-heart related motion of said body;

generating a third signal by using said second signal to subtract at least a portion said second acoustic component from said first signal;

generating said heart related parameters from said third signal; and generating a fourth signal related to said ambient noise, said step of generating said third signal further comprising using said fourth signal to subtract at least a portion of said third acoustic component from said first signal.

208. An apparatus for detecting at least one of human physiological and contextual information from the body of a wearer which is mounted on said body in conjunction with a garment, comprising:

a housing;

a garment suitable to be worn on a portion of the body which restrains and supports said housing in a position proximate to the upper arm of said body;

one or more sensors supported by said housing, said one or more sensors selected from the group consisting of physiological sensors and contextual sensors; and a processing unit supported by said housing in electronic communication with said one or more sensors;

said one or more sensors comprising a sensor for sensing one or more heart related parameters including at least one of pulse oximetry, heart-related sounds, and parameters relating to the mechanical action of the heart.

209. An apparatus for detecting at least one of human physiological and contextual information from the body of a wearer, comprising:

a self-contained housing suitable to be worn on the upper arm portion of said body;

one or more sensors within said housing, said one or more sensors selected from the group consisting of physiological sensors and contextual sensors; and a processing unit within said housing in electronic communication with said one or more sensors;

said one or more sensors comprising a sensor for sensing one or more heart related parameters including at least one of pulse oximetry, heart-related sounds, and parameters relating to the mechanical action of the heart.

210. An apparatus for detecting from the body of a wearer parameters relating to the heart of the wearer, comprising:

an acoustic-based non-ECG heart parameter sensor that generates a first signal including a first physiological acoustic component generated from the motion of said heart, a second physiological acoustic component generated from non-heart related motion of said body of said wearer, and a third acoustic component generated from ambient noise; and one or more filtering sensors for generating a second signal related to said non-heart related motion of said body and a third signal related to said ambient noise, said second signal being used to subtract at least a portion of said second physiological acoustic component from said first signal and said third signal being used to subtract at least a portion of said third acoustic component from said first signal to generate a fourth signal, said fourth signal being used to generate said heart related parameters.

211. An apparatus according to claim 210, said acoustic-based non-ECG heart parameter sensor including a sound transducer coupled to a pad containing an acoustic transmission material.

212. A method for detecting from the body of a wearer parameters relating to the heart of the wearer, comprising:

generating a first physiological acoustic signal including a first physiological acoustic component generated from the motion of said heart, a second acoustic component generated from non-heart related motion of said body, and a third acoustic component generated from ambient noise;

generating a second signal related to said non-heart related motion of said body;

generating a third signal related to said ambient noise;

generating a fourth signal by (i) using said second signal to subtract at least a portion of said second acoustic component from said first signal, and (ii) using said third signal to subtract at least a portion of said third acoustic component from said first signal;

generating said heart related parameters from said fourth signal.

213. An apparatus for detecting at least one of human physiological and contextual information from the body of a wearer, comprising:

a housing support section for engaging at least a portion of said body;

a housing removably attached to and supported by said housing support section;

a strap attached to said housing support section for securing said housing support section to said body;

one or more sensors supported by said housing, said one or more sensors selected from the group consisting of physiological sensors and contextual sensors; and a processing unit supported by said housing in electronic communication with said one or more sensors.

214. An apparatus according to claim 213, said one or more sensors comprising at least one of a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

215. An apparatus according to claim 213, said housing support section comprising a flexible section.

216. An apparatus according to claim 215, said housing being selectively removably attached to said housing support section.

217. An apparatus for detecting at least one of human physiological and contextual information from the body of a wearer, comprising:

a housing suitable to be worn on said body;

housing support section for engaging at least a portion of said body, said housing being attached to said housing support section;

one or more sensors supported by said housing, said one or more sensors selected from the group consisting of physiological sensors and contextual sensors;

a processing unit supported by said housing in electronic communication with said one or more sensors; and a wireless transceiver for receiving information from and transmitting information to a computing device, said computing device displaying information to an individual and enabling said individual to input information, said computing device and said processing unit being adapted to engage in shared computing.

218. An apparatus according to claim 217, said housing support section comprising a flexible section.

219. An apparatus according to claim 218, said housing being selectively removably attached to said housing support section.

220. An apparatus for detecting at least one of human physiological and contextual information from the body of a wearer, comprising:

a housing suitable to be worn on said body;

one or more sensors supported by said housing, said one or more sensors selected from the group consisting of physiological sensors and contextual sensors, said sensors generate data indicative of at least a detected parameter of the wearer;

a processing unit supported by said housing in electronic communication with said one or more sensors and generating derived data comprising a derived parameter based on said detected parameter, being an individual status parameter that cannot be directly detected by one of said one or more sensors.; and a wireless transceiver for receiving information from and transmitting information to a computing device, said computing device displaying information to an individual and enabling said individual to input information, said computing device and said processing unit being adapted to engage in shared computing.

221. An apparatus for detecting from the body of a wearer parameters relating to the heart of the wearer, comprising:

an acoustic-based non-ECG heart parameter sensor that generates a first signal including a first physiological acoustic component generated from the motion of said heart and a second physiological acoustic component generated from non-heart related motion of said body of said wearer, said non-heart related motion comprising footfalls of said wearer; and one or more filtering sensors comprising an accelerometer for generating a second signal related to said non-heart related motion of said body, said second signal being used to subtract at least a portion of said second physiological acoustic component from said first signal to generate a third signal, said third signal being used to generate said heart related parameters.

222. An apparatus according to claim 221, said acoustic-based non-ECG heart parameter sensor including a sound transducer coupled to a pad containing an acoustic transmission material.

* * * * *

UNITED STATES PATENT AND TRADEMARK OFFICE
CERTIFICATE OF CORRECTION

| | |
|---|---|
| PATENT NO. | : 7,020,508 B2 |
| APPLICATION NO. | : 10/227575 |
| DATED | : March 28, 2006 |
| INVENTOR(S) | : John M. Stivoric et al. |

It is certified that error appears in the above-identified patent and that said Letters Patent is hereby corrected as shown below:

Delete the title and substitute therefore the attached title page consisting of the corrected number of drawing sheets in patent.

Delete drawing sheets 1-36 and substitute therefore the attached drawing sheets 1-37.

Delete the entire specification and claims and replace with the attached reprinted specification and claims.

This certificate supersedes the Certificate of Correction issued September 4, 2007 and March 1, 2011.

Signed and Sealed this
Eleventh Day of October, 2011

David J. Kappos
*Director of the United States Patent and Trademark Office*

(12) United States Patent
Stivoric et al.

(10) Patent No.: US 7,020,508 B2
(45) Date of Patent: Mar. 28, 2006

(54) APPARATUS FOR DETECTING HUMAN PHYSIOLOGICAL AND CONTEXTUAL INFORMATION

(75) Inventors: John M. Stivoric, Pittsburgh, PA (US); Scott K. Boehmke, Pittsburgh, PA (US); Eric Teller, Pittsburgh, PA (US); Christopher D. Kasabach, Pittsburgh, PA (US)

(73) Assignee: BodyMedia, Inc., Pittsburgh, PA (US)

( * ) Notice: Subject to any disclaimer, the term of this patent is extended or adjusted under 35 U.S.C. 154(b) by 60 days.

(21) Appl. No.: 10/227,575

(22) Filed: Aug. 22, 2002

(65) Prior Publication Data
US 2004/0039254 A1 Feb. 26, 2004

(51) Int. Cl.
*A61B 5/04* (2006.01)

(52) U.S. Cl. ....................... 600/390; 600/513

(58) Field of Classification Search ................ 600/372, 600/382–384, 386, 388–391, 393, 481, 483, 600/508, 509, 544–547, 549
See application file for complete search history.

(56) References Cited

U.S. PATENT DOCUMENTS

| 4,031,365 A | 6/1977 | Raggiotti et al. | 702/131 |
|---|---|---|---|
| 4,052,979 A | 10/1977 | Scherr et al. | 600/503 |
| 4,129,125 A | 12/1978 | Lester et al. | 600/484 |
| 4,148,304 A | 4/1979 | Mull | 600/549 |
| 4,151,831 A | 5/1979 | Lester | 600/549 |
| 4,192,000 A | 3/1980 | Lipsey | |
| 4,377,171 A | 3/1983 | Wada | 600/549 |
| 4,407,295 A | 10/1983 | Steuer et al. | 600/483 |
| 4,488,558 A * | 12/1984 | Simbruner et al. | 600/376 |
| 4,509,531 A | 4/1985 | Ward | 600/549 |
| 4,531,527 A | 7/1985 | Reinhold, Jr. et al. | 600/509 |
| 4,557,273 A | 12/1985 | Stoller et al. | 600/551 |
| 4,608,987 A | 9/1986 | Mills | 600/389 |
| 4,622,979 A | 11/1986 | Katchis et al. | 600/515 |
| 4,672,977 A * | 6/1987 | Kroll | 600/528 |
| 4,676,254 A | 6/1987 | Frohn | 600/549 |

(Continued)

FOREIGN PATENT DOCUMENTS

DE 198 32 361 A1 2/2000

(Continued)

OTHER PUBLICATIONS

"Georgia Tech Researchers Develop First 'Smart T-shirt'," Nov. 14, 1997 press release, Georgia Institute of Technology.

(Continued)

*Primary Examiner*—Carl Layno
(74) *Attorney, Agent, or Firm*—Metz Lewis LLC; Barry I. Friedman

(57) ABSTRACT

A detecting apparatus includes a housing support section(s), a housing removably attached thereto, one or more sensors and a processor. An alternate apparatus measures heat flux and includes a known resistivity base member, a processing unit and two temperature measuring devices, one in thermal communication with the body through a thermal energy communicator and the other in thermal communication with the ambient environment. A further alternate apparatus includes a housing or flexible section having an adhesive material on a surface thereof for removably attaching the apparatus to the body. A further alternate apparatus includes a housing having an inner surface having a concave shape in a first direction and convex shape in a second direction substantially perpendicular thereto. Also, an apparatus for detecting heart related parameters includes one or more filtering sensors for generating filtering signals related to the non-heart related motion of the body.

222 Claims, 37 Drawing Sheets

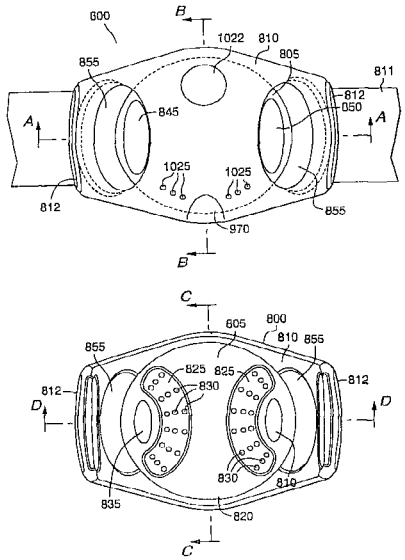

APPARATUS FOR DETECTING HUMAN PHYSIOLOGICAL AND CONTEXTUAL INFORMATION

FIELD OF THE INVENTION

The present invention also relates to a number of embodiments of an apparatus which includes one or more sensors for collecting and storing data relating to an individual's physiological state and various contextual parameters.

BACKGROUND OF THE INVENTION

Research has shown that a large number of the top health problems in society are either caused in whole or in part by an unhealthy lifestyle. More and more, our society requires people to lead fast-paced, achievement-oriented lifestyles that often result in poor eating habits, high stress levels, lack of exercise, poor sleep habits and the inability to find the time to center the mind and relax. Recognizing this fact, people are becoming increasingly interested in establishing a healthier lifestyle.

Traditional medicine, embodied in the form of an HMO or similar organizations, does not have the time, the training, or the reimbursement mechanism to address the needs of those individuals interested in a healthier lifestyle. There have been several attempts to meet the needs of these individuals, including a perfusion of fitness programs and exercise equipment, dietary plans, self-help books, alternative therapies, and most recently, a plethora of health information web sites on the Internet. Each of these attempts are targeted to empower the individual to take charge and get healthy. Each of these attempts, however, addresses only part of the needs of individuals seeking a healthier lifestyle and ignores many of the real barriers that most individuals face when trying to adopt a healthier lifestyle. These barriers include the fact that the individual is often left to himself or herself to find motivation, to implement a plan for achieving a healthier lifestyle, to monitor progress, and to brainstorm solutions when problems arise; the fact that existing programs are directed to only certain aspects of a healthier lifestyle, and rarely come as a complete package; and the fact that recommendations are often not targeted to the unique characteristics of the individual or his life circumstances.

SUMMARY OF THE INVENTION

An apparatus is disclosed for detecting human physiological or contextual information from the body of an individual wearing the apparatus. The apparatus includes a flexible section that is adapted to engage a portion of the wearer's body, and a housing that is removably attached to the flexible section. The housing supports one or more physiological and/or contextual sensors and a processor in electrical communication with the sensors. According to one embodiment, the apparatus may include multiple flexible sections that may be selectively attached to the housing. The apparatus may also have operating parameters that are adjustable depending on the particular flexible section that is attached to the housing at a particular time. The operating parameters, for example, may be adjusted through the interaction of a switch or switches provided on or in the housing and a switch activator or switch activators provided on or in each of the flexible sections. Various structures for removably attaching the housing to the flexible section are described, including, but not limited to, tongues and grooves, adhesives, magnets, and elastic bands. The apparatus may also include a wireless transceiver for transmitting information to and receiving information from a computing device.

Also described is an apparatus that is adapted to measure heat flux between the body of the wearer and the ambient environment. The apparatus includes a housing and a base member having a preselected, known resistivity mounted within the housing. The base member may comprise a printed circuit board. A first temperature measuring device is attached to a first side of the base member and a second temperature measuring device is attached to a second side of the base member. The temperature measuring devices may comprise, for example, a thermistor, a thermocouple, or a thermopile. The apparatus further includes a thermal energy communicator mounted between a portion of the body of the wearer and the first temperature measuring device. The thermal energy communicator may include one or more of a heat conduit, a thermally conductive interface material or materials, and a thermally conductive interface component in various combinations. The second temperature measuring device is in thermal communication with the ambient environment. The apparatus may include a thermal interface material and/or a thermally conductive interface component for providing thermal communication between the ambient environment and the second temperature measuring device. A processing unit is provided in the housing and is in electrical communication with the temperature measuring devices. The apparatus may further include a flexible section attached to the housing adapted to engage a portion of the body of the wearer, or a plurality of flexible sections adapted to be selectively attached to the housing. According to one embodiment, the apparatus has operating parameters that may be adjusted depending on the particular flexible section that is attached to the housing.

An apparatus for detecting, monitoring and reporting at least one of human physiological and contextual information from the body of a wearer is also described. The apparatus includes a housing having an adhesive material on at least a portion of an external surface thereof that enables the housing to be removably attached to a portion of the body of the wearer. At least two physiological and/or contextual sensors are supported by the housing. The physiological sensors are adapted to facilitate the generation of data indicative of one or more physiological parameters of the wearer and the contextual sensors are adapted to facilitate the generation of data indicative of one or more contextual parameters of the wearer. A processor is also included and is an electrical communication with the sensors. The processor generates: (i) derived data from at least one of at least a portion of the data indicative of physiological parameters and at least a portion of the data indicative of contextual parameters; and (ii) analytical status data from at least a portion of at least one of the data indicative of physiological parameters, the data indicative of contextual parameters, the derived data and the analytical status data. The apparatus further includes an electronic memory for retrievably storing at least one of the data indicative of physiological parameters, the data indicative of contextual parameters, the derived data and the analytical status data. The apparatus is adapted to transmit to the wearer at least one of the data indicative of physiological parameters, the data indicative of contextual parameters, the derived data and the analytical status data. The housing may be made of a rigid material or a flexible material, such as a flexible plastic film. The apparatus may include a number of displays for transmitting information, including, but not limited to, an LED or an electrochemical display. The apparatus may further include a wireless transceiver for receiving information from and transmitting information to a computing device. The processor of the apparatus and the computing device may be adapted to engage in shared computing. Furthermore, a computing device may be included in the apparatus for transmitting information to the wearer. The computing device may be coupled to the processor, and the processor may be adapted to cause the computing device to trigger an event upon detection of one or more physiological conditions of the individual. The apparatus may further include various structures for manually entering information into the apparatus, such as a button or a touch pad or keyboard provided on the apparatus or on a computing device coupled to the processor. According to one embodiment, the apparatus monitors the degree to which the wearer has followed a predetermined routine. In this embodiment, the analytical status data comprises feedback to the individual relating to the degree to which the individual has followed the predetermined routine, with the feedback being generated from at least a portion of at least one of the data indicative of one or more physiological parameters of the individual, the derived data, and manually entered data. Also described is an apparatus for detecting human physiological or contextual information from the body of an individual wearing the apparatus that includes a housing having an inner surface for mounting adjacent the body and an outer surface opposite the inner surface. The inner surface includes a longitudinal axis and a transverse axis, with the inner surface being generally concave in a first direction and having an axis of concavity coincident with the longitudinal axis and generally convex in a second direction perpendicular to the first direction and having an axis of concavity coincident with the transverse axis. The inner surface may have first and second lateral ends at opposite ends of the axis of concavity, and the housing may have a first radiused portion adjacent to and including the first lateral end and a second radiused portion adjacent to and including the second lateral end. The inner surface may also have third and fourth lateral ends at opposite ends of the axis of convexity, and the housing may have a third radiused portion adjacent to and including the third lateral end and a fourth radiused portion adjacent to and including the fourth lateral end. Further, the outer surface of the housing may have a convex shape between a first lateral side and a second lateral side of the outer surface. According to one embodiment, the housing includes a width dimension as measured between a first lateral side and a second lateral side of the housing, with at least a portion of the first lateral side and second lateral side each having a taper such that the width dimension generally decreases in a direction from the inner surface to the outer surface. The apparatus may include a flexible section attached to the housing that engages the body of the wearer and has a generally convex outer surface.

Also described is an apparatus for detecting from the body of a wearer parameters relating to the heart of the wearer including an acoustic-based non-ECG heart parameter sensor that generates a first signal including a first acoustic component generated from the motion of the wearers heart and a second acoustic component generated from non-heart related motion of the body of the wearer, such as, for example, from footfalls. The apparatus also includes one or more filtering sensors, such as an accelerometer, for generating a second signal related to the non-heart related motion of the body. The second signal is used to subtract the second acoustic component from the first signal to generate a third signal, with the third signal being used to generate the heart related parameters. The first signal may also include an acoustic component generated from ambient noise, and the apparatus may include an ambient noise sensor. In this configuration, the signal from the ambient noise sensor is used to subtract out the acoustic component generated from ambient noise from the signal that is used to generate the heart related parameters.

In addition, a method is disclosed for detecting from the body of a wearer parameters relating to the heart of the wearer. The method comprises steps of generating a first acoustic signal including a first acoustic component generated from the motion of the wearer's heart and a second acoustic component generated from non-heart related motion of the body of the wearer, generating a second signal related to the non-heart related motion of the body, generating a third signal by using the second signal to subtract the second acoustic component from the first signal, and generating the heart related parameters from the third signal. The first acoustic signal may further include a third acoustic component generated from ambient noise and the method may further comprise generating a fourth signal related to the ambient noise with the step of generating the third signal further comprising using the fourth signal to subtract the third acoustic component from the first signal.

BRIEF DESCRIPTION OF THE DRAWINGS

Further features and advantages of the present invention will be apparent upon consideration of the following detailed description of the present invention, taken in conjunction with the following drawings, in which like reference characters refer to like parts, and in which:

FIG. 1 is a diagram of an embodiment of a system for monitoring physiological data and lifestyle over an electronic network according to the present invention;

FIG. 2 is a block diagram of an embodiment of the sensor device shown in FIG. 1;

FIG. 3 is a block diagram of an embodiment of the central monitoring unit shown in FIG. 1;

FIG. 4 is a block diagram of an alternate embodiment of the central monitoring unit shown in FIG. 1;

FIG. 5 is a representation of a preferred embodiment of the Health Manager web page according to an aspect of the present invention;

FIG. 6 is a representation of a preferred embodiment of the nutrition web page according to an aspect of the present invention;

FIG. 7 is a representation of a preferred embodiment of the activity level web page according to an aspect of the present invention;

FIG. 8 is a representation of a preferred embodiment of the mind centering web page according to an aspect of the present invention;

FIG. 9 is a representation of a preferred embodiment of the sleep web page according to an aspect of the present invention;

FIG. 10 is a representation of a preferred embodiment of the daily activities web page according to an aspect of the present invention;

FIG. 11 is a representation of a preferred embodiment of the Health Index web page according to an aspect of the present invention;

FIG. 12 is a front view of a specific embodiment of the sensor device shown in FIG. 1;

FIG. 13 is a back view of a specific embodiment of the sensor device shown in FIG. 1;

FIG. 14 is a side view of a specific embodiment of the sensor device shown in FIG. 1;

FIG. 15 is a bottom view of a specific embodiment of the sensor device shown in FIG. 1;

FIGS. 16 and 17 are front perspective views of a specific embodiment of the sensor device shown in FIG. 1;

FIG. 18 is an exploded side perspective view of a specific embodiment of the sensor device shown in FIG. 1;

FIG. 19 is a side view of the sensor device shown in FIGS. 12 through 18 inserted into a battery recharger unit;

FIG. 20 is a block diagram illustrating all of the components either mounted on or coupled to the printed circuit board forming a part of the sensor device shown in FIGS. 12 through 18; and FIG. 21 is a block diagram of an apparatus for monitoring health, wellness and fitness according to an alternate embodiment of the present invention;

FIG. 22 is a front view of an alternate embodiment of a sensor device according to the present invention;

FIG. 23 is a back view of an alternate embodiment of a sensor device according to the present invention;

FIG. 24 is a cross-sectional view of the sensor device shown in FIG. 22 taken along lines A—A;

FIG. 25 is a cross-sectional view of the sensor device shown in FIG. 22 taken along lines B—B;

FIG. 26 is a cross-sectional view of the sensor device shown in FIG. 22 taken along lines A—A showing the internal components of the housing of the sensor device;

FIG. 27 is a block diagram illustrating the components mounted on or coupled to the printed circuit board forming a part of an embodiment of the sensor device shown in FIGS. 22 through 26;

FIG. 28 is a front view of an alternate embodiment of a sensor device according to the present invention including an LCD;

FIG. 29 is a block diagram illustrating the components mounted on or coupled to the printed circuit board forming a part of an alternate embodiment of the sensor device shown in FIGS. 22 through 26;

FIGS. 30 and 31 are isometric views of an alternate embodiment of a sensor device according to the present invention having a housing adapted to be removably attached to a flexible section;

FIG. 32 is an isometric view of a further alternate embodiment of a sensor device according to the present invention having a housing adapted to be removably attached to a flexible section;

FIG. 33 is an isometric view of an embodiment of a sensor device having adjustable operating parameters according to an aspect of the present invention;

FIG. 34 is an isometric view of an alternate embodiment of a sensor device according to the present invention having a housing having an adhesive material on an external surface thereof for removably attaching the housing to the body;

FIGS. 35A and B are cross-sectional views of a housing for a prior art sensor device;

FIGS. 35C through H are cross-sectional views of various embodiments of a housing for a sensor device according to an aspect of the present invention taken along lines C—C in FIG. 23.

FIG. 36A is a cross-sectional view of a housing for a prior art sensor device;

FIGS. 36B through H are cross-sectional views of various embodiments of a housing for a sensor device according to an aspect of the present invention taken along lines D—D in FIG. 23;

FIG. 37 is an isometric view of an embodiment of a housing for a sensor device according to the present invention having a bottom or inner surface having a concavity in one direction and a convexity in another direction;

FIGS. 38A through D are cross-sectional views of a housing for a sensor device having a flat top surface and flat lateral ends;

FIGS. 39A through F are cross-sectional views of various embodiments of a housing for a sensor device having surfaces designed to deflect objects and prevent movement of the housing; and FIG. 39G is a cross-sectional view of the housing shown in FIG. 39E attached to a flexible section.

FIG. 40A is an elevational drawing of the sensor device mounted within a garment on the upper arm of a wearer.

FIG. 40B is an elevational drawing of the sensor device mounted within a garment on the left chest area of a wearer.

DESCRIPTION OF THE PREFERRED EMBODIMENTS

In general, according to the present invention, data relating to the physiological state, the lifestyle and certain contextual parameters of an individual is collected and transmitted, either subsequently or in real-time, to a site, preferably remote from the individual, where it is stored for later manipulation and presentation to a recipient, preferably over an electronic network such as the Internet. Contextual parameters as used herein means parameters relating to the environment, surroundings and location of the individual, including, but not limited to, air quality, sound quality, ambient temperature, global positioning and the like. Referring to FIG. 1, located at user location 5 is sensor device 10 adapted to be placed in proximity with at least a portion of the human body. Sensor device 10 is preferably worn by an individual user on his or her body, for example as part of a garment such as a form fitting shirt, or as part of an arm band or the like. Sensor device 10, includes one or more sensors, which are adapted to generate signals in response to physiological characteristics of an individual, and a microprocessor. Proximity as used herein means that the sensors of sensor device 10 are separated from the individual's body by a material or the like, or a distance such that the capabilities of the sensors are not impeded.

Sensor device 10 generates data indicative of various physiological parameters of an individual, such as the individual's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and UV radiation exposure and absorption. In certain cases, the data indicative of the various physiological parameters is the signal or signals themselves generated by the one or more sensors and in certain other cases the data is calculated by the microprocessor based on the signal or signals generated by the one or more sensors. Methods for generating data indicative of various physiological parameters and sensors to be used therefor are well known. Table 1 provides several examples of such well known methods and shows the parameter in question, the method used, the sensor device used, and the signal that is generated. Table 1 also provides an indication as to whether further processing based on the generated signal is required to generate the data.

TABLE 1

| Parameter | Method | Sensor | Signal | Further Processing |
|---|---|---|---|---|
| Heart Rate | EKG | 2 Electrodes | DC Voltage | Yes |
| Pulse Rate | BVP | LED Emitter and Optical Sensor | Change in Resistance | Yes |
| Beat-to-Beat Variability | Heart Rate | 2 Electrodes | DC Voltage | Yes |
| EKG | Skin Surface Potentials | 3–10 Electrodes | DC Voltage | No |
| Respiration Rate | Chest Volume Change | Strain Gauge | Change in Resistance | Yes |
| Skin Temperature | Surface Temperature Probe | Thermistors | Change in Resistance | Yes |
| Core Temperature | Esophageal or Rectal Probe | Thermistors | Change in Resistance | Yes |
| Heat Flow | Heat Flux | Thermopile | DC Voltage | Yes |
| Galvanic Skin Response | Skin Conductance | 2 Electrodes | Change in Resistance | No |
| EMG | Skin Surface Potentials | 3 Electrodes | DC Voltage | No |
| EEG | Skin Surface Potentials | Multiple Electrodes | DC Voltage | Yes |
| EOG | Eye Movement | Thin Film Piezoelectric Sensors | DC Voltage | Yes |
| Blood Pressure | Non-Invasive Korotkuff Sounds | Electronic Sphygromarometer | Change in Resistance | Yes |
| Body Fat | Body Impedance | 2 Active Electrodes | Change in Impedance | Yes |
| Activity in Interpreted G Shocks per Minute | Body Movement | Accelerometer | DC Voltage, Capacitance Changes | Yes |
| Oxygen Consumption | Oxygen Uptake | Electro-chemical | DC Voltage Change | Yes |
| Glucose Level | Non-Invasive | Electro-chemical | DC Voltage Change | Yes |
| Body Position (e.g. supine, erect, sitting) | N/A | Mercury Switch Array | DC Voltage Change | Yes |
| Muscle Pressure | N/A | Thin Film Piezoelectric Sensors | DC Voltage Change | Yes |
| UV Radiation Absorption | N/A | UV Sensitive Photo Cells | DC Voltage Change | Yes |

The types of data listed in Table 1 are intended to be examples of the types of data that can be generated by sensor device 10. It is to be understood that other types of data relating to other parameters can be generated by sensor device 10 without departing from the scope of the present invention.

The microprocessor of sensor device 10 may be programmed to summarize and analyze the data. For example, the microprocessor can be programmed to calculate an average, minimum or maximum heart rate or respiration rate over a defined period of time, such as ten minutes. Sensor device 10 may be able to derive information relating to an individual's physiological state based on the data indicative of one or more physiological parameters. The microprocessor of sensor device 10 is programmed to derive such information using known methods based on the data indicative of one or more physiological parameters. Table 2 provides examples of the type of information that can be derived, and indicates some of the types of data that can be used therefor.

TABLE 2

| Derived Information | Data Used |
|---|---|
| Ovulation | Skin temperature, core temperature, oxygen consumption |
| Sleep onset/wake | Beat-to-beat variability, heart rate, pulse rate, respiration rate, skin temperature, core temperature, heat flow, galvanic skin response, EMG, EEG, EOG, blood pressure, oxygen consumption |
| Calories burned | Heart rate, pulse rate, respiration rate, heat flow, activity, oxygen consumption |
| Basal metabolic rate | Heart rate, pulse rate, respiration rate, heat flow, activity, oxygen consumption |
| Basal temperature | Skin temperature, core temperature |
| Activity level | Heart rate, pulse rate, respiration rate, heat flow, activity, oxygen consumption |
| Stress level | EKG, beat-to-beat variability, heart rate, pulse rate, respiration rate, skin temperature, heat flow, galvanic skin response, EMG, EEG, blood pressure, activity, oxygen consumption |
| Relaxation level | EKG, beat-to-beat variability, heart rate, pulse rate, respiration rate, skin temperature, heat flow, galvanic skin response, EMG, EEG, blood pressure, activity, oxygen consumption |

TABLE 2-continued

| Derived Information | Data Used |
| --- | --- |
| Maximum oxygen consumption rate | EKG, heart rate, pulse rate, respiration rate, heat flow, blood pressure, activity, oxygen consumption |
| Rise time or the time it takes to rise from a resting rate to 85% of a target maximum | Heart rate, pulse rate, heat flow, oxygen consumption |
| Time in zone or the time heart rate was above 85% of a target maximum | Heart rate, pulse rate, heat flow, oxygen consumption |
| Recovery time or the time it takes heart rate to return to a resting rate after heart rate was above 85% of a target maximum | Heart rate, pulse rate, heat flow, oxygen consumption |

Additionally, sensor device 10 may also generate data indicative of various contextual parameters relating to the environment surrounding the individual. For example, sensor device 10 can generate data indicative of the air quality, sound level/quality, light quality or ambient temperature near the individual, or even the global positioning of the individual. Sensor device 10 may include one or more sensors for generating signals in response to contextual characteristics relating to the environment surrounding the individual, the signals ultimately being used to generate the type of data described above. Such sensors are well known, as are methods for generating contextual parametric data such as air quality, sound level/quality, ambient temperature and global positioning.

FIG. 2 is a block diagram of an embodiment of sensor device 10. Sensor device 10 includes at least one sensor 12 and microprocessor 20. Depending upon the nature of the signal generated by sensor 12, the signal can be sent through one or more of amplifier 14, conditioning circuit 16, and analog-to-digital converter 18, before being sent to microprocessor 20. For example, where sensor 12 generates an analog signal in need of amplification and filtering, that signal can be sent to amplifier 14, and then on to conditioning circuit 16, which may, for example, be a band pass filter. The amplified and conditioned analog signal can then be transferred to analog-to-digital converter 18, where it is converted to a digital signal. The digital signal is then sent to microprocessor 20. Alternatively, if sensor 12 generates a digital signal, that signal can be sent directly to microprocessor 20.

A digital signal or signals representing certain physiological and/or contextual characteristics of the individual user may be used by microprocessor 20 to calculate or generate data indicative of physiological and/or contextual parameters of the individual user. Microprocessor 20 is programmed to derive information relating to at least one aspect of the individual's physiological state. It should be understood that microprocessor 20 may also comprise other forms of processors or processing devices, such as a microcontroller, or any other device that can be programmed to perform the functionality described herein.

The data indicative of physiological and/or contextual parameters can, according to one embodiment of the present invention, be sent to memory 22, such as flash memory, where it is stored until uploaded in the manner to be described below. Although memory 22 is shown in FIG. 2 as a discrete element, it will be appreciated that it may also be part of microprocessor 20. Sensor device 10 also includes input/output circuitry 24, which is adapted to output and receive as input certain data signals in the manners to be described herein. Thus, memory 22 of the sensor device 10 will build up, over time, a store of data relating to the individual user's body and/or environment. That data is periodically uploaded from sensor device 10 and sent to remote central monitoring unit 30, as shown in FIG. 1, where it is stored in a database for subsequent processing and presentation to the user, preferably through a local or global electronic network such as the Internet. This uploading of data can be an automatic process that is initiated by sensor device 10 periodically or upon the happening of an event such as the detection by sensor device 10 of a heart rate below a certain level, or can be initiated by the individual user or some third party authorized by the user, preferably according to some periodic schedule, such as every day at 10:00 p.m. Alternatively, rather than storing data in memory 22, sensor device 10 may continuously upload data in real time.

The uploading of data from sensor device 10 to central monitoring unit 30 for storage can be accomplished in various ways. In one embodiment, the data collected by sensor device 10 is uploaded by first transferring the data to personal computer 35 shown in FIG. 1 by means of physical connection 40, which, for example, may be a serial connection such as an RS232 or USB port. This physical connection may also be accomplished by using a cradle, not shown, that is electronically coupled to personal computer 35 into which sensor device 10 can be inserted, as is common with many commercially available personal digital assistants. The uploading of data could be initiated by then pressing a button on the cradle or could be initiated automatically upon insertion of sensor device 10. The data collected by sensor device 10 may be uploaded by first transferring the data to personal computer 35 by means of short-range wireless transmission, such as infrared or RF transmission, as indicated at 45.

Once the data is received by personal computer 35, it is optionally compressed and encrypted by any one of a variety of well known methods and then sent out over a local or global electronic network, preferably the Internet, to central monitoring unit 30. It should be noted that personal computer 35 can be replaced by any computing device that has access to and that can transmit and receive data through the electronic network, such as, for example, a personal digital assistant such as the Palm VII sold by Palm, Inc., or the Blackberry 2-way pager sold by Research in Motion, Inc.

Alternatively, the data collected by sensor device 10, after being encrypted and, optionally, compressed by microprocessor 20, may be transferred to wireless device 50, such as a 2-way pager or cellular phone, for subsequent long distance wireless transmission to local telco site 55 using a wireless protocol such as e-mail or as ASCII or binary data. Local telco site 55 includes tower 60 that receives the wireless transmission from wireless device 50 and computer 65 connected to tower 60. According to the preferred embodiment, computer 65 has access to the relevant electronic network, such as the Internet, and is used to transmit the data received in the form of the wireless transmission to the central monitoring unit 30 over the Internet. Although wireless device 50 is shown in FIG. 1 as a discrete device coupled to sensor device 10, it or a device having the same or similar functionality may be embedded as part of sensor device 10.

Sensor device 10 may be provided with a button to be used to time stamp events such as time to bed, wake time, and time of meals. These time stamps are stored in sensor device 10 and are uploaded to central monitoring unit 30 with the rest of the data as described above. The time stamps may include a digitally recorded voice message that, after being uploaded to central monitoring unit 30, are translated using voice recognition technology into text or some other information format that can be used by central monitoring unit 30.

In addition to using sensor device 10 to automatically collect physiological data relating to an individual user, a kiosk could be adapted to collect such data by, for example, weighing the individual, providing a sensing device similar to sensor device 10 on which an individual places his or her hand or another part of his or her body, or by scanning the individual's body using, for example, laser technology or an iStat blood analyzer. The kiosk would be provided with processing capability as described herein and access to the relevant electronic network, and would thus be adapted to send the collected data to the central monitoring unit 30 through the electronic network. A desktop sensing device, again similar to sensor device 10, on which an individual places his or her hand or another part of his or her body may also be provided. For example, such a desktop sensing device could be a blood pressure monitor in which an individual places his or her arm. An individual might also wear a ring having a sensor device 10 incorporated therein. A base, not shown, could then be provided which is adapted to be coupled to the ring. The desktop sensing device or the base just described may then be coupled to a computer such as personal computer 35 by means of a physical or short range wireless connection so that the collected data could be uploaded to central monitoring unit 30 over the relevant electronic network in the manner described above. A mobile device such as, for example, a personal digital assistant, might also be provided with a sensor device 10 incorporated therein. Such a sensor device 10 would be adapted to collect data when mobile device is placed in proximity with the individual's body, such as by holding the device in the palm of one's hand, and upload the collected data to central monitoring unit 30 in any of the ways described herein.

Furthermore, in addition to collecting data by automatically sensing such data in the manners described above, individuals can also manually provide data relating to various life activities that is ultimately transferred to and stored at central monitoring unit 30. An individual user can access a web site maintained by central monitoring unit 30 and can directly input information relating to life activities by entering text freely, by responding to questions posed by the web site, or by clicking through dialog boxes provided by the web site. Central monitoring unit 30 can also be adapted to periodically send electronic mail messages containing questions designed to elicit information relating to life activities to personal computer 35 or to some other device that can receive electronic mail, such as a personal digital assistant, a pager, or a cellular phone. The individual would then provide data relating to life activities to central monitoring unit 30 by responding to the appropriate electronic mail message with the relevant data. Central monitoring unit 30 may also be adapted to place a telephone call to an individual user in which certain questions would be posed to the individual user. The user could respond to the questions by entering information using a telephone keypad, or by voice, in which case conventional voice recognition technology would be used by central monitoring unit 30 to receive and process the response. The telephone call may also be initiated by the user, in which case the user could speak to a person directly or enter information using the keypad or by voice/voice recognition technology. Central monitoring unit 30 may also be given access to a source of information controlled by the user, for example the user's electronic calendar such as that provided with the Outlook product sold by Microsoft Corporation of Redmond, Wash., from which it could automatically collect information. The data relating to life activities may relate to the eating, sleep, exercise, mind centering or relaxation, and/or daily living habits, patterns and/or activities of the individual. Thus, sample questions may include: What did you have for lunch today? What time did you go to sleep last night? What time did you wake up this morning? How long did you run on the treadmill today?

Feedback may also be provided to a user directly through sensor device 10 in a visual form, for example through an LED or LCD or by constructing sensor device 10, at least in part, of a thermochromatic plastic, in the form of an acoustic signal or in the form of tactile feedback such as vibration. Such feedback may be a reminder or an alert to eat a meal or take medication or a supplement such as a vitamin, to engage in an activity such as exercise or meditation, or to drink water when a state of dehydration is detected. Additionally, a reminder or alert can be issued in the event that a particular physiological parameter such as ovulation has been detected, a level of calories burned during a workout has been achieved or a high heart rate or respiration rate has been encountered.

As will be apparent to those of skill in the art, it may be possible to "download" data from central monitoring unit 30 to sensor device 10. The flow of data in such a download process would be substantially the reverse of that described above with respect to the upload of data from sensor device 10. Thus, it is possible that the firmware of microprocessor 20 of sensor device 10 can be updated or altered remotely, i.e., the microprocessor can be reprogrammed, by downloading new firmware to sensor device 10 from central monitoring unit 30 for such parameters as timing and sample rates of sensor device 10. Also, the reminders/alerts provided by sensor device 10 may be set by the user using the web site maintained by central monitoring unit 30 and subsequently downloaded to the sensor device 10.

Referring to FIG. 3, a block diagram of an embodiment of central monitoring unit 30 is shown. Central monitoring unit 30 includes CSU/DSU 70 which is connected to router 75, the main function of which is to take data requests or traffic, both incoming and outgoing, and direct such requests and traffic for processing or viewing on the web site maintained by central monitoring unit 30. Connected to router 75 is firewall 80. The main purpose of firewall 80 is to protect the remainder of central monitoring unit 30 from unauthorized or malicious intrusions. Switch 85, connected to firewall 80, is used to direct data flow between middleware servers 95a through 95c and database server 110. Load balancer 90 is provided to spread the workload of incoming requests among the identically configured middleware servers 95a through 95c. Load balancer 90, a suitable example of which is the F5 ServerIron product sold by Foundry Networks, Inc. of San Jose, Calif., analyzes the availability of each middleware server 95a through 95c, and the amount of system resources being used in each middleware server 95a through 95c, in order to spread tasks among them appropriately.

Central monitoring unit 30 includes network storage device 100, such as a storage area network or SAN, which acts as the central repository for data. In particular, network storage device 100 comprises a database that stores all data gathered for each individual user in the manners described above. An example of a suitable network storage device 100 is the Symmetrix product sold by EMC Corporation of Hopkinton, Mass. Although only one network storage device 100 is shown in FIG. 3, it will be understood that multiple network storage devices of various capacities could be used depending on the data storage needs of central monitoring unit 30. Central monitoring unit 30 also includes database server 110 which is coupled to network storage device 100. Database server 110 is made up of two main components: a large scale multiprocessor server and an enterprise type software server component such as the 8/8i component sold by Oracle Corporation of Redwood City, Calif., or the 506 7 component sold by Microsoft Corporation of Redmond, Wash. The primary functions of database server 110 are that of providing access upon request to the data stored in network storage device 100, and populating network storage device 100 with new data. Coupled to network storage device 100 is controller 115, which typically comprises a desktop personal computer, for managing the data stored in network storage device 100.

Middleware servers 95a through 95c, a suitable example of which is the 22OR Dual Processor sold by Sun Microsystems, Inc. of Palo Alto, Calif., each contain software for generating and maintaining the corporate or home web page or pages of the web site maintained by central monitoring unit 30. As is known in the art, a web page refers to a block or blocks of data available on the World-Wide Web comprising a file or files written in Hypertext Markup Language or HTML, and a web site commonly refers to any computer on the Internet running a World-Wide Web server process. The corporate or home web page or pages are the opening or landing web page or pages that are accessible by all members of the general public that visit the site by using the appropriate uniform resource locator or URL. As is known in the art, URLs are the form of address used on the World-Wide Web and provide a standard way of specifying the location of an object, typically a web page, on the Internet. Middleware servers 95a through 95c also each contain software for generating and maintaining the web pages of the web site of central monitoring unit 30 that can only be accessed by individuals that register and become members of central monitoring unit 30. The member users will be those individuals who wish to have their data stored at central monitoring unit 30. Access by such member users is controlled using passwords for security purposes. Preferred embodiments of those web pages are described in detail below and are generated using collected data that is stored in the database of network storage device 100.

Middleware servers 95a through 95c also contain software for requesting data from and writing data to network storage device 100 through database server 110. When an individual user desires to initiate a session with the central monitoring unit 30 for the purpose of entering data into the database of network storage device 100, viewing his or her data stored in the database of network storage device 100, or both, the user visits the home web page of central monitoring unit 30 using a browser program such as Internet Explorer distributed by Microsoft Corporation of Redmond, Wash., and logs in as a registered user. Load balancer 90 assigns the user to one of the middleware servers 95a through 95c, identified as the chosen middleware server. A user will preferably be assigned to a chosen middleware server for each entire session. The chosen middleware server authenticates the user using any one of many well known methods, to ensure that only the true user is permitted to access the information in the database. A member user may also grant access to his or her data to a third party such as a health care provider or a personal trainer. Each authorized third party may be given a separate password and may view the member user's data using a conventional browser. It is therefore possible for both the user and the third party to be the recipient of the data.

When the user is authenticated, the chosen middleware server requests, through database server 110, the individual user's data from network storage device 100 for a predetermined time period. The predetermined time period is preferably thirty days. The requested data, once received from network storage device 100, is temporarily stored by the chosen middleware server in cache memory. The cached data is used by the chosen middleware server as the basis for presenting information, in the form of web pages, to the user again through the user's browser. Each middleware server 95a through 95c is provided with appropriate software for generating such web pages, including software for manipulating and performing calculations utilizing the data to put the data in appropriate format for presentation to the user. Once the user ends his or her session, the data is discarded from cache. When the user initiates a new session, the process for obtaining and caching data for that user as described above is repeated. This caching system thus ideally requires that only one call to the network storage device 100 be made per session, thereby reducing the traffic that database server 110 must handle. Should a request from a user during a particular session require data that is outside of a predetermined time period of cached data already retrieved, a separate call to network storage device 100 may be performed by the chosen middleware server. The predetermined time period should be chosen, however, such that such additional calls are minimized. Cached data may also be saved in cache memory so that it can be reused when a user starts a new session, thus eliminating the need to initiate a new call to network storage device 100.

As described in connection with Table 2, the microprocessor of sensor device 10 may be programmed to derive information relating to an individual's physiological state based on the data indicative of one or more physiological parameters. Central monitoring unit 30, and preferably middleware servers 95a through 95c, may also be similarly programmed to derive such information based on the data indicative of one or more physiological parameters.

It is also contemplated that a user will input additional data during a session, for example, information relating to the user's eating or sleeping habits. This additional data is preferably stored by the chosen middleware server in a cache during the duration of the user's session. When the user ends the session, this additional new data stored in a cache is transferred by the chosen middleware server to database server 110 for population in network storage device 100. Alternatively, in addition to being stored in a cache for potential use during a session, the input data may also be immediately transferred to database server 110 for population in network storage device 100, as part of a write-through cache system which is well known in the art.

Data collected by sensor device 10 shown in FIG. 1 is periodically uploaded to central monitoring unit 30. Either by long distance wireless transmission or through personal computer 35, a connection to central monitoring unit 30 is made through an electronic network, preferably the Internet. In particular, connection is made to load balancer 90 through CSU/DSU 70, router 75, firewall 80 and switch 85. Load balancer 90 then chooses one of the middleware servers 95a through 95c to handle the upload of data, hereafter called the chosen middleware server. The chosen middleware server authenticates the user using any one of many well known methods. If authentication is successful, the data is uploaded to the chosen middleware server as described above, and is ultimately transferred to database server 110 for population in the network storage device 100.

Referring to FIG. 4, an alternate embodiment of central monitoring unit 30 is shown. In addition to the elements shown and described with respect to FIG. 3, the embodiment of the central monitoring unit 30 shown in FIG. 4 includes a mirror network storage device 120 which is a redundant backup of network storage device 100. Coupled to mirror network storage device 120 is controller 122. Data from network storage device 100 is periodically copied to mirror network storage device 120 for data redundancy purposes.

Third parties such as insurance companies or research institutions may be given access, possibly for a fee, to certain of the information stored in mirror network storage device 120. Preferably, in order to maintain the confidentiality of the individual users who supply data to central monitoring unit 30, these third parties are not given access to such user's individual database records, but rather are only given access to the data stored in mirror network storage device 120 in aggregate form. Such third parties may be able to access the information stored in mirror network storage device 120 through the Internet using a conventional browser program. Requests from third parties may come in through CSU/DSU 70, router 75, firewall 80 and switch 85. In the embodiment shown in FIG. 4, a separate load balancer 130 is provided for spreading tasks relating to the accessing and presentation of data from mirror drive array 120 among identically configured middleware servers 135a through 135c. Middleware servers 135a through 135c each contain software for enabling the third parties to, using a browser, formulate queries for information from mirror network storage device 120 through separate database server 125. Middleware servers 135a through 135c also contain software for presenting the information obtained from mirror network storage device 120 to the third parties over the Internet in the form of web pages. In addition, the third parties can choose from a series of prepared reports that have information packaged along subject matter lines, such as various demographic categories.

As will be apparent to one of skill in the art, instead of giving these third parties access to the backup data stored in mirror network storage device 120, the third parties may be given access to the data stored in network storage device 100. Also, instead of providing load balancer 130 and middleware servers 135a through 135c, the same functionality, although at a sacrificed level of performance, could be provided by load balancer 90 and middleware servers 95a through 95c.

When an individual user first becomes a registered user or member, that user completes a detailed survey. The purposes of the survey are to: identify unique characteristics/circumstances for each user that they might need to address in order to maximize the likelihood that they will implement and maintain a healthy lifestyle as suggested by central monitoring unit 30; gather baseline data which will be used to set initial goals for the individual user and facilitate the calculation and display of certain graphical data output such as the Health Index pistons; identify unique user characteristics and circumstances that will help central monitoring unit 30 customize the type of content provided to the user in the Health Manager's Daily Dose; and identify unique user characteristics and circumstances that the Health Manager can guide the user to address as possible barriers to a healthy lifestyle through the problem-solving function of the Health Manager.

The specific information to be surveyed may include: key individual temperamental characteristics, including activity level, regularity of eating, sleeping, and bowel habits, initial response to situations, adaptability, persistence, threshold of responsiveness, intensity of reaction, and quality of mood; the user's level of independent functioning, i.e., self-organization and management, socialization, memory, and academic achievement skills; the user's ability to focus and sustain attention, including the user's level of arousal, cognitive tempo, ability to filter distractions, vigilance, and self-monitoring; the user's current health status including current weight, height, and blood pressure, most recent general physician visit, gynecological exam, and other applicable physician/healthcare contacts, current medications and supplements, allergies, and a review of current symptoms and/or health-related behaviors; the user's past health history, i.e., illnesses/surgeries, family history, and social stress events, such as divorce or loss of a job, that have required adjustment by the individual; the user's beliefs, values and opinions about health priorities, their ability to alter their behavior and, what might contribute to stress in their life, and how they manage it; the user's degree of self-awareness, empathy, empowerment, and self-esteem, and the user's current daily routines for eating, sleeping, exercise, relaxation and completing activities of daily living; and the user's perception of the temperamental characteristics of two key persons in their life, for example, their spouse, a friend, a co-worker, or their boss, and whether there are clashes present in their relationships that might interfere with a healthy lifestyle or contribute to stress.

Each member user will have access, through the home web page of central monitoring unit 30, to a series of web pages customized for that user, referred to as the Health Manager. The opening Health Manager web page 150 is shown in FIG. 5. The Health Manager web pages are the main workspace area for the member user. The Health Manager web pages comprise a utility through which central monitoring unit 30 provides various types and forms of data, commonly referred to as analytical status data, to the user that is generated from the data it collects or generates, namely one or more of: the data indicative of various physiological parameters generated by sensor device 10; the data derived from the data indicative of various physiological parameters; the data indicative of various contextual parameters generated by sensor device 10; and the data input by the user. Analytical status data is characterized by the application of certain utilities or algorithms to convert one or more of the data indicative of various physiological parameters generated by sensor device 10, the data derived from the data indicative of various physiological parameters, the data indicative of various contextual parameters generated by sensor device 10, and the data input by the user into calculated health, wellness and lifestyle indicators. For example, based on data input by the user relating to the foods he or she has eaten, things such as calories and amounts of proteins, fats, carbohydrates, and certain vitamins can be calculated. As another example, skin temperature, heart rate, respiration rate, heat flow and/or GSR can be used to provide an indicator to the user of his or her stress level over a desired time period. As still another example, skin temperature, heat flow, beat-to-beat heart variability, heart rate, pulse rate, respiration rate, core temperature, galvanic skin response, EMG, EEG, EOG, blood pressure, oxygen consumption, ambient sound and body movement or motion as detected by a device such as an accelerometer can be used to provide indicators to the user of his or her sleep patterns over a desired time period.

Located on the opening Health Manager web page 150 is Health Index 155. Health Index 155 is a graphical utility used to measure and provide feedback to member users regarding their performance and the degree to which they have succeeded in reaching a healthy daily routine suggested by central monitoring unit 30. Health Index 155 thus provides an indication for the member user to track his or her progress. Health Index 155 includes six categories relating to the user's health and lifestyle: Nutrition, Activity Level, Mind Centering, Sleep, Daily Activities and How You Feel. The Nutrition category relates to what, when and how much a person eats and drinks. The Activity Level category relates to how much a person moves around. The Mind Centering category relates to the quality and quantity of time a person spends engaging in some activity that allows the body to achieve a state of profound relaxation while the mind becomes highly alert and focused. The Sleep category relates to the quality and quantity of a person's sleep. The Daily Activities category relates to the daily responsibilities and health risks people encounter. Finally, the How You Feel category relates to the general perception that a person has about how they feel on a particular day. Each category has an associated level indicator or piston that indicates, preferably on a scale ranging from poor to excellent, how the user is performing with respect to that category.

When each member user completes the initial survey described above, a profile is generated that provides the user with a summary of his or her relevant characteristics and life circumstances. A plan and/or set of goals is provided in the form of a suggested healthy daily routine. The suggested healthy daily routine may include any combination of specific suggestions for incorporating proper nutrition, exercise, mind centering, sleep, and selected activities of daily living in the user's life. Prototype schedules may be offered as guides for how these suggested activities can be incorporated into the user's life. The user may periodically retake the survey, and based on the results, the items discussed above will be adjusted accordingly.

The Nutrition category is calculated from both data input by the user and sensed by sensor device 10. The data input by the user comprises the time and duration of breakfast, lunch, dinner and any snacks, and the foods eaten, the supplements such as vitamins that are taken, and the water and other liquids consumed during a relevant, pre-selected time period. Based upon this data and on stored data relating to known properties of various foods, central monitoring unit 30 calculates well known nutritional food values such as calories and amounts of proteins, fats, carbohydrates, vitamins, etc., consumed.

The Nutrition Health Index piston level is preferably determined with respect to the following suggested healthy daily routine: eat at least three meals; eat a varied diet consisting of 6–11 servings of bread, pasta, cereal, and rice, 2–4 servings fruit, 3–5 servings of vegetables, 2–3 servings of fish, meat, poultry, dry beans, eggs, and nuts, and 2–3 servings of milk, yogurt and cheese; and drink 8 or more 8 ounce glasses of water. This routine may be adjusted based on information about the user, such as sex, age, height and/or weight. Certain nutritional targets may also be set by the user or for the user, relating to daily calories, protein, fiber, fat, carbohydrates, and/or water consumption and percentages of total consumption. Parameters utilized in the calculation of the relevant piston level include the number of meals per day, the number of glasses of water, and the types and amounts of food eaten each day as input by the user.

Nutritional information is presented to the user through nutrition web page 160 as shown in FIG. 6. The preferred nutritional web page 160 includes nutritional fact charts 165 and 170 which illustrate actual and target nutritional facts, respectively as pie charts, and nutritional intake charts 175 and 180 which show total actual nutritional intake and target nutritional intake, respectively as pie charts. Nutritional fact charts 165 and 170 preferably show a percentage breakdown of items such as carbohydrates, protein and fat, and nutritional intake charts 175 and 180 are preferably broken down to show components such as total and target calories, fat, carbohydrates, protein, and vitamins. Web page 160 also includes meal and water consumption tracking 185 with time entries, hyperlinks 190 which allow the user to directly access nutrition-related news items and articles, suggestions for refining or improving daily routine with respect to nutrition and affiliate advertising elsewhere on the network, and calendar 195 for choosing between views having variable and selectable time periods. The items shown at 190 may be selected and customized based on information learned about the individual in the survey and on their performance as measured by the Health Index.

The Activity Level category of Health Index 155 is designed to help users monitor how and when they move around during the day and utilizes both data input by the user and data sensed by sensor device 10. The data input by the user may include details regarding the user's daily activities, for example the fact that the user worked at a desk from 8 a.m. to 5 p.m. and then took an aerobics class from 6 p.m. to 7 p.m. Relevant data sensed by sensor device 10 may include heart rate, movement as sensed by a device such as an accelerometer, heat flow, respiration rate, calories burned, GSR and hydration level, which may be derived by sensor device 60 or central monitoring unit 30. Calories burned may be calculated in a variety of manners, including: the multiplication of the type of exercise input by the user by the duration of exercise input by the user; sensed motion multiplied by time of motion multiplied by a filter constant; or sensed heat flux multiplied by time multiplied by a filter constant.

The Activity Level Health Index piston level is preferably determined with respect to a suggested healthy daily routine that includes: exercising aerobically for a pre-set time period, preferably 20 minutes, or engaging in a vigorous lifestyle activity for a pre-set time period, preferably one hour, and burning at least a minimum target number of calories, preferably 205 calories, through the aerobic exercise and/or lifestyle activity. The minimum target number of calories may be set according to information about the user, such as sex, age, height and/or weight. Parameters utilized in the calculation of the relevant piston level include the amount of time spent exercising aerobically or engaging in a vigorous lifestyle activity as input by the user and/or sensed by sensor device 10, and the number of calories burned above pre-calculated energy expenditure parameters.

Information regarding the individual user's movement is presented to the user through activity level web page 200 shown in FIG. 7, which may include activity graph 205 in the form of a bar graph, for monitoring the individual user's activities in one of three categories: high, medium and low intensity with respect to a pre-selected unit of time. Activity percentage chart 210, in the form of a pie chart, may also be provided for showing the percentage of a pre-selected time period, such as one day, that the user spent in each category. Activity level web page 200 may also include calorie section 215 for displaying items such as total calories burned, daily target calories burned, total caloric intake, and duration of aerobic activity. Finally, activity level web page 200 may include at least one hyperlink 220 to allow a user to directly access relevant news items and articles, suggestions for refining or improving daily routine with respect to activity level and affiliate advertising elsewhere on the network. Activity level web page 200 may be viewed in a variety of formats, and may include user-selectable graphs and charts such as a bar graph, pie chart, or both, as selectable by Activity level check boxes 225. Activity level calendar 230 is provided for selecting among views having variable and selectable time periods. The items shown at 220 may be selected and customized based on information learned about the individual in the survey and on their performance as measured by the Health Index.

The Mind Centering category of Health Index 155 is designed to help users monitor the parameters relating to time spent engaging in certain activities which allow the body to achieve a state of profound relaxation while the mind becomes focused, and is based upon both data input by the user and data sensed by the sensor device 10. In particular, a user may input the beginning and end times of relaxation activities such as yoga or meditation. The quality of those activities as determined by the depth of a mind centering event can be measured by monitoring parameters including skin temperature, heart rate, respiration rate, and heat flow as sensed by sensor device 10. Percent change in GSR as derived either by sensor device 10 or central monitoring unit 30 may also be utilized.

The Mind Centering Health Index piston level is preferably calculated with respect to a suggested healthy daily routine that includes participating each day in an activity that allows the body to achieve profound relaxation while the mind stays highly focused for at least fifteen minutes. Parameters utilized in the calculation of the relevant piston level include the amount of time spent in a mind centering activity, and the percent change in skin temperature, heart rate, respiration rate, heat flow or GSR as sensed by sensor device 10 compared to a baseline which is an indication of the depth or quality of the mind centering activity.

Information regarding the time spent on self-reflection and relaxation is presented to the user through mind centering web page 250 shown in FIG. 8. For each mind centering activity, referred to as a session, the preferred mind centering web page 250 includes the time spent during the session, shown at 255, the target time, shown at 260, comparison section 265 showing target and actual depth of mind centering, or focus, and a histogram 270 that shows the overall level of stress derived from such things as skin temperature, heart rate, respiration rate, heat flow and/or GSR. In comparison section 265, the human figure outline showing target focus is solid, and the human figure outline showing actual focus ranges from fuzzy to solid depending on the level of focus. The preferred mind centering web page may also include an indication of the total time spent on mind centering activities, shown at 275, hyperlinks 280 which allow the user to directly access relevant news items and articles, suggestions for refining or improving daily routine with respect to mind centering and affiliate advertising, and a calendar 285 for choosing among views having variable and selectable time periods. The items shown at 280 may be selected and customized based on information learned about the individual in the survey and on their performance as measured by the Health Index.

The Sleep category of Health Index 155 is designed to help users monitor their sleep patterns and the quality of their sleep. It is intended to help users learn about the importance of sleep in their healthy lifestyle and the relationship of sleep to circadian rhythms, being the normal daily variations in body functions. The Sleep category is based upon both data input by the user and data sensed by sensor device 10. The data input by the user for each relevant time interval includes the times the user went to sleep and woke up and a rating of the quality of sleep. As noted in Table 2, the data from sensor device 10 that is relevant includes skin temperature, heat flow, beat-to-beat heart variability, heart rate, pulse rate, respiration rate, core temperature, galvanic skin response, EMG, EEG, EOG, blood pressure, and oxygen consumption. Also relevant is ambient sound and body movement or motion as detected by a device such as an accelerometer. This data can then be used to calculate or derive sleep onset and wake time, sleep interruptions, and the quality and depth of sleep.

The Sleep Health Index piston level is determined with respect to a healthy daily routine including getting a minimum amount, preferably eight hours, of sleep each night and having a predictable bed time and wake time. The specific parameters which determine the piston level calculation include the number of hours of sleep per night and the bed time and wake time as sensed by sensor device 10 or as input by the user, and the quality of the sleep as rated by the user or derived from other data.

Information regarding sleep is presented to the user through sleep web page 290 shown in FIG. 9. Sleep web page 290 includes a sleep duration indicator 295, based on either data from sensor device 10 or on data input by the user, together with user sleep time indicator 300 and wake time indicator 305. A quality of sleep rating 310 input by the user may also be utilized and displayed. If more than a one day time interval is being displayed on sleep web page 290, then sleep duration indicator 295 is calculated and displayed as a cumulative value, and sleep time indicator 300, wake time indicator 305 and quality of sleep rating 310 are calculated and illustrated as averages. Sleep web page 290 also includes a user-selectable sleep graph 315 which calculates and displays one sleep related parameter over a pre-selected time interval. For illustrative purposes, FIG. 9 shows heat flow over a one-day period, which tends to be lower during sleeping hours and higher during waking hours. From this information, a person's bio-rhythms can be derived. Sleep graph 315 may also include a graphical representation of data from an accelerometer incorporated in sensor device 10 which monitors the movement of the body. The sleep web page 290 may also include hyperlinks 320 which allow the user to directly access sleep related news items and articles, suggestions for refining or improving daily routine with respect to sleep and affiliate advertising available elsewhere on the network, and a sleep calendar 325 for choosing a relevant time interval. The items shown at 320 may be selected and customized based on information learned about the individual in the survey and on their performance as measured by the Health Index.

The Activities of Daily Living category of Health Index 155 is designed to help users monitor certain health and safety related activities and risks and is based entirely on data input by the user. The Activities of Daily Living category is divided into four sub-categories: personal hygiene, which allows the user to monitor activities such as brushing and flossing his or her teeth and showering; health maintenance, that tracks whether the user is taking prescribed medication or supplements and allows the user to monitor tobacco and alcohol consumption and automobile safety such as seat belt use; personal time, that allows the user to monitor time spent socially with family and friends, leisure, and mind centering activities; and responsibilities, that allows the user to monitor certain work and financial activities such as paying bills and household chores.

The Activities of Daily Living Health Index piston level is preferably determined with respect to the healthy daily routine described below. With respect to personal hygiene, the routine requires that the users shower or bathe each day, brush and floss teeth each day, and maintain regular bowel habits. With respect to health maintenance, the routine requires that the user take medications and vitamins and/or supplements, use a seat belt, refrain from smoking, drink moderately, and monitor health each day with the Health Manager. With respect to personal time, the routine requires the users to spend at least one hour of quality time each day with family and/or friends, restrict work time to a maximum of nine hours a day, spend some time on a leisure or play activity each day, and engage in a mind stimulating activity. With respect to responsibilities, the routine requires the users to do household chores, pay bills, be on time for work, and keep appointments. The piston level is calculated based on the degree to which the user completes a list of daily activities as determined by information input by the user.

Information relating to these activities is presented to the user through daily activities web page 330 shown in FIG. 10. In preferred daily activities web page 330, activities chart 335, selectable for one or more of the sub-categories, shows whether the user has done what is required by the daily routine. A colored or shaded box indicates that the user has done the required activity, and an empty, non-colored or shaded box indicates that the user has not done the activity. Activities chart 335 can be created and viewed in selectable time intervals. For illustrative purposes, FIG. 10 shows the personal hygiene and personal time sub-categories for a particular week. In addition, daily activities web page 330 may include daily activity hyperlinks 340 which allow the user to directly access relevant news items and articles, suggestions for improving or refining daily routine with respect to activities of daily living and affiliate advertising, and a daily activities calendar 345 for selecting a relevant time interval. The items shown at 340 maybe selected and customized based on information learned about the individual in the survey and on their performance as measured by the Health Index.

The How You Feel category of Health Index 155 is designed to allow users to monitor their perception of how they felt on a particular day, and is based on information, essentially a subjective rating, that is input directly by the user. A user provides a rating, preferably on a scale of 1 to 5, with respect to the following nine subject areas: mental sharpness; emotional and psychological well being; energy level; ability to cope with life stresses; appearance; physical well being; self-control; motivation; and comfort in relating to others. Those ratings are averaged and used to calculate the relevant piston level.

Referring to FIG. 11, Health Index web page 350 is shown. Health Index web page 350 enables users to view the performance of their Health Index over a user selectable time interval including any number of consecutive or non-consecutive days. Using Health Index selector buttons 360, the user can select to view the Health Index piston levels for one category, or can view a side-by-side comparison of the Health Index piston levels for two or more categories. For example, a user might want to just turn on Sleep to see if their overall sleep rating improved over the previous month, much in the same way they view the performance of their favorite stock. Alternatively, Sleep and Activity Level might be simultaneously displayed in order to compare and evaluate Sleep ratings with corresponding Activity Level ratings to determine if any day-to-day correlations exist. Nutrition ratings might be displayed with How You Feel for a pre-selected time interval to determine if any correlation exists between daily eating habits and how they felt during that interval. For illustrative purposes, FIG. 11 illustrates a comparison of Sleep and Activity Level piston levels for the week of June 10 through June 16. Health Index web page 350 also includes tracking calculator 365 that displays access information and statistics such as the total number of days the user has logged in and used the Health Manager, the percentage of days the user has used the Health Manager since becoming a subscriber, and percentage of time the user has used the sensor device 10 to gather data.

Referring again to FIG. 5, opening Health Manager web page 150 may include a plurality of user selectable category summaries 156a through 156f, one corresponding to each of the Health Index 155 categories. Each category summary 156a through 156f presents a pre-selected filtered subset of the data associated with the corresponding category. Nutrition category summary 156a displays daily target and actual caloric intake. Activity Level category summary 156b displays daily target and actual calories burned. Mind Centering category summary 156c displays target and actual depth of mind centering or focus. Sleep category summary 156d displays target sleep, actual sleep, and a sleep quality rating. Daily Activities category summary 156e displays a target and actual score based on the percentage of suggested daily activities that are completed. The How You Feel category summary 156f shows a target and actual rating for the day.

Opening Health Manager web page 150 also may include Daily Dose section 157 which provides, on a daily time interval basis, information to the user, including, but not limited to, hyperlinks to news items and articles, commentary and reminders to the user based on tendencies, such as poor nutritional habits, determined from the initial survey. The commentary for Daily Dose 157 may, for example, be a factual statement that drinking 8 glasses of water a day can reduce the risk of colon cancer by as much as 32%, accompanied by a suggestion to keep a cup of water by your computer or on your desk at work and refill often. Opening Health Manager web page 150 also may include a Problem Solver section 158 that actively evaluates the user's performance in each of the categories of Health Index 155 and presents suggestions for improvement. For example, if the system detects that a user's Sleep levels have been low, which suggest that the user has been having trouble sleeping, Problem Solver 158 can provide suggestions for way to improve sleep. Problem Solver 158 also may include the capability of user questions regarding improvements in performance. Opening Health Manager web page 150 may also include a Daily Data section 159 that launches an input dialog box. The input dialog box facilitates input by the user of the various data required by the Health Manager. As is known in the art, data entry may be in the form of selection from pre-defined lists or general free form text input. Finally, opening Health Manager web page 150 may include Body Stats section 161 which may provide information regarding the user's height, weight, body measurements, body mass index or BMI, and vital signs such as heart rate, blood pressure or any of the identified physiological parameters.

Referring to FIGS. 12–17, a specific embodiment of sensor device 10 is shown which is in the form of an armband adapted to be worn by an individual on his or her upper arm, between the shoulder and the elbow. The specific embodiment of sensor device 10 shown in FIGS. 12–17 will, for convenience, be referred to as armband sensor device 400. Armband sensor device 400 includes computer housing 405, flexible wing body 410, and, as shown in FIG. 17, elastic strap 415. Computer housing 405 and flexible wing body 410 are preferably made of a flexible urethane material or an elastomeric material such as rubber or a rubber-silicone blend by a molding process. Flexible wing body 410 includes first and second wings 418 each having a thru-hole 420 located near the ends 425 thereof. First and second wings 418 are adapted to wrap around a portion of the wearer's upper arm.

Elastic strap 415 is used to removably affix armband sensor device 400 to the individual's upper arm. As seen in FIG. 17, bottom surface 426 of elastic strap 415 is provided with Velcro loops 416 along a portion thereof. Each end 427 of elastic strap 415 is provided with Velcro hook patch 428 on bottom surface 426 and pull tab 429 on top surface 430. A portion of each pull tab 429 extends beyond the edge of each end 427.

In order to wear armband sensor device 400, a user inserts each end 427 of elastic strap 415 into a respective thru-hole 420 of flexible wing body 410. The user then places his arm through the loop created by elastic strap 415, flexible wing body 410 and computer housing 405. By pulling each pull tab 429 and engaging Velcro hook patches 428 with Velcro loops 416 at a desired position along bottom surface 426 of elastic strap 415, the user can adjust elastic strap 415 to fit comfortably. Since Velcro hook patches 428 can be engaged with Velcro loops 416 at almost any position along bottom surface 426, armband sensor device 400 can be adjusted to fit arms of various sizes. Also, elastic strap 415 may be provided in various lengths to accommodate a wider range of arm sizes. As will be apparent to one of skill in the art, other means of fastening and adjusting the size of elastic strap may be used, including, but not limited to, snaps, buttons, or buckles. It is also possible to use two elastic straps that fasten by one of several conventional means including Velcro, snaps, buttons, buckles or the like, or merely a single elastic strap affixed to wings 418.

Alternatively, instead of providing thru-holes 420 in wings 418, loops having the shape of the letter D, not shown, may be attached to ends 425 of wings 418 by one of several conventional means. For example, a pin, not shown, may be inserted through ends 425, wherein the pin engages each end of each loop. In this configuration, the D-shaped loops would serve as connecting points for elastic strap 415, effectively creating a thru-hole between each end 425 of each wing 418 and each loop.

As shown in FIG. 18, which is an exploded view of armband sensor device 400, computer housing 405 includes a top portion 435 and a bottom portion 440. Contained within computer housing 405 are printed circuit board or PCB 445, rechargeable battery 450, preferably a lithium ion battery, and vibrating motor 455 for providing tactile feedback to the wearer, such as those used in pagers, suitable examples of which are the Model 12342 and 12343 motors sold by MG Motors Ltd. of the United Kingdom.

Top portion 435 and bottom portion 440 of computer housing 405 sealingly mate along groove 436 into which O-ring 437 is fit, and may be affixed to one another by screws, not shown, which pass through screw holes 438a and stiffeners 438b of bottom portion 440 and apertures 439 in PCB 445 and into threaded receiving stiffeners 451 of top portion 435. Alternately, top portion 435 and bottom portion 440 may be snap fit together or affixed to one another with an adhesive. Preferably, the assembled computer housing 405 is sufficiently water resistant to permit armband sensor device 400 to be worn while swimming without adversely affecting the performance thereof.

As can be seen in FIG. 13, bottom portion 440 includes, on a bottom side thereof, a raised platform 430. Affixed to raised platform 430 is heat flow or flux sensor 460, a suitable example of which is the micro-foil heat flux sensor sold by RdF Corporation of Hudson, N.H. Heat flux sensor 460 functions as a self-generating thermopile transducer, and preferably includes a carrier made of a polyamide film. Bottom portion 440 may include on a top side thereof, that is on a side opposite the side to which heat flux sensor 460 is affixed, a heat sink, not shown, made of a suitable metallic material such as aluminum. Also affixed to raised platform 430 are GSR sensors 465, preferably comprising electrodes formed of a material such as conductive carbonized rubber, gold or stainless steel. Although two GSR sensors 465 are shown in FIG. 13, it will be appreciated by one of skill in the art that the number of GSR sensors 465 and the placement thereof on raised platform 430 can vary as long as the individual GSR sensors 465, i.e., the electrodes, are electrically isolated from one another. By being affixed to raised platform 430, heat flux sensor 460 and GSR sensors 465 are adapted to be in contact with the wearer's skin when armband sensor device 400 is worn. Bottom portion 440 of computer housing 405 may also be provided with a removable and replaceable soft foam fabric pad, not shown, on a portion of the surface thereof that does not include raised platform 430 and screw holes 438a. The soft foam fabric is intended to contact the wearer's skin and make armband sensor device 400 more comfortable to wear.

Electrical coupling between heat flux sensor 460, GSR sensors 465, and PCB 445 may be accomplished in one of various known methods. For example, suitable wiring, not shown, may be molded into bottom portion 440 of computer housing 405 and then electrically connected, such as by soldering, to appropriate input locations on PCB 445 and to heat flux sensor 460 and GSR sensors 465. Alternatively, rather than molding wiring into bottom portion 440, thru-holes may be provided in bottom portion 440 through which appropriate wiring may pass. The thru-holes would preferably be provided with a water tight seal to maintain the integrity of computer housing 405.

Rather than being affixed to raised platform 430 as shown in FIG. 13, one or both of heat flux sensor 460 and GSR sensors 465 may be affixed to the inner portion 466 of flexible wing body 410 on either or both of wings 418 so as to be in contact with the wearer's skin when armband sensor device 400 is worn. In such a configuration, electrical coupling between heat flux sensor 460 and GSR sensors 465, whichever the case may be, and the PCB 445 may be accomplished through suitable wiring, not shown, molded into flexible wing body 410 that passes through one or more thru-holes in computer housing 405 and that is electrically connected, such as by soldering, to appropriate input locations on PCB 445. Again, the thru-holes would preferably be provided with a water tight seal to maintain the integrity of computer housing 405. Alternatively, rather than providing thru-holes in computer housing 405 through which the wiring passes, the wiring may be captured in computer housing 405 during an overmolding process, described below, and ultimately soldered to appropriate input locations on PCB 445.

As shown in FIGS. 12, 16, 17 and 18, computer housing 405 includes a button 470 that is coupled to and adapted to activate a momentary switch 585 on PCB 445. Button 470 may be used to activate armband sensor device 400 for use, to mark the time an event occurred or to request system status information such as battery level and memory capacity. When button 470 is depressed, momentary switch 585 closes a circuit and a signal is sent to processing unit 490 on PCB 445. Depending on the time interval for which button 470 is depressed, the generated signal triggers one of the events just described. Computer housing 405 also includes LEDs 475, which may be used to indicate battery level or memory capacity or to provide visual feedback to the wearer. Rather than LEDs 475, computer housing 405 may also include a liquid crystal display or LCD to provide battery level, memory capacity or visual feedback information to the wearer. Battery level, memory capacity or feedback information may also be given to the user tactily or audibly.

Armband sensor device 400 may be adapted to be activated for use, that is collecting data, when either of GSR sensors 465 or heat flux sensor 460 senses a particular condition that indicates that armband sensor device 400 has been placed in contact with the user's skin. Also, armband sensor device 400 may be adapted to be activated for use when one or more of heat flux sensor 460, GSR sensors 465, accelerometer 495 or 550, or any other device in communication with armband sensor device 400, alone or in combination, sense a particular condition or conditions that indicate that the armband sensor device 400 has been placed in contact with the user's skin for use. At other times, armband sensor device 400 would be deactivated, thus preserving battery power.

Computer housing 405 is adapted to be coupled to a battery recharger unit 480 shown in FIG. 19 for the purpose of recharging rechargeable battery 450. Computer housing 405 includes recharger contacts 485, shown in FIGS. 12, 15, 16 and 17, that are coupled to rechargeable battery 450. Recharger contacts 485 may be made of a material such as brass, gold or stainless steel, and are adapted to mate with and be electrically coupled to electrical contacts, not shown, provided in battery recharger unit 480 when armband sensor device 400 is placed therein. The electrical contacts provided in battery recharger unit 480 may be coupled to recharging circuit 481a provided inside battery recharger unit 480. In this configuration, recharging circuit 481 would be coupled to a wall outlet, such as by way of wiring including a suitable plug that is attached or is attachable to battery recharger unit 480. Alternatively, electrical contacts 480 may be coupled to wiring that is attached to or is attachable to battery recharger unit 480 that in turn is coupled to recharging circuit 481b external to battery recharger unit 480. The wiring in this configuration would also include a plug, not shown, adapted to be plugged into a conventional wall outlet.

Also provided inside battery recharger unit 480 is RF transceiver 483 adapted to receive signals from and transmit signals to RF transceiver 565 provided in computer housing 405 and shown in FIG. 20. RF transceiver 483 is adapted to be coupled, for example by a suitable cable, to a serial port, such as an RS 232 port or a USB port, of a device such as personal computer 35 shown in FIG. 1. Thus, data may be uploaded from and downloaded to armband sensor device 400 using RF transceiver 483 and RF transceiver 565. It will be appreciated that although RF transceivers 483 and 565 are shown in FIGS. 19 and 20, other forms of wireless transceivers may be used, such as infrared transceivers. Alternatively, computer housing 405 may be provided with additional electrical contacts, not shown, that would be adapted to mate with and be electrically coupled to additional electrical contacts, not shown, provided in battery recharger unit 480 when armband sensor device 400 is placed therein. The additional electrical contacts in the computer housing 405 would be coupled to the processing unit 490 and the additional electrical contacts provided in battery recharger unit 480 would be coupled to a suitable cable that in turn would be coupled to a serial port, such as an RS R32 port or a USB port, of a device such as personal computer 35. This configuration thus provides an alternate method for uploading of data from and downloading of data to armband sensor device 400 using a physical connection.

FIG. 20 is a schematic diagram that shows the system architecture of armband sensor device 400, and in particular each of the components that is either on or coupled to PCB 445.

As shown in FIG. 17, PCB 445 includes processing unit 490, which may be a microprocessor, a microcontroller, or any other processing device that can be adapted to perform the functionality described herein. Processing unit 490 is adapted to provide all of the functionality described in connection with microprocessor 20 shown in FIG. 2. A suitable example of processing unit 490 is the Dragonball EZ sold by Motorola, Inc. of Schaumburg, Ill. PCB 445 also has thereon a two-axis accelerometer 495, a suitable example of which is the Model ADXL210 accelerometer sold by Analog Devices, Inc. of Norwood, Mass. Two-axis accelerometer 495 is preferably mounted on PCB 445 at an angle such that its sensing axes are offset at an angle substantially equal to 45 degrees from the longitudinal axis of PCB 445 and thus the longitudinal axis of the wearer's arm when armband sensor device 400 is worn. The longitudinal axis of the wearer's arm refers to the axis defined by a straight line drawn from the wearer's shoulder to the wearer's elbow. The output signals of two-axis accelerometer 495 are passed through buffers 500 and input into analog to digital converter 505 that in turn is coupled to processing unit 490. GSR sensors 465 are coupled to amplifier 510 on PCB 445. Amplifier 510 provides amplification and low pass filtering functionality, a suitable example of which is the Model AD8544 amplifier sold by Analog Devices, Inc. of Norwood, Mass. The amplified and filtered signal output by amplifier 510 is input into amp/offset 515 to provide further gain and to remove any bias voltage and into filter/conditioning circuit 520, which in turn are each coupled to analog to digital converter 505. Heat flux sensor 460 is coupled to differential input amplifier 525, such as the Model INA amplifier sold by Burr-Brown Corporation of Tucson, Ariz., and the resulting amplified signal is passed through filter circuit 530, buffer 535 and amplifier 540 before being input to analog to digital converter 505. Amplifier 540 is configured to provide further gain and low pass filtering, a suitable example of which is the Model AD8544 amplifier sold by Analog Devices, Inc. of Norwood, Mass. PCB 445 also includes thereon a battery monitor 545 that monitors the remaining power level of rechargeable battery 450. Battery monitor 545 preferably comprises a voltage divider with a low pass filter to provide average battery voltage. When a user depresses button 470 in the manner adapted for requesting battery level, processing unit 490 checks the output of battery monitor 545 and provides an indication thereof to the user, preferably through LEDs 475, but also possibly through vibrating motor 455 or ringer 575. An LCD may also be used.

PCB 445 may include three-axis accelerometer 550 instead of or in addition to two-axis accelerometer 495. The three-axis accelerometer outputs a signal to processing unit 490. A suitable example of three-axis accelerometer is the μPAM product sold by I.M. Systems, Inc. of Scottsdale, Ariz. Three-axis accelerometer 550 is preferably tilted in the manner described with respect to two-axis accelerometer 495.

PCB 445 also includes RF receiver 555 that is coupled to processing unit 490. RF receiver 555 may be used to receive signals that are output by another device capable of wireless transmission, shown in FIG. 20 as wireless device 558, worn by or located near the individual wearing armband sensor device 400. Located near as used herein means within the transmission range of wireless device 558. For example, wireless device 558 may be a chest mounted heart rate monitor such as the Tempo product sold by Polar Electro of Oulu, Finland. Using such a heart rate monitor, data indicative of the wearer's heart rate can be collected by armband sensor device 400. Antenna 560 and RF transceiver 565 are coupled to processing unit 490 and are provided for purposes of uploading data to central monitoring unit 30 and receiving data downloaded from central monitoring unit 30. RF transceiver 565 and RF receiver 555 may, for example, employ Bluetooth technology as the wireless transmission protocol. Also, other forms of wireless transmission may be used, such as infrared transmission.

The fact that RF Transceiver 565 may be used for wirelessly uploading data from and wirelessly downloading data to armband sensor device 400 is advantageous because it eliminates the need to remove armband sensor device 400 to perform these functions, as would be required with a physical connection. For example, if armband sensor device 400 was being worn under the user's clothing, requiring removal of armband sensor device 400 prior to uploading and/or downloading data increases user inconvenience. In addition, the wearing of armband sensor device 400 has an effect on the user's skin and underlying blood vessels, which in turn may affect any measurements being made with respect thereto. It may be necessary for a period of time during which armband sensor device 400 is worn by the user to elapse before a steady state is achieved and consistent, accurate measurements can be made. By providing armband sensor device 400 with wireless communications capability, data can be uploaded and downloaded without disturbing an established steady state equilibrium condition. For example, programming data for processing unit 490 that controls the sampling characteristics of armband sensor device 400 can be downloaded to armband sensor device 400 without disturbing the steady state equilibrium condition.

In addition, antenna 560 and RF transceiver 565 permit armband sensor device 400 to communicate wirelessly with other devices capable of wireless communication, i.e., transmit information to and receive information from those devices. The devices may include, for example, devices that are implanted in the body of the person using armband sensor device 400, such as an implantable heart pacemaker or an implantable insulin dispensing device, for example the MiniMed® 2007 implantable insulin pump sold by MiniMed Inc. of Northridge, Calif., devices worn on the body of the person using armband sensor device 400, or devices located near the person using armband sensor device 400 at any particular time, such as an electronic scale, a blood pressure monitor, a glucose monitor, a cholesterol monitor or another armband sensor device 400. With this two-way wireless communication capability, armband sensor device 400 may be adapted to transmit information that activates or deactivates such a device for use or information that programs such a device to behave in a particular way. For example, armband sensor device 400 may be adapted to activate a piece of exercise equipment such as a treadmill and program it to operate with certain parameters that are dictated or desired by or optimal for the user of armband sensor device 400. As another example, armband sensor device 400 may be adapted to adjust a computer controlled thermostat in a home based on the detected skin temperature of the wearer or turn off a computer controlled lighting system, television or stereo when the wearer is determined to have fallen asleep.

Vibrating motor 455 is coupled to processing unit 490 through vibrator driver 570 and provides tactile feedback to the wearer. Similarly, ringer 575, a suitable example of which is the Model SMT916A ringer sold by Projects Unlimited, Inc. of Dayton, Ohio, is coupled to processing unit 490 through ringer driver 580, a suitable example of which is the Model MMBTA14 CTI darlington transistor driver sold by Motorola, Inc. of Schaumburg, Ill., and provides audible feedback to the wearer. Feedback may include, for example, celebratory, cautionary and other threshold or event driven messages, such as when a wearer reaches a level of calories burned during a workout.

Also provided on PCB 445 and coupled to processing unit 490 is momentary switch 585. Momentary switch 585 is also coupled to button 470 for activating momentary switch 585. LEDs 475, used to provide various types of feedback information to the wearer, are coupled to processing unit 490 through LED latch/driver 590.

Oscillator 595 is provided on PCB 445 and supplies the system clock to processing unit 490. Reset circuit 600, accessible and triggerable through a pin-hole in the side of computer housing 405, is coupled to processing unit 490 and enables processing unit 490 to be reset to a standard initial setting.

Rechargeable battery 450, which is the main power source for the armband sensor device 400, is coupled to processing unit 490 through voltage regulator 605. Finally, memory functionality is provided for armband sensor device 400 by SRAM 610, which stores data relating to the wearer of armband sensor device 400, and flash memory 615, which stores program and configuration data, provided on PCB 445. SRAM 610 and flash memory 615 are coupled to processing unit 490 and each preferably have at least 512K of memory.

In manufacturing and assembling armband sensor device 400, top portion 435 of computer housing 405 is preferably formed first, such as by a conventional molding process, and flexible wing body 410 is then overmolded on top of top portion 435. That is, top portion 435 is placed into an appropriately shaped mold, i.e., one that, when top portion 435 is placed therein, has a remaining cavity shaped according to the desired shape of flexible wing body 410, and flexible wing body 410 is molded on top of top portion 435. As a result, flexible wing body 410 and top portion 435 will merge or bond together, forming a single unit. Alternatively, top portion 435 of computer housing 405 and flexible wing body 410 may be formed together, such as by molding in a single mold, to form a single unit. The single unit however formed may then be turned over such that the underside of top portion 435 is facing upwards, and the contents of computer housing 405 can be placed into top portion 435, and top portion 435 and bottom portion 440 can be affixed to one another. As still another alternative, flexible wing body 410 may be separately formed, such as by a conventional molding process, and computer housing 405, and in particular top portion 435 of computer housing 405, may be affixed to flexible wing body 410 by one of several known methods, such as by an adhesive, by snap-fitting, or by screwing the two pieces together. Then, the remainder of computer housing 405 would be assembled as described above. It will be appreciated that rather than assembling the remainder of computer housing 405 after top portion 435 has been affixed to flexible wing body 410, the computer housing 405 could be assembled first and then affixed to flexible wing body 410.

Referring to FIG. 21, a block diagram of an alternate embodiment of the present invention is shown. This alternate embodiment includes stand alone sensor device 700 which functions as an independent device, meaning that it is capable of collecting and/or generating the various types of data described herein in connection with sensor device 10 and sensor device 400 and providing analytical status data to the user without interaction with a remotely located apparatus such as central monitoring unit 30. Stand alone sensor device 700 includes a processor that is programmed and/or otherwise adapted to include the utilities and algorithms necessary to create analytical status data from the data indicative of various physiological and/or contextual parameters of the user, the data derived therefrom, and the data input by the user, all of which is stored in and accessed as needed from memory provided in stand alone sensor device 700. Stand alone sensor device 700 may comprise sensor device 10 shown in FIGS. 1 and 2 that includes microprocessor 20 and memory 22 or armband sensor device 400 shown in FIGS. 12–17 that includes processing unit 490 and SRAM 610.

As shown schematically in FIG. 21, data may be input into stand alone sensor device 700 in a number of ways. Stand alone sensor device 700 may include one or more physiological sensors 705 as described herein for facilitating the collection of data indicative of various physiological parameters of the user. Stand alone sensor device 700 may also include one or more contextual sensors 710 as described herein for facilitating the collection of data indicative of various contextual parameters of the user. As indicated by reference number 715, stand alone sensor device 700 may be adapted to enable the manual entry of data by the user. For example, stand alone sensor device 700 may include a data input button, such as a button 470 of armband sensor device 400, through which a user could manually enter information such as information relating to various life activities of the user as described herein or information relating to the operation and/or control of stand alone sensor device 700, for example, the setting of reminders or alerts as described herein. In this example, activation of button 470 may simply record or time stamp that an event such as a meal has occurred, with the wearer needing to assign a meaning to that time stamp through data entry at a later time. Alternatively, activation of button 470 in certain sequences, such as one activation, two successive activations, three successive activations, etc., can be preset to have different specific meanings. A wearer would need to follow a menu or guide of such preset activation sequences to input relevant data. Alternatively, stand alone sensor device 700 may include a more sophisticated means for manual entry of information such as a keypad, a touch screen, a microphone, or a remote control device, for example a remote control device incorporated into a wristwatch. In the case of a microphone, the processor of stand alone sensor device 700 would be provided with well known voice recognition software or the like for converting the input speech into usable data.

As indicated by reference numbers 720 and 725, information comprising data indicative of various physiological and/or contextual parameters and data derived therefrom may be input into stand alone sensor device 700 through interaction with other devices. In addition, information such as handshake data or data indicative of various physiological and/or contextual parameters and data derived therefrom may be output from stand alone sensor device 700 to such other devices. According to one embodiment, the interaction is in the form of wireless communication between stand alone sensor device 700 and another device capable of wireless communication by way of a wireless transceiver provided in stand alone sensor device 700, such as wireless transceiver 565 shown and described in connection with FIG. 20. The device-to-device interaction may, as shown by reference number 720, be explicit, meaning that the user of stand alone sensor device 700 has knowingly initiated the interaction. For example, a user may activate a button on a scale to upload data to stand alone sensor device 700. The device-to-device interaction may also, as shown by reference number 725, be hidden, meaning that the user of stand alone sensor device 700 does not knowingly initiate the interaction. For example, a gym may have a sensor that wirelessly transmits a signal to sensing device 700 when the user enters and leaves the gym to time stamp when the user began and ended a workout.

As shown schematically in FIG. 21, information may be output or transmitted from stand alone sensor device 700 in a number of ways. Such information may include the data indicative of various physiological parameters and/or contextual parameters, the data derived therefrom, the data manually input by the user, the analytical status data, or any combination thereof. As shown by reference numbers 730, 735 and 740, information may be output or transmitted in an audible fashion such as by a series of tones or beeps or a recorded voice by a device such as a speaker, in a visual fashion such as by one or more LEDs, or in a tactile fashion such as by vibration. For example, stand alone sensor device 700 may be adapted to output a tone or tones, light an LED or LEDs, or vibrate as a reminder for an event, such as a reminder to eat or exercise at a particular time, or when a goal has been reached, such as a target number of calories burned during a workout, or a condition has been sensed, such as ovulation. Alternatively, stand alone sensor device 700 may be provided with a more sophisticated visual output means such as an LCD similar to those found on commercially available cell phones, pagers and personal digital assistants. With an LCD or a similar device and the expanded visual output capabilities it would provide, stand alone sensor device 700 may be adapted to output or transmit some or all of the information described in connection with FIGS. 5 through 11 in the same or a similar format. For example, stand alone sensor device 700 could provide analytical status data in the form of the Health Index to the user. As a further alternative, stand alone sensor device 700 may be coupled to computing device 750 such as a personal computer, a cell phone, a pager, a personal digital assistant, another stand alone sensor device 700 or any other device having a processor by either wired connection 755 or wireless connection 760. For example, battery recharger unit 480 shown in FIG. 19 may be used to provide the wired connection 755 or wireless connection 760. In this configuration, the display of the computing device could be used to visually output information from stand alone sensor device 700. It will be appreciated that since computing device 750 includes a sophisticated output means such as an LCD, it may be used to output or transmit to the user some or all of the information described in connection with FIGS. 5 through 11, such as the Health Index, in the same or a similar format.

Also, computing device 750 may in turn be used to control other devices, such as the lights or thermostat in a home, based on data output by stand alone sensor device 700, such as the fact that the wearer has fallen asleep or the fact that the wearer's skin temperature has reached a certain level. In other words, stand alone sensor device 700, and in particular its processor, may be adapted to cause a computing device 750 to trigger an event upon detection of one or more physiological and/or contextual conditions by stand alone sensor device 700. Alternatively, stand alone sensor device 700 may be adapted to cause a computing device 750 to trigger an event based upon information received from another computing device 750.

Stand alone sensor device 700 may be adapted to interact with and influence an interactive electronic media device, such as a video game, or non-interactive electronic media device, such as on a display device such as a DVD or digital video disc player playing a digitally recorded movie. For example, stand alone sensor device 700 may be adapted to transmit information relating to the physiological state of the wearer to the video game, which in turn adjusts the characteristics of the game, such as the level of difficulty. As another example, stand alone sensor device 700 may be adapted to transmit information relating to the physiological state of the wearer to the device displaying the digitally recorded movie which in turn adjusts the characteristics, such as the outcome, of the movie.

Furthermore, stand alone sensor device 700 may include location sensing device 765, such as an ultrasonic or a radio-frequency identification tag, for enabling a computing device 750 to detect the geographic location of stand alone sensor device 700, such as the location of stand alone sensor device 700 within a defined space such as a building. In one embodiment, a location indication causes computing device 750 to trigger an event, such as lowering the temperature in a room corresponding to the indicated location, preferably based on the detection by stand alone sensor device 700 of one or more physiological conditions of the wearer, such as skin temperature. In another embodiment, the location indication causes computing device 750 to trigger an event, such as lowering the temperature in a room corresponding to the indicated location, if stand alone sensor device 700 detects one or more physiological conditions, such as a skin temperature of the wearer being above a certain level. In addition, the input means of the computing device, such as the mouse and keyboard of a personal computer, the keypad of a cell phone or pager, or the touch screen of a personal digital assistant, may be used to manually input information into stand alone sensor device 700.

The different modes of output may be used in combination to provide different types and levels of information to a user. For example, stand alone sensor device 700 could be worn by an individual while exercising and an LED or a tone can be used to signal that a goal of a certain number of calories burned has been reached. The user could then transmit additional data wirelessly from stand alone sensor device 700 to a computing device 750 such as a cell phone after he or she is finished exercising to view data such as heart rate and/or respiration rate over time.

As a further alternative embodiment of the present invention, rather than the processor provided in stand alone sensor device 700 being programmed and/or otherwise adapted to generate the derived data and to include the utilities and algorithms necessary to create analytical status data, computing device 750 could be so programmed. In this embodiment, stand alone sensor device 700 collects and/or generates the data indicative of various physiological and/or contextual parameters of the user, the data manually input by the user, and/or data input as a result of device-to-device interaction shown at 720 and 725, all of which is stored in the memory provided in stand alone sensor device 700. This data is then periodically uploaded to computing device 750 which in turn generates derived data and/or analytical status data. Alternatively, the processor of stand alone sensor device 700 could be programmed to generate the derived data with computing device 750 being programmed and/or otherwise adapted to include the utilities and algorithms necessary to create analytical status data based on data indicative of one or more physiological and/or contextual parameters, data derived therefrom, data manually input by the user and/or data input as a result of device-to-device interaction shown at 720 and 725 uploaded from stand alone sensor device 700. As still a further alternative, the processor of stand alone sensor device 700 could be programmed and/or otherwise adapted to include the utilities and algorithms necessary to create analytical status data based on data indicative of one or more physiological and/or contextual parameters, data derived therefrom, data manually input by the user and/or data input as a result of device-to-device interaction shown at 720 and 725 uploaded from stand alone sensor device 700 with computing device 750 being programmed to generate the derived data. In either alternative, any or all of the data indicative of physiological and/or contextual parameters of the user, the data derived therefrom, the data manually input by the user, the data input as a result of device-to-device interaction shown at 720 and 725 and the analytical status data may then be viewed by the user using the output means of the programmed computing device 750 or another computing device 750 to which the data is downloaded. In the latter alternative, everything but the analytical status data may also be output by stand alone sensor device 700 as described herein.

Computing device 750 in these alternative embodiments may be connected to an electronic network, such as the Internet, to enable it to communicate with central monitoring unit 30 or the like. The programming of computing device 750 that enables it to generate the derived data and/or the analytical status data may, with such a configuration, be modified or replaced by downloading the relevant data to computing device 750 over the electronic network.

As still a further alternative embodiment, computing device 750 may be provided with a custom written plug-in adapted to provide data display functionality through use of a well known browser program. In this embodiment, stand alone sensor device 700 collects and/or generates the data indicative of various physiological and/or contextual parameters of the user, the derived data, the data input by the user, data input as a result of device-to-device interaction shown at 720 and 725, and/or analytical status data based thereon and uploads this data to computing device 750. The plug-in provided in computing device 750 then generates appropriate display pages based on the data which may be viewed by the user using the browser provided with computing device 750. The plug-in may be modified/updated from a source such as central monitoring unit 30 over an electronic network such as the Internet.

Referring to FIGS. 22–26, an alternate embodiment of a sensor device is shown at 800. Sensor device 800 may be a specific embodiment of either sensor device 10 described in connection with FIGS. 1–11 or stand alone sensor device 700 described in connection with FIG. 21. Sensor device 800 includes housing 805 affixed to flexible section 810, which is similar to flexible wing body 410 shown in FIGS. 12–17. Flexible section 810 is adapted to engage, such as by wrapping around or conforming to, at least a portion of the human body, such as the upper arm, to enable sensor device 800, in combination with a removable strap 811 inserted through slots 812 provided in flexible section 810, to be worn on the body. Preferably, flexible section 810 is made of a material having a durometer of between 75 and 85 Shore A. Flexible section 810 may take on a variety of shapes and may be made of a cloth material, a flexible plastic film, or an elastic material having an adhesive similar in structure to a Band-Aid® disposable adhesive bandage. In the embodiment shown in FIGS. 22–26, housing 805 is permanently affixed to flexible section 810, such as by an over molding or co-molding process, through the use of an adhesive material, or by a fastening mechanism such as one or more screws. Housing 805 includes top portion 815 affixed to bottom portion 820 by any known means, including, for example, an adhesive material, screws, snap fittings, sonic welding, or thermal welding. According to a preferred embodiment, a watertight seal is provided between top portion 815 and bottom portion 820. Such a water-tight seal is provided when sonic welding or thermal welding is used. Alternatively, an O-ring could be provided between top portion 815 and bottom portion 820 to create the water-tight seal.

As can be seen most readily in FIGS. 23, 24 and 26, affixed to bottom portion 820 of housing 805 are GSR sensors 825. GSR sensors 825 measure the conductivity of the skin between two points and may comprise electrodes formed of a material such as stainless steel, gold or a conductive carbonized rubber. Preferably, GSR sensors 825 have an oblong, curved shape as shown in FIG. 23, much like a kidney bean shape, that allows some portion of GSR sensors 825 to maintain contact with the body even if sensor device 800 is rocking or otherwise moving while being worn. Most preferably, GSR sensors 825 include raised bumps 830, or some other three-dimensional textured surface, along the surface thereof to perturb the skin and push between hairs to ensure good contact with the skin. In addition, raised bumps 830 provide channels for the movement of sweat underneath sensor device 800, rather than trapping sweat, no matter the orientation of sensor device with respect to the body. Also affixed to bottom portion 820 are heat flux skin interface component 835 and skin temperature skin interface component 840, each comprising a plate made of a thermally conductive material such as stainless steel. Preferably, heat flux skin interface component 835 and skin temperature skin interface component 840 are made of a material having thermal conduction properties of at least 12.9 W/mK, such as 304 stainless steel. Preferably, GSR sensors 825 are spaced at least 0.44 inches apart from one another, and at least 0.09 inches apart from heat flux skin interface component 835 and skin temperature skin interface component 840. GSR sensors 825, heat flux skin interface component 835 and skin temperature skin interface component 840 are adapted to be in contact with the wearer's skin when sensor device 800 is worn, and facilitate the measurement of GSR, heat flux from the body and skin temperature data. As can be seen most readily in FIGS. 22, 24 and 26, affixed to top portion 815 of housing 805 are heat flux ambient interface component 845 and ambient temperature interface component 850, which also are made of a thermally conductive material such as stainless steel, preferably a material having thermal conduction properties of at least 12.9 W/mK, such as 304 stainless steel. Heat flux ambient interface component 845 and ambient temperature interface component 850 facilitate the measurement of heat flux from the body and ambient temperature, respectively, by providing a thermal interface to the surrounding environment. To further enhance the measurement of these parameters, holes 855 are provided in flexible section 810 to expose heat flux ambient interface component 845 and ambient temperature interface component 850 to the ambient air. Preferably, holes 855 are sized so that flexible section 810 occludes as little skin as possible in the regions surrounding heat flux ambient interface component 845 and ambient temperature interface component 850 so as to allow air flowing off of the skin of the wearer to pass these components.

GSR Sensors 825, heat flux, skin interface component 835, skin temperature skin interface component 840, or any other sensing component that comes into contact with the skin may be provided with a plurality of microneedles for, among other things, enhancing electrical contact with the skin and providing real time access to interstitial fluid in and below the epidermis, which access may be used to measure various parameters such as pH level of the skin through electrochemical, impedance based or other well known methods. Microneedles enhance electrical contact by penetrating the stratum corneum of the skin to reach the epidermis. Such microneedles are well known in the art and may be made of a metal or plastic material. Prior art microneedles are described in, for example, U.S. Pat. No. 6,312,612 owned by the Procter and Gamble Company. Based on the particular application, the number, density, length, width at the point or base, distribution and spacing of the microneedles will vary.

Referring to FIG. 26, which is a cross-section taken along lines A—A in FIG. 22, the internal components of sensor device 800, housed within housing 805, are shown. Printed circuit board or PCB 860 is affixed to top portion 815 of housing 805 and receives and supports the electronic components provided inside housing 805. Affixed to a bottom side of PCB 860 and electronically coupled to GSR sensors 825 are contacts 865, which preferably comprise gold plated contact pins such as the Pogo® contacts available from Everett Charles Technologies in Pomona, Calif. Also affixed to the bottom side of PCB 860 is skin temperature thermistor 870, a suitable example of which is the model 100K6D280 thermistor manufactured by BetaTherm Corporation in Shrewsbury, Mass. Skin temperature thermistor 870 is, according to a preferred embodiment, thermally coupled to skin temperature skin interface component 840 by a thermally conductive interface material 875. Thermally conductive interface material 875 may be any type of thermally conductive interface known in the art, including, for example, thermally conductive gap fillers, thermally conductive phase change interface materials, thermally conductive tapes, thermally conductive cure-in-place compounds or epoxies, and thermal greases. Suitable thermally conductive interface materials include a boron nitride filled expanded polytetrafluoroethylene matrix sold under the trademark PolarChip CP8000 by W. L. Gore & Associates, Inc. and a boron nitride and alumina filled silicone elastomer on an adhesive backed 5 mil. (0.013 cm) thick aluminum foil carrier called A574, which is available from the Chomerics division of Parker Hannefin Corp. located in Woburn, Mass. Provided on top of PCB 860 is near-body ambient temperature thermistor 880, a suitable example of which is the model NTHS040ZN0IN100KJ thermistor manufactured by Vishay Intertechnology, Inc. in Malvern, Pa. Near-body ambient temperature thermistor 880 is thermally coupled to ambient temperature interface component 850 by thermally conductive interface material 875.

Still referring to FIG. 26, a preferred embodiment of sensor device 800 includes a particular embodiment of an apparatus for measuring heat flux between a living body and the ambient environment described in U.S. Pat. No. 6,595,929 B2 owned by the assignee hereof, the disclosure of which is incorporated herein by reference in its entirety. Specifically, heat conduit 885 is provided within housing 805. As used herein, the term heat conduit refers to one or more heat conductors which are adapted to singly or jointly transfer heat from one location to another, such as a conductor made of stainless steel. Heat conduit 885 is thermally coupled to heat flux skin interface component 835 by thermally conductive interface material 875. Provided on the bottom side of PCB 860 is a first heat flux thermistor 890A, and provided on the top side of PCB 860 is a second heat flux thermistor 890B. PCB 860 acts as a base member for supporting these components. It will be appreciated that a base member separate and apart from PCB 860 may be substituted therefor as an alternative configuration. A suitable example of both heat flux thermistors 890A and 890B is the model 100K6D280 thermistor manufactured by Beta Therm Corporation in Shrewsbury, Mass. Heat flux Thermistor 890A and 890B are soldered to pads provided on PCB 860. The second heat flux thermistor 890B is thermally coupled to heat flux ambient interface 845 by thermally conductive interface material 875. As is well-known in the art, PCB 860 is made of a rigid or flexible material, such as a fiberglass, having a preselected, known thermal resistance or resistivity K. The heat flux off of the body of the wearer can be determined by measuring a first voltage V1 with heat flux thermistor 890A and a second voltage V2 with heat flux thermistor 890B. These voltages are then electrically differenced, such as by using a differential amplifier, to provide a voltage value that, as is well known in the art, can be used to calculate the temperature difference (T2−T1) between the top and bottom sides of PCB 860. Heat flux can then be calculated according to the following formula:

Heat Flux=$K(T2-T1)$

The combination of PCB 860 and heat flux thermistors 890A and 890B are thus a form of a heat flux sensor. One advantage of the configuration of the apparatus for measuring heat flux shown in FIG. 26 is that, due to the vertical orientation of the components, assembly of the apparatus for measuring heat flux, and thus sensor device 800 as a whole, is simplified. Also adding to the simplicity is the fact that thermally conductive interface materials that include a thin adhesive layer on one or both sides may be used for thermally conductive interface materials 875, enabling components to be adhered to one another. In addition, thermistors 890A and 890B are relatively inexpensive components, as compared to an integral heat flux sensor such as those commercially available from RdF Corporation of Hudson, N.H., thereby reducing the cost of sensor device 800. Although heat flux thermistors 890A and 890B are described as being provided on PCB 860 in the embodiment shown in FIG. 26, it will be appreciated that any piece of material having a known resistivity K may be used. Furthermore, other temperature measuring devices known in the art, such as a thermocouple or thermopile, may be substituted for heat flux thermistors 890A and 890B. As a further alternative, heat conduit 885 may be omitted such that thermal communication between heat flux thermistor 890A and heat flux skin interface component 835 is provided by one or more pieces of thermally conductive interface material 875. As still a further alternative, heat flux skin interface component 835 may be omitted such that thermal communication between heat flux thermistor 890A and the skin is provided by either or both of heat conduit 885 and one or more pieces of thermally conductive interface material 875. In any of the embodiments described herein, the combination of one or more of heat conduit 885, one or more pieces of thermally conductive interface material 875, and heat flux skin interface component 835 act as a thermal energy communicator for placing heat flux thermistor 890A in thermal communication with the body of the wearer of sensor device 800.

FIG. 27 is a schematic diagram that shows an embodiment of the system architecture of sensor device 800, and in particular each of the components that is either provided on or coupled to PCB 860.

As shown in FIG. 27, PCB 860 includes processing unit 900, which may be a microprocessor, a microcontroller, or any other processing device that can be adapted to perform the functionality described herein, in particular the functionality described in connection with microprocessor 20 shown in FIG. 2, processing unit 490 shown in FIG. 20, or stand alone sensor device 700 shown in FIG. 21. A suitable example of processing unit 900 is the Dragonball EZ sold by Motorola, Inc. of Schaumburg, Ill. Also provided on PCB 860 is accelerometer 905, which may be either a two-axis or a three-axis accelerometer. A suitable example of a two-axis accelerometer is the Model ADXL202 accelerometer sold by Analog Devices, Inc. of Norwood, Mass., and a suitable example of a three-axis accelerometer is the model ACH-04-08-05 accelerator sold by Measurement Specialties Incorporated in Norristown, Pa. The output signals of accelerometer 905 are passed through buffers 910 and input analog to digital, referred to as A/D, converter 915 that in turn is coupled to processing unit 900. GSR sensors 825 are coupled to A/D converter 915 through current loop 920, low pass filter 925, and amplifier 930. Current loop 920 comprises an opamp and a plurality of resistors, and applies a small, fixed current between the two GSR sensors 825 and measures the voltage across them. The measured voltage is directly proportional to the resistance of the skin in contact with the electrodes. Similarly, heat flux thermistors 890A and 890B are coupled to A/D converter 915 and processing unit 900, where the heat flux calculations are performed, through low pass filter 935 and amplifier 940.

Battery monitor 945, preferably comprising a voltage divider with low pass filter to provide average battery voltage, monitors the remaining power level of rechargeable battery 950. Rechargeable battery 950 is preferably a LiIon/LiPolymer 3.7 V Cell. Rechargeable battery 950, which is the main power source for sensor device 800, is coupled to processing unit 900 through voltage regulator 955. Rechargeable battery 950 may be recharged either using recharger 960 or USB cable 965, both of which may be coupled to sensor device 800 through USB interface 970. Preferably, USB interface 970 is hermetically sealable, such as with a removable plastic or rubber plug, to protect the contacts of USB interface 970 when not in use.

PCB 860 further includes skin temperature thermistor 870 for sensing the temperature of the skin of the wearer of sensor device 800, and near-body ambient temperature thermistor 880 for sensing the ambient temperature in the area near the body of the wearer of sensor device 800. Each of these components is biased and coupled to processing unit 900 through A/D converter 915.

According to a specific embodiment of sensor device 800, PCB 860 may include one or both of an ambient light sensor and an ambient sound sensor, shown at 975 in FIG. 27, coupled to A/D converter 915. The ambient light sensor and ambient sound sensor may be adapted to merely sense the presence or absence of ambient light or sound, the state where a threshold ambient light or sound level has been exceeded, or a reading reflecting the actual level of ambient light or sound. A suitable example of an ambient sound sensor is the WM-60A Condenser Microphone Cartridge sold by Matsushita Electric Corporation of America located in Secaucus, N.J., and suitable examples of an ambient light sensor are the Optek OPR5500 phototransistor and the Optek OPR5910 photodiode sold by Optek Technology, Inc. located in Carrollton, Tex. In addition, PCB 860 may include ECG sensor 980, including two or more electrodes, for measuring the heart rate of the wearer, and impedance sensor 985, also including a plurality of electrodes, for measuring the impedance of the skin of the wearer. Impedance sensor 985 may also be an EMG sensor which gives an indication of the muscular activity of the wearer. The electrodes forming part of ECG sensor 980 or impedance sensor 985 may be dedicated electrodes for such sensors, or may be the electrodes from GSR sensors 825 multiplexed for appropriate measurements. ECG sensor 980 and impedance sensor 985 are each coupled to A/D converter 915.

PCB 860 further includes RF transceiver 990, coupled to processing unit 900, and antenna 995 for wirelessly transmitting and receiving data to and from wireless devices in proximity to sensor device 800. RF transceiver 990 and antenna 995 may be used for transmitting and receiving data to and from a device such as a treadmill being used by a wearer of sensor device 800 or a heart rate monitor worn by the wearer of sensor device 800, or to upload and download data to and from a computing device such as a PDA or a PC. In addition, RF transceiver 990 and antenna 995 may be used to transmit information to a feedback device such as a bone conductivity microphone worn by a fireman to let the fireman know if a condition that may threaten the fireman's safety, such as hydration level or fatigue level, has been sensed by sensor device 800. As described in detail in connection with FIG. 21, stand alone sensor device 700 may be coupled to computing device 750 to enable data to be communicated therebetween. Thus, as a further alternative, RF transceiver 990 and antenna 995 may be used to couple sensor device 800 to a computing device such as computing device 750 shown in FIG. 21. Such a configuration would enable sensor device 800 to transmit data to and receive data from the computing device 750, for example a computing device worn on the wrist. The computing device could be used to enable a user to input data, which may then be stored therein or transmitted to sensor device 800, and to display data, including data transmitted from sensor device 800. The configuration would also allow for computing tasks to be divided between sensor device 800 and computing device 750, referred to herein as shared computing, as described in detail in connection with FIG. 21.

As shown in FIG. 27, PCB 860 may include proximity sensor 1000 which is coupled to processing unit 900 for sensing whether sensor device 800 is being worn on the body. Proximity sensor 1000 may also be used as a way to automatically power on and off sensor device 800. Proximity sensor 1000 preferably comprises a capacitor, the electrical capacitance of which changes as sensor device 800 gets closer to the body. PCB 860 may also include sound transducer 1005, such as a ringer, coupled to processing unit 900 through driver 1010.

Sensor device 800 may also be provided with sensors in addition to those shown in FIG. 27, such as those taught by U.S. Pat. No. 5,853,005, the disclosure of which is incorporated herein by reference. The '005 patent teaches a sound transducer coupled to a pad containing an acoustic transmission material. The pad and sound transducer may be used to sense acoustic signals generated by the body which in turn may be converted into signals representative of physiological parameters such as heart rate or respiration rate. In addition, rather than being integrated in sensor device 800 as part of one or more of housing 805, flexible section 810 or strap 811, a sensing apparatus as taught by the '005 patent may be provided separate from sensor device 800 and be coupled, wired or wirelessly, to sensor device 800. According to the '005 patent, the sound or acoustic transducer is preferably a piezoelectric, electret, or condenser-based hydrophone, similar to those used by the Navy in sonar applications, but can be any other type of waterproof pressure and motion sensing type of sensor.

The sensing apparatus as taught by the '005 patent is an example of what shall be referred to herein as a non-ECG heart parameter sensor, meaning that it has the following two qualities: (1) it does not need to make measurements across the torso using at least two contacts separated by some distance; and (2) it does not measure electrical activity of the heart. The sensing apparatus as taught by the '005 patent has been shown to be capable of detecting heart rate information and information relating to individual beats of the heart with high reliability under certain circumstances, depending primarily on factors including the proximity of the apparatus to the heart, the level of ambient noise, and motion related sound artifacts caused by the movement of the body. As a result, the sensing apparatus as taught by the '005 patent is most reliable when worn in an ambient environment with a low level of ambient noise and when the body is not moving.

Certain characteristics, sensors and sensing capabilities of sensor device 800 are able to improve the reliability and accuracy of an acoustic-based non-ECG heart parameter sensor 1012 such as the sensing apparatus as taught by the '005 patent that is incorporated therein or coupled thereto. For example, in one specific embodiment, sensor device 800 is particularly suited to be worn on the upper arm. The upper arm is a good location for a sensor device 800 having an acoustic-based non-ECG heart parameter sensor 1012 incorporated therein because it is near the heart and provides a space for sensor device 800 that allows it to be unobtrusive and comfortable to wear. In addition, ambient sound sensor shown at 975 in FIG. 27 may be used to filter out ambient noise from the signals detected by the acoustic-based non-ECG heart parameter sensor 1012 in order to isolate the sound signal originating from the body. Filtering of the signal produced by an acoustic-based non-ECG heart parameter sensor 1012 such as the sensing apparatus as taught by the '005 patent in this manner may be used both in the case where such an apparatus is incorporated in sensor device 800 and in the case where it is separated from but coupled to sensor device 800 as described above. Furthermore, the sound generated from the motion of the body that is not created by the heart can be accounted for and adjusted for through the use of a sensor or sensors that detect or that may be used to identify body sounds generated as a result of motion of the body, such as accelerometer 905 shown in FIGS. 27 and 29 or the body position or muscle pressure sensors identified in Table 1. For example, footfalls create sound within the body that can lower the signal to noise ratio of an acoustic-based non-ECG heart parameter sensor 1012, which will likely result in false positive and false negative heart beat identifications. As is well known in the art, accelerometer 905 may function as a footfall indicator. Accelerometer 905 may thus be used to filter or subtract out from the signal detected by the acoustic-based non-ECG heart parameter sensor 1012 signals related sound motion artifacts caused by the movement of the body such as by footfalls.

Several methodologies for performing the filtering or subtracting of signals described herein are known to those of ordinary skill in the art. Such filtering or subtracting of signals used in connection with the monitoring of disparate signals, some used for noise cancellation and some used for their direct measure, is also known as data integration.

Sensor device 800 may also be used to put parameters around and provide a context for the readings made by a non-ECG heart parameter sensor 1012 so that inaccurate readings can be identified and compensated for. For example, sensor device 800 may be used to detect real time energy expenditure of the wearer as well as the type of activity in which the wearer is engaging, such as running or riding a bike. Thus, as another example of how the sensors and sensing capabilities of sensor device 800 may be used to increase the reliability and accuracy of a non-ECG heart parameter sensor 1012 through data integration, the energy expenditure and activity type information can be used to provide a context in which the heart related parameters detected by the non-ECG heart parameter sensor 1012 can be assessed and possibly filtered. For example, if sensor device 800 detects that a person is burning 13 calories per minute and is biking, and the non-ECG heart parameter sensor 1012 is indicating that the wearer's heart rate is 60 beats per minute, then it is highly likely that further filtration of the signal from the non-ECG heart parameter sensor 1012 is necessary.

Other well known non-ECG heart parameter sensing devices include, for example, those based on micro-power impulse radar technology, those based on the use of piezo-electric based strain gauges, and those based on plethysmography, which involves the measurement of changes in the size of a body part as modified by the circulation of blood in that part. It will be appreciated that the performance of these devices may also be enhanced through the use of data integration as described herein.

Another sensor that may be incorporated into the sensor device 800 measures the pressure with which sensor device 800 is held against the body of the wearer. Such a sensor could be capacitive or resistive in nature. One such instantiation places a piezo-resistive strain gauge on the back of the enclosure to measure the small deflection of the plastic as increasing force is applied. Data gathered from such a sensor can be used to compensate the readings of other sensors in sensor device 800 according to the readings of such a sensor.

Also provided on PCB 860 and coupled to processing unit 900 is switch 1015. Switch 1015 is also coupled to button 1020 provided on housing 805. Button 1020, by activating switch 1015, may be used to enter information into sensor device 800, such as a time stamp to mark the occurrence of an event such as taking medication. Preferably, button 1020 has a tactile, positive detent feedback when depressed, and a concave shape to prevent accidental depression. Also, in the embodiment shown in FIGS. 22–26, flexible section 810 includes membrane 1022 that covers and seals button 1020. In the embodiments shown in FIGS. 30–32, a similar membrane 1022 may be provided on flexible section 810, and, preferably, also on housing 805 such that button 1020 is sealed when housing 805 is removed from flexible section 810. Alternatively, a hole may be provided in flexible section 810 exposing button 1020 and membrane 1022 when housing 805 is attached to flexible section 810. In addition, coupled to processing unit 900 on PCB 860 are LCDs and/or LEDs 1025 for outputting information to the wearer. FIG. 28 shows an alternate embodiment of sensor device 800 in which LCD 1025 is provided on a top face of housing t As an alternative to LCDs or LEDs 1025, sensor device 800 may include a prior art electrochemical display that retains its ability to display information even when power is no longer being provided thereto. Such a display is described in U.S. Pat. No. 6,368,287 B1, the disclosure of which is incorporated herein by reference, and includes a plurality of markers comprising a miniature heating element and a coating of heat sensitive material. When current is passed through one of the heating elements, it heats up, thereby inducing a change in the color of the coating material. The color change is permanent, even after the heating element cools down. Such displays are relatively inexpensive and thus are well adapted for use in embodiments of sensor device 800 that are designed to be disposable, possibly single use, items.

Oscillator 1030 is provided on PCB 860 and supplies the system clock to processing unit 900. Reset circuit 1035 is coupled to processing unit 900 and enables processing unit 900 to be reset to a standard initial setting.

Finally, non-volatile data storage device 1040, such as a FLASH memory chip, is provided for storing information collected and/or generated by sensor device 800. Preferably, data storage device 1040 includes at least 128K of memory. Non-volatile program storage device 1045, such as a FLASH ROM chip, is provided for storing the programs required to operate sensor device 800.

As an alternative, a microprocessor with integral A/D converters, data storage, and program storage may be substituted for processing unit 900, A/D converter 915, data storage device 1040 and non-volatile memory 1045. A suitable example of such a microprocessor is the Texas Instruments Model MSP430 processor.

Any component forming a part of sensor device 800 that comes in contact with the wearer's skin should not, in a preferred embodiment, degrade in durometer, elasticity, color or other physical or chemical properties when exposed to skin oils, perspiration, deodorant, suntan oils or lotions, skin moisturizers, perfume or isopropyl alcohol. In addition, such components preferably are hypoallergenic.

FIG. 29 shows an alternate embodiment of PCB 860 in which rechargeable battery 950, voltage regulator 955, recharger 960 and USB cable 965 have been replaced by disposable AAA battery 1050 and boost converter 1055. Boost converter 1055 uses an inductor to boost the voltage of AAA battery 1050 to the 3.0–3.3 V required to run the electronics on PCB 860. A suitable boost converter 1055 is the model MAX1724 sold by Maxim Integrated Products, Inc. of Sunnydale, Calif.

Referring to FIGS. 30 and 31, an alternate embodiment of sensor device 800 is shown in which housing 805 is removably attached to flexible section 810. As shown in FIGS. 30 and 31, housing 805 is provided with groove 1060 along the outer edge thereof which is adapted to receive therein tongue 1065 provided on the bottom side of flexible section 810 for securely but removably attaching housing 805 to flexible section 810. Through the interaction of groove 1060 and tongue 1065, housing 805 may thus be readily popped in and out of flexible section 810. Such a configuration enables housing 805 to be readily attached to multiple flexible sections having sizes and shapes that are different than flexible section 810 as long as the flexible section includes a tongue similar to tongue 1065. Such alternate flexible sections may be sized and shaped to fit on particular parts of the body, such as the calf or thigh, and may comprise a garment such as a shirt having the tongue or tongues located in places of interest, such as the upper arm or upper left chest, the latter enabling housing 805 to be positioned over the heart of the wearer, as shown in FIGS. 40A and 40B. U.S. Pat. No. 6,527,711, owned by the assignee of the present application and incorporated herein by reference, identifies several locations on the body that are particularly well adapted to receive particularly sized and shaped sensor devices so as to avoid interference with the motion and flexibility of the body. As will be appreciated by those of skill in the art, groove 1060 and tongue 1065 may be swapped such that groove 1060 is provided in flexible section 810 and tongue 1065 is provided on housing 805. As will also be appreciated by those of skill in the art, multiple alternative structures exist for securely but removably attaching housing 805 to flexible section 810. These alternative structures include, without limitation, temporary adhesives, screws, a tight fit between housing 805 and flexible section 810 that holds the two together by friction, magnets provided in each of housing 805 and flexible section 810, well-known snaps and snapping mechanisms, a threaded portion provided on housing 805 adapted to be received by threads in flexible section 810, an O-ring or similar elastic band adapted to fit around a portion of flexible section 810 and into a groove provided in housing 805 when flexible section 810 is placed over housing 805, or merely pressure when housing 805 is placed on the body and flexible section 810 is placed thereover and attached to the body such as by strap 811. Referring to FIG. 32, a still further alternative structure for removably securing flexible section 810 to housing 805 is shown in which flexible section 810 comprises an elastic or similar band that is adapted to fit into a groove 1062 provided in housing 805. Housing 805 and flexible section 810 may then be placed on the body and held in place by strap 811 or the like inserted through gaps 1064 between housing 805 and flexible section 810.

FIG. 33 shows an alternate embodiment of sensor device 800 as shown in FIGS. 30 and 31 that is adapted to automatically adjust or alter the operating parameters of sensor device 800, such as its functionality, settings or capabilities, depending on the particular flexible section to which housing 805 is attached. For example, the calculation of a parameter, such as energy expenditure, may depend on information that is particular each individual, such as age, height, weight, and sex. Rather than having each individual enter that information in sensor device 800 each time he or she wants to wear the device 800, each individual that is going to wear the device could enter the information once and have their own flexible section that causes sensor device 800 to make measurements based on his or her particular information. Alternatively, the memory in sensor device 800 for storage of user data may be divided into several compartments, one for each user, so as to avoid co-mingling of user data. Sensor device 800 may be adapted to alter where collected data is stored depending on the particular flexible section that is being used. In addition, sensor device 800 may be calibrated and recalibrated differently over time depending on the particular flexible section to which housing 805 is attached as it learns about each particular wearer and his or her habits, demographics and/or activities.

According to a particular embodiment, housing 805 is provided with first magnetic switch 1070 and second magnetic switch 1075, each on PCB 860. Provided on or inside flexible section 810, such as by an insert molding technique, is magnet 1080. Magnet 1080 is positioned on or inside flexible section 810 such that it aligns with and thereby activates one of first magnetic switch 1080 and second magnetic switch 1075 when housing 805 is attached to flexible section 810. In the embodiment shown in FIG. 33, second magnetic switch 1075 will be activated. A second flexible section 810 similar to flexible section 810 shown in FIG. 33 will also be provided, the difference being that the magnet 1080 provided therewith will be positioned such that first magnetic switch 1070 is activated when housing 805, the same housing 805 shown in FIG. 33, is attached to the second flexible section 810. Housing 805, and in particular processing unit 900, may be programmed to alter its functionality, settings or capabilities depending on which one of first magnetic switch 1070 and second magnetic switch 1075 is activated, i.e., which particular flexible section 810 is being used. Thus, a husband and wife may share a single housing 805 but have different flexible wings 810 with magnets 1080 located in different places. In such a case, housing 805 may be programmed to operate with functionality, settings or capabilities particular to the husband when first magnetic switch 1070 is activated, and with functionality, settings or capabilities particular to the wife when second magnetic switch 1075 is activated. Although only two magnetic switches are shown in FIG. 33, it will be appreciated that multiple magnetic switches and multiple flexible sections may be used to allow sensor device 800 to be programmed for multiple wearers, such as an entire family, with each family member having his or her own flexible section. As still a further alternative, multiple flexible sections may be provided that are adapted to be worn on different parts of the body, each having a magnet placed in a different location. Housing 805 may then be programmed to have functionality, settings or capabilities particular to the type of sensing to be done on each different part of the body, with magnetic switches placed so as to be activated when housing 805 is attached to the appropriate flexible section. Sensor device 800 according to this embodiment is thus a "smart" device. As will be appreciated by one of skill in the art, many alternatives to first and second magnetic switches 1070 and 1075 and magnet 1080 may be used to provide the functionality described in connection with FIG. 33. Such alternatives include, without limitation, mechanical switches provided in housing 805 that are activated by a protruding portion, such as a pin, provided at a particular location on flexible section 810, optical switches comprising an array of light sensors provided in housing 805 that are activated when the surrounding light is blocked, reflected or filtered in a particular way with one or more translucent sections and a single opaque, reflective or filtering section being selectively provided on flexible section 810 at particular locations, the translucent sections not activating the corresponding optical switches and the opaque, reflective or filtering section activating the corresponding optical switch, electronic switches provided in housing 805 activated by a conductor provided in particular locations in flexible section 810. As still a further alternative, housing 805 may be provided with multiple switches and each flexible section 810 may be provided with one or more switch activators positioned to activate certain selected switches. The operating parameters of housing 805 would in this embodiment be adapted to change depending upon the particular set of one or more switches that are activated. This embodiment thus employs an encoding scheme to alter the operating parameters of housing 805 depending on which flexible section 810 is used. As still a further alternative, housing 805 may be provided with a single switch adapted to alter the operating parameters of housing 805 depending upon the way in which or state in which it is activated, such as by the properties of the switch activators. For example, the switch may be a magnetic switch that is activated a plurality of different ways depending upon the magnetic level or strength of the magnet provided in each flexible section 810. A plurality of flexible sections 810 could then be provided, each having a magnet of a different strength. In addition, any particular flexible section 810 may be provided with a plurality of magnets having different strengths with each magnet being able to activate the switch in housing 805 in a different manner. Such a flexible section 810 would be able to selectively trigger different operating parameters of housing 805, such as by rotating a portion of flexible wing 805 to align a particular magnet with the switch. As an alternative, the switch could be an electrical switch and the switch activators could be conductors having different resistances. The switch would, in this embodiment, be activated in different ways depending on the measured resistance of the switch activator that closes the circuit.

Referring to FIG. 34, as still a further embodiment of sensor device 800, housing 805 may be provided with adhesive material 1085 on a back side thereof to enable housing 805 to be removably attached to selected portions of the body, such as the upper left chest over the heart, without flexible section 810. Adhesive material 1085 may be any well-known adhesive that would securely attach housing 805 to the body and enable it to be worn for a period of time, but that would also readily enable housing 805 to be removed from the body after use. Adhesive material 1085 may comprise, for example, a double sided adhesive foam backing that would allow for comfortable attachment of housing 805 to the body. Furthermore, housing 805 may be made of a well-known flexible plastic film or the like, such as that taught in U.S. Pat. No. 6,368,287 B1, the disclosure of which is incorporated herein by reference, that would, due to low cost, enable sensor device 800 to be disposable. Such a disposable sensor device may also include an electrochemical display described above to enhance its disposability. In an embodiment adapted for placement over the upper left chest or any other appropriate region for detecting heart related parameters, sensor device 800 would include one or more sensors described herein for sensing heart related parameters such as heart rate, beat-to-beat or interbeat variability, ECG or EKG, pulse oximetry, heart sounds, such as detected with a microphone, and mechanical action of the heart, such as detected with ultrasound or micro-pulse radar devices.

FIGS. 35A–H and 36A–H illustrate aspects of the present invention relating to the ergonomic design of sensor device 800. Referring to FIGS. 35A and 35B, a housing 1100 of a prior art sensor device having a rectangular cross-section is shown resting on the body 1110 of a wearer of the prior art sensor device. As seen in FIG. 35B, when body 1110 flexes and forms a concavity, as may happen many times each minute on various parts of the body or for extended periods of time depending on the position of various body parts during particular activities, a significant portion of housing 1100 is caused to be removed from body 1110. When housing 1100 is caused to be removed in this manner, the ability of the prior art sensor device to accurately make measurements and collect data will be jeopardized, especially for any readings to be taken near the center of the cross-section indicated by the arrows in FIG. 35B.

FIGS. 35C–H illustrate a cross-section of housing 805 of sensor device 800 taken along lines C—C shown in FIG. 23 according to various aspects of the present invention. The cross-section shown in FIGS. 35C–H is taken near the middle portion of housing 805 shown in FIG. 23 between GSR sensors 825. As seen in FIG. 35C, bottom surface 1115 of housing 805 is provided with a generally convex shape such that, when body 1110 flexes and forms a concavity, a substantial portion of bottom surface 1115 of housing 805 remains in contact with body 1110 by fitting into the concavity. As seen in FIG. 35D, when body 1110 flexes in the opposite direction so as to create a convexity, the center portion of housing 805, indicated by the arrow in FIG. 35D, remains in contact with body 1110. As shown in FIG. 35E, this is true even if housing 805 were to rock within the concavity formed in body 1110. Referring to FIG. 35F, body 1110 may, at times, flex to an extreme degree, i.e., more than the anticipated maximum that it was designed for, such that, even if bottom surface 1115 is provided with a convex shape, it may still cause bottom surface 1115 to be removed from body 1110. A solution to this problem is illustrated in FIG. 35G, wherein the lateral ends 1120A and 1120B of housing 805 are provided with radiused portions 1125A and 1125B, respectively adjacent to and including opposite lateral ends of bottom surface 1115. Radiused portions 1125A and 1125B enable housing 805 to sit lower and fit into the concavity created when body 1110 flexes to an extreme degree. In addition, radiused portions 1125A and 1125B provide for more comfortable wear as they eliminate sharp edges 1130A and 1130B shown in FIG. 35F that contact body 1110. FIG. 35H shows how body 1110 will tend to conform to the shape of housing 805 due at least in part to the viscosity of the skin when body 1110 is in a relaxed condition.

FIG. 36A shows a cross-section of housing 1100 of prior art sensor device taken along a line perpendicular to the line on which the cross-section shown in FIGS. 35A and 35B was taken. As seen in FIG. 36A, when housing 1100 is placed on a convex portion of body 1110, significant portions of housing 1100, specifically the lateral ends thereof indicated by the arrows in FIG. 36A, are not in contact with body 1110. FIGS. 36B–H show a cross-section of housing 805 according to various aspects of the present invention taken along lines D—D shown in FIG. 23. As seen in FIG. 36B, bottom surface 1115 of housing 805 is provided with a generally concave shape adapted to receive the convex portion of body 1110. Referring to FIG. 36C, lateral ends 1130A and 1130B may be provided with radiused portions 1135A and 1135B adjacent to and including opposite lateral ends of bottom surface 1115, which allow housing 805 to rest in closer contact with body 1110, even when body 1110 flexes to an extreme degree, i.e., more than the anticipated maximum that it was designed for, and remove sharp edges 1140A and 1140B shown in FIG. 36B, providing for more comfortable wear. As shown in FIG. 36D, body 1110 will tend to conform to the shape of housing 805 when body 1110 is in a relaxed condition. As shown in FIGS. 36E and 36F, good contact with body 1110 is maintained at the points illustrated by the arrows when body 1110 is flexed in a manner that decreases the convex shape thereof or that creates a convexity therein. Thus, it will be appreciated that it is advantageous to place sensors or sensing elements at the points indicated by the arrows because those points will tend to remain in contact with body 1110. FIGS. 36G and 36H, showing, for example, heat flux skin interface component 835 and skin temperature skin interface component 840 placed at the points indicated by the arrows, illustrate this point. As seen in FIGS. 36G and 36H, there is more than point contact between body 1110 and skin temperature skin interface component 840.

FIG. 37 is an isometric view of housing 805 according to an embodiment of the present invention in which bottom surface 1115 has both the generally convex shape shown in FIGS. 35C–H and the generally concave shape shown in FIGS. 36B–H. Specifically, bottom surface 1115, which is the inner surface of housing 805 for mounting adjacent to the body of the wearer, includes a longitudinal axis 1141 and a transverse axis 1142. Bottom surface 1115 has a generally concave shape having an axis of concavity 1143 that is coincident with longitudinal axis 1141, meaning that it runs in a first direction from first lateral end 1144 of inner surface 1115 to second lateral end 1145 of inner surface 1115. Bottom surface 1115 has a generally convex shape having an axis of convexity 1146 that is coincident with transverse axis 1142, meaning that it runs in a second direction from third lateral end 1147 of inner surface 1115 to fourth lateral end 1148 of inner surface 1115. As seen in FIG. 37, the first and second directions, and longitudinal axis 1141 and transverse axis 1142, are generally perpendicular to one another.

Referring to FIGS. 38A–D, it will be appreciated that housing 805 having a flat top surface 1150 and flat lateral ends 1130A and 1130B may tend to be jostled and bumped by object 1155, such as a wall or door or the corner or edge of a drawer, cabinet or desk, thereby moving housing 805 on body 1110 because such flat surfaces are not well adapted to deflect object 1155. Movement of housing 805 on body 1110 will detrimentally effect the ability of sensor device 800 to accurately make measurements and collect data. FIGS. 39A–G illustrate various aspects of the present invention that are adapted to deflect object 1155 and substantially prevent movement of housing 805 on body 1110. In addition, the forms shown in FIGS. 39A–G increase the durability of sensor device 800 and make it easier to put on and wear clothing and the like, such as a wetsuit, over sensor device 800. As seen in FIG. 39A, housing 805 may have tapered sides 1160A and 1160B such that the width of housing 805 decreases in the direction from bottom surface 1115 to top surface 1150. Alternatively, referring to FIG. 39B, top surface 1150 of housing 805 may have a convex shape. As a further alternative, as seen in FIG. 39C, housing 805 may be provided with radiused portions 1165A and 1165B that meet with radiused portions 1135A and 1135B such that the lateral ends of housing 805 have a substantially semicircular shape. As shown in FIG. 39D, housing 805 may have both tapered sides 1160A and 1160B and a top surface 1150 with a convex shape. FIG. 39E is a modification of housing 805 shown in FIG. 39E in which the points 1170A and 1170B where radiused portions 1135A and 1135B meet tapered sides 1160A and 1160B, respectively, are themselves radiused. FIG. 39F is a variation of housing 805 shown in FIG. 39E having elongated tapered sides 1160A and 1160B. FIG. 39G shows how the ability of housing 805, such as the embodiment shown in FIG. 39E, to deflect object 1155 may be enhanced by the addition of flexible section 810 having a substantially convex outer surface. In addition, an air channel is provided between flexible section 810 and body 1110 to allow for heat to flow away from body 1110.

The terms and expressions which have been employed herein are used as terms of description and not as limitation, and there is no intention in the use of such terms and expressions of excluding equivalents of the features shown and described or portions thereof, it being recognized that various modifications are possible within the scope of the invention claimed. Although particular embodiments of the present invention have been illustrated in the foregoing detailed description, it is to be further understood that the present invention is not to be limited to just the embodiments disclosed, but that they are capable of numerous rearrangements, modifications and substitutions.

What is claimed is:

1. An apparatus for detecting at least one of human physiological and contextual information from the body of a wearer, comprising:
   a flexible section for engaging at least a portion of said body;
   a housing removably attached to and supported by said flexible section;
   a strap attached to said flexible section for securing said flexible section to said body;
   one or more sensors supported by said housing, said one or more sensors selected from the group consisting of physiological sensors and contextual sensors; and
   a processing unit supported by said housing in electronic communication with said one or more sensors.

2. An apparatus according to claim 1, further comprising a groove provided said housing and a tongue provided on said flexible section, said groove being suitable to receive said tongue.

3. An apparatus according to claim 1, further comprising a tongue provided on said housing and a groove provided in said flexible section, said groove being suitable to receive said tongue.

4. An apparatus according to claim 1, further comprising an adhesive material for removably attaching said housing to said flexible section.

5. An apparatus according to claim 1, further comprising a magnet supported by each of said housing and said flexible section.

6. An apparatus according to claim 1, further comprising a stretchable band and a groove provided in said housing, said band suitable to fit around a portion of said flexible section and into said groove when said flexible section is placed over said housing.

7. An apparatus according to claim 1, said housing further comprising a display.

8. An apparatus according to claim 1, said one or more sensors comprising at least one of a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

9. An apparatus according to claim 1, said one or more sensors comprising at least two sensors.

10. An apparatus for detecting at least one of human physiological and contextual information from the body of a wearer, comprising:
    a housing support section for engaging at least a portion of said body;
    a housing removably attached to and supported by said housing support section;
    one or more sensors supported by said housing, said one or more sensors selected from the group consisting of physiological sensors and contextual sensors;
    a processing unit supported by said housing in electronic communication with said one or more sensors; and
    one or more additional housing support sections that may be selectively removably attached to said housing.

11. An apparatus according to claim 10, said housing support section and at least one of said additional housing support sections being suitable to engage different body portions of said wearer.

12. An apparatus according to claim 10, said apparatus having adjustable operating parameters, further comprising means for adjusting said operating parameters depending on the particular one of said housing support section and said one or more additional housing support sections to which said housing is removably attached.

13. An apparatus according to claim 12, said means for adjusting said operating parameters comprising a plurality of switches supported by said housing and a switch activator supported by said housing support section and each of said additional housing support sections, said switches being coupled to said processing unit, said operating parameters being adjusted in dependence on the particular one of said switches that is activated.

14. An apparatus according to claim 13, each of said switch activators being supported by a respective one of said housing support section and said additional housing support sections in a position such that a different one of said switches is activated depending on the particular one of said housing support section and said additional housing support sections to which said housing is removably attached.

15. An apparatus according to claim 13, said switches comprising magnetic switches and said switch activators each comprising a magnet.

16. An apparatus according to claim 13, said switches comprising mechanical switches.

17. An apparatus according to claim 16, each of said switch activators comprising a protruding element.

18. An apparatus according to claim 13, said switches comprising optical switches, said switch activators comprising one of means for obscuring light, means for reflecting light and means for filtering light.

19. An apparatus according to claim 13, said switches comprising electrical switches and said switch activators each comprising a conductor.

20. An apparatus according to claim 12, said means for adjusting said operating parameters comprising a plurality of switches supported by said housing and one or more switch activators supported by each of said housing support section and said additional housing support sections, said operating parameters being adjusted in dependence on the particular one or more of said switches that are activated.

21. An apparatus according to claim 12, said means for adjusting said operating parameters comprising a switch supported by said housing and at least one switch activator supported by each of said housing support section and said additional housing support sections, said switch being activatable according to a plurality of states depending upon a property of the particular switch activator activating said switch, said operating parameters being adjusted in dependence on said activation state of said switch.

22. An apparatus according to claim 10, further comprising a groove provided in said housing and a tongue provided on said housing support section and each of said additional housing support sections, said groove being suitable to receive each of said tongues.

23. An apparatus according to claim 10, further comprising a tongue provided on said housing and a groove provided in said housing support section and each of said additional housing support sections, said grooves being suitable to receive said tongue.

24. An apparatus according to claim 10, further comprising an adhesive material for removably attaching said housing to said housing support section and said additional housing support sections.

25. An apparatus according to claim 10, further comprising a magnet supported by each of said housing, said housing support section and said additional housing support sections.

26. An apparatus according to claim 10, further comprising a stretchable band and a groove provided in said housing, said stretchable band suitable to fit around a portion of one of said housing support section and said additional housing support section and into said groove when said one of said housing support section and said additional housing support sections is placed over said housing.

27. An apparatus according to claim 10, further comprising a wireless communications device for at least one of receiving information from and transmitting information to a computing device.

28. An apparatus according to claim 27, said computing device displaying information to an individual and enabling said individual to input information.

29. An apparatus according to claim 28, said computing device and said processing unit being adapted to engage in shared computing.

30. An apparatus according to claim 10, at least one of said housing section and said additional housing support sections comprising a garment.

31. An apparatus according to claim 30, said one or more sensors comprising a sensor for sensing one or more heart related parameters.

32. An apparatus according to claim 31, said one or more heart related parameters including at least one of heart rate, beat-to-beat variability, ECG, pulse oximetry, heart-related sounds and parameters relating to the mechanical action of the heart.

33. An apparatus according to claim 32, at least one of said additional housing support sections being suitable to engage a portion of said body comprising the left chest.

34. An apparatus according to claim 10, said housing support section and said one or more additional housing support sections each comprising a flexible section.

35. An apparatus according to claim 10, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

36. An apparatus for detecting at least one of human physiological and contextual information from the body of a wearer, comprising:
   a self-contained housing suitable to be worn on the left chest portion of said body;
   one or more sensors within said housing, said one or more sensors selected from the group consisting of physiological sensors and contextual sensors; and
   a processing unit within said housing in electronic communication with said one or more sensors;
   said one or more sensors comprising a sensor for sensing one or more heart related parameters including at least one of heart rate, beat-to-beat variability, ECG, pulse oximetry, heart-related sounds, and parameters relating to the mechanical action of the heart.

37. An apparatus according to claim 36, further comprising a housing support section for engaging at least a portion of said body, said housing being attached to said housing support section.

38. An apparatus according to claim 37, said housing support section comprising a flexible section.

39. An apparatus according to claim 38, said housing being selectively removably attached to said housing support section.

40. An apparatus according to claim 36, wherein said sensors generate data indicative of at least a detected parameter of the wearer and said processing unit generates derived data comprising a derived parameter based on said detected parameter, being an individual status parameter that cannot be directly detected by one of said one or more sensors.

41. An apparatus for detecting at least one of human physiological and contextual information from the body of a wearer which is mounted on said body in conjunction with a garment, comprising:
- a housing;
- a garment suitable to be worn on a portion of the body which restrains and supports said housing in a position proximate to the left chest of said body;
- one or more sensors supported by said housing, said one or more sensors selected from the group consisting of physiological sensors and contextual sensors; and
- a processing unit supported by said housing in electronic communication with said one or more sensors;
- said one or more sensors comprising a sensor for sensing one or more heart related parameters including at least one of heart rate, beat-to-beat variability, ECG, pulse oximetry, heart-related sounds, and parameters relating to the mechanical action of the heart.

42. An apparatus for detecting at least one of human physiological and contextual information from the body of a wearer in an ambient environment, comprising:
- a housing;
- a base member having a preselected resistivity mounted within said housing;
- a first temperature measuring device attached to a first side of said base member;
- a thermal energy communicator mounted adjacent to said first temperature measuring device for placing said first temperature measuring device in thermal communication with a portion of said body, said thermal energy communicator being located between said first temperature measuring device and said portion of said body when said apparatus is being worn on said body;
- a second temperature measuring device attached to a second side of said base member, said second temperature measuring device in thermal communication with said ambient environment; and
- a processing unit provided in said housing, said first and second temperature measuring devices being in electronic communication with said processing unit;
- wherein said apparatus is adapted to measure heat flux between said body and said ambient environment.

43. An apparatus according to claim 42, said first temperature measuring device comprising a first thermistor and said second temperature measuring device comprising a second thermistor.

44. An apparatus according to claim 43, said first thermistor measuring a first voltage, said second thermistor measuring a second voltage, said first voltage and said second voltage being used to generate a temperature difference (T2−T1), said heat flux being calculated according to the following formula:

heat flux =$K(T2-T1)$, wherein $K$ is said preselected resistivity.

45. An apparatus according to claim 42, said first temperature measuring device measuring a first parameter, said second temperature measuring device measuring a second parameter, said first parameter and said second parameter being used to generate a temperature difference (T2−T1), said heat flux being calculated according to the following formula:

heat flux =$K(T2-T1)$, wherein $K$ is said preselected resistivity.

46. An apparatus according to claim 42, said thermal energy communicator comprising a heat conduit having a first surface in thermal communication with said body portion when said apparatus is being worn and a second surface in thermal communication with said first temperature measuring device.

47. An apparatus according to claim 46, said thermal energy communicator further comprising a skin-side thermally conductive interface component in thermal communication with said body portion when said apparatus is being worn and said first surface of said heat conduit.

48. An apparatus according to claim 47, said skin-side thermally conductive interface component comprising a stainless steel plate.

49. An apparatus according to claim 47, said thermal energy communicator further comprising a first skin-side thermally conductive interface material located between said first thermally conductive interface component and said first surface of said heat conduit, and a second skin-side thermally conductive interface material located between said second surface of said heat conduit and said first temperature measuring device.

50. An apparatus according to claim 49, said first and second skin-side thermally conductive interface materials selected from the group consisting of thermally conductive gap fillers, thermally conductive phase change interface materials, thermally conductive tapes, thermally conductive cure-in-place compounds and epoxies, and thermal greases.

51. An apparatus according to claim 49, said skin-side thermally conductive interface component, said first skin-side thermally conductive interface material, said heat conduit, said second skin-side thermally conductive interface material, said first temperature measuring device, said base member, and said second temperature measuring device attached to one another along a direction substantially normal to said first and second side of said base member.

52. An apparatus according to claim 51, said base member comprising a printed circuit board.

53. An apparatus according to claim 52, said processing unit being attached to said printed circuit board.

54. An apparatus according to claim 42, further comprising an ambient-side thermally conductive interface component in thermal communication with said ambient environment and said second temperature measuring device.

55. An apparatus according to claim 54, further comprising an ambient-side thermally conductive interface material located between said ambient-side thermally conductive interface component and said second temperature measuring device.

56. An apparatus according to claim 55, said ambient-side thermally conductive interface material selected from the group consisting of thermally conductive gap fillers, thermally conductive phase change interface materials, thermally conductive tapes, thermally conductive cure-in-place compounds and epoxies, and thermal greases.

57. An apparatus according to claim 54, said ambient-side thermally conductive interface component comprising a stainless steel plate.

58. An apparatus according to claim 54, further comprising a housing support section for holding said housing in engagement with said body of said wearer, said housing support section exposing said ambient-side thermally conductive interface component to said ambient environment.

59. An apparatus according to claim 42, said thermal energy communicator comprising a thermally conductive interface material in thermal communication with said body portion when said apparatus is worn and said first temperature measuring device.

60. An apparatus according to claim 59, said thermally conductive interface material selected from the group consisting of thermally conductive gap fillers, thermally conductive phase change interface materials, thermally conductive tapes, thermally conductive cure-in-place compounds and epoxies, and thermal greases.

61. An apparatus according to claim 42, further comprising a housing support section attached to said housing, said housing support section being suitable to engage at least a portion of said body of said wearer.

62. An apparatus according to claim 42, further comprising a housing support section for engaging at least a portion of said body of said wearer, said housing support section being removably attached to said housing.

63. An apparatus according to claim 42, further comprising a plurality of housing support sections each suitable to engage at least a portion of said body of said wearer, and means for removably attaching said housing to any one of said housing support sections.

64. An apparatus according to claim 63, said apparatus having adjustable operating parameters, further comprising means for adjusting said operating parameters depending on the particular one of said housing support sections to which said housing is removably attached.

65. An apparatus for detecting at least one of human physiological and contextual information from the body of a wearer in an ambient environment, comprising:
a housing;
a printed circuit board supported by said housing, said printed circuit board having a preselected resistivity;
a first thermistor attached to a first side of said printed circuit board and a second thermistor attached to a second side of said printed circuit board;
a processing unit supported by said housing, said first thermistor and said second thermistor in electrical communication with said processing unit;
a heat conduit, said heat conduit having a first surface and a second surface;
a first thermally conductive interface component, said first thermally conductive interface component being in thermal communication with said body of said wearer when said apparatus is being worn;
a second thermally conductive interface component in thermal communication with said ambient environment when said apparatus is being worn; and
a first thermally conductive interface material located between said first thermally conductive interface component and said first surface of said heat conduit, a second thermally conductive interface material located between said second surface of said heat conduit and said first thermistor, and a third thermally conductive interface material located between said second thermistor and said second thermally conductive interface component;
wherein said apparatus is adapted to measure heat flux between said body and said ambient environment.

66. An apparatus according to claim 65, said first thermally conductive interface component, said first thermally conductive interface material, said heat conduit, said second thermally conductive interface material, said first thermistor, said printed circuit board, said second thermistor, said third thermally conductive interface material and said second thermally conductive interface component attached to one another along a direction substantially normal to said first and second sides of said printed circuit board.

67. An apparatus according to claim 65, further comprising a housing support section for holding said housing in engagement with said body of said wearer, said housing support section exposing said second thermally conductive interface component to said ambient environment.

68. An apparatus for detecting, monitoring and reporting at least one of human physiological and contextual information from the body of a wearer, comprising:
a housing having an adhesive material on at least a portion of an external surface thereof, said adhesive material enabling said housing to be removably attached to a portion of said body;
at least two sensors supported by said housing selected from the group consisting of physiological sensors and contextual sensors, said physiological sensors adapted to facilitate the generation of data indicative of one or more detected physiological parameters of said wearer, said contextual sensors adapted to facilitate the generation of data indicative of one or more detected contextual parameters of said wearer;
a processing unit in electrical communication with said sensors, said processing unit being adapted to generate at least one of: (i) derived data from at least one of at least a portion of said data indicative of physiological parameters, (ii) derived data from at least a portion of said data indicative of contextual parameters, said derived data comprising a calculated parameter based on at least one of said detected parameters, being an individual status parameter that cannot be directly detected by any of said at least two sensors and (iii) analytical status data from at least a portion of at least one of said data indicative of physiological parameters, said data indicative of contextual parameters and said derived data;
an electronic memory in electrical communication with said processing unit for retrievably storing at least one of said data indicative of physiological parameters, data indicative of contextual parameters, derived data and analytical status data; and
means for transmitting to an individual at least one of said data indicative of physiological parameters, data indicative of contextual parameters, derived data and analytical status data.

69. An apparatus according to claim 68, said housing being made of a rigid material.

70. An apparatus according to claim 69, said analytical status data being generated from at least a portion of said manually entered information.

71. An apparatus according to claim 68, said housing being made of a flexible material.

72. An apparatus according to claim 71, said flexible material comprising a flexible plastic film.

73. An apparatus according to claim 68, said means for transmitting comprising an electrochemical display.

74. An apparatus according to claim 68, said portion of said body comprising the left chest, said data indicative of one or more physiological parameters of said wearer comprising heart related parameters.

75. An apparatus according to claim 74, said housing being made of a flexible material.

76. An apparatus according to claim 75, said flexible material comprising a flexible plastic film.

77. An apparatus according to claim 76, said means for transmitting comprising an electrochemical display.

78. An apparatus according to claim 68, further comprising a wireless communications device for at least one of receiving information from and transmitting information to a computing device.

79. An apparatus according to claim 78, said processing unit and said computing device adapted to engage in shared computing.

80. An apparatus according to claim 68, said means for transmitting comprising a computing device coupled to said processing unit.

81. An apparatus according to claim 80, said computing device being coupled to said processing unit by a physical connection.

82. An apparatus according to claim 80, said computing device being coupled to said processing unit by a wireless connection.

83. An apparatus according to claim 69, further comprising means for manually entering information into said apparatus.

84. An apparatus according to claim 83, said apparatus monitoring the degree to which said individual has followed a predetermined routine, said analytical status data comprising feedback to said individual relating to the degree to which said individual has followed said predetermined routine, said feedback being generated from at least a portion of at least one of said data indicative of one or more physiological parameters of said individual, said derived data and said manually entered data.

85. An apparatus according to claim 84, wherein said routine comprises a plurality of categories and said feedback is generated and provided with respect to each of said categories.

86. An apparatus according to claim 68, said means for transmitting comprising a computing device coupled to said processing unit, said processing unit being adapted to cause said computing device to trigger an event upon detection of one or more physiological conditions of said wearer.

87. An apparatus according to claim 68, said processing unit being adapted to cause a computing device to trigger an event upon detection of one or more physiological conditions of said individual.

88. An apparatus according to claim 68, said at least two sensors being selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

89. An apparatus for detecting at least one of human physiological and contextual information from the body of a wearer, comprising:
a housing, said housing having an inner surface for mounting adjacent said body and an outer surface opposite said inner surface;
said inner surface having a longitudinal axis and a transverse axis, said inner surface being generally concave in a first direction and having an axis of concavity coincident with said longitudinal axis, said inner surface being generally convex in a second direction generally perpendicular to said first direction and having an axis of convexity coincident with said transverse axis.

90. An apparatus according to claim 89, said inner surface having first and second lateral ends located at opposite ends of said axis of concavity, said housing having a first radiused portion adjacent to and including said first lateral end and a second radiused portion adjacent to and including said second lateral end.

91. An apparatus according to claim 90, said inner surface having third and fourth lateral ends located at opposite ends of said axis of convexity, said housing having a third radiused portion adjacent to and including said third lateral end and a fourth radiused portion adjacent to and including said fourth lateral end.

92. An apparatus according to claim 90, further comprising one or more sensors located adjacent to at least one of said first and second lateral ends.

93. An apparatus according to claim 90, said outer surface having a convex shape between a first lateral side and a second lateral side of said outer surface.

94. An apparatus according to claim 93, said housing having a width dimension as measured between a first lateral side and a second lateral side of said housing, at least a portion of said first lateral side and said second lateral side each having a taper such that said width dimension gradually decreases in a third direction from said inner surface to said outer surface.

95. An apparatus according to claim 93, said housing having a third radiused portion adjacent to and including said first lateral side of said outer surface and a fourth radiused portion adjacent to and including said second lateral side of said outer surface.

96. An apparatus according to claim 94, said housing having a third radiused portion adjacent to and including said first lateral side of said outer surface and a fourth radiused portion adjacent to and including said second lateral side of said outer surface.

97. An apparatus according to claim 89, said outer surface having a convex shape between a first lateral side and a second lateral side of said outer surface.

98. An apparatus according to claim 97, said housing having a width dimension as measured between a first lateral side and a second lateral side of said housing, at least a portion of said first lateral side and said second lateral side each having a taper such that said width dimension gradually decreases in a third direction from said inner surface to said outer surface.

99. An apparatus according to claim 89, further comprising a housing support section attached to said housing for engaging said body of said wearer, said housing support section having a generally convex outer surface.

100. An apparatus according to claim 89, further comprising one or more sensors supported by said housing, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

101. An apparatus for detecting at least one of human physiological and contextual information from the body of a wearer, comprising:
a housing suitable to be worn on said body;
one or more sensors supported by said housing, said one or more sensors selected from the group consisting of physiological sensors and contextual sensors; and
a processing unit supported by said housing in electronic communication with said one or more sensors, said one or more sensors comprising a sensor for measuring GSR including at least two electrical contacts, said electrical contacts having a textured surface.

102. An apparatus according to claim 101, said textured surface comprising a plurality of raised bumps.

103. An apparatus according to claim 101, said electrical contacts having an oblong, curved shape.

104. An apparatus according to claim 101, said sensor for measuring GSR further comprising a current loop for applying a current between said electrical contacts and measuring a voltage across said electrical contacts.

105. An apparatus according to claim 101, further comprising a housing support section for engaging at least a portion of said body, said housing being attached to said housing support section.

106. An apparatus according to claim 105, said housing support section comprising a flexible section.

107. An apparatus according to claim 106, said housing being selectively removably attached to said housing support section.

108. An apparatus for detecting at least one of human physiological and contextual information from the body of a wearer, comprising:
 a housing suitable to be worn on said body;
 one or more sensors supported by said housing, said one or more sensors selected from the group consisting of physiological sensors and contextual sensors;
 a processing unit supported by said housing in electronic communication with said one or more sensors; and
 a proximity sensor for sensing whether said apparatus is being worn.

109. An apparatus according to claim 108, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.
 a proximity sensor for sensing whether said apparatus is being worn.

110. An apparatus according to claim 108, further comprising a housing support section for engaging at least a portion of said body, said housing being attached to said housing support section.

111. An apparatus according to claim 110, said housing support section comprising a flexible section.

112. An apparatus according to claim 111, said housing being selectively removably attached to said housing support section.

113. An apparatus for detecting at least one of human physiological and contextual information from the body of a wearer, comprising:
 a housing suitable to be worn on said body;
 one or more sensors supported by said housing, said one or more sensors selected from the group consisting of physiological sensors and contextual sensors;
 a processing unit supported by said housing in electronic communication with said one or more sensors; and
 a proximity sensor for automatically powering said apparatus on and off.

114. An apparatus according to claim 113, further comprising a housing support section for engaging at least a portion of said body, said housing being attached to said housing support section.

115. An apparatus according to claim 114, said housing support section comprising a flexible section.

116. An apparatus according to claim 115, said housing being selectively removably attached to said housing support section.

117. An apparatus according to claim 113, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

118. An apparatus for detecting at least one of human physiological and contextual information from the body of a wearer, comprising:
 a housing suitable to be worn on said body;
 one or more sensors supported by said housing, said one or more sensors selected from the group consisting of physiological sensors and contextual sensors, said sensors generating data indicative of at least a detected parameter of the wearer;
 a processing unit supported by said housing in electronic communication with said one or more sensors generating derived data comprising a calculated parameter based on said detected parameter, being an individual status parameter that cannot be directly detected by one of said one or more sensors, said processing unit being in electronic communication with a feedback device for providing feedback information to a wearer of said device.

119. An apparatus according to claim 118, further comprising a housing support section for engaging at least a portion of said body, said housing being attached to and supported by said housing support section.

120. An apparatus according to claim 119, said housing support section comprising a flexible section.

121. An apparatus according to claim 120, said housing being selectively removably attached to said housing support section.

122. An apparatus according to claim 118, said one or more sensors comprising two sensors supported by said housing.

123. An apparatus according to claim 118, further comprising at least one additional sensor in electrical communication with said processing unit.

124. An apparatus according to claim 123, wherein said additional sensor is external to said housing.

125. An apparatus according to claim 118, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor and a sensor for measuring heart related parameters.

126. A method for detecting from the body of a wearer parameters relating to the heart of the wearer, comprising:
 generating a first physiological acoustic signal including a first physiological acoustic component generated from the motion of said heart and a second physiological acoustic component generated from non-heart related motion of said body of said wearer, said non-heart related motion comprising footfalls of said wearer;
 generating a second signal related to said non-heart related motion of said body;
 generating a third signal by using said second signal to subtract at least a portion of said second physiological acoustic component from said first signal; and
 generating said heart related parameters from said third signal.

127. A method according to claim 126, wherein said information relating to said footfalls is generated using an accelerometer.

128. An apparatus for detecting, monitoring and reporting at least one of human physiological and contextual information from the body of a wearer, comprising:
- a housing having an adhesive material on at least a portion of an external surface thereof, said adhesive material enabling said housing to be removably attached to a portion of said body;
- at least two sensors supported by said housing, said at least two sensors being selected from the group consisting of physiological sensors and contextual sensors, said sensors generating data indicative of at least a first parameter and a second parameter of the wearer;
- a processor, said processor generating derived data based on said data indicative of at least a first parameter and a second parameter, said derived data comprising a third parameter of said wearer, said third parameter being an individual status parameter that cannot be directly detected by any of said at least two sensors;
- a memory for retrievably storing at least one of said data indicative of at least a first parameter and a second parameter and said derived data; and
- means for transmitting to an individual at least one of said data indicative of at least a first parameter and a second parameter and said derived data.

129. An apparatus according to claim 128, said housing being made of a rigid material.

130. An apparatus according to claim 128, said housing being made of a flexible material.

131. An apparatus according to claim 130, said flexible material comprising a flexible plastic film.

132. An apparatus according to claim 128, said means for transmitting comprising an electrochemical display.

133. An apparatus according to claim 128, said portion of said body comprising the left chest, said data indicative of at least a first parameter and a second parameter of the wearer comprising heart related parameters, said derived data relating to the heart of said wearer.

134. An apparatus according to claim 133, said housing being made of a flexible material.

135. An apparatus according to claim 133, said flexible material comprising a flexible plastic film.

136. An apparatus according to claim 133, said means for transmitting comprising an electrochemical display.

137. An apparatus according to claim 128, further comprising a wireless communications device for at least one of receiving information from and transmitting information to a computing device.

138. An apparatus according to claim 137, said processor and said computing device adapted to engage in shared computing.

139. An apparatus according to claim 128, said means for transmitting comprising a computing device in electronic communication with said processor.

140. An apparatus according to claim 128, said means for transmitting comprising a computing device in electronic communication with said processor, said processor being adapted to cause said computing device to trigger an event upon detection of one or more physiological conditions of said individual.

141. An apparatus according to claim 128, said processor being adapted to cause a computing device to trigger an event upon detection of one or more physiological conditions of said wearer.

142. An apparatus according to claim 128, said at least two sensors being selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

143. An apparatus for detecting at least one of human physiological and contextual information from the body of a wearer, comprising:
- a housing suitable to be worn on said body;
- housing support section for engaging at least a portion of said body, said housing being attached to said housing support section;
- one or more sensors supported by said housing, said one or more sensors selected from the group consisting of physiological sensors and contextual sensors; and
- a processing unit supported by said housing in electronic communication with said one or more sensors, said one or more sensors comprising a sensing component for contacting the skin of a wearer, said sensing component comprising a plurality of microneedles.

144. An apparatus according to claim 143, said housing support section comprising a flexible section.

145. An apparatus according to claim 144, said housing being selectively removably attached to said housing support section.

146. An apparatus for detecting at least one of human physiological and contextual information from the body of a wearer, comprising:
- a self-contained housing suitable to be worn on said body;
- one or more sensors within said housing, said one or more sensors selected from the group consisting of physiological sensors and contextual sensors; and
- a processing unit within said housing in electronic communication with said one or more sensors, said one or more sensors comprising one or more electrical contacts, said electrical contacts having a textured surface.

147. An apparatus according to claim 146, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

148. An apparatus according to claim 146, said textured surface comprising a plurality of raised bumps.

149. An apparatus according to claim 146, further comprising a housing support section for engaging at least a portion of said body, said housing being attached to said housing support section.

150. An apparatus according to claim 149, said housing support section comprising a flexible section.

151. An apparatus according to claim 150, said housing being selectively removably attached to said housing support section.

152. An apparatus for detecting at least one of human physiological and contextual information from the body of a wearer, comprising:
- a housing suitable to be worn on said body;
- a housing support section for engaging at least a portion of said body, said housing being attached to said housing support section;

one or more sensors supported by said housing, said one or more sensors selected from the group consisting of physiological sensors and contextual sensors; and a processing unit supported by said housing in electronic communication with said one or more sensors and with a sensing component placed in contact with the skin of said wearer, said sensing component comprising a plurality of microneedles.

153. An apparatus according to claim 152, said housing support section comprising a flexible section.

154. An apparatus according to claim 153, said housing being selectively removably attached to said housing support section.

155. An apparatus for detecting at least one of human physiological and contextual information from the body of a wearer, comprising:
- a housing suitable to be worn on said body;
- one or more sensors supported by said housing, said one or more sensors comprising at least one of: an ambient temperature sensor, an ambient light sensor, an ambient sound sensor, an EMG sensor, a skin impedance sensor and a heat flux sensor;
- a processing unit supported by said housing in electronic communication with said one or more sensors; and
- a wireless transceiver for receiving information from and transmitting information to a computing device, said computing device displaying information to an individual and enabling said individual to input information, said computing device and said processing unit being adapted to engage in shared computing.

156. An apparatus according to claim 155, further comprising a housing support section for engaging at least a portion of said body, said housing being attached to said housing support section.

157. An apparatus according to claim 156, said housing support section comprising a flexible section.

158. An apparatus according to claim 157, said housing being selectively removably attached to said housing support section.

159. An apparatus according to claim 155, further comprising two sensors.

160. An apparatus according to claim 155, wherein said sensors generate data indicative of at least a detected parameter of the wearer and said processing unit generates derived data comprising a derived parameter based on said detected parameter, being an individual status parameter that cannot be directly detected by one of said one or more sensors.

161. An apparatus for detecting at least one of human physiological and contextual information from the body of a wearer, comprising:
- a housing suitable to be worn on said body;
- one or more sensors supported by said housing, said one or more sensors further comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters; and
- a processing unit supported by said housing in electronic communication with said one or more sensors, said one or more sensors comprising a sensing component for contacting the skin of said wearer, said sensing component comprising a plurality of microneedles.

162. An apparatus for detecting at least one of human physiological and contextual information from the body of a wearer, comprising:
- a housing suitable to be worn on said body;
- an ECG sensor and an accelerometer supported by said housing;
- a processing unit supported by said housing in electronic communication with said sensors, said processing unit being in electronic communication with a feedback device for providing feedback information to a wearer of said device.

163. An apparatus for detecting at least one of human physiological and contextual information from the body of a wearer, comprising:
- a self-contained housing suitable to be worn on the upper arm portion of said body;
- one or more sensors within said housing, said one or more sensors selected from the group consisting of physiological sensors and contextual sensors, said one or more sensors comprising at least one of: an ambient temperature sensor, an ambient light sensor, an ambient sound sensor, an EMG sensor, a skin impedance sensor, and a heat flux sensor; and
- a processing unit within said housing in electronic communication with said one or more sensors.

164. An apparatus for detecting at least one of human physiological and contextual information from the body of a wearer, comprising:
- a housing support section for engaging at least a portion of said body, said housing support section having an adhesive material on a surface thereof for attaching said housing support section to said body;
- a housing located between said housing support section and said body, said housing being held against said body by said housing support section;
- one or more sensors supported by said housing, said one or more sensors selected from the group consisting of physiological sensors and contextual sensors; and
- a processing unit supported by said housing in electronic communication with said one or more sensors.

165. An apparatus according to claim 164, said housing support section comprising a flexible section.

166. An apparatus according to claim 164, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

167. An apparatus according to claim 164, said housing being selectively removably attached to said housing support section.

168. An apparatus according to claim 164, said housing having an inner surface for mounting adjacent said body and an outer surface opposite said inner surface, said inner surface having a generally concave cross section.

169. An apparatus according to claim 164, said housing having an inner surface for mounting adjacent said body and an outer surface opposite said inner surface, said inner surface having a generally convex cross section.

170. An apparatus according to claim 164, said housing having an inner surface for mounting adjacent said body and an outer surface opposite said inner surface, said inner surface having a longitudinal axis and a transverse axis, said inner surface being generally concave in a first direction and having an axis of concavity coincident with said longitudinal axis, said inner surface being generally convex in a second direction generally perpendicular to said first direction and having an axis of convexity coincident with said transverse axis.

171. An apparatus for detecting at least one of human physiological and contextual information from the body of a wearer, comprising:
   a housing, said housing engaging said body;
   one or more sensors supported by said housing, said one or more sensors selected from the group consisting of physiological sensors and contextual sensors;
   a processing unit supported by said housing in electronic communication with said one or more sensors;
   a housing support section placed over said housing, said housing support section engaging said body and securing said housing in place against said body by way of pressure alone.

172. An apparatus according to claim 171, said housing support section comprising a flexible section.

173. An apparatus according to claim 171, said one or more sensors comprising at least one of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

174. An apparatus according to claim 171, said housing having an inner surface for mounting adjacent said body and an outer surface opposite said inner surface, said inner surface having a generally concave cross section.

175. An apparatus according to claim 171, said housing having an inner surface for mounting adjacent said body and an outer surface opposite said inner surface, said inner surface having a generally convex cross section.

176. An apparatus according to claim 171, said housing having an inner surface for mounting adjacent said body and an outer surface opposite said inner surface, said inner surface having a longitudinal axis and a transverse axis, said inner surface being generally concave in a first direction and having an axis of concavity coincident with said longitudinal axis, said inner surface being generally convex in a second direction generally perpendicular to said first direction and having an axis of convexity coincident with said transverse axis.

177. An apparatus for detecting at least one of human physiological and contextual information from the body of a wearer, comprising:
   a housing suitable to be worn on said body;
   one or more sensors supported by said housing, said one or more sensors selected from the group consisting of physiological sensors and contextual sensors;
   a processing unit supported by said housing in electronic communication with said one or more sensors, said processing unit being in electronic communication with a feedback device having a sensor for providing feedback information to a wearer of said device.

178. An apparatus for detecting at least one of human physiological and contextual information from the body of a wearer, comprising:
   a housing;
   a housing support section comprising a flexible section for receiving and supporting the insertion of said housing, said housing support section engaging at least a portion of said body;
   one or more sensors supported by said housing, said one or more sensors selected from the group consisting of physiological sensors and contextual sensors; and
   a processing unit supported by said housing in electronic communication with said one or more sensors, said processing unit being in electronic communication with a feedback device for providing feedback information to a wearer of said device.

179. An apparatus according to claim 178, said housing being selectively removably attached to said housing support section.

180. An apparatus for detecting at least one of human physiological and contextual information from the body of a wearer, comprising:
   a housing suitable to be worn on a portion of said body;
   a housing support section for engaging at least a portion of said body, said housing being attached to said housing support section;
   one or more sensors supported by said housing, said one or more sensors selected from the group consisting of physiological sensors and contextual sensors; and
   a processing unit supported by said housing in electronic communication with said one or more sensors;
   said one or more sensors comprising a sensor for sensing one or more heart related parameters including at least one of heart rate, beat-to-beat variability, ECG, pulse oximetry, heart-related sounds, and parameters relating to the mechanical action of the heart, said portion of said body comprising the left chest.

181. An apparatus according to claim 180, said housing support section comprising a flexible section.

182. An apparatus according to claim 180, said housing being selectively removably attached to said housing support section.

183. An apparatus for detecting at least one of human physiological and contextual information from the body of a wearer, comprising:
   a housing suitable to be worn on said body;
   a housing support section comprising a flexible section for engaging at least a portion of said body, said housing being selectively removably attached to said housing support section;
   one or more sensors supported by said housing, said one or more sensors selected from the group consisting of physiological sensors and contextual sensors; and
   a processing unit supported by said housing in electronic communication with said one or more sensors, said one or more sensors comprising one or more electrical contacts, said electrical contacts having a textured surface comprising a plurality of raised bumps.

184. An apparatus for detecting at least one of human physiological and contextual information from the body of a wearer, comprising:
   a housing suitable to be worn on said body;
   one or more sensors supported by said housing, said one or more sensors selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters; and
   a processing unit supported by said housing in electronic communication with said one or more sensors and with a sensing component placed in contact with the skin of said wearer, said sensing component comprising a plurality of microneedles.

185. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and an electrochemical display for transmitting to an individual at least one of said data indicative of physiological parameters, data indicative of contextual parameters, derived data and analytical status data.

186. An apparatus for detecting, monitoring and reporting at least one of human physiological and contextual information from the body of a wearer, comprising:

a flexible housing comprising plastic film, said flexible housing having an adhesive material on at least a portion of an external surface thereof, said adhesive material enabling said housing to be removably attached to the left chest area of said body;

at least two sensors supported by said housing selected from the group consisting of physiological sensors and contextual sensors, said physiological sensors adapted to facilitate the generation of data indicative of one or more heart related physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least one of at least a portion of said data indicative of said heart related physiological parameters and at least a portion of said data indicative of contextual parameters, and (ii) analytical status data from at least a portion of at least one of said data indicative of said heart related physiological parameters, said data indicative of contextual parameters and said derived data;

an electronic memory in electrical communication with said processing unit for retrievably storing at least one of said data indicative of said heart related physiological parameters, data indicative of contextual parameters, derived data and analytical status data; and an electrochemical display for transmitting to an individual at least one of said data indicative of said heart related physiological parameters, data indicative of contextual parameters, derived data and analytical status data.

187. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least one of at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data;

means for transmitting to an individual at least one of said data indicative of physiological parameters, data indicative of contextual parameters, derived data and analytical status data; and a wireless communications device for at least one of receiving information from and transmitting information to a computing device wherein said processing unit and said computing device are adapted to engage in shared computing.

188. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and a computing device coupled to said processing unit by a physical connection for transmitting to an individual at least one of said data indicative of physiological parameters, data indicative of contextual parameters, derived data and analytical status data.

189. An apparatus for detecting, monitoring and reporting at least one of human physiological and contextual information from the body of a wearer, comprising:

a rigid housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and means for transmitting to an individual at least one of said data indicative of physiological parameters, data indicative of contextual parameters, derived data and analytical status data.

190. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data;

means for transmitting to an individual at least one of said data indicative of physiological parameters, data indicative of contextual parameters, derived data and analytical status data; and means for manually entering information into said apparatus.

191. An apparatus for detecting, monitoring and reporting at least one of human physiological and contextual information from the body of a wearer, comprising:

a rigid housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data;

means for transmitting to an individual at least one of said data indicative of physiological parameters, data indicative of contextual parameters, derived data and analytical status data; and means for manually entering information into said apparatus, said analytical status data being generated from at least a portion of manually entered information.

192. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and a computing device coupled to said processing unit for transmitting to an individual at least one of said data indicative of physiological parameters, data indicative of contextual parameters, derived data and analytical status data;

wherein said processing unit is adapted to cause said computing device to trigger an event upon detection of one or more physiological conditions of said wearer.

193. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data and to cause a computing device to trigger an event upon detection of one or more physiological conditions of said wearer;

an electronic memory in electrical communication with said processing unit for retrievably storing at least one of said data indicative of physiological parameters, data indicative of contextual parameters, derived data and analytical status data; and means for transmitting to an individual at least one of said data indicative of physiological parameters, data indicative of contextual parameters, derived data and analytical status data.

194. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of physiological sensors and contextual sensors, said physiological sensors adapted to facilitate the generation of data indicative of one or more physiological parameters of said wearer, said contextual sensors adapted to facilitate the generation of data indicative of one or more contextual parameters of said wearer;

a processing unit in electrical communication with said sensors, said processing unit being adapted to generate at least one of: (i) derived data from at least one of at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data;

means for transmitting to an individual at least one of said data indicative of physiological parameters, data indicative of contextual parameters, derived data and analytical status data; and means for manually entering information into said apparatus;

said apparatus monitoring the degree to which said individual has followed a predetermined routine, said analytical status data comprising feedback to said individual relating to the degree to which said individual has followed said predetermined routine, said feedback being generated from at least a portion of at least one of said data indicative of one or more physiological parameters of said individual, said derived data and said manually entered data.

195. An apparatus according to claim 194, wherein said routine comprises a plurality of categories and said feedback is generated and provided with respect to each of said categories.

196. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters, said sensors adapted to facilitate the generation of data indicative of one or more physiological parameters or contextual parameters of said wearer;

a processing unit in electrical communication with said sensors, said processing unit being adapted to generate at least one of: (i) derived data from at least a portion of said data indicative of physiological parameters and at least a portion of said data indicative of contextual parameters, and (ii) analytical status data from at least a portion of at least one of said data indicative of physiological parameters, said data indicative of contextual parameters and said derived data;

an electronic memory in electrical communication with said processing unit for retrievably storing at least one of said data indicative of physiological parameters, data indicative of contextual parameters, derived data and analytical status data; and means for transmitting to an individual at least one of said data indicative of physiological parameters, data indicative of contextual parameters, derived data and analytical status data.

197. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of physiological sensors and contextual sensors, said sensors generating data indicative of at least a first parameter and a second parameter of the wearer;

a processor, said processor generating derived data based on said data indicative of at least a first parameter and a second parameter;

a memory for retrievably storing at least one of said data indicative of at least a first parameter and a second parameter and said derived data; and an electrochemical display for transmitting to an individual at least one of said data indicative of at least a first parameter and a second parameter and said derived data.

198. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to the left chest area of said body;

at least two sensors supported by said housing, said at least two sensors being selected from the group consisting of physiological sensors and contextual sensors, said sensors generating data indicative of at least a first heart related parameter and a second heart related parameter of the wearer;

a processor, said processor generating derived data based on at least a portion of said first and second parameters, said derived data comprising heart related derived data;

a memory for retrievably storing at least one of said data indicative of at least a first heart related parameter and a second heart related parameter and said heart related derived data; and an electrochemical display for transmitting to an individual at least one of said data indicative of at least a first heart related parameter, said data indicative of at least a second heart related parameter, and said derived data.

199. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of physiological sensors and contextual sensors, said sensors generating data indicative of at least a first parameter and a second parameter of the wearer;

a processor, said processor generating derived data based on said data indicative of at least a first parameter and a second parameter;

a memory for retrievably storing at least one of said data indicative of at least a first parameter and a second parameter and said derived data;

means for transmitting to an individual at least one of said data indicative of at least a first parameter and a second parameter and said derived data; and a wireless communications device for at least one of receiving information from and transmitting information to a computing device, wherein said processor and said computing device adapted to engage in shared computing.

200. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of physiological sensors and contextual sensors, said sensors generating data indicative of at least a first parameter and a second parameter of the wearer;

a processor, said processor generating derived data based on said data indicative of at least a first parameter and a second parameter;

a memory for retrievably storing at least one of said data indicative of at least a first parameter and a second parameter and said derived data; and a computing device in electronic communication with said processor for transmitting to an individual at least one of said data indicative of at least a first parameter and a second parameter and said derived data, said processor being adapted to cause said computing device to trigger an event upon detection of one or more physiological conditions of said individual.

201. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of physiological sensors and contextual sensors, said sensors generating data indicative of at least a first parameter and a second parameter of the wearer;

a processor, said processor generating derived data based on said data indicative of at least a first parameter and a second parameter and adapted to cause a computing device to trigger an event upon detection of one or more physiological conditions of said wearer;

a memory for retrievably storing at least one of said data indicative of at least a first parameter and a second parameter and said derived data; and means for transmitting to an individual at least one of said data indicative of at least a first parameter and a second parameter and said derived data.

202. An apparatus for detecting, monitoring and reporting at least one of human physiological and contextual information from the body of a wearer, comprising:

a housing having an adhesive material on at least a portion of an external surface thereof, said adhesive material enabling said housing to be removably attached to a portion of said body;

at least two sensors supported by said housing, said at least two sensors being selected from the group consisting of: a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters, said sensors generating data indicative of at least a first parameter and a second parameter of the wearer;

a processor, said processor generating derived data based on said data indicative of at least a first parameter and a second parameter;

a memory for retrievably storing at least one of said data indicative of at least a first parameter and a second parameter and said derived data; and means for transmitting to an individual at least one of said data indicative of at least a first parameter and a second parameter and said derived data.

203. An apparatus for detecting from the body of a wearer parameters relating to the heart of the wearer, comprising:

an acoustic-based non-ECG heart parameter sensor that generates a first signal including a first acoustic component generated from the motion of said heart and a second acoustic component generated from footfalls created by said body of said wearer; and one or more filtering accelerometer sensors for generating a second signal related to said footfalls created by said body, said second signal being used to subtract at least a portion of said second acoustic component from said first signal to generate a third signal, said third signal being used to generate said heart related parameters.

204. An apparatus for detecting from the body of a wearer parameters relating to the heart of the wearer, comprising:

an acoustic-based non-ECG heart parameter sensor that generates a first signal including a first acoustic component generated from the motion of said heart and a second acoustic component generated from non-heart related motion of said body of said wearer, said first signal further including a third acoustic component generated from ambient noise;

one or more filtering sensors for generating a second signal related to said non-heart related motion of said body, said second signal being used to subtract at least a portion of said second acoustic component from said first signal to generate a third signal, said third signal being used to generate said heart related parameters; and an ambient noise sensor that generates a fourth signal related to said ambient noise, said fourth signal being used to subtract at least a portion of said third acoustic component from said first signal to generate said third signal.

205. A method for detecting from the body of a wearer parameters relating to the heart of the wearer, comprising:

generating a first acoustic signal including a first acoustic component generated from the motion of said heart and a second acoustic component generated from footfalls created by said body of said wearer;

generating a second signal related to said footfalls;

generating a third signal by using said second signal to subtract at least a portion said second acoustic component from said first signal; and generating said heart related parameters from said third signal.

206. A method according to claim 205, wherein said information relating to said footfalls is generated using an accelerometer.

207. A method for detecting from the body of a wearer parameters relating to the heart of the wearer, comprising:

generating a first acoustic signal including a first acoustic component generated from the motion of said heart and a second acoustic component generated from non-heart related motion of said body of said wearer, said first acoustic signal further including a third acoustic component generated from ambient noise;

generating a second signal related to said non-heart related motion of said body;

generating a third signal by using said second signal to subtract at least a portion said second acoustic component from said first signal;

generating said heart related parameters from said third signal; and generating a fourth signal related to said ambient noise, said step of generating said third signal further comprising using said fourth signal to subtract at least a portion of said third acoustic component from said first signal.

208. An apparatus for detecting at least one of human physiological and contextual information from the body of a wearer which is mounted on said body in conjunction with a garment, comprising:

a housing;

a garment suitable to be worn on a portion of the body which restrains and supports said housing in a position proximate to the upper arm of said body;

one or more sensors supported by said housing, said one or more sensors selected from the group consisting of physiological sensors and contextual sensors; and a processing unit supported by said housing in electronic communication with said one or more sensors;

said one or more sensors comprising a sensor for sensing one or more heart related parameters including at least one of pulse oximetry, heart-related sounds, and parameters relating to the mechanical action of the heart.

209. An apparatus for detecting at least one of human physiological and contextual information from the body of a wearer, comprising:

a self-contained housing suitable to be worn on the upper arm portion of said body;

one or more sensors within said housing, said one or more sensors selected from the group consisting of physiological sensors and contextual sensors; and a processing unit within said housing in electronic communication with said one or more sensors;

said one or more sensors comprising a sensor for sensing one or more heart related parameters including at least one of pulse oximetry, heart-related sounds, and parameters relating to the mechanical action of the heart.

210. An apparatus for detecting from the body of a wearer parameters relating to the heart of the wearer, comprising:

an acoustic-based non-ECG heart parameter sensor that generates a first signal including a first physiological acoustic component generated from the motion of said heart, a second physiological acoustic component generated from non-heart related motion of said body of said wearer, and a third acoustic component generated from ambient noise; and one or more filtering sensors for generating a second signal related to said non-heart related motion of said body and a third signal related to said ambient noise, said second signal being used to subtract at least a portion of said second physiological acoustic component from said first signal and said third signal being used to subtract at least a portion of said third acoustic component from said first signal to generate a fourth signal, said fourth signal being used to generate said heart related parameters.

211. An apparatus according to claim 210, said acoustic-based non-ECG heart parameter sensor including a sound transducer coupled to a pad containing an acoustic transmission material.

212. A method for detecting from the body of a wearer parameters relating to the heart of the wearer, comprising:

generating a first physiological acoustic signal including a first physiological acoustic component generated from the motion of said heart, a second acoustic component generated from non-heart related motion of said body, and a third acoustic component generated from ambient noise;

generating a second signal related to said non-heart related motion of said body;

generating a third signal related to said ambient noise;

generating a fourth signal by (i) using said second signal to subtract at least a portion of said second acoustic component from said first signal, and (ii) using said third signal to subtract at least a portion of said third acoustic component from said first signal;

generating said heart related parameters from said fourth signal.

213. An apparatus for detecting at least one of human physiological and contextual information from the body of a wearer, comprising:

a housing support section for engaging at least a portion of said body;

a housing removably attached to and supported by said housing support section;

a strap attached to said housing support section for securing said housing support section to said body;

one or more sensors supported by said housing, said one or more sensors selected from the group consisting of physiological sensors and contextual sensors; and a processing unit supported by said housing in electronic communication with said one or more sensors.

214. An apparatus according to claim 213, said one or more sensors comprising at least one of a sensor for measuring GSR including at least two electrical contacts, a skin temperature sensor, an ambient temperature sensor, an accelerometer, an ambient light sensor, an ambient sound sensor, an EMG sensor, an ECG sensor, a skin impedance sensor, a heat flux sensor, and a sensor for measuring heart related parameters.

215. An apparatus according to claim 213, said housing support section comprising a flexible section.

216. An apparatus according to claim 215, said housing being selectively removably attached to said housing support section.

217. An apparatus for detecting at least one of human physiological and contextual information from the body of a wearer, comprising:

a housing suitable to be worn on said body;

housing support section for engaging at least a portion of said body, said housing being attached to said housing support section;

one or more sensors supported by said housing, said one or more sensors selected from the group consisting of physiological sensors and contextual sensors;

a processing unit supported by said housing in electronic communication with said one or more sensors; and a wireless transceiver for receiving information from and transmitting information to a computing device, said computing device displaying information to an individual and enabling said individual to input information, said computing device and said processing unit being adapted to engage in shared computing.

218. An apparatus according to claim 217, said housing support section comprising a flexible section.

219. An apparatus according to claim 218, said housing being selectively removably attached to said housing support section.

220. An apparatus for detecting at least one of human physiological and contextual information from the body of a wearer, comprising:

a housing suitable to be worn on said body;

one or more sensors supported by said housing, said one or more sensors selected from the group consisting of physiological sensors and contextual sensors, said sensors generate data indicative of at least a detected parameter of the wearer;

a processing unit supported by said housing in electronic communication with said one or more sensors and generating derived data comprising a derived parameter based on said detected parameter, being an individual status parameter that cannot be directly detected by one of said one or more sensors.; and a wireless transceiver for receiving information from and transmitting information to a computing device, said computing device displaying information to an individual and enabling said individual to input information, said computing device and said processing unit being adapted to engage in shared computing.

221. An apparatus for detecting from the body of a wearer parameters relating to the heart of the wearer, comprising:

an acoustic-based non-ECG heart parameter sensor that generates a first signal including a first physiological acoustic component generated from the motion of said heart and a second physiological acoustic component generated from non-heart related motion of said body of said wearer, said non-heart related motion comprising footfalls of said wearer; and one or more filtering sensors comprising an accelerometer for generating a second signal related to said non-heart related motion of said body, said second signal being used to subtract at least a portion of said second physiological acoustic component from said first signal to generate a third signal, said third signal being used to generate said heart related parameters.

222. An apparatus according to claim 221, said acoustic-based non-ECG heart parameter sensor including a sound transducer coupled to a pad containing an acoustic transmission material.

* * * * *